US008178490B2

(12) United States Patent
Glinka et al.

(10) Patent No.: US 8,178,490 B2
(45) Date of Patent: May 15, 2012

(54) POLYBASIC BACTERIAL EFFLUX PUMP INHIBITORS AND THERAPEUTIC USES THEREOF

(75) Inventors: Tomasz Glinka, Cupertino, CA (US); Olga Rodny, Mountain View, CA (US); Keith A. Bostian, Atherton, CA (US); David M. Wallace, San Diego, CA (US); Robert I. Higuchi, Solana Beach, CA (US); Chun Chow, San Diego, CA (US); Chi Ching Mak, San Diego, CA (US); Gavin Hirst, San Diego, CA (US); Brian Eastman, San Diego, CA (US)

(73) Assignee: Rempex Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 12/613,329

(22) Filed: Nov. 5, 2009

(65) Prior Publication Data

US 2010/0152098 A1 Jun. 17, 2010

Related U.S. Application Data

(63) Continuation-in-part of application No. 12/116,172, filed on May 6, 2008, now abandoned.

(60) Provisional application No. 60/917,616, filed on May 11, 2007, provisional application No. 61/111,674, filed on Nov. 5, 2008.

(51) Int. Cl.
*A61K 38/00* (2006.01)

(52) U.S. Cl. ........................................................ 514/2.4

(58) Field of Classification Search ........................ None
See application file for complete search history.

(56) References Cited

U.S. PATENT DOCUMENTS

| | | | |
|---|---|---|---|
| 5,883,074 | A | 3/1999 | Boggs et al. |
| 5,989,832 | A | 11/1999 | Trias et al. |
| 6,114,310 | A | 9/2000 | Chamberland et al. |
| 6,133,261 | A | 10/2000 | Harris |
| 6,204,279 | B1 | 3/2001 | Leger et al. |
| 6,245,746 | B1 | 6/2001 | Chamberland et al. |
| 6,362,229 | B1 | 3/2002 | Markham et al. |
| 6,395,713 | B1 | 5/2002 | Beigelman et al. |
| 6,399,629 | B1 | 6/2002 | Chamberland et al. |
| 6,436,980 | B1 | 8/2002 | Leger et al. |
| 6,777,388 | B1 | 8/2004 | Grasso et al. |
| 7,056,917 | B2 | 6/2006 | Nakayama et al. |
| 2003/0092720 | A1 | 5/2003 | Nakayama et al. |

FOREIGN PATENT DOCUMENTS

| | | | |
|---|---|---|---|
| DE | 43 31 135 | A1 | 3/1995 |
| EP | 1 227 084 | A1 | 7/2002 |
| EP | 1 389 463 | A1 | 2/2004 |
| GB | 1299080 | | 12/1972 |
| GB | 2354771 | A | 4/2001 |
| WO | WO 99/37667 | | 7/1999 |
| WO | WO 00/01714 | | 1/2000 |
| WO | WO 2004/062674 | A2 | 7/2004 |
| WO | WO 2005/089738 | A2 | 9/2005 |
| WO | WO 2005/113579 | A1 | 12/2005 |
| WO | WO 2008/141010 | A2 | 11/2008 |

OTHER PUBLICATIONS

Bodor, et al., Soft Drug Design: General Principles and Recent Applications, Med. Res. Rev., 2000, p. 58-101, vol. 20 (1), John Wiley & Sons, Inc.

Lomovskaya, et al., Efflux Pumps: Their Role in Antibacterial Drug Discovery, Current Medicinal Chemistry, 2001, p. 1699-1711, vol. 8, Bentham Science publishers, Ltd.

Minks, et al., Noninvasive Tracing of Recombinant Proteins with "Fluorophenylalanine-Fingers", Analytical Biochemistry, 2000, p. 29-34, vol. 284, Academic Press.

PCT, International Preliminary Report on Patentability, dated Nov. 26, 2009, for PCT/US2008/062796.

PCT, International Preliminary Report on Patentability, dated Nov. 26, 2009, for PCT/US2008/062785.

PCT, International Search Report and The Written Opinion, dated Sep. 7, 2005, for PCT/US2005/017841.

PCT, International Search Report and The Written Opinion, dated Jun. 25, 2010, for PCT/US2009/063426.

Renau, et al., Addressing the Stability of C-Capped Dipeptide Efflux Pump Inhibitors that Potentiate the Activity of Levofloxacin in *Pseudomonas aeruginosa*, Bioorganic & Medicinal Chemistry Letters, 2001, p. 663-667, vol. 11, Elsevier Science Ltd.

Renau, et al., Addressing the Stability of C-Capped Dipeptide Efflux Pump Inhibitors that Potentiate the activity of Levofloxacin in *Pseudomonas aeruginosa*, Poster Presented at 40th Interscience Conference on Antimicrobial Agents and Chemotherapy, Sep. 17-20, 2000, Toronto, Canada.

Renau, et al., Conformationally-Restricted Analogues of Efflux Pump Inhibitors that Potentiate the Activity of Levofloxacin in *Pseudomonas aeruginosa*, Bioorganic & Medicinal Chemistry Letters, 2003, p. 2755-2758, vol. 13, Elsevier, Ltd.

Yoshida, et al., MexAB-OprM Specific Efflux Pump Inhibitors in *Pseudomonas aeruginosa*. Part 7: Highly Soluble and in Vivo Active Quaternary Ammonium Analogue D13-9001, a Potential Preclinical Candidate, Bioorganic & Medicinal Chemistry, 2007, p. 7087-7097, vol. 15, Elsevier, Ltd.

*Primary Examiner* — Cecilia J Tsang
*Assistant Examiner* — Thomas Heard
(74) *Attorney, Agent, or Firm* — Knobbe, Martens, Olson & Bear LLP

(57) ABSTRACT

Disclosed are compounds having polybasic functionalities. The compounds inhibit bacterial efflux pump inhibitors and are used in combination with an anti-bacterial agent to treat or prevent bacterial infections. These combinations can be effective against bacterial infections that have developed resistance to anti-bacterial agents through an efflux pump mechanism.

15 Claims, No Drawings

POLYBASIC BACTERIAL EFFLUX PUMP INHIBITORS AND THERAPEUTIC USES THEREOF

RELATED APPLICATIONS

This application is a continuation-in-part of U.S. application Ser. No. 12/116,172, filed May 6, 2008, which claims the benefit of U.S. Provisional Application No. 60/917,616, filed May 11, 2007. This application also claims the benefit of U.S. Provisional Application No. 61/111,674, filed Nov. 5, 2008.

BACKGROUND OF THE INVENTION

1. Field of the Invention

This invention relates to the field of antimicrobial agents and more specifically it relates to Efflux Pump Inhibitor (EPI) compounds to be co-administered with antimicrobial agents for the treatment of infections caused by drug resistant pathogens. The invention includes novel compounds useful as efflux pump inhibitors, compositions and devices comprising such efflux pump inhibitors, and therapeutic use of such compounds.

2. Description of the Related Art

Antibiotics have been effective tools in the treatment of infectious diseases during the last half-century. From the development of antibiotic therapy to the late 1980s there was almost complete control over bacterial infections in developed countries. However, in response to the pressure of antibiotic usage, multiple resistance mechanisms have become widespread and are threatening the clinical utility of antibacterial therapy. The increase in antibiotic resistant strains has been particularly common in major hospitals and care centers. The consequences of the increase in resistant strains include higher morbidity and mortality, longer patient hospitalization, and an increase in treatment costs.

Bacteria have developed several different mechanisms to overcome the action of antibiotics. These mechanisms of resistance can be specific for a molecule or a family of antibiotics, or can be non-specific and be involved in resistance to unrelated antibiotics. Several mechanisms of resistance can exist in a single bacterial strain, and those mechanisms may act independently or they may act synergistically to overcome the action of an antibiotic or a combination of antibiotics. Specific mechanisms include degradation of the drug, inactivation of the drug by enzymatic modification, and alteration of the drug target. There are, however, more general mechanisms of drug resistance, in which access of the antibiotic to the target is prevented or reduced by decreasing the transport of the antibiotic into the cell or by increasing the efflux of the drug from the cell to the outside medium. Both mechanisms can lower the concentration of drug at the target site and allow bacterial survival in the presence of one or more antibiotics that would otherwise inhibit or kill the bacterial cells. Some bacteria utilize both mechanisms, combining a low permeability of the cell wall (including membranes) with an active efflux of antibiotics.

In recent years interest in efflux-mediated resistance in bacteria has been triggered by the growing amount of data implicating efflux pumps in clinical isolates. The phenomenon of antibiotic efflux was first discovered in 1980, in the context of the mechanism of tetracycline resistance in enterobacteria. Since then, it has been shown that efflux of antibiotics can be mediated by more than one pump in a single organism and that almost all antibiotics are subject to resistance by this mechanism.

Some efflux pumps selectively extrude specific antibiotics. Examples of such pumps include the Tet or CmlA transporters, which can extrude tetracycline or chloramphenicol, respectively. Other efflux pumps, so-called multi-drug resistance (MDR) pumps, extrude a variety of structurally diverse compounds. In the latter case, a single efflux system may confer resistance to multiple antibiotics with different modes of action. In this respect, bacterial MDR pumps are similar to mammalian MDR transporters. In fact, one such pump, P-glycoprotein, the first discovered MDR pump, confers multiple drug resistance on cancer cells and is considered to be one of the major reasons tumor resistance to anti-cancer therapy. A typical example of bacterial MDR pump is MexAB-OprM from *Pseudomonas aeruginosa*. This pump has been shown to affect the susceptibility of the organism to almost all antibiotic classes which fluoroquinolones, β-lactams, macrolides, phenicols, tetracyclines, and oxazolidinones.

Efflux pumps in gram-positive bacteria excrete their substrates across a single cytoplasmic membrane. This is also the case for some pumps in gram-negative bacteria, and as a result their substrates are effluxed into the periplasmic space. Other efflux pumps from gram-negative bacteria efflux their substrates directly into the external medium, bypassing the periplasm and the outer membrane. These pumps are organized in complex three component structures, which traverse both inner and outer membranes. They consist of a transporter located in the cytoplasmic membrane, an outer membrane channel and a periplasmic 'linker' protein, which brings the other two components into contact. It is clearly advantageous for gram-negative bacteria to efflux drugs by bypassing the periplasm and outer membrane. In gram-negative bacteria the outer membrane significantly slows down the entry of both lipophilic and hydrophilic agents. The former, such as erythromycin and fusidic acid, are hindered by the lipopolysaccharide components of the outer leaflet of the outer membrane bilayer. Hydrophilic agents cross the outer membrane through water-filled porins whose size prevents rapid diffusion, even for small compounds such as fluoroquinolones and some β-lactams. Thus, direct efflux creates the possibility for two different mechanisms to work synergistically to provide the cell with a potent defense mechanism. Furthermore, direct efflux into the medium leads to decreased amounts of drugs not only in the cytoplasmic but also in the periplasmic space. This could explain the apparently paradoxical finding that efflux pumps protect gram-negative bacteria from β-lactam antibiotics whose target penicillin-binding proteins are found in the periplasm.

Many MDR pumps are encoded by the genes, which are normal constituents of bacterial chromosomes. In this case increased antibiotic resistance is a consequence of over-expression of these genes. Thus bacteria have the potential to develop multi-drug resistance without the acquisition of multiple specific resistance determinants. In some cases, the simultaneous operation of efflux pumps and other resistance mechanisms in the same cell results in synergistic effects.

While some genes encoding efflux pumps are not expressed in wild type cells and require induction or regulatory mutations for expression to occur, other efflux genes are expressed constitutively. As a result wild type cells have basal level of efflux activity. This basal activity of multi-drug efflux pumps in wild type cells contribute to intrinsic antibiotic resistance, or more properly, decreased antibiotic susceptibility. This intrinsic resistance may be low enough for the bacteria to still be clinically susceptible to therapy. However, the bacteria might be even more susceptible if efflux pumps were rendered non-functional, allowing lower doses of antibiotics to be effective. To illustrate, *P. aeruginosa* laboratory-derived mutant strain PAM1626, which does not produce any measurable amounts of efflux pump is 8 to 10 fold more susceptible to levofloxacin and meropenem than the parent strain *P. aeruginosa* PAM1020, which produces the basal level of MexAB-OprM efflux pump. Were it not for efflux pumps, the spectrum of activity of many so-called 'gram-positive' antibiotics could be expanded to previously non-susceptible gram-negative species. This can be applied to 'narrow-spectrum' β-lactams, macrolides, lincosamides, streptogramins, rifamycins, fusidic acid, and oxazolidinones—all of which have a potent antibacterial effect against engineered mutants lacking efflux pumps.

It is clear that in many cases, a dramatic effect on the susceptibility of problematic pathogens would be greatly enhanced if efflux-mediated resistance were to be nullified. Two approaches to combat the adverse effects of efflux on the efficacy of antimicrobial agents can be envisioned: identification of derivatives of known antibiotics that are not effluxed and development of therapeutic agents that inhibit transport activity of efflux pumps and could be used in combination with existing antibiotics to increase their potency.

There are several examples when the first approach has been successfully reduced to practice. These examples include new fluoroquinolones, which are not affected by multidrug resistance pumps in *Staphylococcus aureus* or *Streptococcus pneumoniae* or new tetracycline and macrolide derivatives, which are not recognized by the corresponding antibiotic-specific pumps. However, this approach appears to be much less successful in the case of multidrug resistance pumps from gram-negative bacteria. In gram-negative bacteria, particular restrictions are imposed on the structure of successful drugs: they must be amphiphilic in order to cross both membranes. It is this very property that makes antibiotics good substrates of multi-drug resistance efflux pumps from gram-negative bacteria. In the case of these bacteria the efflux pump inhibitory approach becomes the major strategy in improving the clinical effectiveness of existing antibacterial therapy.

The efflux pump inhibitory approach was first validated in the case of mammalian P-glycoprotein. And the first inhibitors have been found among compounds with previously described and quite variable pharmacological activities. For example, P-glycoprotein-mediated resistance, can be reversed by calcium channel blockers such as verpamyl and azidopine, immunosuppressive agents cyclosporin A and FK506 as well as antifungal agents such as rapamycin and FK520 (Raymond et al, 1994). It is important that efflux pump inhibitory activity was by no means connected to other activities of these compounds. In fact, the most advanced inhibitor of P-glycoprotein is a structural derivative of cyclosporin A and is devoid if immunosuppressive activity.

SUMMARY OF THE INVENTION

Some embodiments disclosed herein include bacterial efflux pump inhibitors having polybasic functionality. Other embodiments disclosed herein include pharmaceutical compositions and methods of treatment using these compounds.

One embodiment disclosed herein includes a compound having the structure of formula I, II or III:

I

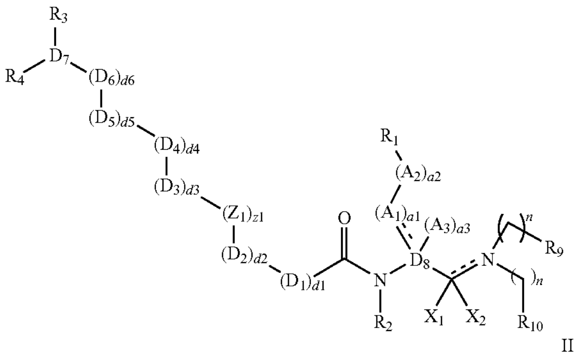

II

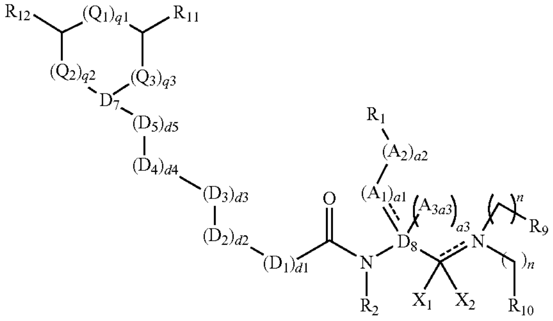

III

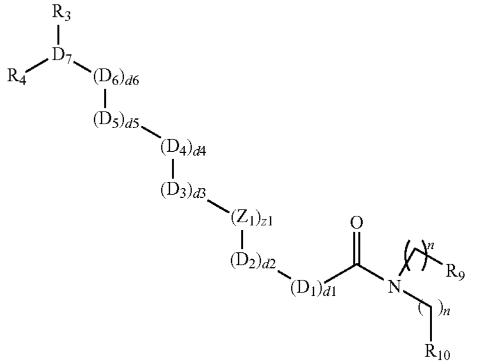

or a pharmaceutically acceptable salt or pro-drug thereof wherein;

each bond represented by a dashed and solid line represents a bond selected from the group consisting of a single bond and a double bond;

each $R_1$ is independently selected from $C_1$-$C_6$ alkyl, $C_3$-$C_7$ carbocyclyl, heterocyclyl, aryl and heteroaryl, each optionally substituted with up to 3 substituents independently selected from the group consisting of a halide, alkyl, carbocyclyl, heterocycle, $—(CH_2)_n$aryl, $—OR_2$, $—OR_{10}$, $—S(R_2)_2$, $—SO_2NHR_{10}$, $—(CH_2)_nSH$, $—CF_3$, $—OCF_3$, $—N(R_2)_2$, $—NO_2$, —CN, $—CO_2$alkyl, $—CO_2$aryl and —C(O)aryl;

each $R_2$ is independently selected from H, —OH, and $C_1$-$C_6$ alkyl;

$R_3$ is selected from $—(CH_2)_nCHR_5R_6$, $—(CH_2)_nNR_5R_6$, and $—(CH_2)_mC(═O)NR_5R_6$;

each $R_4$ is independently selected from $—NHR_2$, $—(CH_2)_n CHR_5R_6$, $—(CH_2)_nNR_5R_6$, $—(CH_2)_mC(═O)NR_5R_6$, and $—C(═NR_5)NR_5R_5$;

each $R_5$ is independently selected from H and $—(CH_2)_m NH_2$;

each $R_6$ is independently selected from $—(CH_2)_nNHR_7$, $—(CH_2)_nNHC(=NH)NH_2$, $—(CH_2)_nNHC(R_2)=NH$, $—(CH_2)_nC(=NH)NH_2$, and $—(CH_2)_nN^+(CH_3)_3$;

each $R_7$ is independently selected from H, alkyl, $—C(=O)CH(R_{13})(NH_2)$, $—C(=O)A_2CH_2NH_2$, Alanine, Arginine, Asparagine, Aspartic acid, Glutamic acid, Glutamine, Cysteine, Glycine, Histidine, Isoleucine, Leucine, Lysine, Methionine, Phenylalanine, Proline, Serine, Threonine, Tryptophan, Tyrosine, Valine, 3-benzyloxy alanine, and ornithine;

$R_8$ is selected from H, alkyl, aryl, SH and OH;

$R_9$ is selected from H, $C_1$-$C_6$ alkyl, $C_3$-$C_{10}$ carbocyclyl, heterocyclyl, aryl, heteroaryl, —C(O)O-heteroaryl, and —NHC(O)-aryl, each optionally substituted with up to 3 substituents independently selected from the group consisting of a halide, alkyl optionally substituted with $—CF_3$ or —OH, carbocyclyl optionally substituted with halide, $—(CH_2)_nR_1$, $—(CH=CH)_nR_1$, $—OR_2$, $—OR_1$, =O, $—S(R_2)_2$, $—SR_1$, $—SO_2NR_1R_2$, $SO_2CF_3$, $—(CH_2)_nSH$, $—CF_3$, $—OCF_3$, $—N(R_2)_2$, $—NO_2$, —CN, $—(C=X)R_1$, $—(C=X)R_2$, $—CO_2$alkyl, $—CO_2$aryl, heteroaryl optionally substituted with $C_1$-$C_6$ alkyl, and aryl optionally substituted with $C_1$-$C_6$ alkyl; or $R_9$ is absent;

$R_{10}$ is selected from $C_1$-$C_6$ alkyl, $C_3$-$C_{10}$ carbocyclyl, heterocyclyl, aryl, heteroaryl, —C(O)O-heteroaryl, and —NHC(O)-aryl, each optionally substituted with up to 3 substituents independently selected from the group consisting of a halide, alkyl optionally substituted with $—CF_3$ or —OH, carbocyclyl optionally substituted with halide, $—(CH_2)_nR_1$, $—OR_2$, $—OR_1$, =O, $—S(R_2)_2$, $—SR_1$, $—SO_2NR_1R_2$, $—SO_2CF_3$, $—(CH_2)_nSH$, $—CF_3$, $—OCF_3$, $—N(R_2)_2$, $—NO_2$, —CN, $—(C=X)R_1$, $—(C=X)R_2$, $—CO_2$alkyl, and $—CO_2$aryl;

$R_9$ and $R_{10}$ are optionally linked to form a ring;

$R_{11}$ is selected from H, $—(CH_2)_nNHR_2$ and $—(CH_2)_nCHR_5R_6$;

$R_{12}$ is selected from H, $—(CH_2)_nNHR_2$ and $—(CH_2)_nCHR_5R_6$, wherein at least one of $R_{11}$ and $R_{12}$ is not H;

$R_{13}$ is selected from $—(CH_2)_nCHR_5(CH_2)_nNH_2$, $—(CH_2)_mNR_5(CH_2)_nNH_2$ and $—(CH_2)_mC(=O)NR_5(CH_2)_nNH_2$;

$A_1$ is $—[C(R_2R_8)]_m—$ or $=CR_2[C(R_2R_8)]_m—$, wherein if $A_1$ is $=CR_2[C(R_2R_8)]_m—$, then a3 is 0;

$A_2$ is $—(CH_2)_m—$, $—C(=X)—$, $—O(CH_2)_n—$, $—S(CH_2)_n—$, —CH=CH—, $—C(=N—OR_2)—$, or $—NR_2—$;

$A_3$ is H, $—CF_3$, $C_1$-$C_6$ alkyl, a lone electron pair when $D_8$ is N, or $A_3$ is $—CH_2—$ bonded to $A_1$, $A_2$ or $R_1$ to form a ring;

a1, a2 and a3 are independently equal to 0 or 1;

$D_1$ is selected from $—CH_2—$, $—N(NHR_7)—$, $—CH(NHR_7)—$, $—CH[(CH_2)_mNHR_7]—$, $—CH(R_2)—$, and $—CH(CH_2SH)—$;

$D_2$, $D_3$, $D_4$, $D_5$ and $D_6$ are independently selected from the group consisting of $—(CH_2)_m—$, $—CH(R_2)—$, $—CH(NHR_7)—$, $—N(R_5)—$, —O—, —S—, —C(=X)—, —S(=O)— and $—SO_2—$, wherein any two atoms of $D_2$, $D_3$, $D_4$, $D_5$ and $D_6$ are optionally linked to form a three, four, five or six membered saturated ring;

$D_7$ is selected from N, =C< where the carbon forms a double bond with an adjacent carbon in one of $D_1$-$D_6$, CH and $CR_4$;

$D_8$ is selected from C and N;

d1, d2, d3, d4, d5 and d6 are independently equal to 0 or 1;

$Q_1$ is selected from $—CH_2—$, $—N(R_2)N(R_2)—$, and $—N(R_2)—$;

$Q_2$ and $Q_3$ are independently selected from the group consisting of $—CH_2—$, $CH_2CH_2—$, and $—N(R_2)—$;

with the proviso that no more than one of $Q_1$, $Q_2$, and $Q_3$ comprises a nitrogen;

q1, q2, and q3 are independently equal to 0 or 1;

$X_1$ and $X_2$ are each hydrogen or taken together are =O or =S, or $X_1$ is hydrogen and $X_2$ is —O— or —S— bonded to $R_{10}$ to form a 5- or 6-membered heterocyclyl, or $X_1$ is absent and $X_2$ is —O— or —S— bonded to $R_{10}$ to form a 5- or 6-membered heterocyclyl or heteroaryl, wherein when $X_1$ is absent, the bond to nitrogen represented by a dashed and solid line is a double bond;

each X is independently O or S;

$Z_1$ is an aryl, heteroaryl, carbocyclyl, or heterocyclyl;

z1 is 0 or 1;

if z1 is 0 then at least one from the group consisting of d1, d2, d3, d4, d5 and d6 are equal to 1, if z1 is 1 then at least one from the group consisting of d1, d2, d3, d4, d5 and d6 is equal to 1, wherein in the structure of formula III when z1 is 0 then d1 is 1, d2 is 1, and $D_2$ is selected from the group consisting of $—(CH_2)_m—$, $—CH(R_2)—$, $—CH(NHR_7)—$, —O—, —S—, —C(=X)—, —S(=O)— and $—SO_2—$;

each n is independently an integer of 0 to 4; and each m is independently an integer of 1 to 3.

Another embodiment disclosed herein includes a compound having the structure of formula IV:

(IV)

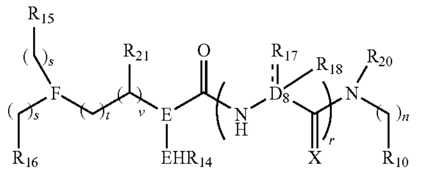

or a pharmaceutically acceptable salt or prodrug thereof, wherein:

$D_8$ is selected from C and N;

each E is independently CH or N;

F is selected from the group consisting of:

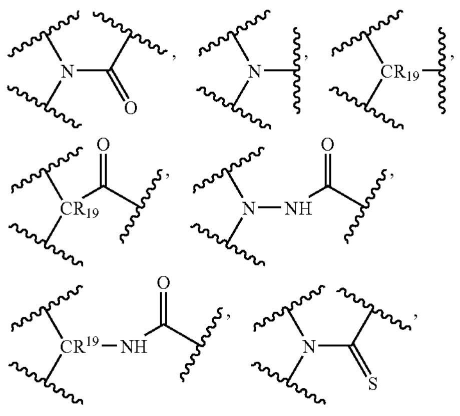

-continued

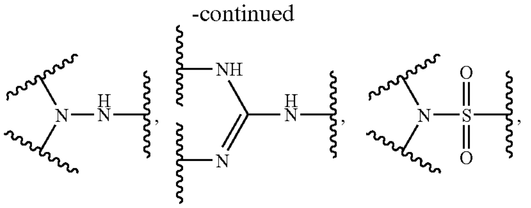

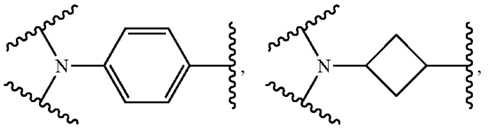

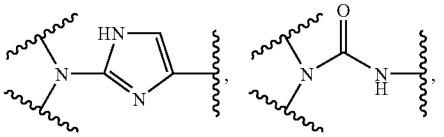

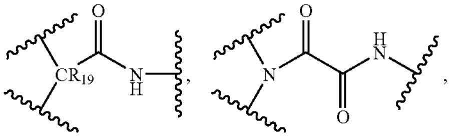

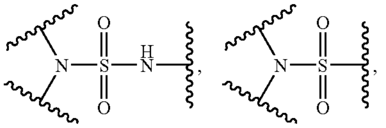

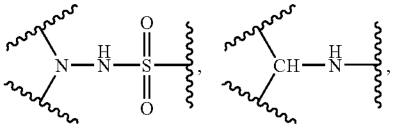

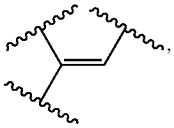
and

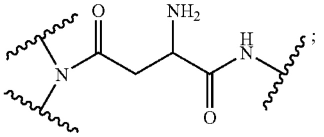

X is O or S;

$R_{10}$ is selected from carbocyclyl, heterocyclyl, aryl, heteroaryl, —NHC(O)-aryl, and aralkyl, each optionally substituted with up to 3 substituents independently selected from the group consisting of a halide, alkyl optionally substituted with —$CF_3$ or —OH, alkylaminoalkoxy, —$CF_3$, —$OCF_3$, —$NO_2$, —CN, —OH, =O, carbocyclyl optionally substituted with halide, heterocyclyl, aryl optionally substituted with halide or —OH, heteroaryl optionally substituted with alkyl, —O-aryl optionally substituted with —O—$C_1$-$C_6$ alkyl, alkyl, or heterocyclyl, —O-heteroaryl optionally substituted with halide or —$CF_3$, —O-heterocyclyl, —$SO_2$NH-heteroaryl, —O—$C_1$-$C_6$ alkyl, optionally substituted with halide, —$SO_2N(alkyl)_2$, SMe, —$SO_2CF_3$, di($C_1$-$C_6$) alkylamino, —$CH_2$-heterocyclyl optionally substituted with alkyl, —$CH_2$-aryl, —C(O)aryl, and —CH=CH-aryl;

$R_{14}$ is selected from H, —C(O)—CH(Me)($NH_2$), —C(O)—CH($CH_2$OH)($NH_2$), —C(O)CH($NH_2$)(arylether), —C(O)CH($NH_2$)(aminoalkyl), and —$(CH_2)_tNH_2$;

$R_{15}$ and $R_{16}$ are independently selected from —$NH_2$, —NHC(=NH)$NH_2$, —$N^+(CH_3)_3$, —$NHCH_2CH_2NH_2$, —$N(CH_2CH_2NH_2)_2$, —$C(O)N(CH_2CH_2NH_2)_2$, —$CH(CH_2NH_2)_2$, and —$CH_2(NH_2)(CH_2NH_2)$, or $R_{15}$ and $R_{16}$ together with F form a heterocyclyl substituted with one or more substituents independently selected from —$(CH_2)_sNH_2$, —$(CH_2)_sNHC(=NH)NH_2$, —$(CH_2)_sN^+(CH_3)_3$, —$(CH_2)_sNHCH_2CH_2NH_2$, —$(CH_2)_sN(CH_2CH_2NH_2)_2$, —$(CH_2)_sC(O)N(CH_2CH_2NH_2)_2$, and —$(CH_2)_sCH(CH_2NH_2)_2$;

$R_{17}$ is selected from alkyl, aralkyl, arylthioether, arylether, heteroaralkyl, carbocyclyl-alkyl, heterocyclyl-alkyl, aryl, and carbocyclyl, each optionally substituted with up to 3 substituents independently selected from the group consisting of —$CF_3$, —OH, —$OCF_3$, halide, —CN, alkyl, —O-aralkyl, aryl, —$S(CH_3)_2$, —C(O)aryl, —S-aralkyl optionally substituted with —OMe, =O, and =N—OH;

$R_{18}$ is H, alkyl, or absent, or $R_{17}$ together with $R_{18}$ form a carbocyclyl optionally substituted with aryl or heteroaryl;

$R_{19}$ is H, —$NH_2$, —$CH_2NH_2$, or —$CH_2CH_2NH_2$;

$R_{20}$ is H, alkyl, or heteroaryl;

$R_{21}$ is $NH_2$, —OH, alkyl, each t is independently an integer from 0 to 4;

each s is independently an integer from 0 to 3;

r is 0 or 1;

v is 0 or 1; and n is an integer from 0 to 4.

Other embodiments disclosed herein include methods of inhibiting a bacterial efflux pump by administering to a subject infected with a bacteria a compound according to any of the above formulas.

Another embodiment disclosed herein includes a method of treating or preventing a bacterial infection by co-administering to a subject infected with a bacteria or subject to infection with a bacteria, a compound according to any of the above formulas and another anti-bacterial agent.

Another embodiment disclosed herein includes a pharmaceutical composition that has a compound according to any of the above formulas and a pharmaceutically acceptable carrier, diluent, or excipient.

It is to be understood that both the foregoing general description and the following detailed description are exemplary and explanatory only and are not restrictive of the invention, as claimed.

DETAILED DESCRIPTION OF THE PREFERRED EMBODIMENT

Compositions and methods for inhibiting intrinsic drug resistance and/or preventing acquired drug resistance in microbes would be of tremendous benefit. Certain embodiments provide such compositions and methods.

Some embodiments relate to a method for treating a microbial infection whose causative microbe employs an efflux pump resistance mechanism, comprising contacting the microbial cell with an efflux pump inhibitor in combination with an antimicrobial agent. The efflux pump inhibitors of preferred embodiments can comprise polybasic structures, as disclosed herein.

Some embodiments include a method for prophylactic treatment of a mammal. In this method, an efflux pump inhibitor is administered to a mammal at risk of a microbial infection, e.g., a bacterial infection. In some embodiments, an antimicrobial agent is administered in combination with or coadministered with the efflux pump inhibitor.

Some embodiments also feature a method of enhancing the antimicrobial activity of an antimicrobial agent against a microbe, in which such a microbe is contacted with a efflux pump inhibitor, and an antibacterial agent.

In some embodiments, pharmaceutical compositions are provided that are effective for treatment of an infection of an animal, e.g., a mammal, by a microbe, such as a bacterium or a fungus. The composition includes a pharmaceutically acceptable carrier and an efflux pump inhibitor as described herein. Some embodiments provide antimicrobial formulations that include an antimicrobial agent, an efflux pump inhibitor, and a carrier. In some embodiments, the antimicrobial agent is an antibacterial agent.

In some embodiments, the efflux pump inhibitor is administered to the lungs as an aerosol. In some such embodiments, a co-administered antimicrobial agent may be administered in conjunction with the efflux pump inhibitor by any known means.

Definitions

In this specification and in the claims, the following terms have the meanings as defined. As used herein, "alkyl" means a branched, or straight chain chemical group containing only carbon and hydrogen, such as methyl, isopropyl, isobutyl, sec-butyl and pentyl. Alkyl groups can either be unsubstituted or substituted with one or more substituents, e.g., halogen, alkoxy, acyloxy, amino, amido, cyano, nitro, hydroxyl, mercapto, carboxy, carbonyl, benzyloxy, aryl, heteroaryl, or other functionality that may be suitably blocked, if necessary for purposes of the invention, with a protecting group. Alkyl groups can be saturated or unsaturated (e.g., containing —C═C— or —C≡C— subunits), at one or several positions. Typically, alkyl groups will comprise 1 to 8 carbon atoms, preferably 1 to 6, and more preferably 1 to 4 carbon atoms.

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. Carbocyclyl groups can either be unsubstituted or substituted with one or more substituents, e.g., halogen, alkoxy, acyloxy, amino, amido, cyano, nitro, hydroxyl, mercapto, carboxy, carbonyl, benzyloxy, aryl, heteroaryl, or other functionality that may be suitably blocked, if necessary for purposes of the invention, with a protecting group. Typically, carbocyclyl groups will comprise 3 to 10 carbon atoms, preferably 3 to 6.

As used herein, "lower alkyl" means a subset of alkyl, and thus is a hydrocarbon substituent, which is linear, or branched. Preferred lower alkyls are of 1 to about 4 carbons, and may be branched or linear. Examples of lower alkyl include butyl, propyl, isopropyl, ethyl, and methyl. Likewise, radicals using the terminology "lower" refer to radicals preferably with 1 to about 4 carbons in the alkyl portion of the radical.

As used herein, "amido" means a H—CON— or alkyl-CON—, aryl-CON— or heterocyclyl-CON group wherein the alkyl, cycloalkyl, aryl, heteroaryl or heterocyclyl group is as herein described.

As used herein, "aryl" means an aromatic radical having a single-ring (e.g., phenyl) or multiple condensed rings (e.g., naphthyl or anthryl) with only carbon atoms present in the ring backbone. Aryl groups can either be unsubstituted or substituted with one or more substitutents, e.g., amino, cyano, hydroxyl, lower alkyl, haloalkyl, alkoxy, nitro, halo, mercapto, and other substituents. A preferred carbocyclic aryl is phenyl.

As used herein, the term "heteroaryl" means an aromatic radical having one or more heteroatom(s) (e.g., N, O, or S) in the ring backbone and may include a single ring (e.g., pyridine) or multiple condensed rings (e.g., quinoline). Heteroaryl groups can either be unsubstituted or substituted with one or more substituents, e.g., amino, cyano, nitro, hydroxyl, alkyl, cycloalkyl, haloalkyl, alkoxy, aryl, halo, and mercapto. Examples of heteroaryl include thienyl, pyridyl, furyl, oxazolyl, oxadiazolyl, pyrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl and others.

In these definitions it is clearly contemplated that substitution on the aryl and heteroaryl rings is within the scope of certain embodiments. Where substitution occurs, the radical is called substituted aryl or substituted heteroaryl. Preferably one to three and more preferably one or two substituents occur on the aryl ring. Though many substituents will be useful, preferred substituents include those commonly found in aryl compounds, such as alkyl, cycloalkyl, hydroxy, alkoxy, cyano, halo, haloalkyl, mercapto and the like.

As used herein, "amide" includes both RNR'CO— (in the case of R=alkyl, alkaminocarbonyl-) and RCONR'— (in the case of R=alkyl, alkyl carbonylamino-).

As used herein, the term "ester" includes both ROCO— (in the case of R=alkyl, alkoxycarbonyl-) and RCOO— (in the case of R=alkyl, alkylcarbonyloxy-).

As used herein, the term "ether" (including the ether portion of an arylether group) includes an alkyl group in which one or more carbon atoms in the alkyl backbone have been replaced with an oxygen atom.

As used herein, "acyl" means an H—CO— or alkyl-CO—, aryl-CO— or heterocyclyl-CO— group wherein the alkyl, cycloalkyl, aryl or heterocyclyl group is as herein described. Preferred acyls contain a lower alkyl. Exemplary alkyl acyl groups include formyl, acetyl, propanoyl, 2-methylpropanoyl, t-butylacetyl, butanoyl and palmitoyl.

As used herein, "halo or halide" is a chloro, bromo, fluoro or iodo atom radical. Chloro, bromo and fluoro are preferred halides. The term "halo" also contemplates terms sometimes referred to as "halogen", or "halide".

As used herein, "haloalkyl" means a hydrocarbon substituent, which is linear or branched or cyclic alkyl, alkenyl or alkynyl substituted with chloro, bromo, fluoro or iodo atom(s). Most preferred of these are fluoroalkyls, wherein one or more of the hydrogen atoms have been substituted by fluoro. Preferred haloalkyls are of 1 to about 3 carbons in length, More preferred haloalkyls are 1 to about 2 carbons, and most preferred are 1 carbon in length. The skilled artisan will recognize then that as used herein, "haloalkylene" means a diradical variant of haloalkyl, such diradicals may act as spacers between radicals, other atoms, or between the parent ring and another functional group.

As used herein, "heterocyclyl" means a cyclic ring system comprising at least one heteroatom in the ring system backbone. Heterocyclyls may include multiple fused rings. Heterocyclyls may have any degree of saturation provided that at least one ring in the ring system is not aromatic. Heterocyclyls may be substituted or unsubstituted, and are attached to other groups via any available valence, preferably any available carbon or nitrogen. More preferred heterocycles are of 5 or 6 members. In six membered monocyclic heterocycles, the heteroatom(s) are selected from one up to three of O, N or S, and wherein when the heterocycle is five membered, preferably it has one or two heteroatoms selected from O, N, or S.

As used herein quaternary ammonium refers to a positively charged nitrogen atom linked to four aliphatic carbon atoms or a positively charged nitrogen of the heteroaryl ring linked to an aliphatic carbon as in N-pyridinium, N-thiazolium, N-imidazolium, N-triazolium and like.

As used herein, "substituted amino" means an amino radical which is substituted by one or two alkyl, cycloalkyl, aryl, heteroaryl or heterocyclyl groups, wherein the alkyl, aryl or heterocyclyl are defined as above.

As used herein, "substituted thiol" means RS— group wherein R is an alkyl, an aryl, or a heterocyclyl group, wherein the alkyl, cycloalkyl, aryl, heteroaryl or heterocyclyl are defined as above.

As used herein, "sulfonyl" means an alkyl$SO_2$, aryl$SO_2$ or heterocyclyl-$SO_2$ group wherein the alkyl, cycloalkyl, aryl, heteroaryl or heterocyclyl are defined as above.

As used herein, "sulfamido" means an alkyl-N—$S(O)_2$N—, aryl-$NS(O)_2N$— or heterocyclyl-$NS(O)_2N$— group wherein the alkyl, cycloalkyl, aryl, heteroaryl or heterocycyl group is as herein described.

As used herein, "sulfonamido" means an alkyl-$S(O)_2N$—, aryl-$S(O)_2N$— or heterocyclyl-$S(O)_2N$— group wherein the alkyl, cycloalkyl, aryl, heteroaryl or heterocycicyl group is as herein described.

As used herein, "ureido" means an alkyl-NCON—, aryl-NCON— or heterocyclyl-NCON— group wherein the alkyl, cycloalkyl, aryl, heteroaryl or heterocycyl group is as herein described As used herein, when two groups are indicated to be "linked" or "bonded" to form a "ring," it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions, and it is within the purview of the skilled artisan to both envision such rings and the methods of their formations. Preferred are rings having from 3-7 members, more preferably 5 or 6 members. As used herein the term "ring" or "rings" when formed by the combination of two radicals refers to heterocyclic, carbocyclic, aryl, or heteroaryl rings.

The skilled artisan will recognize that some structures described herein may be resonance forms or tautomers of compounds that may be fairly represented by other chemical structures, even when kinetically, the artisan recognizes that such structures are only a very small portion of a sample of such compound(s). Such compounds are clearly contemplated within the scope of this invention, though such resonance forms or tautomers are not represented herein.

The term "administration" or "administering" refers to a method of giving a dosage of an antimicrobial pharmaceutical composition to a vertebrate or invertebrate, including a mammal, a bird, a fish, or an amphibian, where the method is, e.g., intrarespiratory, topical, oral, intravenous, intraperitoneal, or intramuscular. The preferred method of administration can vary depending on various factors, e.g., the components of the pharmaceutical composition, the site of the potential or actual bacterial infection, the microbe involved, and the severity of an actual microbial infection.

A "diagnostic" as used herein is a compound, method, system, or device that assists in the identification and characterization of a health or disease state. The diagnostic can be used in standard assays as is known in the art.

The term "efflux pump" refers to a protein assembly that exports substrate molecules from the cytoplasm or periplasm of a cell, in an energy dependent fashion. Thus an efflux pump will typically be located in the cytoplasmic membrane of the cell (spanning the cytoplasmic membrane). In Gram-negative bacteria the pump may span the periplasmic space and there may also be portion of the efflux pump, which spans the outer membrane.

An "efflux pump inhibitor" ("EPI") is a compound that specifically interferes with the ability of an efflux pump to export its normal substrate, or other compounds such as an antibiotic. The inhibitor may have intrinsic antimicrobial (e.g., antibacterial) activity of its own, but at least a significant portion of the relevant activity is due to the efflux pump inhibiting activity.

The term "mammal" is used in its usual biological sense. Thus, it specifically includes humans, cattle, horses, dogs, and cats, but also includes many other species.

The term "microbial infection" refers to the invasion of the host organism, whether the organism is a vertebrate, invertebrate, fish, plant, bird, or mammal, by pathogenic microbes. This includes the excessive growth of microbes that are normally present in or on the body of a mammal or other organism. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal. Specifically, this description applies to a bacterial infection. Note that the compounds of preferred embodiments are also useful in treating microbial growth or contamination of cell cultures or other media, or inanimate surfaces or objects, and nothing herein should limit the preferred embodiments only to treatment of higher organisms, except when explicitly so specified in the claims.

The term "multidrug resistance pump" refers to an efflux pump that is not highly specific to a particular antibiotic. The term thus includes broad substrate pumps (efflux a number of compounds with varying structural characteristics). These pumps are different from pumps, which are highly specific for tetracyclines. Tetracycline efflux pumps are involved in specific resistance to tetracycline in bacteria. However, they do not confer resistance to other antibiotics. The genes for the tetracycline pump components are found in plasmids in Gram-negative as well as in Gram-positive bacteria.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); *Goodman and Gilman's: The Pharmacological Basis of Therapeutics,* 8th Ed., Pergamon Press.

The term "pharmaceutically acceptable salt" refers to salts that retain the biological effectiveness and properties of the compounds of the preferred embodiments and, which are not biologically or otherwise undesirable. In many cases, the compounds of the preferred embodiments are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in World Patent Publication 87/05297, Johnston et al., published Sep. 11, 1987 (incorporated by reference herein).

"Solvate" refers to the compound formed by the interaction of a solvent and an EPI, a metabolite, or salt thereof. Suitable solvates are pharmaceutically acceptable solvates including hydrates.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

In the context of the response of a microbe, such as a bacterium, to an antimicrobial agent, the term "susceptibility" refers to the sensitivity of the microbe for the presence of the antimicrobial agent. So, to increase the susceptibility means that the microbe will be inhibited by a lower concentration of the antimicrobial agent in the medium surrounding the microbial cells. This is equivalent to saying that the microbe is more sensitive to the antimicrobial agent. In most cases the minimum inhibitory concentration (MIC) of that antimicrobial agent will have been reduced.

By "therapeutically effective amount" or "pharmaceutically effective amount" is meant an amount of an efflux pump inhibitor, or amounts individually of an efflux pump inhibitor and an antimicrobial agent, as disclosed in the preferred embodiments, which have a therapeutic effect, which generally refers to the inhibition to some extent of the normal metabolism of microbial cells causing or contributing to a microbial infection. The doses of efflux pump inhibitor and antimicrobial agent, which are useful in combination as a treatment, are therapeutically effective amounts. Thus, as used herein, a therapeutically effective amount means those amounts of efflux pump inhibitor and antimicrobial agent which, when used in combination, produce the desired therapeutic effect as judged by clinical trial results and/or model animal infection studies. In particular embodiments, the efflux pump inhibitor and antimicrobial agent are combined in pre-determined proportions and thus a therapeutically effective amount would be an amount of the combination. This amount and the amount of the efflux pump inhibitor and antimicrobial agent individually can be routinely determined by one of skill in the art, and will vary, depending on several factors, such as the particular microbial strain involved and the particular efflux pump inhibitor and antimicrobial agent used. This amount can further depend upon the patient's height, weight, sex, age and medical history. For prophylactic treatments, a therapeutically effective amount is that amount which would be effective if a microbial infection existed.

A therapeutic effect relieves, to some extent, one or more of the symptoms of the infection, and includes curing an infection. "Curing" means that the symptoms of active infection are eliminated, including the elimination of excessive members of viable microbe of those involved in the infection. However, certain long-term or permanent effects of the infection may exist even after a cure is obtained (such as extensive tissue damage).

"Treat," "treatment," or "treating," as used herein refers to administering a pharmaceutical composition for prophylactic and/or therapeutic purposes. The term "prophylactic treatment" refers to treating a patient who is not yet infected, but who is susceptible to, or otherwise at risk of, a particular infection. The term "therapeutic treatment" refers to administering treatment to a patient already suffering from an infection. Thus, in preferred embodiments, treating is the administration to a mammal (either for therapeutic or prophylactic purposes) of therapeutically effective amounts of an efflux pump inhibitor and an antibacterial (or antimicrobial) agent in combination (either simultaneously or serially).

Compounds

Some embodiments include compounds containing within the Box A fragment at least two basic nitrogen functionalities basic enough to be protonated to an appreciable degree at physiological pH of 7.4. One embodiment includes a compound having the structure of formula (I):

I

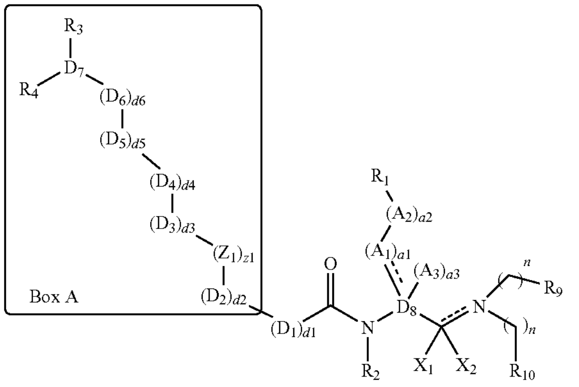

or a pharmaceutically acceptable salt or pro-drug thereof wherein;

each bond represented by a dashed and solid line represents a bond selected from the group consisting of a single bond and a double bond;

each $R_1$ is independently selected from $C_1$-$C_6$ alkyl, $C_3$-$C_7$ carbocyclyl, heterocyclyl, aryl and heteroaryl, each optionally substituted with up to 3 substituents independently selected from the group consisting of a halide, alkyl, carbocyclyl, heterocyclyl, —$(CH_2)_n$aryl, —$OR_2$, —$OR_{10}$, —$S(R_2)_2$, —$SO_2NHR_{10}$, —$(CH_2)_n$SH, —$CF_3$, —$OCF_3$, —$N(R_2)_2$, —$NO_2$, —CN, —$CO_2$alkyl, —$CO_2$aryl and —C(O)aryl;

each $R_2$ is independently selected from H, —OH, and $C_1$-$C_6$ alkyl;

$R_3$ is selected from —$(CH_2)_n CHR_5R_6$, —$(CH_2)_n NR_5R_6$, and —$(CH_2)_m C(=O)NR_5R_6$;

each $R_4$ is independently selected from $-NHR_2$, $-(CH_2)_nCHR_5R_6$, $-(CH_2)_nNR_5R_6$, $-(CH_2)_mC(=O)NR_5R_6$, and $-C(=NR_5)NR_5R_5$;

each $R_5$ is independently selected from H and $-(CH_2)_mNH_2$;

each $R_6$ is independently selected from $-(CH_2)_nNHR_7$, $-(CH_2)_nNHC(=NH)NH_2$, $-(CH_2)_nNHC(R_2)=NH$, $-(CH_2)_nC(=NH)NH_2$, and $-(CH_2)_nN^+(CH_3)_3$;

each $R_7$ is independently selected from H, alkyl, $-C(=O)CH(R_{13})(NH_2)$, $-C(=O)A_2CH_2NH_2$, Alanine, Arginine, Asparagine, Aspartic acid, Glutamic acid, Glutamine, Cysteine, Glycine, Histidine, Isoleucine, Leucine, Lysine, Methionine, Phenylalanine, Proline, Serine, Threonine, Tryptophan, Tyrosine, Valine, 3-benzyloxy alanine, and ornithine;

$R_8$ is selected from H, alkyl, aryl, SH and OH;

$R_9$ is selected from H, $C_1$-$C_6$ alkyl, $C_3$-$C_{10}$ carbocyclyl, heterocyclyl, aryl, heteroaryl, —C(O)O-heteroaryl, and —NHC(O)-aryl, each optionally substituted with up to 3 substituents independently selected from the group consisting of a halide, alkyl optionally substituted with $-CF_3$ or —OH, carbocyclyl optionally substituted with halide, $-(CH_2)_nR_1$, $-(CH=CH)_nR_1$, $-OR_2$, $-OR_1$, =O, $-S(R_2)_2$, $-SR_1$, $-SO_2NR_1R_2$, $-SO_2CF_3$, $-(CH_2)_nSH$, $-CF_3$, $-OCF_3$, $-N(R_2)_2$, $-NO_2$, —CN, $-(C=X)R_1$, $-(C=X)R_2$, $-CO_2$alkyl, $-CO_2$aryl, heteroaryl optionally substituted with $C_1$-$C_6$ alkyl, and aryl optionally substituted with $C_1$-$C_6$ alkyl; or $R_9$ is absent;

$R_{10}$ is selected from $C_1$-$C_6$ alkyl, $C_3$-$C_{10}$ carbocyclyl, heterocyclyl, aryl, heteroaryl, —C(O)O-heteroaryl, and —NHC(O)-aryl, each optionally substituted with up to 3 substituents independently selected from the group consisting of a halide, alkyl optionally substituted with $-CF_3$ or —OH, carbocyclyl optionally substituted with halide, $-(CH_2)_nR_1$, $-OR_2$, $-OR_1$, =O, $-S(R_2)_2$, $-SR_1$, $-SO_2NR_1R_2$, $-SO_2CF_3$, $-(CH_2)_nSH$, $-CF_3$, $-OCF_3$, $-N(R_2)_2$, $-NO_2$, —CN, $-(C=X)R_1$, $-(C=X)R_2$, $-CO_2$alkyl, and $-CO_2$aryl;

$R_9$ and $R_{10}$ are optionally linked to form a ring;

$R_{13}$ is selected from $-(CH_2)_nCHR_5(CH_2)_nNH_2$, $-(CH_2)_mNR_5(CH_2)_nNH_2$ and $-(CH_2)_mC(=O)NR_5(CH_2)_nNH_2$;

$A_1$ is $-[C(R_2R_8)]_m-$ or $=CR_2[C(R_2R_8)]_m-$, wherein if $A_1$ is $=CR_2[C(R_2R_8)]_m-$, then a3 is 0;

$A_2$ is $-(CH_2)_m-$, $-C(=X)-$, $-O(CH_2)_n-$, $-S(CH_2)_n-$, —CH=CH—, $-C(=N-OR_2)-$, or $-NR_2-$, $A_3$ is H, $-CF_3$, $C_1$-$C_6$ alkyl, a lone electron pair when $D_8$ is N, or $A_3$ is $-CH_2-$ bonded to $A_1$, $A_2$ or $R_1$ to form a ring;

a1, a2 and a3 are independently equal to 0 or 1;

$D_1$ is selected from $-CH_2-$, $-N(NHR_7)-$, $-CH(NHR_7)-$, $-CH[(CH_2)_mNHR_7]-$, $-CH(R_2)-$, and $-CH(CH_2SH)-$;

$D_2$, $D_3$, $D_4$, $D_5$ and $D_6$ are independently selected from the group consisting of $-(CH_2)_m-$, $-CH(R_2)-$, $-CH(NHR_7)-$, $-N(R_5)-$, —O—, —S—, $-C(=X)-$, $-S(=O)-$ and $-SO_2-$, wherein any two atoms of $D_2$, $D_3$, $D_4$, $D_5$ and $D_6$ are optionally linked to form a three, four, five or six membered saturated ring;

$D_7$ is selected from N, =C< where the carbon forms a double bond with an adjacent carbon in one of $D_1$-$D_6$, CH and $CR_4$;

$D_8$ is selected from C and N;

d1, d2, d3, d4, d5 and d6 are independently equal to 0 or 1;

$X_1$ and $X_2$ are each hydrogen or taken together are =O or =S, or $X_1$ is hydrogen and $X_2$ is —O— or —S— bonded to $R_{10}$ to form a 5- or 6-membered heterocyclyl, or $X_1$ is absent and $X_2$ is —O— or —S— bonded to $R_{10}$ to form a 5- or 6-membered heterocyclyl or heteroaryl, wherein when $X_1$ is absent, the bond to nitrogen represented by a dashed and solid line is a double bond;

each X is independently O or S;

$Z_1$ is an aryl, heteroaryl, carbocyclyl, or heterocyclyl;

z1 is 0 or 1;

if z1 is 0 then at least one from the group consisting of d1, d2, d3, d4, d5 and d6 are equal to 1, if z1 is 1 then at least one from the group consisting of d1, d2, d3, d4, d5 and d6 is equal to 1;

each n is independently an integer of 0 to 4; and each m is independently an integer of 1 to 3.

In another embodiment, the compounds have the structure of formula (II)

Formula (II)

II

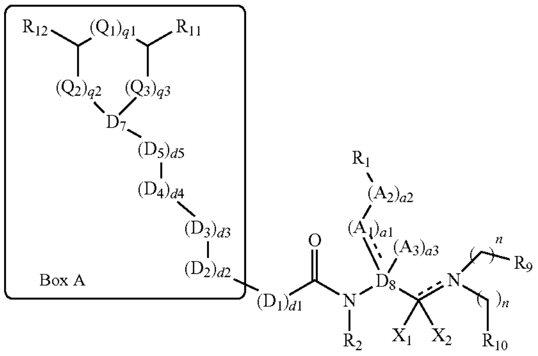

or a pharmaceutically acceptable salt or pro-drug thereof wherein;

each bond represented by a dashed and solid line represents a bond selected from the group consisting of a single bond and a double bond;

each $R_1$ is independently selected from $C_1$-$C_6$ alkyl, $C_3$-$C_7$ carbocyclyl, heterocyclyl, aryl and heteroaryl, each optionally substituted with up to 3 substituents independently selected from the group consisting of a halide, alkyl, carbocyclyl, heterocyclyl, $-(CH_2)_n$aryl, $-OR_2$, $-OR_{10}$, $-S(R_2)_2$, $-SO_2NHR_{10}$, $-(CH_2)_nSH$, $-CF_3$, $-OCF_3$, $-N(R_2)_2$, $-NO_2$, —CN, $-CO_2$alkyl, $-CO_2$aryl and —C(O)aryl;

each $R_2$ is independently selected from H, —OH, and $C_1$-$C_6$ alkyl;

$R_3$ is selected from $-(CH_2)_nCHR_5R_6$, $-(CH_2)_nNR_5R_6$, and $-(CH_2)_mC(=O)NR_5R_6$;

each $R_4$ is independently selected from $-NHR_2$, $-(CH_2)_nCHR_5R_6$, $-(CH_2)_nNR_5R_6$, $-(CH_2)_mC(=O)NR_5R_6$, and $-C(NR_5)NR_5R_5$;

each $R_5$ is independently selected from H and $-(CH_2)_mNH_2$;

each $R_6$ is independently selected from $-(CH_2)_nNHR_7$, $-(CH_2)_nNHC(=NH)NH_2$, $-(CH_2)_nNHC(R_2)=NH$, $-(CH_2)_nC(=NH)NH_2$, and $-(CH_2)_nN^+(CH_3)_3$;

each $R_7$ is independently selected from H, alkyl, $-C(=O)CH(R_{13})(NH_2)$, $-C(=O)A_2CH_2NH_2$, Alanine, Arginine, Asparagine, Aspartic acid, Glutamic acid, Glutamine, Cysteine, Glycine, Histidine, Isoleucine, Leucine, Lysine, Methionine, Phenylalanine, Proline, Serine, Threonine, Tryptophan, Tyrosine, Valine, 3-benzyloxy alanine, and ornithine;

$R_8$ is selected from H, alkyl, aryl, SH and OH;

$R_9$ is selected from H, $C_1$-$C_6$ alkyl, $C_3$-$C_{10}$ carbocyclyl, heterocyclyl, aryl, heteroaryl, —C(O)O-heteroaryl, and —NHC(O)-aryl, each optionally substituted with up to 3 substituents independently selected from the group consisting of a halide, alkyl optionally substituted with $—CF_3$ or —OH, carbocyclyl optionally substituted with halide, $—(CH_2)_nR_1$, $—(CH{=}CH)_nR_1$, $—OR_2$, $—OR_1$, =O, $—S(R_2)_2$, $—SR_1$, $—SO_2NR_1R_2$, $—SO_2CF_3$, $—(CH_2)_nSH$, $—CF_3$, $—OCF_3$, $—N(R_2)_2$, $—NO_2$, —CN, $—(C{=}X)R_1$, $—(C{=}X)R_2$, $—CO_2$alkyl, $—CO_2$aryl, heteroaryl optionally substituted with $C_1$-$C_6$ alkyl, and aryl optionally substituted with $C_1$-$C_6$ alkyl; or $R_9$ is absent;

$R_{10}$ is selected from $C_1$-$C_6$ alkyl, $C_3$-$C_{10}$ carbocyclyl, heterocyclyl, aryl, heteroaryl, —C(O)O-heteroaryl, and —NHC(O)-aryl, each optionally substituted with up to 3 substituents independently selected from the group consisting of a halide, alkyl optionally substituted with $—CF_3$ or —OH, carbocyclyl optionally substituted with halide, $—(CH_2)_nR_1$, $—OR_2$, $—OR_1$, =O, $—S(R_2)_2$, $—SO_2NR_1R_2$, $—SO_2CF_3$, $—(CH_2)_nSH$, $—CF_3$, $—OCF_3$, $—N(R_2)_2$, $—NO_2$, —CN, $—(C{=}X)R_1$, $—(C{=}X)R_2$, $—CO_2$alkyl, and $—CO_2$aryl;

$R_9$ and $R_{10}$ are optionally linked to form a ring;

$R_{11}$ is selected from H, $—(CH_2)_nNHR_2$ and $—(CH_2)_nCHR_5R_6$;

$R_{12}$ is selected from H, $—(CH_2)_nNHR_2$ and $—(CH_2)_nCHR_5R_6$, wherein at least one of $R_{11}$ and $R_{12}$ is not H;

$R_{13}$ is selected from $—(CH_2)_nCHR_5(CH_2)_nNH_2$, $—(CH_2)_mNR_5(CH_2)_nNH_2$ and $—(CH_2)_mC({=}O)NR_5(CH_2)_nNH_2$;

$A_1$ is $—[C(R_2R_8)]_m—$ or $=CR_2[C(R_2R_8)]_m—$, wherein if $A_1$ is $=CR_2[C(R_2R_8)]_m—$, then a3 is 0;

$A_2$ is $—(CH_2)_m—$, $—C({=}X)—$, $—O(CH_2)_n—$, $—S(CH_2)_n—$, $—CH{=}CH—$, $—C({=}N—OR_2)—$, or $—NR_2—$;

$A_3$ is H, $—CF_3$, $C_1$-$C_6$ alkyl, a lone electron pair when $D_8$ is N, or $A_3$ is $—CH_2—$ bonded to $A_1$, $A_2$ or $R_1$ to form a ring;

a1, a2 and a3 are independently equal to 0 or 1;

$D_1$ is selected from $—CH_2—$, $—N(NHR_7)—$, $—CH(NHR_7)—$, $—CH[(CH_2)_mNHR_7]—$, $—CH(R_2)—$, and $—CH(CH_2SH)—$;

$D_2$, $D_3$, $D_4$, $D_5$ and $D_6$ are independently selected from the group consisting of $—(CH_2)_m—$, $—CH(R_2)—$, $—CH(NHR_7)—$, $—N(R_5)—$, —O—, —S—, $—C({=}X)—$, $—S({=}O)—$ and $SO_2—$, wherein any two atoms of $D_2$, $D_3$, $D_4$, $D_5$ and $D_6$ are optionally linked to form a three, four, five or six membered saturated ring;

$D_7$ is selected from N, =C< where the carbon forms a double bond with an adjacent carbon in one of $D_1$-$D_6$, CH and $CR_4$;

$D_8$ is selected from C and N;

d1, d2, d3, d4, d5 and d6 are independently equal to 0 or 1;

$Q_1$ is selected from $—CH_2—$, $—N(R_2)N(R_2)—$, and $—N(R_2)—$;

$Q_2$ and $Q_3$ are independently selected from the group consisting of $—CH_2—$, $—CH_2CH_2—$, and $—N(R_2)—$;

with the proviso that no more than one of $Q_1$, $Q_2$, and $Q_3$ comprises a nitrogen;

q1, q2, and q3 are independently equal to 0 or 1;

$X_1$ and $X_2$ are each hydrogen or taken together are =O or =S, or $X_1$ is hydrogen and $X_2$ is —O— or —S— bonded to $R_{10}$ to form a 5- or 6-membered heterocyclyl, or $X_1$ is absent and $X_2$ is —O— or —S— bonded to $R_{10}$ to form a 5- or 6-membered heterocyclyl or heteroaryl, wherein when $X_1$ is absent, the bond to nitrogen represented by a dashed and solid line is a double bond;

each X is independently O or S;

each n is independently an integer of 0 to 4; and each m is independently an integer of 1 to 3.

In another embodiment, the compounds have the structure of formula (III):

Formula (III)

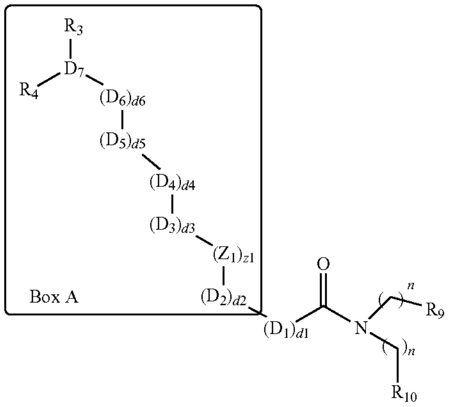

or a pharmaceutically acceptable salt or pro-drug thereof wherein;

each bond represented by a dashed and solid line represents a bond selected from the group consisting of a single bond and a double bond;

each $R_1$ is independently selected from $C_1$-$C_6$ alkyl, $C_3$-$C_7$ carbocyclyl, heterocyclyl, aryl and heteroaryl, each optionally substituted with up to 3 substituents independently selected from the group consisting of a halide, alkyl, carbocyclyl, heterocyclyl, $—(CH_2)_n$aryl, $—OR_2$, $—OR_{10}$, $—S(R_2)_2$, $—SO_2NHR_{10}$, $—(CH_2)_nSH$, $—CF_3$, $—OCF_3$, $—N(R_2)_2$, $—NO_2$, —CN, $—CO_2$alkyl, $—CO_2$aryl and —C(O)aryl;

each $R_2$ is independently selected from H, —OH, and $C_1$-$C_6$ alkyl;

$R_3$ is selected from $—(CH_2)_nCHR_5R_6$, $—(CH_2)_nNR_5R_6$, and $—(CH_2)_mC({=}O)NR_5R_6$;

each $R_4$ is independently selected from $—NHR_2$, $—(CH_2)_nCHR_5R_6$, $—(CH_2)_nNR_5R_6$, $—(CH_2)_mC({=}O)NR_5R_6$, and $—C({=}NR_5)NR_5R_5$;

each $R_5$ is independently selected from H and $—(CH_2)_mNH_2$;

each $R_6$ is independently selected from $—(CH_2)_nNHR_7$, $—(CH_2)_nNHC({=}NH)NH_2$, $—(CH_2)_nNHC(R_2){=}NH$, $—(CH_2)_nC({=}NH)NH_2$, and $—(CH_2)_nN^+(CH_3)_3$;

each $R_7$ is independently selected from H, alkyl, $—C({=}O)CH(R_{13})(NH_2)$, $—C({=}O)A_2CH_2NH_2$, Alanine, Arginine, Asparagine, Aspartic acid, Glutamic acid, Glutamine, Cysteine, Glycine, Histidine, Isoleucine, Leucine, Lysine, Methionine, Phenylalanine, Proline, Serine, Threonine, Tryptophan, Tyrosine, Valine, 3-benzyloxy alanine, and ornithine;

$R_8$ is selected from H, alkyl, aryl, SH and OH;

$R_9$ is selected from H, $C_1$-$C_6$ alkyl, $C_3$-$C_{10}$ carbocyclyl, heterocyclyl, aryl, heteroaryl, —C(O)O-heteroaryl, and —NHC(O)-aryl, each optionally substituted with up to 3 substituents independently selected from the group consisting of a halide, alkyl optionally substituted with —$CF_3$ or —OH, carbocyclyl optionally substituted with halide, —$(CH_2)_nR_1$, —$(CH{=}CH)_nR_1$, —$OR_2$, —$OR_1$, =O, —$S(R_2)_2$, —$SR_1$, —$SO_2NR_1R_2$, —$SO_2CF_3$, —$(CH_2)_nSH$, —$CF_3$, —$OCF_3$, —$N(R_2)_2$, —$NO_2$, —CN, —(C=X)$R_1$, —(C=X)$R_2$, —$CO_2$alkyl, —$CO_2$aryl, heteroaryl optionally substituted with $C_1$-$C_6$ alkyl, and aryl optionally substituted with $C_1$-$C_6$ alkyl; or $R_9$ is absent;

$R_{10}$ is selected from $C_1$-$C_6$ alkyl, $C_3$-$C_{10}$ carbocyclyl, heterocyclyl, aryl, heteroaryl, —C(O)O-heteroaryl, and —NHC(O)-aryl, each optionally substituted with up to 3 substituents independently selected from the group consisting of a halide, alkyl optionally substituted with —$CF_3$ or —OH, carbocyclyl optionally substituted with halide, —$(CH_2)_nR_1$, —$OR_2$, —$OR_1$, =O, —$S(R_2)_2$, —$SR_1$, —$SO_2NR_1R_2$, —$SO_2CF_3$, —$(CH_2)_nSH$, —$CF_3$, —$OCF_3$, —$N(R_2)_2$, —$NO_2$, —CN, —(C=X)$R_1$, —(C=X)$R_2$, —$CO_2$alkyl, and —$CO_2$aryl;

$R_9$ and $R_{10}$ are optionally linked to form a ring;

$R_{13}$ is selected from —$(CH_2)_nCHR_5(CH_2)_nNH_2$, —$(CH_2)_mNR_5(CH_2)_nNH_2$ and —$(CH_2)_mC(=O)NR_5(CH_2)_nNH_2$;

$A_1$ is —$[C(R_2R_8)]_m$— or =$CR_2[C(R_2R_8)]_m$—, wherein if $A_1$ is =$CR_2[C(R_2R_8)]_m$—, then a3 is 0;

$A_2$ is —$(CH_2)_m$—, —C(=X)—, —$O(CH_2)_n$—, —$S(CH_2)_n$—, —CH=CH—, —C(=N—$OR_2$)—, or —$NR_2$—;

$A_3$ is H, —$CF_3$, $C_1$-$C_6$ alkyl, a lone electron pair when $D_8$ is N, or $A_3$ is —$CH_2$— bonded to $A_1$, $A_2$ or $R_1$ to form a ring;

a1, a2 and a3 are independently equal to 0 or 1;

$D_1$ is selected from —$CH_2$—, —$N(NHR_7)$—, —$CH(NHR_7)$—, —$CH[(CH_2)_mNHR_7]$—, —$CH(R_2)$—, and —$CH(CH_2SH)$—;

$D_2$, $D_3$, $D_4$, $D_5$ and $D_6$ are independently selected from the group consisting of —$(CH_2)_m$—, —$CH(R_2)$—, —$CH(NHR_7)$—, —$N(R_5)$—, —O—, —S—, —C(=X)—, —S(=O)— and —$SO_2$—, wherein any two atoms of $D_2$, $D_3$, $D_4$, $D_5$ and $D_6$ are optionally linked to form a three, four, five or six membered saturated ring;

$D_7$ is selected from N, =C< where the carbon forms a double bond with an adjacent carbon in one of $D_1$-$D_6$, CH and $CR_4$;

$D_8$ is selected from C and N;

d1, d2, d3, d4, d5 and d6 are independently equal to 0 or 1;

$X_1$ and $X_2$ are each hydrogen or taken together are =O or =S, or $X_1$ is hydrogen and $X_2$ is —O— or —S— bonded to $R_{10}$ to form a 5- or 6-membered heterocyclyl, or $X_1$ is absent and $X_2$ is —O— or —S— bonded to $R_{10}$ to form a 5- or 6-membered heterocyclyl or heteroaryl, wherein when $X_1$ is absent, the bond to nitrogen represented by a dashed and solid line is a double bond;

each X is independently O or S;

$Z_1$ is an aryl, heteroaryl, carbocyclyl, or heterocyclyl;

z1 is 0 or 1;

if z1 is 0 then d1 is 1, d2 is 1, and $D_2$ is selected from the group consisting of —$(CH_2)_m$—, —$CH(R_2)$—, —$CH(NHR_7)$—, —O—, —S—, —C(=X)—, —S(=O)— and —$SO_2$—, if z1 is 1 then at least one from the group consisting of d1, d2, d3, d4, d5 and d6 is equal to 1;

each n is independently an integer of 0 to 4; and each m is independently an integer of 1 to 3.

In another embodiment, the compounds have the structure of formula (IV):

(IV)

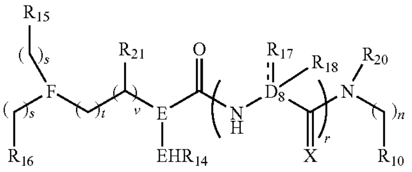

or a pharmaceutically acceptable salt or prodrug thereof, wherein:

$D_8$ is selected from C and N;

each E is independently CH or N;

F is selected from the group consisting of:

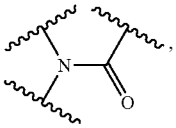, 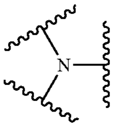, 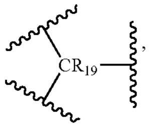, 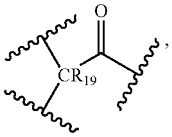, 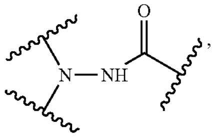, 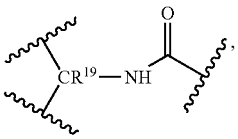, 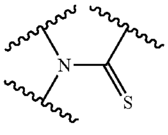, 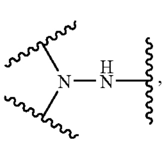, 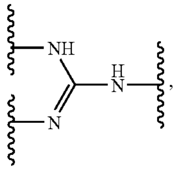, 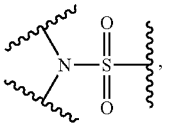, 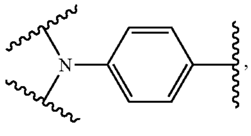, 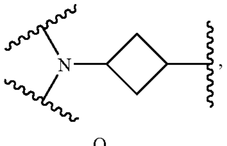, 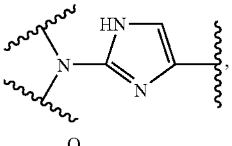, 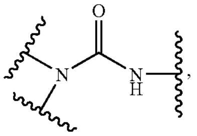, 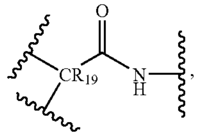, 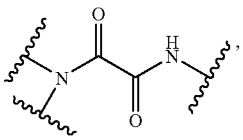, 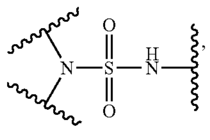, -continued

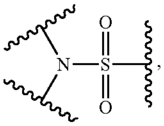,
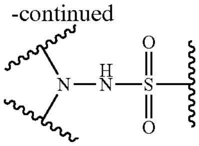,

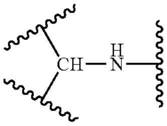,
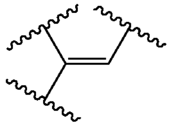, and

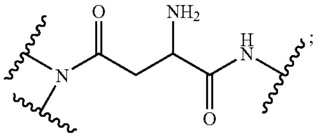;

X is O or S;

$R_{10}$ is selected from carbocyclyl, heterocyclyl, aryl, heteroaryl, —NHC(O)-aryl, and aralkyl, each optionally substituted with up to 3 substituents independently selected from the group consisting of a halide, alkyl optionally substituted with —$CF_3$ or —OH, alkylaminoalkoxy, —$CF_3$, —$OCF_3$, —$NO_2$, —CN, —OH, ═O, carbocyclyl optionally substituted with halide, heterocyclyl, aryl optionally substituted with halide or —OH, heteroaryl optionally substituted with alkyl, —O-aryl optionally substituted with —O—$C_1$-$C_6$ alkyl, alkyl, or heterocyclyl, —O-heteroaryl optionally substituted with halide or —$CF_3$, —O-heterocyclyl, —$SO_2$NH-heteroaryl, —O—$C_1$-$C_6$ alkyl, optionally substituted with halide, —$SO_2$N(alkyl)$_2$, SMe, —$SO_2CF_3$, di($C_1$-$C_6$) alkylamino, —$CH_2$-heterocyclyl optionally substituted with alkyl, —$CH_2$-aryl, —C(O)aryl, and —CH═CH-aryl;

$R_{14}$ is selected from H, —C(O)—CH(Me)($NH_2$), —C(O)—CH($CH_2$OH)($NH_2$), —C(O)CH($NH_2$) (arylether), —C(O)CH($NH_2$)(aminoalkyl), and —$(CH_2)_tNH_2$;

$R_{15}$ and $R_{16}$ are independently selected from —$NH_2$, —NHC(═NH)$NH_2$, —$N^+(CH_3)_3$, —$NHCH_2CH_2NH_2$, —$N(CH_2CH_2NH_2)_2$, —C(O)$N(CH_2CH_2NH_2)_2$, —CH$(CH_2NH_2)_2$, and —$CH_2(NH_2)(CH_2NH_2)$, or $R_{15}$ and $R_{16}$ together with F form a heterocyclyl substituted with one or more substituents independently selected from —$(CH_2)_sNH_2$, —$(CH_2)_s$NHC(═NH)$NH_2$, —$(CH_2)_sN^+(CH_3)_3$, —$(CH_2)_sNHCH_2CH_2NH_2$, —$(CH_2)_sN(CH_2CH_2NH_2)_2$, —$(CH_2)_s$C(O)N$(CH_2CH_2NH_2)_2$, and —$(CH_2)_s$CH$(CH_2NH_2)_2$;

$R_{17}$ is selected from alkyl, aralkyl, arylthioether, arylether, heteroaralkyl, carbocyclyl-alkyl, heterocyclyl-alkyl, aryl, and carbocyclyl, each optionally substituted with up to 3 substituents independently selected from the group consisting of —$CF_3$, —OH, —$OCF_3$, halide, —CN, alkyl, —O-aralkyl, aryl, —$S(CH_3)_2$, —C(O)aryl, —S-aralkyl optionally substituted with —OMe, ═O, and ═N—OH;

$R_{18}$ is H, alkyl, or absent, or $R_{17}$ together with $R_{18}$ form a carbocyclyl optionally substituted with aryl or heteroaryl;

$R_{19}$ is H, —$NH_2$, —$CH_2NH_2$, or —$CH_2CH_2NH_2$;

$R_{20}$ is H, alkyl, or heteroaryl;

$R_{21}$ is —$NH_2$, —OH, alkyl, each t is independently an integer from 0 to 4;

each s is independently an integer from 0 to 3;

r is 0 or 1;

v is 0 or 1; and n is an integer from 0 to 4.

Some embodiments of the compounds of formulas (I)-(VI) and analogous compounds are shown below. Although the structures are shown with defined configurations at selected stereocenters, the shown stereochemistries are not meant to be limiting and all possible stereoisomers of the shown structures are contemplated. Compounds of any absolute and relative configurations at the stereocenters as well as mixtures of enantiomers and diastereoisomers of any given structure are also contemplated.

1

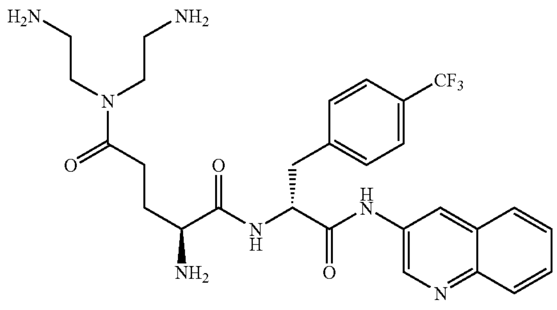

2

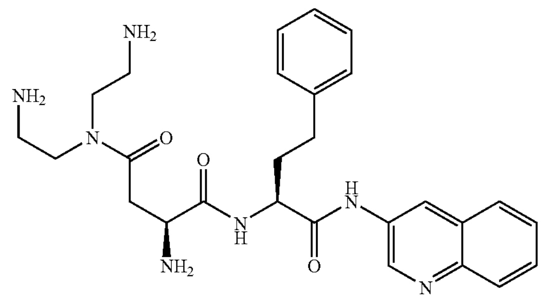

3

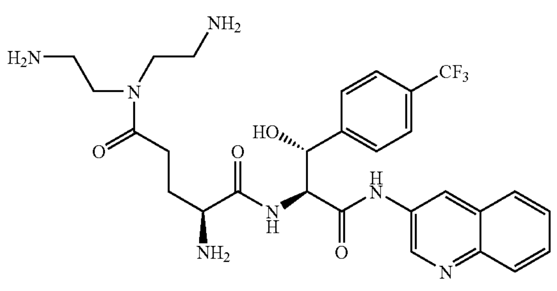

4

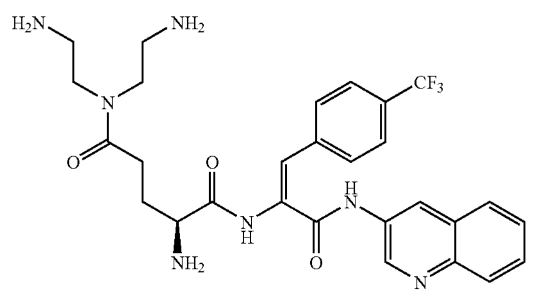

-continued
5
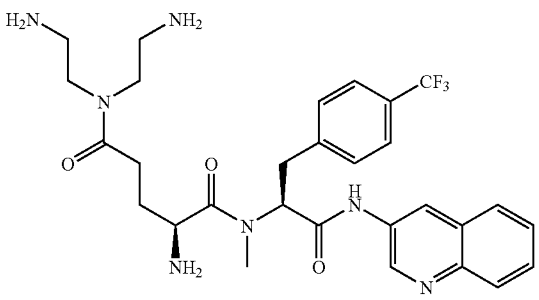
6
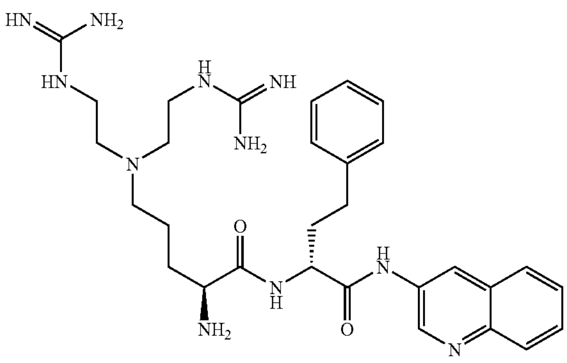
7
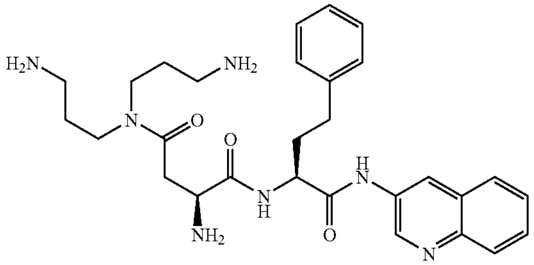
8
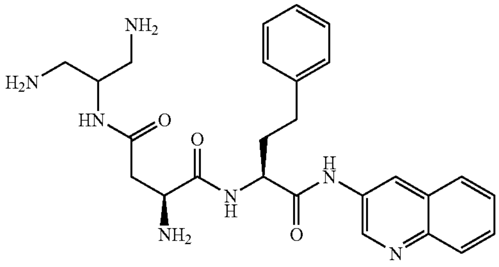
9
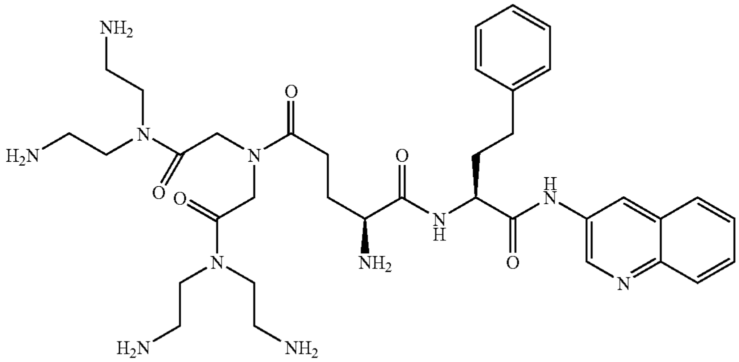
10
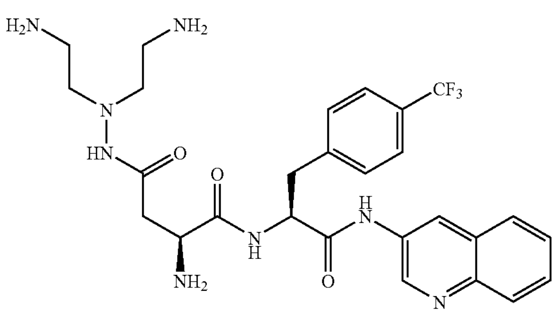
11
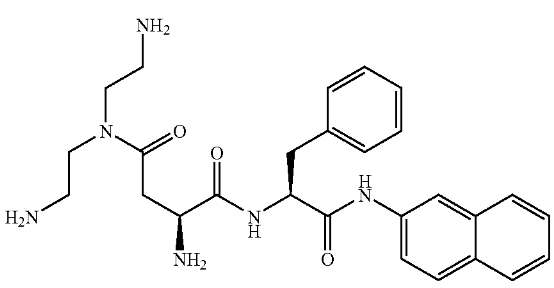
12
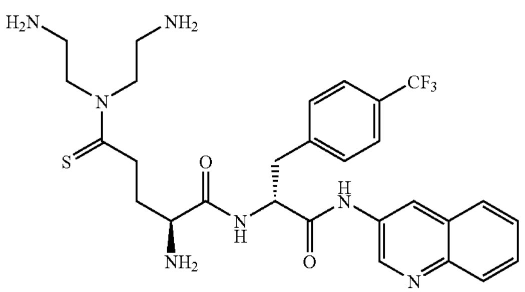
13
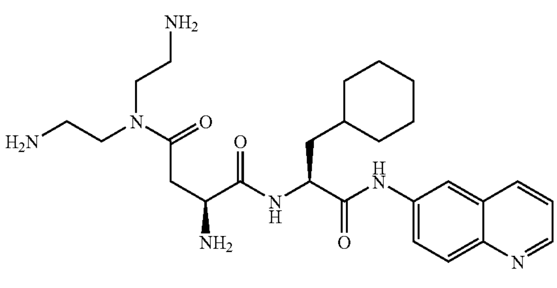

-continued
14
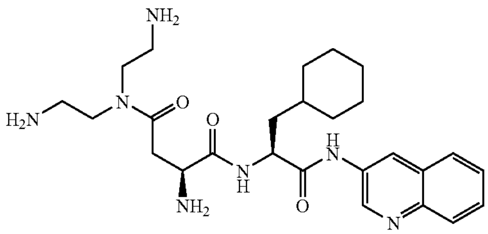
15
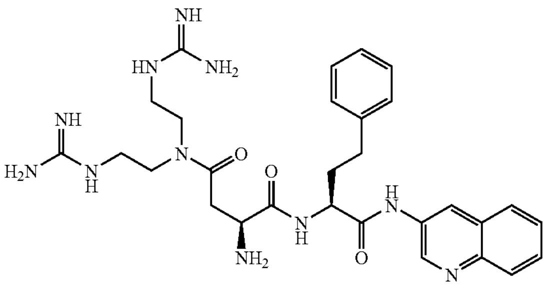
16
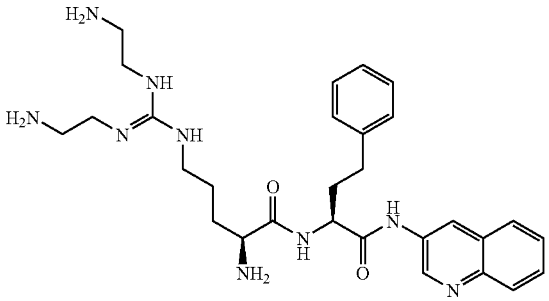
17
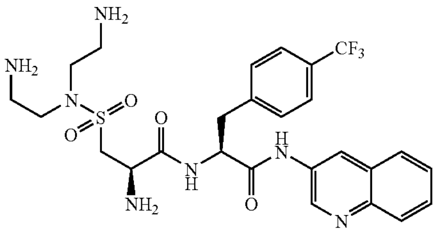
18
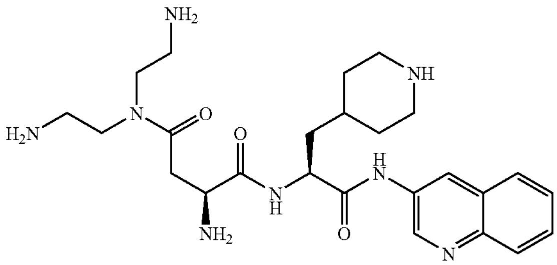
19
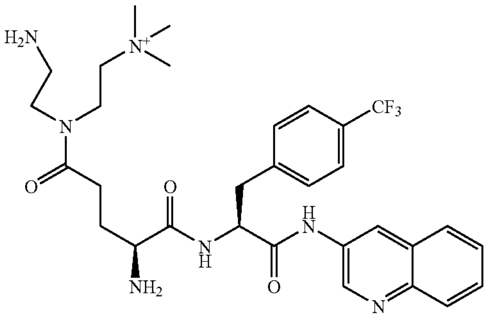
20
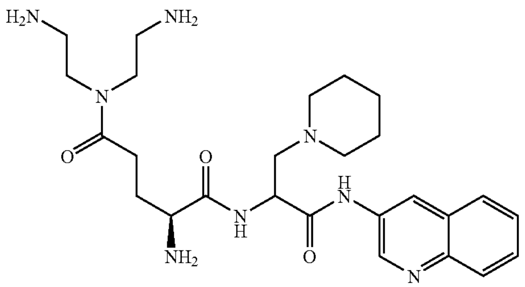
21
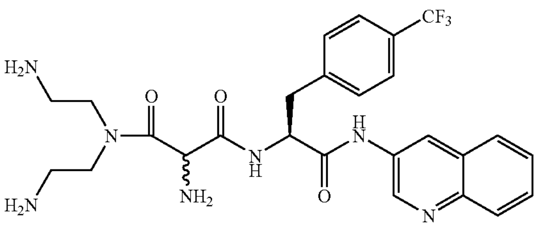
22
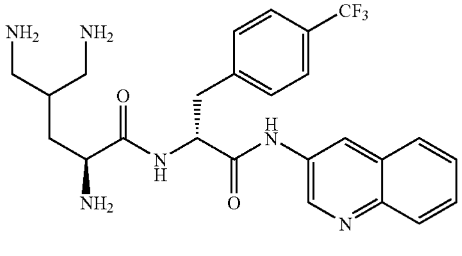
23
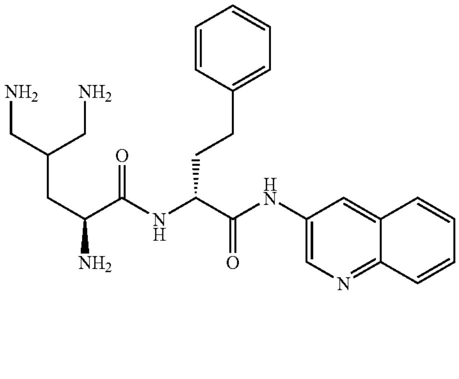

-continued
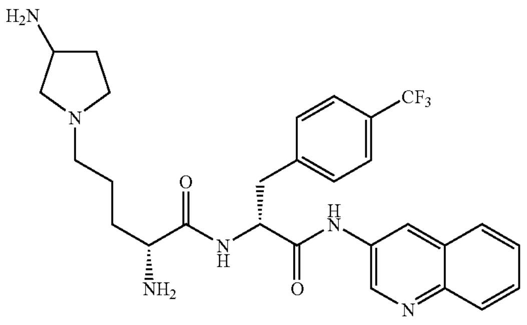
24
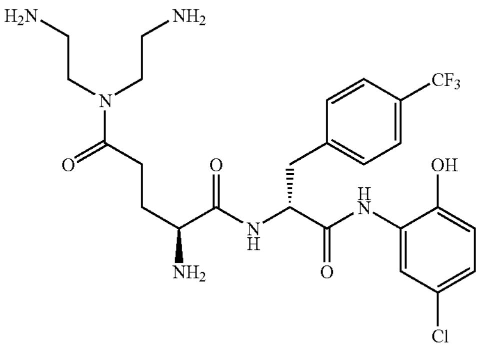
25
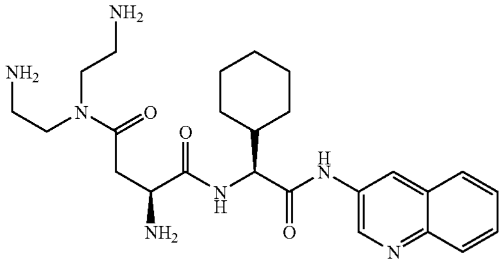
26
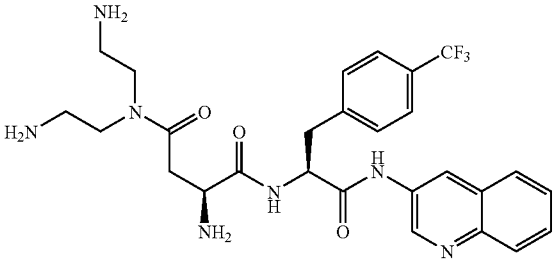
27
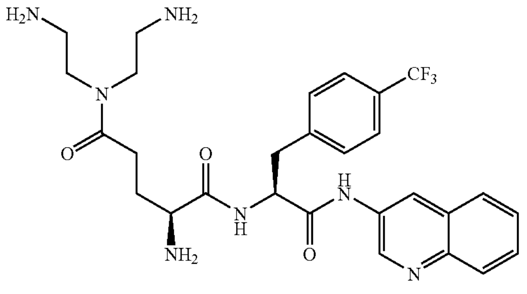
28
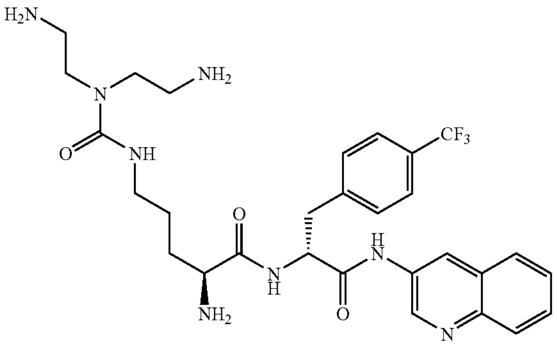
29
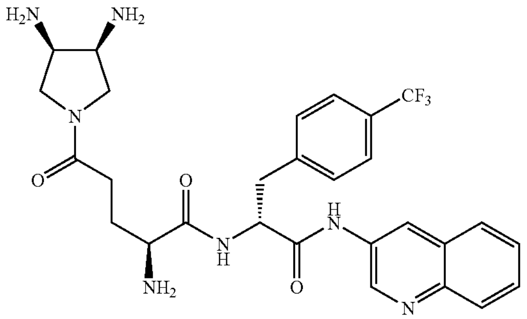
30
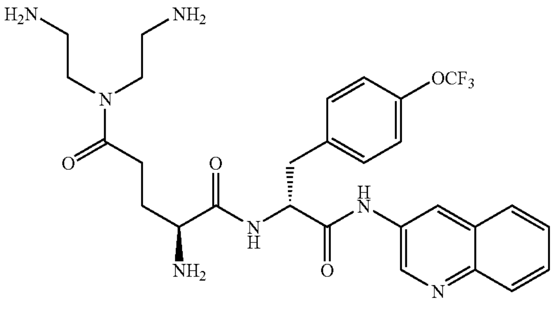
31

-continued
32
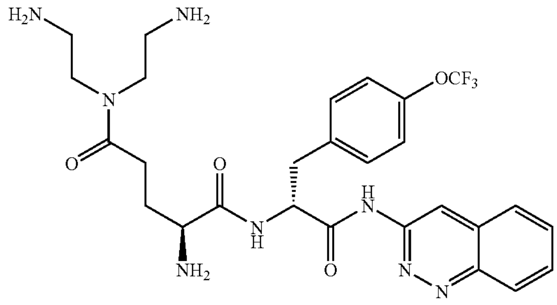
33
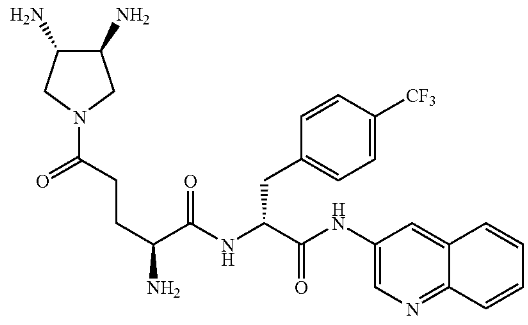
34
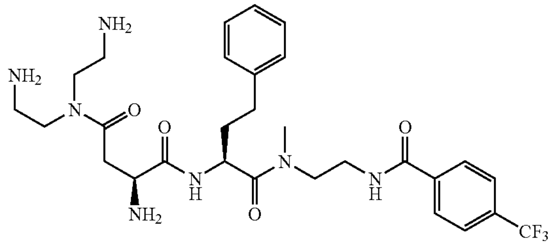
35
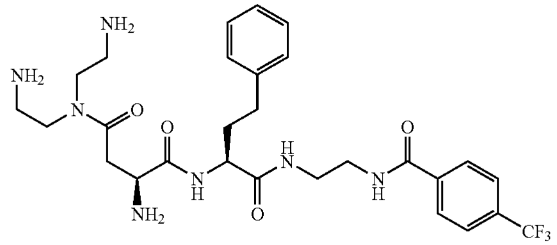
36
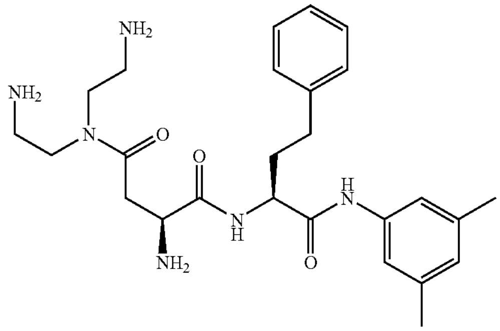
37
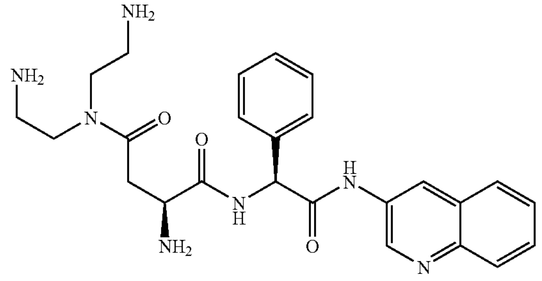
38
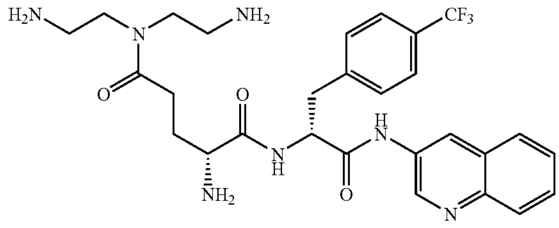
39
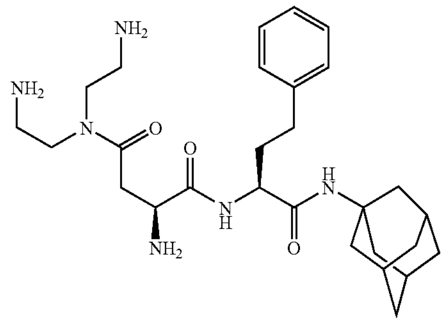
40
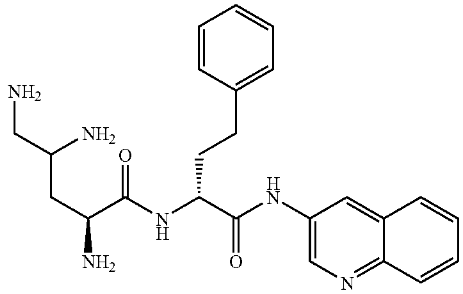
41
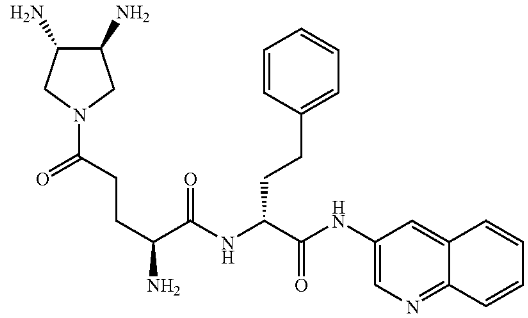

-continued
42
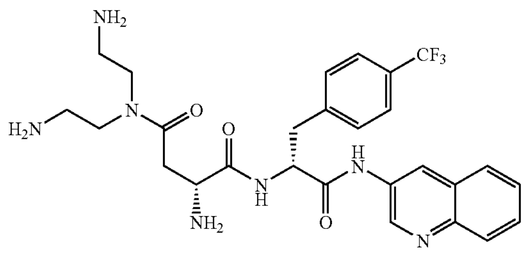
43
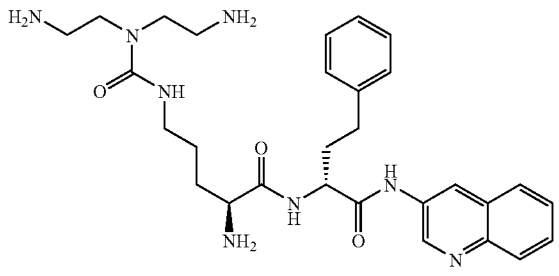
44
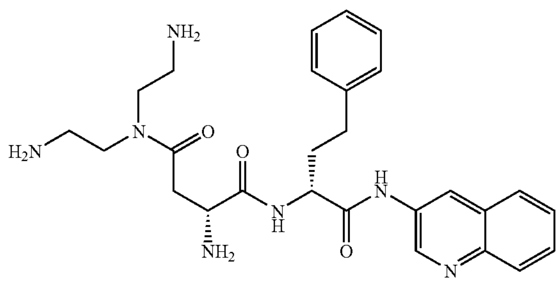
45
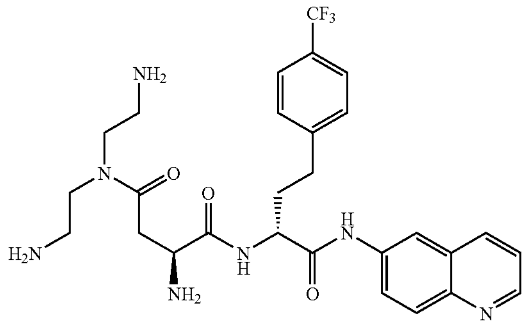
46
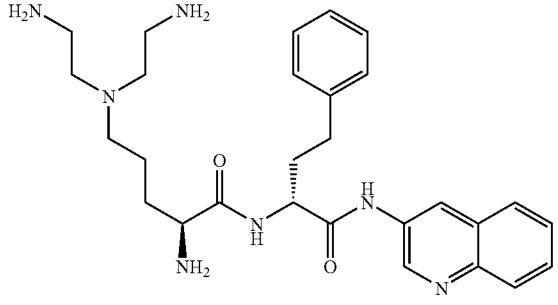
47
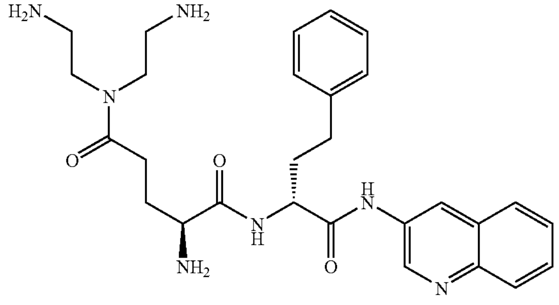
48
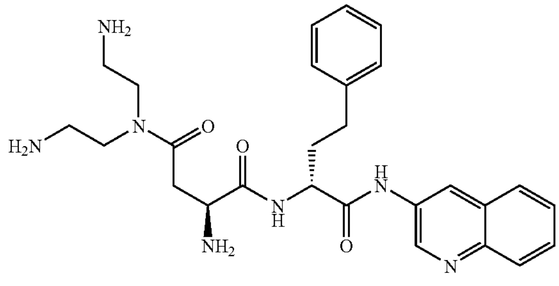
49
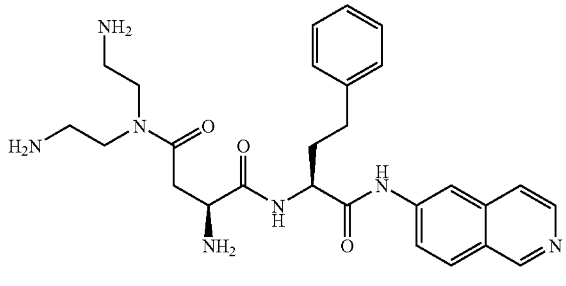
50
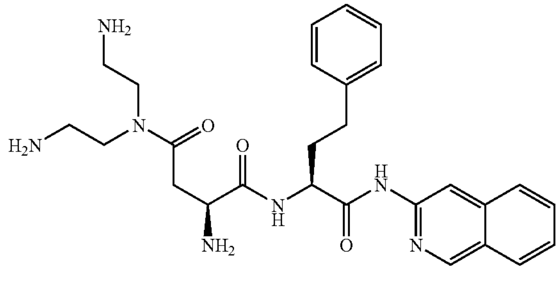
51
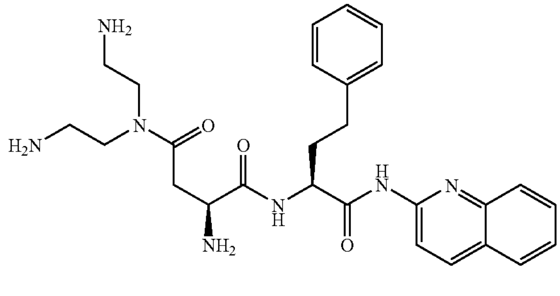

-continued
52
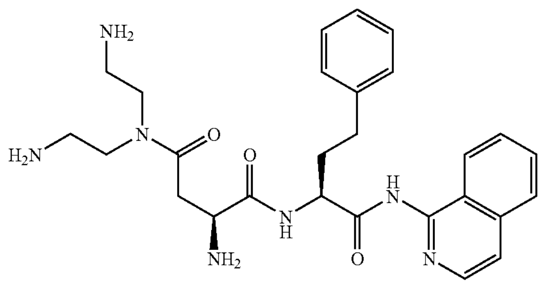
53
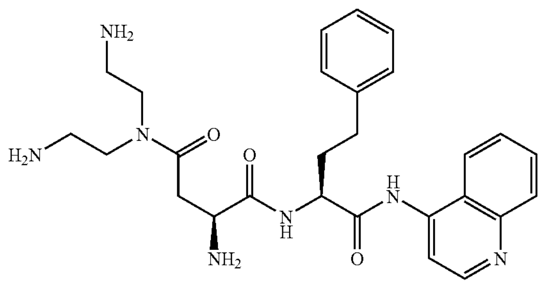
54
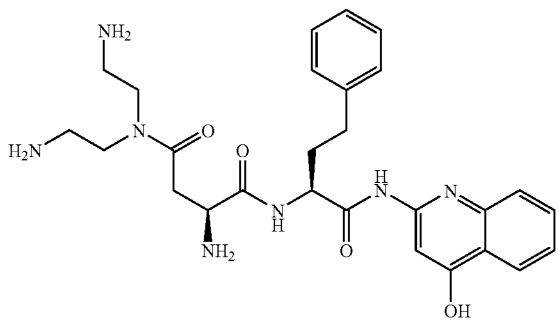
55
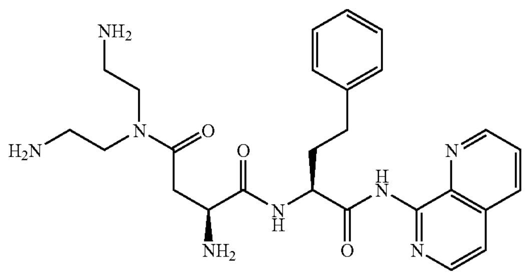
56
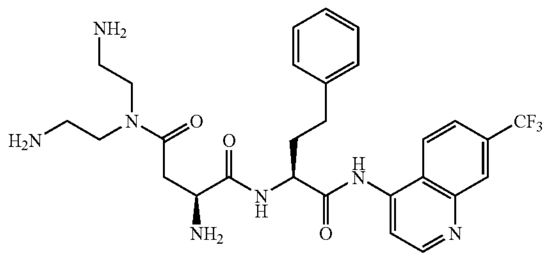
57
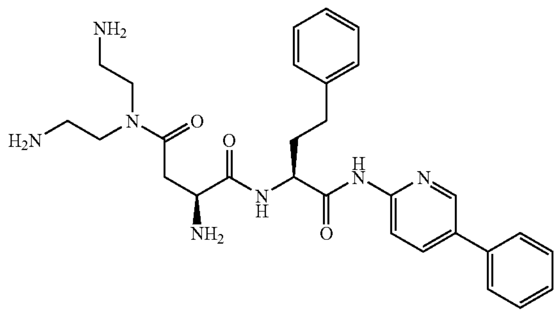
58
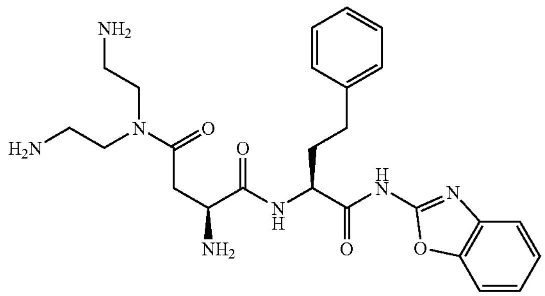
59
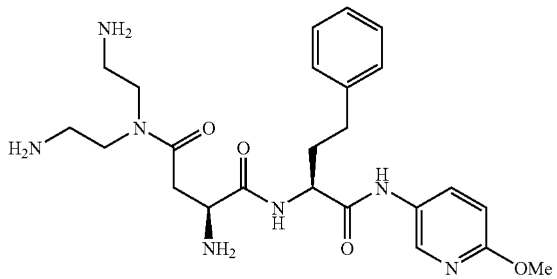
60
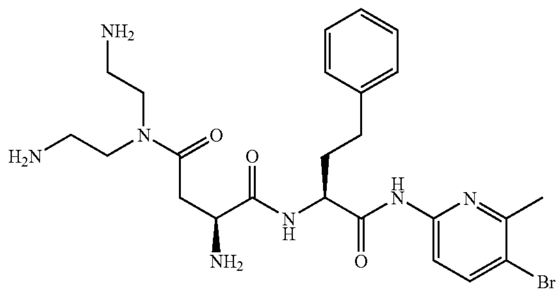
61
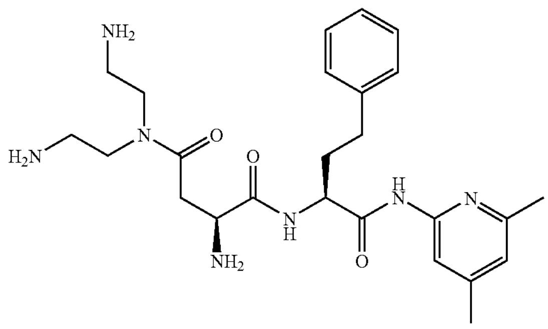

-continued
62
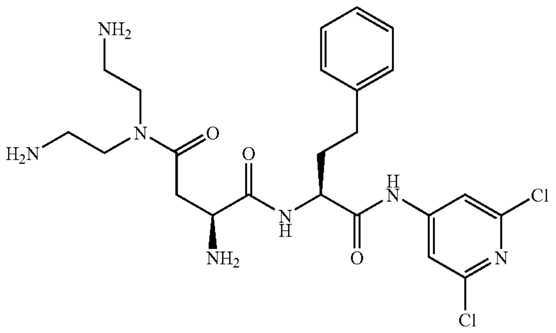
63
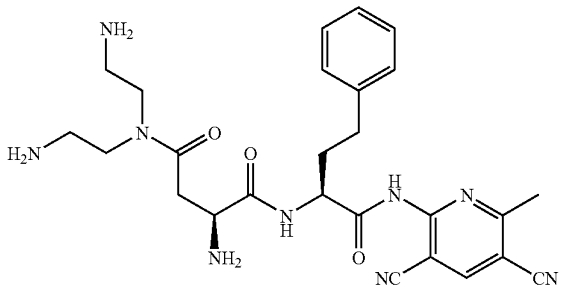
64
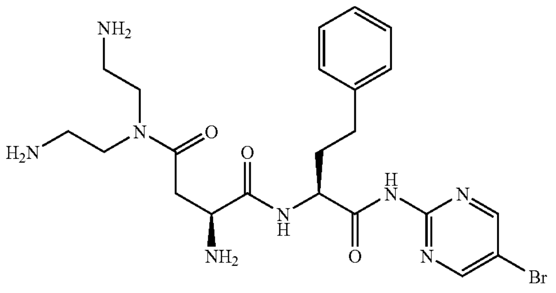
65
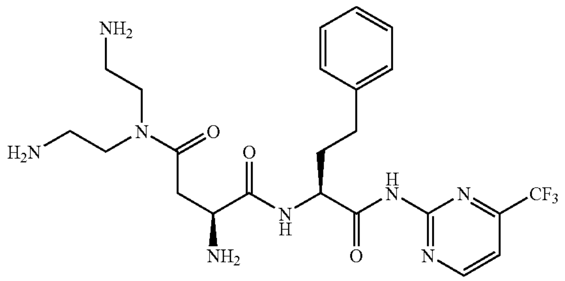
66
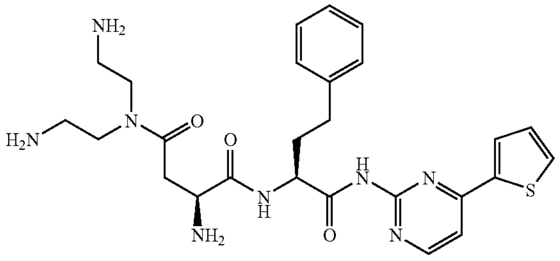
67
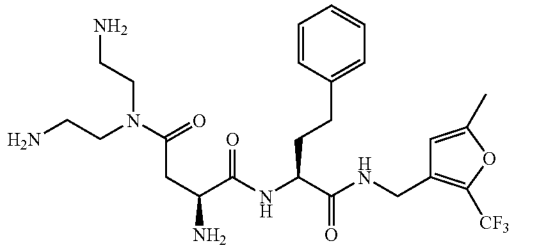
68
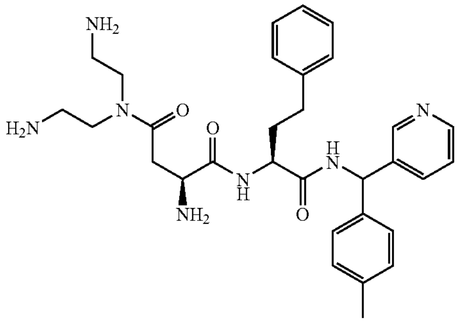
69
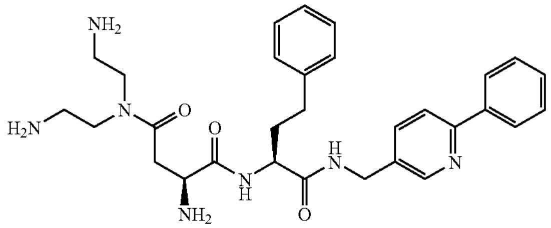
70
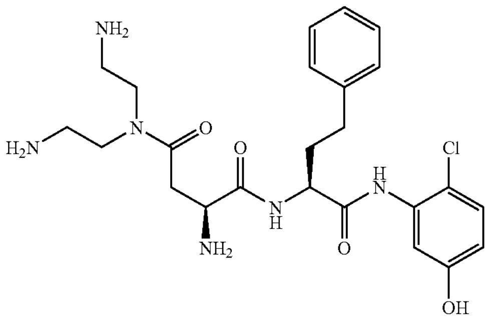
71
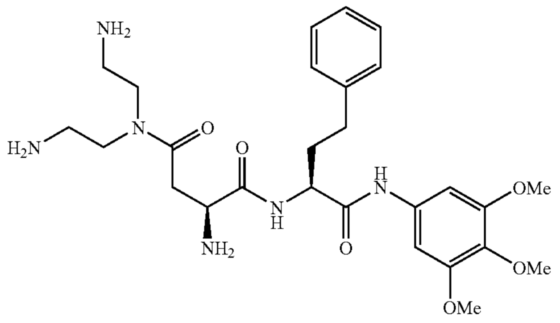

-continued
72
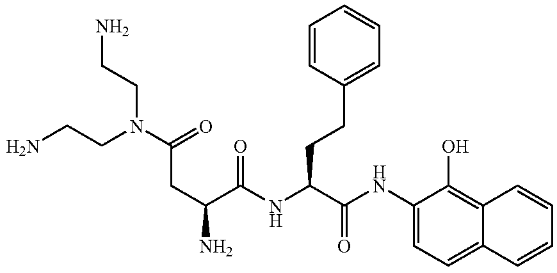
73
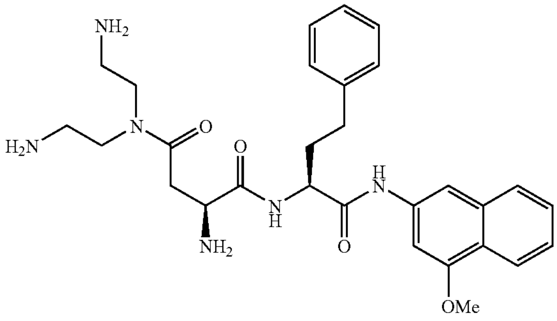
74
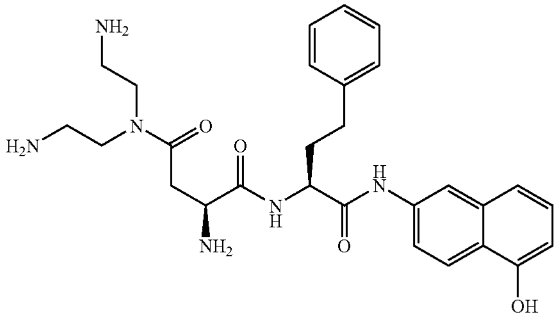
75
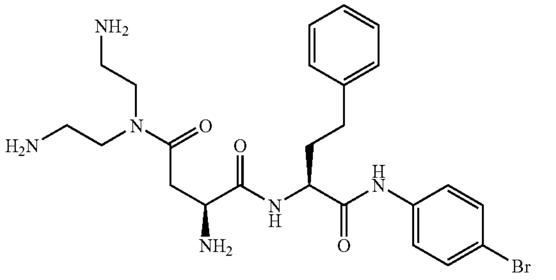
76
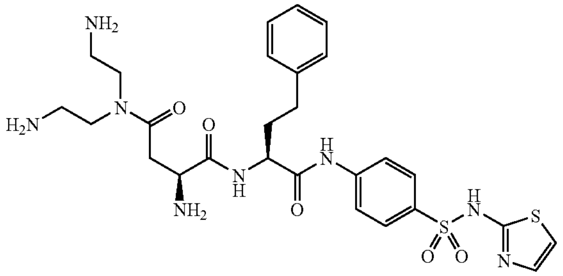
77
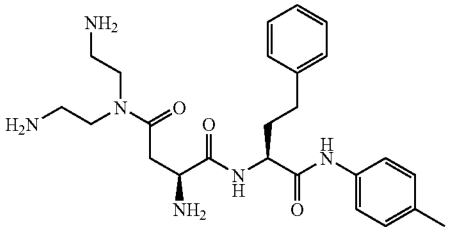
78
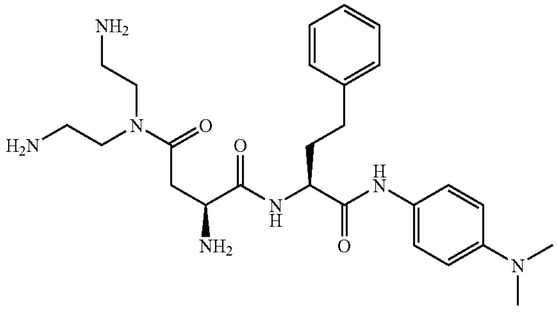
79
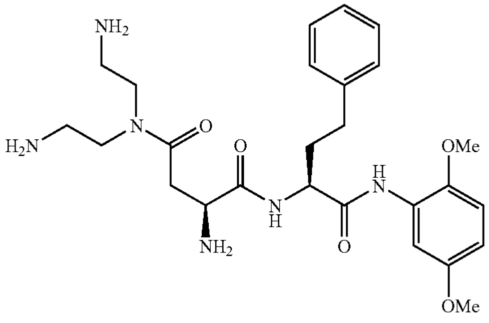
80
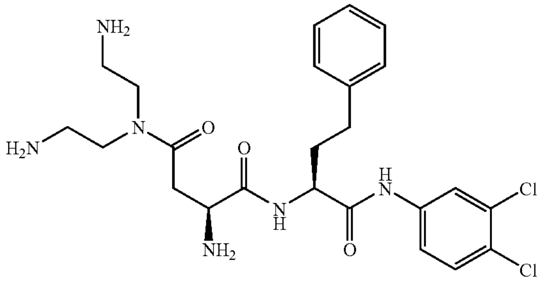
81
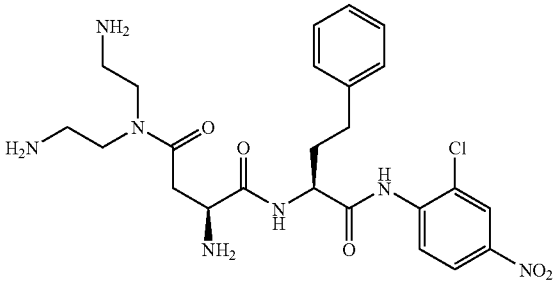

-continued
82
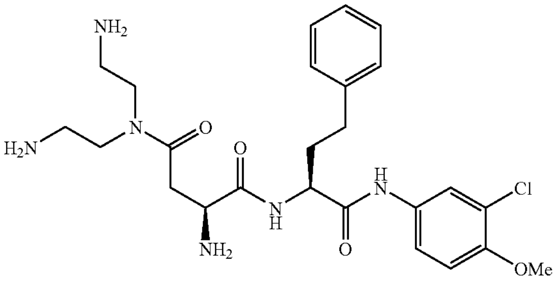
83
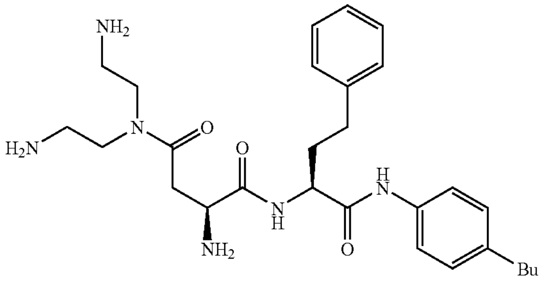
84
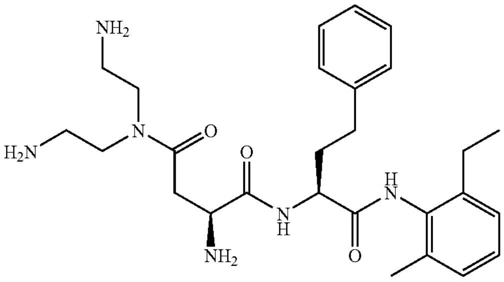
85
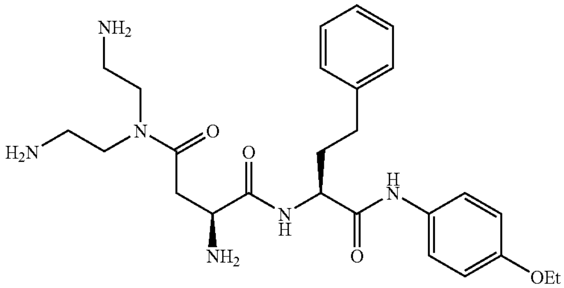
86
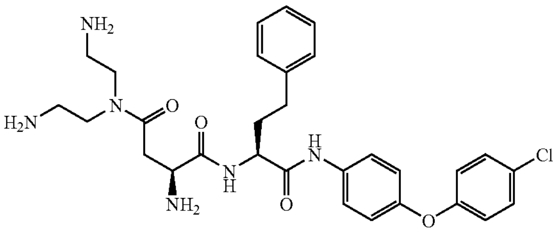
87
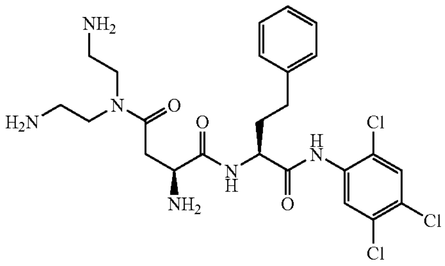
88
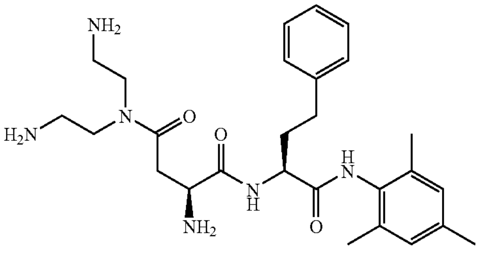
89
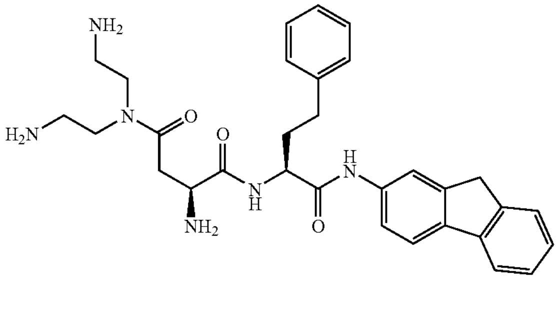
90
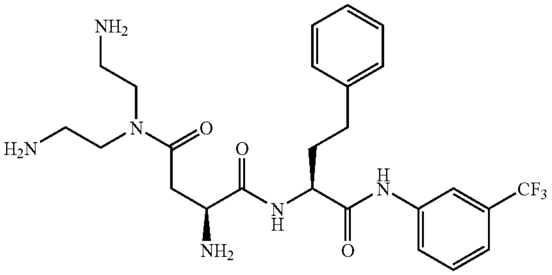
91
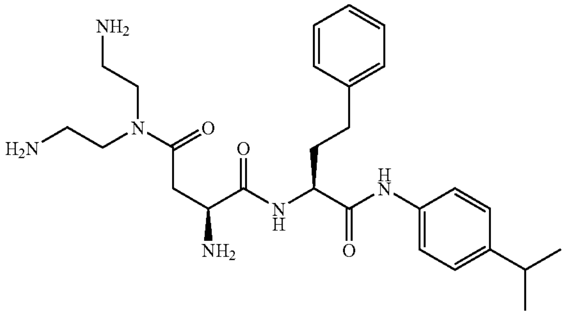

-continued
92
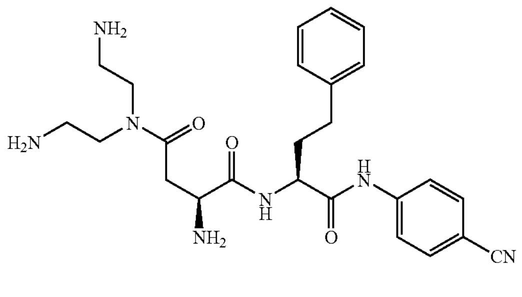
93
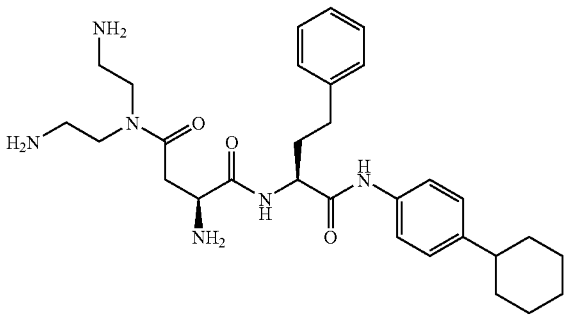
94
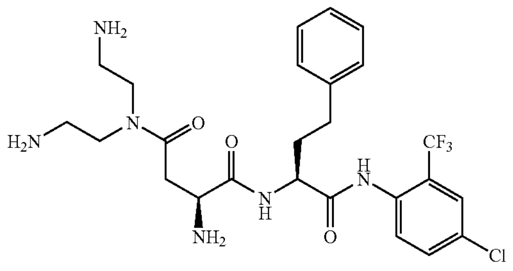
95
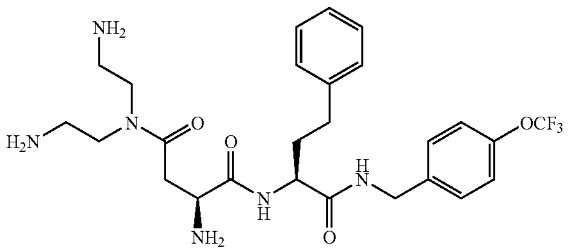
96
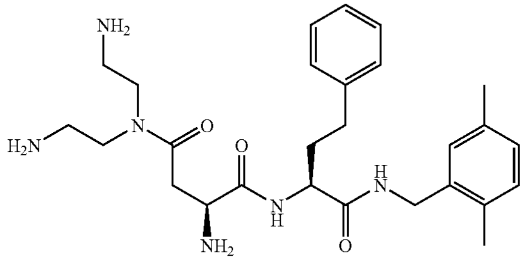
97
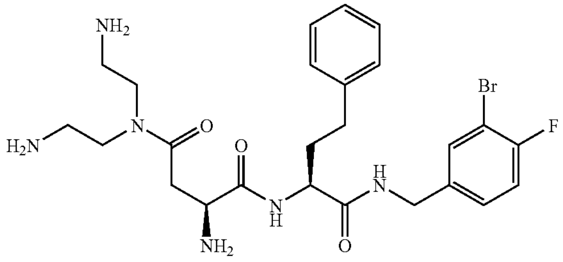
98
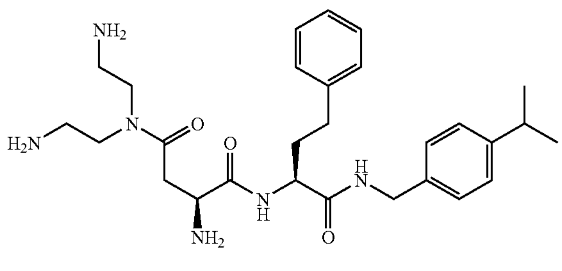
99
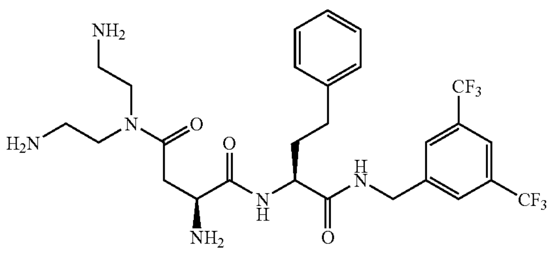
100
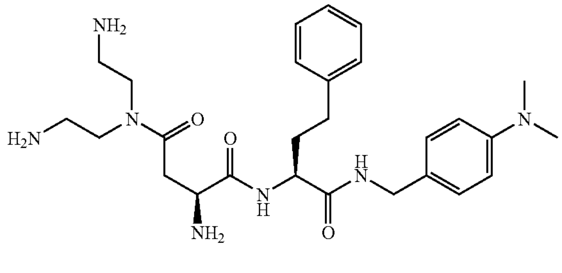
101
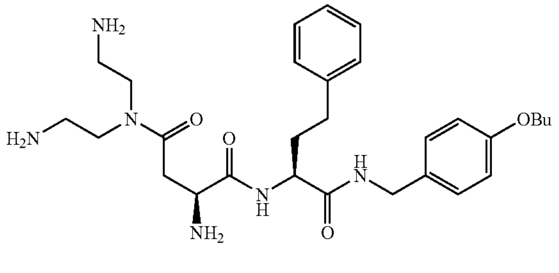

-continued
102
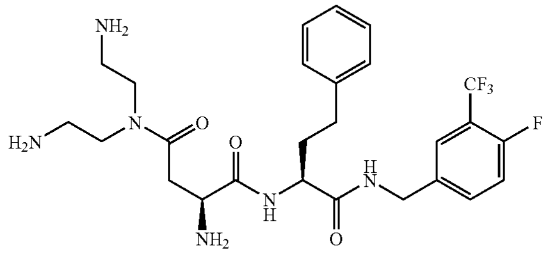
103
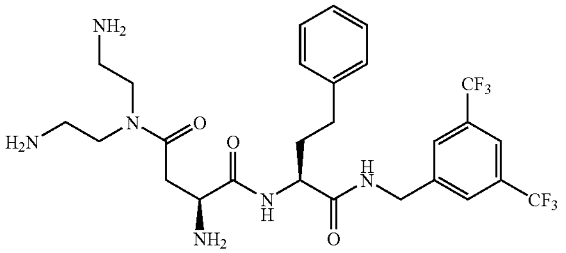
104
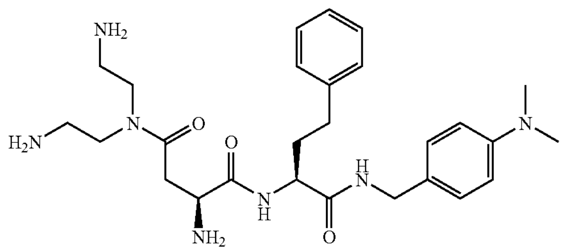
105
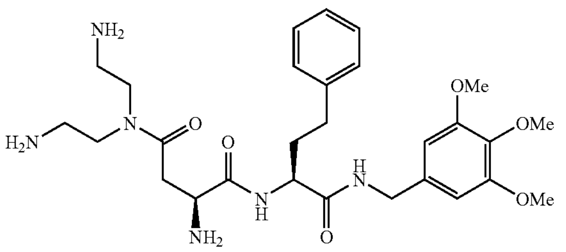
106
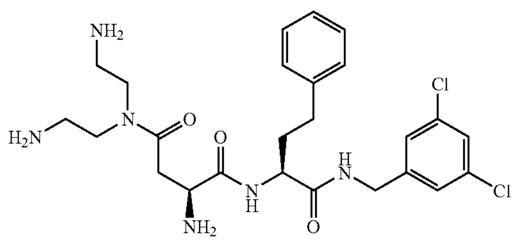
107
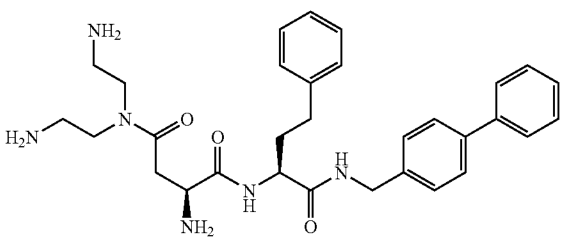
108
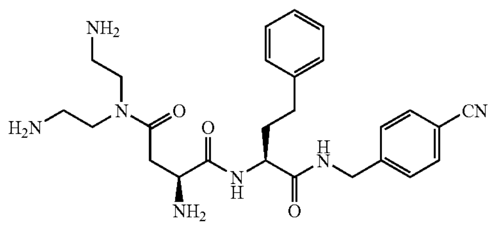
109
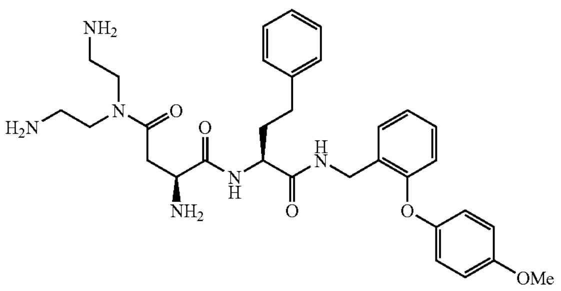
110
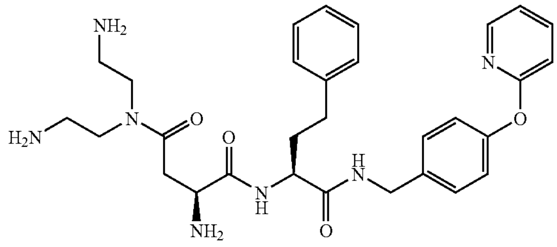
111
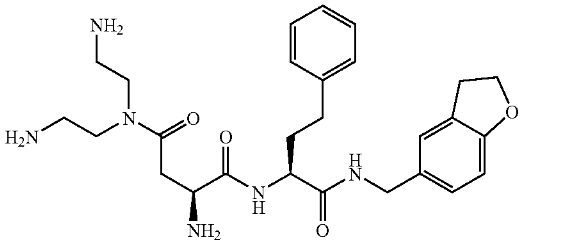
112
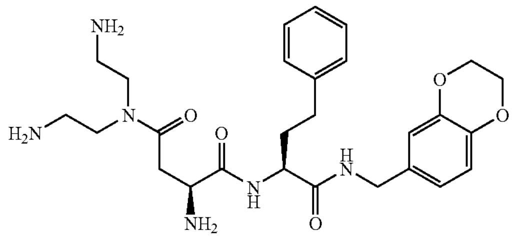
113
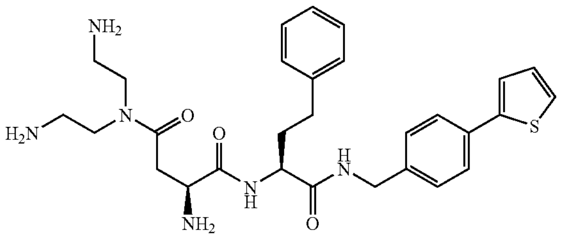

-continued
114
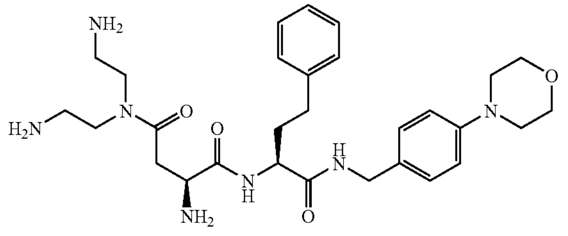
116
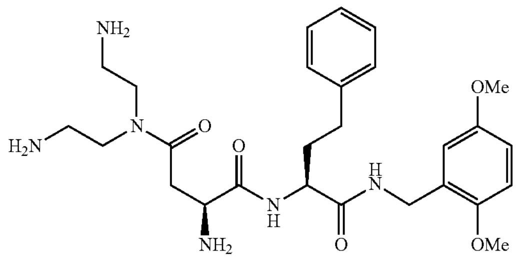
118
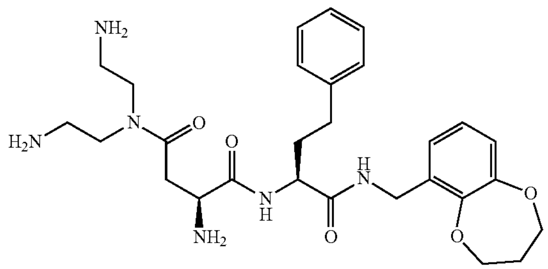
120
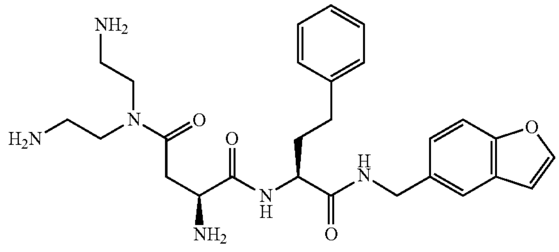
122
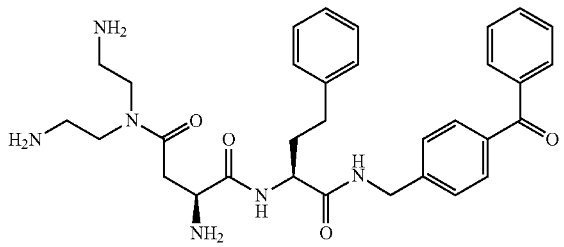
114
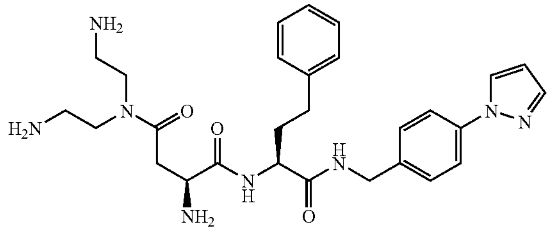
117
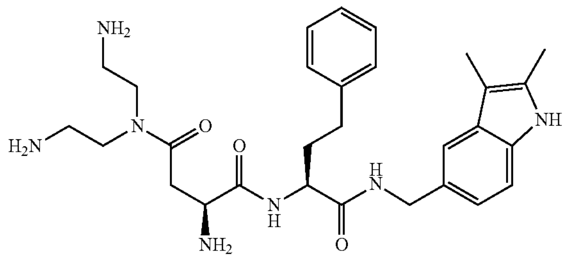
119
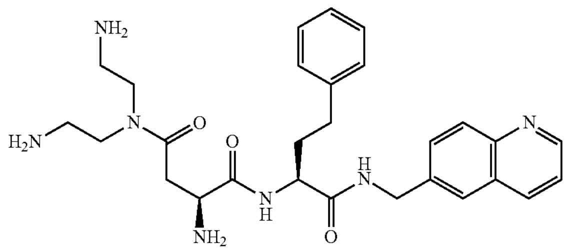
121
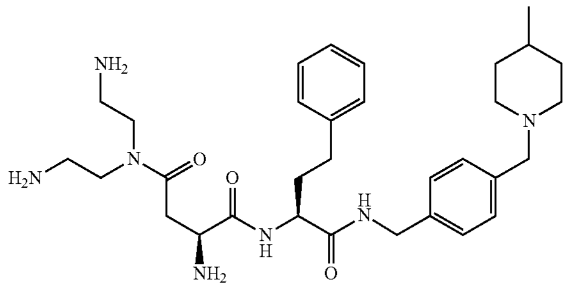
123
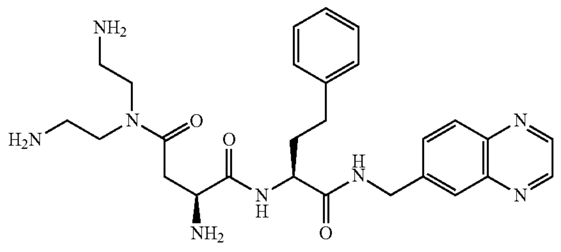

-continued
124
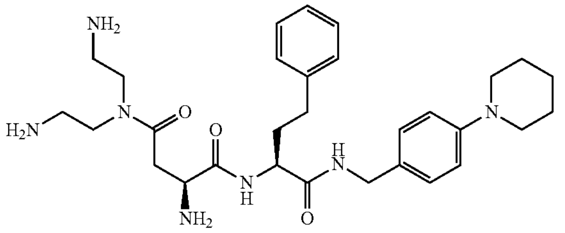
125
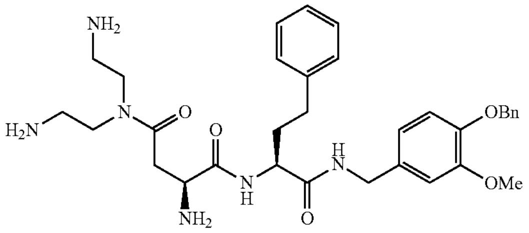
126
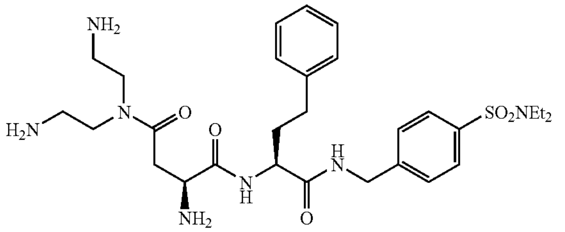
127
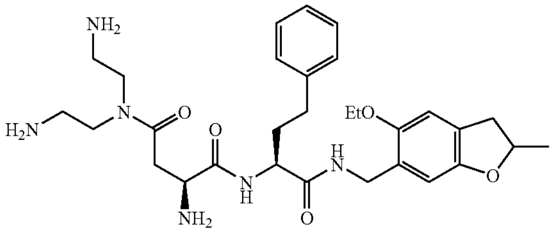
128
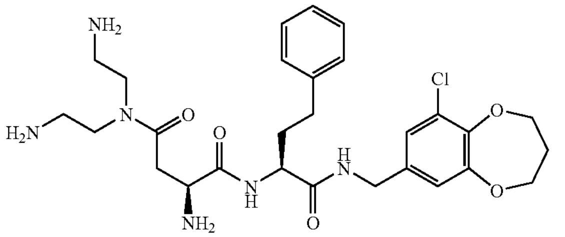
129
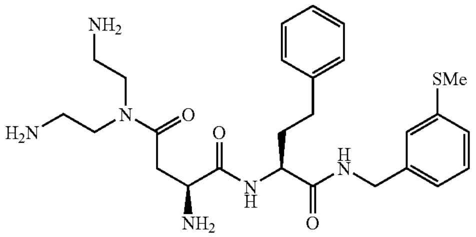
130
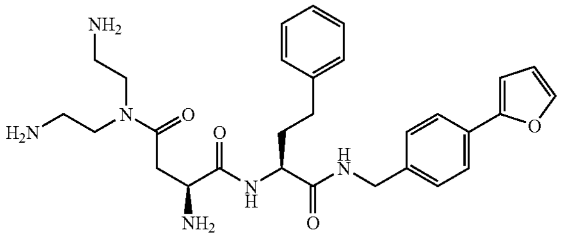
131
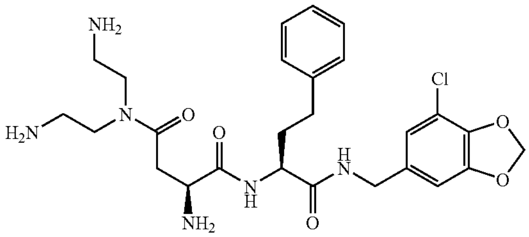
132
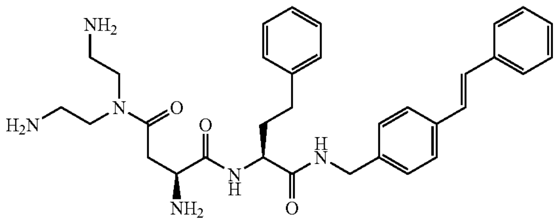
133
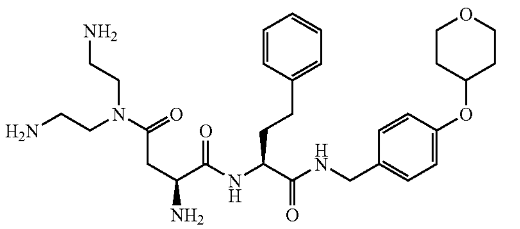
134
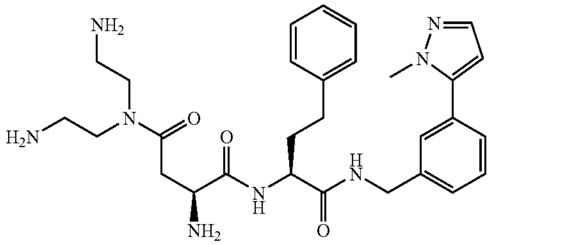
135
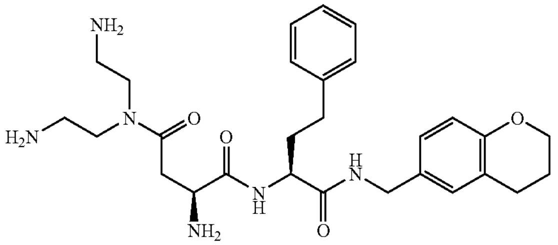

-continued
136
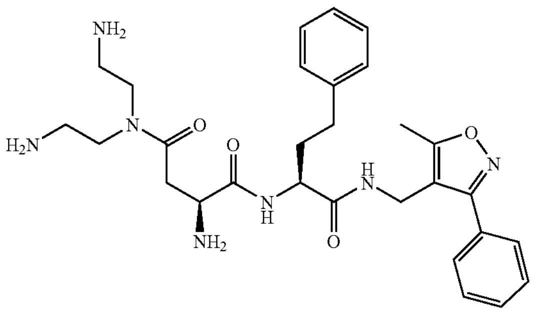
137
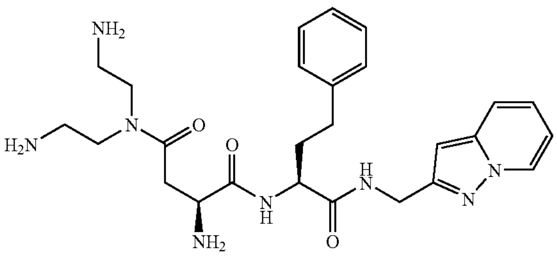
138
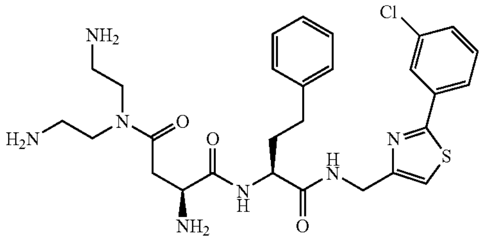
139
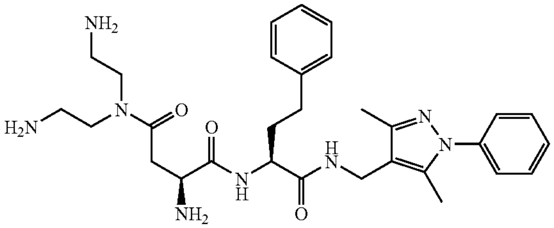
140
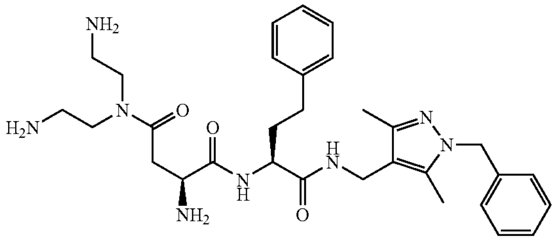
141
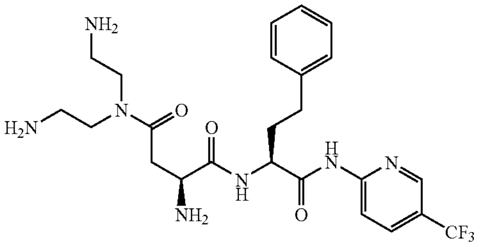
142
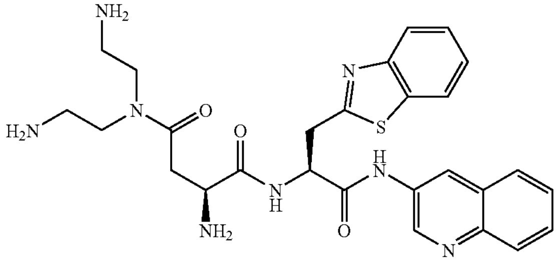
143
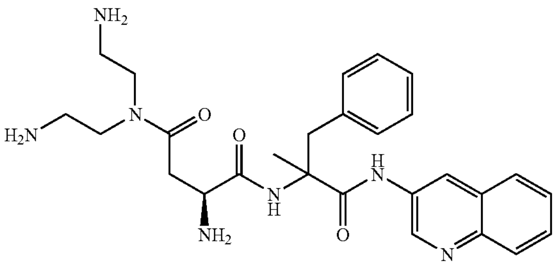
144
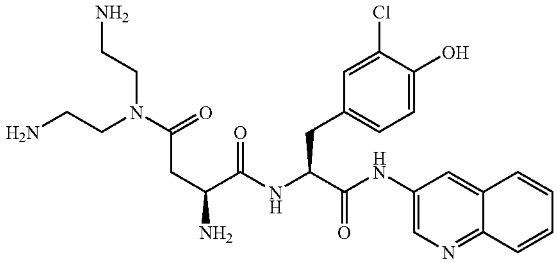
145
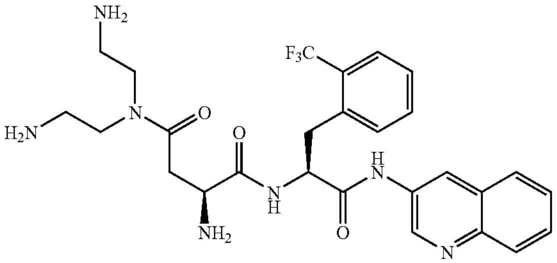

-continued
146
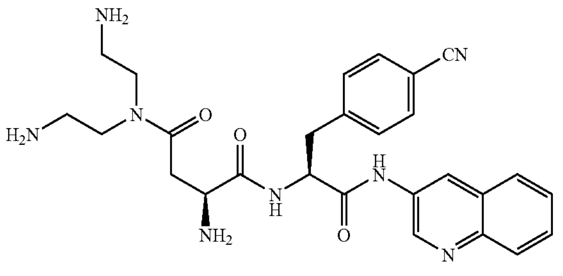
147
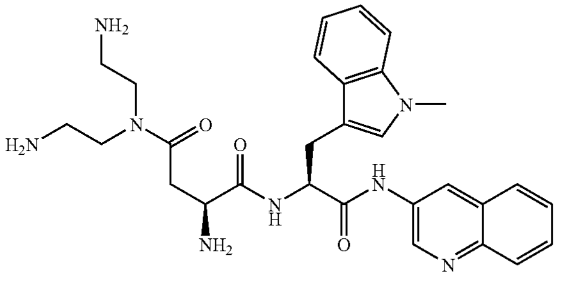
148
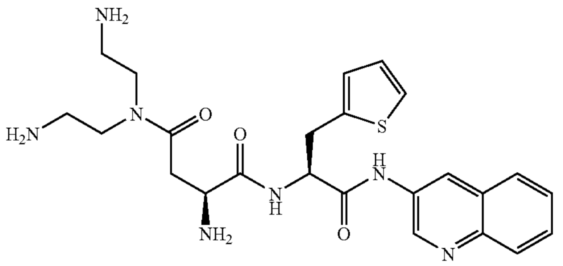
149
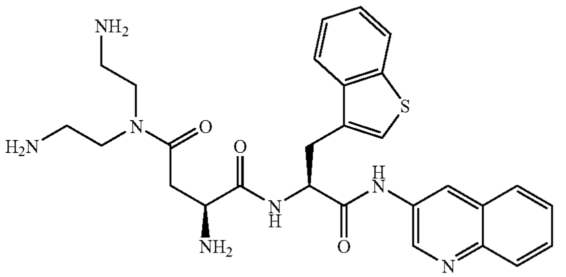
150
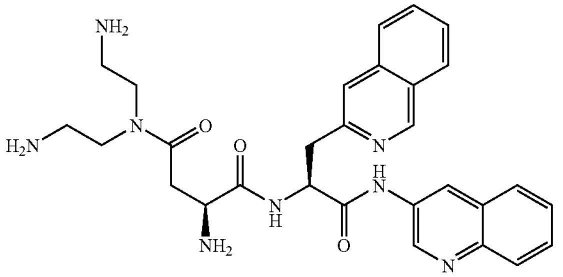
151
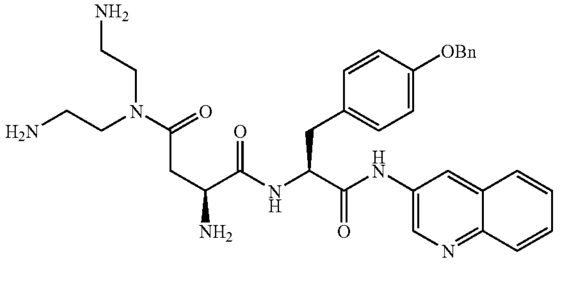
152
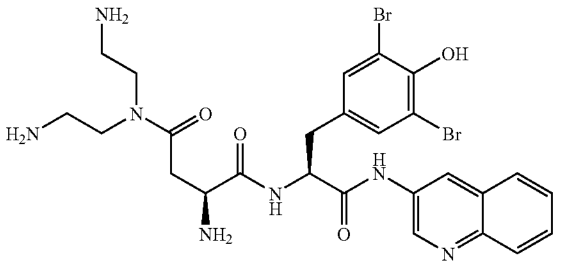
153
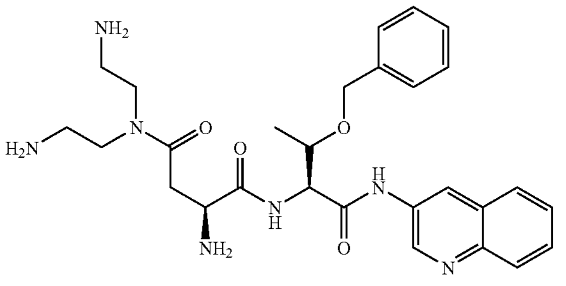
154
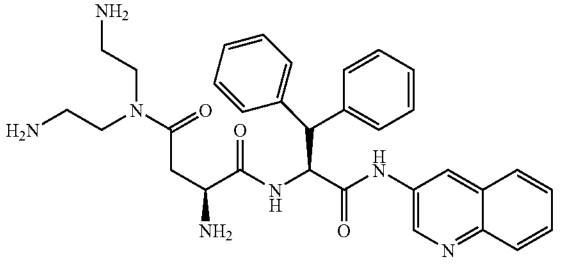
155
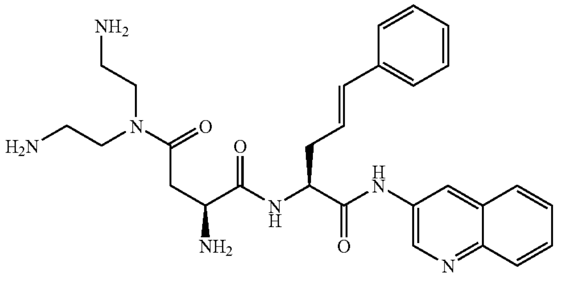

-continued
156
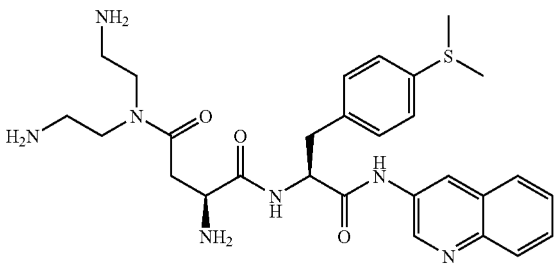
157
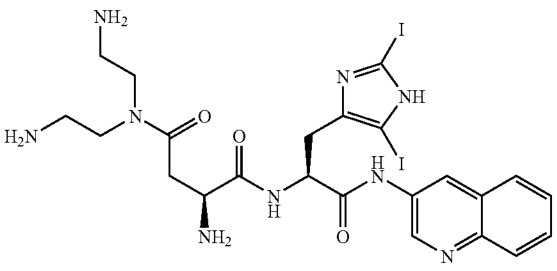
158
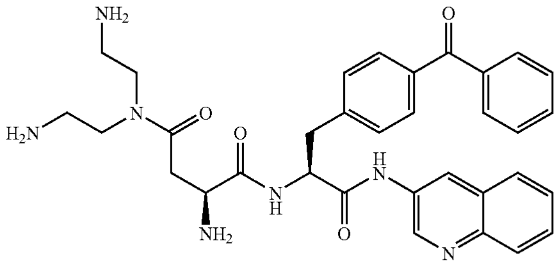
159
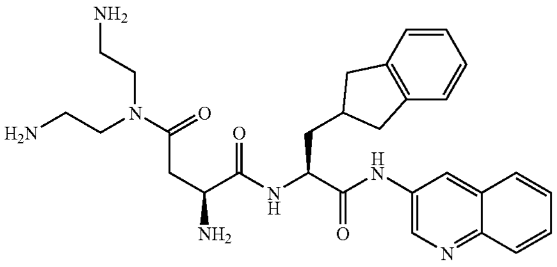
160
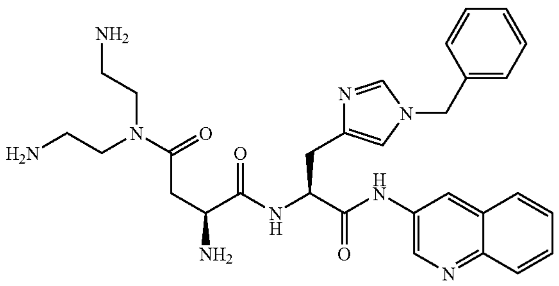
161
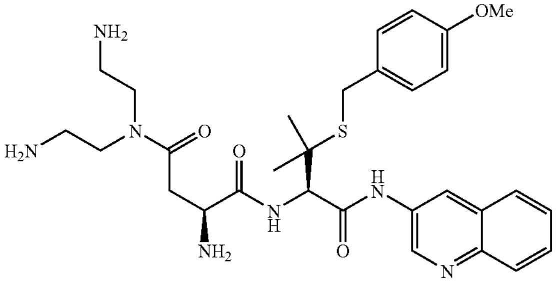
162
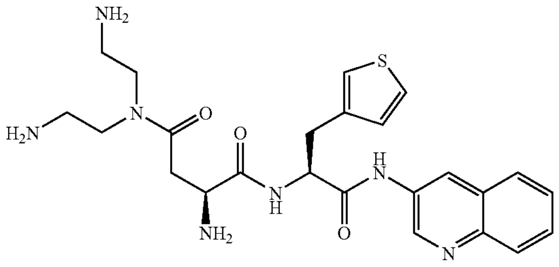
163
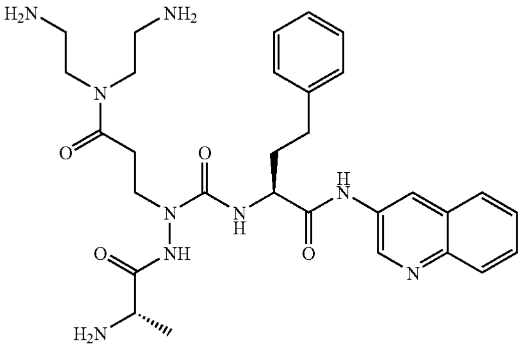
164
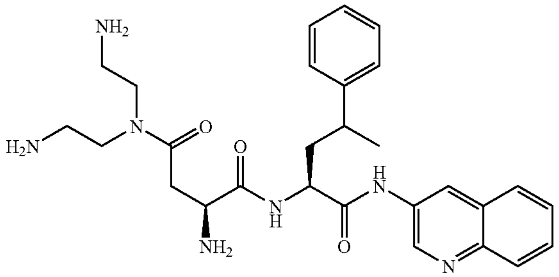
165
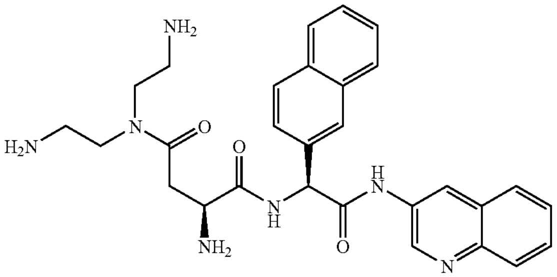

-continued
166
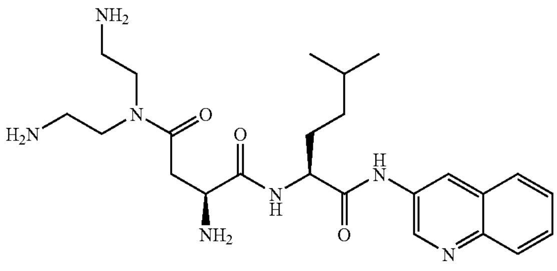
167
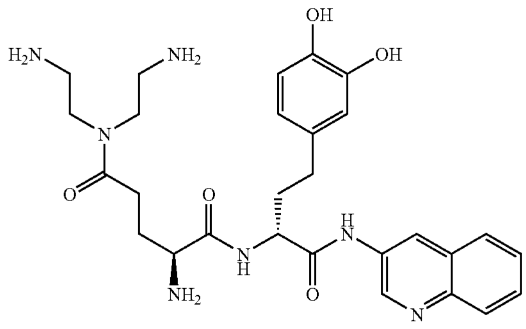
168
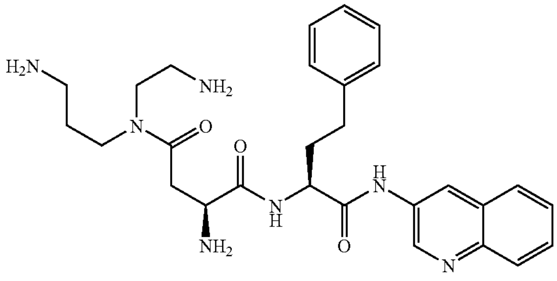
169
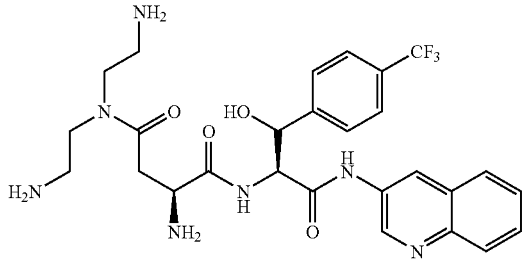
170
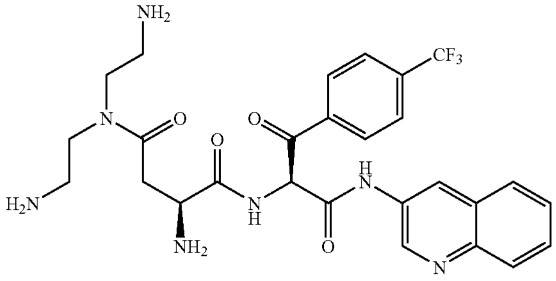
171
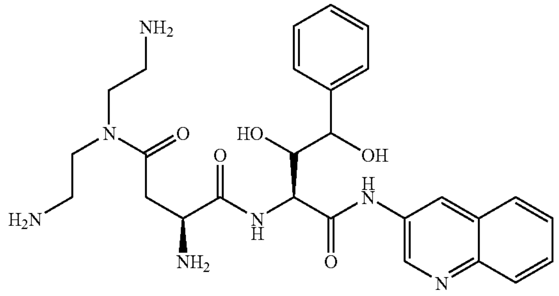
172
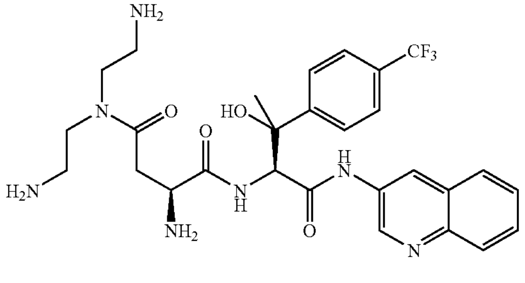
173
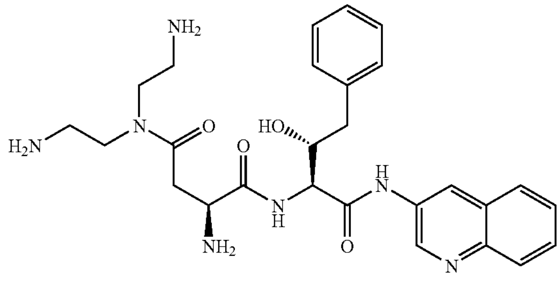

-continued
174
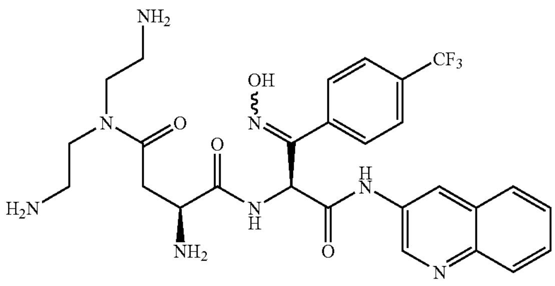
175
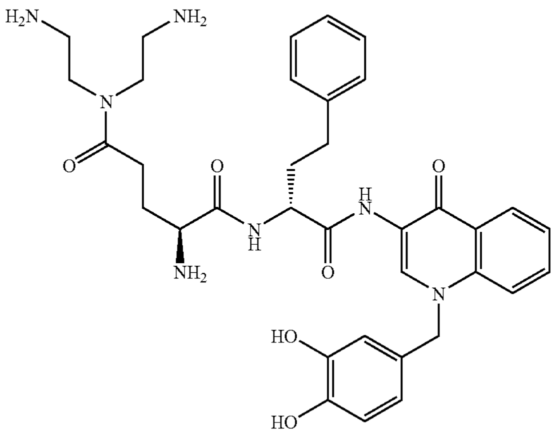
176
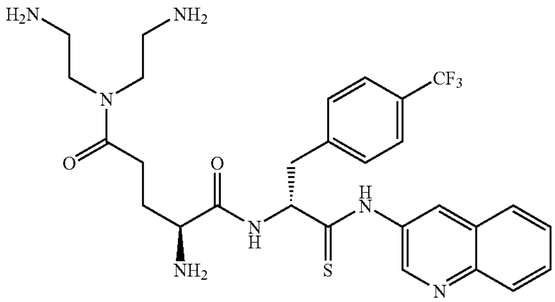
177
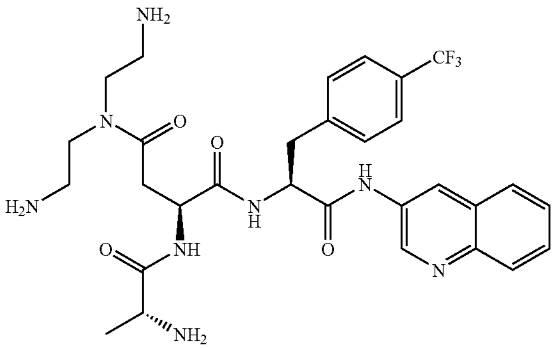
178
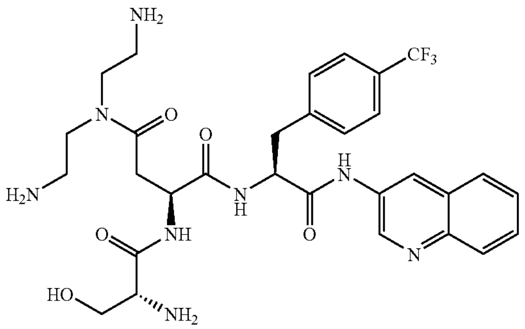
179
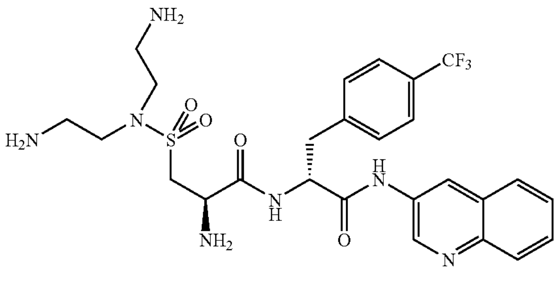
180
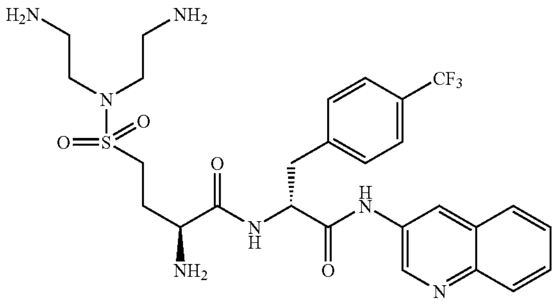
181
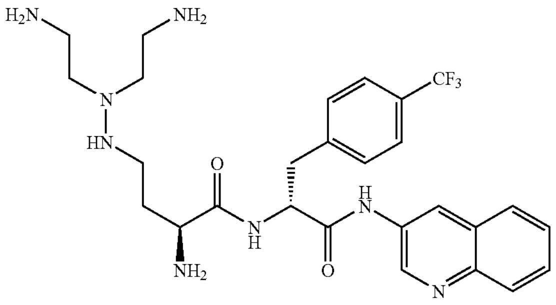

-continued
182
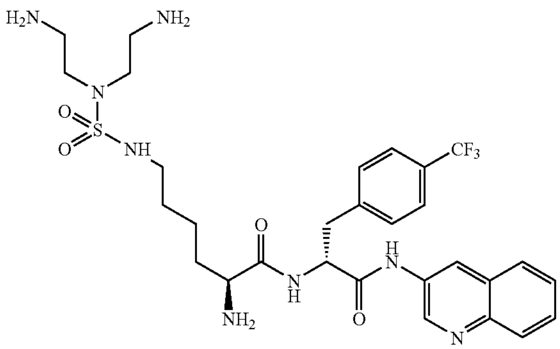
183
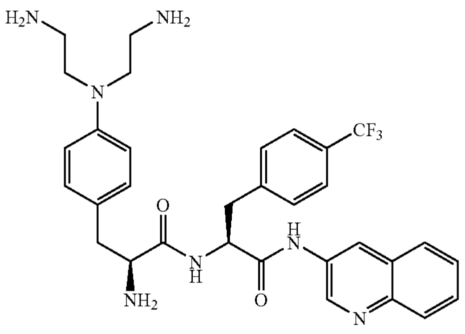
184
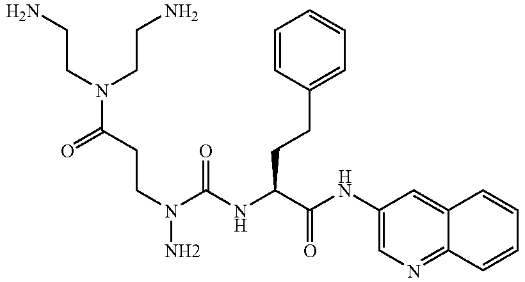
185
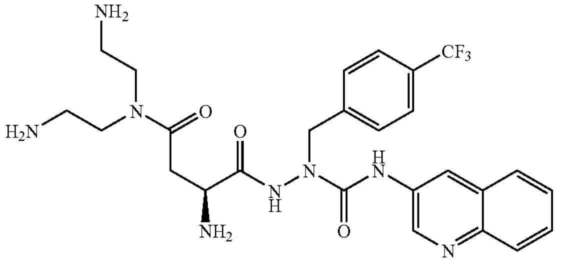
186
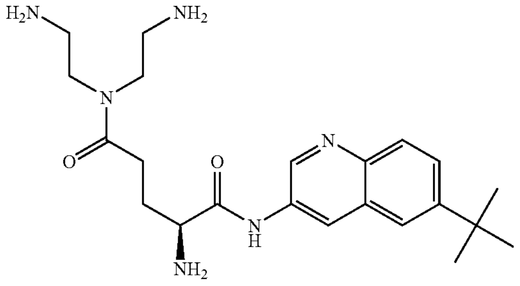
187
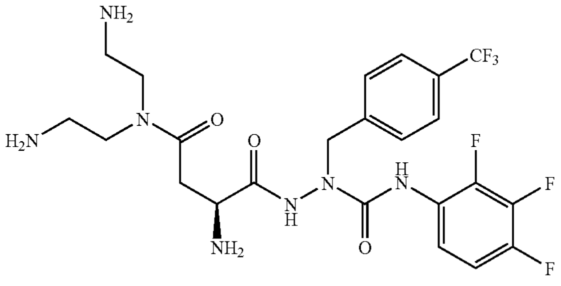
188
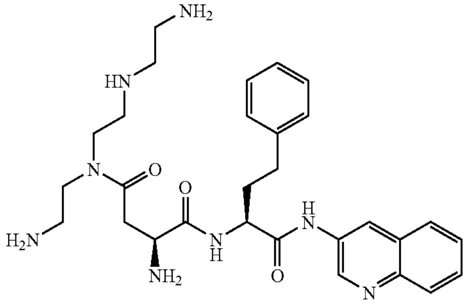
189
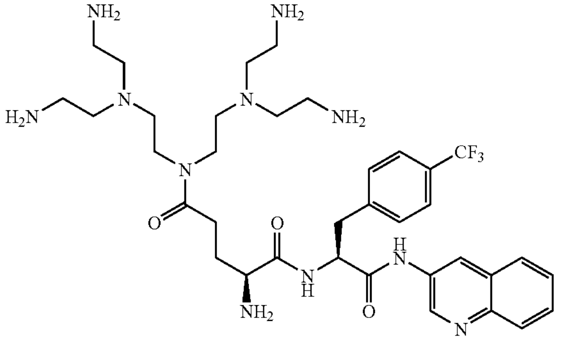

-continued
190
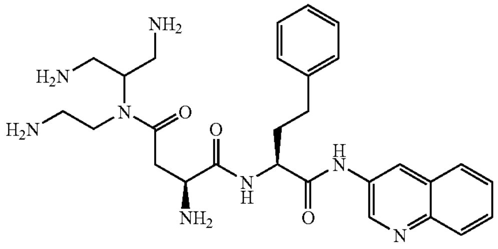
191
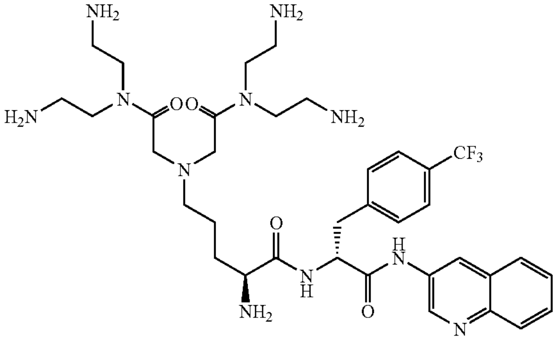
192
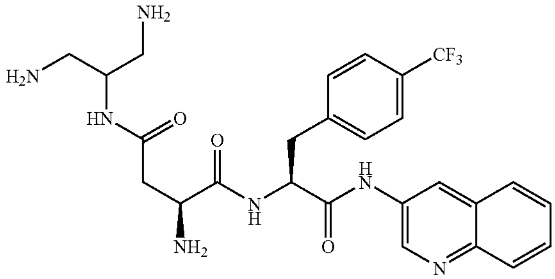
193
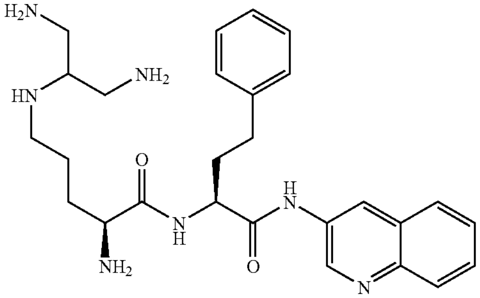
194
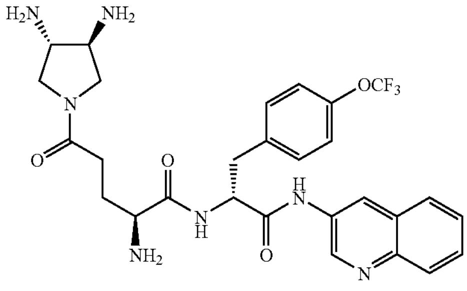
195
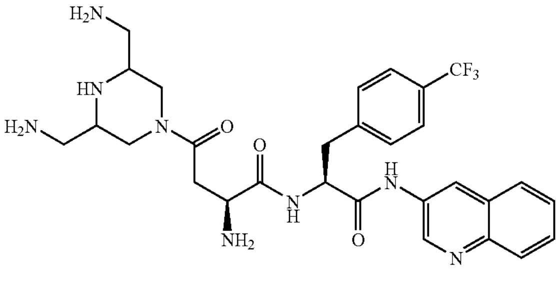
196
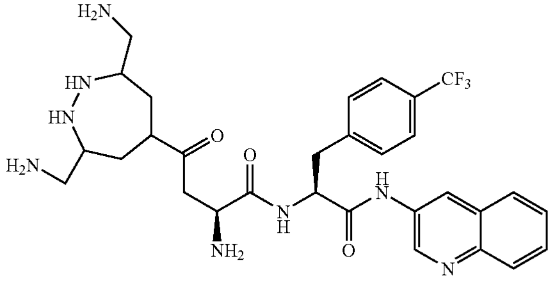
197
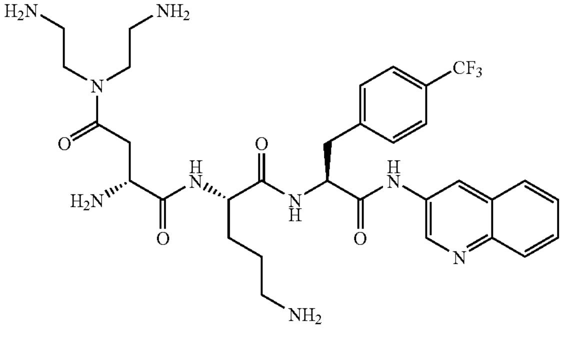

-continued
198
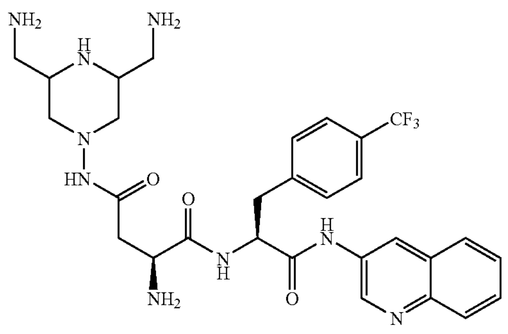
199
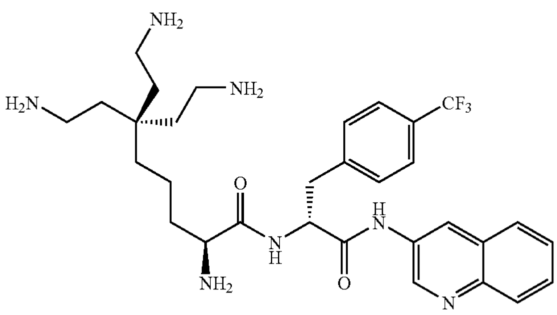
200
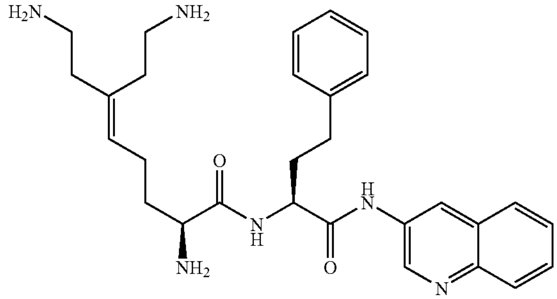
201
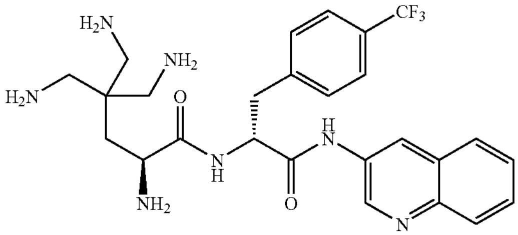
202
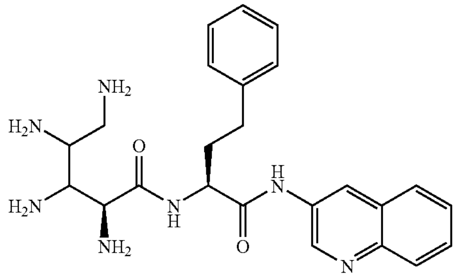
203
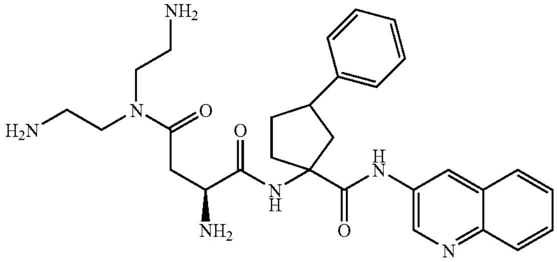
204
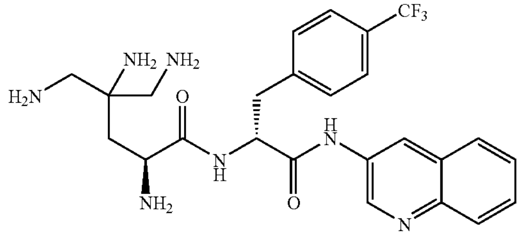
205
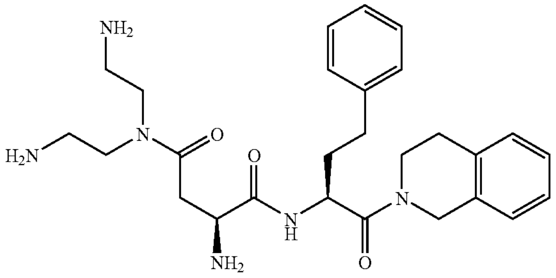
206
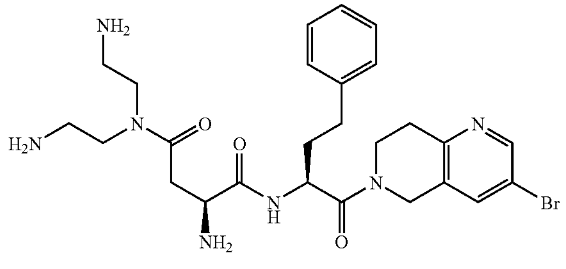
207
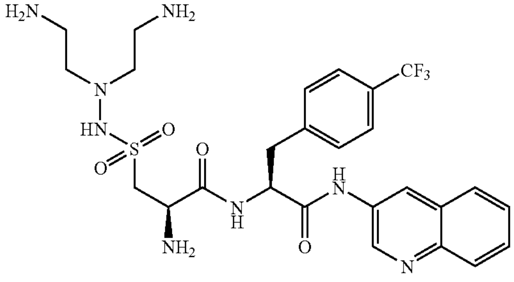

-continued
208
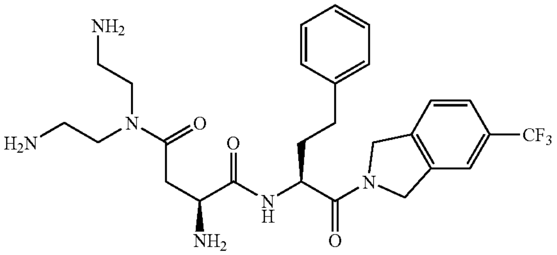
209
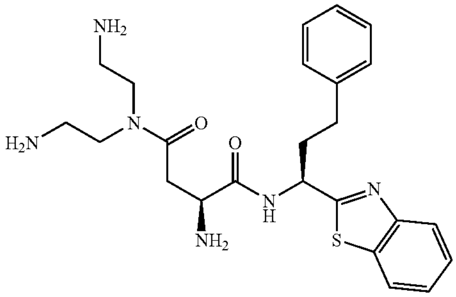
210
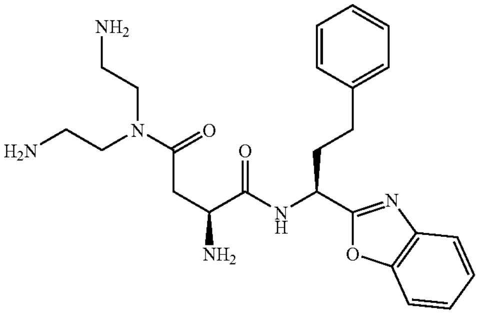
211
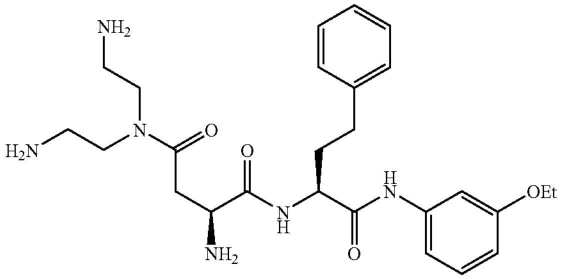
212
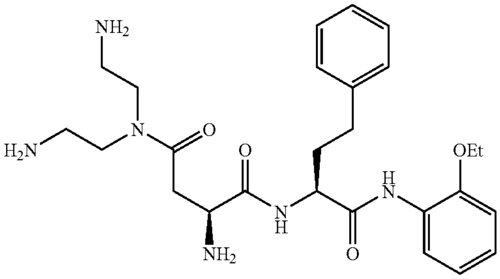
213
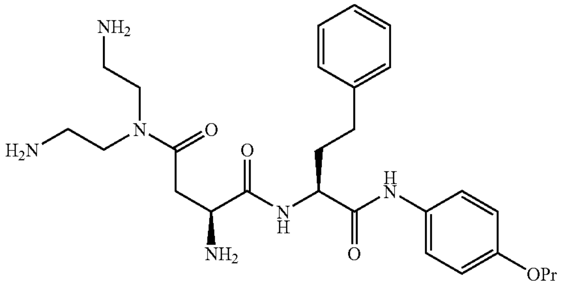
214
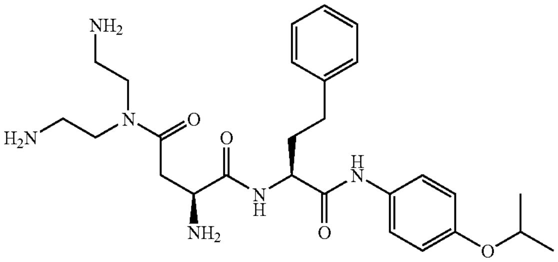
215
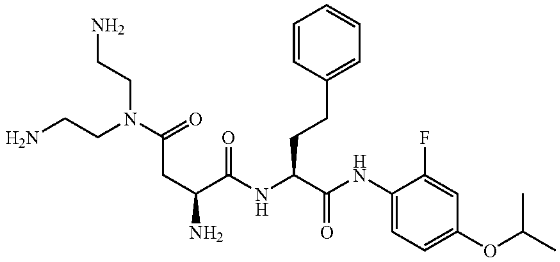
216
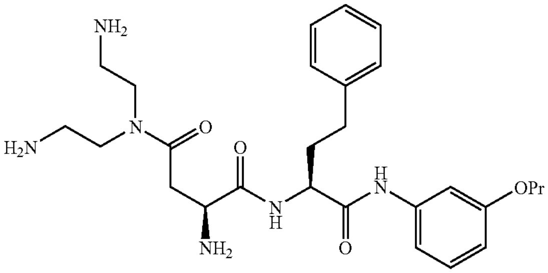
217
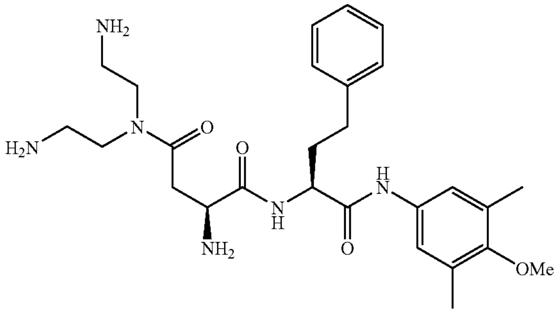

-continued
218
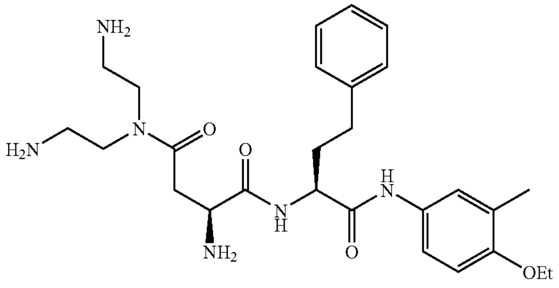
219
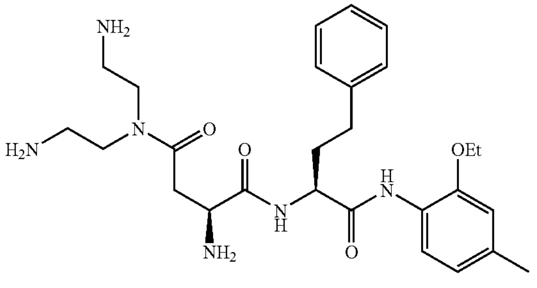
220
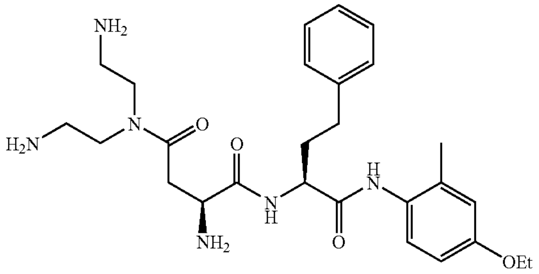
221
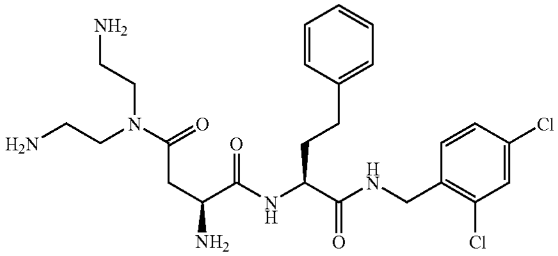
222
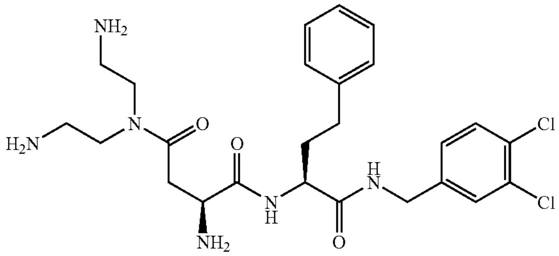
223
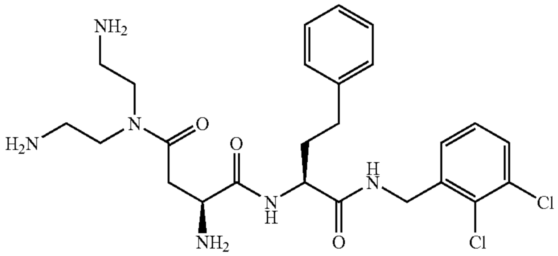
224
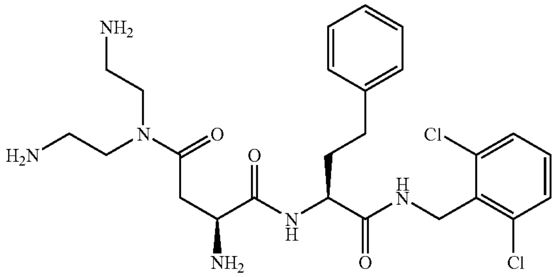
225
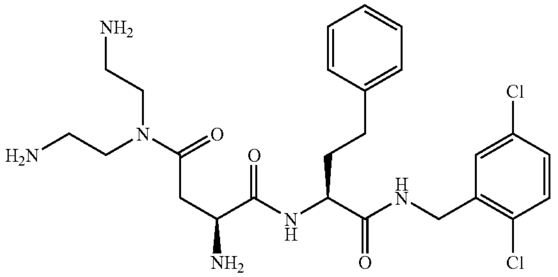
226
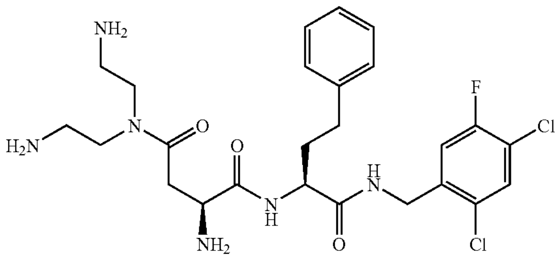
227
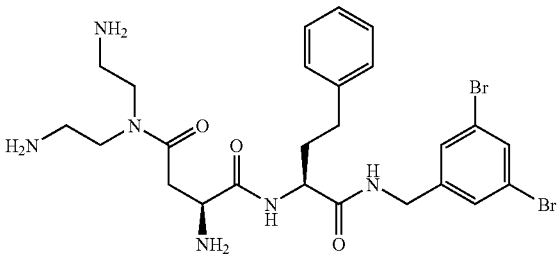

-continued
228
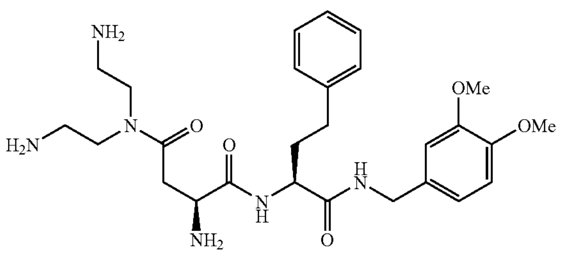
229
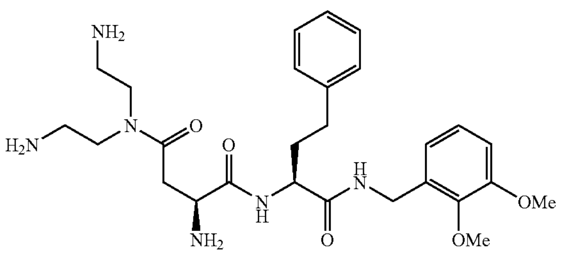
230
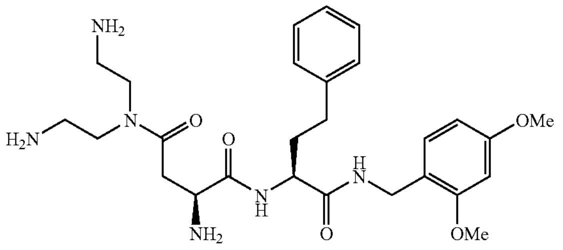
231
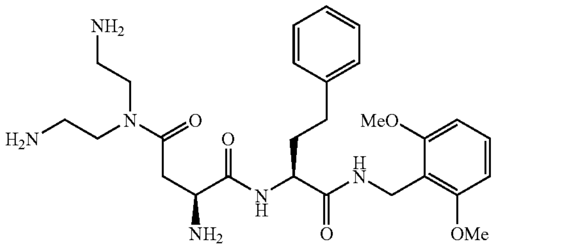
232
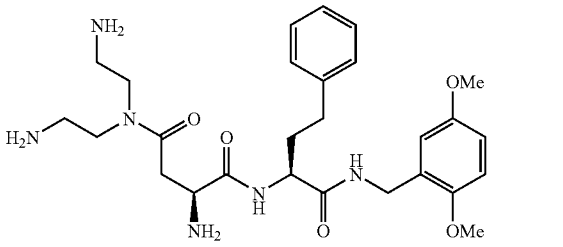
233
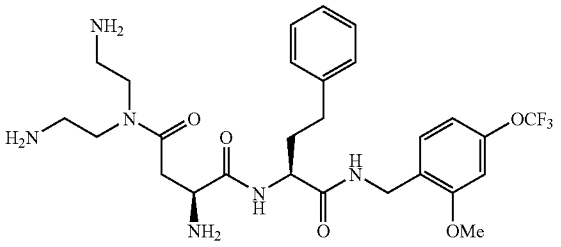
234
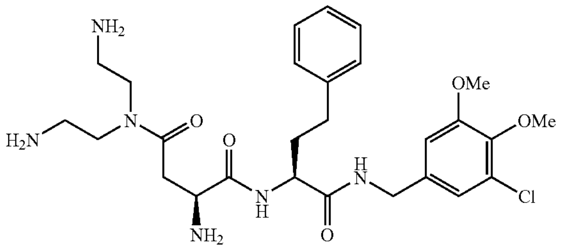
235
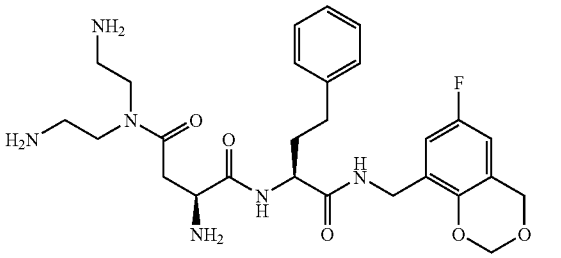
236
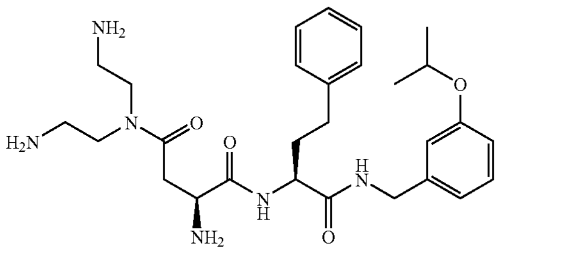
237
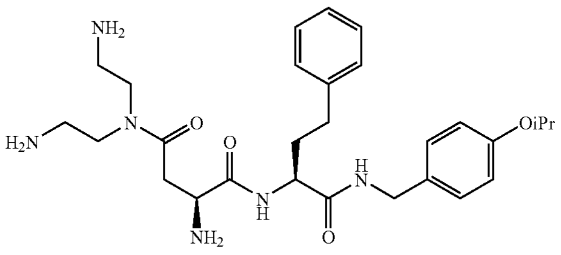

-continued
238
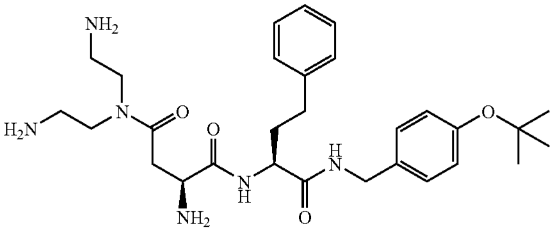
239
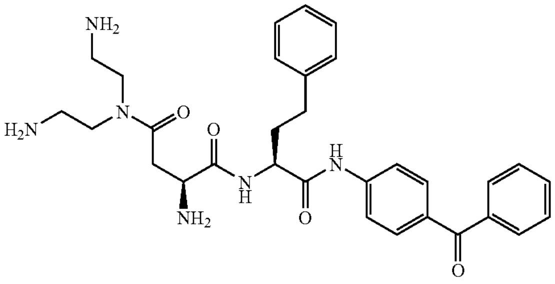
240
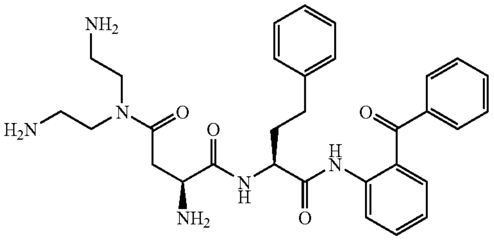
241
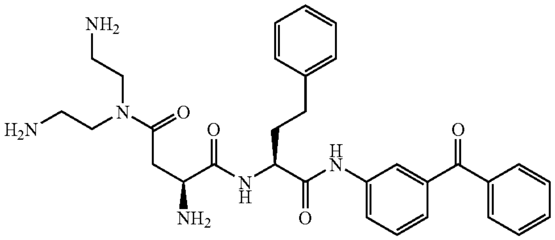
242
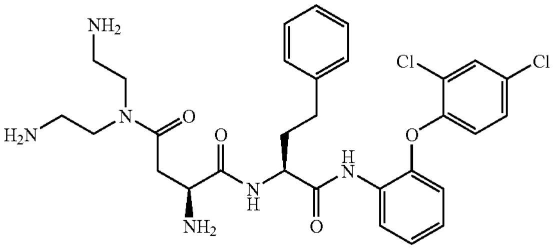
243
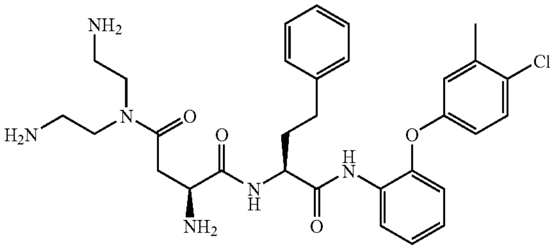
244
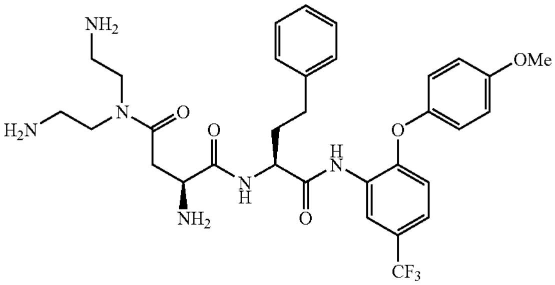
245
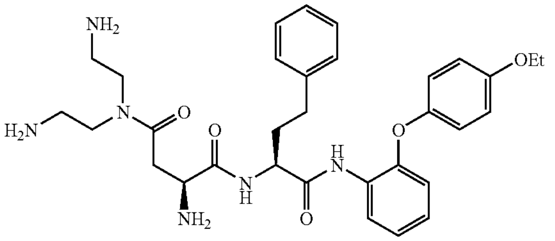
246
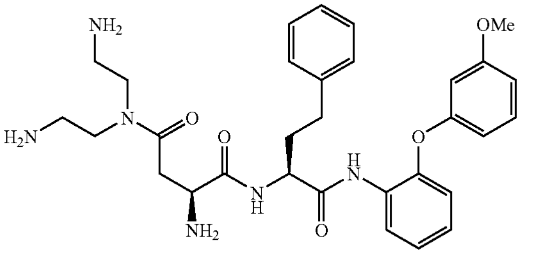
247
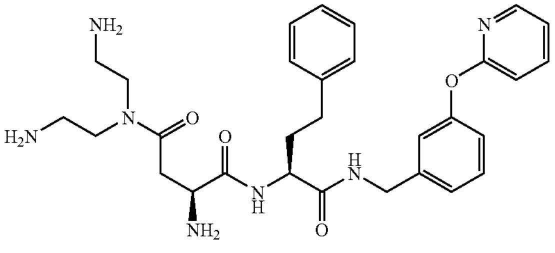

-continued
248
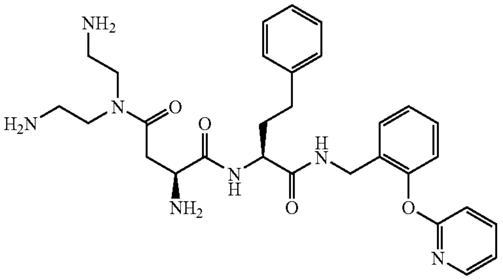
249
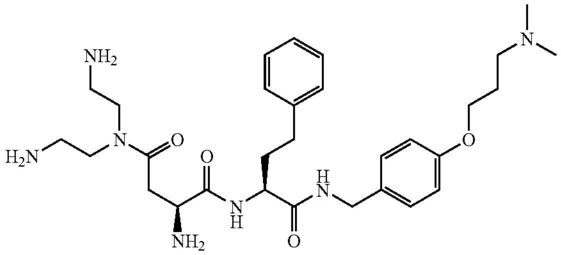
250
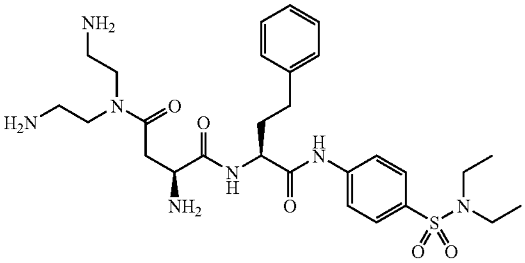
251
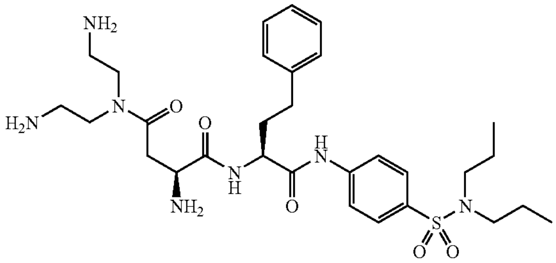
252
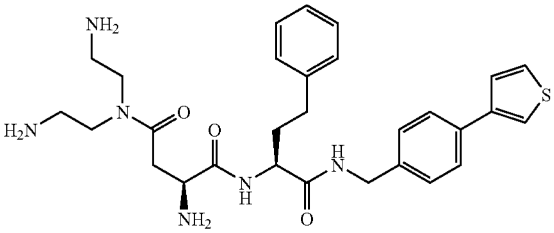
253
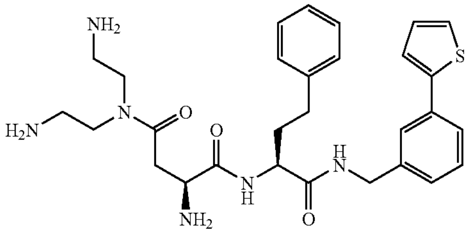
254
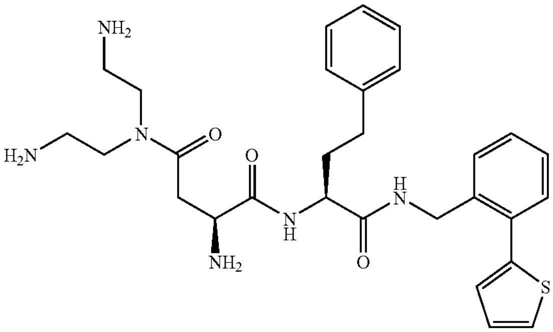
255
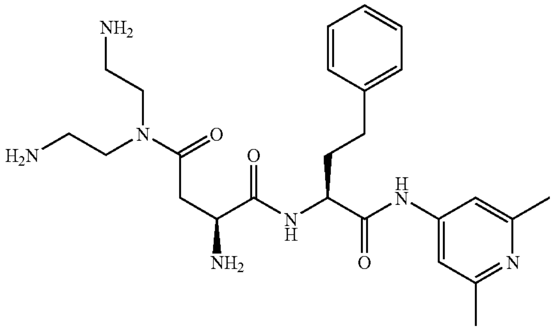
256
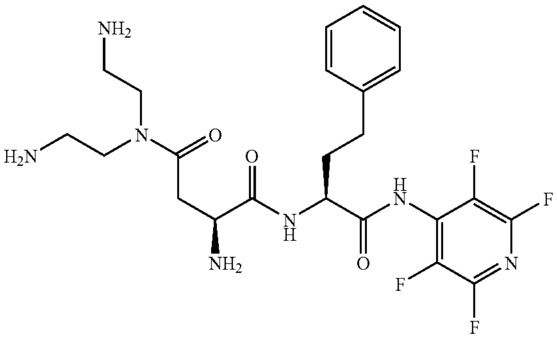
257
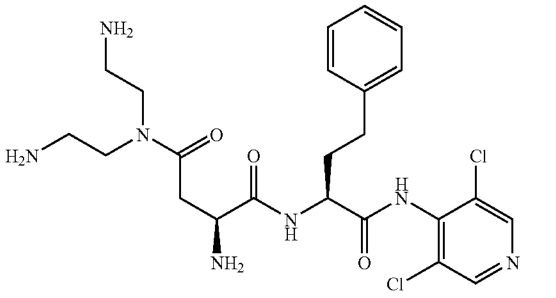

-continued
258
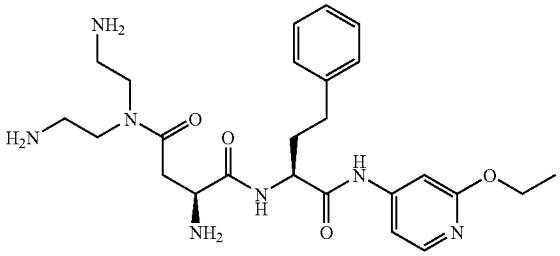
259
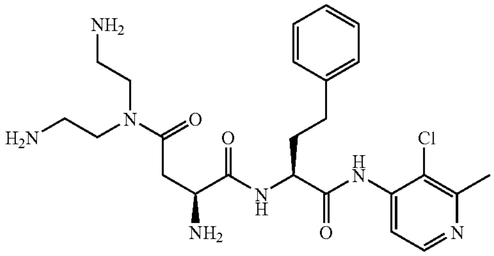
260
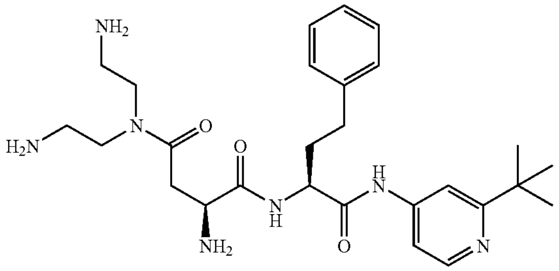
261
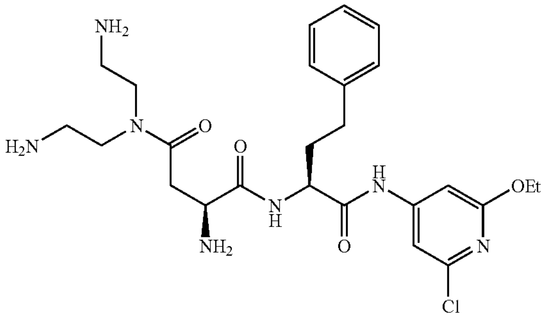
262
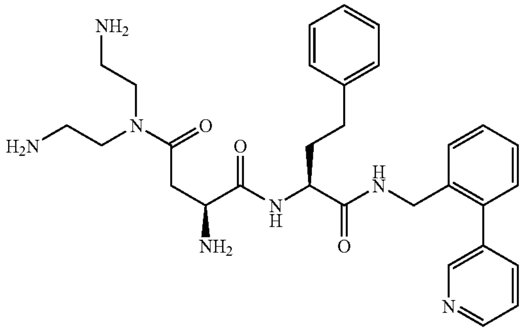
263
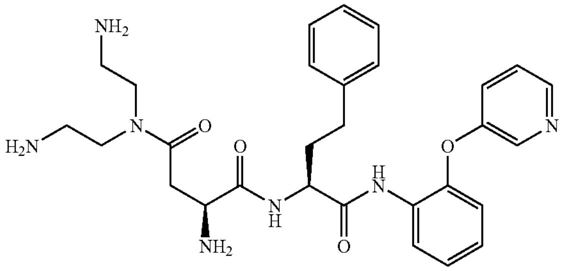
264
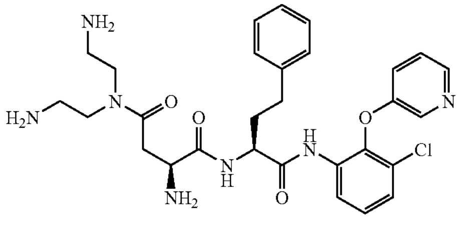
265
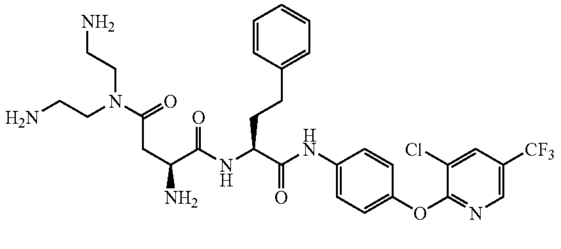
266
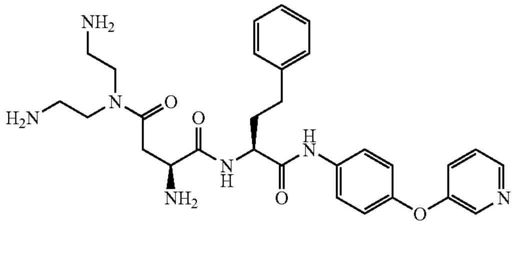
267
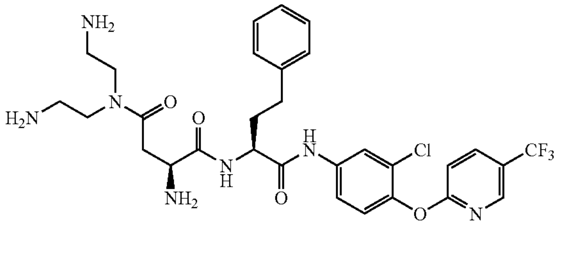

-continued
268
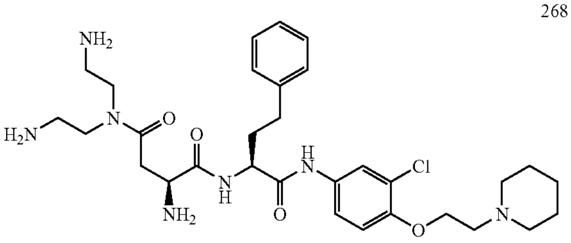
269
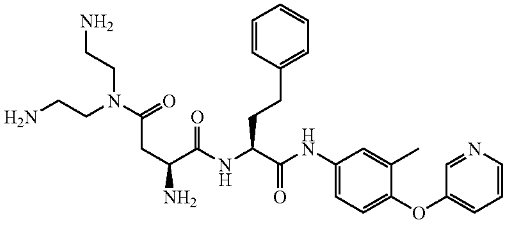
270
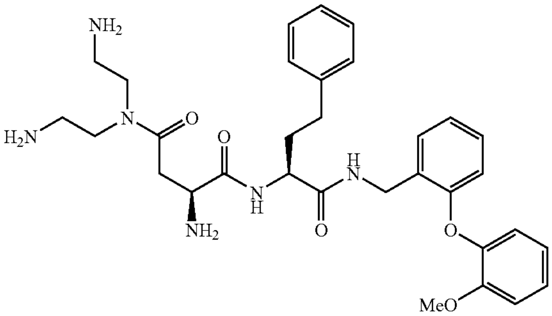
271
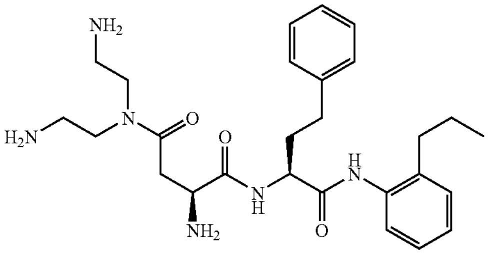
272
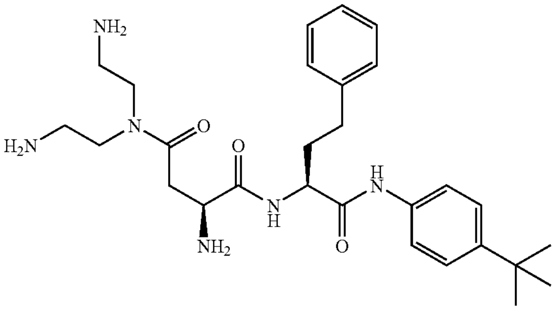
273
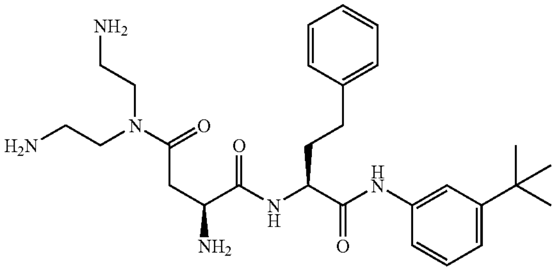
274
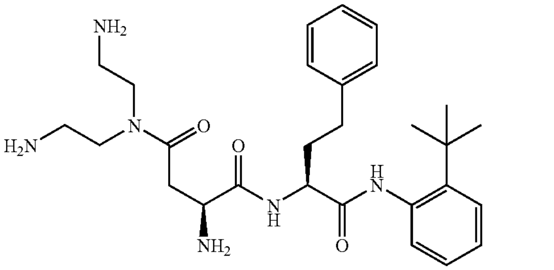
275
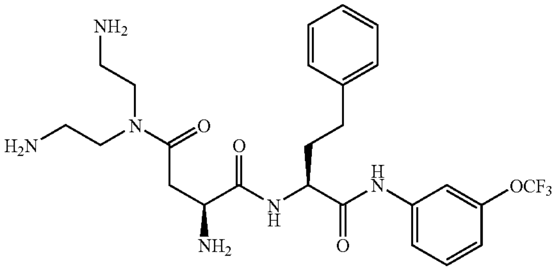
276
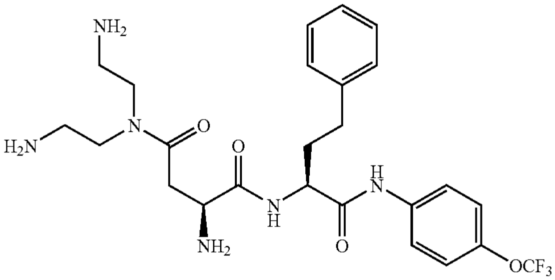
277
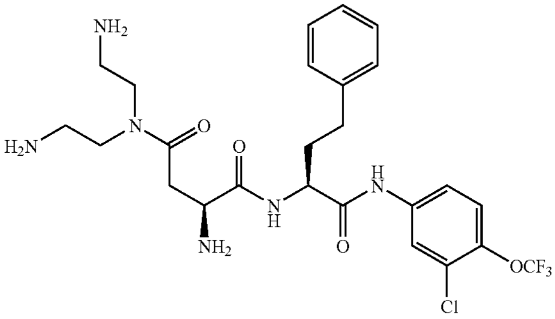

-continued
278
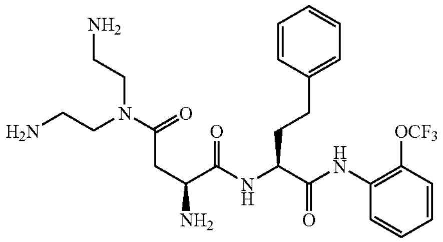
279
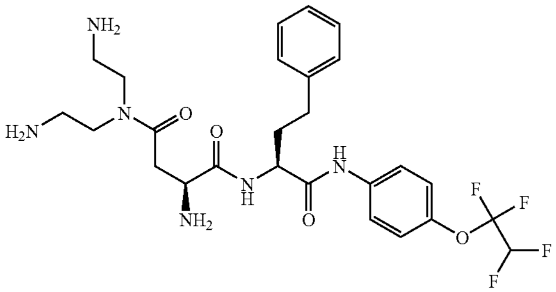
280
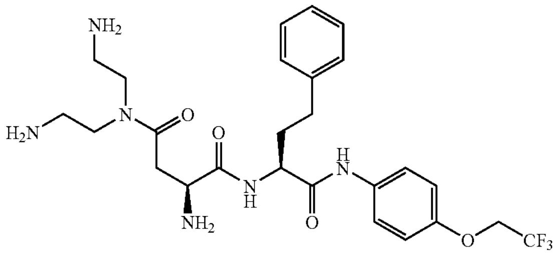
281
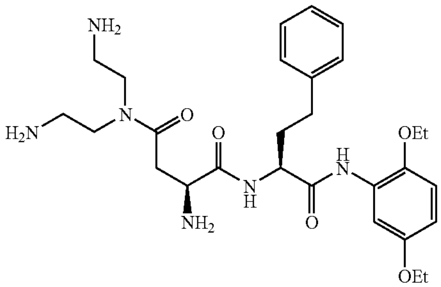
282
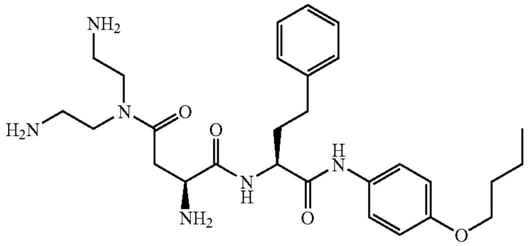
283
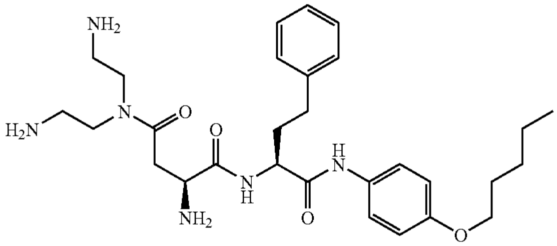
284
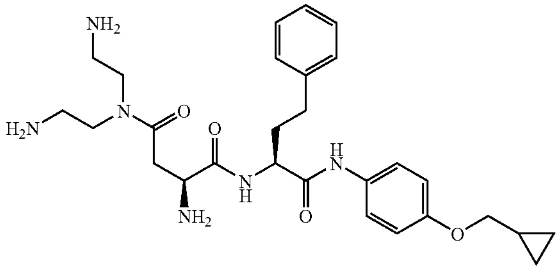
285
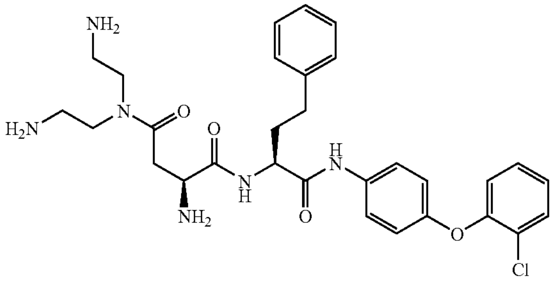
286
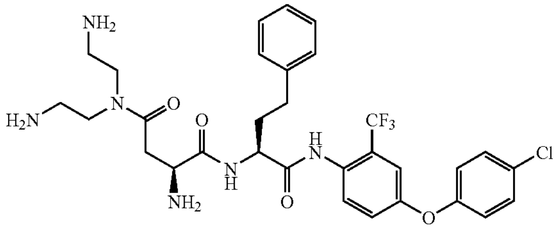
287
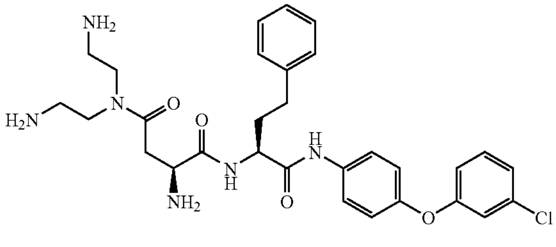

-continued
288
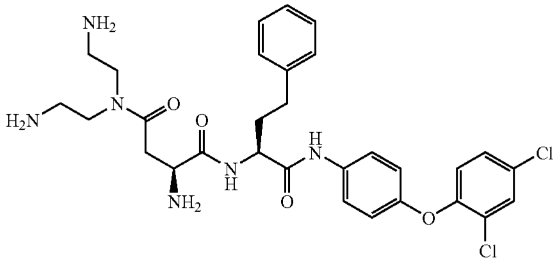
289
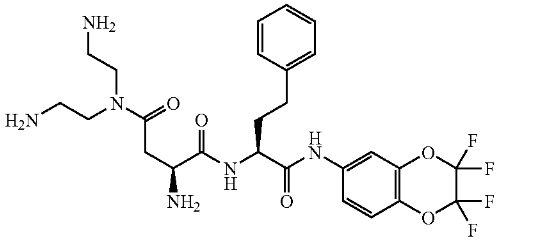
290
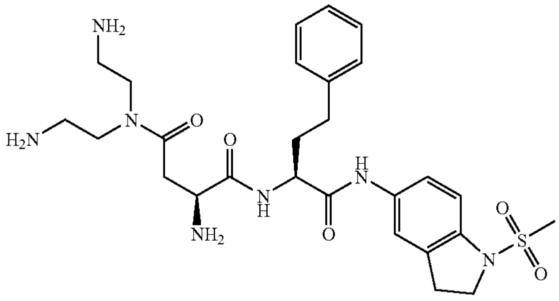
291
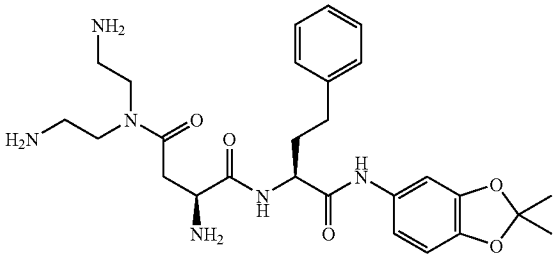
292
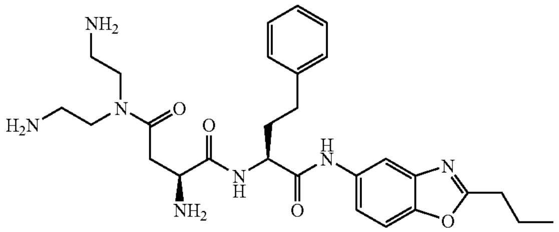
293
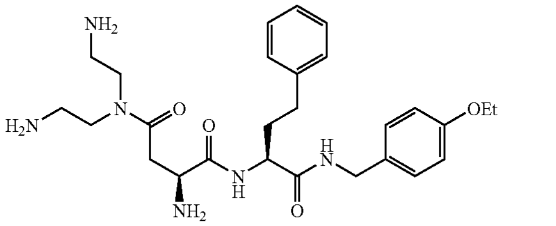
294
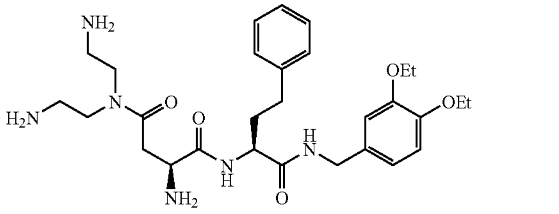
295
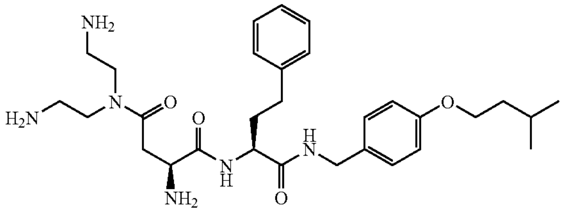
296
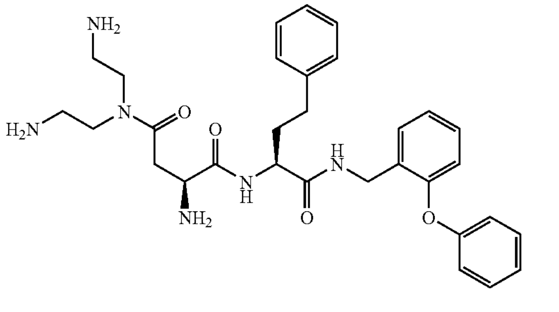
297
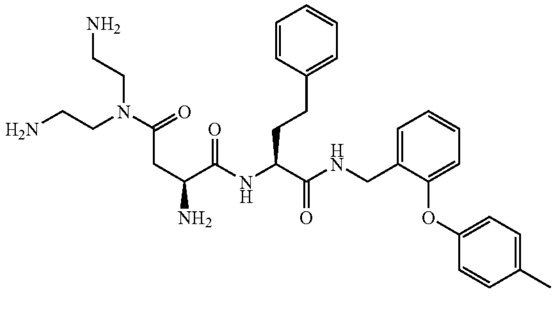

-continued
298
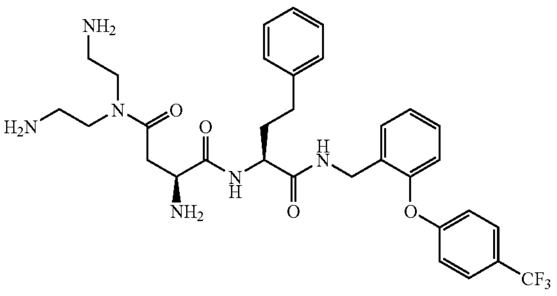
299
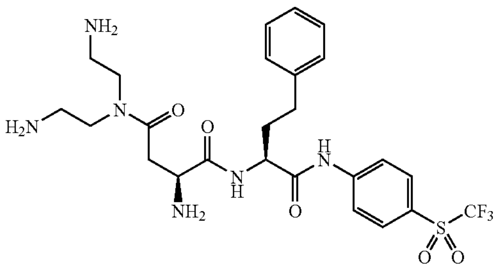
300
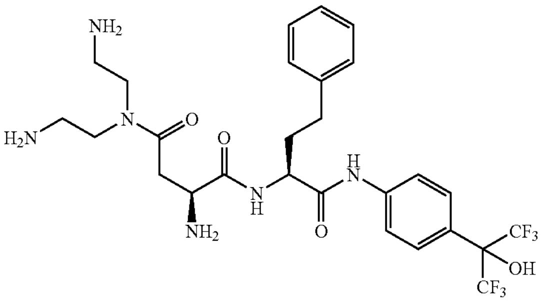
301
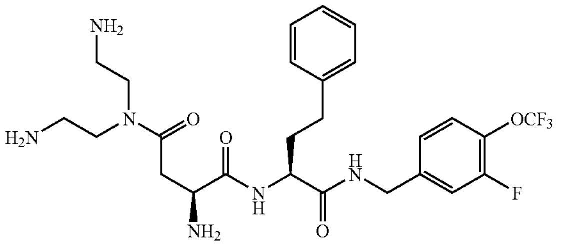
302
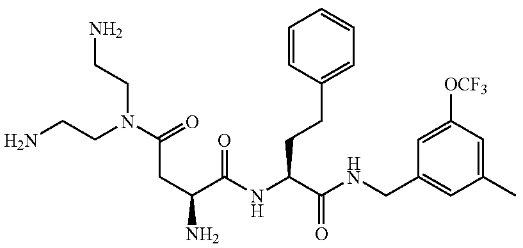
303
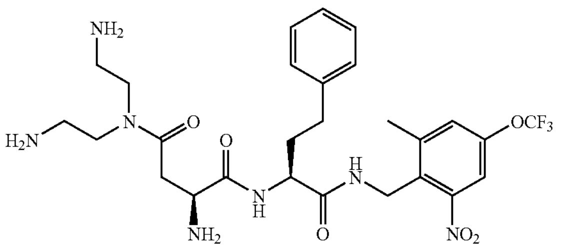
304
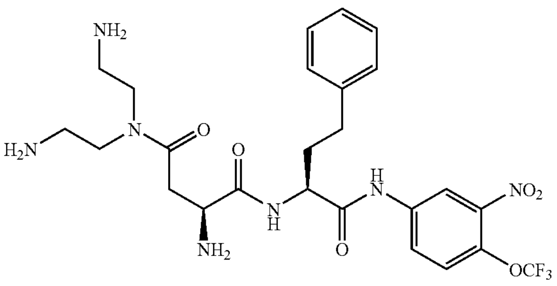
305
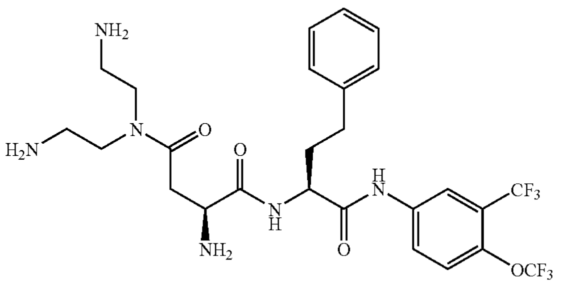
306
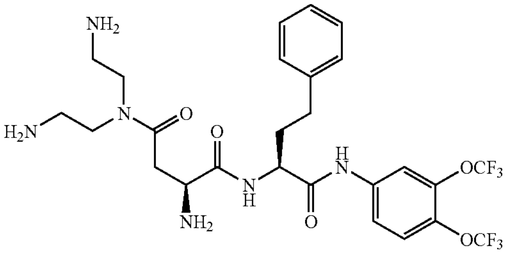
307
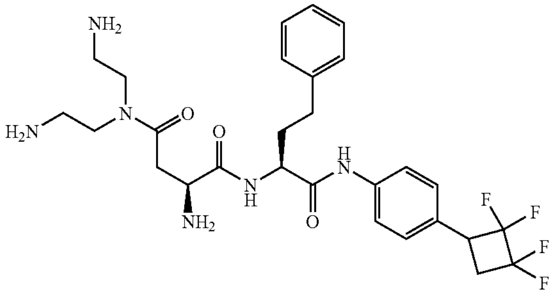

-continued
308
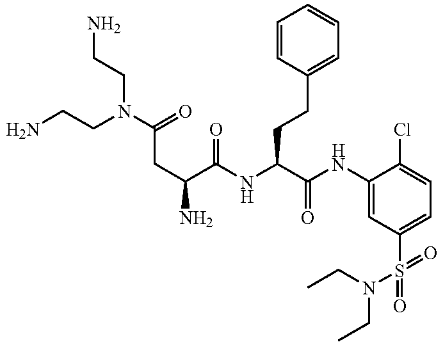
309
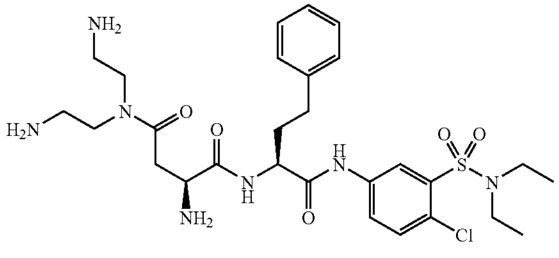
310
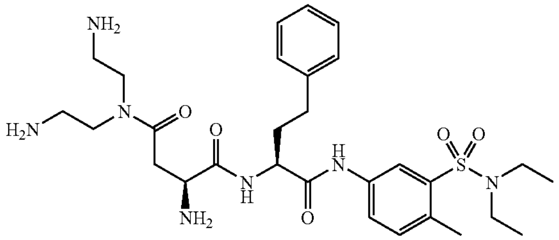
311
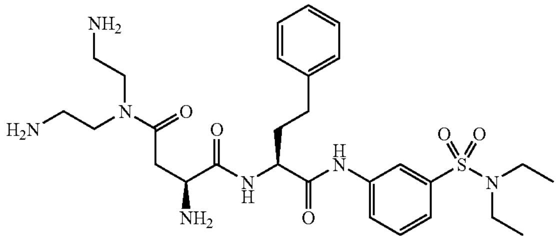
312
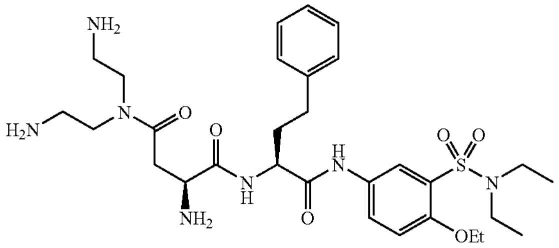
313
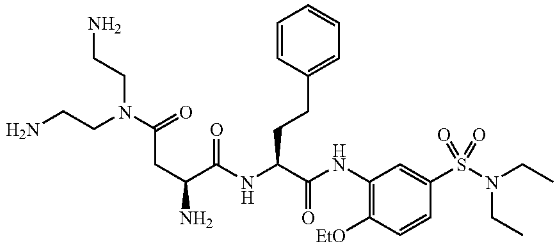
314
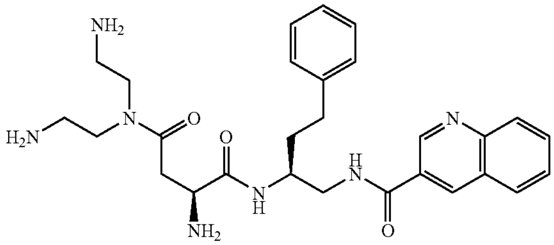
315
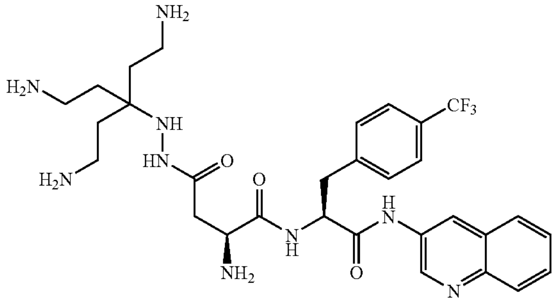
316
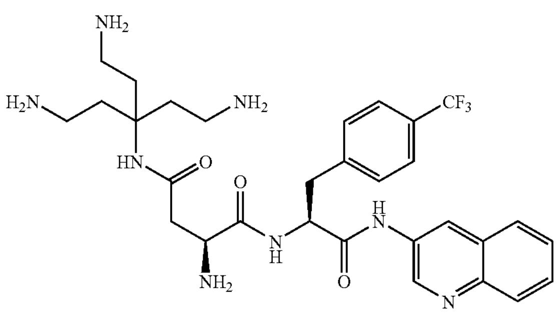
317
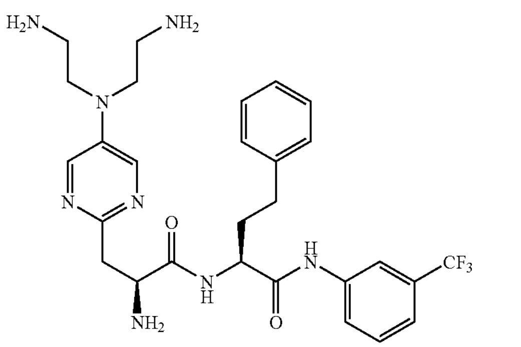

-continued
318
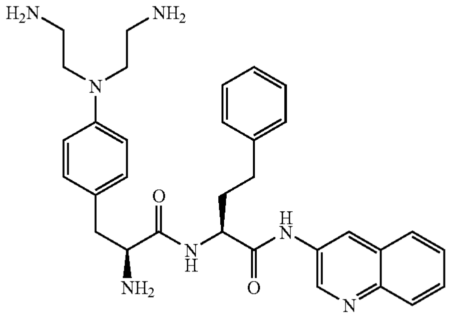
319
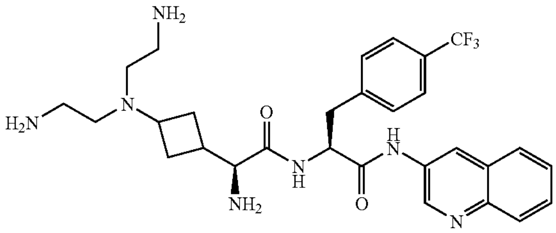
320
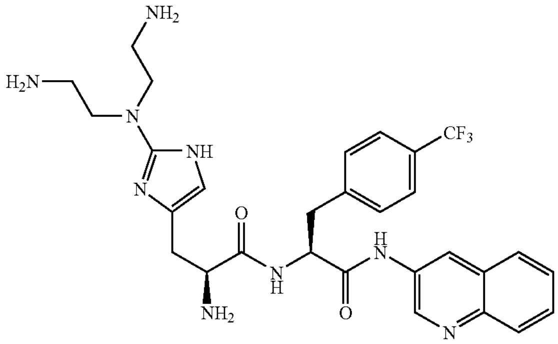
321
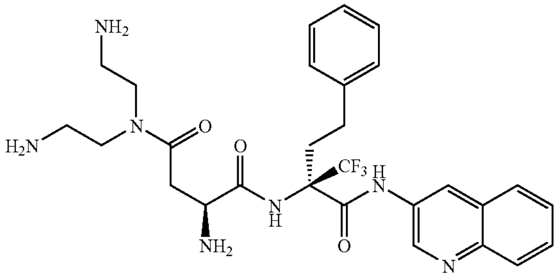
322
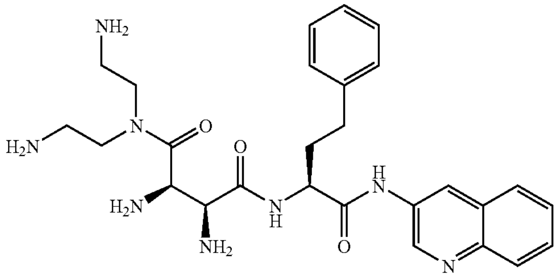
323
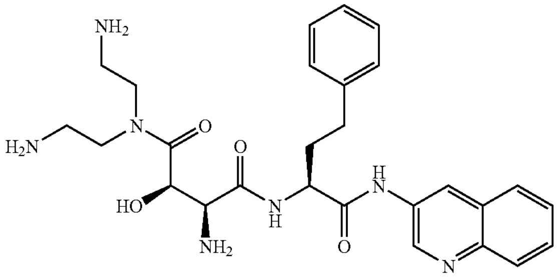
324
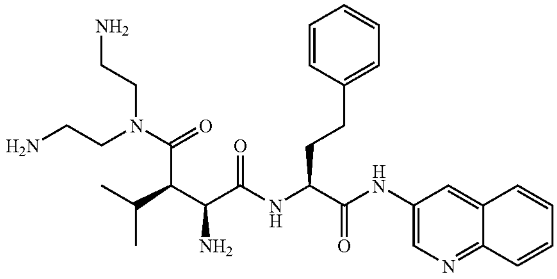
325
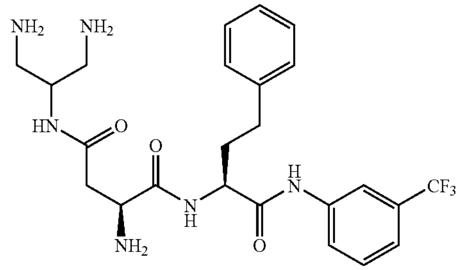
326
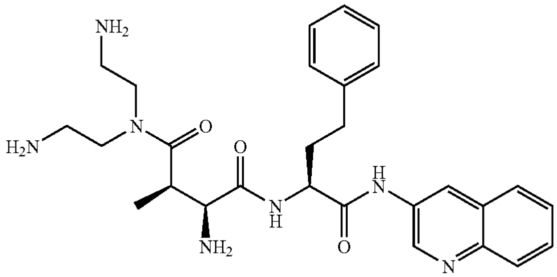
327
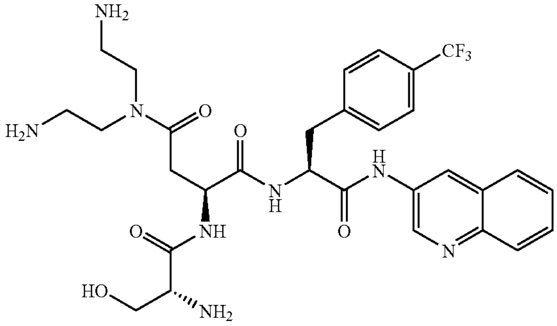

-continued
328
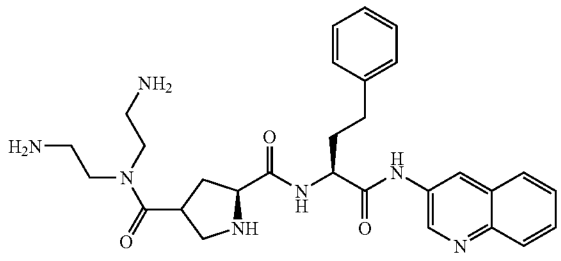
329
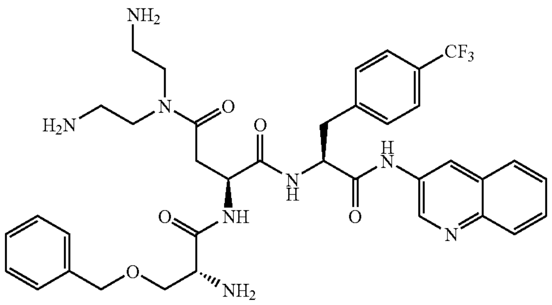
330
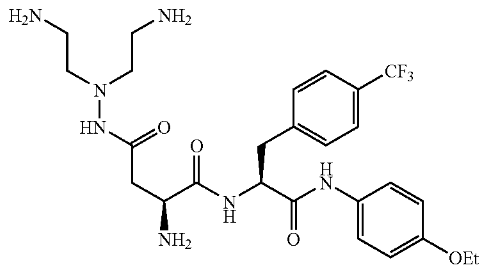
331
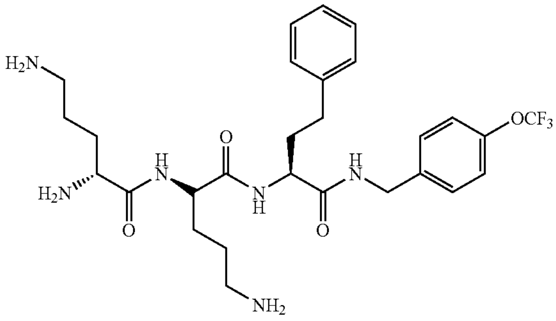
332
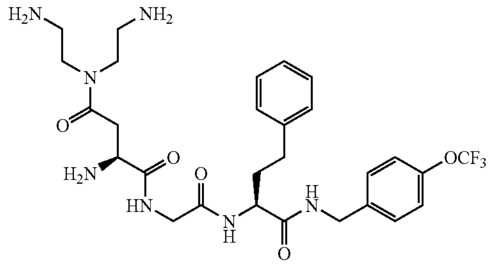
333
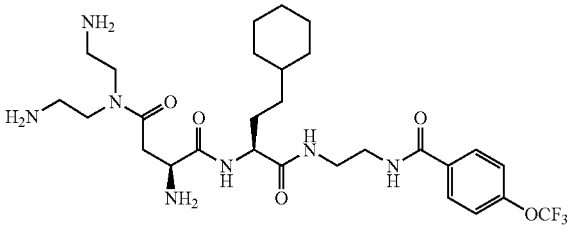
334
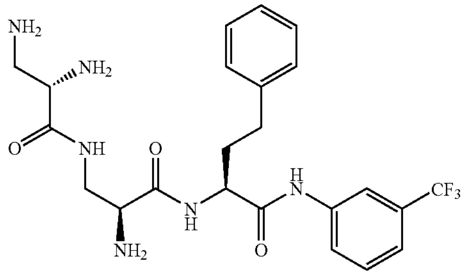
335
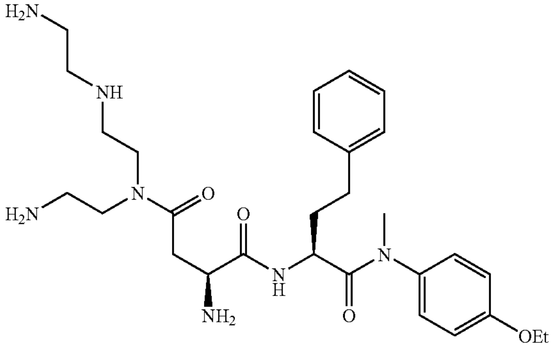

-continued
336
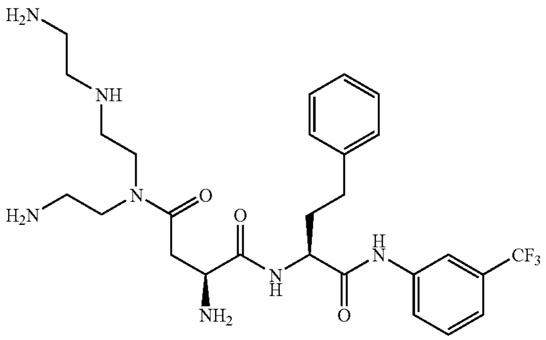
337
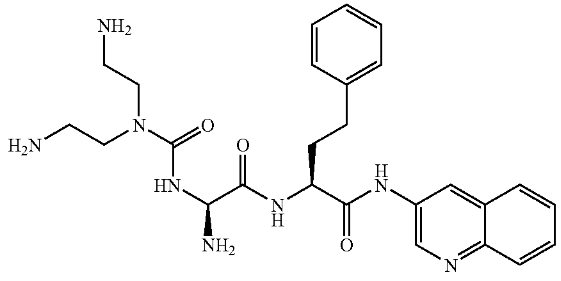
338
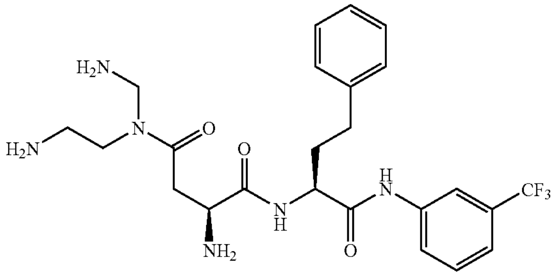
339
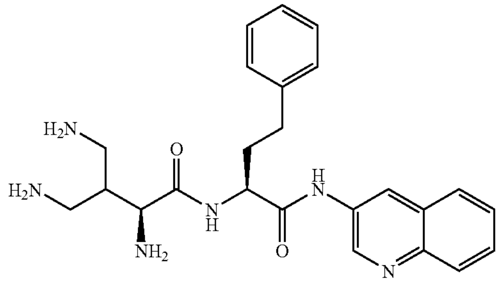
340
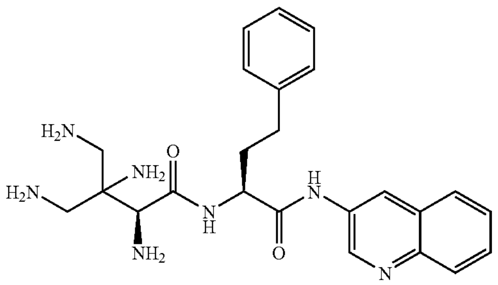
341
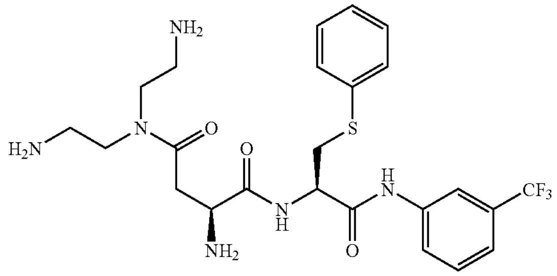
342
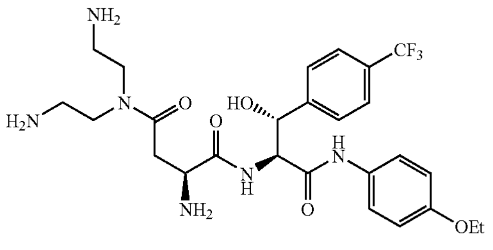
343
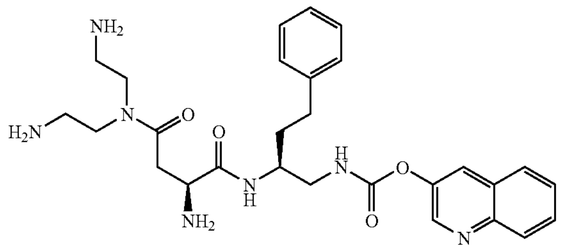
344
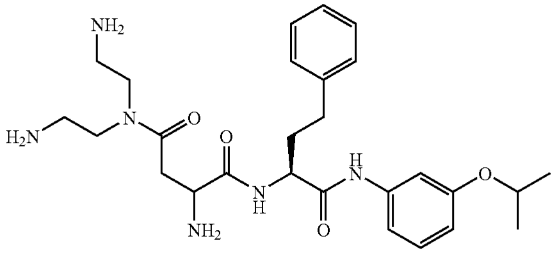
345
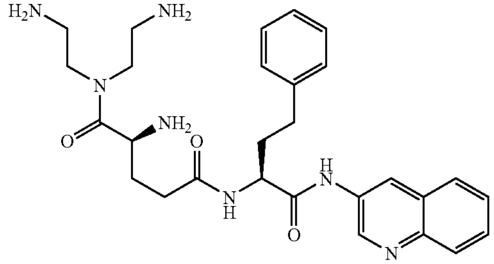

-continued
346
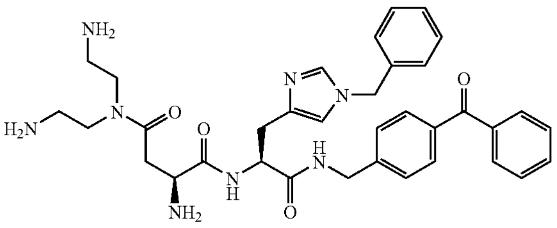
347
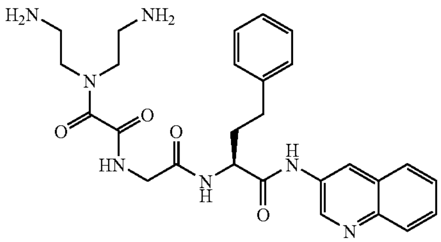
348
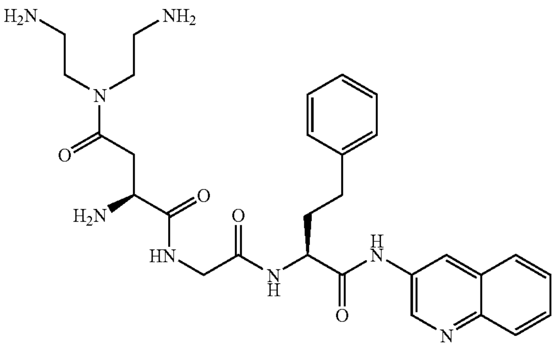
349
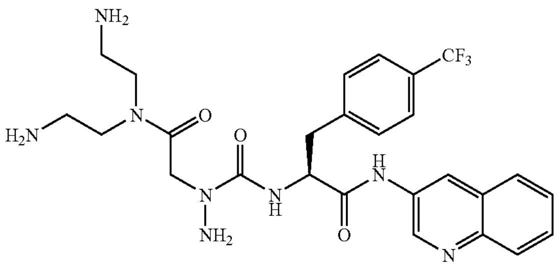
350
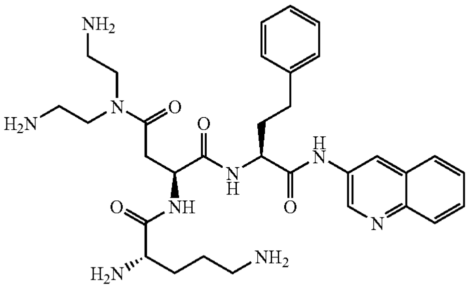
351
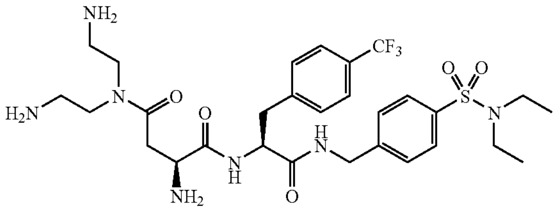
352
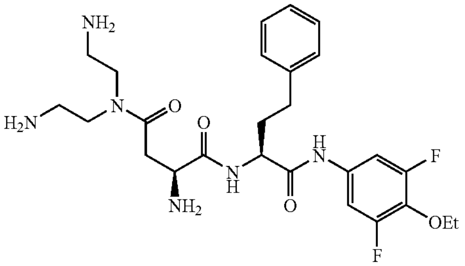
353
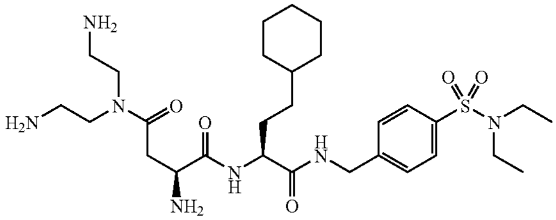
354
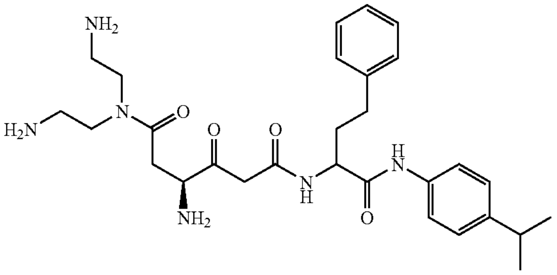
355
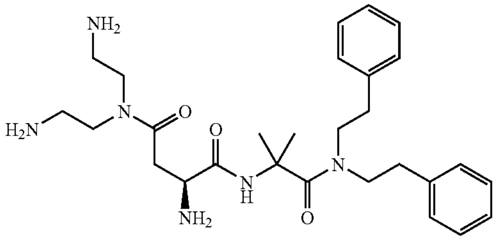

-continued
356
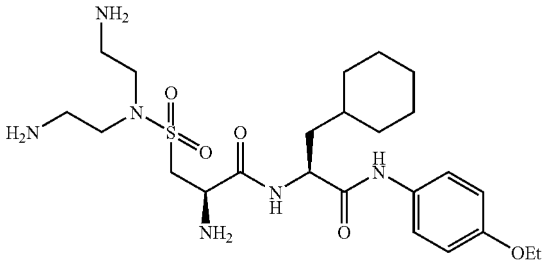
357
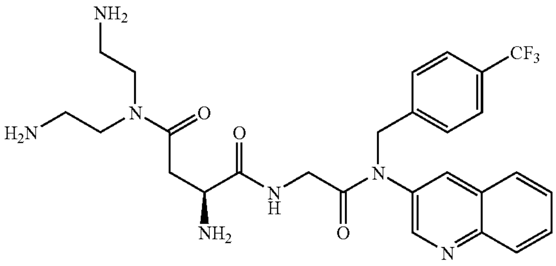
358
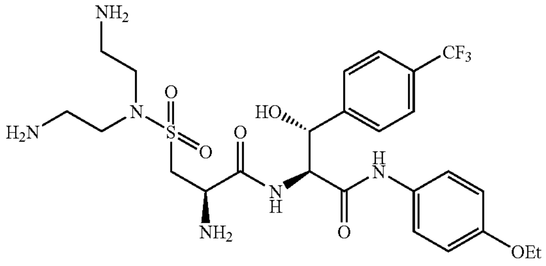
359
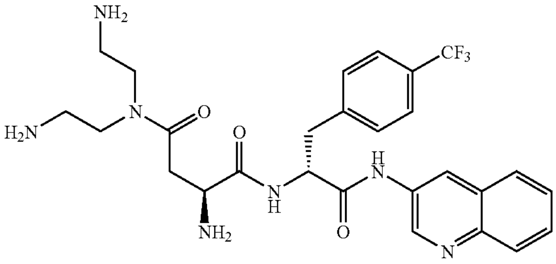
360
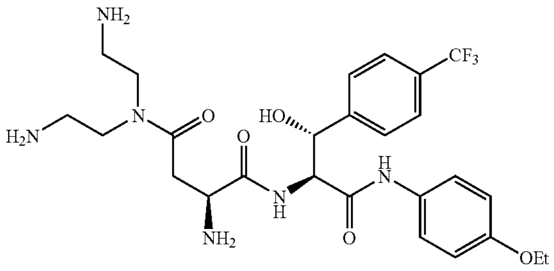
361
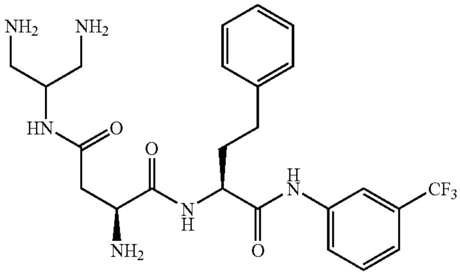
362
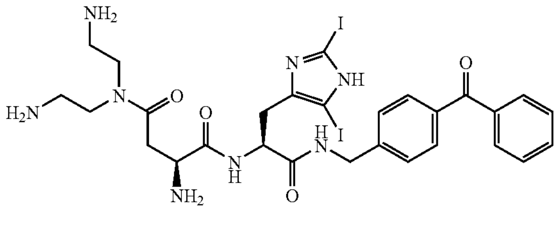
363
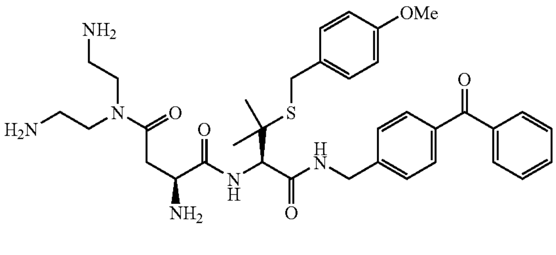
364
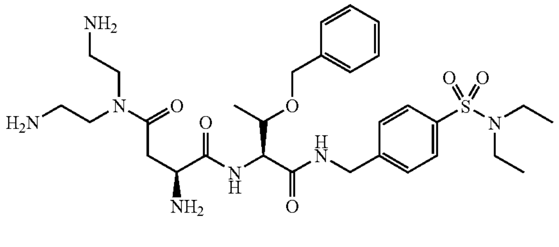
365
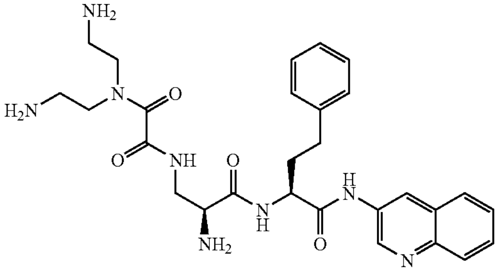

-continued
366
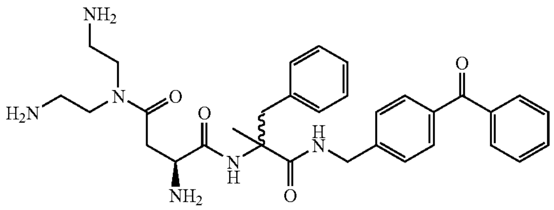
367
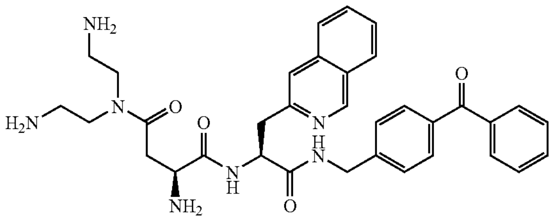
368
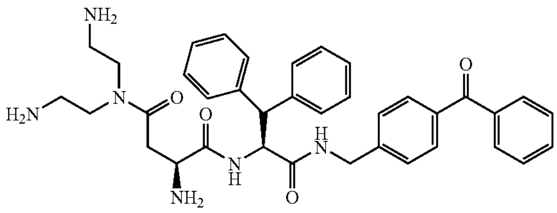
369
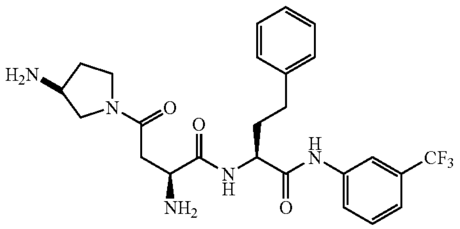
370
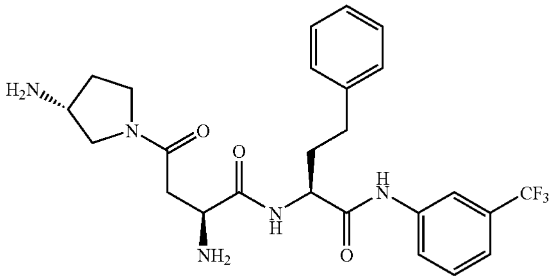
371
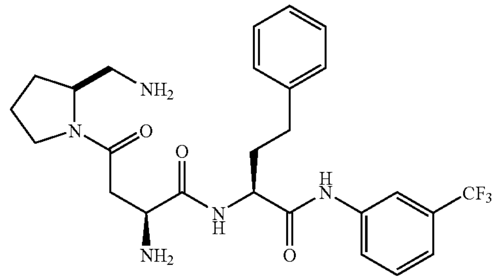
372
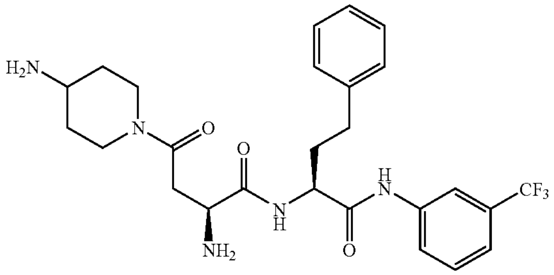
373
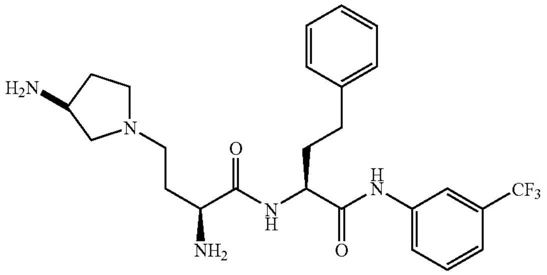
374
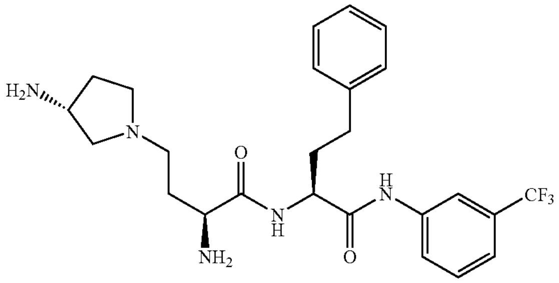
375
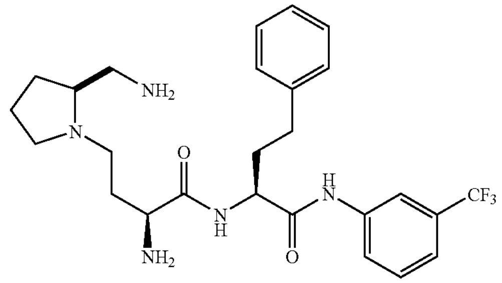

-continued
376
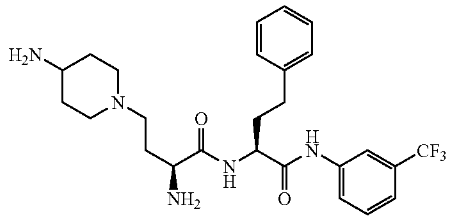
377
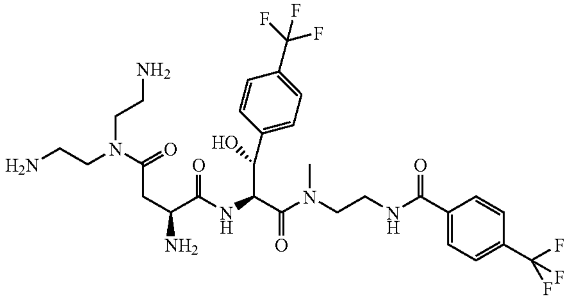
378
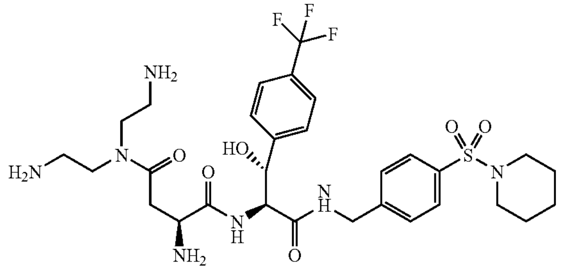
379
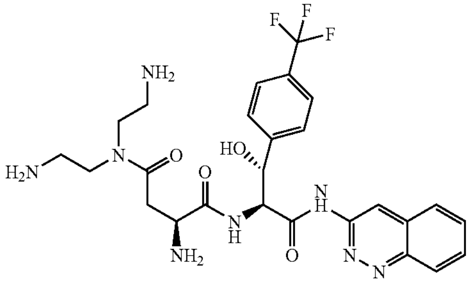
380
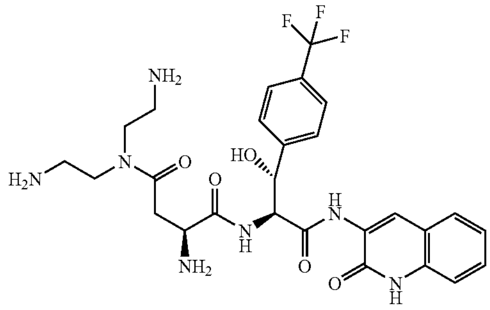
381
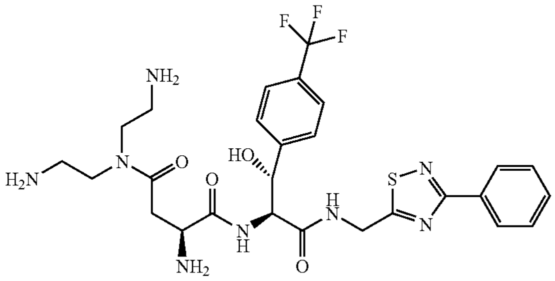
382
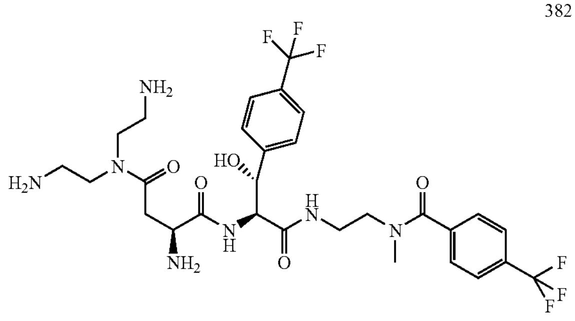
383
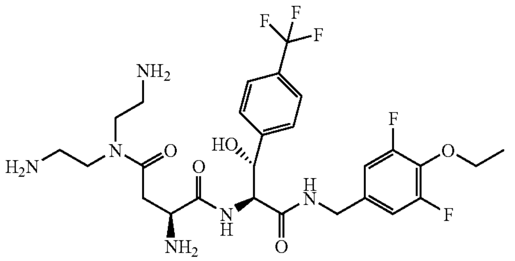
384
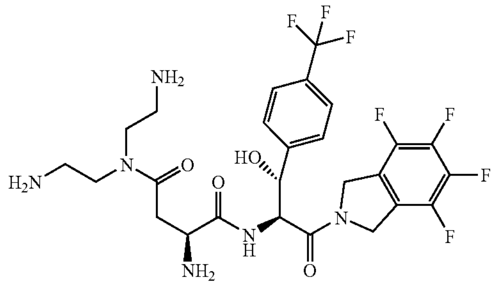
385
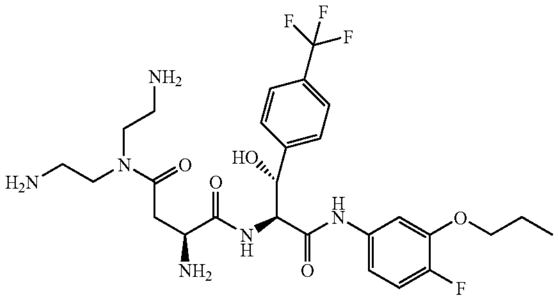

-continued
386
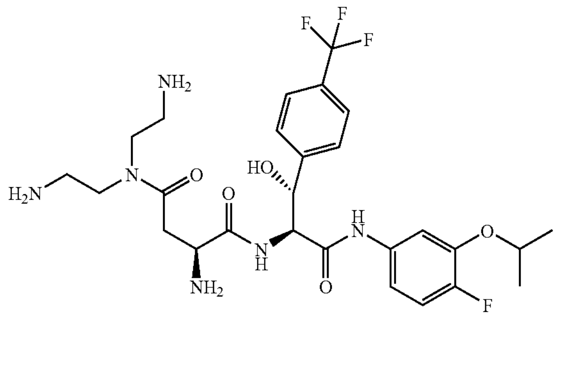
387
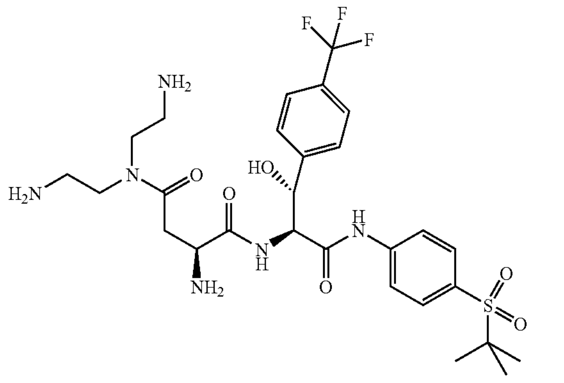
388
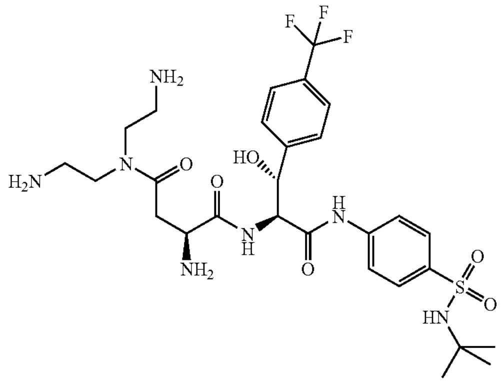
389
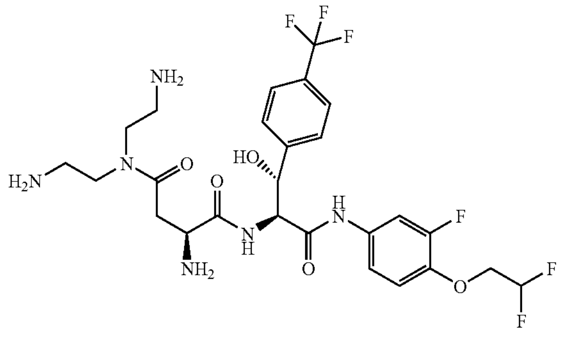
390
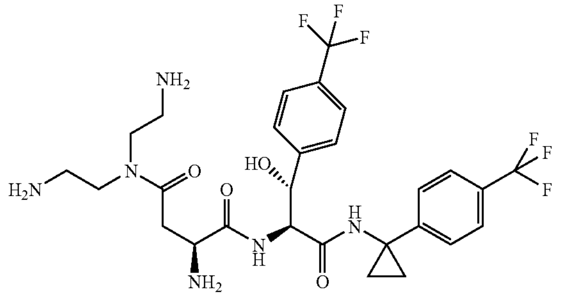
391
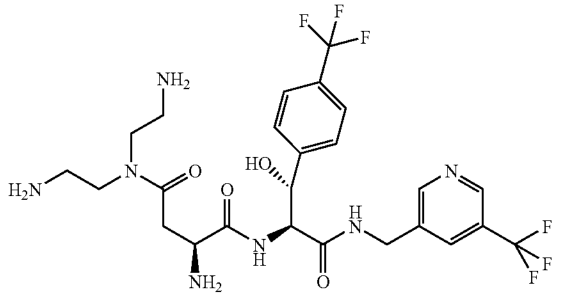
392
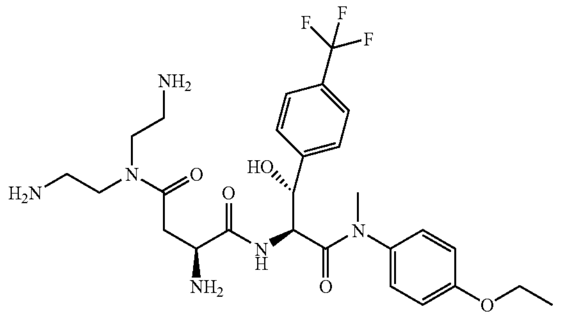
393
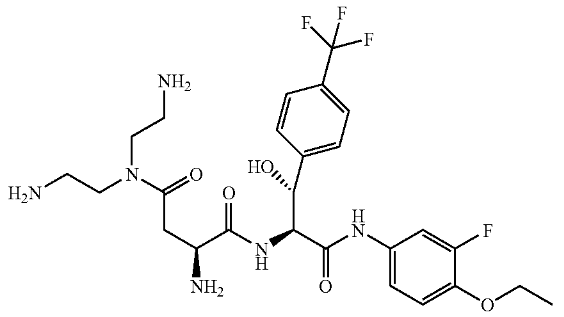

-continued
394
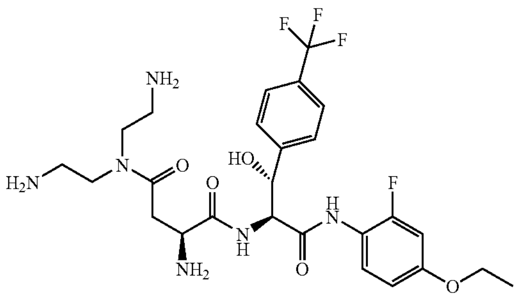
395
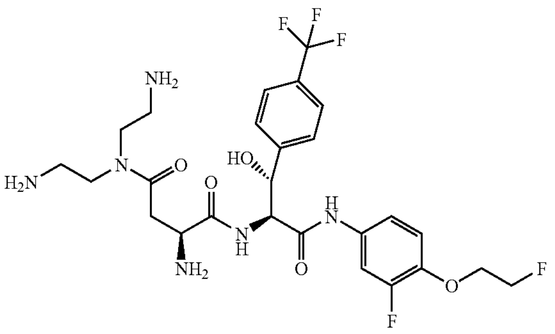
396
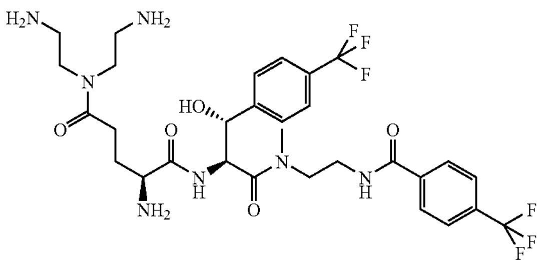
397
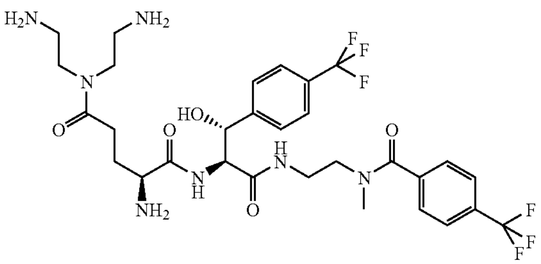
398
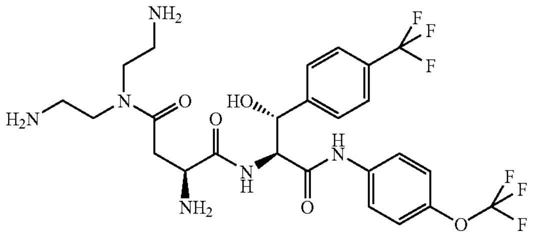
399
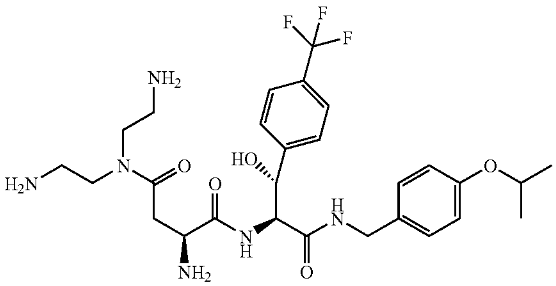
400
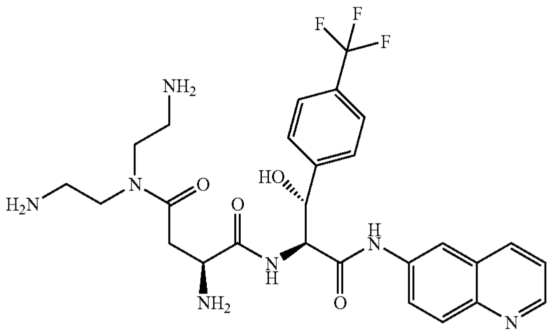
401
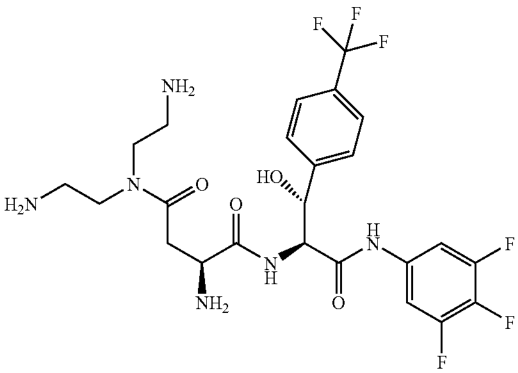

-continued
402
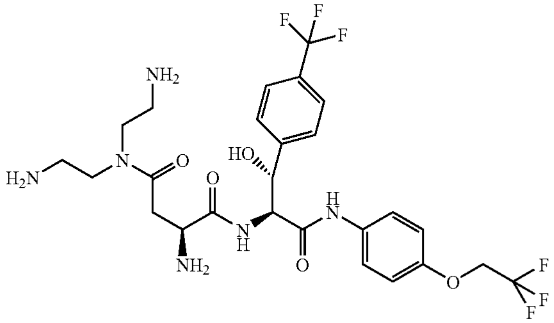
403
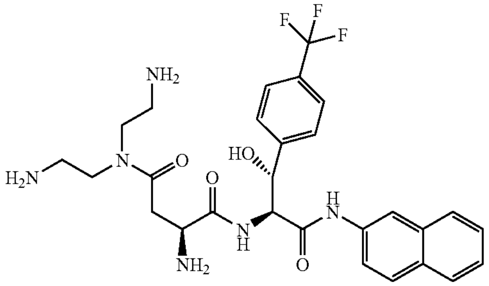
404
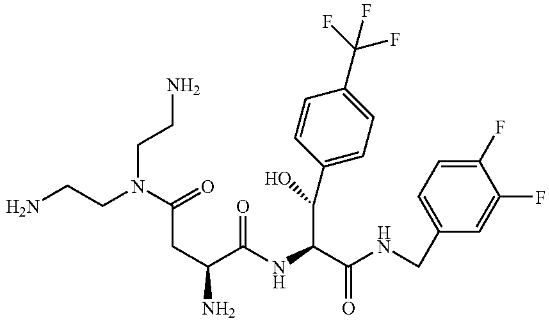
405
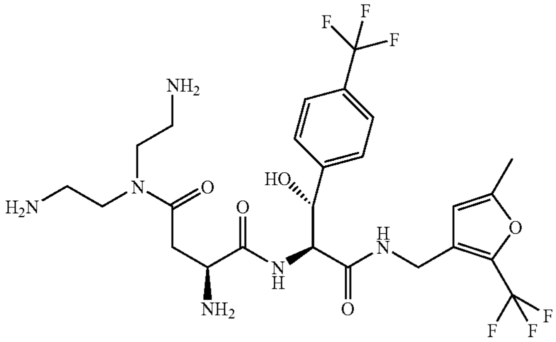
406
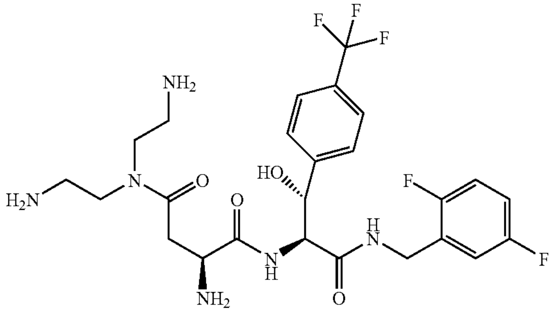
407
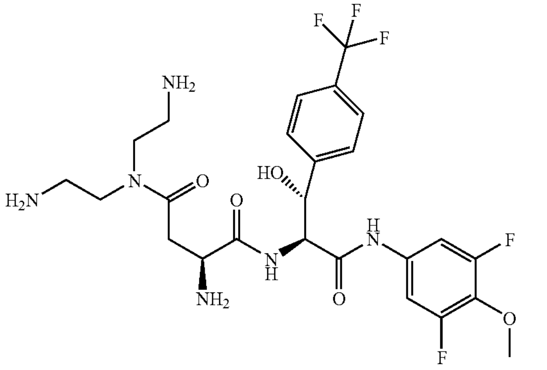
408
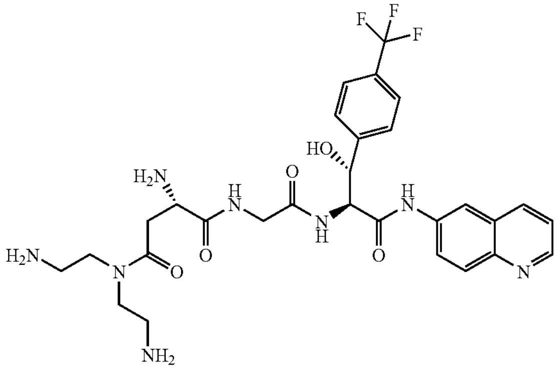
409
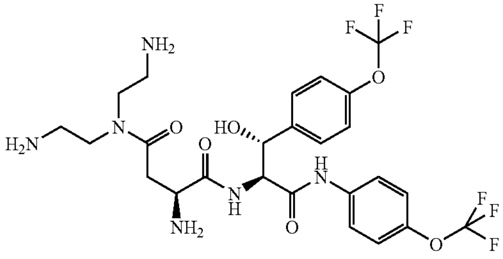

-continued
410
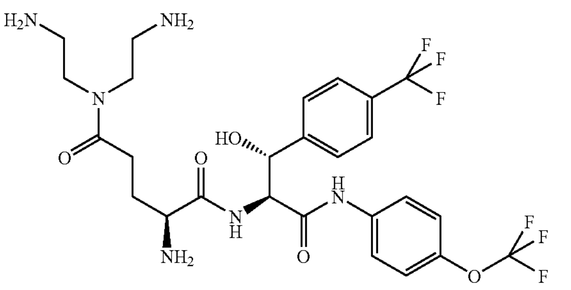
411
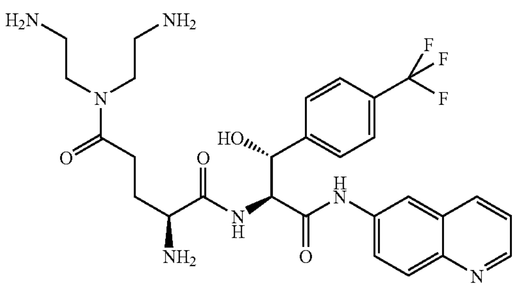
412
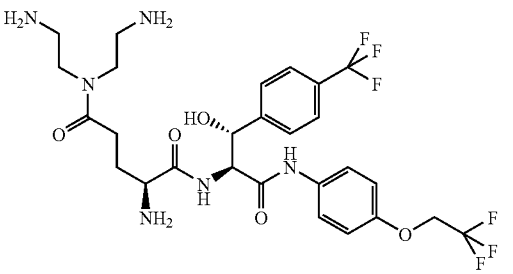
413
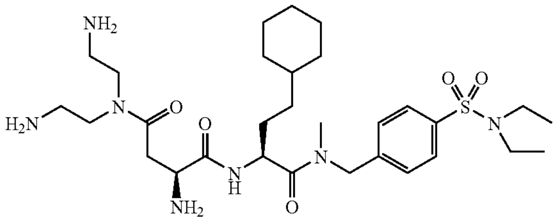
414
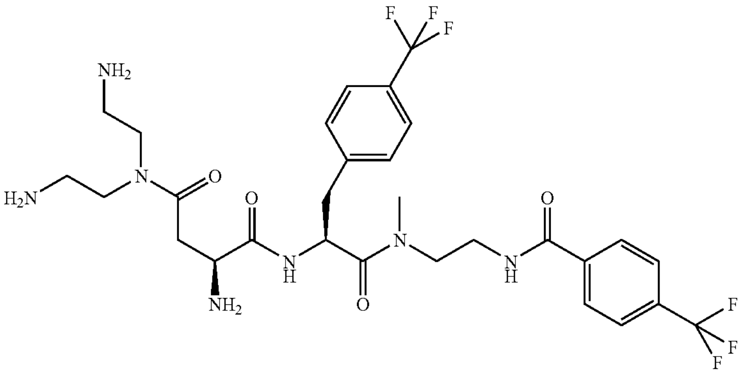
415
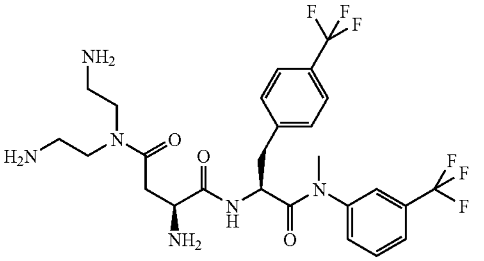
416
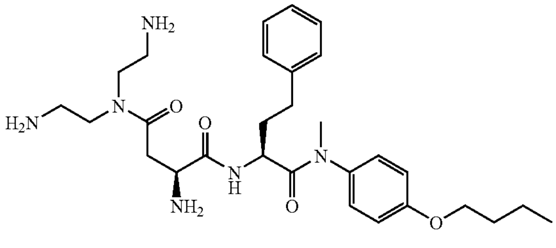
417
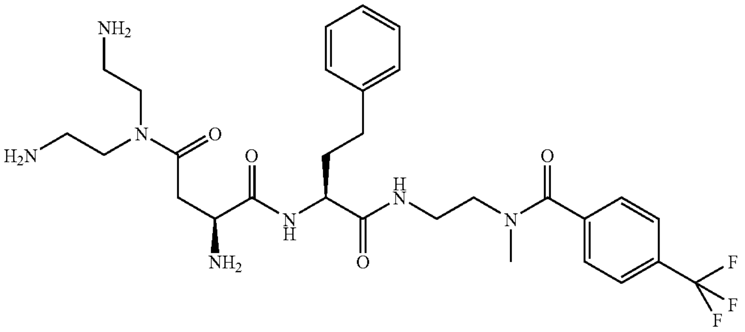

-continued
418
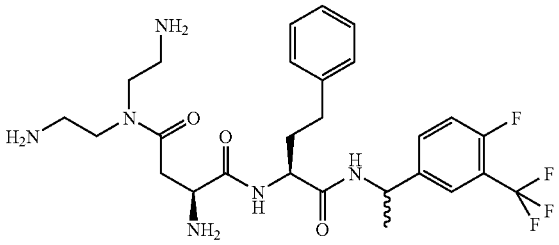
419
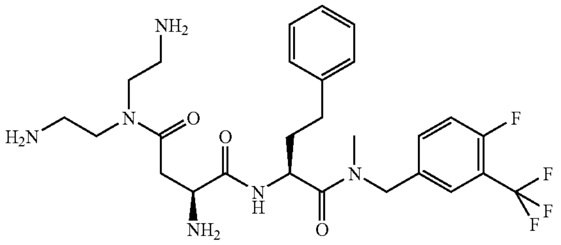
420
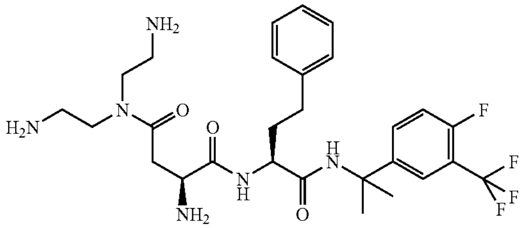
421
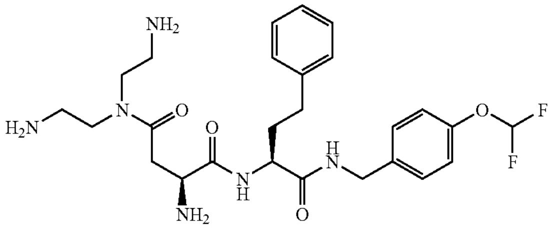
422
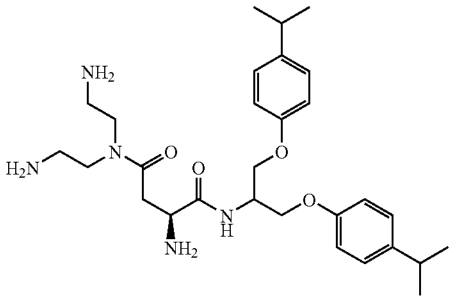
423
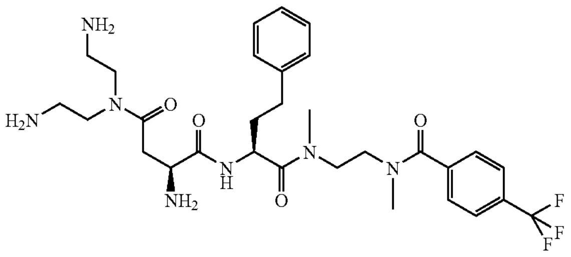
424
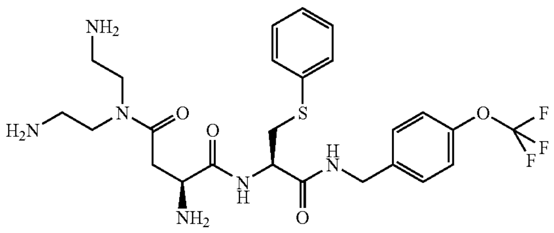
425
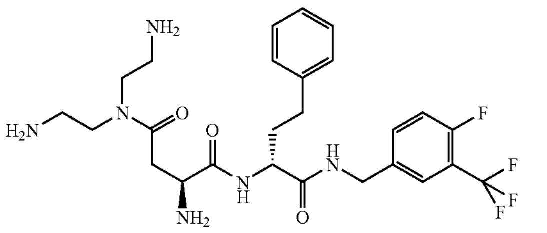
426
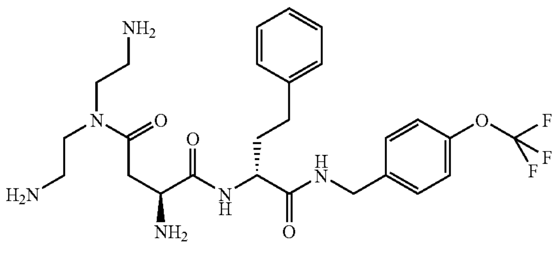
427
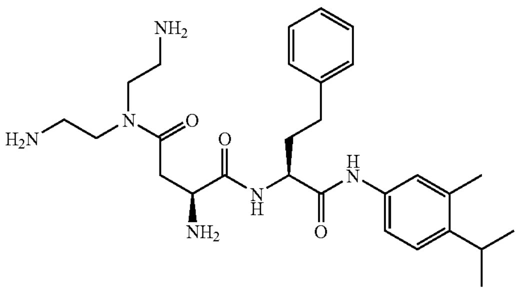

-continued
428
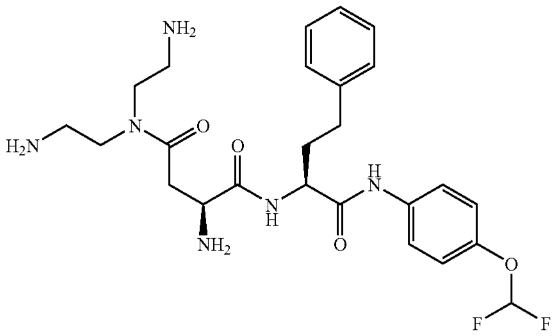
429
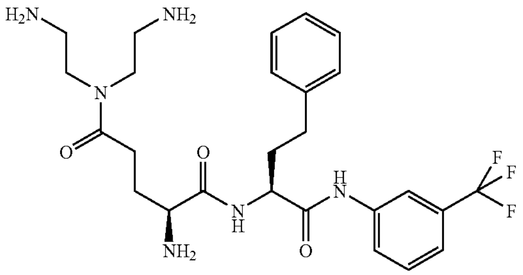
430
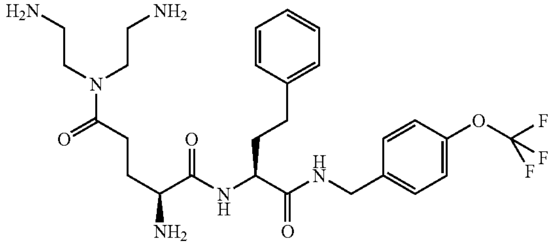
431
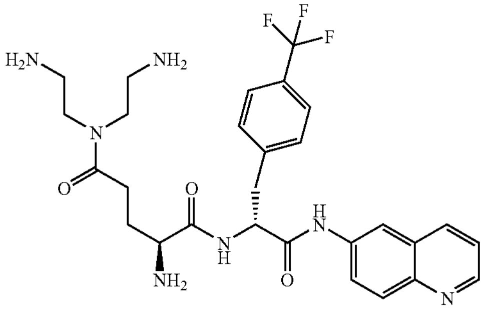
432
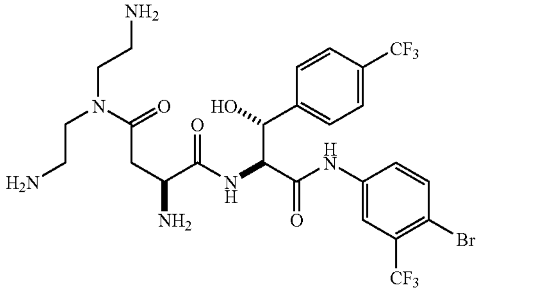
433
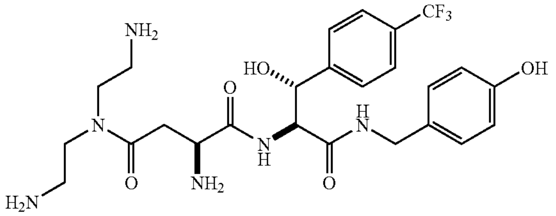
434
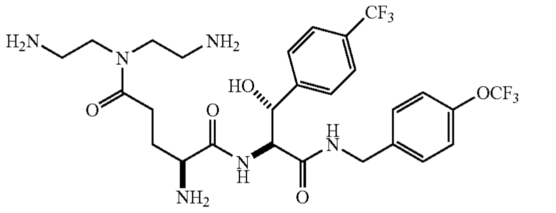
435
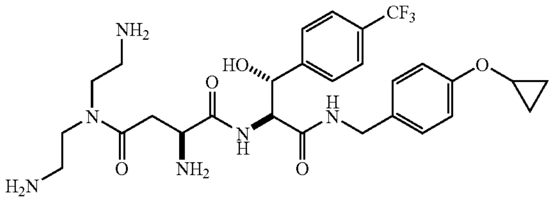
436
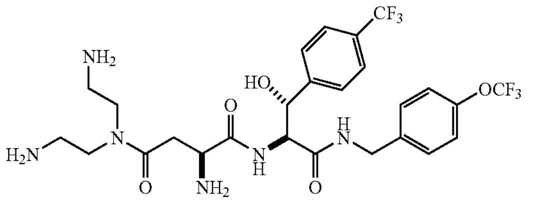
437
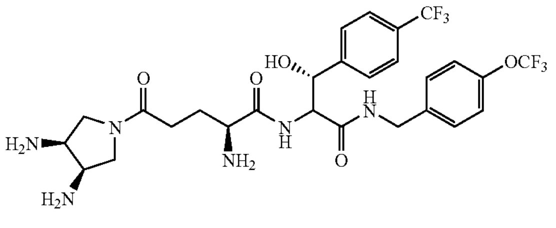

-continued
438
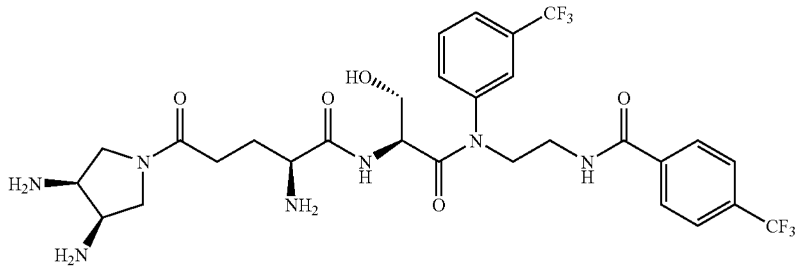
439
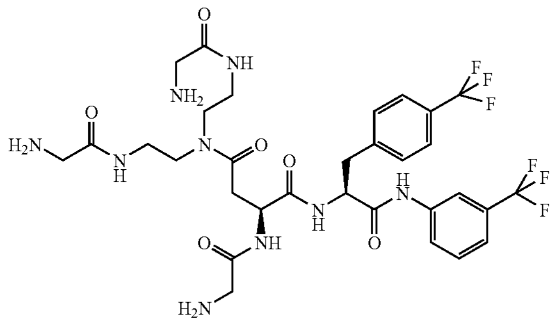
440
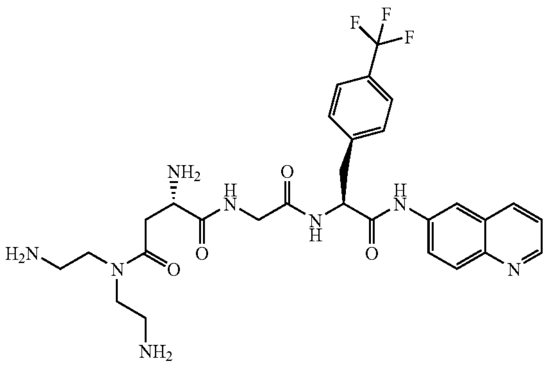
441
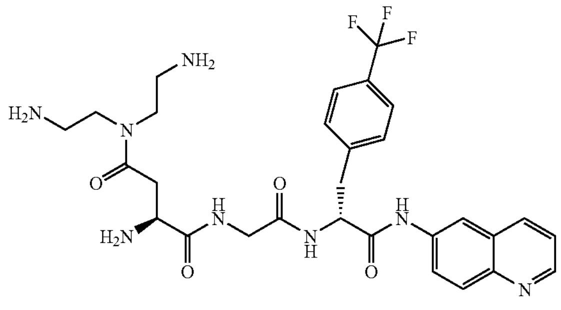
442
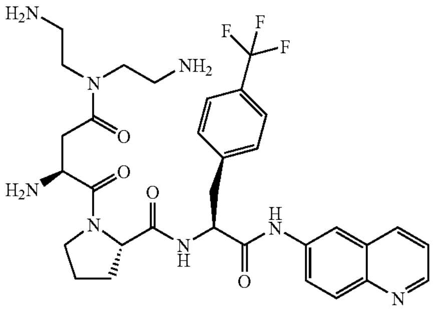
443
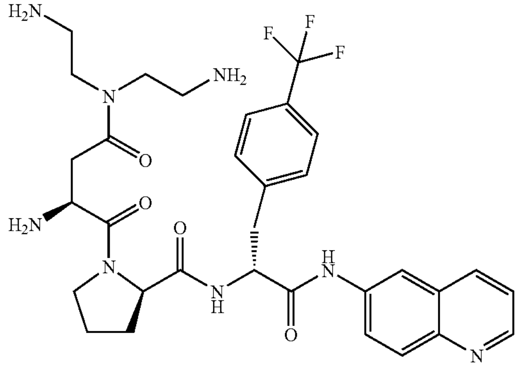
444
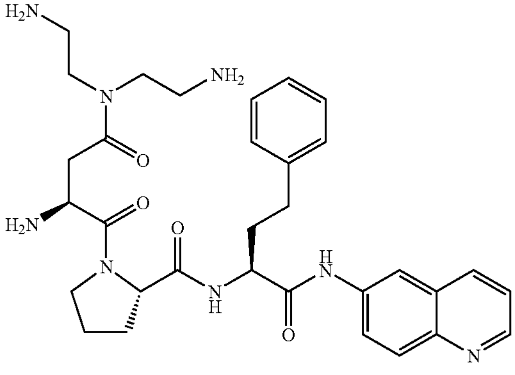

-continued
445
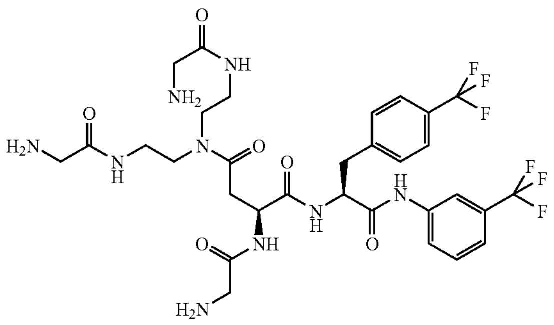
446
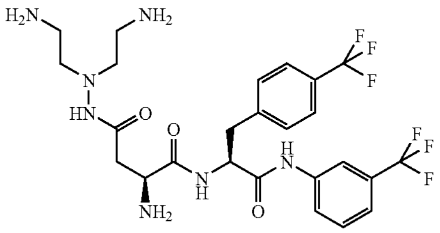
447
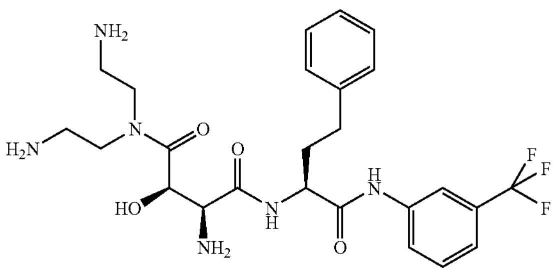
448
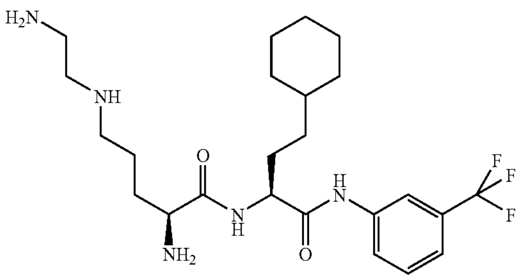
449
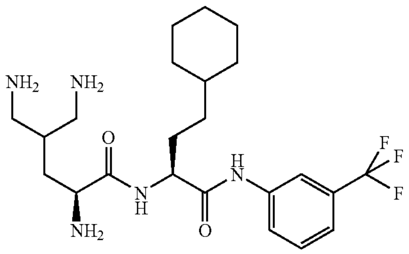
450
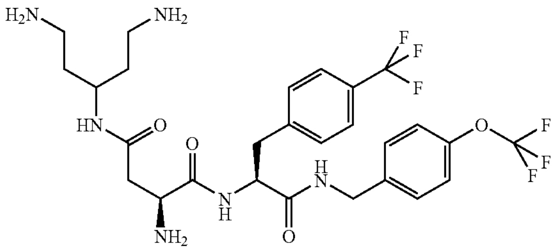
451
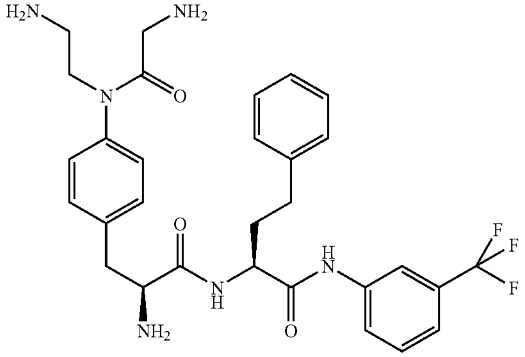
452
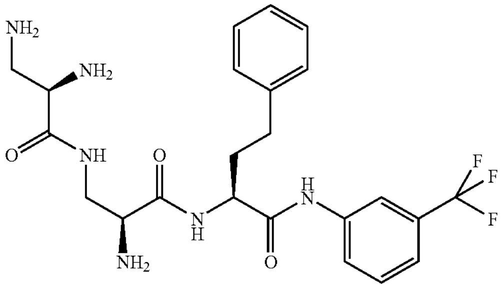
453
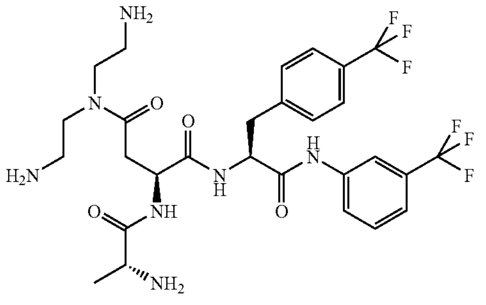
454
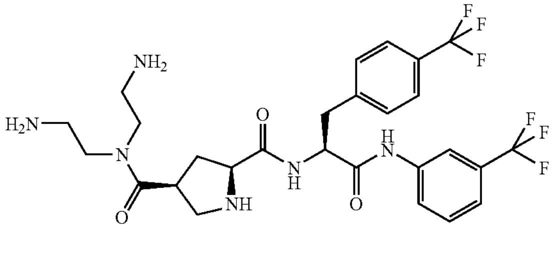

-continued
455
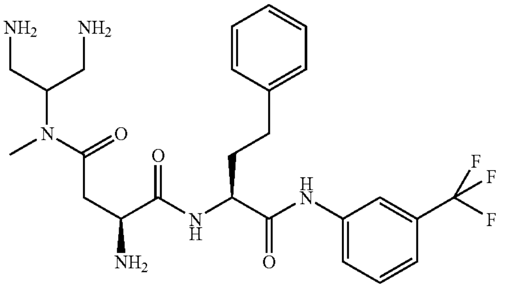
456
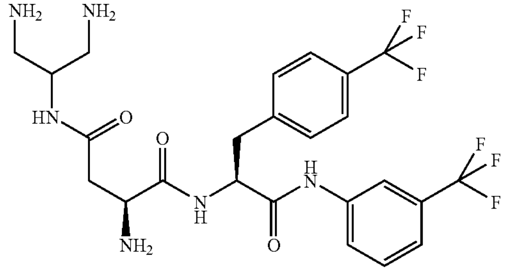
457
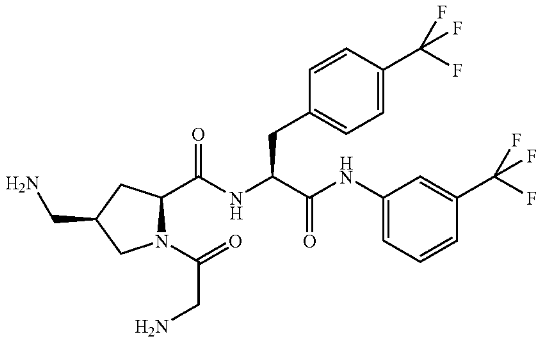
458
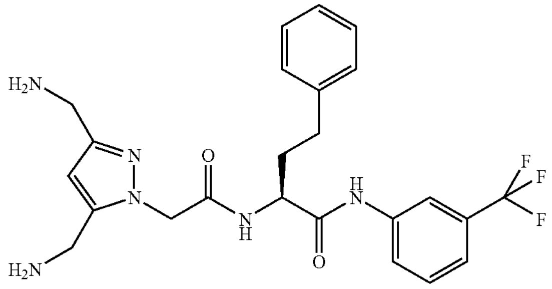
459
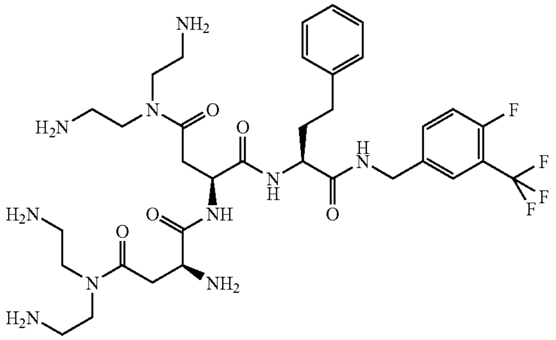
460
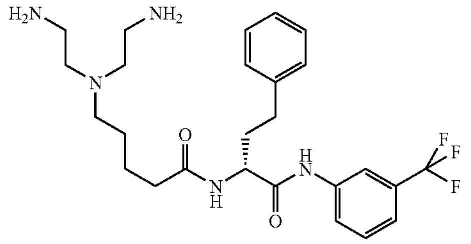
461
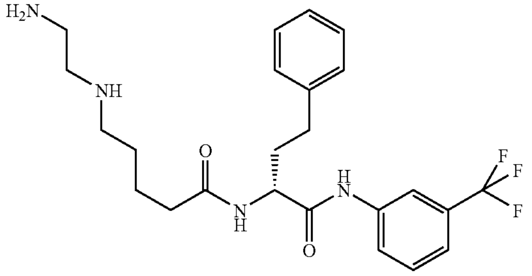
462
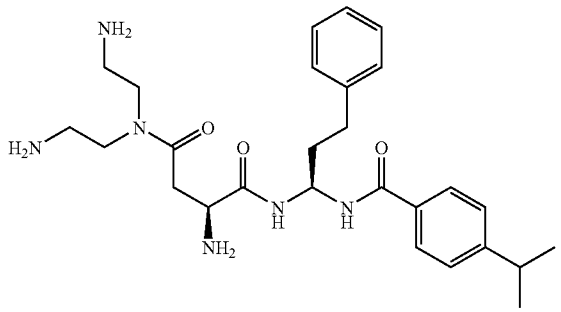
463
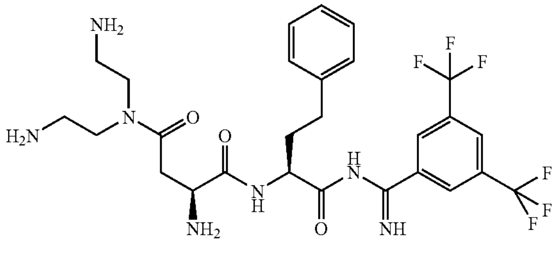
464
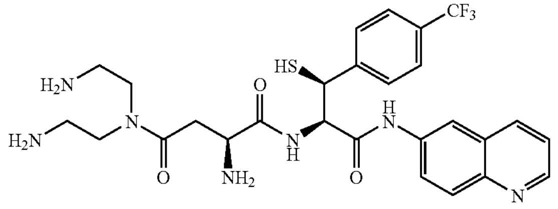

-continued

465

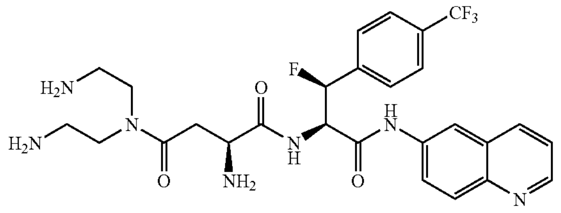

466

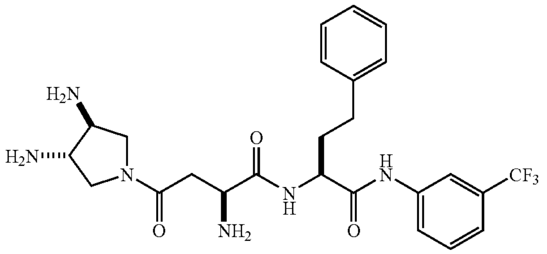

467

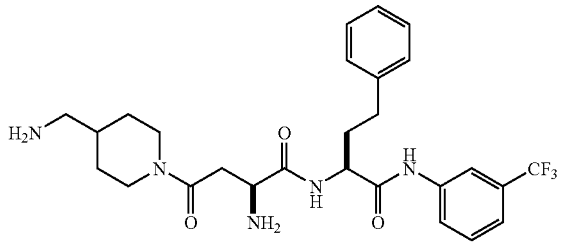

468

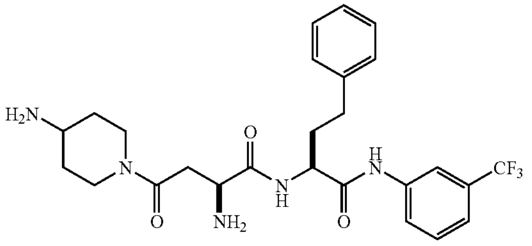

469

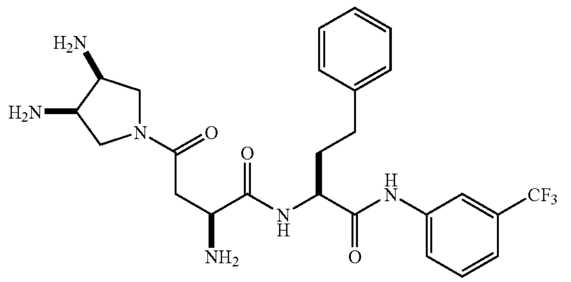

Compound Preparation

The starting materials used in preparing the compounds of the invention are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the claimed compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as *March's Advanced Organic Chemistry: Reactions, Mechanisms, and Structure* 6th Ed., John Wiley & Sons (2007), Carey and Sundberg, *Advanced Organic Chemistry* 5th Ed., Springer (2007) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts *Protecting Groups in Organic Synthesis,* 4th Ed., John Wiley & Sons (2006).

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application. Chemical names comport with IUPAC nomenclature and have been determined through the use of Marvin Java tools, available from ChemAxon Kft., MAramaros koz 3/a, Budapest, 1037 Hungary (http://www.chemaxon.com/).

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

$^1$H nuclear magnetic resonance spectra (NMR) were measured in the indicated solvents on either a Bruker NMR spectrometer (Avance TM DRX500, 500 MHz for 1H) or Varian NMR spectrometer (Mercury 400BB, 400 MHz for 1H). Peak positions are expressed in parts per million (ppm) downfield from tetramethylsilane. The peak multiplicities are denoted as follows, s, singlet; d, doublet; t, triplet; m, multiplet.

The following abbreviations have the indicated meanings:

atm=atmosphere
Bn=benzyl
$Boc_2O$=di-tert-butyldicarbonate
brine=saturated aqueous sodium chloride
Cbz=carboxybenzyl
CbzOSu=N-(benzyl-oxycarbonyloxy)succinimide
CDI=1,1'-carbonyldiimidazole
CDMT=2-chloro-4,6-dimethoxy-1,3,5-triazine
DCM=dichloromethane
DIBAL=diisobutylaluminum hydride
DIPEA=diisopropylethylamine
DMAP=4-(dimethylamino)-pyridine
DMF=N,N-dimethylformamide
DMT-MM=4-(4,6-dimethoxy-1,3,5-triazin-2-yl)-4-methylmorpholinium chloride
EDC=1-ethyl-3-(3-dimethylaminopropyl) carbodiimide hydrochloride
ESIMS=electron spray mass spectrometry
EtOAc=ethyl acetate
EtOH=ethyl alcohol
HATU=2-(1H-7-azabenzotriazol-1-yl)-1,1,3,3-tetramethyl uronium hexafluorophosphate methanaminium
HOBt=1-hydroxybenzotriazole
Lawesson's reagent=2,4-bis(4-methoxyphenyl)-1,3,2,4-dithiadiphosphetane-2,4-disulfide
MsCl=methanesulfonyl chloride
$Na_2EDTA$=disodium ethylene diamine tetraacetic acid
NMR=nuclear magnetic resonance
Pd/C=palladium on activated carbon
r.t.=room temperature
TBTU=O-(benzotriazol-1-yl)-N,N,N',N'-tetramethyluronium tetrafluoroborate
TEA=triethylamine
TFA=trifluoroacetic acid
THF=tetrahydrofuran
Tr=triphenylmethyl
p-TsOH=para-toluenesulfonic acid
TLC=thin layer chromatography
TMS=trimethylsilyl
n-Bu=normal butyl Synthesis of 6-[(1S)-2-[bis(2-azaniumylethyl)carbamoyl]-1-{[(1R)-1-carbamoyl-3-[4-(trifluoromethyl)phenyl]propyl]carbamoyl}ethan-1-aminium]quinolin-1-ium tetrachloride 45 is depicted below in scheme 1 and example 1

Scheme 1

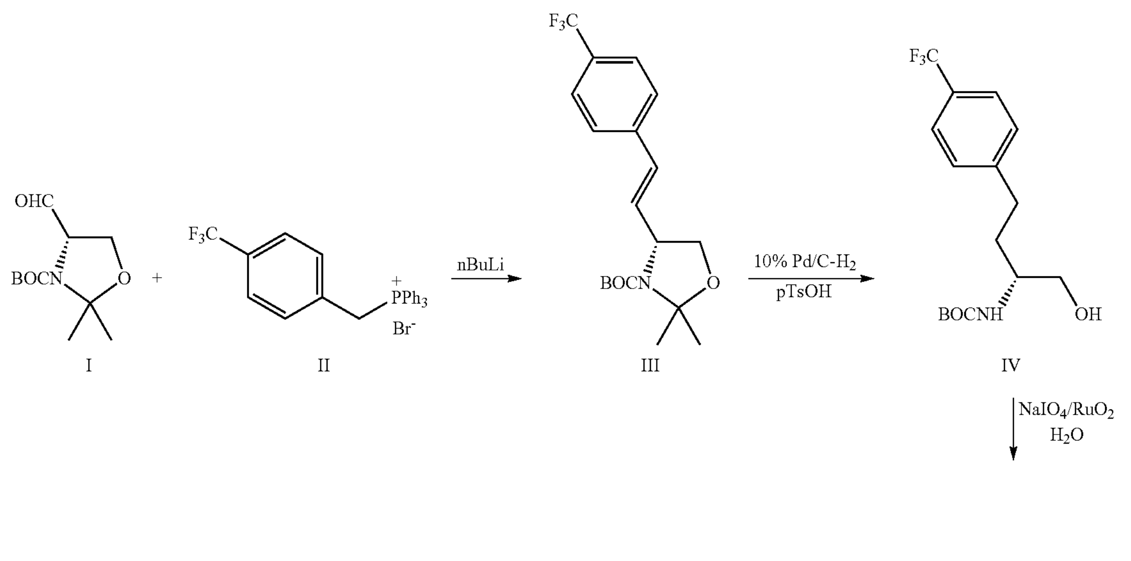

I II III IV

-continued

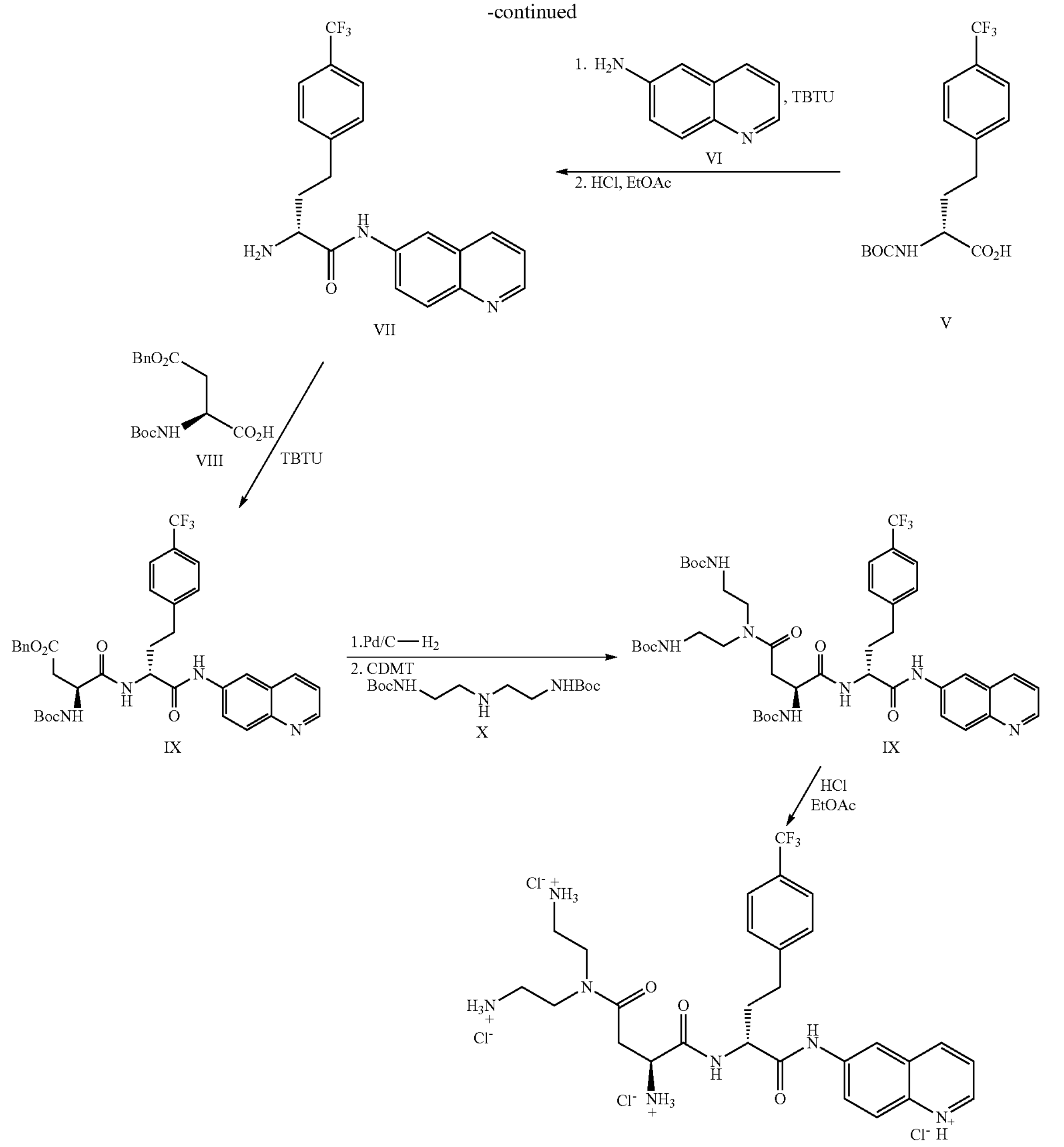

45

EXAMPLE 1

Step 1

To a solution of triphenyl({[4-(trifluoromethyl)phenyl] methyl}) phosphonium bromide II (80.2 g; 0.16 mol) in THF (640 mL) under argon and cooled to −68° C. was added n-BuLi (100 mL; 0.56 mol; as 2.5 M solution in hexanes). After 10 minutes the reaction mixture was warmed to −40° C. until the precipitate disappeared. The mixture was cooled to −68° C. again and a solution of Garner's aldehyde I (36.7 g; 0.16 mol) (obtained from L-serine) in THF (50 mL) was added dropwise over 25 minutes. The reaction was warmed to r.t. and stirred overnight before quenching with methanol (250 mL) for an additional 30 minutes. The solvent was removed under reduced pressure and the residue was then purified on a silica gel column (20:1 hexane:EtOAc) to give (R,Z-E)-tert-butyl-2,2-dimethyl-4-(4-trifluoromethylstyryl) oxazolidine-3-carboxylate III as a light-yellow oil (47.3 g, 0.128 mol, 80% yield). ESIMS found for $C_{19}H_{24}F_3NO_3$ m/z 372.4 (M+H).

Step 2

To a solution of the olefin III (47.2 g; 0.127 mol) in methanol (500 mL) was added 10% Pd/C (4 g) and para-toluenesulfonic acid monohydrate (0.24 g; 1.27 mmol). The suspension was stirred under hydrogen at normal pressure and r.t. overnight. The mixture was filtered through Celite and concentrated under reduced pressure to produce compound IV as a white solid (41.7 g, 125.1 mmol, 98% yield). ESIMS found for $C_{16}H_{22}F_3NO_3$ m/z 334.3 (M+H).

Step 3

To a solution of tert-butyl (1R)-1-(hydroxymethyl)-3-[4-(trifluoromethyl)phenyl]propylcarbamate IV (41.3 g; 0.124 mol) in 60% aqueous acetone was added a solid sodium (meta)periodate (266 g; 1.24 mol) followed by ruthenium(II) oxide hydrate (1.65 g; 12.4 mmol). The greenish suspension was stirred for 3 h before adding propan-2-ol (500 mL) and stirring for an additional 30 min to consume excess oxidant. The resulting suspension was filtered through Celite, and the filtrate was concentrated under reduced vacuum to give a brown oil. To the brown foam was added 1 N HCl to pH=1 which was followed by extraction with EtOAc. The organic layer was washed with brine and dried with $MgSO_4$. The crude residue was then purified on a silica gel column (10:1 hexane:EtOAc) to obtain (2R)-2-[(tert-butoxycarbonyl)amino]-4-[4-(trifluoromethyl)phenyl]butanoic acid V (18 g; 51.8 mmol, 42% yield). $^1H$ NMR ($CDCl_3$) 1.46 (brs, 9H), 1.93-2.30 (m, 2H), 2.68-2.87 (m, 2H), 4.12-4.47 (m, 1H), 5.04-5.23 (m, 1H), 7.30 (d, J=8, 2H), 7.55 (d, J=8, 2H); ESIMS found for $C_{16}H_{20}F_3NO_4$ m/z 348.3 (M+H).

Step 4

To a solution of (2R)-2-{[(tert-butoxy)carbonyl]amino}-4-[4-(trifluoromethyl)phenyl]butanoic acid V (0.97 g, 2.79 mmol) and 3-aminoquinoline VI (0.45 g, 3.10 mmol) in ethyl acetate (30 mL) was added DMT-MM (1.0 g, 3.63 mmol). After being stirred at r.t. overnight, the reaction was washed with water, 1N HCl, aq. sat. $NaHCO_3$, water and dried over $Na_2SO_4$. The solvent was removed under reduced pressure to afford tert-butyl N-[(1R)-1-[(quinolin-3-yl)carbamoyl]-3-[4-(trifluoromethyl)phenyl]propyl]carbamate (1.23 g, 2.59 mmol, 93% yield). ESIMS found for $C_{25}H_{26}F_3N_3O_3$ m/z 474 (M+H).

Step 5 tert-butyl N-[(1R)-1-[(quinolin-3-yl)carbamoyl]-3-[4-(trifluoromethyl)phenyl]propyl]carbamate (1.23 g, 2.60 mmol) in trifluoroacetic acid (10 mL) and was stirred at r.t. for 1 h. The solvent was removed under reduced pressure before treating with DCM (2×20 mL) and evaporated. Crude VII was obtained as the trifluoroacetate before suspending in EtOAc (20 mL) and treating with TEA (0.72 mL, 5.2 mmol) while the mixture became homogeneous. This solution was used in the next step.

Step 6

To the solution of (2S)-4-(benzyloxy)-2-{[(tert-butoxy)carbonyl]amino}-4-oxobutanoic acid VIII (430 mg, 1.33 mmol) in DCM (10 mL) was added DIPEA (0.65 mL, 3.75 mmol), (2R)-2-amino-N-(quinolin-6-yl)-4-[4-(trifluoromethyl)phenyl]butanamide VII (540 mg 1.21 mmol) and TBTU (428 mg, 1.33 mmol). The mixture was stirred at r.t. overnight. The reaction mixture was then washed with 1 M $K_2CO_3$, 1 M HCl, brine and dried over $MgSO_4$. The residue was then purified on a silica gel column (50:1 $CHCl_3$/methanol) to yield benzyl (3S)-3-{[(tert-butoxy)carbonyl]amino}-3-{[(1R)-1-[(quinolin-6-yl)carbamoyl]-3-[4-(trifluoromethyl)phenyl]propyl]carbamoyl}propanoate IX (680 mg, 1.00 mmol, 75% yield). $^1H$ NMR ($CDCl_3$) 1.46 (s, 9H), 1.88-2.20 (m, 2H), 2.40-2.64 (m, 1H), 2.66-2.88 (m, 1H), 2.92 (d, J=6 Hz, 1H), 3.27 (dd, J=5 Hz, J=17 Hz, 1H), 4.49-4.70 (m, 2H), 5.12 (d, J=5 Hz, 2H), 5.59 (d, J=8 Hz, 1H), 7.07 (d, J=8 Hz, 1H), 7.22-7.42 (m, 8H), 7.53 (s, 1H), 7.57 (s, 1H), 7.72 (dd, J=2 Hz, J=9 Hz, 1H), 8.00 (d, J=9 Hz, 1H), 8.08 (d, J=8 Hz, 1H), 8.41 (d, J=2 Hz, 1H), 8.82 (d, J=4 Hz, 1H), 8.89 (s, 1H); $^{19}F$ NMR (DMSO-$d_6$) −61.73 (s, 3F); ESIMS found for $C_{36}H_{37}F_3N_4O_6$ m/z 679 (M+H).

Step 7

To a solution of benzyl (3S)-3-{[(tert-butoxy)carbonyl]amino}-3-{[(1R)-1-[(quinolin-6-yl)carbamoyl]-3-[4-(trifluoromethyl)phenyl]propyl]carbamoyl}propanoate IX (570 mg, 0.84 mmol) in EtOH/water (15 mL/2 mL) under argon was added 10% Pd/C catalyst (catalytic amount). The mixture was stirred under an atmosphere of hydrogen at r.t. overnight. The mixture was then filtered through Celite and evaporated to dryness. The oily residue was suspended in ethyl ether and filtered to afford the free acid as a white crystalline solid (110 mg, 0.18 mmol, 32% yield). ESIMS found for $C_{29}H_{31}F_3N_4O_6$ m/z 589 (M+H).

Step 8

To a solution of CDMT (37 mg, 0.20 mmol) in DCM (10 mL) and cooled to 0° C. was added N-methylmorpholine (0.023 mL, 0.20 mmol). The mixture was stirred for min before adding (3S)-3-{[(tert-butoxy)carbonyl]amino}-3-{[(1R)-1-[(quinolin-6-yl)carbamoyl]-3-[4-(trifluoromethyl)phenyl]propyl]carbamoyl}propanoic acid (110 mg, 0.18 mmol). The solution was stirred for 60 min at 0° C. The tert-butyl N-{2-[(2-{[(tert-butoxy)carbonyl]amino}ethyl)amino]ethyl}carbamate X was then added and the mixture stirred at r.t. overnight. The solution was washed with 1 M aq. $K_2CO_3$, 1 M aq. HCl, brine and dried over anhydrous $MgSO_4$. The crude product was then purified on a silica gel column (100:1 $CHCl_3$/MeOH) and finally crystallized from ethyl ether/hexane to give tert-butyl N-[(1S)-2-[bis(2-{[(tert-butoxy)carbonyl]amino}ethyl)carbamoyl]-1-{[(1R)-1-[(quinolin-6-yl)carbamoyl]-3-[4-(trifluoromethyl)phenyl]propyl]carbamoyl}ethyl]carbamate XI (110 mg, 0.13 mmol, 72% yield). $^1H$ NMR ($CDCl_3$) 1.43 (s, 18H), 1.50 (s, 9H), 1.69 (brs, 2H), 2.03 (brs, 2H), 2.78 (brs, 2H), 3.23 (brs, 2H), 3.46 (brs, 4H), 4.60 (brs, 4H), 4.96-5.11 (m, 1H), 5.98-6.14 (m, 1H), 6.91-7.01 (m, 1H), 7.28-7.38 (m, 3H), 7.47-7.58 (m, 3H), 7.88-8.03 (m, 2H), 8.12 (d, J=7 Hz, 1H), 8.52 (s, 1H), 8.81 (brs, 1H), 9.31 (brs, 1H); $^{19}F$ NMR (DMSO-$d_6$) −61.75 (s, 3F); ESIMS found for $C_{43}H_{58}F_3N_7O_9$ m/z 874 (M+H).

Step 9

To a solution of tert-butyl N-[(1S)-2-[bis(2-{[(tert-butoxy)carbonyl]amino}ethyl)carbamoyl]-1-{[(1R)-1-[(quinolin-6-yl)carbamoyl]-3-[4-(trifluoromethyl)phenyl]propyl]carbamoyl}ethyl]carbamate XI (110 mg, 0.13 mmol) in EtOAc (5 mL) was added HCl (4.5 M solution in EtOAc, 5 mL). The reaction mixture was stirred for 15 min at r.t. before adding ethyl ether (20 mL). The precipitate was filtered and washed with ether to give 6-[(1S)-2-[bis(2-azaniumylethyl)carbamoyl]-1-{[(1R)-1-carbamoyl-3-[4-(trifluoromethyl)phenyl]propyl]carbamoyl}ethan-1-aminium]quinolin-1-ium tetrachloride 45 as a white crystalline solid (88 mg, 0.12 mmol, 92% yield). $^1H$ NMR (DMSO-$d_6$) 2.01-2.26 (m, 2H), 2.68-2.88 (m, 2H), 2.92-3.29 (m, 8H), 4.24-4.37 (m, 1H), 4.40-4.56 (m, 1H), 7.50 (d, J=8 Hz, 2H), 7.62 (d, J=8 Hz, 2H), 7.77-7.89 (m, 1H), 8.09 (brs, 3H), 8.17-8.24 (brs, 2H), 8.34 (brs, 6H), 8.61 (s, 1H), 8.82 (d, J=9 Hz, 1H), 9.03 (d, J=4 Hz, 1H), 9.16 (d, J=7 Hz, 1H), 10.90 (s, 1H); $^{19}F$ NMR (DMSO-$d_6$) −60.06 (s, 3F); ESIMS found for $C_{28}H_{34}F_3N_7O_3$ m/z 574 (M+H).

The following compounds have been prepared (or, in the case of compounds 370 and 371, are to be prepared) in accordance with the procedure described in the above Example 1.

2

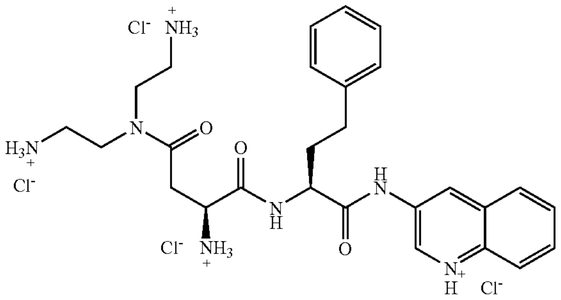

3-[(1S)-2-[bis(2-azaniumylethyl)carbamoyl]-1-{[(1S)-1-carbamoyl-3-phenylpropyl]carbamoyl}ethan-1-aminium] quinolin-1-ium tetrachloride 2

$^1$H NMR (DMSO-$d_6$) 2.02-2.22 (m, 2H), 2.65-2.87 (m, 2H), 2.96-3.05 (m, 2H), 3.06-3.27 (m, 4H), 3.52-3.59 (m, 4H), 4.38-4.45 (m, 1H), 4.47-4.53 (m, 1H), 7.16-7.31 (m, 5H), 7.63 (t, J=8 Hz, 1H), 7.71 (t, J=8 Hz, 1H), 7.97-8.02 (m, 2H), 8.04 (brs, 3H), 8.25 (brs, 3H), 8.36 (brs, 3H), 8.80 (s, 1H), 9.11 (d, J=3 Hz, 1H), 9.17 (d, J=7 Hz, 1H), 10.80 (s, 1H); ESIMS found for $C_{27}H_{35}N_7O_3$ m/z 506 (M+H).

13

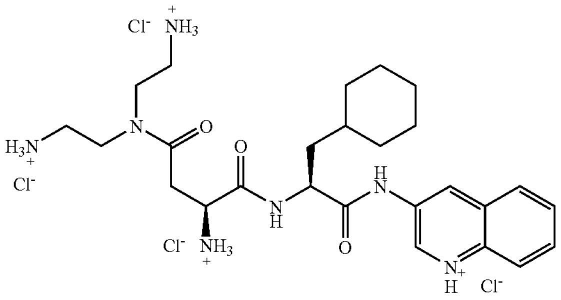

6-[(1S)-2-[bis(2-azaniumylethyl)carbamoyl]-1-{[(1S)-1-carbamoyl-2-cyclohexylethyl]carbamoyl}ethan-1-aminium] quinolin-1-ium tetrachloride 13

$^1$H NMR (DMSO-$d_6$) 0.91-0.99 (m, 2H), 1.14-1.24 (m, 4H), 1.43-1.50 (m, 1H), 1.60-1.80 (m, 6H), 2.99-3.02 (m, 2H), 3.08-3.15 (m, 2H), 3.22-3.28 (m, 2H), 3.53-3.70 (m, 3H), 4.32-4.35 (m, 1H), 4.52-4.57 (m, 1H), 7.89 (dd, J=9 Hz, J=5 Hz, 1H), 8.13 (brs, 3H), 8.20 (dd, J=9 Hz, J=2 Hz, 1H), 8.31 (s, 1H), 8.35 (brs, 6H), 8.36 (s, 1H), 8.70 (d, J=2 Hz, 1H), 8.95-8.99 (m, 2H), 9.07 (d, J=5 Hz, 1H), 10.82 (s, 1H); ESIMS found for $C_{26}H_{39}N_7O_3$ m/z 498 (M+H).

14

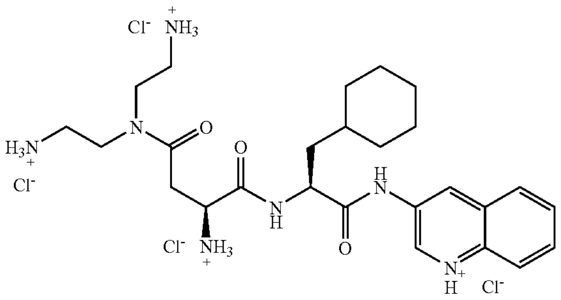

3-[(1S)-2-[bis(2-azaniumylethyl)carbamoyl]-1-{[(1S)-1-carbamoyl-2-cyclohexylethyl]carbamoyl}ethan-1-aminium] quinolin-1-ium tetrachloride 14

$^1$H NMR (DMSO-$d_6$) 0.92-0.97 (m, 2H), 1.15-1.24 (m, 4H), 1.46-1.52 (m, 1H), 1.60-1.78 (m, 6H), 2.98-3.02 (m, 2H), 3.06-3.16 (m, 2H), 3.21-3.29 (m, 2H), 3.55-3.72 (m, 4H), 4.29-4.35 (m, 1H), 4.51-4.56 (m, 1H), 7.68 (t, J=8 Hz, 1H), 7.78 (t, J=8 Hz, 1H), 8.00 (s, 1H), 8.09 (brs, 4H), 8.34 (brs, 6H), 8.94 (s, 1H), 9.00 (d, J=7 Hz, 1H), 9.22 (s, 1H), 10.90 (s, 1H); ESIMS found for $C_{26}H_{39}N_7O_3$ m/z 498 (M+H).

369

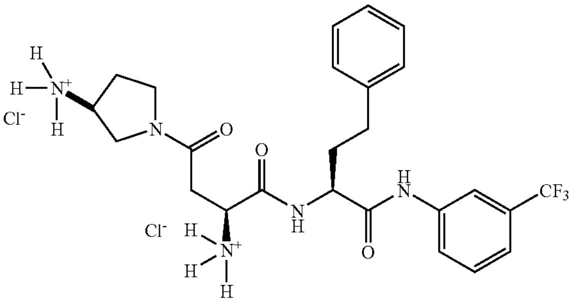

(3S)-1-[(3S)-3-Azaniumyl-3-{[(1S)-3-phenyl-1-{[3-(trifluoromethyl)phenyl]carbamoyl}propyl]carbamoyl}propanoyl]pyrrolidin-3-aminium dichloride 369. $^1$H NMR (500 MHz, MeOH-$d_4$): 8.07 (d, J=12.4 Hz, 1H), 7.77 (t, J=8.4 Hz, 1H), 7.51 (t, J=8.0 Hz, 1H), 7.40 (d, J=7.6 Hz, 1H), 7.30-7.23 (m, 4H), 7.20-7.16 (m, 1H), 4.55-4.50 (m, 1H), 4.40-4.36 (m, 1H), 4.05-3.90 (m, 1H), 3.84-3.60 (m, 4H), 3.15-3.00 (m, 2H), 2.90-2.80 (m, 1H), 2.80-2.70 (m, 1H), 2.50-2.30 (m, 1H), 2.27-2.00 (m, 3H) MS (ESI): m/z for $C_{25}H_{30}F_3N_5O_3$ calcd 505.2, found 528.2 $[M+Na]^+$.

370

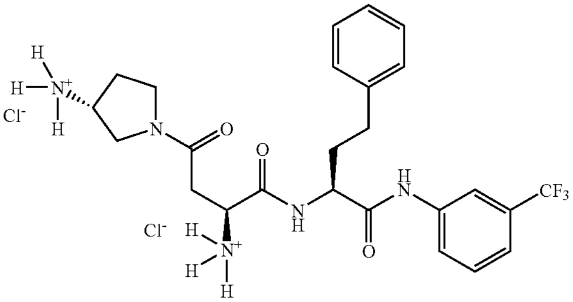

(3R)-1-[(3S)-3-Azaniumyl-3-{[(1S)-3-phenyl-1-{[3-(trifluoromethyl)phenyl]carbamoyl}propyl]carbamoyl}propanoyl]pyrrolidin-3-aminium dichloride 370.

371

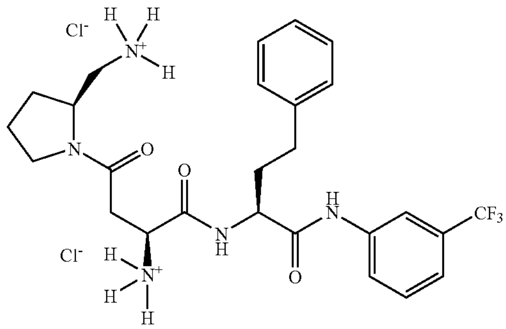

(1S)-3-[(2S)-2-(azaniumylmethyl)pyrrolidin-1-yl]-3-oxo-1-{[(1S)-3-phenyl-1-{[3-(trifluoromethyl)phenyl]carbamoyl}propyl]carbamoyl}propan-1-aminium dichloride 371.

372

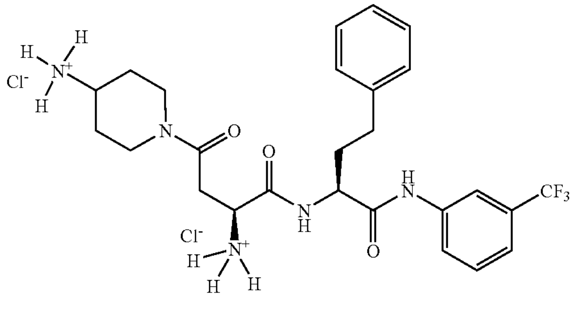

1-[(3S)-3-azaniumyl-3-{[(1S)-3-phenyl-1-{[3-(trifluoromethyl)phenyl]carbamoyl}propyl]carbamoyl}propanoyl]piperidin-4-aminium dichloride 372. $^1$H NMR (500 MHz, MeOH-$d_4$): 8.05 (d, J=15.2 Hz, 1H), 7.76 (d, J=8.2 Hz, 1H), 7.51 (t, J=8.0 Hz, 1H), 7.40 (d, J=7.8 Hz, 1H), 7.30-7.23 (m, 4H), 7.20-7.16 (m, 1H), 4.70-4.60 (m, 1H), 4.60-4.50 (m, 1H), 4.40-4.30 (m, 1H), 4.10-4.00 (m, 1H), 3.35-3.45 (m, 1H), 3.20-3.10 (m, 3H), 2.90-2.70 (m, 3H), 2.30-2.20 (m, 1H), 2.20-2.00 (m, 3H), 1.75-1.65 (m, 1H), 1.55-1.45 (m, 1H). MS (ESI): m/z for $C_{26}H_{32}F_3N_5O_3$ calcd 519.3, found 542.2 $[M+Na]^+$.

15

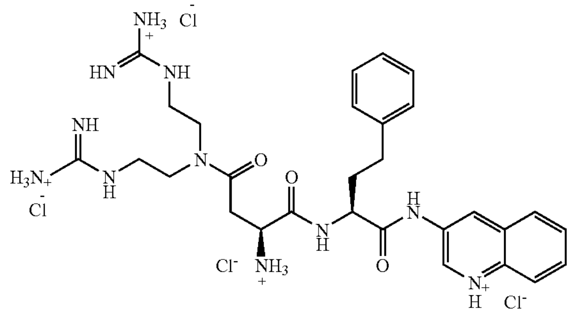

Prepared using procedures from Example 1, 5 and 8. 3-[(1S)-2-[bis({2-[(azaniumylmethanimidoyl)amino]ethyl})carbamoyl]-1-{[(1S)-1-carbamoyl-3-phenylpropyl]carbamoyl}ethan-1-aminium]quinolin-1-ium tetrachloride 15

$^1$H NMR (DMSO-$d_6$) 1.99-2.21 (m, 2H), 2.62-2.72 (m, 1H), 2.74-2.87 (m, 1H), 3.11-3.20 (m, 2H), 3.26-3.33 (m, 2H), 3.33-3.69 (m, 6H), 4.29-4.40 (m, 1H), 4.43-4.51 (m1H), 6.81-7.54 (brs, 4H), 7.12-7.19 (m, 1H), 7.23-7.30 (m, 4H), 7.54-7.59 (m, 2H), 7.61-7.68 (m, 1H), 7.72-7.83 (m, 2H), 7.90-7.97 (m, 2H), 8.30 (s, 3H), 8.69 (s, 1H), 9.01 (s, 1H), 9.14 (d, J=7 Hz, 1H), 10.58 (s, 1H).

26

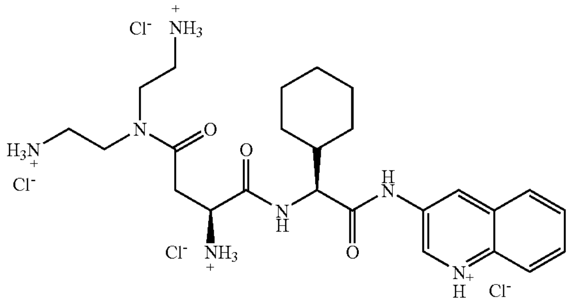

3-[(1S)-2-[bis(2-azaniumylethyl)carbamoyl]-1-{[(S)-carbamoyl (cyclohexyl)methyl]carbamoyl}ethan-1-aminium]quinolin-1-ium tetrachloride 26

$^1$H NMR (DMSO-$d_6$) 1.12-1.26 (m, 6H), 1.61-1.71 (m, 4H), 1.80 (d, J=8 Hz, 1H), 2.99-3.05 (m, 4H), 3.12-3.20 (m, 2H), 3.51-3.60 (m, 1H), 3.60-3.68 (m, 4H), 4.37-4.40 (m, 1H), 7.66 (t, J=8 Hz, 1H), 7.75 (t, J=8 Hz, 1H), 8.05 (s, 1H), 8.07 (s, 1H), 8.09 (brs, 3H), 8.34 (brs, 6H), 8.88 (d, J=7 Hz, 1H), 8.90 (s, 1H), 9.17 (d, J=2 Hz, 1H), 10.98 (s, 1H); ESIMS found for $C_{25}H_{37}N_7O_3$ m/z 484 (M+H).

27

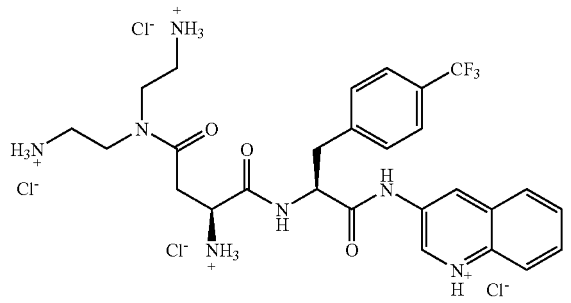

3-[(1S)-2-[bis(2-azaniumylethyl)carbamoyl]-1-{[(1S)-1-carbamoyl-2-[4-(trifluoromethyl)phenyl]ethyl]carbamoyl}ethan-1-aminium]quinolin-1-ium tetrachloride 27

$^1$H NMR (DMSO-$d_6$) 2.88-3.27 (m, 6H), 3.28-3.45 (m, 2H), 3.49-3.74 (m, 4H), 4.15-4.22 (m, 1H), 4.72-4.87 (m, 1H), 7.61-7.87 (m, 6H), 8.11 (brs, 3H), 8.15 (brs, 1H), 8.26 (brs, 3H), 8.35 (brs, 4H), 9.00 (s, 1H), 9.21 (d, J=7 Hz, 1H), 9.29 (d, J=2 Hz, 1H), 11.49 (s, 1H); $^{19}$F NMR (DMSO-$d_6$) −60.09 (s, 3F); ESIMS found for $C_{27}H_{32}F_3N_7O_3$ m/z 560 (M+H).

36

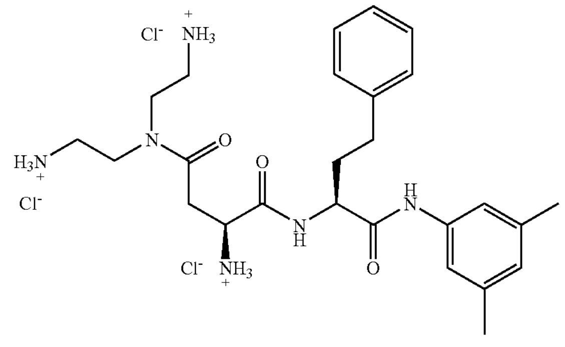

(1S)-2-[bis(2-azaniumylethyl)carbamoyl]-1-{[(1S)-1-[(3,5-dimethylphenyl)carbamoyl]-3-phenylpropyl]carbamoyl}ethan-1-aminium trichloride 36

$^{1}H$ NMR (DMSO-$d_6$) 1.96-2.08 (m, 2H), 2.19-2.24 (m, 6H), 2.60-2.66 (m, 1H), 2.71-2.80 (m, 1H), 2.90-3.13 (m, 5H), 3.18-3.29 (m, 1H), 3.64-3.68 (m, 4H), 4.34-4.44 (m, 2H), 6.68 (brs, 1H), 7.14-7.19 (m, 1H), 7.21-7.31 (m, 7H), 8.15 (brs, 3H), 8.31-8.49 (m, 6H), 9.07-9.11 (m, 1H), 9.98 (brs, 1H); ESIMS found for $C_{26}H_{38}N_6O_3$ m/z 483 (M+H).

37

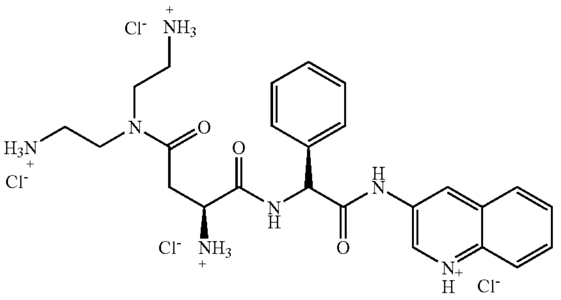

3-[(1S)-2-[bis(2-azaniumylethyl)carbamoyl]-1-{[carbamoyl(phenyl)methyl]carbamoyl}ethan-1-aminium]quinolin-1-ium tetrachloride 37

$^{1}H$ NMR (DMSO-$d_6$) 2.92-3.19 (m, 6H), 3.47-3.59 (m, 4H), 4.43 (brs, 1H), 5.77 (brs, 1H), 7.52 (d, J=8 Hz, 1H), 7.39-7.45 (m, 2H), 7.60-7.68 (m, 3H), 7.73 (d, J=8 Hz, 1H), 7.97-8.04 (m, 2H), 8.08 (brs, 3H), 8.28 (brs, 3H), 8.33 (brs, 3H), 8.85 (s, 1H), 9.17 (brs, 1H0, 9.42 (d, J=8 Hz, 1H), 11.40 (s, 1H); ESIMS found for $C_{25}H_{31}N_7O_3$ m/z 478 (M+H).

39

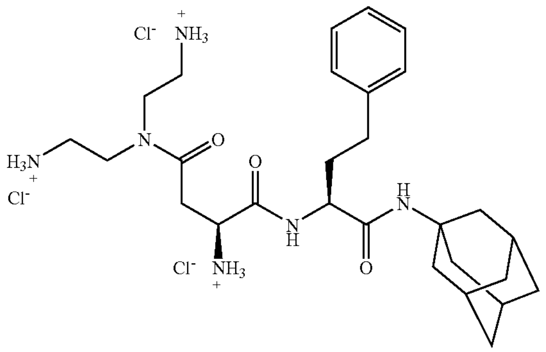

(1S)-1-{[(1S)-1-[(adamantan-1-yl)carbamoyl]-3-phenylpropyl]carbamoyl}-2-[bis(2-azaniumylethyl)carbamoyl]ethan-1-aminium trichloride 39

$^{1}H$ NMR (DMSO-$d_6$) 1.15 (s, 1H), 1.48 (s, 1H), 1.51 (s, 1H), 1.69 (s, 2H), 1.72-1.84 (m, 9H), 1.87-1.96 (m, 4H), 2.04-2.07 (m, 1H), 3.00-3.12 (m, 4H), 3.17-3.24 (m, 2H), 3.58-3.63 (m, 4H), 4.32-4.35 (m, 1H), 4.50-4.53 (m, 1H), 7.18-7.30 (m, 5H), 7.92 (d, J=8 Hz, 1H), 8.03 (brs, 3H), 8.35 (brs, 6H), 8.85 (d, J=8 Hz, 1H); ESIMS found for $C_{28}H_{44}N_6O_3$ m/z 513 (M+H).

42

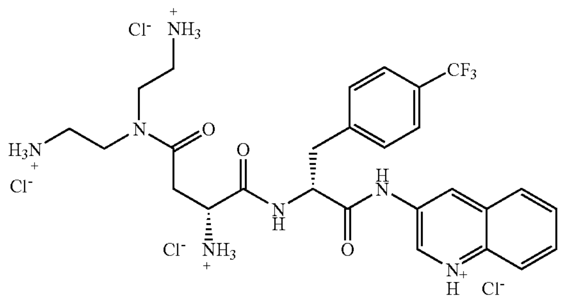

3-[(1R)-2-[bis(2-azaniumylethyl)carbamoyl]-1-{[(1R)-1-carbamoyl-2-[4-(trifluoromethyl)phenyl]ethyl]carbamoyl}ethan-1-aminium]quinolin-1-ium tetrachloride 42

$^{1}H$ NMR (DMSO-$d_6$) 2.93-3.26 (m, 8H), 4.04-4.29 (m, 4H), 4.41-4.64 (m, 1H), 4.72-4.92 (m, 1H), 6.73-6.93 (m, 1H), 6.95-7.22 (m, 1H), 7.42-7.84 (m, 5H), 7.98-8.13 (m, 4H), 8.16-8.40 (m, 6H), 8.41-8.54 (m, 1H), 8.77-8.98 (m, 1H), 9.10-9.29 (m, 1H), 11.34 (brs, 1H); $^{19}F$ NMR (DMSO-$d_6$) −60.09 (s, 3F); ESIMS found for $C_{27}H_{32}F_3N_7O_3$ m/z 560 (M+H).

44

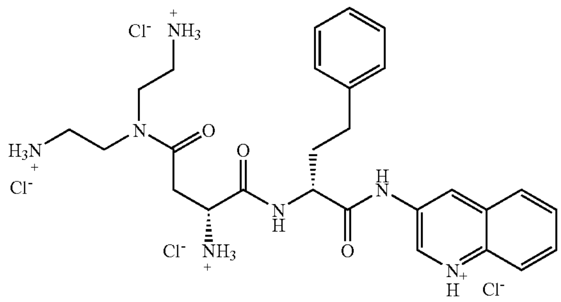

3-[(1R)-2-[bis(2-azaniumylethyl)carbamoyl]-1-{[(1R)-1-carbamoyl-3-phenylpropyl]carbamoyl}ethan-1-aminium]quinolin-1-ium tetrachloride 44

$^{1}H$ NMR (DMSO-$d_6$) 1.95-2.19 (m, 2H), 2.59-2.82 (m, 2H), 2.95-3.02 (m, 2H), 3.03-3.15 (m, 4H), 3.48-3.66 (m, 4H), 4.31-4.40 (m, 1H), 4.45-4.55 (m, 1H), 7.09-7.31 (m, 5H), 7.65-7.83 (m, 2H), 8.04 (d, J=8 Hz, 2H), 8.84 (brs, 1H), 8.97-9.06 (m, 1H), 9.14 (brs, 1H), 10.93 (s, 1H); ESIMS found for $C_{27}H_{35}N_7O_3$ m/z 506 (M+H).

48

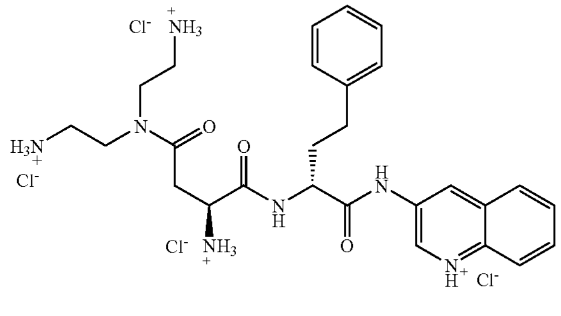

3-[(1S)-2-[bis(2-azaniumylethyl)carbamoyl]-1-{[(1R)-1-carbamoyl-3-phenylpropyl]carbamoyl}ethan-1-aminium]quinolin-1-ium tetrachloride 48

$^1$H NMR (DMSO-$d_6$) 2.02-2.19 (m, 2H), 2.61-2.78 (m, 2H), 2.96 (brs, 2H), 3.07 (brs, 2H), 3.14-3.30 (m, 2H), 3.58 (brs, 2H), 3.65 (brs, 2H), 4.34 (brs, 2H), 4.44 (brs, 2H), 7.10-7.15 (m, 1H), 7.22-7.26 (m, 1H), 7.74 (t, J=8 Hz, 1H), 7.85 (t, J=8 Hz, 1H), 8.12-8.21 (m, 5H), 8.41 (brs, 6H), 9.11 (bs, 1H), 9.20 (d, J=7 Hz, 1H), 9.40 (d, J=2 Hz, 1H), 11.30 (s, 1H); ESIMS found for $C_{27}H_{35}N_7O_3$ m/z 506 (M+H).

169

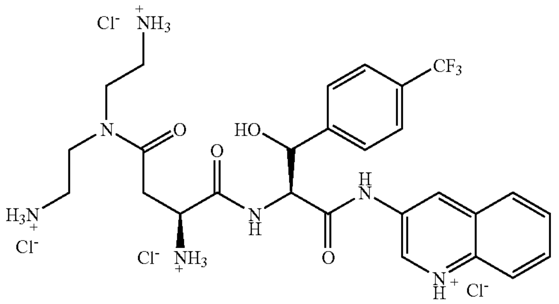

3-[(1S)-2-[bis(2-azaniumylethyl)carbamoyl]-1-{[(1S)-1-carbamoyl-2-hydroxy-2-[4-(trifluoromethyl)phenyl]ethyl]carbamoyl}ethan-1-aminium]quinolin-1-ium tetrachloride 169

$^1$H NMR (DMSO-$d_6$) 2.91-3.19 (m, 6H), 3.51-3.67 (m, 4H), 4.20-4.37 (m, 1H), 4.79-4.88 (m, 1H), 5.47 (d, J=2 Hz, 1H), 7.63-7.53 (m, 4H), 7.53-7.85 (m, 2H), 7.96-8.09 (m, 5H), 8.15-8.33 (m, 6H), 8.81 (brs, 2H), 9.18 (d, J=2 Hz, 1H), 11.29 (s, 1H); $^{19}$F NMR (DMSO-$d_6$) −60.09 (s); ESIMS found for $C_{27}H_{32}F_3N_7O_4$ m/z 576.4 (M+H).

345

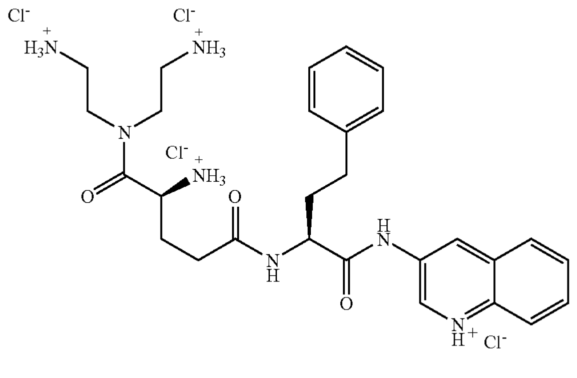

3-[(1S)-1-[bis(2-azaniumylethyl)carbamoyl]-3-{[(1S)-1-carbamoyl-3-phenylpropyl]carbamoyl}propan-1-aminium]quinolin-1-ium tetrachloride 345

$^1$H NMR (DMSO-$d_6$) 1.98-2.14 (m, 4H), 2.63-2.87 (m, 2H), 2.96-3.05 (m, 4H), 3.67-3.77 (m, 4H), 3.77-3.88 (m, 4H), 4.46-4.56 (m, 2H), 7.16-7.20 (m, 1H), 7.23-7.30 (m, 5H), 7.63 (t, J=8 Hz, 1H), 7.71 (t, J=8 Hz, 1H), 8.00 (t, J=8 Hz, 2H), 8.09 (brs, 3H), 8.31 (brs, 3H), 8.45 (brs, 3H), 8.66 (d, J=8 Hz, 1H), 8.79 (d, J=2 Hz, 1H), 9.11 (d, J=2 Hz, 1H), 10.87 (s, 1H); ESIMS found for $C_{28}H_{37}N_7O_3$ m/z 520 (M+H).

351

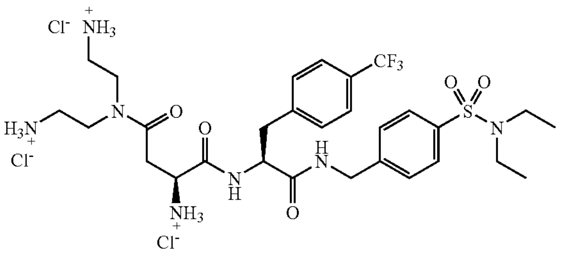

(1S)-2-[bis(2-azaniumylethyl)carbamoyl]-1-{[(1S)-1-({[4-(diethylsulfamoyl)phenyl]methyl}carbamoyl)-2-[4-(trifluoromethyl)phenyl]ethyl]carbamoyl}ethan-1-aminium trichloride 351

$^1$H NMR (DMSO-$d_6$) 1.02 (t, J=7 Hz, 6H), 2.87-3.24 (m, 6H), 3.12 (q, J=7 Hz, 4H), 3.47-3.71 (m, 6H), 4.11-4.65 (m, 4H), 7.34 (d, J=8 Hz, 2H), 7.52 (d, J=8 Hz, 2H), 7.62 (d, J=11 Hz, 2H), 7.67 (d, J=11 Hz, 2H), 8.06 (brs, 3H), 8.26 (brs, 6H), 8.81 (t, J=6 Hz, 1H), 9.02 (d, J=8 Hz, 1H), $^{19}$F NMR (DMSO-$d_6$) −60.10 (s); ESIMS found for $C_{29}H_{42}F_3N_7O_5S$ m/z 658.6 (M+H).

352

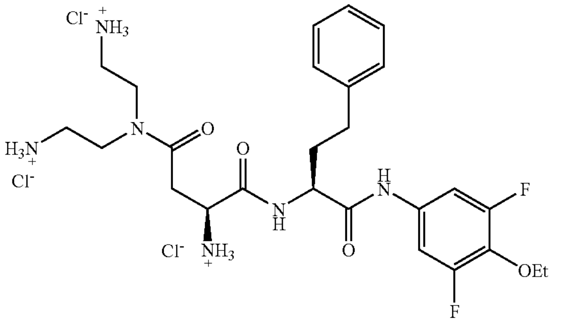

(1S)-2-[bis(2-azaniumylethyl)carbamoyl]-1-{[(1S)-1-[(4-ethoxy-3,5-difluorophenyl)carbamoyl]-3-phenylpropyl]carbamoyl}ethan-1-aminium trichloride 352

$^1$H NMR (DMSO-$d_6$/$D_2O$) 1.24 (t, J=7 Hz, 3H), 1.81-2.12 (m, 4H), 2.67 (brs, 2H), 2.95 (brs, 8H), 4.07 (q, J=7 Hz, 2H), 4.36 (brs, 2H), 7.11-7.31 (m, 5H), 7.43 (s, 1H), 7.48 (s, 1H), 10.51 (s, 1H), $^{19}$F NMR (DMSO-$d_6$/$D_2O$) −127.08 (s); ESIMS found for $C_{26}H_{36}F_2N_6O_4$ m/z 535.6 (M+H).

353

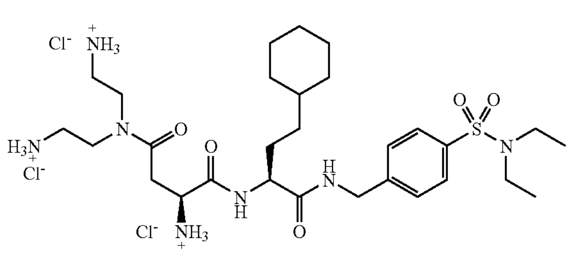

(1S)-2-[bis(2-azaniumylethyl)carbamoyl]-1-{[(1S)-3-cyclohexyl-1-({[4-(diethylsulfamoyl)phenyl]methyl}carbamoyl)propyl]carbamoyl}ethan-1-aminium trichloride 353

$^1$H NMR (DMSO-$d_6$) 0.69-0.90 (m, 2H), 1.01 (t, J=7 Hz, 6H), 1.07-1.24 (m, 6H), 1.44-1.75 (m, 8H), 2.92 (brs, 5H), 3.12 (q, J=7 Hz, 4H), 3.47-3.71 (m, 4H), 4.07-4.42 (m, 4H), 7.45 (d, J=8 Hz, 2H), 7.70 (d, J=8 Hz, 2H), 8.10 (brs, 3H), 8.34 (brs, 6H), 8.68 (d, J=6 Hz, 1H), 8.80 (d, J=7 Hz, 1H), ESIMS found for $C_{29}H_{51}N_7O_5S$ m/z 610.7 (M+H).

354

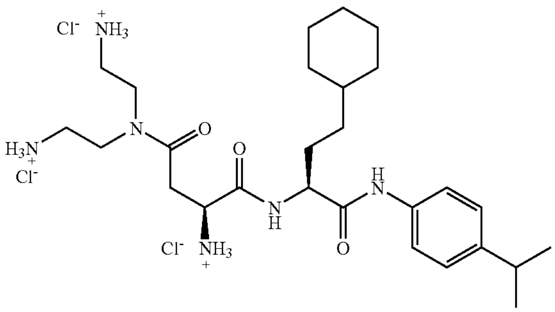

(1S)-2-[bis(2-azaniumylethyl)carbamoyl]-1-{[(1S)-3-cyclohexyl-1-{[4-(propan-2-yl)phenyl]carbamoyl}propyl]carbamoyl}ethan-1-aminium trichloride 354

$^1$H NMR (DMSO-$d_6$) 0.69-0.96 (m, 2H), 1.03-1.26 (m, 12H), 1.53-1.78 (m, 7H), 2.72-2.87 (m, 1H), 2.90-3.17 (m, 6H), 3.52-3.70 (m, 4H), 4.31 (brs, 2H), 7.15 (d, J=8 Hz, 2H), 7.52 (d, J=8 Hz, 2H), 8.10 (brs, 3H), 8.31 (brs, 6H), 8.83 (d, J=7 Hz, 1H), 10.04 (s, 1H); ESIMS found for $C_{27}H_{46}N_6O_3$ m/z 503.6 (M+H).

359

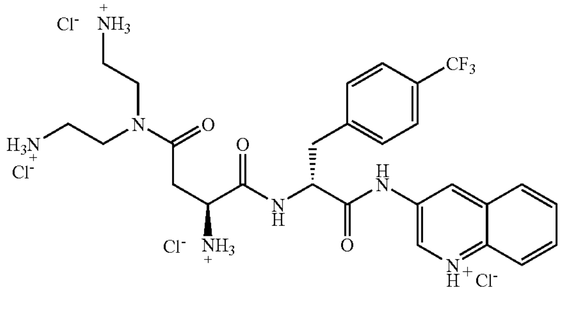

3-[(1S)-2-[bis(2-azaniumylethyl)carbamoyl]-1-{[(1R)-1-carbamoyl-2-[4-(trifluoromethyl)phenyl]ethyl]carbamoyl}ethan-1-aminium]quinolin-1-ium tetrachloride 359

$^1$H NMR (DMSO-$d_6$) 3.03 (brs, 6H), 4.24 (brs, 1H), 4.70-5.07 (m, 7H), 7.58-7.86 (m, 6H), 8.02-8.18 (m, 5H), 8.28 (brs, 3H), 8.41 (brs, 3H), 8.95 (d, J=2 Hz, 1H), 9.19 (d, J=8 Hz, 1H), 9.27 (d, J=2 Hz, 1H), 11.41 (s, 1H); $^{19}$F NMR (DMSO-$d_6$) −59.99 (s); ESIMS found for $C_{27}H_{32}F_3N_7O_3$ m/z 560.6 (M+H).

360

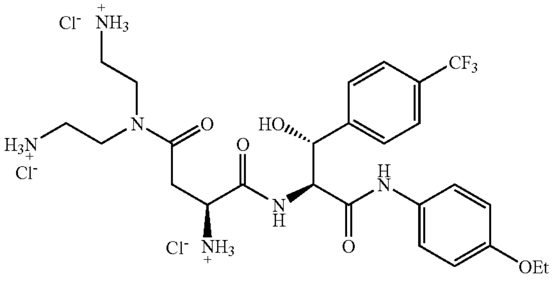

(1S)-2-[bis(2-azaniumylethyl)carbamoyl]-1-{[(1S,2R)-1-[(4-ethoxyphenyl)carbamoyl]-2-hydroxy-2-[4-(trifluoromethyl)phenyl]ethyl]carbamoyl}ethan-1-aminium trichloride 360

$^1$H NMR (DMSO-$d_6$) 1.26 (t, J=7 Hz, 3H), 2.90-3.18 (m, 6H), 3.52-3.60 (m, 4H), 3.92 (q, J=7 Hz, 2H), 4.66 (dd, J=5 Hz, J=10 Hz, 1H), 5.26 (brs, 1H), 6.09 (brs, 1H), 6.68 (d, J=9 Hz, 2H), 7.46 (d, J=9 Hz, 2H), 7.64 (d, J=8 Hz, 2H), 7.70 (d, J=8 Hz, 2H), 8.03 (brs, 3H), 8.20 (brs, 3H), 8.26 (brs, 3H), 8.65 (d, J=8 Hz, 1H), 10.19 (s, 1H), $^{19}$F NMR (DMSO-$d_6$) −60.07 (s); ESIMS found for $C_{26}H_{35}F_3N_6O_5$ m/z 569.6 (M+H).

Synthesis of 3-[(1S)-3-[bis(2-azaniumylethyl)carbamothioyl]-1-{[(1R)-1-carbamoyl-2-[4-(trifluoromethyl)phenyl]ethyl]carbamoyl}propan-1-aminium]quinolin-1-ium tetrachloride 12 is depicted below in scheme 2 and example 2

Scheme 2

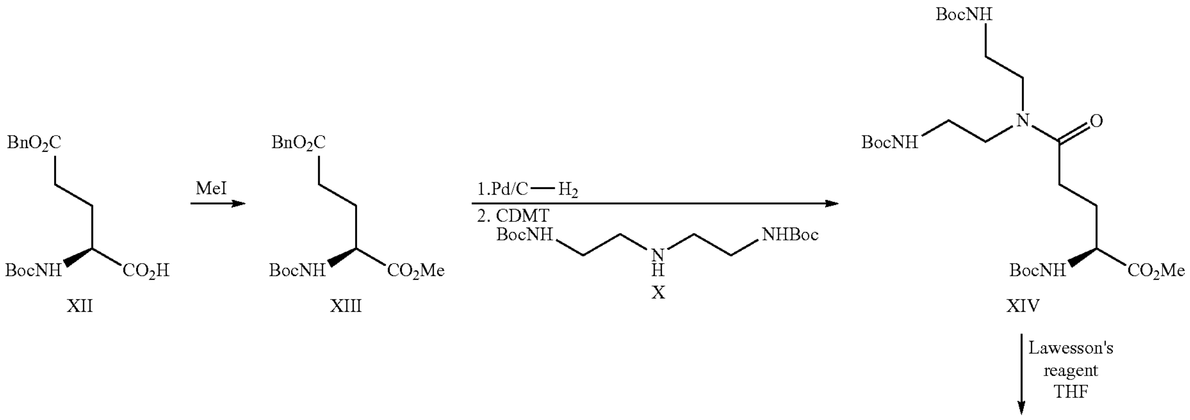

-continued

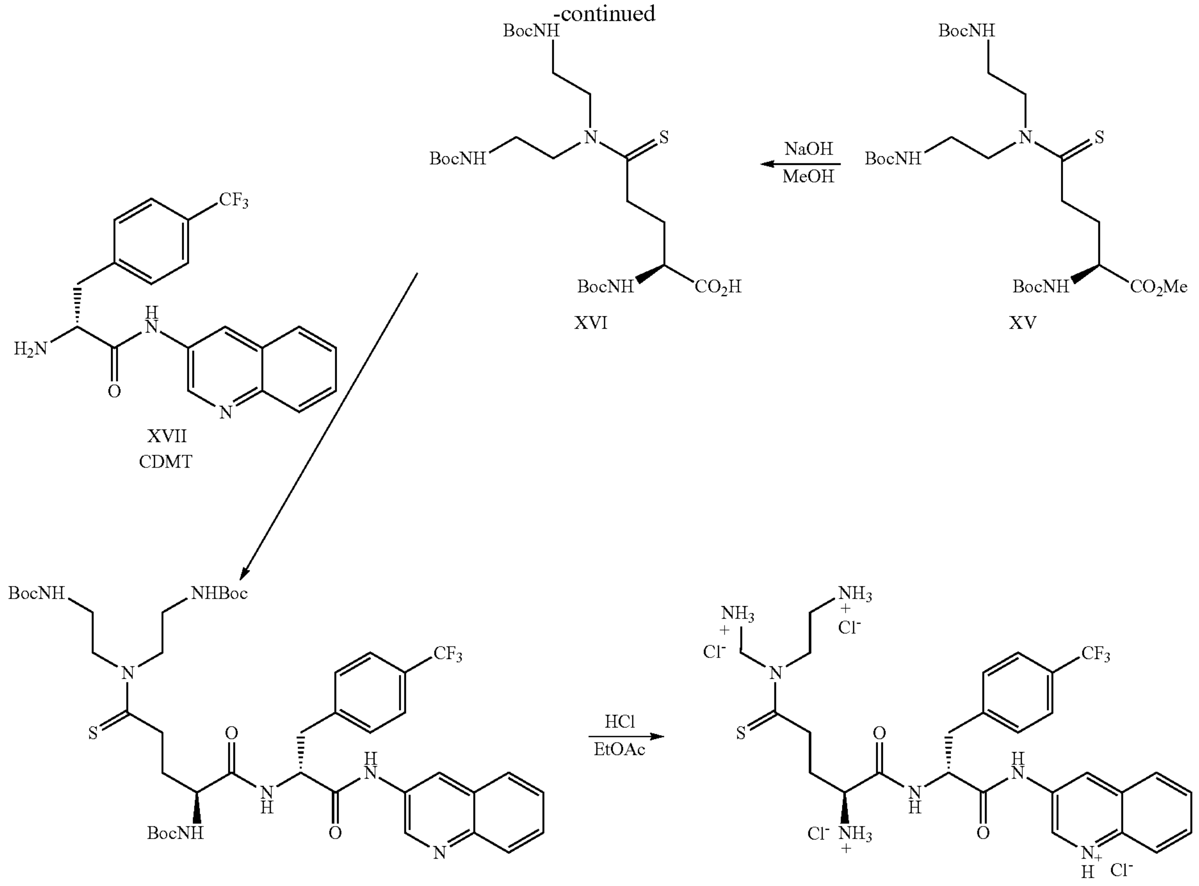

XVI XV XVII XVII 12

EXAMPLE 2

Step 1

Methyl iodide (1.01 mL, 16.3 mmol) was added dropwise to a solution of (2S)-5-(benzyloxy)-2-{[(tert-butoxy)carbonyl]amino}-5-oxopentanoic acid XII (5.00 g, 14.82 mmol) and $K_2CO_3$ (2.25 g, 16.3 mmol) in DMF (25 mL) at r.t. The reaction mixture was stirred about 3 h at r.t. before adding additional methyl iodide (1.01 mL, 16.3 mmol). EtOAc was then added to the reaction and washed 3x10% $Na_2S_2O_3$ and dried over $MgSO_4$. The solvent was removed under reduced pressure and the crude product was purified on a silica gel column (100:1 and then 50:1 $CHCl_3$/MeOH) to give 5-benzyl 1-methyl (2S)-2-{[(tert-butoxy)carbonyl] amino}pentanedioate XIII (4.20 g, 12.23 mmol, 82% yield). ESIMS found for $C_{18}H_{25}NO_6$ m/z 352 (M+H).

Step 2

To a solution of 5-benzyl 1-methyl (2S)-2-{[(tert-butoxy) carbonyl]amino}pentanedioate XIII (4.2 g, 12.23 mmol) in EtOH/water (40 mL/6 mL) under argon was added 10% Pd/C catalyst (catalytic amount). The mixture was stirred under an atmosphere of hydrogen for 6 h at r.t. The mixture was then filtered through Celite and evaporated to dryness to afford the free acid (3.0 g, 11.48 mmol, 32% yield). ESIMS found for $C_{32}H_{61}N_7O_{10}$ m/z 262 (M+H).

Step 3

To a solution of CDMT (2.22 g, 12.62 mmol) in DCM (40 mL) and cooled to 0° C. was added N-methylmorpholine (1.38 mL, 12.63 mmol). The mixture was stirred for 10 min before adding (4S)-4-{[(tert-butoxy)carbonyl]amino}-5-methoxy-5-oxopentanoic acid (3.0 g, 11.48 mmol). The solution was stirred for 60 min at 0° C. The tert-butyl N-{2-[(2-{[(tert-butoxy)carbonyl]amino}ethyl)amino] ethyl}carbamate X was then added and the mixture stirred at r.t. overnight. The solution was washed with 1 M aq. $K_2CO_3$, 1 M aq. HCl, brine and dried over anhydrous $MgSO_4$. The crude product was crystallized from DCM/hexane to give methyl (2S)-4-[bis(2-{[(tert-butoxy)carbonyl]amino}ethyl) carbamoyl]-2-{[(tert-butoxy)carbonyl]amino}butanoate XIV (4.91 g, 8.98 mmol, 72% yield). $^1H$ NMR (DMSO-$d_6$) 1.35-1.47 (m, 27H), 1.80-1.91 (m, 1H), 2.19-2.32 (m, 1H), 2.33-2.42 (m, 1H), 2.46-2.57 (m, 1H), 3.11-3.38 (m, 6H), 3.40-3.53 (m, 1H), 3.54-3.62 (m, 1H), 3.73 (s, 3H), 4.26-4.38 (m, 1H), 4.99-5.09 (brs, 1H), 5.31-5.46 (m, 2H); ESIMS found for $C_{25}H_{46}N_4O_9$ m/z 547 (M+H).

Step 4

To the solution of methyl (2S)-4-[bis(2-{[(tert-butoxy)carbonyl]amino}ethyl)carbamoyl]-2-{[(tert-butoxy)carbonyl] amino}butanoate XIV (610 mg, 1.12 mmol) in THF (10 mL) under argon was added Lawesson's reagent (680 mg, 1.68 mmol) and DMAP (13 mg, 0.11 mmol). The mixture was stirred at r.t. for 2 h and then refluxed over weekend. An additional two portions of Lawesson's reagent (900 mg, 2.24 mmol) and was added and the reaction was refluxed for another 4 h. The solvent was evaporated under reduced pressure and the crude product was purified on a silica gel column (1:6 EtOAc/hexane) to give methyl (2S)-4-[bis(2-{[(tert-butoxy)carbonyl]amino}ethyl)carbamothioyl]-2-{[(tert-butoxy)carbonyl]amino}butanoate XV (290 mg, 0.51 mmol, 45% yield). ESIMS found for $C_{25}H_{46}N_4O_8S$ m/z 563 (M+H).

Step 5

To the solution of the ester XV (290 mg, 0.51 mmol) in MeOH (10 mL) was added 4 M NaOH dropwise until pH=13. The mixture was stirred overnight at r.t. before evaporating the MeOH under reduced pressure. The residue was mixed with water and washed with ether. After acidifying to pH~3 with 2 M HCl, the product was extracted with DCM, dried over $MgSO_4$ and concentrated under vacuum to give (2S)-4-[bis(2-{[(tert-butoxy)carbonyl]amino}ethyl)carbamothioyl]-2-{[(tert-butoxy)carbonyl]amino}butanoic acid XVI (250 mg, 0.45 mmol, 88% yield). ESIMS found for $C_{24}H_{44}N_4O_8S$ m/z 549 (M+H).

Step 6

To a solution of CDMT (86 mg, 0.49 mmol) in DCM (10 mL) and cooled to 0° C. was added N-methylmorpholine (0.2 mL, 1.86 mmol). The mixture was stirred for 10 min before adding (2S)-4-[bis(2-{[(tert-butoxy)carbonyl]amino}ethyl) carbamothioyl]-2-{[(tert-butoxy)carbonyl]amino}butanoic acid XVI (250 mg, 0.45 mmol). The solution was stirred for 60 min at 0° C. The (2R)-2-amino-N-(quinolin-3-yl)-3-[4-(trifluoromethyl)phenyl]propanamide XVII (210 mg, 0.49 mmol) was then added and the mixture stirred at r.t. overnight. The solution was washed with 1 M aq. $K_2CO_3$, 1 M aq. HCl, brine and dried over anhydrous $MgSO_4$. The crude product was then purified on a silica gel column (50:1 $CHCl_3$/MeOH) to give tert-butyl N-{2-[(2S)-2-{[(tert-butoxy)carbonyl] amino}-4-[N-(2-{[(tert-butoxy)carbonyl]amino}ethyl) methanethioamido]-N-[(1R)-1-[(quinolin-3-yl)carbamoyl]-2-[4-(trifluoromethyl)phenyl]ethyl]butanamide] ethyl}carbamate XVIII (210 mg, 0.24 mmol, 53% yield). $^1H$ NMR ($CDCl_3$) 1.34-1.41 (m, 9H), 1.42-1.56 (m, 18H), 2.02-2.14 (m, 2H), 2.51-2.74 (m, 1H), 2.82-3.00 (m, 1H), 3.21-3.41 (m, 3H), 3.46-3.53 (m, 1H), 3.54-3.72 (m, 2H), 3.73-4.00 (m, 2H), 4.21-4.43 (m, 2H), 4.88-5.00 (m, 1H), 5.49-5.71 (m, 1H), 7.44-7.54 (m, 2H), 7.56-7.70 (m, 3H), 7.81 (d, J=8 Hz, 1H), 8.05 (d, J=8 Hz, 1H), 8.74-8.9 (m, 2H), 9.01-9.09 (m, 1H); $^{19}F$ NMR (DMSO-$d_6$) −61.75 (s, 3F); ESIMS found for $C_{43}H_{58}F_3N_7O_8S$ m/z 890 (M+H).

Step 7

To a solution of tert-butyl N-{2-[(2S)-2-{[(tert-butoxy)carbonyl]amino}-4-[N-(2-{[(tert-butoxy)carbonyl] amino}ethyl)methanethioamido]-N-[(1R)-1-[(quinolin-3-yl)carbamoyl]-2-[4-(trifluoromethyl)phenyl]ethyl] butanamide]ethyl}carbamate XVIII (210 mg, 0.24 mmol) in EtOAc (5 mL) was added HCl (4.5 M solution in EtOAc, 5 mL). The reaction mixture was stirred for 15 min at r.t. before adding ethyl ether (20 mL). The precipitate was filtered and washed with ether to give 3-[(1S)-3-[bis(2-azaniumylethyl) carbamothioyl]-1-{[(1R)-1-carbamoyl-2-[4-(trifluoromethyl)phenyl]ethyl]carbamoyl}propan-1-aminium]quinolin-1-ium methane tetrachloride 12 as a white crystalline solid (140 mg, 0.19 mmol, 79% yield). $^1H$ NMR (DMSO-$d_6$) 1.76-1.84 (m, 1H), 2.00-2.09 (m, 1H), 2.55-2.65 (m, 2H), 2.80-2.91 (m, 1H), 3.00-3.15 (m, 5H), 3.27-3.36 (m, 2H), 3.82-4.07 (m, 2H), 4.13-4.19 (brs, 1H), 4.89-4.94 (brs, 1H), 7.49-7.69 (m, 6H), 7.94 (t, J=8 Hz, 2H), 7.99-8.13 (brs, 3H), 8.64-8.74 (s, 1H), 8.95-9.03 (s, 1H), 9.19 (d, J=8 Hz, 1H), 10.89-10.99 (s, 1H); $^{19}F$ NMR (DMSO-$d_6$) −60.12 (s, 3F).

The following compounds were prepared in accordance with the procedure described in the above example 2. Most examples skip Step 4.

1

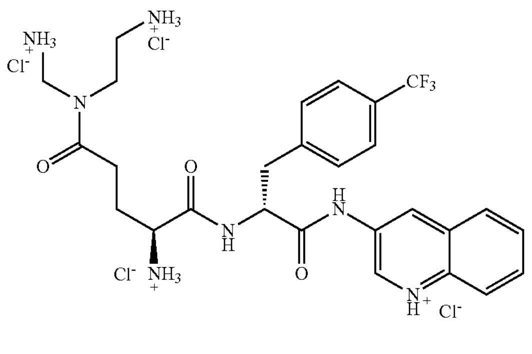

3-[(1S)-3-[bis(2-azaniumylethyl)carbamoyl]-1-{[(1R)-1-carbamoyl-2-[4-(trifluoromethyl)phenyl]ethyl] carbamoyl}propan-1-aminium]quinolin-1-ium tetrachloride 1

$^1H$ NMR (DMSO-$d_6$) 1.64-1.95 (m, 2H), 2.78-3.18 (m, 6H), 3.26-3.43 (m, 2H), 3.47-3.69 (m, 4H), 3.77-4.10 (m, 1H), 4.75-5.08 (m, 1H), 7.60-7.63 (m, 4H), 7.64-7.82 (m, 2H), 7.92-8.16 (m, 5H), 8.35 (brs, 6H), 8.80-8.92 (m, 1H), 9.08-9.33 (m, 2H), 11.27 (brs, 1H); $^{19}F$ NMR (DMSO-$d_6$) −60.06 (s, 3F); ESIMS found for $C_{28}H_{34}F_3N_7O_3$ m/z 574 (M+H).

3

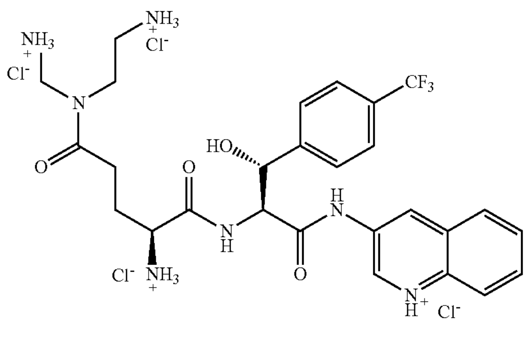

3-[(1S)-3-[bis(2-azaniumylethyl)carbamoyl]-1-{[(1S, 2R)-1-carbamoyl-2-hydroxy-2-[4-(trifluoromethyl)phenyl] ethyl]carbamoyl}propan-1-aminium]quinolin-1-ium tetrachloride 3

$^1H$ NMR (DMSO-$d_6$) 1.87-2.13 (m, 2H), 2.59-2.73 (m, 1H), 2.77-2.86 (m, 1H), 2.87-2.98 (m, 2H), 3.02-3.13 (m, 2H), 3.48-3.58 (m, 2H), 3.60-3.72 (m, 2H), 4.84 (dd, J=8 Hz, J=7 Hz, 1H), 5.46-5.58 (m, 1H), 6.03-6.43 (m, 1H), 7.59-7.80 (m, 4H), 7.88 (d, J=8 Hz, 2H), 7.94-8.03 (brs, 3H), 8.04-8.12 (m, 2H), 8.19-8.28 (brs, 3H), 8.27-8.41 (brs, 3H), 8.80-8.99 (m, 2H), 9.22 (s, 1H), 11.46 (s, 1H); $^{19}F$ NMR (DMSO-$d_6$) −60.07 (s, 3F); ESIMS found for $C_{28}H_{34}F_3N_7O_4$ m/z 590 (M+H).

7

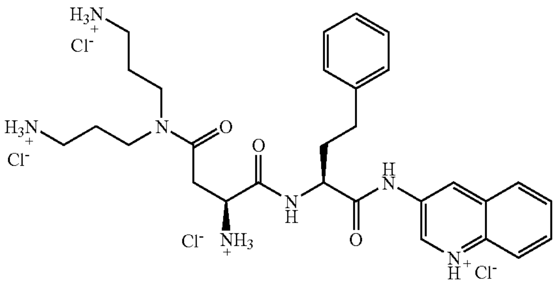

3-[(1S)-2-[bis(3-azaniumylpropyl)carbamoyl]-1-{[(1S)-1-carbamoyl-3-phenylpropyl]carbamoyl}ethan-1-aminium]quinolin-1-ium tetrachloride 7

$^1$H NMR (DMSO-$d_6$) 1.83-1.88 (m, 2H), 1.96-2.03 (m, 2H), 2.05-2.24 (m, 2H), 2.72-2.92 (m, 6H), 3.16-3.22 (m, 2H), 3.40-3.55 (m, 4H), 4.30-4.33 (m, 1H), 4.50-4.54 (m, 1H), 7.15-7.20 (m, 1H), 7.28-7.30 (m, 5H), 7.65-7.69 (m, 1H), 7.77-7.78- (m, 1H), 8.03-8.08 (m, 2H), 8.17 (brs 3H), 8.32 (brs 3H), 8.50 (brs, 3H), 8.96 (d, J=2 Hz, 1H), 9.26 (d, J=2 Hz, 1H), 11.02 (s, 1H); ESIMS found for $C_{29}H_{39}N_7O_3$ m/z 534 (M+H).

11

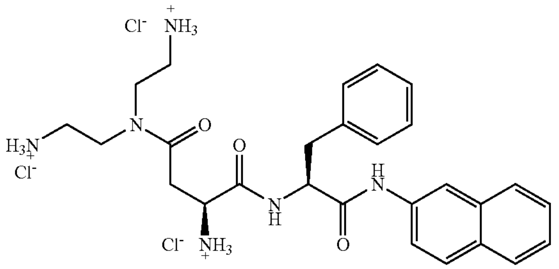

(1S)-2-[bis(2-azaniumylethyl)carbamoyl]-1-{[(1S)-1-[(naphthalen-2-yl)carbamoyl]-2-phenylethyl]carbamoyl}ethan-1-aminium trichloride 11

$^1$H NMR (DMSO-$d_6$) 3.78-3.21 (m, 8H), 3.46-3.81 (m, 4H), 4.16 (brs, 1H), 4.72 (brs, 1H), 7.05-7.53 (m, 7H), 7.67 (brs, 1H), 7.80 (brs, 3H), 8.00-8.54 (m, 10H), 9.07 (brs, 1H), 10.60 (brs, 1H); ESIMS found for $C_{27}H_{34}N_6O_3$ m/z 491 (M+H).

25

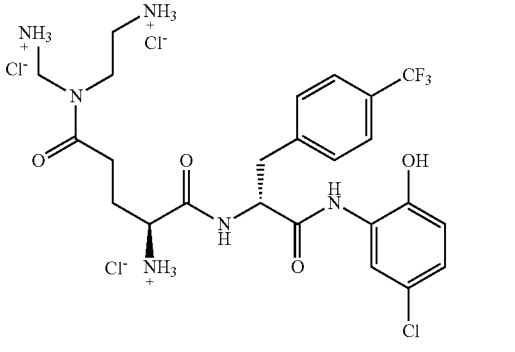

(1S)-3-[bis(2-azaniumylethyl)carbamoyl]-1-{[(1R)-1-[(5-chloro-2-hydroxyphenyl)carbamoyl]-2-[4-(trifluoromethyl)phenyl]ethyl]carbamoyl}propan-1-aminium trichloride 25

$^1$H NMR (DMSO-$d_6$) 1.62-1.72 (m, 1H), 1.75-1.82 (m, 1H), 2.37-2.49 (m, 2H), 2.92-3.06 (m, 6H), 3.46-3.61 (m, 4H), 3.89 (brs, 1H), 5.05-5.12 (m, 1H), 6.93-7.01 (m, 2H), 7.59-7.65 (m, 3H), 7.97 (d, J=2 Hz, 1H), 8.01 (brs, 3H), 8.26 (brs, 3H), 8.32 (brs, 3H), 9.04 (d, J=9 Hz, 1H), 9.75 (s, 1H), 10.38 (s, 1H), 11.98 (brs, 1H); ESIMS found for $C_{25}H_{32}N_6O_4ClF_3$ m/z 573 (M+H).

28

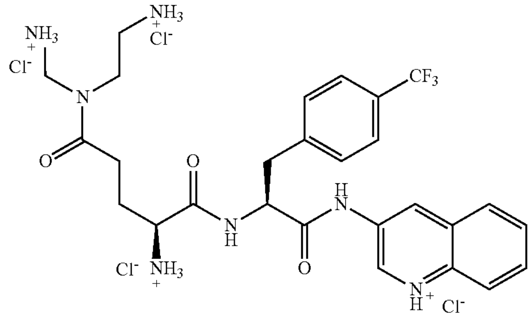

3-[(1S)-3-[bis(2-azaniumylethyl)carbamoyl]-1-{[(1S)-1-carbamoyl-2-[4-(trifluoromethyl)phenyl]ethyl]carbamoyl}propan-1-aminium]quinolin-1-ium tetrachloride 28

$^1$H NMR (DMSO-$d_6$) 1.64-1.95 (m, 2H), 2.78-3.18 (m, 6H), 3.26-3.43 (m, 2H), 3.47-3.69 (m, 4H), 3.77-4.10 (m, 1H), 4.75-5.08 (m, 1H), 7.60-7.63 (m, 4H), 7.64-7.82 (m, 2H), 7.92-8.16 (m, 5H), 8.35 (brs, 6H), 8.80-8.92 (m, 1H), 9.08-9.33 (m, 2H), 11.27 (brs, 1H); $^{19}$F NMR (DMSO-$d_6$) −60.06 (s, 3F); ESIMS found for $C_{28}H_{34}F_3N_7O_3$ m/z 574 (M+H).

30

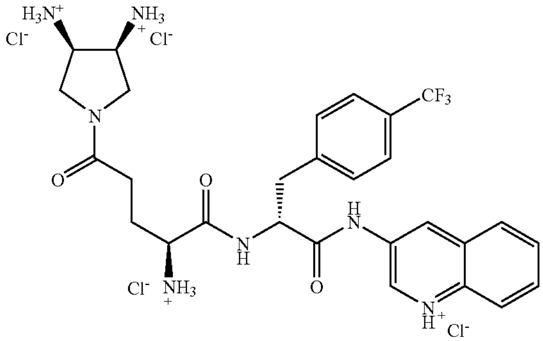

3-[(1S)-1-{[(1R)-1-carbamoyl-2-[4-(trifluoromethyl)phenyl]ethyl]carbamoyl}-4-[(3R,4S)-3,4-diazaniumylpyrrolidin-1-yl]-4-oxobutan-1-aminium]quinolin-1-ium tetrachloride 30

$^1$H NMR (DMSO-$d_6$) 1.56-1.85 (m, 4H), 2.04-2.28 (m, 2H), 2.89-3.14 (m, 2H), 3.30-3.40 (m, 2H), 3.97-4.10 (m, 3H), 4.81-5.05 (m, 1H), 7.68-7.91 (m, 4H), 8.06-8.20 (m, 4H), 8.30 (brs, 3H), 8.92 (brs, 3H), 8.99-9.12 (m, 4H), 9.24 (d, J=8 Hz, 1H), 9.31-9.38 (m, 1H), 11.51 (brs, 1H); $^{19}$F NMR (DMSO-$d_6$) −60.06 (s, 3F); ESIMS found for $C_{28}H_{32}F_3N_7O_3$ m/z 572 (M+H).

31

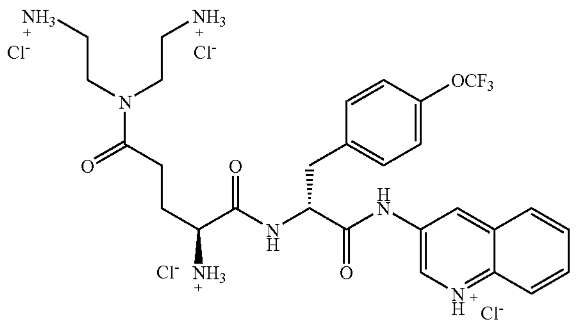

3-[(1S)-3-[bis(2-azaniumylethyl)carbamoyl]-1-{[(1R)-1-carbamoyl-2-[4-(trifluoromethoxy)phenyl]ethyl]carbamoyl}propan-1-aminium]quinolin-1-ium tetrachloride $^1$H NMR (DMSO-$d_6$) 1.66-1.93 (m, 2H), 2.80-3.14 (m, 6H), 3.21-3.37- (m, 2H), 3.50-3.78 (m, 4H), 3.88-4.01 (m, 1H), 4.81-4.97 (m, 1H), 7.26 (d, J=8 Hz, 2H), 7.53 (d, J=8 Hz, 2H), 7.63-7.84 (m, 2H), 8.03 (s, 1H), 8.06 (brs, 3H), 8.10 (s, 1H), 8.35 (brs, 6H), 8.89 (d, J=2 Hz, 1H), 9.19 (s, 1H), 9.24 (d, J=2 Hz, 1H), 11.35 (s, 1H); $^{19}$F NMR (DMSO-$d_6$) −56.13 (s, 3F); ESIMS found for $C_{28}H_{34}F_3N_7O_4$ m/z 590 (M+H).

32

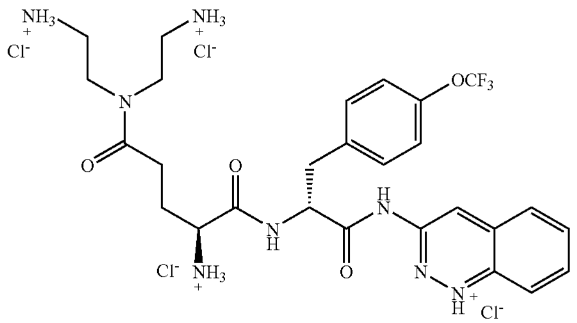

3-[(1S)-3-[bis(2-azaniumylethyl)carbamoyl]-1-{[(1R)-1-carbamoyl-2-[4-(trifluoromethoxy)phenyl]ethyl]carbamoyl}propan-1-aminium]cinnolin-1-ium tetrachloride 32

$^1$H NMR ($CD_3OD$) 1.65-1.79 (m, 1H), 1.90-2.10 (m, 1H), 2.64-2.74 (m, 2H), 3.15-3.26 (m, 4H), 3.60-3.75 (m, 4H), 4.08-4.16 (m, 1H), 4.20-4.36 (m, 1H), 4.95-5.00 (m, 1H), 5.04-5.13 (m, 1H), 7.22 (d, J=8 Hz, 2H), 7.50 (d, J=8 Hz, 2H), 7.83-7.88 (m, 2H), 7.96-8.02 (m, 1H), 8.35-8.40 (m, 1H), 8.86 (s, 1H); $^{19}$F NMR (DMSO-$d_6$) −58.82 (s, 3F); ESIMS found for $C_{27}H_{33}F_3N_8O_4$ m/z 591 (M+H).

33

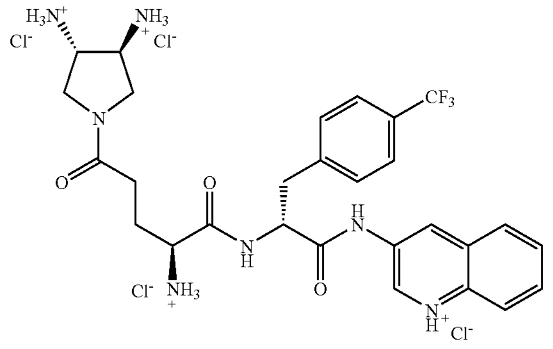

3-[(1S)-1-{[(1R)-1-carbamoyl-2-[4-(trifluoromethyl)phenyl]ethyl]carbamoyl}-4-[(3S,4S)-3,4-diazaniumylpyrrolidin-1-yl]-4-oxobutan-1-aminium]quinolin-1-ium tetrachloride 33

$^1$H NMR (DMSO-$d_6$) 1.56-1.85 (m, 4H), 2.04-2.28 (m, 2H), 2.89-3.14 (m, 2H), 3.30-3.40 (m, 2H), 3.97-4.10 (m, 3H), 4.81-5.05 (m, 1H), 7.68-7.91 (m, 4H), 8.06-8.20 (m, 4H), 8.30 (brs, 3H), 8.92 (brs, 3H), 8.99-9.12 (m, 4H), 9.24 (d, J=8 Hz, 1H), 9.31-9.38 (m, 1H), 11.51 (brs, 1H); $^{19}$F NMR (DMSO-$d_6$) −60.06 (s, 3F); ESIMS found for $C_{28}H_{32}F_3N_7O_3$ m/z 572 (M+H).

38

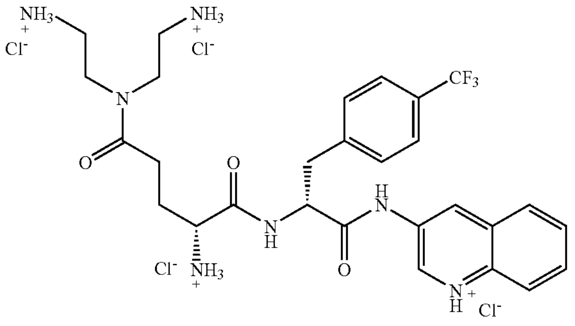

3-[(1R)-3-[bis(2-azaniumylethyl)carbamoyl]-1-{[(1R)-1-carbamoyl-2-[4-(trifluoromethyl)phenyl]ethyl]carbamoyl}propan-1-aminium]quinolin-1-ium tetrachloride 38

$^1$H NMR (DMSO-$d_6$) 1.88-2.04 (m, 2H), 2.86-3.19 (m, 6H), 3.21-3.41 (m, 2H), 3.47-3.60 (m, 2H), 3.63-3.74 (m, 2H), 3.83-3.95 (m, 1H), 4.75-5.02 (m, 1H), 7.60-7.71 (m, 3H), 7.72-7.85 (m, 3H), 7.98-8.16 (m, 5H), 8.36 (brs, 6H), 8.93 (brs, 1H), 9.19-9.30 (m, 1H), 9.53 (d, J=7 Hz, 1H), 11.66 (brs, 1H); ESIMS found for $C_{28}H_{34}F_3N_7O_3$ m/z 574 (M+H).

41

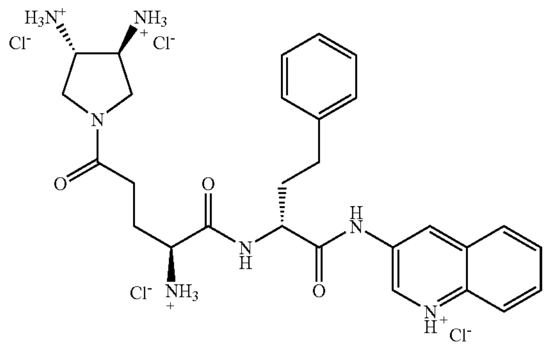

3-[(1S)-1-{[(1R)-1-carbamoyl-3-phenylpropyl]carbamoyl}-4-[(3S,4S)-3,4-diazaniumylpyrrolidin-1-yl]-4-oxobutan-1-aminium]quinolin-1-ium tetrachloride 41

$^1$H NMR (DMSO-$d_6$) 2.13-2.20 (m, 1H), 2.40-2.46 (m, 2H), 2.57-2.85 (m, 2H), 3.46-3.64 (m, 2H), 3.79-3.88 (m, 3H), 3.93-4.13 (m, 5H), 4.48-4.57 (m, 1H), 7.12-7.20 (m, 1H), 7.21-7.35 (m, 4H), 7.65-7.73 (m, 1H), 7.75-7.84 (m, 1H), 8.02-8.15 (m, 1H), 8.44 (brs, 3H), 8.89 (brs, 3H), 8.94 (brs, 1H), 9.01 (brs, 3H), 9.19-9.37 (m, 2H), 11.11 (brs, 1H); ESIMS found for $C_{28}H_{35}N_7O_3$ m/z 518 (M+H).

47

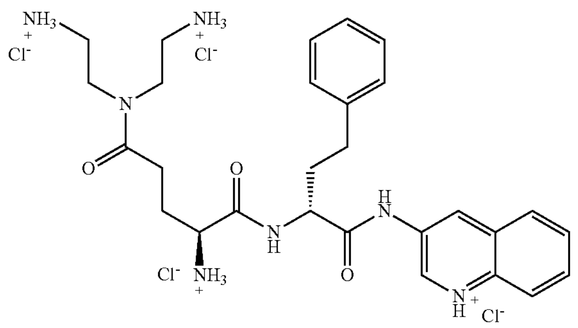

3-[(1S)-3-[bis(2-azaniumylethyl)carbamoyl]-1-{[(1R)-1-carbamoyl-3-phenylpropyl]carbamoyl}propan-1-aminium] quinolin-1-ium tetrachloride 47

$^1$H NMR (DMSO-$d_6$) 1.98-2.18 (m, 4H), 2.55-2.67 (m, 2H), 2.69-2.80 (m, 2H), 2.87-2.97 (m, 2H), 2.97-3.07 (m, 2H), 3.56-3.66 (m, 4H), 4.00-4.05 (m, 1H), 4.45-4.55 (m, 1H), 7.12-7.28 (m, 5H), 7.62 (t, J=7 Hz, 1H), 7.72 (t, J=7 Hz, 1H), 7.95 (brs, 3H), 7.98 (d, J=9 Hz, 1H), 8.01 (d, J=8 Hz, 1H), 8.28 (brs, 3H), 8.40 (brs, 3H), 8.81 (s, 1H), 9.14 (d, J=2 Hz, 1H), 9.21 (d, J=7 Hz, 1H), 10.94 (s, 1H); ESIMS found for $C_{28}H_{37}N_7O_3$ m/z 520 (M+H).

Synthesis of 3-[(1S)-3-[bis(2-azaniumylethyl)carbamoyl]-1-{[(1E)-1-carbamoyl-2-[4-(trifluoromethyl)phenyl]eth-1-en-1-yl]carbamoyl}propan-1-aminium]quinolin-1-ium tetrachloride 4 is depicted below in scheme 3 and example 3.

Scheme 3

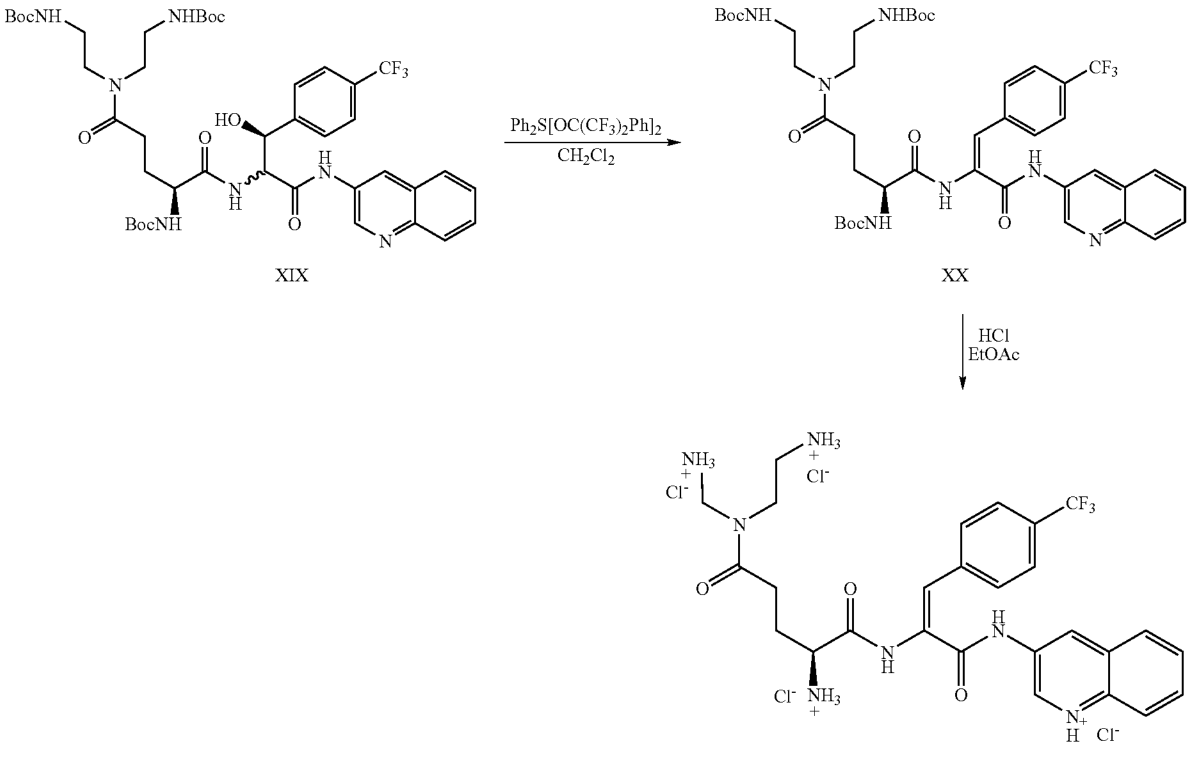

XIX

XX

4

EXAMPLE 3

Preparation of tert-butyl N-{2-[(2S)-2-{[(tert-butoxy)carbonyl]amino}-N-(2-{[(tert-butoxy)carbonyl]amino}ethyl)-N'-[(2S)-2-hydroxy-1-[(quinolin-3-yl)carbamoyl]-2-[4-(trifluoromethyl)phenyl]ethyl]pentanediamido]ethyl}carbamate XIX was performed following procedures listed in example 2.

Step 1

To a solution of compound XIX (0.26 g, 0.29 mmol) in dry DCM (5 mL) was added Martin's sulfurane (0.29 g, 0.43 mmol). The reaction mixture was stirred overnight at r.t. before the solvent was removed under reduced pressure. The residue was purified on a silica gel column (100:1 DCM:MeOH) to produce tert-butyl N-{2-[(2S)-2-{[(tert-butoxy)carbonyl]amino}-N-(2-{[(tert-butoxy)carbonyl]amino}ethyl)-N'-[(1E)-1-[(quinolin-3-yl)carbamoyl]-2-[4-(trifluoromethyl)phenyl]eth-1-en-1-yl]pentanediamido]ethyl}carbamate XX (0.13 g, 0.15 mmol, 52% yield). ESIMS found for $C_{43}H_{56}F_3N_7O_9$ m/z 872 (M+H).

Step 2

Procedure can be found in examples 1-2. The final compound 4 was isolated as the hydrochloride salt. $^1$H NMR (DMSO-$d_6$) 2.71-2.83 (m, 1H), 2.87-3.16 (m, 5H), 3.45-3.68 (m, 6H), 4.11-4.25 (m, 1H), 7.28 (s, 1H), 7.56-7.67 (m, 1H), 7.70-7.84 (m, 3H), 7.88-8.12 (m, 7H), 8.29 (brs, 3H), 8.57 (brs, 3H), 8.87 (brs, 1H), 9.25 (brs, 1H), 10.64 (brs, 1H), 10.96 (brs, 1H); $^{19}$F NMR (DMSO-$d_6$) −60.48 (s, 3F); ESIMS found for $C_{28}H_{32}F_3N_7O_3$ m/z 572 (M+H).

Synthesis of 3-[(1S)-3-[bis(2-azaniumylethyl)carbamoyl]-1-{[(1S)-1-carbamoyl-2-[4-(trifluoromethyl)phenyl]ethyl](methyl)carbamoyl}propan-1-aminium]quinolin-1-ium tetrachloride 5 is depicted below in scheme 4 and example 4.

Scheme 4

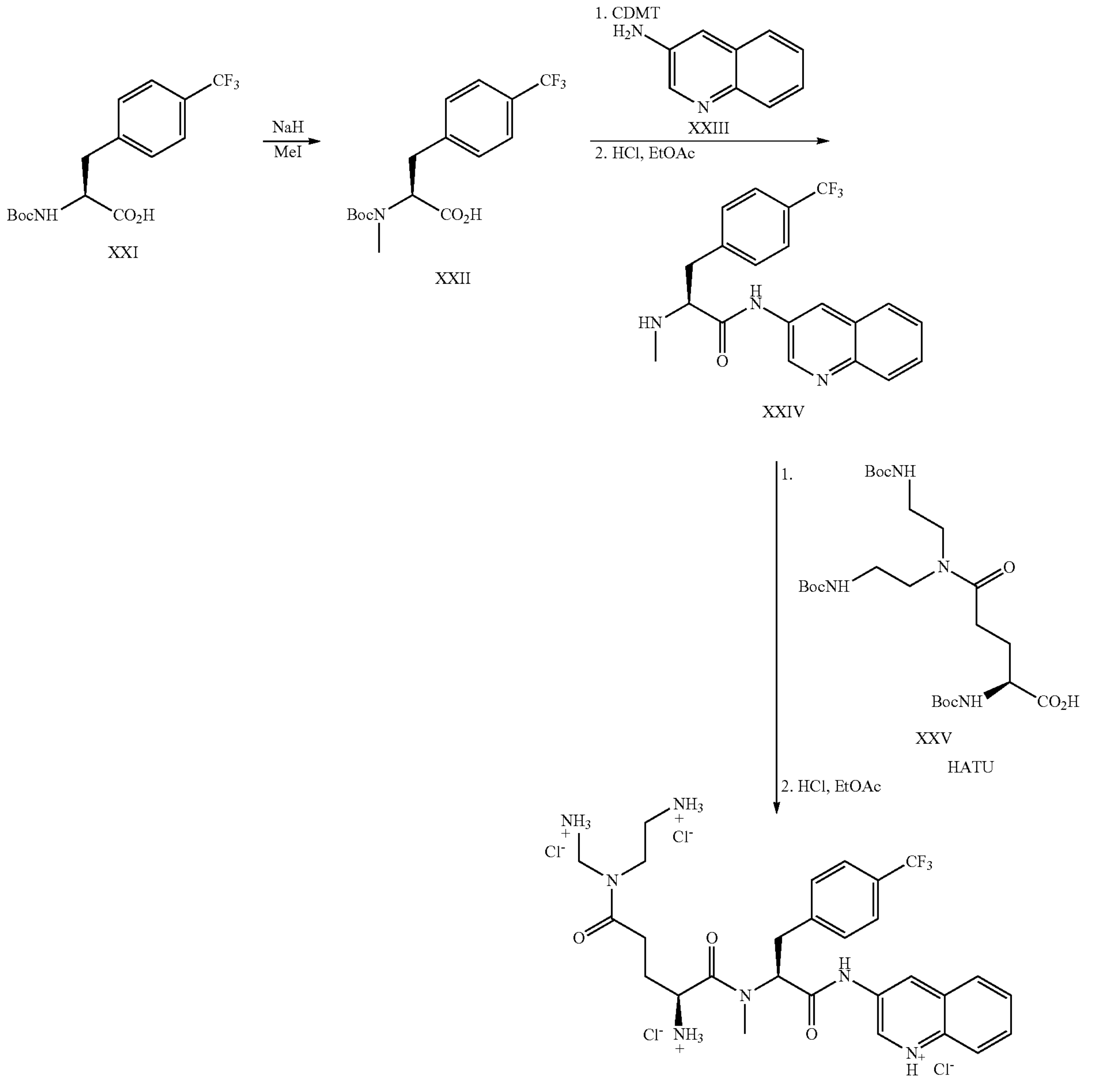

XXI XXII XXIII XXIV XXV

EXAMPLE 4

Step 1

To a solution of (2R)-2-[(tert-butoxycarbonyl)amino]-3-[4-(trifluoromethyl)phenyl]propanoic acid XXI (1 g, 3 mmol) in dry THF (10 mL) was added sodium hydride (60% suspension in mineral oil) (0.72 g, 18 mmol; 6 eq. of pure NaH) in portions. Methyl iodide (1.12 mL, 18 mmol) was then added and the mixture was stirring at r.t. for 3 days. The mixture was then treated with water before removing the THF under reduced pressure. The aqueous phase was acidified and extracted 2× EtOAc. The combined EtOAc was washed with sodium thiosulfate, dried and evaporated under reduced pressure. The residue was crystallized to produce (2R)-2-[(tert-butoxycarbonyl)(methyl)amino]-3-[4-(trifluoromethyl)phenyl]-propanoic acid XXII (0.73 g, 2 mmol, 70% yield).

Step 2-5

Procedures can be found in examples 1-2. The final compound 5 was isolated as the hydrochloride salt. $^{1}$H NMR (DMSO-$d_6$) 2.64-287 (m, 2H), 2.89-3.00 (m, 2H), 3.00-3.05 (m, 2H), 3.14 (s, 3H), 3.20-3.46 (m, 2H), 3.47-3.74 (m, 6H), 4.40 (s, 1H), 5.32 (s, 1H), 7.53-7.80 (m, 6H), 7.95-8.15 (m, 5H), 8.25-8.45 (m, 6H), 8.89 (s, 1H), 9.18 (s, 1H), 11.02 (s, 1H); $^{19}$F NMR (DMSO-$d_6$) −60.10 (s, 3F); ESIMS found for $C_{30}H_{37}F_3N_6O_3$ m/z 588 (M+).

Synthesis of 3-[(1S)-4-[bis({2-[(azaniumylmethanimidoyl)amino]ethyl}) amino]-1-{[(1R)-1-carbamoyl-3-phenylpropyl]carbamoyl}butan-1-aminium]quinolin-1-ium tetrachloride 6 is depicted below in scheme 5 and example 5.

Scheme 5

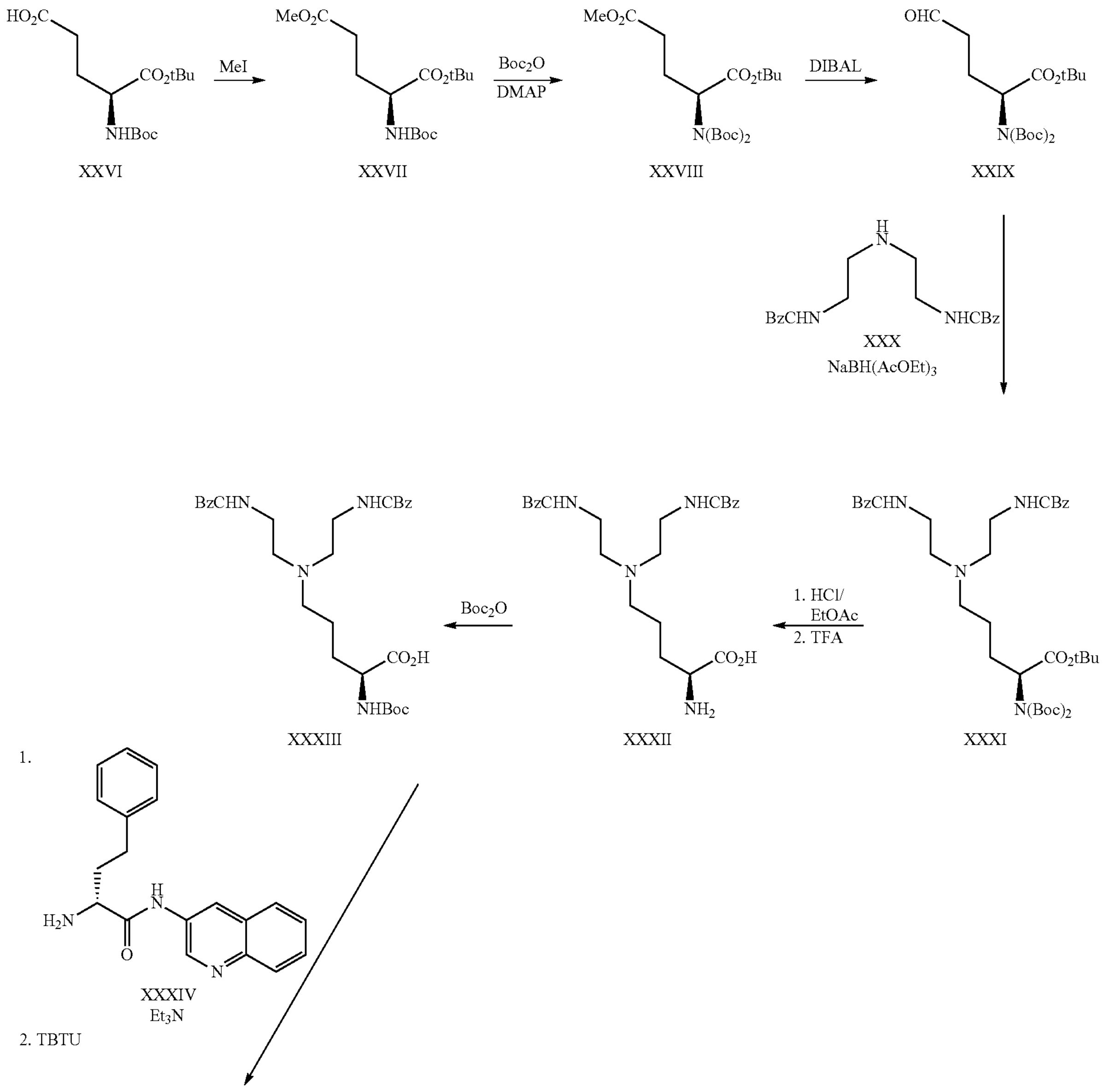

XXVI XXVII XXVIII XXIX XXX XXXI XXXII XXXIII XXXIV

-continued

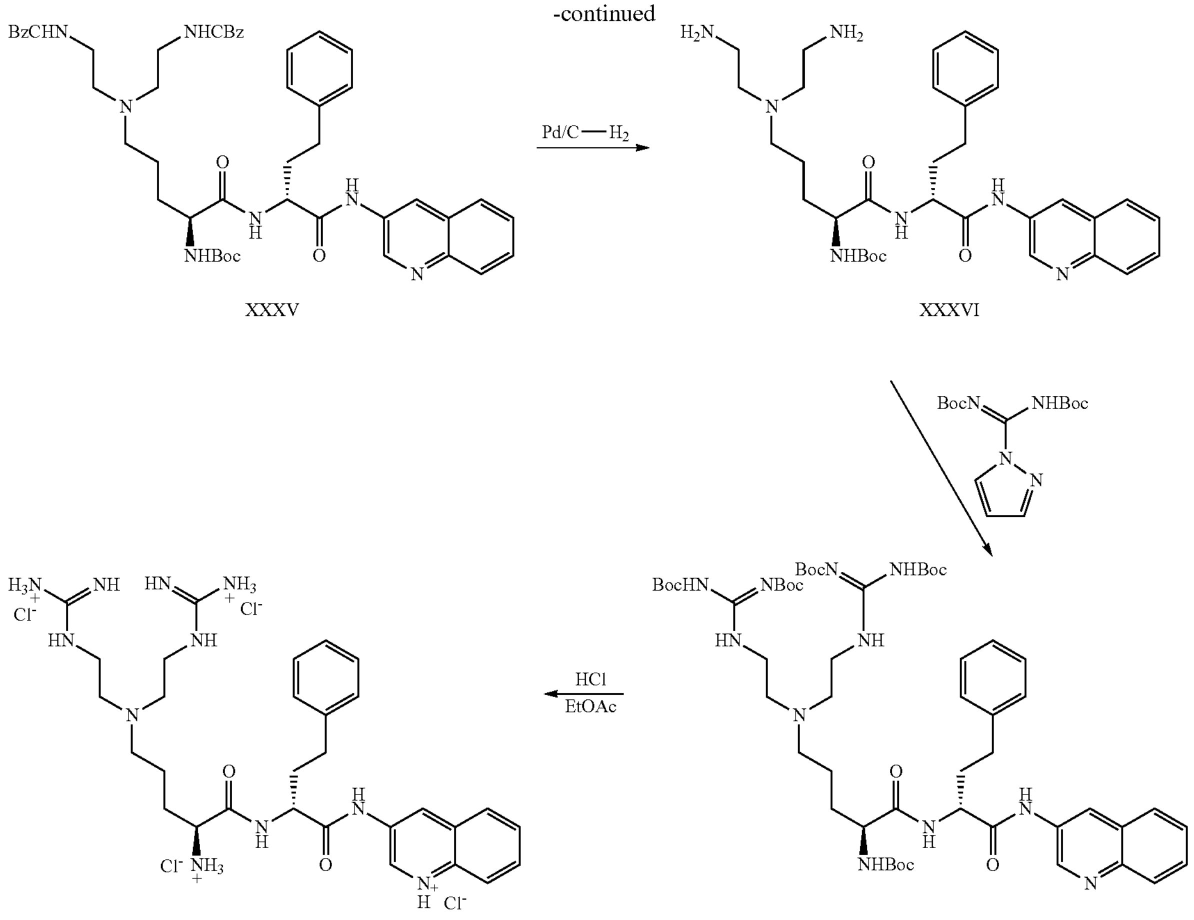

XXXV XXXVI XXXVII 6

EXAMPLE 5

Step 1

To a solution of Boc-glutamic acid tert-butyl ester XXVI (50 g, 164.8 mmol) and $K_2CO_3$ (34.2 g, 247.2 mmol) in DMF (250 mL) was added MeI (10.8 ml, 173.1 mmol) dropwise. The reaction mixture was stirred at r.t. for 2 h before adding ethyl acetate. The organic extract was washed 10% $Na_2S_2O_3$ (3×) and dried over $MgSO_4$. The solvent was removed under reduced pressure and the crude product was crystallized from hexane to give the product XXVII as a white solid (50.7 g, 159.8 mmol, 95% yield). $^1$H NMR ($CDCl_3$) 1.44 (s, 9H), 1.46 (s, 9H), 1.86-1.96 (m. 11H), 2.08-2.20 (m, 1H), 2.32-2.46 (m, 2H), 3.46 (m, 2H), 3.68 (s, 3H), 4.17-4.21 (m, 1H); ESIMS found for $C_{15}H_{27}NO_6$ m/z 318 (M+H).

Step 2

To a solution of 1-tert-butyl 5-methyl (2S)-2-{[(tert-butoxy)carbonyl]amino}pentanedioate XXVII (50.7 g, 159.8 mmol), TEA (26.6 mL, 191.7 mmol) and DMAP (19.5 g, 159.8 mmol) in MeCN (480 mL) was added di-tert-butyl dicarbonate (69.7 g, 319.5 mmol). The reaction mixture was stirred at r.t. overnight before adding additional TEA (11.1 mL, 79.0 mmol), DMAP (9.8 g, 79.9 mmol) and $Boc_2O$ (34.8 g, 159.8 mmol) and stirring for another 2 days. The solvent was removed under reduced pressure and residue was purified on a silica gel column (1:100-1:50-1:30 EtOAc:hexane) to give pure product XXVIII as colorless oil. (50.0 g, 119.8 mmol, 75% yield). $^1$H NMR ($CDCl_3$) 1.44 (s, 9H), 1.49 (s, 18H), 2.15 (ddd, J=3 Hz, J=8 Hz, J=19 Hz, 1H), 2.33-2.46 (m, 3H), 3.66 (s, 3H), 4.75 (m, 1H); ESIMS found for $C_{20}H_{35}NO_8$ m/z 857 (2M+23).

Step 3

To a solution of 1-tert-butyl 5-methyl (2S)-2-{bis[(tert-butoxy)carbonyl]amino}pentanedioate XXVIII (50.0 g, 119.8 mmol) in dry ethyl ether (120 mL) at −78° C. under Ar was added a solution of DIBAL (65.0 mL, 65.0 mmol). The reaction mixture was stirred 1.5-2.5 hours at −78° C. The mixture was treated with MeOH (240 mL) and allowed to warm to r.t. The suspension was filtered through Celite and washed with methanol. The solvent was removed under reduced pressure and the residue was purified on a silica gel column (1:20 EtOAc:hexane) to give pure product XXIX as a colorless oil. (37.1 g, 95.8 mmol, 80% yield). $^1$H NMR ($CDCl_3$) 1.44 (s, 9H), 1.47 (s, 18H), 2.07-2.15 (m, 1H), 2.37-2.56 (m, 3H), 4.70 (dd, J=5 Hz, J=10 Hz, 1H), 9.73 (s, 1H); ESIMS found for $C_{19}H_{33}NO_7$ m/z 410 (M+23).

Step 4

To a solution of benzyl N-{2-[(2-{[(benzyloxy)carbonyl]amino}ethyl)amino]ethyl}carbamate XXX (13.34 g, 35.92 mmol) in dry DCM (100 mL) was added acetic acid (9.34 mL, 163.25 mmol). The mixture was cooled with water/ice bath before adding tert-butyl (2S)-2-{bis[(tert-butoxy)carbonyl] amino}-5-oxopentanoate XXIX. The reaction mixture was stirred for 1 h at 0° C. and then sodium triacetoxyborohydride (10.37 g, 48.98 mmol) was added in portions. The reaction mixture was stirred at r.t. overnight. The reaction was washed with water, 1 M HCl, brine and dried over $MgSO_4$. The solvent was removed under reduced pressure and product was purified on a silica gel column (ethyl acetate:hexane (1:15→1:10→1:10→1:1 EtOAc:hexane→100% EtOAc) to give the protected amino acid XXXI as yellow oil (15.12 g, 20.35 mmol, 57% yield). $^1$H NMR ($CDCl_3$) 1.44 (s, 9H), 1.50 (s, 18H), 1.70-1.98 (m, 4H), 2.00-2.16 (m, 2H), 3.15 (brs, 4H), 3.56 (brs, 4H), 4.55-4.67 (m, 1H), 5.08 (s, 4H), 6.36 (brs, 2H), 7.32 (brs, 10H); ESIMS found for $C_{39}H_{58}N_4O_{10}$ m/z 743 (M+H).

Step 5

To a solution of tert-butyl (2S)-5-[bis(2-{[(benzyloxy)carbonyl]amino}ethyl)amino]-2-{bis[(tert-butoxy)carbonyl] amino}pentanoate XXXI (3.00 g, 4.04 mmol) in ethyl acetate (20 mL) was added HCl (3.5 M solution in EtOAc, 20 mL). The reaction mixture was stirred for 30 min at r.t. before adding ethyl ether (about 50 mL). The precipitate was filtered and washed with ether to give (2S)-5-[bis(2-{[(benzyloxy) carbonyl]amino}ethyl)amino]-2-{bis[(tert-butoxy)carbonyl]amino}pentanoic acid as a white crystalline solid (1.82 g, 3.14 mmol, 78% yield).

Step 6

A solution of (2S)-5-[bis(2-{[(benzyloxy)carbonyl] amino}ethyl)amino]-2-{bis[(tert-butoxy)carbonyl] amino}pentanoic acid (1.82 g, 3.14 mmol) in TFA (20 mL) was stirred overnight. The TFA was removed under reduced pressure to give (2S)-2-amino-5-[bis(2-{[(benzyloxy)carbonyl]amino}ethyl)amino]pentanoic acid XXXII as a light brown foam (1.70 g, 2.83 mmol, 90% yield). ESIMS found for $C_{25}H_{34}N_4O_6$ m/z 487 (M+H).

Step 7

To a solution of (2S)-2-amino-5-[bis(2-{[(benzyloxy)carbonyl]amino}ethyl)amino]pentanoic acid XXXII (1.70 g, 2.83 mmol) in water (20 mL) was added $K_2CO_3$ followed by a solution of $Boc_2O$ (0.80 g, 3.68 mmol) in acetone (15 mL). The reaction mixture was stirred for 1 h with additional portions of $K_2CO_3$ being added to maintain the pH of 10. The mixture was stirred overnight and then the acetone was evaporated under reduced pressure and alkalized to pH=12. The aqueous residue was washed with diethyl ether (2×) and acidified with 6 N HCl to pH=2. The aqueous phase was washed with DCM (4×) and the combined DCM extracts were washed with brine and dried over $MgSO_4$. The solvent was removed under reduced pressure and product was purified on a silica gel column (100:1→50:1→30:1→20:1 EtOAc:MeOH) to give (2S)-5-[bis(2-{[(benzyloxy)carbonyl]amino}ethyl)amino]-2-{[(tert-butoxy)carbonyl] amino}pentanoic acid XXXIII (1.35 g, 3.30 mmol, 81% yield). $^1$H NMR ($CDCl_3$) 1.41 (s, 9H), 1.83 (brs, 4H), 3.25 (brs, 6H), 3.55 (brs, 4H), 4.23 (brs, 1H), 5.07 (s, 4H), 5.72 (brs, 1H), 6.10 (brs, 1H), 6.68 (brs, 1H), 7.32 (brs, 10H); ESIMS found for $C_{30}H_{42}N_4O_8$ m/z 587 (M+H).

Step 8-9

Procedures can be found in examples 1-2.

Step 10

A solution of pyrazolecarboxamidine (1.15 g, 3.70 mmol) and tert-butyl N-[(1S)-4-[bis(2-aminoethyl)amino]-1-{[(1R)-3-phenyl-1-[(quinolin-3-yl)carbamoyl]propyl] carbamoyl}butyl]carbamate XXXVI (0.75 g, 1.20 mmol) in THF/MeOH (10 mL/10 mL) was stirred at r.t. overnight. The solvent was removed under vacuum and the residue was dissolved in DCM washed with 1 M HCl, brine and dried over $MgSO_4$. The crude product was purified on a silica gel column (1:1→3:1→5:1 EtOAc:hexane→100% EtOAc→100:1 EtOAc/MeOH) to give tert-butyl N-[(1Z)-{[(tert-butoxy)carbonyl]amino}({2-[(2-{[(1Z)-{[(tert-butoxy)carbonyl] amino}({[(tert-butoxy)carbonyl]imino})methyl] amino}ethyl)[(4S)-4-{[(tert-butoxy)carbonyl]amino}-4-{[(1R)-3-phenyl-1-[(quinolin-3-yl)carbamoyl]propyl] carbamoyl}butyl]amino]ethyl}amino)methylidene]carbamate XXXVII (120 mg, 0.11 mmol, 15% yield). ESIMS found for $C_{56}H_{84}N_{10}O_{12}$ m/z 1090 (M+H).

Step 11

Procedure can be found in examples 1-2. The final compound 6 was isolated as the hydrochloride salt. $^1$H NMR (DMSO-$d_6$) 1.58-1.81 (m, 4H), 1.82-1.90 (m, 1H), 1.91-1.99 (m, 1H), 2.41-2.50 (m, 1H), 2.52-2.63 (m, 1H), 3.09 (brs, 6H), 3.24-3.31 (m, 1H), 3.52 (brs, 3H), 3.86 (brs, 1H), 4.26-4.33 (m, 1H), 6.92 (brs, 1H), 7.04 (brs, 4H), 7.38 (brs, 3H), 7.49-7.55 (m, 1H), 7.59-7.65 (m, 1H), 7.81-7.91 (m, 2H), 7.93-7.98 (m, 1H), 8.34 (brs, 3H), 8.42 (brs, 3H), 8.73 (s, 1H), 8.85 (s, 1H), 9.16 (s, 1H), 10.99 (s, 1H), 11.09 (s, 1H), 11.26 (brs, 1H); ESIMS found for $C_{30}H_{43}N_{11}O_2$ m/z 590 (M+).

The following compounds were prepared in accordance with the procedure described in the above example 5.

46

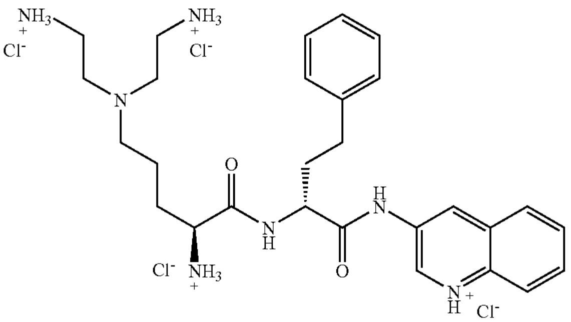

3-[(1S)-4-[bis(2-azaniumylethyl)amino]-1-{[(1R)-1-carbamoyl-3-phenylpropyl]carbamoyl}butan-1-aminium] quinolin-1-ium tetrachloride 46

$^1$H NMR (DMSO-$d_6$) 1.78-2.00 (m, 4H), 2.01-2.20 (m, 2H), 2.61-2.82 (m, 4H), 3.21-3.40 (m, 4H), 3.53-3.69 (m, 4H), 4.01 (brs, 1H), 4.51-4.59 (m, 1H), 7.16-7.21 (m, 1H), 7.22-7.32 (m, 4H), 7.62 (t, J=8 Hz, 1H), 7.71 (t, J=8 Hz, 1H), 7.97 (d, J=8 Hz, 1H), 8.00 (d, J=8 Hz, 1H), 8.41 (brs, 9H), 8.77 (s, 1H), 9.11 (brs, 1H), 9.24 (d, J=8 Hz, 1H), 10.89 (s, 1H); ESIMS found for $C_{28}H_{39}N_7O_2$ m/z 506 (M+H).

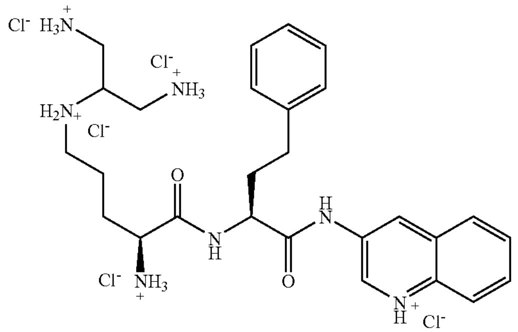

193

3-[(2S)-2-[(4S)-1-N-(1,3-diazaniumylpropan-2-yl)-4-formamidobutane-1,4-bis(aminium)]-4-phenylbutanamido]quinolin-1-ium pentachloride 193

$^1$H NMR (DMSO-$d_6$) 1.71-1.98 (m, 4H), 1.99-2.17 (m, 2H), 2.62-2.73 (m, 1H), 2.76-2.87 (m, 1H), 3.19 (brs, 2H), 3.37-3.46 (m, 5H), 3.79 (brs, 1H), 4.06 (brs, 1H), 4.51-4.60 (m, 1H), 7.11-7.16 (m, 1H), 7.24 (brs, 2H), 7.25 (brs, 2H), 7.64 (dd, J=7 Hz, J=7 Hz, 1H), 7.73 (dd, J=7 Hz, J=7 Hz, 1H), 7.98-8.10 (m, 2H), 8.40 (brs, 3H), 8.59 (brs, 6H), 8.90 (brs, 1H), 9.15 (d, J=1 Hz, 1H), 9.21 (d, J=7 Hz, 1H), 9.95 (brs, 1H), 11.15 (brs, 1H); ESIMS found for $C_{27}H_{37}N_7O_2$ m/z 492.5 (M+H).

Synthesis of 3-[(1S)-4-[bis({2-[(azaniumylmethanimidoyl)amino]ethyl}) amino]-1-{[(1R)-1-carbamoyl-3-phenylpropyl]carbamoyl}butan-1-aminium]quinolin-1-ium tetrachloride 8 is depicted below in scheme 6 and example 6.

Scheme 6

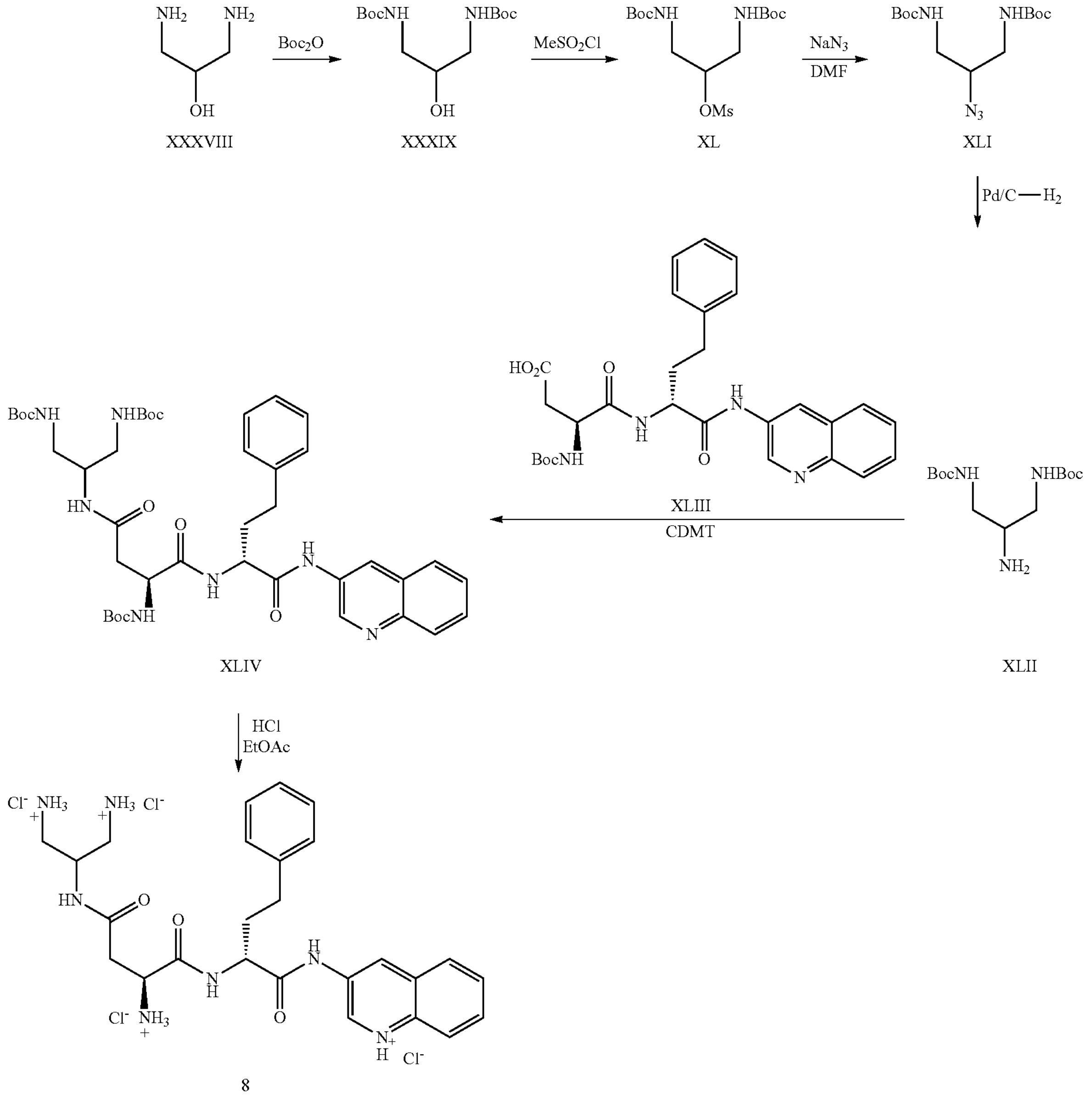

XXXVIII XXXIX XL XLI

XLIV XLII

8

EXAMPLE 6

Step 1

To a solution of 1,3-diamine-2-hydroxypropane (10 g, 110 mmol) in 5% $NaHCO_3$ (pH~9) was added a solution of $Boc_2O$ (97 g, 440 mmol) in acetone (200 mL). The reaction mixture was stirred overnight. The acetone was evaporated under vacuum and aqueous residue was washed 5× EtOAc. The organic layer was washed with brine and dried over $MgSO_4$. The solvent was removed under reduced pressure to give crude product. The product was purified on a silica gel column (1:200→1:150→1:120→100:1→80:1→50:1 MeOH: DCM) to give the pure tert-butyl N-(3-{[(tert-butoxy)carbonyl]amino}-2-hydroxypropyl)carbamate XXXIX as white solid (20.10 g, 69.3 mmol, 62% yield). ESIMS found for $C_{13}H_{26}N_2O_5$ m/z 291 (M+H).

Step 2

To a solution of tert-butyl N-(3-{[(tert-butoxy)carbonyl] amino}-2-hydroxypropyl)carbamate XXXIX (1.83 g, 6.3 mmol) in DCM was added TEA (1.38 mL, 10 mmol) was added. The mixture was cooled to 10° C. before adding mesyl chloride (0.77 mL, 10 mmol) dropwise. The reaction mixture was stirred for 30 min and then the solvent was removed under reduced pressure. The residue was dissolved in DCM, washed 1 M HCl (3×), 5% $NaHCO_3$ and dried over $MgSO_4$. The solvent was again removed under vacuum to give tert-butyl N-(3-{[(tert-butoxy)carbonyl]amino}-2-(methanesulfonyloxy)propyl)carbamate XL (2.31 g, 6.3 mmol, 99% yield). ESIMS found for $C_{14}H_{28}N_2O_7S$ m/z 369 (M+H).

Step 3

To a solution of tert-butyl N-(3-{[(tert-butoxy)carbonyl] amino}-2-(methanesulfonyloxy)propyl)carbamate XL (2.31 g, 6.6 mmol) in DMF was added $NaN_3$. The mixture was heated overnight at 60° C., diluted with DCM and washed with 10% $Na_2S_2O_3$ (5×), 5% $NaHCO_3$, brine and dried over $MgSO_4$. The solvent was evaporated under vacuum to give crude product (1.75 g). The product was purified on a silica gel column (1:10 EtOAc:hexane) to give the pure tert-butyl N-(2-azido-3-{[(tert-butoxy)carbonyl]amino}propyl)carbamate XLI as white crystals (1.33 g, 4.2 mmol, 67% yield). $^1$H NMR ($CDCl_3$) 1.47 (s, 18H), 3.07-3.26 (m, 2H), 3.27-3.53 (m, 2H), 3.59-3.75 (m, 1H), 5.06 (brs, 2H); ESIMS found for $C_{13}H_{25}N_5O_4$ m/z 316 (M+H).

Step 4

To a solution of the azide XLI (1.33 g, 4.22 mmol) in a mixture of ethanol/water (9:1) was added a catalytic amount of Pd/C. The mixture was stirred under hydrogen overnight. The mixture was filtered through a pad of Celite and the filtrate was concentrated to dryness under vacuum to give tert-butyl N-(2-amino-3-{[(tert-butoxy)carbonyl] amino}propyl)carbamate XLII (0.85 g, 2.94 mmol, 70% yield). $^1$H NMR ($CDCl_3$) 1.46 (s, 18H), 2.88-3.00 (m, 1H), 3.00-3.27 (m, 4H), 5.12 (brs, 2H); ESIMS found for $C_{13}H_{27}N_3O_4$ m/z 290 (M+H).

Step s 5-6

Procedures can be found in examples 1-2. The final compound 8 was isolated as the hydrochloride salt. $^1$H NMR (DMSO-$d_6$) 1.98-2.07 (m, 1H), 2.10-2.17 (m, 1H), 2.65-2.71 (m, 1H), 2.75-2.85 (m, 2H), 2.91-2.96 (m, 2H), 3.04-3.12 (m, 2H), 4.20-4.31 (m, 2H), 4.40-4.52 (m, 2H), 7.13-7.19 (m, 1H), 7.25-7.26 (m, 4H), 7.61 (dd, J=8 Hz, J=8 Hz, 1H), 7.69 (dd, J=8 Hz, J=7 Hz, 1H), 7.97-8.09 (m, 2H), 8.25 (brs, 6H), 8.20-8.32 (m, 3H), 8.63 (d, J=8 Hz, 1H), 8.78 (s, 1H), 9.06-9.10 (m, 1H), 9.23 (d, J=7 Hz, 1H), 10.86 (s, 1H); ESIMS found for $C_{26}H_{33}N_7O_3$ m/z 492 (M+H).

The following compounds were prepared in accordance with the procedure described in the above example 6:

190

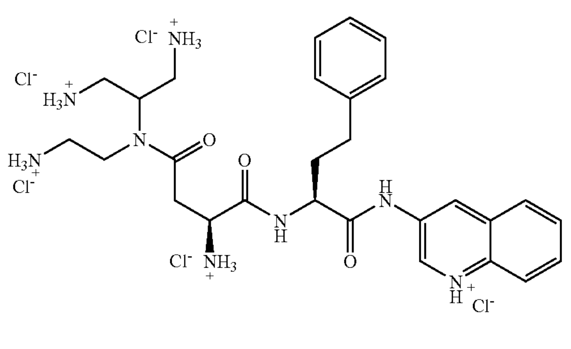

3-[(1S)-2-[(2-azaniumylethyl)(1,3-diazaniumylpropan-2-yl)carbamoyl]-1-{[(1S)-1-carbamoyl-3-phenylpropyl] carbamoyl}ethan-1-aminium]quinolin-1-ium pentachloride 190

$^1$H NMR (DMSO-$d_6$) 2.66-2.88 (m, 2H), 3.07-3.56 (m, 8H), 3.56-3.92 (m, 4H), 4.38-4.59 (m, 3H), 7.09-7.35 (m, 5H), 7.55-7.78 (m, 2H), 8.01 (d, J=8 Hz, 2H), 8.22-8.65 (brs, 8H), 8.81 (s, 1H), 9.05-9.22 (m, 2H), 10.78 (s, 1H); ESIMS found for $C_{28}H_{38}N_8O_3$ m/z 535.7 (M+H).

361

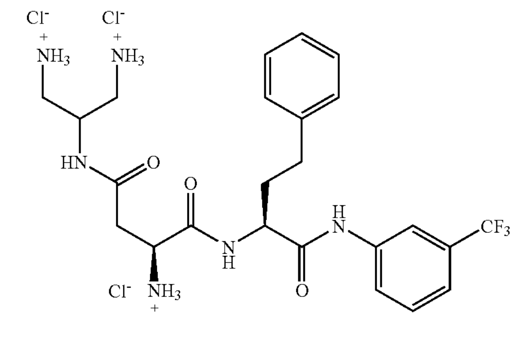

(1S)-2-[(1,3-diazaniumylpropan-2-yl)carbamoyl]-1-{[(1S)-3-phenyl-1-{[3-(trifluoromethyl)phenyl] carbamoyl}propyl]carbamoyl}ethan-1-aminium trichloride 361

$^1$H NMR (DMSO-$d_6$) 1.87-2.07 (m, 2H), 2.57-2.76 (m, 3H), 2.84-2.95 (m, 3H), 2.98-3.06 (m, 2H), 4.19 (brs, 1H), 4.34-4.42 (m, 2H), 7.10 (dd, J=4 Hz, J=4 Hz, 1H), 7.20 (d, J=4 Hz, 4H), 7.32 (d, J=8 Hz, 1H), 7.48 (t, J=8 Hz, 1H), 7.78 (d, J=8 Hz, 1H), 8.09 (s, 1H), 8.23-8.38 (brs, 9H), 8.58 (d, J=8 Hz, 1H), 9.14 (d, J=7 Hz, 1H), 10.65 (s, 1H); $^{19}$F NMR (DMSO-$d_6$) −60.66 (s, 3F); ESIMS found for $C_{24}H_{31}F_3N_6O_3$ m/z 509.7 (M+H).

Synthesis of 3-[(1S)-3-[bis({[bis(2-azaniumylethyl)carbamoyl]methyl}) carbamoyl]-1-{[(1S)-1-carbamoyl-3-phenylpropyl]carbamoyl}propan-1-aminium]quinolin-1-ium hexachloride 9 is depicted below in scheme 7 and example 7.

Scheme 7
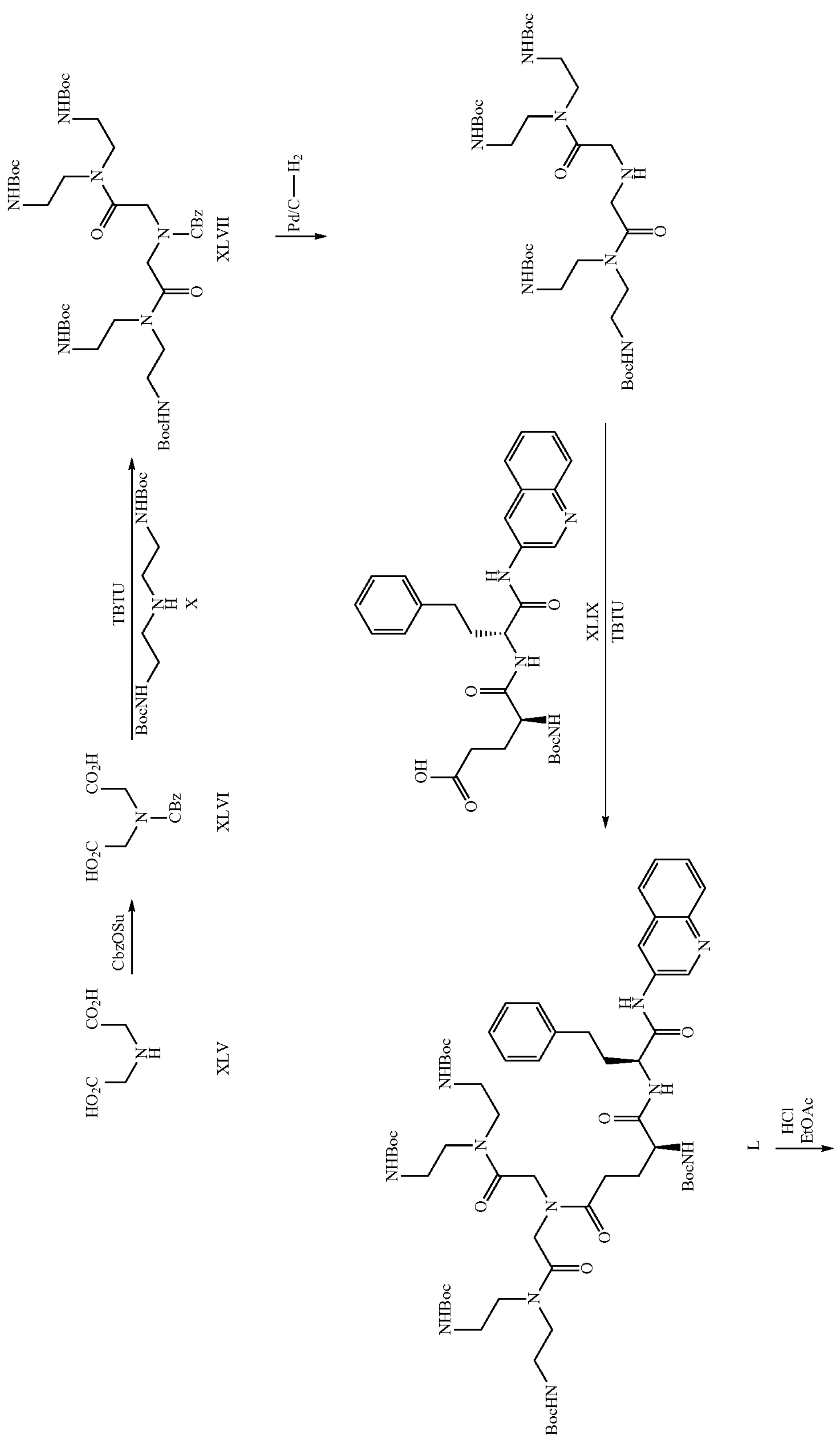

-continued
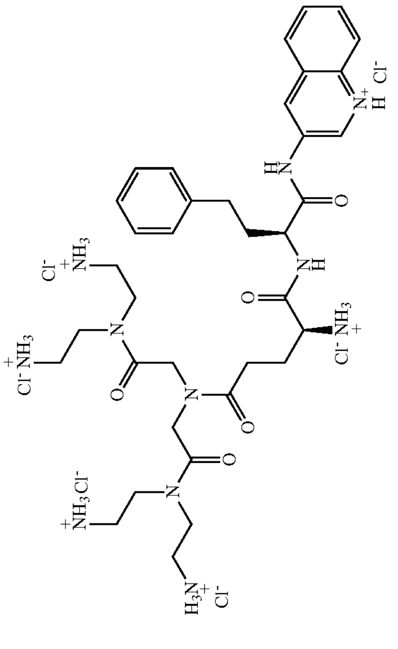
9

EXAMPLE 7

Step 1

To the solution of iminodiacetic acid XLV (10 g, 75.13 mmol) and $K_2CO_3$ (41.53 g, 300.52 mmol) in water (225 mL) was added a solution of CBzOsu (20.6 g, 82.64 mmol) in acetone (150 mL). The mixture was stirred at r.t. overnight. The acetone was evaporated under reduced pressure and the remaining water was washed with ethyl ether (2×). The aqueous layer was acidified to pH=2 with 2 M aq. HCl and then saturated with NaCl, washed with EtOAc (3×). The combined EtOAc was dried over $MgSO_4$ and evaporated under reduced pressure to give 2-{[(benzyloxy)carbonyl](carboxymethyl)amino}acetic acid XLVI (15 g, 56.17 mmol, 75% yield). ESIMS found for $C_{12}H_{13}NO_6$ m/z 290 (M+Na).

Step 2

To the solution of 2-{[(benzyloxy)carbonyl](carboxymethyl)amino}acetic acid XLVI (2 g, 7.5 mmol) in DCM (25 mL) was added DIPEA (3.26 mL, 18.75 mmol), tert-butyl N-{2-[(2-{[(tert-butoxy)carbonyl]amino}ethyl)amino]ethyl}carbamate X (5.69 g 18.75 mmol) and TBTU (6.02 g, 18.75 mmol). The mixture was stirred at r.t. overnight. The reaction mixture was then washed with 1 M $K_2CO_3$, 1 M HCl, brine and dried over $MgSO_4$. The residue was purified on a silica gel column (1:20 EtOAc:hexane) to give tert-butyl N-[2-(2-{[(benzyloxy)carbonyl]({[bis(2-{[(tert-butoxy)carbonyl]amino}ethyl)carbamoyl]methyl})amino}-N-(2-{[(tert-butoxy)carbonyl]amino}ethyl)acetamido)ethyl]carbamate XLVII (5.09 g, 6.07 mmol, 81% yield). $^1H$ NMR ($CDCl_3$) 1.36-1.49 (m, 36H), 3.08-3.59 (m, 20H), 4.02-4.35 (m, 4H), 5.16 (s, 2H), 7.30-7.39 (m, 5H); ESIMS found for $C_{40}H_{67}N_7O_{12}$ m/z 838 (M+H).

Step 3

To the solution of compound XLVII (5.09 g, 6.07 mmol) in EtOH/water (50 mL/8 mL) under an argon atmosphere was added 10% Pd/C (catalytic amount). The reaction was flushed with hydrogen and stirred overnight in r.t. The catalyst was removed by filtration through Celite and the solvents removed under reduced pressure to give tert-butyl N-{2-[2-({[bis(2-{[(tert-butoxy)carbonyl]amino}ethyl)carbamoyl]methyl}amino)-N-(2-{[(tert-butoxy)carbonyl]amino}ethyl)acetamido]ethyl}carbamate XLVIII (4.02 g, 5.71 mmol, 94% yield). ESIMS found for $C_{32}H_{61}N_7O_{10}$ m/z 704 (M+H).

Step 4

To the solution of (4S)-4-{[(tert-butoxy)carbonyl]amino}-4-{[(1S)-3-phenyl-1-[(quinolin-3-yl)carbamoyl]propyl]carbamoyl}butanoic acid XLIX (290 mg; 0.54 mmol) in DCM (10 mL) and DIPEA (0.113 mL; 0.65 mmol) was added the amine XLVIII (460 mg; 0.65 mmol) and TBTU (210 mg; 0.65 mmol). The reaction mixture was stirred overnight before it was diluted with DCM (40 mL), washed once with water, 1 M aqueous HCl (2×), 5% $NaHCO_3$ (2×), water and dried over anhydrous $MgSO_4$. The solvent was evaporated under reduced pressure and crude product crystallized from EtOAc/hexane to give pure tert-butyl N-(2-{2-[(2S)—N-{[bis(2-{[(tert-butoxy)carbonyl]amino}ethyl)carbamoyl]methyl}-2-[{(tert-butoxy)carbonyl]amino}-N'-[(1S)-3-phenyl-1-[(quinolin-3-yl)carbamoyl]propyl]pentanediamido]-N-(2-{[(tert-butoxy)carbonyl]amino}ethyl)acetamido}ethyl)carbamate L as white solid (150 mg; 0.123 mmol; 22.8% yield). $^1H$ NMR ($CDCl_3$) 1.33-1.46 (m, 1H), 1.97-2.06 (m, 1H), 2.07-2.16 (m, 1H), 2.21-2.32 (m, 1H), 2.36-2.49 (brs, 2H), 2.60-2.70 (m, 1H), 2.72-2.85 (m, 2H), 3.13-3.52 (m, 16H), 4.01-4.20 (brs, 2H), 4.25-4.47 (m, 3H), 4.53-4.66 (m, 1H), 5.21-5.35 (m, 1H), 5.38-5.51 (brs, 1H), 5.69-5.81 (m, 1H), 5.82-5.92 (brs, 1H), 6.04-6.11 (brs, 1H), 7.18-7.24 (m, 2H), 7.25-7.31 (m, 6H), 7.50 (dd, J=7 Hz, 1H), 7.59 (dd, J=7 Hz, 1H), 7.78 (d, J=8 Hz, 1H), 8.03 (d, J=9 Hz, 1H), 8.73-8.84 (m, 1H); ESIMS found for $C_{61}H_{93}N_{11}O_{15}$ m/z 1220 (M+H).

Step 5

Procedure can be found in examples 1-2. The final compound 9 was isolated as the hydrochloride salt. $^1H$ NMR (DMSO-$d_6$) 1.84-1.97 (m, 1H), 1.98-2.06 (m, 2H), 2.07-2.19 (m, 1H), 2.61-2.72 (m, 1H), 2.76-2.84 (m, 2H), 2.86-2.96 (m, 2H), 2.97-3.05 (m, 4H), 3.07-3.19 (m, 2H), 3.44-3.56 (m, 6H), 3.57-3.68 (m, 3H), 4.24-4.44 (brs, 3H), 4.50-4.63 (brs, 3H), 7.11-7.17 (m, 1H), 7.21-7.30 (m, 4H), 7.65 (dd, J=7 Hz, J=7 Hz, 1H), 7.74 (dd, J=7 Hz, J=7 Hz, 1H), 8.01-8.10 (m, 5H), 8.11-8.17 (brs, 3H), 8.18-8.25 (brs, 3H), 8.27-8.40 (brs, 3H), 8.41-8.55 (brs, 3H), 8.82-8.90 (brs, 1H), 9.12-9.18 (brs, 1H), 9.24 (d, J=7 Hz, 1H), 11.21-11.31 (brs, 1H); ESIMS found for $C_{36}H_{53}N_{11}O_5$ m/z 720 (M+H).

Synthesis of 3-[(1S)-2-[N',N'-bis(2-azaniumylethyl)hydrazinecarbonyl]-1-{[(1S)-1-carbamoyl-2-[4-(trifluoromethyl)phenyl]ethyl]carbamoyl}ethan-1-aminium]quinolin-1-ium tetrachloride 10 is depicted below in scheme 8 and example 8.

Scheme 8

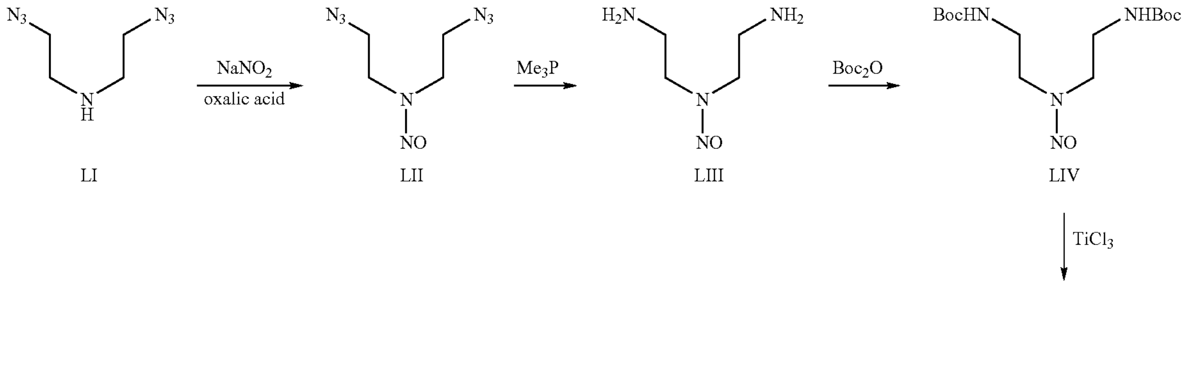

LI LII LIII LIV

-continued

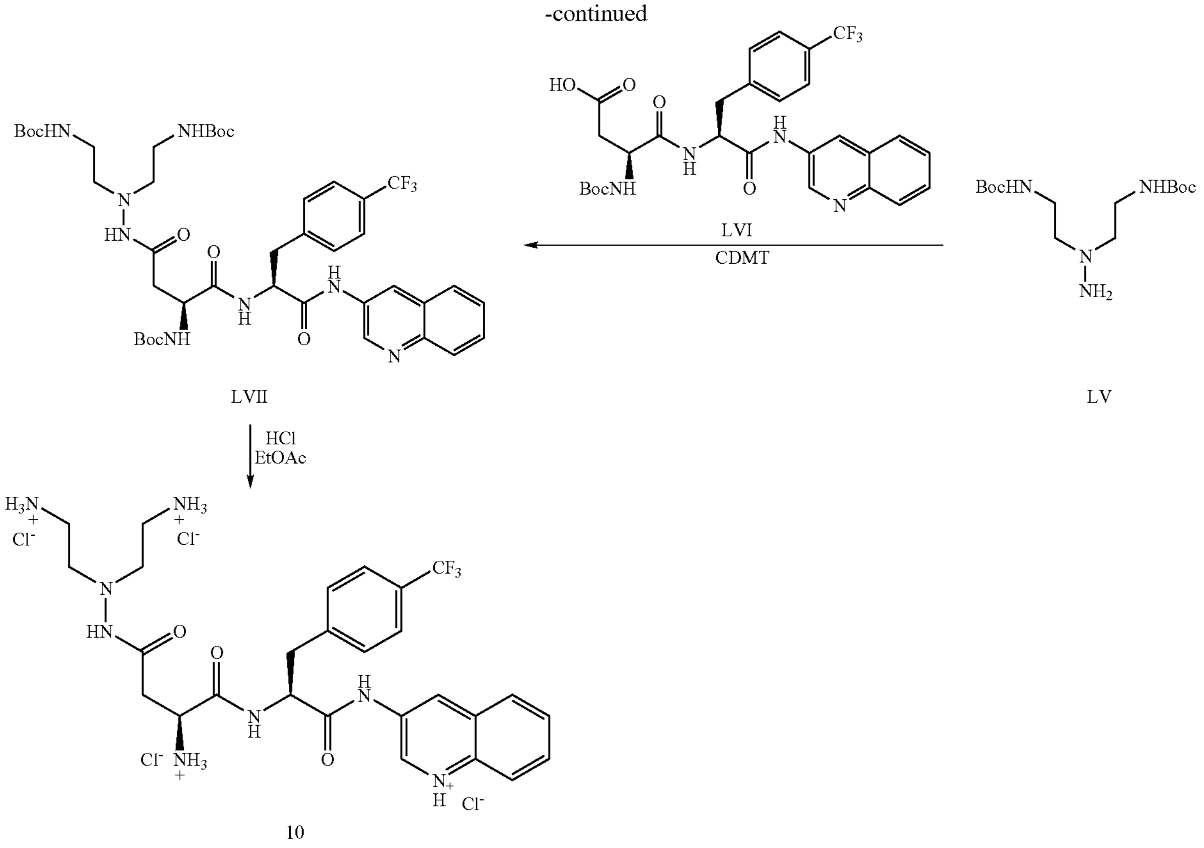

EXAMPLE 8

Step 1

A suspension of sodium nitrate (13.4 g; 0.194 mol), oxalic acid (24.4 g; 0.194 mol) and N,N-bis(2-azidoethyl)amine LI (15 g; 0.097 mol) in DCM (300 mL) was stirred vigorously at r.t. for 2.5 h. Silica gel (20 g) and hexane (200 mL) was added to the reaction mixture and the resulting suspension was filtered. The solids were washed (1:1 hexane/DCM, 200 mL). The solvent was evaporated under reduced pressure to afford N,N-bis(2-azidoethyl)-N-nitrosoamine LII (15 g; 0.081 mol; 84% yield).

Step 2

To a solution of N,N-bis(2-azidoethyl)-N-nitrosoamine LII (15 g; 0.081 mol) in dry THF was slowly added trimethylphosphine (1 M solution in THF; excess) while cooling the mixture reaction in cold water bath. The mixture was stirred overnight. The solution was evaporated under reduced pressure and crude N,N-bis(2-aminoethyl)-N-nitrosoamine LIII (12 g; quantitative yield) was used directly for step 3. ESIMS found for $C_4H_{12}N_4O$ m/z 132.9 (M+H).

Step 3

To a solution of the crude N,N-bis(2-aminoethyl)-N-nitrosoamine LIII (0.081 mol) in acetone (160 mL) was added 1 M aq. $NaHCO_3$ until the pH was 9-10. Di-tert-butyl dicarbonate (53 g; 0.243 mol) was the added in portions and stirred for 3 h. The acetone was evaporated and aqueous solution was extracted with EtOAc (3×). The combined organic phase was dried over $MgSO_4$ and then evaporated. The crude product was purified on a silica gel column (10:1→2:1 hexane/EtOAc) to give tert-butyl N-{2-[(2-{[(tert-butoxy)carbonyl]amino}ethyl)(nitroso)amino]ethyl}carbamate LIV (23.66 g; 0.071 mol; 88% yield). $^1$H NMR ($CDCl_3$) 1.39 (s, 9H), 1.41 (s, 9H), 3.24 (dt, J=6 Hz, J=5 Hz, 2H), 3.52 (dt, J=6 Hz, J=5 Hz, 2H), 3.71 (t, J=6 Hz, 2H), 4.20 (t, J=6 Hz, 2H), 4.93 (brs, 1H), 5.07 (brs, 1H); ESIMS found for $C_{14}H_{28}N_4O_5$ m/z 333.2 (M+H).

Step 4

To a solution of tert-butyl N-{2-[(2-{[(tert-butoxy)carbonyl]amino}ethyl)(nitroso)amino]ethyl}carbamate LIV (2 g; 6.02 mmol) in methanol (15 mL) was added a solution of titanium (III) chloride (3.7 g; 24.07 mmol) in water (20 mL). The mixture was stirred for 1.5 h and then cooled in a ice/water bath before adding KOH (12 g) in portions for 40 min. Stirring was continued for an additional 1 h at r.t. The reaction was filtered, solvent evaporated and purified on a silica gel column (1:1 chloroform/methanol) to obtain crude tert-butyl N-{2-[1-(2-{[(tert-butoxy)carbonyl]amino}ethyl)hydrazin-1-yl]ethyl}carbamate LV (0.85 g) used directly for step 5. ESIMS found for $C_{15}H_{32}N_3O_4$ m/z 319.4 (M+H).

Step 5

Procedure can be found in examples 1-2.

Step 6

Procedure can be found in examples 1-2. The final compound 10 was isolated as the hydrochloride salt. $^1$H NMR (DMSO-$d_6$) 2.70 (dd, J=8 Hz, J=16 Hz, 1H), 2.85-2.94 (m, 5H), 2.99-3.04 (m, 4H), 3.08 (dd, J=11 Hz, J=14 Hz, 1H), 3.25-3.28 (m, 1H), 4.15-4.19 (m, 1H), 4.79-4.84 (m, 1H), 7.64 (d, J=8 Hz, 2H), 7.62-7.66 (m, 1H), 7.70 (d, J=8 Hz, 2H), 7.77 (dd, J=8 Hz, J=8 Hz, 1H), 7.97 (brs, 6H), 8.04 (d, J=9 Hz, 1H), 8.06 (d, J=9 Hz, 1H), 8.29 (brs, 6H), 8.87 (s, 1H), 9.19-9.21 (m, 2H), 9.68 (s, 1H), 11.51 (s, 1H); ESIMS found for $C_{27}H_{33}F_3N_8O_3$ m/z 575.5 (M+H).

The following compound was prepared in accordance with the procedure described in the above example 8.

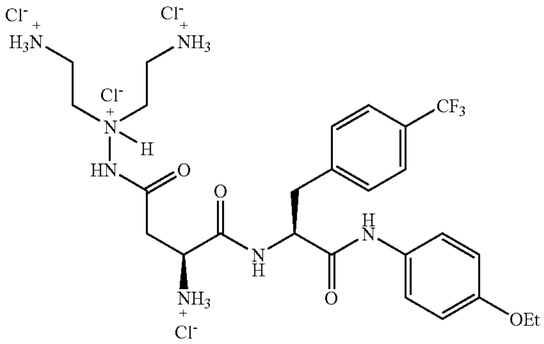

330 bis(2-azaniumylethyl)[(1S)-1-{[(1S)-1-[(4-ethoxyphenyl)carbamoyl]-2-[4-(trifluoromethyl)phenyl]ethyl]carbamoyl}-2-formamidoethan-1-aminium]azanium pentachloride 330

$^{9}$F NMR (DMSO-$d_6$) −60.08 (s,); ESIMS found for $C_{27}H_{38}F_3N_7O_4$ m/z 582.7 (M+H).

Synthesis of 3-[(1S)-4-[2,1-bis(2-azaniumylethyl)carbamimidamido]-1-{[(1S)-1-carbamoyl-3-phenylpropyl]carbamoyl}butan-1-aminium]quinolin-1-ium tetrachloride 16 is depicted below in scheme 9 and example 9.

Scheme 9

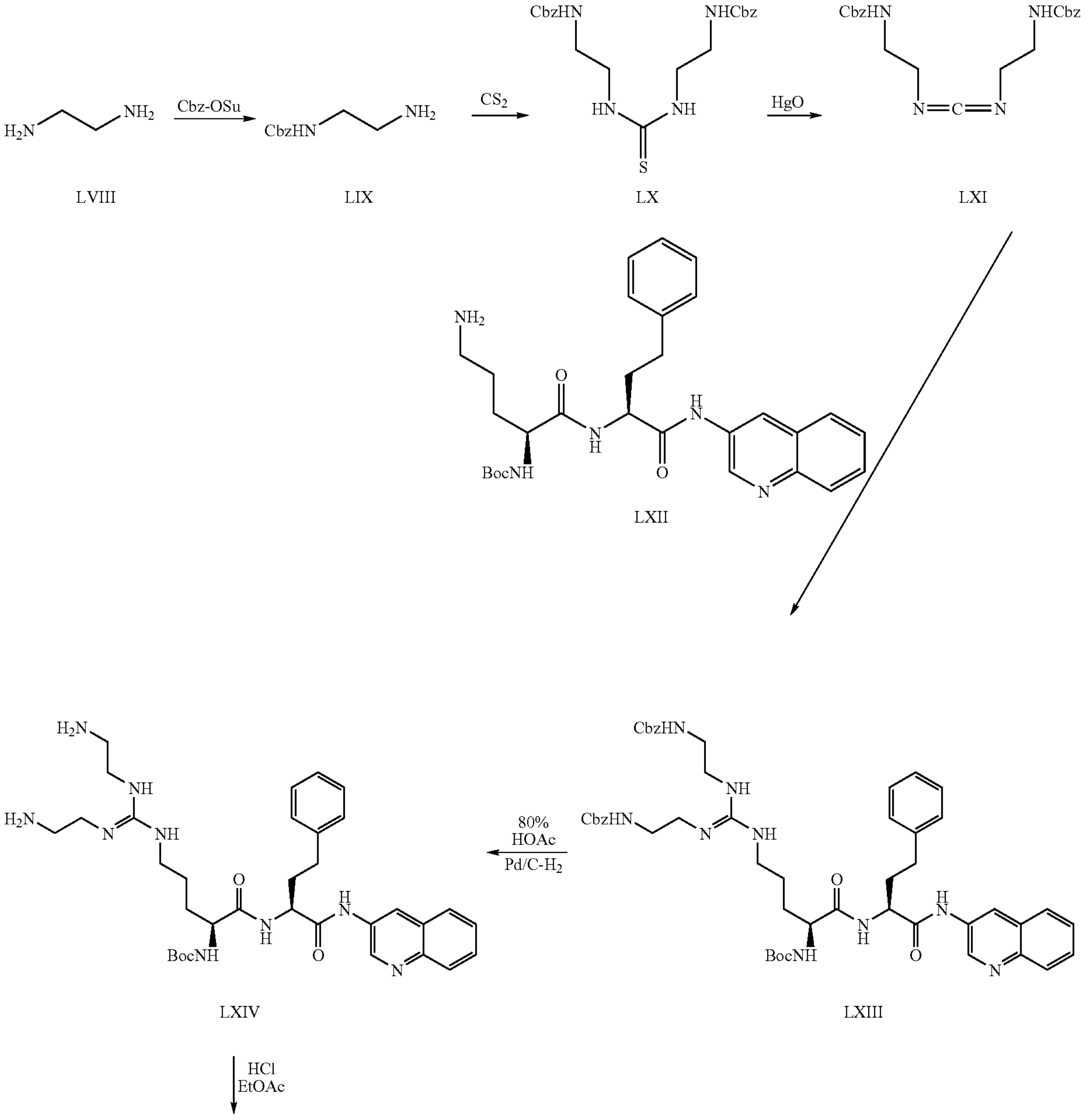

LVIII LIX LX LXI

LXII

LXIV LXIII

-continued

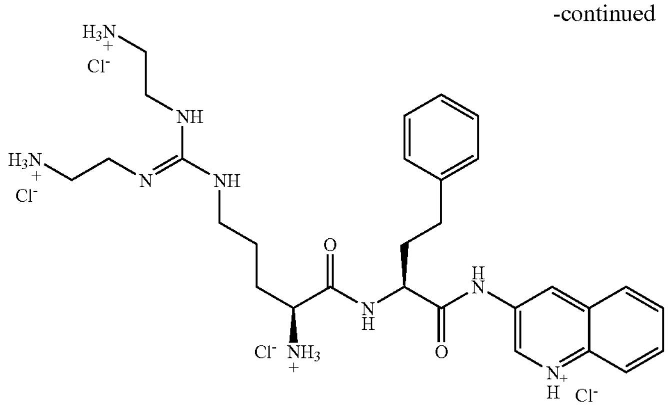

16

EXAMPLE 9

Step 1

To a solution of 2-aminoethylamine LVIII (150 mL; 2.25 mol) in chloroform (1.5 L), cooled to 0° C. was added a solution of carbobenzoxy N-hydroxysuccinimide (112.14 g; 0.45 mol) in water (0.5 L) with vigorously stirring for one hour. The solid was filtered and the solution was washed with brine (3×), once with water and dried over anhydrous $MgSO_4$. The solvent was evaporated under reduced pressure and the residue was purified on a silica gel column (100:1→30:1 DCM:MeOH) to yield benzyl 2-aminoethylcarbamate LIX as a colorless viscous oil (350 g; 1.80 mol; 80% yield). $^1H$ NMR ($CDCl_3$) 2.79-2.83 (m, 2H), 3.21-3.28 (m, 2H), 5.10 (s, 2H), 5.19 (brs, 1H), 7.29-7.34 (m, 1H), 7.35-7.38 (m, 4H); ESIMS found for $C_{10}H_{14}N_2O_2$ m/z 195.2 (M+H).

Step 2

To a suspension of benzyl 2-aminoethylcarbamate LIX (3 g; 15.45 mmol) in anhydrous ethanol (20 mL) was added carbon disulfide (0.47 mL; 7.73 mmol). The mixture was heated under gently reflux for 22 h. After cooling to r.t., the product precipitated and was filtered, washed with anhydrous ethanol (3×) and air dried. Benzyl N-(2-{[(2-{[(benzyloxy)carbonyl]amino}ethyl)carbamothioyl]amino}ethyl)carbamate LX was obtained as white solid (2.97 g; 6.90 mmol; 89.3% yield). $^1H$ NMR (DMSO-$d_6$) 3.10-3.14 (m, 4H), 3.37-3.42 (m, 4H), 5.00 (s, 4H), 7.30-7.37 (m, 12H), 7.54 (brs, 2H); ESIMS found for $C_{21}H_{26}N_4O_4S$ m/z 431.4 (M+H).

Step 3

To a suspension of benzyl N-(2-{[(2-{[(benzyloxy)carbonyl]amino}ethyl)carbamothioyl]amino}ethyl)carbamate LX (500 mg; 1.16 mmol) in DCM (20 mL) was added yellow mercuric (II) oxide (580 mg; 2.67 mmol). The mixture was stirred for 72 h before filtering the solid. The solution was evaporated under reduced pressure and the crude benzyl N-[2-({[(2-{[(benzyloxy)carbonyl]amino}ethyl)imino]methylidene}amino)ethyl]carbamate LXI was used for step 4 without further purification. ESIMS found for $C_{21}H_{24}N_4O_4$ m/z 397.4 (M+H).

Step 4

To a solution of crude carbodiimide LXI in dry THF (30 mL) was added and tert-butyl N-[(1S)-4-amino-1-{[(1S)-3-phenyl-1-[(quinolin-3-yl)carbamoyl]propyl]carbamoyl}butyl]carbamate LXII (790 mg; 1.5 mmol). The mixture was refluxed for 20 h. After cooling, the solvent was evaporated under vacuum to afford a brown foam. The residue was dissolved in DCM and washed with 1 M HCl (2×), water and dried over anhydrous $MgSO_4$. The solvent was removed under vacuum and the residue was purified on a silica gel column (100% $CHCl_3$→50:3 $CHCl_3$/MeOH) to give benzyl N-{2-[(Z)-{[(2-{[(benzyloxy)carbonyl]amino}ethyl)amino]({[(4S)-4-{[(tert-butoxy)carbonyl]amino}-4-{[(1S)-3-phenyl-1-[(quinolin-3-yl)carbamoyl]propyl]carbamoyl}butyl]amino})methylidene}amino]ethyl}carbamate LXIII as an amorphous white solid (424 mg; 0.463 mmol; 40% yield for 2 steps). ESIMS found for $C_{50}H_{61}N_9O_8$ m/z 916.7 (M+H).

Step 5

To a solution of benzyl N-{2-[(Z)-{[(2-{[(benzyloxy)carbonyl]amino}ethyl)amino]({[(4S)-4-{[(tert-butoxy)carbonyl]amino}-4-{[(1S)-3-phenyl-1-[(quinolin-3-yl)carbamoyl]propyl]carbamoyl}butyl]amino})methylidene}amino]ethyl}carbamate LXIII (420 mg; 0.46 mmol) in 80% of acetic acid (25 mL) was added 10% Pd/C (catalytic amount). The mixture was stirred under hydrogen for three days before filtering through Celite and concentrated under reduced pressure. The residue was co-evaporated with toluene (3×) and dried under vacuum to give tert-butyl N-[(1S)-4-[2,1-bis(2-aminoethyl)carbamimidamido]-1-{[(1S)-3-phenyl-1-[(quinolin-3-yl)carbamoyl]propyl]carbamoyl}butyl]carbamate LXIV as a off-white foam (260 mg; 0.40 mmol; 87% yield). ESIMS found for $C_{34}H_{49}N_9O_4$ m/z 648.8 (M+H).

Step 6

Procedure can be found in examples 1-2. The final compound 16 was isolated as the hydrochloride salt. $^1H$ NMR (DMSO-$d_6$) 1.73-1.80 (m, 2H), 1.84-1.93 (m, 2H), 2.04-2.11 (m, 1H), 2.13-2.19 (m, 1H), 2.69-2.75 (m, 1H), 2.82-2.88 (m, 1H), 3.01-3.10 (m, 4H), 3.38-3.43 (m, 2H), 3.60-3.66 (m, 4H), 4.09-4.13 (m, 1H) 4.57-4.62 (m, 1H), 7.15-7.19 (m, 1H), 7.22-7.33 (m, 4H), 7.72 (dd, J=8 Hz, J=8 Hz, 1H), 7.82 (dd, J=8 Hz, J=8 Hz, 1H), 8.07 (brs, 2H), 8.14-8.16 (m, 3H), 8.33 (brs, 6H), 8.44 (brs, 3H), 8.99 (s, 1H), 9.28 (s, 1H), 9.33 (d, J=7 Hz, 1H), 11.44 (s, 1H); ESIMS found for $C_{29}H_{41}N_9O_2$ m/z 548.7 (M+H).

Synthesis of 3-[(1R)-2-[bis(2-azaniumylethyl)sulfamoyl]-1-{[(1S)-1-carbamoyl-2-[4-(trifluoromethyl)phenyl]ethyl]carbamoyl}ethan-1-aminium]quinolin-1-ium tetrachloride 17 is depicted below in scheme 10 and example 10.

Scheme 10

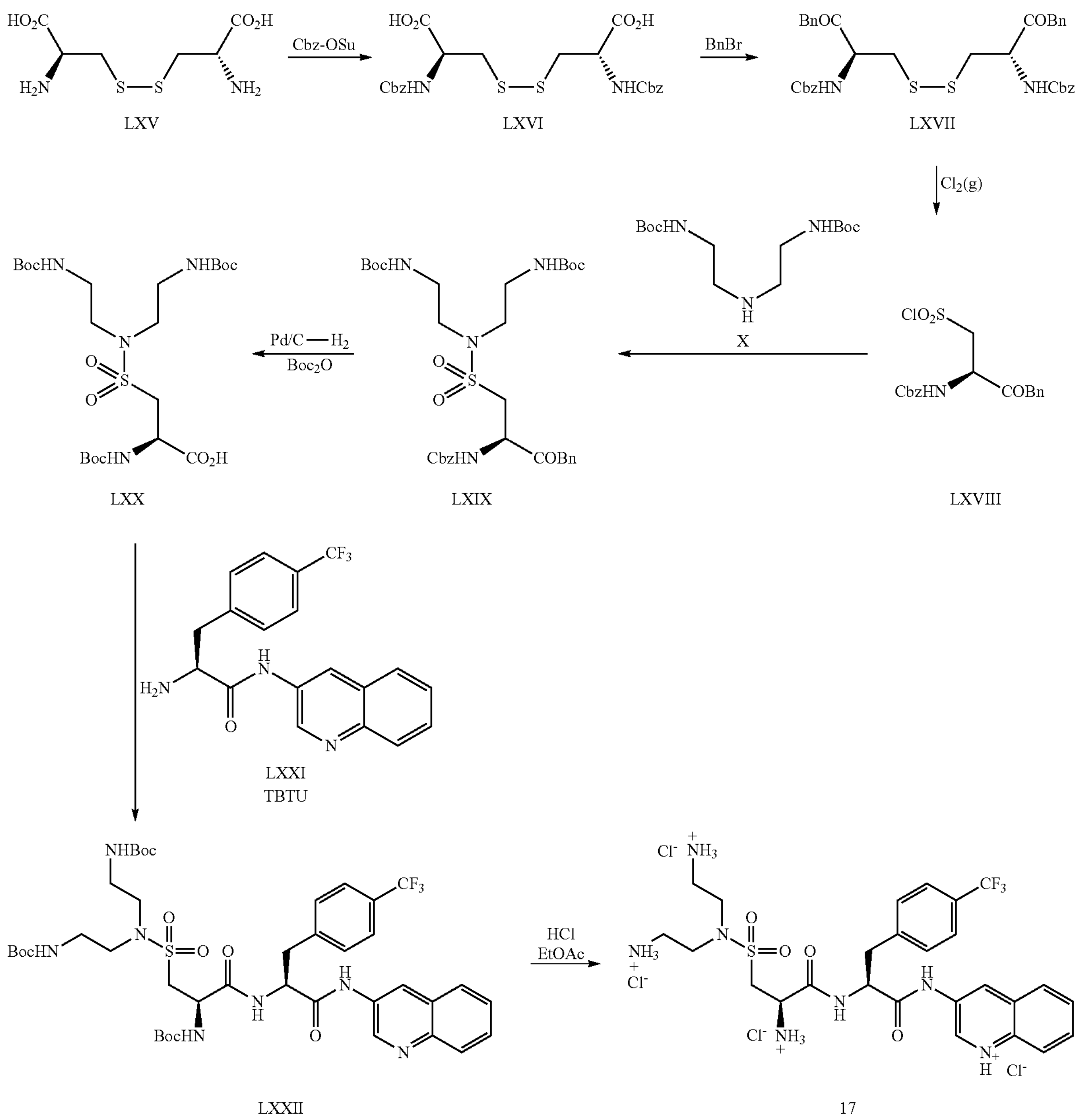

EXAMPLE 10

Step 1

To a solution of L-Cystine (3 g; 12.5 mmol) in acetone (25 mL) was added 1 M NaOH (20 mL), water (16 mL) and carbobenzoxy N-hydroxysuccinimide (7.5 g; 30 mmol). The mixture was stirred overnight at r.t. before the acetone was removed. The remaining aqueous phase was adjusted to pH=11 with 1 M NaOH, washed with diethyl ether and acidified to pH~5. The white precipitate was filtered, washed with water and dried. The crude product was purified on a silica gel column (100% $CHCl_3$→100:7 $CHCl_3$/MeOH) to give (2S)-2-{[(benzyloxy)carbonyl]amino}-3-{[(2S)-2-{[(benzyloxy)carbonyl]amino}-2-carboxyethyl]disulfanyl}propanoic acid LXVI (3.52 g; 6.92 mmol; 55% yield). $^1$H NMR (DMSO-$d_6$) 2.91 (dd, J=13 Hz, J=10 Hz, 2H), 3.14 (dd, J=13 Hz, J=4 Hz, 2H), 4.27 (ddd, J=13 Hz, J=10 Hz, J=4 Hz, 2H), 5.00-5.06 (m, 4H), 7.29-7.32 (m, 2H), 7.34-7.37 (m, 8H), 7.74 (d, J=8 Hz, 2H), 13.03 (brs, 2H); ESIMS found for $C_{22}H_{24}N_2O_8S_2$ m/z 509.2 (M+H).

Step 2

To a solution of (2S)-2-{[(benzyloxy)carbonyl]amino}-3-{[(2S)-2-{[(benzyloxy)carbonyl]amino}-2-carboxyethyl] disulfanyl}propanoic acid LXVI (5.6 g; 11 mmol) and anhydrous potassium carbonate (6.08 g; 44.0 mmol) in DMF (50 mL) cooled to 0° C. was added benzyl bromide (7.8 mL; 66.0 mmol). The mixture was stirred overnight at r.t. Water (150 mL) was added, and solution was extracted once with DCM (40 mL). The solvent was evaporated under reduced pressure and the residue was dissolved in diethyl ether (60 mL). The ether was washed with 10% aq $Na_2S_2O_3$ until all the DMF was removed and once with water. The organic phase was dried over anhydrous $MgSO_4$, evaporated and the residue purified on a silica gel column (100% $CHCl_3$→200:3 $CHCl_3$: MeOH). Benzyl (2S)-3-{[(2S)-3-(benzyloxy)-2-{[(benzyloxy)carbonyl]amino}-3-oxopropyl]disulfanyl}-2-{[(benzyloxy)carbonyl]amino}propanoate LXVII was obtained as a light-green viscous oil (5.9 g; 8.56 mmol; 77.8% yield). $^1H$ NMR ($CDCl_3$) 3.04-3.18 (m, 4H), 4.62-4.76 (m, 2H), 5.12 (s, 2H), 5.17 (s, 2H), 5.62-5.76 (m, 2H), 7.28-7.40 (m, 20H); ESIMS found for $C_{36}H_{36}N_2O_8S_2$ m/z 689.5 (M+H).

Step 3

To a solution of Benzyl (2S)-3-{[(2S)-3-(benzyloxy)-2-{[(benzyloxy)carbonyl]amino}-3-oxopropyl]disulfanyl}-2-{[(benzyloxy)carbonyl]amino}propanoate LXVII (5.85 g; 8.50 mmol) in carbon tetrachloride (60 mL) and anhydrous ethanol (15 mL) was bubbled gaseous chlorine for 40 minutes while cooling in an ice/water bath. The excess chlorine was removed by bubbling argon through the mixture. The solvent was removed under reduced pressure to give crude benzyl (2S)-2-{[(benzyloxy)carbonyl]amino}-3-(chlorosulfonyl) propanoate LXVIII as a white solid (5.95 g; 12.7 mmol; 75% yield). ESIMS found for $C_{18}H_{18}ClNO_6S$ m/z 412.3/414.3 ($^{35}Cl/^{37}Cl$) (M+H).

Step 4

To a solution of crude compound LXVIII (5.93 g; 12.66 mmol) in DCM (90 mL) cooled in an ice/water bath was added tert-butyl N-{2-[(2-{[(tert-butoxy)carbonyl]amino}ethyl)amino]ethyl}carbamate X (4.8 g; 15.84 mmol). After 10 min, TEA (3 mL; 21.6 mmol) was added and after another 30 min the reaction was warmed to r.t. and stirred overnight. DCM (100 mL) was then added and washed with 1 M HCl (2×150 mL), 5% aq $NaHCO_3$ (100 mL) and dried over anhydrous $MgSO_4$. The solvent was removed under reduced pressure and the residue was purified on a silica gel column (100% hexane→3:4 hexane/EtOAc). The product was further crystallized from hexane to give benzyl (2S)-2-{[(benzyloxy)carbonyl]amino}-3-[bis(2-{[(tert-butoxy)carbonyl]amino}ethyl)sulfamoyl]propanoate LXIX (1.82 g; 2.68 mmol; 21% yield). ESIMS found for $C_{32}H_{46}N_4O_{10}S$ m/z 679.5 (M+H).

Step 5

To a solution of benzyl (2S)-2-{[(benzyloxy)carbonyl]amino}-3-[bis(2-{[(tert-butoxy)carbonyl]amino}ethyl)sulfamoyl]propanoate LXIX (1.80 g; 2.65 mmol) in EtOAc (45 mL) was added TEA (0.4 mL; 2.9 mmol), di-tert-butyl dicarbonate (633 mg; 2.9 mmol) and 10% Pd/C (200 mg). The mixture was stirred under an hydrogen atmosphere overnight at r.t. before filtering through Celite and concentrating under reduced pressure. The product was purified on a silica gel column (100% $CHCl_3$→100:3 $CHCl_3$:MeOH) to obtain (2S)-3-[bis(2-{[(tert-butoxy)carbonyl]amino}ethyl)sulfamoyl]-2-{[(tert-butoxy)carbonyl]amino}propanoic acid LXX as colorless viscously oil (1.24 g; 2.23 mmol; 84.4% yield). ESIMS found for $C_{22}H_{42}N_4O_{10}S$ m/z 555.6 (M+H).

Step 6

Procedure can be found in examples 1-2.

Step 7

Procedure can be found in examples 1-2. The final compound 17 was isolated as the hydrochloride salt. $^1H$ NMR (DMSO-$d_6$) 3.02-3.07 (m, 4H), 3.18 (dd, J=8 Hz, J=14 Hz, 1H), 3.27-3.34 (m, 1H), 3.61-3.64 (m, 4H), 3.68 (dd, J=8 Hz, J=14 Hz, 1H), 3.86 (dd, J=4 Hz, J=14 Hz, 1H), 4.37-4.43 (m, 1H), [4.81 (dd, J=8 Hz, J=14 Hz, $1^{st}$ rotamer), 4.87 (dd, J=8 Hz, J=14 Hz, $2^{nd}$ rotamer), 1H], [7.58 (d, J=8 Hz, $2^{nd}$ rotamer), 7.63 (d, J=8 Hz, $1^{st}$ rotamer), 2H], 7.64-7.66 (m, 3H), 7.72 (dd, J=7 Hz, J=8 Hz, 1H), [7.99 (d, J=8 Hz, $2^{nd}$ rotamer), 8.03 (d, J=8 Hz, $1^{st}$ rotamer), 1H], 8.02 (d, J=7 Hz, 1H), [8.22 (brs, $1^{st}$ rotamer), 8.25 (brs, $2^{nd}$ rotamer), 6H], [8.61 (brs, $1^{st}$ rotamer), 8.64 (brs, $2^{nd}$ rotamer), 3H], [8.77 (s, $2^{nd}$ rotamer), 8.80 (s, $1^{st}$ rotamer), 1H], 9.12 (s, 1H), 9.55 (d, J=7 Hz, 1H), [11.12 (s, $2^{nd}$ rotamer), 11.22 (s, $1^{st}$ rotamer), 1H]; $^{19}F$ NMR (DMSO-$d_6$) −60.06 ($1^{st}$ rotamer), −60.13 ($2^{nd}$ rotamer) (s, 3F); ESIMS found for $C_{26}H_{32}F_3N_7O_4S$ m/z 596.6 (M+H).

The following compounds were prepared in accordance with the procedure described in the above example 10.

356

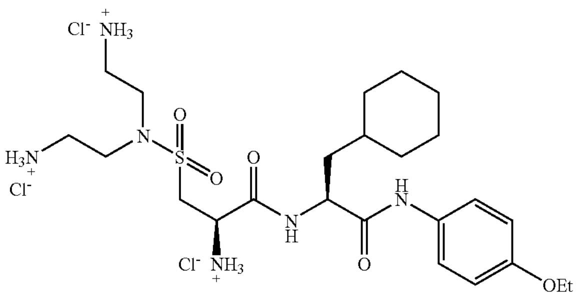

(2S)-2-[(1R)-2-[bis(2-azaniumylethyl)sulfamoyl]-1-formamidoethan-1-aminium]-3-cyclohexyl-N-(4-ethoxyphenyl)propanamide trichloride 356 mixture of diastereoisomers; $^1H$ NMR (DMSO-$d_6$) 0.79-0.93 (m, 2H), 1.04-1.21 (m, 4H), 1.26 (t, J=7 Hz, 3H), 1.35-1.43 (brs, 1H), 1.50-1.76 (m, 7H), 2.96-3.09 (brs, 4H), 3.45-3.58 (brs, 4H), 3.62-3.77 (m, 2H), 3.93 (d, J=7 Hz, 2H), [4.34 (brs), 4.40 (brs), 2H], 6.82 (d, J=8 Hz, 2H), 7.47 (d, J=8 Hz, 2H), 8.13-8.26 (brs, 6H), 8.59-8.70 (brs, 3H), 9.15 (d, J=7 Hz, 1H), [9.89 (s), 9.96 (s), 1H]; ESIMS found for $C_{24}H_{42}N_6O_5S$ m/z 527.6 (M+H).

358

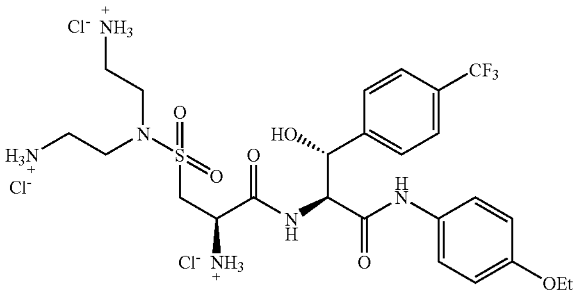

(2S,3R)-2-[(1R)-2-[bis(2-azaniumylethyl)sulfamoyl]-1-formamidoethan-1-aminium]-N-(4-ethoxyphenyl)-3-hydroxy-3-[4-(trifluoromethyl)phenyl]propanamide trichloride 358 mixture of diastereoisomers; $^1H$ NMR (DMSO-$d_6$) [1.06 (t, J=7 Hz,), 1.28 (t, J=7 Hz,), 3H], 3.05 (brs, 4H), 3.56 (brs, 2H), 3.69-3.80 (m, 4H), 3.94 (q, J=7 Hz, 2H), 4.47 (brs, 1H), 4.64-4.82 (m, 1H), [5.24 (d, J=1 Hz) 5.32 (d, J=1 Hz), 1H], 6.83 (d, J=9 Hz, 2H), 7.42 (d, J=9 Hz, 2H), 7.58-7.77 (m, 4H), 8.29 (brs, 6H), 8.58 (brs, 3H), [9.14 (d, J=8 Hz), 9.20 (brs), 1H], [10.15 (s), 10.20 (s), 1H], $^{19}F$ NMR (DMSO-$d_6$); −60.08 (s), −59.99 (s), ESIMS found for $C_{25}H_{35}F_3N_6O_6S$ m/z 605.6 (M+H).

Synthesis of 3-[(1S)-2-[bis(2-aminioethyl)carbamoyl]-1-{[(1S)-1-carbamoyl-2-(piperidin-1-ium-4-yl)ethyl]carbamoyl}ethanaminium]quinolin-1-ium pentachloride 18 is depicted below in scheme 11 and example 11.
Scheme 11
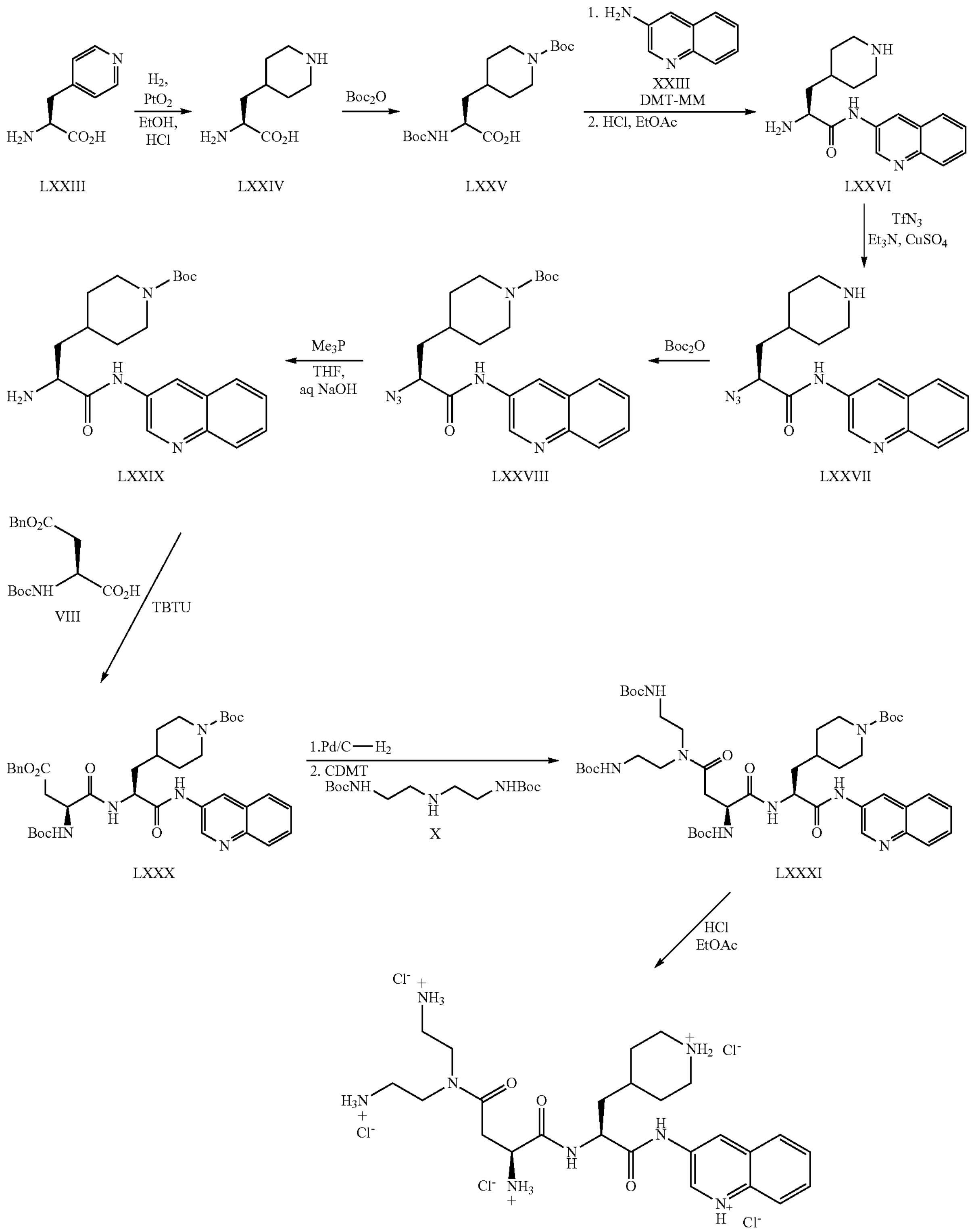

EXAMPLE 11

Step 1

To a solution of (2S)-2-amino-3-(pyridin-4-yl)propanoic acid LXXIII (660 mg, 4.0 mmol) in ethanol (120 mL) was added 1 N HCl (10 mL) and $PtO_2$ (150 mg). The mixture was vigorously shaken 70 psi $H_2$ in a Parr apparatus for 48 h. The mixture was filtered through Celite and the filtrate was concentrated to dryness giving crude (2S)-2-amino-3-(piperidin-4-yl)propanoic acid LXXIV as the hydrochloride salt (988 mg). ESIMS found for $C_8H_{16}NO_2$ m/z 172.0 (M+).

Step 2

To a suspension of (2S)-2-amino-3-(piperidin-4-yl)propanoic acid LXXIV (988 mg) in DCM (30 mL) was added TEA (3.3 mL, 24 mmol) and $Boc_2O$ (2.0 g, 8.8 mmol). The mixture was stirred at r.t. overnight. It was evaporated to dryness under reduced pressure before adding water (100 mL) and extracting with diethyl ether. Water layer was separated and acidified with 1 N HCl until pH=3 and extracted with ethyl acetate. The organic layer was dried over $Na_2SO_4$ and concentrated to dryness to obtain crude (2S)-2-{[(tert-butoxy)carbonyl]amino}-3-{1-[(tert-butoxy)carbonyl]piperidin-4-yl}propanoic acid LXXV (1.25 g). ESIMS found for $C_{18}H_{32}N_2O_6$ m/z 373 (M+H).

Step 3

To a solution of (2S)-2-{[(tert-butoxy)carbonyl]amino}-3-{1-[(tert-butoxy)carbonyl]piperidin-4-yl}propanoic acid LXXV (450 mg 1.21 mmol) and 3-aminoquinoline (187 mg, 1.30 mmol) in DCM (20 mL) was added DMT-MM (387 mg, 1.4 mmol). The mixture was stirred at r.t. overnight. The reaction was washed with water, 1 N HCl, satd. aq. $NaHCO_3$, water and dried over $Na_2SO_4$. The product was purified on a silica gel column (1:1 EtOAc:hexane) to give tert-butyl 4-[(2S)-2-{[(tert-butoxy)carbonyl]amino}-2-[(quinolin-3-yl)carbamoyl]ethyl]piperidine-1-carboxylate (425 mg, 0.85 mmol, 70% yield). $^1H$ NMR (DMSO-$d_6$) 1.02-1.10 (m, 2H), 1.40 (s, 18H), 1.54-1.73 (m, 9H), 4.22-4.25 (m, 1H), 7.20 (d, J=8 Hz, 1H), 7.55-7.66 (m, 2H), 7.94 (t, J=8 Hz, 2H), 8.69 (d, J=2 Hz, 1H), 8.93 (d, J=2 Hz, 1H), 10.44 (s, 1H). ESIMS found for $C_{27}H_{38}N_4O_5$ m/z 499 (M+H).

Step 4

To a solution of tert-butyl 4-[(2S)-2-{[(tert-butoxy)carbonyl]amino}-2-[(quinolin-3-yl)carbamoyl]ethyl]piperidine-1-carboxylate (425 mg, 0.85 mmol) was added HCl/EtOAc (5 M solution, 6 mL) at r.t. overnight. The precipitate was filtered, washed with ethyl acetate, diethyl ether and dried to give crude (2S)-2-amino-3-(piperidin-4-yl)-N-(quinolin-3-yl)propanamide LXXVI as the hydrochloride salt (351 mg). ESIMS found for $C_{17}H_{22}N_4O$ m/z 299 (M+H).

Step 5

To a solution of (2S)-2-amino-3-(piperidin-4-yl)-N-(quinolin-3-yl) propanamide LXXVI in a mixture of methanol (15 mL) and water (5 mL) was added $Et_3N$ (0.60 mL, 4.24 mmol) and $CuSO_4$ (20 mg). The mixture was treated at 0° C. with freshly prepared solution of triflic azide (5.9 mmol) in DCM (10 mL). The mixture was stirred at r.t. for 48 h. The solvent was evaporated under reduced pressure and dissolved in EtOAc, washed with satd. aq. $NaHCO_3$, water and dried over $Na_2SO_4$. The solvent was removed under vacuum to give crude (2S)-2-azido-3-(piperidin-4-yl)-N-(quinolin-3-yl) propanamide LXXVII (320 mg). ESIMS found for $C_{17}H_{20}N_6O$ m/z 325 (M+H).

Step 6

To a solution of (2S)-2-azido-3-(piperidin-4-yl)-N-(quinolin-3-yl) propanamide LXXVII in DCM (10 mL) was added TEA (0.60 mL, 4.25 mmol) followed by $Boc_2O$ (202 mg, 0.93 mmol). The mixture was stirred at r.t. overnight before the solvent was removed under reduced pressure. The residue was purified on a silica gel column (1:1→2:1 EtOAc:hexane) to give tert-butyl 4-[(2S)-2-azido-2-[(quinolin-3-yl)carbamoyl]ethyl]piperidine-1-carboxylate LXXVIII (262 mg, 0.62 mmol, 73% yield for 3 steps). $^1H$ NMR (DMSO-$d_6$) 1.11-1.22 (m, 2H), 1.45 (s, 9H), 1.60-1.79 (m, 9H), 4.30-4.39 (m, 1H), 7.53-7.67 (m, 2H), 7.97 (t, J=8 Hz, 2H), 8.70 (d, J=2 Hz, 1H), 8.95 (d, J=2 Hz, 1H), 10.38 (s, 1H). ESIMS found for $C_{22}H_{28}N_6O_3$ m/z 425 (M+H).

Step 7

To a solution of tert-butyl 4-[(2S)-2-azido-2-[(quinolin-3-yl)carbamoyl]ethyl]piperidine-1-carboxylate LXXVIII (262 mg, 0.62 mmol) in THF (20 mL) and 0.1 M NaOH (2.0 mL) was added $Me_3P$ (1 M in THF, 0.65 mL). The reaction was stirred at r.t. overnight. The solvent was removed under reduced pressure to give crude tert-butyl 4-[(2S)-2-amino-2-[(quinolin-3-yl)carbamoyl]ethyl]piperidine-1-carboxylate LXXIX (275 mg), which was directly used in step 8. ESIMS found for $C_{22}H_{30}N_4O_3$ m/z 399 (M+H).

Step 8-10

Procedures can be found in examples 1-2.

Step 11

Procedure can be found in examples 1-2. The final compound 18 was isolated as the hydrochloride salt. $^1H$ NMR (DMSO-$d_6$) 1.38-1.46 (m, 2H), 1.78-1.88 (m, 2H), 2.82-2.92 (m, 2H), 3.01-3.20 (m, 6H), 3.21-3.29 (m, 4H), 3.58-3.66 (m, 4H), 4.34-4.40 (m, 1H), 4.60-4.66 (m, 1H), 7.65-7.69 (m, 1H), 7.74-7.78 (m, 1H), 8.05-8.09 (m, 5H), 8.10 (brs, 3H), 8.47 (brs, 3H), 8.78-8.82 (m, 1H), 8.90 (d, J=2 Hz, 1H), 8.98-9.01 (m, 1H), 9.10 (d, J=7 Hz, 1H), 9.22 (d, J=2 Hz, 1H), 11.05 (s, 1H). ESIMS found for $C_{25}H_{38}N_8O_3$ m/z 499 (M+H).

Synthesis of 3-[(2S)-2-[(1S)-3-[(2-aminioethyl)[2-(trimethylaminio)ethyl]carbamoyl]-1-formamidopropan-1-aminium]-3-[4-(trifluoromethyl)phenyl]propanamido] quinolin-1-ium tetrachloride 19 is depicted below in scheme 12 and example 12.

Scheme 12

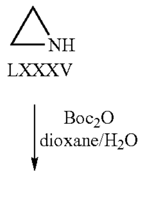

LXXXV

-continued

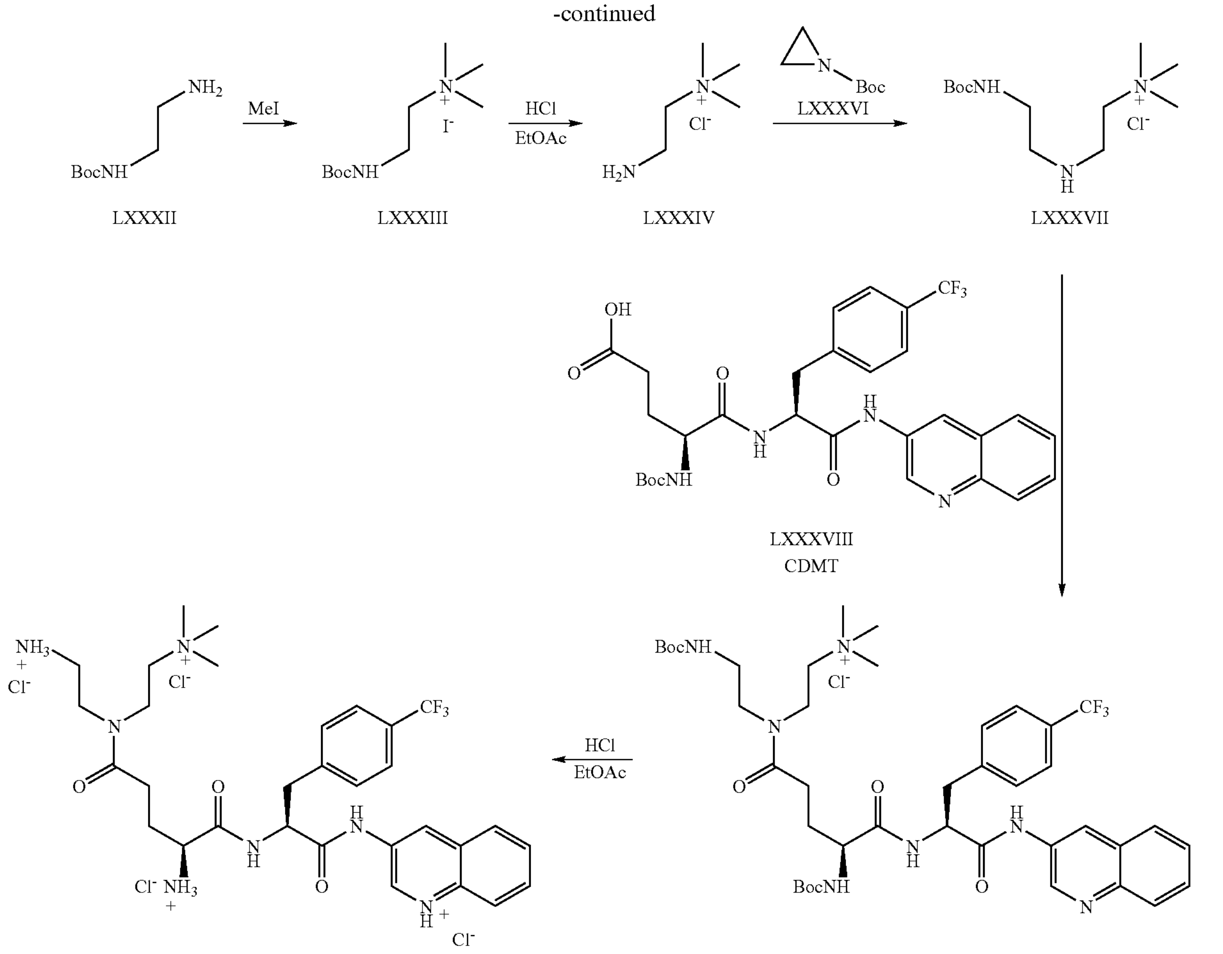

LXXXII LXXXIII LXXXIV LXXXVII

LXXXIX

19

EXAMPLE 12

Step 1

To a solution of tert-butyl N-(2-aminoethyl)carbamate LXXXII (2.6 g; 16.35 mmol) in MeI (5 mL) was added anhydrous potassium carbonate (4.7 g; 34.0 mmol). The mixture was stirred for 24 h at r.t. The MeI was removed under reduced pressure and the residue was crystallized from ethanol and then triturated with ethyl acetate to give tert-butyl N-[2-(trimethylaminio)ethyl]carbamate iodide LXXXIII (3.2 g; 13.40 mmol 82% yield). $^{1}H$ NMR ($CDCl_3$) 1.42 (s, 9H), 3.49 (s, 9H), 3.68-3.72 (m, 2H) 3.82 (t, J=5 Hz, 2H), 5.85-5.92 (m, 1H); ESIMS found for $C_{10}H_{23}N_2O_2$ m/z 203.3 (M+).

Step 2

To a solution of tert-butyl N-[2-(trimethylaminio)ethyl] carbamate iodide LXXXIII (3.2 g; 13.4 mmol) in ethyl acetate cooled in ice/water bath was added HCl (3.5 M solution in EtOAc). The reaction mixture was stirred by 30 min at r.t. The white precipitate was filtered and washed with ether to give (2-aminioethyl)trimethylazanium dichloride LXXXIV (1.9 g; quantitative). ESIMS found for $C_5H_{15}N_2$ m/z 102.9 (M+).

Step 3

To a solution of aziridine (100 g; 2.3 mol) in dioxane (2 L) and water (1 L) the aziridine (100 g; 2.30 mol), cooled to 0° C. in ice water bath, was added di-tert-butyl dicarbonate (530 g; 2.41 mol) in portion over 2 h. The mixture was stirred at r.t. overnight. tert-Butyl aziridine-1-carboxylate LXXXVI was isolated as a mixture with dioxane by distillation.

Step 4

To the solution tert-butyl aziridine-1-carboxylate LXXXVI (excess) in dioxane was added (2-aminioethyl)trimethylazanium dichloride LXXXIV (0.25 g; 1.8 mmol). The mixture was refluxed for 3 days. The solvent was removed under reduced pressure and the residue was purified on a silica gel column (100:1 $CHCl_3$:MeOH) to give crude tert-butyl N-(2-{[2-(trimethylaminio)ethyl]amino}ethyl)carbamate chloride LXXXVII was used directly for step 5.

Step 5

Procedure can be found in examples 1-2.

Step 6

Procedure can be found in examples 1-2. The final compound 19 was isolated as the hydrochloride salt. ESIMS found for $C_{31}H_{41}F_3N_7O_3$ m/z 616 (M+).

Synthesis of 3-[(1S)-3-[bis(2-aminioethyl)carbamoyl]-1-{[1-carbamoyl-2-(piperidin-1-ium-1-yl)ethyl]carbamoyl}propan-1-aminium]quinolin-1-ium pentachloride 20 is depicted below in scheme 13 and example 13.

Scheme 13

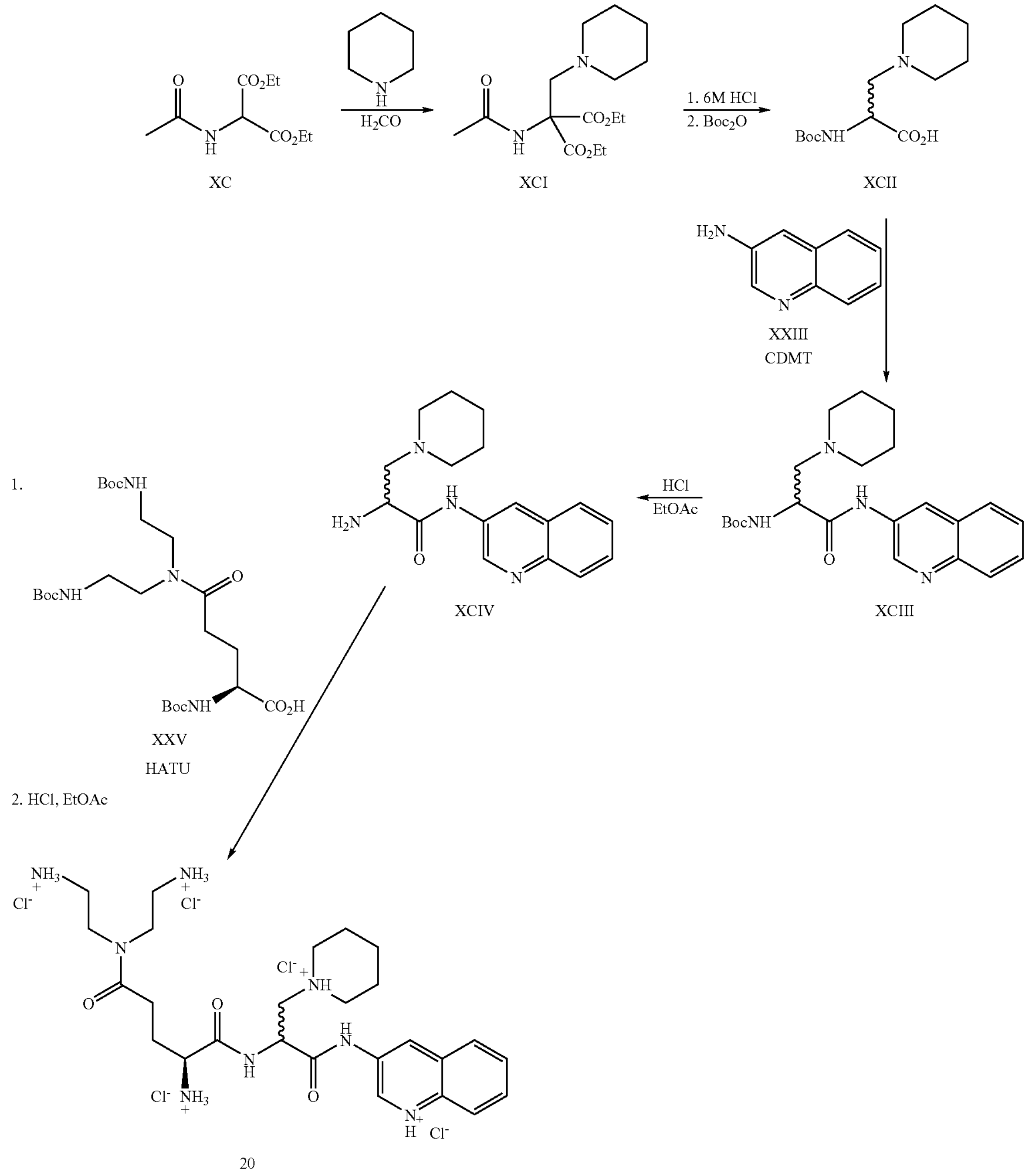

EXAMPLE 13

Step 1

To a solution of diethyl acetamidomalonate XC (1.75 g, 8.05 mmol) in THF (20 mL) was added piperidine (0.62 mL, 6.7 mmol) and 36% aqueous solution formaldehyde (0.23 mL, 8.25 mmol). The reaction mixture was stirred at 60° C. for 5 min. The mixture was cooled to −5° C. and kept at this temperature overnight. The precipitate was filtered to produce 1,3-diethyl 2-acetamido-2-(piperidin-1-ylmethyl)propanedioate XCI as a white crystallized solid (1.01 g, 3.21 mmol, 40% yield). $^1$H NMR ($CDCl_3$) 1.15-1.30 (m, 6H), 1.31-1.56 (m, 6H), 2.03 (s, 3H), 2.30-2.51 (m, 4H), 3.25 (s, 2H), 4.13-4.32 (m, 4H), 6.99 (brs, 1H); ESIMS found for $C_{15}H_{26}N_2O_5$ m/z 315 (M+H).

Step 2

A solution of 1,3-diethyl 2-acetamido-2-(piperidin-1-ylmethyl)propanedioate XCI (1.01 g, 3.21 mmol) in 6 M HCl (20 mL) was refluxed overnight. The reaction mixture was alkalized with 4 M NaOH to pH=11 before adding a solution of $Boc_2O$ (1.40 g, 6.42 mmol) in acetone (25 mL). The reaction mixture was stirred overnight at r.t. The acetone was evaporated under reduced pressure and the remaining water was washed with ethyl ether (2×) and acidified to pH=8 with 2 M aqueous HCl. The water was evaporated under reduced pressure and solid residue was purified on a silica gel column (30:1 $CHCl_3$:MeOH) to give 2-{[(tert-butoxy)carbonyl]amino}-3-(piperidin-1-yl)propanoic acid XCII (0.44 g, 1.61 mmol, 50% yield). $^1$H NMR ($CDCl_3$) 1.41 (s, 9H), 1.77-2.01 (m, 4H), 2.87-3.05 (m, 2H), 3.33-3.42 (m, 2H), 3.44 (brs, 4H), 4.07-4.20 (m, 1H), 5.85 (brs, 1H); ESIMS found for $C_{13}H_{24}N_2O_4$ m/z 273 (M+H).

Step 3

To a solution of 2-{[(tert-butoxy)carbonyl]amino}-3-(piperidin-1-yl)propanoic acid XCII (440 mg, 1.61 mmol) in DCM (15 mL) was added DIPEA (0.33 mL, 1.93 mmol), 3-aminoquinoline XXIII (255 mg 1.77 mmol) and TBTU (568 mg, 1.77 mmol). The mixture was stirred at r.t. overnight. The mixture was washed with 1 M $K_2CO_3$, 1 M HCl, brine and dried over $MgSO_4$. Product was purified on a silica gel column (200:1→100:1 $CHCl_3$:MeOH) and then crystallized from ether to give tert-butyl N-[2-(piperidin-1-yl)-1-[(quinolin-3-yl)carbamoyl]ethyl]carbamate XCIII (450 mg, 1.13 mmol, 70% yield). $^1$H NMR ($CDCl_3$) 1.48 (s, 9H), 1.55-1.67 (m, 4H), 1.68-1.83 (m, 4H), 2.47-2.65 (m, 2H), 2.82-2.98 (m, 2H), 4.39 (brs, 1H), 5.62 (brs, 1H), 7.54 (dd, J=7 Hz, J=7 Hz, 1H), 7.58-7.69 (m, 1H), 7.81 (d, 8 Hz, 1H), 8.03 (d, J=8 Hz, 1H), 8.74 (brs, 2H), 11.78 (brs, 1H); ESIMS found for $C_{22}H_{30}N_4O_3$ m/z 399 (M+H).

Step 4

To a solution of tert-butyl N-[2-(piperidin-1-yl)-1-[(quinolin-3-yl)carbamoyl]ethyl]carbamate XCIII (450 mg, 1.13 mmol) in ethyl acetate (10 mL) was added HCl (4.5 M solution in EtOAc, 10 mL). The reaction mixture was stirred for 20 min at r.t. before adding ethyl ether (20 mL). The precipitate was filtered and washed with ether to give 2-amino-3-(piperidin-1-yl)-N-(quinolin-3-yl)propanamide XCIV as a white crystalline solid (400 mg, 1.07 mmol, 94.7% yield). ESIMS found for $C_{17}H_{22}N_4O$ m/z 299 (M+H).

Step 5

Procedure can be found in examples 1-2.

Step 6

Procedure can be found in examples 1-2. The final compound 20 was isolated as the hydrochloride salt. $^1$H NMR (DMSO-$d_6$) 1.36-1.47 (m, 1H), 1.66-1.74 (m, 1H), 1.76-1.90 (m, 4H), 1.93-2.00 (m, 1H), 2.03-2.15 (m, 2H), 2.61-2.82 (m, 2H), 2.89-2.99 (m, 2H), 3.02-3.11 (m, 2H), 3.44-3.57 (m, 4H), 3.58-3.82 (m, 4H), 3.94-4.04 (m, 1H), 5.00-5.07 (m, 1H), 5.21-5.30 (m, 1H), 7.61-7.79 (m, 2H), 7.94-8.11 (m, 3H), 8.25-8.42 (m, 3H), 8.50-8.68 (m, 3H), 8.82 (brs, 1H), [9.23 (s, 1$^{st}$ diastereoisomer); 9.19 (s, 2$^{nd}$ diastereoisomer), 1H], 9.68-9.53 (m, 1H), [10.21 (brs, 1$^{st}$ diastereoisomer); 10.07 (brs, 2$^{nd}$ diastereoisomer), 1H], [11.73 (s, 1$^{st}$ diastereoisomer); 11.33 (s, 2$^{nd}$ diastereoisomer), 1H]; ESIMS found for $C_{26}H_{40}N_8O_3$ m/z 513 (M+H).

Synthesis of 3-{[bis(2-aminioethyl)carbamoyl]({[(1S)-1-carbamoyl-2-[4-(trifluoromethyl)phenyl]ethyl]carbamoyl})methanaminium}quinolin-1-ium tetrachloride 21 is depicted below in scheme 14 and example 14.

Scheme 14

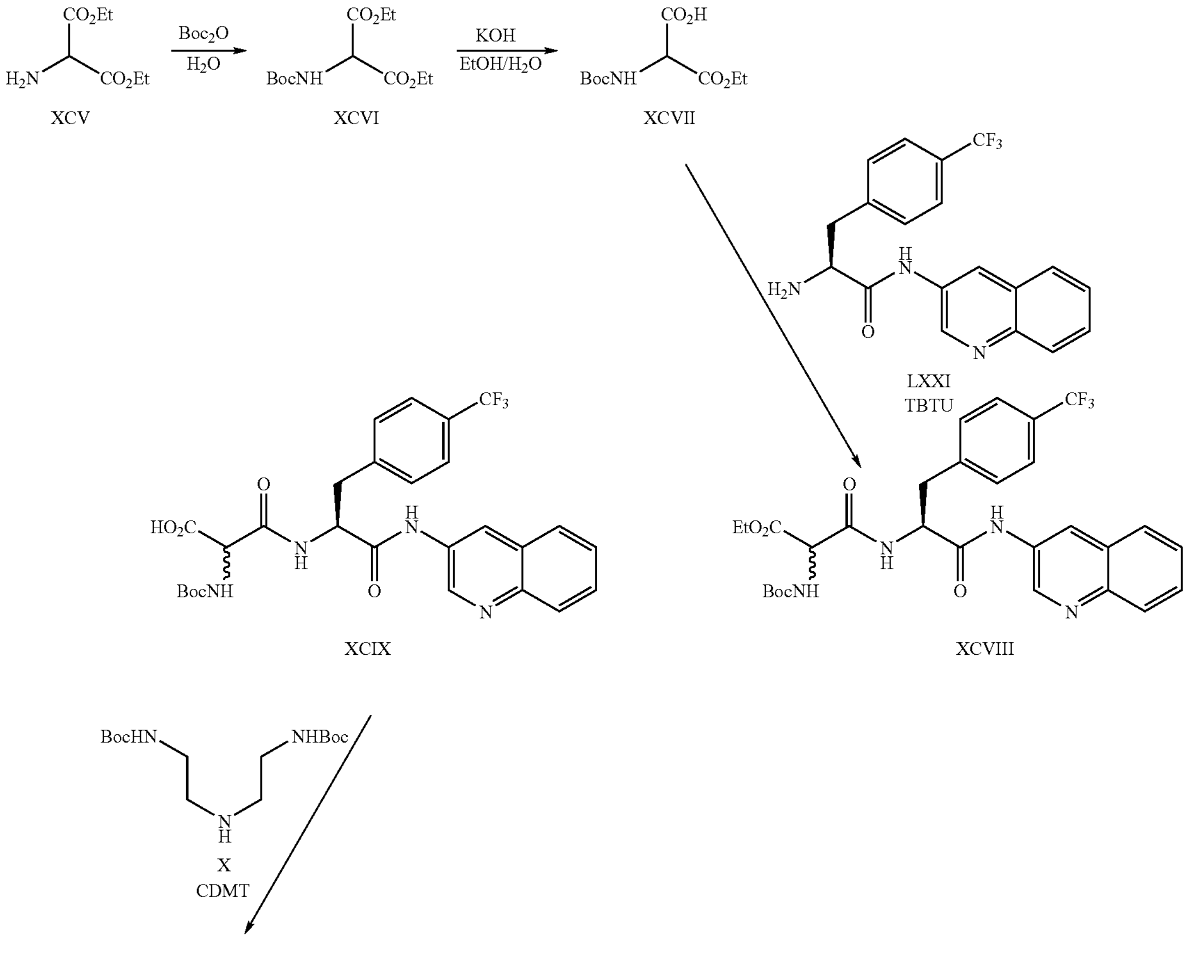

XCV XCVI XCVII LXXI XCIX XCVIII X

-continued

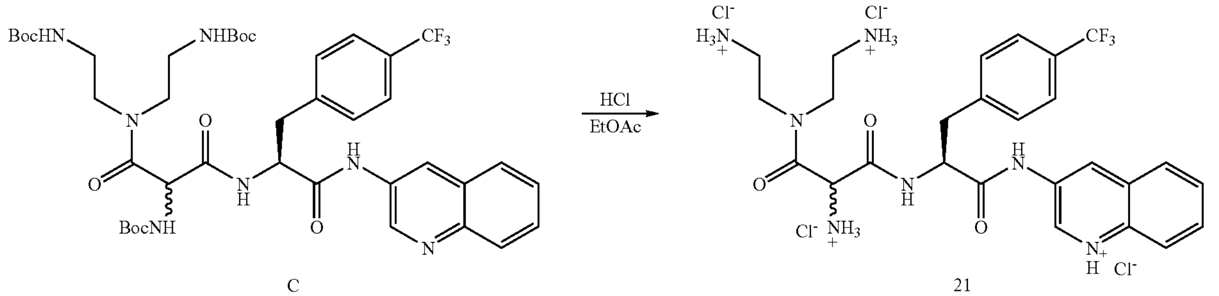

C 21

EXAMPLE 14

Step 1

To a solution of diethyl aminomalonate hydrochloride XCV (2.0 g, 9.45 mmol) in water (45 mL) was added 1 M NaOH to pH~8. $Boc_2O$ (3.72 g, 17.0 mmol) in acetone (15 mL) was then added. The reaction mixture was stirred for 2 days before the acetone was evaporated under reduced pressure. The residue was washed by diethyl ether, and the organic layer was evaporated under vacuum to give the crude 1,3-diethyl 2-{[(tert-butoxy)carbonyl]amino}propanedioate XCVI as a colorless oil (2.22 g, 8 mmol, 85% yield). The crude product was used directly in step 2. ESIMS found for $C_{12}H_{21}NO_6$ m/z 276 (M+H).

Step 2

To a solution of 1,3-diethyl 2-{[(tert-butoxy)carbonyl] amino}propanedioate XCVI (2.22 g, 8 mmol) in a mixture of ethanol/water (45 mL/5 mL) was added KOH (0.45 g, 8 mmol) in water (3 mL) dropwise. The reaction mixture was stirred for 1.5 hours. The ethanol was evaporated and the residue was acidified to pH=2 by 2 M HCl and washed by DCM. The organic layer was washed with brine and dried over $MgSO_4$. The solvent was evaporated to give 2-{[(tert-butoxy)carbonyl]amino}-3-ethoxy-3-oxopropanoic acid XCVII as crystals (1.68 g, 6.8 mmol, 85% yield). $^1H$ NMR ($CDCl_3$) 1.31 (t, J=7 Hz, 3H), 1.41-1.45 (m, 9H), 4.23-4.31 9 m, 2H), 4.76 (d, J=4 Hz, 1H), 7.77 (d, J=4 Hz, 1H), 10.84 (brs, 1H); ESIMS found for $C_{10}H_{17}NO_6$ m/z 248 (M+H).

Step 3

To a solution of 2-{[(tert-butoxy)carbonyl]amino}-3-ethoxy-3-oxopropanoic acid XCVII (0.5 g; 2.02 mmol) and DIPEA (1.20 mL; 7.07 mM) in DCM (30 mL) was added (2S)-2-amino-N-(quinolin-3-yl)-3-[4-(trifluoromethyl)phenyl]propanamide LXXI (0.88 g; 2.02 mmol) and TBTU (0.68 g; 2.12 mmol). The reaction mixture was stirred overnight, diluted with DCM (30 mL), washed with 1 M aq NaOH (2×), 1 M aqueous HCl (2×), brine and dried over anhydrous $MgSO_4$. The solvent was evaporated and the crude product was crystallized from DCM/hexane to give ethyl 2-{[(tert-butoxy)carbonyl]amino}-2-{[(1S)-1-[(quinolin-3-yl)carbamoyl]-2-[4-(trifluoromethyl)phenyl]ethyl] carbamoyl}acetate XCVIII as yellow crystals (0.90 g, 1.53 mmol, 76% yield). ESIMS found for $C_{29}H_{31}F_3N_4O_6$ m/z 589 (M+H).

Step 4

To a solution of ethyl 2-{[(tert-butoxy)carbonyl]amino}-2-{[(1S)-1-[(quinolin-3-yl)carbamoyl]-2-[4-(trifluoromethyl)phenyl]ethyl]carbamoyl}acetate XCVIII (0.90 g, 1.53 mmol) in a mixture of ethanol/water (45 mL/5 mL) was added KOH (0.103 g, 1.84 mmol) in water (10 mL) dropwise. The reaction mixture was stirred for 1.5 h. The ethanol was evaporated under reduced pressure and the residue was acidified to pH=2 by 2 M HCl. The aqueous solution was extracted with DCM. The DCM extract was then washed with brine and dried over $MgSO_4$. The solvent was evaporated to give 2-{[(tert-butoxy)carbonyl]amino}-2-{[(1S)-1-[(quinolin-3-yl) carbamoyl]-2-[4-(trifluoromethyl)phenyl]ethyl] carbamoyl}acetic acid XCIX (0.45 g, 0.80 mmol, 52% yield). The crude product was used directly for step 5.

Step 5

Procedure can be found in examples 1-2.

Step 6

Procedure can be found in examples 1-2. The final compound 21 was isolated as the hydrochloride salt. $^1H$ NMR (DMSO-$d_6$) 2.82-2.98 (m, 2H), 2.98-3.12 (m, 2H), 3.13-3.21 (m, 2H), 3.56-3.91 (m, 4H), 4.74-4.89 (m, 1H), 5.09-5.23 (m, 1H), 7.52-7.61 (m, 1H), 7.61-7.72 (m, 4H), 7.91-8.11 (m, 5H), 8.25-8.31 (brs, 3H), 8.66 (d, J=8 Hz, 1H), 8.71-8.77 (brs, 1H), 8.77-8.83 (brs, 1H), 8.96-9.04 (m, 1H), 9.40 (d, J=8 Hz, 1H), 9.67 (d, J=8 Hz, 1H), 10.88 (s, 1H), 10.93 (s, 1H); ESIMS found for $C_{26}H_{30}F_3N_7O_3$ m/z 546 (M+H).

Synthesis of 3-[(1S)-3-(aminiomethyl)-1-{[(1R)-1-carbamoyl-3-phenylpropyl]carbamoyl}butane-1,4-bis (aminium)]quinolin-1-ium tetrachloride 23 is depicted below in scheme 15 and example 15.

Scheme 15

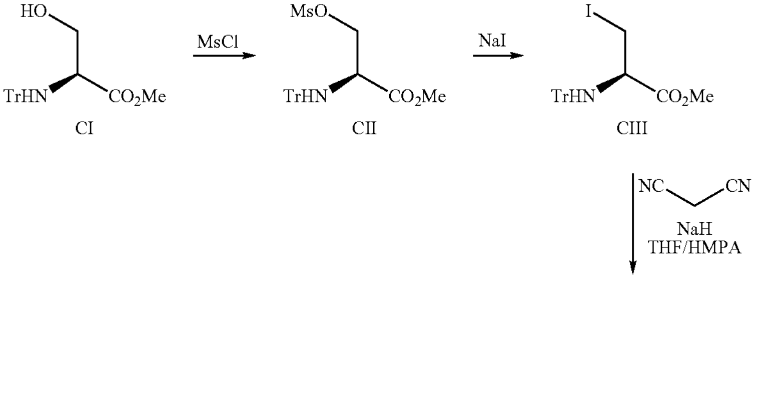

CI CII CIII

-continued

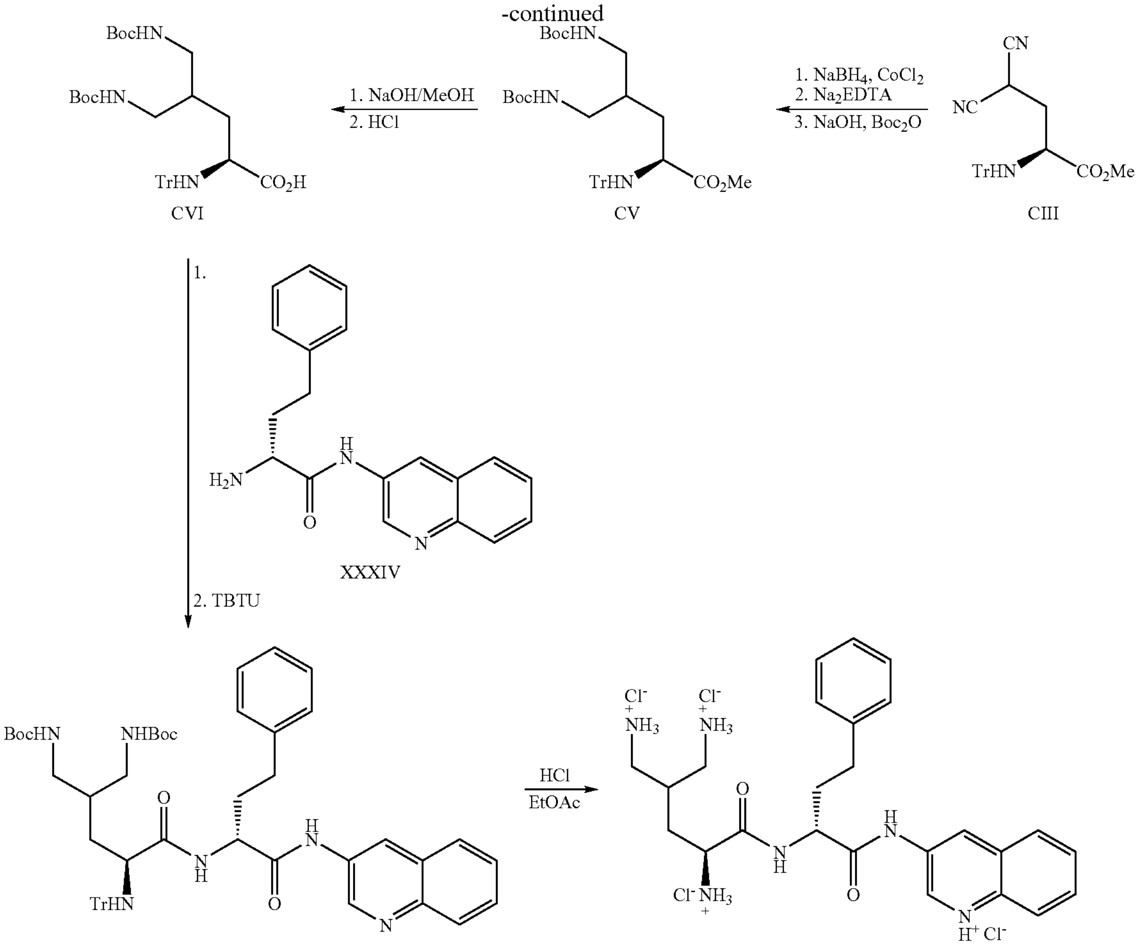

CVI CV CIII XXXIV CVII 23

EXAMPLE 15

Step 1

To a solution of methyl (2S)-3-hydroxy-2-(tritylamino) propanoate CI (24.35 g; 67.37 mmol) and TEA (11.2 mL; 80.8 mmol) in DCM (330 mL) cooled to 0° C. was added methanesulfonyl chloride (6.3 mL; 80.8 mmol) dropwise. The mixture reaction was stirred at r.t. overnight before being diluted with DCM (120 mL), washed with water, 5% aq $NaHCO_3$, 0.5 M aq $KHSO_4$, water, and dried over anhydrous $MgSO_4$. The solvent was removed under reduced pressure to give methyl (2S)-3-[(methylsulfonyl)oxy]-2-(tritylamino) propanoate CII as a off-white foam (22.2 g; 50.51 mmol; 75% yield). $^1$H NMR ($CDCl_3$) 2.89 (d, J=10 Hz, 1H), 3.00 (s, 3H), 3.28 (s, 3H), 3.64-3.68 (m, 1H), 4.25 (dd, J=6 Hz, J=10 Hz, 1H), 4.43 (dd, J=4 Hz, J=10 Hz, 1H), 7.20 (ddd, J=8 Hz, J=8 Hz, J=1 Hz, 3H), 7.28 (dd, J=8 Hz, J=8 Hz, 6H), 7.49 (ddd, J=8 Hz, J=8 Hz, J=1 Hz, 6H); ESIMS found for $C_{24}H_{25}NO_5S$ m/z 440.1 (M+H).

Step 2

To a solution of methyl (2S)-3-[(methylsulfonyl)oxy]-2-(tritylamino)propanoate CII (22 g; 0.05 mol) in acetone (700 mL) was added sodium iodide (150 g; 1.0 mol) and stirred at r.t. for one week under argon. The acetone was evaporated and the residue was dissolved in diethyl ether (1.5 L). The solids were filtered and the solvent reduced to 1 L before washing with 10% aq $Na_2S_2O_3$ (3×) and water (200 mL). The solvent was removed under reduced pressure and the residue purified on a silica gel column (10:1→2:1 hexane/EtOAc) and then crystallized from hexane. The methyl (2R)-3-iodo-2-(tritylamino)propanoate CIII was obtained as yellow foam (21 g; 0.045 mol; 89% yield). $^1$H NMR ($CDCl_3$) [2.25-2.28 (m, $1^{st}$ rotamer), 2.89 (d, J=10 Hz, $2^{nd}$ rotamer), 1H], [2.54 (dd, J=13 Hz, J=6 Hz), 3.21 (dd, J=10 Hz, J=8 Hz), $1^{st}$ rotamer, 1H], [2.69 (dd, J=12 Hz, J=8 Hz), 3.35 (dd, J=10 Hz, J=3 Hz), $2^{nd}$ rotamer, 1H], [3.31 (s, $1^{st}$ rotamer), 3.77 (s, $2^{nd}$ rotamer), 3H], [3.48 (ddd, J=10 Hz, J=7 Hz, J=3 Hz, $2^{nd}$ rotamer), 4.39 (dd, J=8 Hz, J=6 Hz, $1^{st}$ rotamer), 1H], 7.18-7.22 (m, 3H), 7.29 (dd, J=8 Hz, J=7 Hz, 6H), [7.45 (d, J=8 Hz, $1^{st}$ rotamer), 7.50 (d, J=8 Hz, $2^{nd}$ rotamer), 6H].

Step 3

To a solution of malononitrile (0.71 g; 10.6 mmol) in mixture of THF (30 mL) and HMPA (20 mL) was added sodium hydride 60% (0.43 g; 10.6 mmol) and stirred for min. To this mixture was added a solution of methyl (2R)-3-iodo-2-(tritylamino)propanoate CIII (5.0 g; 10.6 mmol) in THF (52 mL) and stirred overnight at r.t. The reaction was quenched with saturated aqueous ammonium chloride and extracted with diethyl ether (5×). The combined organic layers were washed with saturated aqueous ammonium chloride and dried over anhydrous $MgSO_4$. The solvent was removed and the residue was purified on a silica gel column (3:1 hexane/EtOAc) and then crystallized from hexane/EtOAc to give the methyl (2S)-4,4-dicyano-2-(tritylamino)butanoate CIV (2.62 g; 6.4 mmol; 60% yield). $^1$H NMR ($CDCl_3$) 3.02-3.06 (m, 1H), 2.70-2.75 (m, 1H), 2.81-2.86 (m, 1H), 2.95 (dd, J=12 Hz, J=6 Hz, 1H), 3.76 (s, 3H), 4.51 (d, J=6 Hz, 1H), 7.23 (t, J=8 Hz, 3H), 7.32 (dd, J=8 Hz, J=8 Hz, 6H), 7.43 (d, J=8 Hz, 6H); ESIMS found for $C_{26}H_{23}N_3O_2$ m/z 432.3 (M+Na).

Step 4

To a solution of methyl (2S)-4,4-dicyano-2-(tritylamino) butanoate CIV (1.0 g; 2.44 mmol) in methanol (15 mL) and THF (5 mL) was added cobalt (II) chloride hexahydrate (2.9 g; 12.2 mmol) and cooled to −10° C. After 5 min, sodium borohydride (0.92 g; 24.4 mmol) was added and after 20 min the cooling bath was removed and the reaction was stirred for one h at r.t. To the reaction mixture was added 4 M NaOH until pH~10. Disodium EDTA (4.6 g; 12.2 mmol) and di-tert-butyl dicarbonate (1.3 g; 5.86 mmol) were added and the mixture was stirred overnight at r.t. The solids were filtered and washed with methanol. The solvent was evaporated and the remaining aqueous solution was acidified with 2 M HCl to pH~6 and extracted with DCM. The combined organic layers were dried over anhydrous $MgSO_4$ and removed under reduced pressure. The residue was purified on a silica gel column (4:1→1:1 hexane/EtOAc) to afford methyl (2S)-5-{[(tert-butoxy)carbonyl]amino}-4-({[(tert-butoxy)carbonyl] amino}methyl)-2-[(triphenylmethyl)amino]pentanoate CV (0.19 g; 0.31 mmol; 13.7% yield). ESIMS found for $C_{36}H_{47}N_3O_6$ m/z 618.6 (M+H).

Step 5

To a solution of methyl (2S)-5-{[(tert-butoxy) carbonyl] amino}-4-({[(tert-butoxy)carbonyl]amino}methyl)-2-[(triphenylmethyl)amino]pentanoate CV (180 mg; 0.29 mmol) in methanol (15 mL) was added 4 M aq NaOH (3 mL). The mixture was stirred at r.t. for 1 h. Water (20 mL) was then added and the methanol was removed under reduce pressure. The aqueous solution was acidified with 2 M HCl to pH~5-6 and extracted with DCM. The combined organic layers were dried over anhydrous $MgSO_4$ and evaporated to obtain the crude (2S)-5-{[(tert-butoxy)carbonyl]amino}-4-({[(tert-butoxy)carbonyl]amino}methyl)-2-[(triphenylmethyl)amino] pentanoic acid CVI (145 mg). This material was used directly for step 6. ESIMS found for $C_{35}H_{45}N_3O_6$ m/z 604.4 (M+H).

Step 6

Procedure can be found in examples 1-2.

Step 7

Procedure can be found in examples 1-2. The final compound 23 was isolated as the hydrochloride salt. $^1$H NMR ($CD_3OD$) 0.83-0.94 (m, 1H), 2.12-2.33 (m, 2H), 2.76-2.94 (m, 2H), 3.10-3.41 (m, 6H), 4.54-4.61 (m, 1H) 4.87-4.91 (m, 1H), 7.14-7.22 (m, 1H), 7.26-7.29 (m, 4H), 7.60 (ddd, J=8 Hz, J=7 Hz, J=1 Hz, 1H), 7.70 (ddd, J=8 Hz, J=7 Hz, J=1 Hz, 1H), 7.88 (dd, J=8 Hz, J=1 Hz, 1H), 7.99 (dd, J=8 Hz, J=1 Hz, 1H), 8.64 (d, J=2 Hz, 1H), 8.94 (d, J=2 Hz, 1H); ESIMS found for $C_{25}H_{32}N_6O_2$ m/z 449.5 (M+H).

The following compound was prepared in accordance with the procedure described in the above example 15.

22

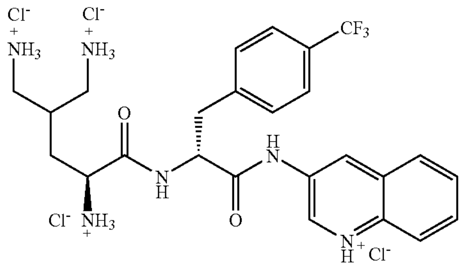

3-[(1S)-3-(azaniumylmethyl)-1-{[(1R)-1-carbamoyl-2-[4-(trifluoromethyl)phenyl]ethyl]carbamoyl}butane-1,4-bis (aminium)]quinolin-1-ium tetrachloride 22

$^1$H NMR ($CD_3OD$) 0.83-0.93 (m, 1H), 2.44-2.52 (m, 1H), 2.59-2.68 (m, 1H), 2.92-3.44 (m, 6H), 4.79-4.99 (m, 2H), 7.56-7.63 (m, 4H), 7.71 (dd, J=8 Hz, J=8 Hz, 1H), 7.83 (dd, J=8 Hz, J=7 Hz, 1H), 7.98 (d, J=7 Hz), 8.06 (d, J=8 Hz), [8.72 (brs, $1^{st}$ rotamer), 8.76 (brs, $2^{nd}$ rotamer), 1H], 9.06 (brs, 1H); $^{19}$F NMR ($CD_3OD$) −63.40 ($1^{st}$ rotamer), −63.33 ($2^{nd}$ rotamer) (s, 3F); ESIMS found for $C_{25}H_{29}F_3N_6O_2$ m/z 503.5 (M+H).

Synthesis of 3-azaniumyl-1-[(4S)-4-azaniumyl-4-{[(1R)-1-[(quinolin-1-ium-3-yl)carbamoyl]-2-[4-(trifluoromethyl) phenyl]ethyl]carbamoyl}butyl]pyrrolidin-1-ium tetrachloride 24 is depicted below in scheme 16 and example 16.

Scheme 16
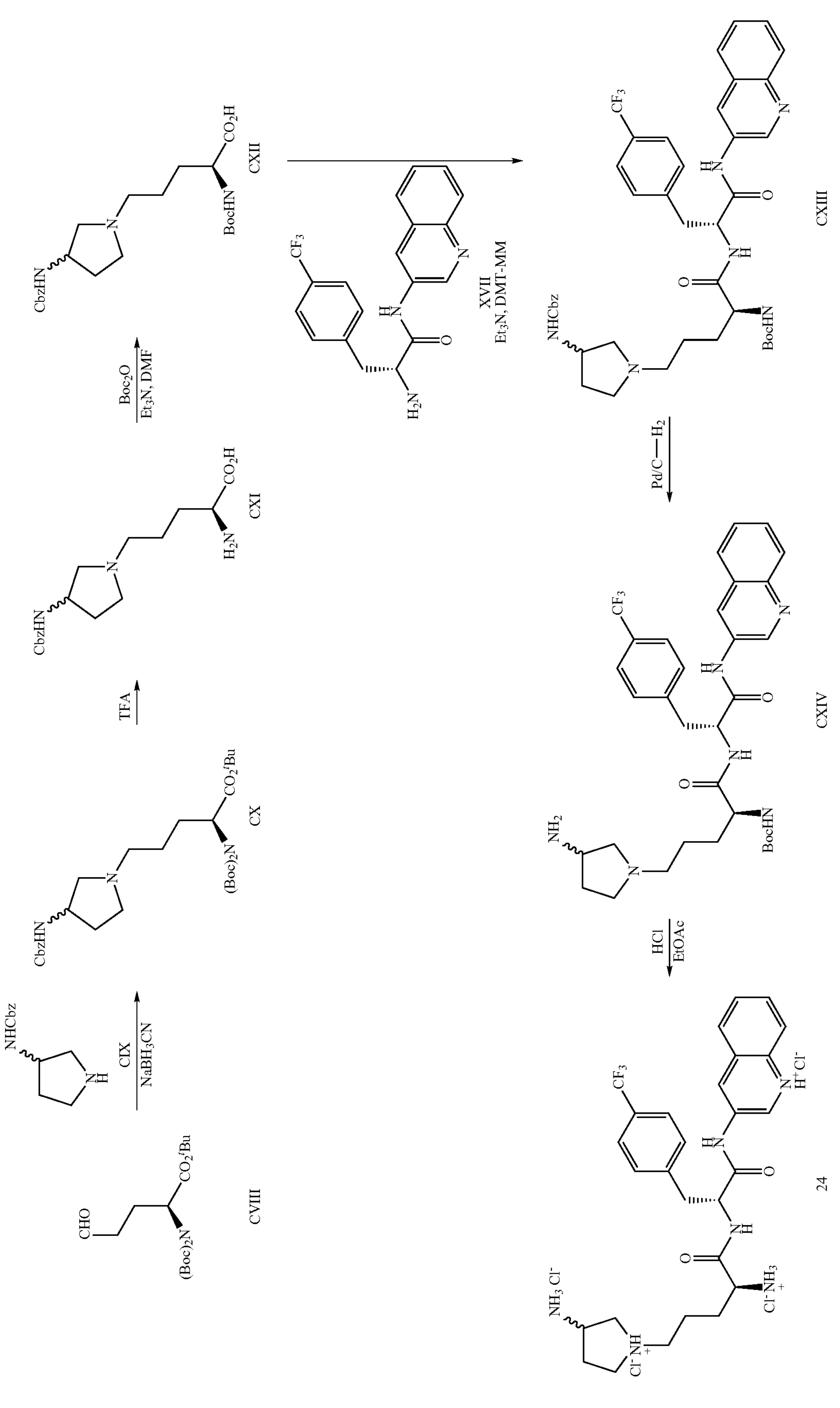
CVIII CX CXI CXII CXIII CXIV 24

EXAMPLE 16

Step 1

To a solution of benzyl N-(pyrrolidin-3-yl)carbamate CIX (622 mg, 2.4 mmol) in DCM (15 mL), cooled down to 0° C. was added acetic acid (0.4 mL, 11 mmol) followed by tert-butyl (2S)-2-{bis[(tert-butoxy)carbonyl]amino}-5-oxopentanoate CVIII (860 mg, 2.2 mmol). The reaction mixture was stirred at 0° C. for 1 h and then sodium cyanoborohydride (208 mg, 3.30 mmol) was added. The mixture was left with stirring overnight at r.t. DCM (30 mL) was added and the mixture was washed with water and brine. The organic layer was dried over $Na_2SO_4$ and evaporated to dryness to obtain crude tert-butyl (2S)-5-(3-{[(benzyloxy)carbonyl]amino}pyrrolidin-1-yl)-2-{bis[(tert-butoxy)carbonyl]amino}pentanoate CX (1.22 g, 2.06 mmol, 93.7% yield). ESIMS found for $C_{31}H_{49}N_3O_8$ m/z 592 (M+H).

Step 2-3

A solution of tert-butyl (2S)-5-(3-{[(benzyloxy)carbonyl]amino}pyrrolidin-1-yl)-2-{bis[(tert-butoxy)carbonyl]amino}pentanoate CX (1.22 g, 2.06 mmol) in trifluoroacetic acid (10 mL) was stirred overnight at r.t. The reaction mixture was concentrated to dryness to give (2S)-2-amino-5-(3-{[(benzyloxy)carbonyl]amino}pyrrolidin-1-yl)pentanoic acid CXI, which was dissolved in DMF (15 mL). TEA (1.4 mL, 10 mmol) was added at r.t. followed by $Boc_2O$ (460 mg, 2.2 mmol) and the mixture was stirred overnight. The solvent was evaporated under reduced pressure and the residue was treated with water (50 mL) and 1N HCl to adjust the pH to 3. The mixture was extracted with ethyl acetate and the organic layer was dried over $Na_2SO_4$ and concentrated to dryness to give crude (2S)-5-(3-{[(benzyloxy)carbonyl]amino}pyrrolidin-1-yl)-2-{[(tert-butoxy)carbonyl]amino}pentanoic acid CXII (1.0 g). ESIMS found for $C_{22}H_{33}N_3O_6$ m/z 436 (M+H).

Step 4

To a solution of (2S)-5-(3-{[(benzyloxy)carbonyl]amino}pyrrolidin-1-yl)-2-{[(tert-butoxy)carbonyl]amino}pentanoic acid CXII (1.0 g) in DCM (10 mL) was added DMT-MM (636 mg, 2.3 mmol). In a separate flask, (2R)-2-amino-N-(quinolin-3-yl)-3-[4-(trifluoromethyl)phenyl]propanamide XVII as the trifluoroacetate salt (700 mg, 1.48 mmol) was suspended in DCM (10 mL) and treated with TEA (0.41 mL, 3.0 mmol) while the mixture became homogeneous. The two solutions were combined and were allowed to react at r.t. overnight. The reaction mixture was washed with water, satd. $NaHCO_3$ and water and dried over $Na_2SO_4$. The solvent was removed under reduced pressure and residue was purified on a silica gel column (1:1 hexane: EtOAc→100% EtOAc→5:1 EtOAc:MeOH) to give tert-butyl N-[(1S)-4-(3-{[(benzyloxy)carbonyl]amino}pyrrolidin-1-yl)-1-{[(1R)-1-[(quinolin-3-yl)carbamoyl]-2-[4-(trifluoromethyl)phenyl]ethyl]carbamoyl}butyl]carbamate CXIII (390 mg, 0.50 mmol, 20% yield). $^1H$ NMR (DMSO-$d_6$) 1.09-1.21 (m, 2H), 1.33 (s, 9H), 1.54-1.60 (m, 2H), 2.01-2.12 (m, 2H), 2.20 (brs, 2H), 2.68-2.74 (m, 2H). 2.96-3.05 (m, 1H), 3.85-3.89 (m, 2H), 3.92-3.98 (m, 1H), 4.10-4.16 (m, 2H), 4.82-4.88 (m, 1H), 5.00 (s, 2H), 7.08 (d, J=7 Hz, 1H), 7.20-7.68 (m, 10H), 7.95-8.02 (m, 4H), 8.52 (d, J=7 Hz, 1H), 8.71 (d, J=2 Hz, 1H), 8.98 (d, J=2 Hz, 1H), 10.40 (s, 1H); ESIMS found for $C_{41}H_{47}N_6O_6F_3$ m/z 777 (M+H).

Step 5

To a solution of tert-butyl N-[(1S)-4-(3-{[(benzyloxy)carbonyl]amino}pyrrolidin-1-yl)-1-{[(1R)-1-[(quinolin-3-yl)carbamoyl]-2-[4-(trifluoromethyl)phenyl]ethyl]carbamoyl}butyl]carbamate CXIII (170 mg, 0.22 mmol) in methanol (20 mL) was added catalytic amount of 10% Pd/C catalyst. The mixture was hydrogenated at normal pressure for 48 h. The catalyst was filtered through Celite and the filtrate was concentrated to give tert-butyl N-[(1S)-4-(3-aminopyrrolidin-1-yl)-1-{[(1R)-1-[(quinolin-3-yl)carbamoyl]-2-[4-(trifluoromethyl)phenyl]ethyl]carbamoyl}butyl]carbamate CXIV (120 mg, 0.19 mmol, 86.4% yield). ESIMS found for $C_{33}H_{41}N_6O_4F_3$ m/z 643 (M+H).

Step 6

Procedure can be found in examples 1-2. The final compound 24 was isolated as the hydrochloride salt. $^1H$ NMR ($CD_3OD$) 1.48-1.73 (m, 4H), 2.05-2.11 (m, 1H), 2.11-2.22 (m, 1H), 3.00-3.11 (m, 2H), 3.13-3.21 (m, 2H), 3.32-3.40 (m, 1H), 3.85-3.97 (m, 4H), 4.03-4.17 (m, 1H), 4.95-4.88 (m, 1H), 7.60-7.70 (m, 6H), 7.98-8.05 (m, 2H), 8.29 (brs, 3H), 8.57 (brs, 1.5H $1^{st}$ diastereoisomer), 8.69 (brs, 1.5H $2^{nd}$ diastereoisomer), 8.74 (d, J=2 Hz, 1H), 9.08 (d, J=2 Hz, 1H), 9.22 (d, J=7 Hz, 1H), 11.12 (s, 1H); ESIMS found for $C_{28}H_{33}N_6O_2F_3$ m/z 543 (M+H).

Synthesis of 3-[(1S)-4-{[bis(2-azaniumylethyl)carbamoyl]amino}-1-{[(1R)-1-carbamoyl-2-[4-(trifluoromethyl)phenyl]ethyl]carbamoyl}butan-1-aminium]quinolin-1-ium tetrachloride 29 is depicted below in scheme 17 and example 17.

Scheme 17

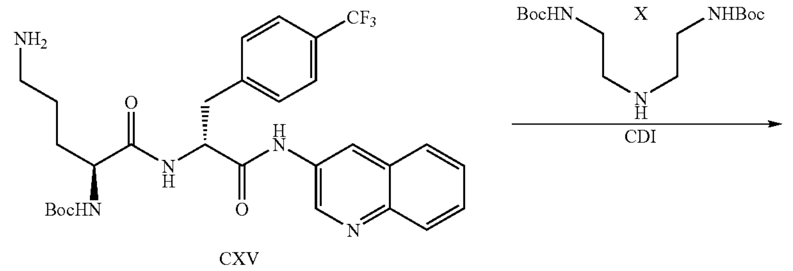

CXV

-continued

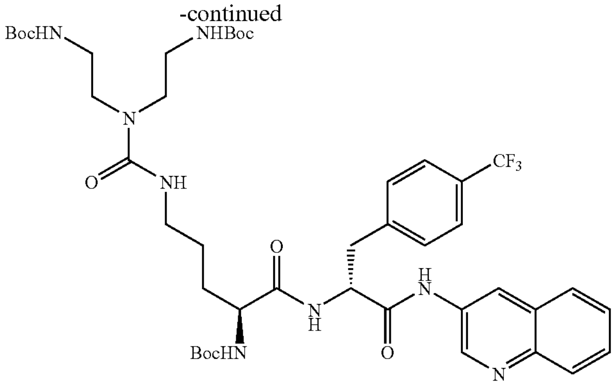

CXVI

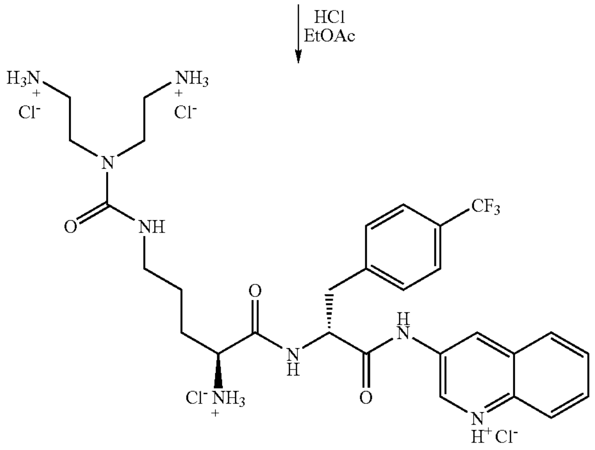

29

EXAMPLE 17

Step 1

To a solution of carbonyldiimidazole (204 mg, 1.25 mmol) in DCM (20 mL) was added tert-butyl N-[(1S)-4-amino-1-{[(1R)-1-[(quinolin-3-yl)carbamoyl]-2-[4-(trifluoromethyl) phenyl]ethyl]carbamoyl}butyl]carbamate CXV (687 mg, 1.20 mmol) and stirred at r.t. for 1 h. To this mixture was added tert-butyl N-{2-[(2-{[(tert-butoxy)carbonyl] amino}ethyl)amino]ethyl}carbamate X (436 mg, 1.44 mmol) and the reaction was stirred overnight at r.t. The mixture was diluted DCM and washed with 1 M HCl, brine, dried over $MgSO_4$ and purified on a silica gel column (100:1→70:1→50:1 $CHCl_3$/MeOH) to give product tert-butyl N-[2-({[(4S)-4-{[(tert-butoxy)carbonyl]amino}-4-{[(1R)-1-[(quinolin-3-yl)carbamoyl]-2-[4-(trifluoromethyl) phenyl]ethyl]carbamoyl}butyl]carbamoyl} (2-{[(tert-butoxy)carbonyl]amino}ethyl)amino)ethyl]carbamate CXVI (500 mg, 0.55 mmol, 44% yield). ESIMS found for $C_{44}H_{61}F_3N_8O_9$ m/z 904 (M+H).

Step 2

Procedure can be found in examples 1-2. The final compound 29 was isolated as the hydrochloride salt. $^1$H NMR ($CD_3OD$) 0.90-1.27 (m, 2H), 1.38-1.68 (m, 2H), 2.72-3.04 (m. 6H), 3.34-3.55 (m, 6H), 4.61-4.75 (m, 1H), 4.88-5.03 (m, 1H), 6.81-6.95 (m, 1H), 7.01-7.19 (m, 1H), 7.42-7.55 (m, 1H), 7.57-7.68 (m, 4H), 7.70-7.82 (m, 2H), 8.21 (brs, 7H), 8.24 (brs, 3H), 8.92 (d, J=2 Hz, 1H), 9.19 (d, J=8 Hz, 1H), 9.27 (d, J=2 Hz, 1H), 11.39 (s, 1H); $^{19}$F NMR (DMSO-$d_6$) −60.08 (s, 3F); ESIMS found for $C_{29}H_{37}F_3N_8O_3$ m/z 604 (M+H).

The following compound was prepared in accordance with the procedure described in the above example 17.

43

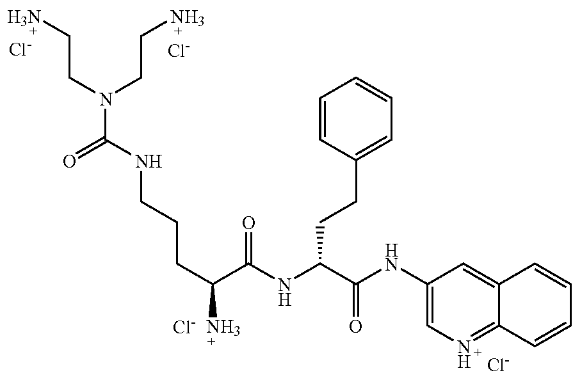

3-[(1S)-4-{[bis(2-azaniumylethyl)carbamoyl]amino}-1-{[(1R)-1-carbamoyl-3-phenylpropyl]carbamoyl}butan-1-aminium]quinolin-1-ium tetrachloride 44

$^1$H NMR (DMSO-$d_6$) 1.40-1.66 (m, 2H), 1.75-1.90 (m, 2H), 1.94-2.18 (m, 2H), 2.57-2.77 (m, 2H), 2.81-2.96 (m, 2H), 3.08 (brs, 2H), 3.38-3.51 (m, 4H), 3.95-4.01 (m, 1H), 4.43-4.55 (m, 2H), 7.04-7.10 (m, 1H), 7.11-7.18 (m, 1H), 7.20-7.28 (m, 4H), 7.71 (dd, J=7 Hz, 1H), 7.81 (dd, J=7 Hz, 1H), 8.08-8.24 (m, 8H), 8.40 (brs, 3H), 9.02 (brs, 1H), 9.25 (d, J=7 Hz, 1H), 9.34 (brs, 1H), 11.21 (s, 1H); ESIMS found for $C_{29}H_{40}N_8O_3$ m/z 549 (M+H).

Synthesis of 2-[bis(2-azaniumylethyl)carbamoyl]-1-{[(1S)-1-[methyl(2-{[4-(trifluoromethyl)phenyl]formamido}ethyl)carbamoyl]-3-phenylpropyl]carbamoyl}ethan-1-aminium trichloride 34 is depicted below in scheme 18 and example 18.

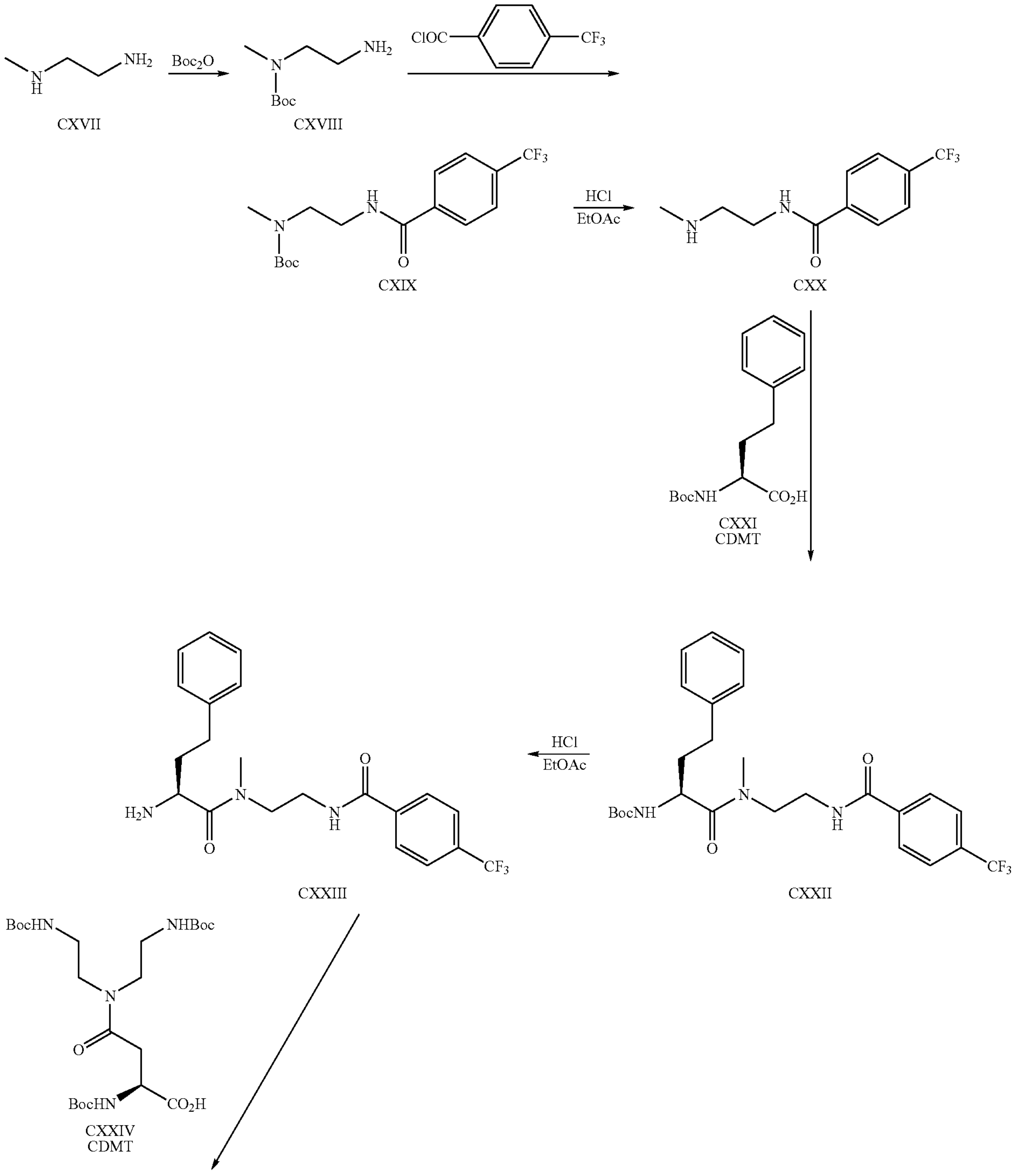

CXVII CXVIII CXIX CXX CXXI CXXII CXXIII CXXIV

-continued

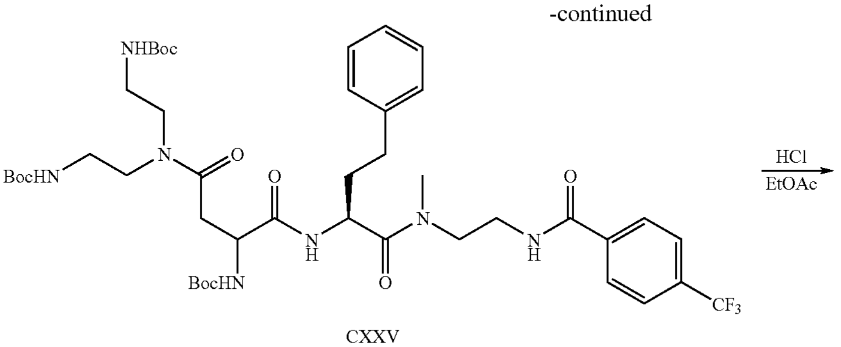

CXXV

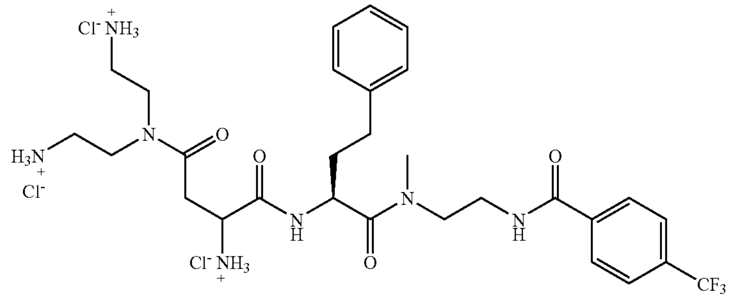

34

EXAMPLE 18

Step 1

To a solution of N-methylethylenediamine (11.8 mL, 134.9 mmol) in acetonitrile (300 mL), cooled to −30° C. was added TEA (7.46 mL, 53.9 mmol) and then a solution of $Boc_2O$ (9.81 g, 45 mmol) in acetonitrile was added dropwise. The mixture was stirred for 2 h at r.t. and then filtered through Celite. The residue was purified on a silica gel column (1:50→1:20→1:10 EtOAc:hexane) to give tert-butyl N-(2-aminoethyl)-N-methylcarbamate CXVIII as a yellow oil (5.2 g, 29.9 mmol, yield 66%). ESIMS found for $C_8H_{18}N_2O_2$ m/z 175 (M+H).

Step 2

To a solution of compound tert-butyl N-(2-aminoethyl)-N-methylcarbamate CXVIII (1.00 g, 5.74 mmol) in DCM (30 mL) was added TEA (0.87 mL, 6.32 mmol) and cooled to 0° C. To this mixture was added a solution of 4-(trifluoromethyl) benzoyl chloride (1.32 g, 6.32 mmol) in DCM (10 mL) dropwise. The reaction mixture was stirred overnight. Ethyl ether was added and the product precipitated (1.06 g, 2.88 mmol, 50% yield). The crude tert-butyl N-methyl-N-(2-{[4-(trifluoromethyl)phenyl]formamido}ethyl)carbamate CXIX was used in step 3 without any purification. ESIMS found for $C_{16}H_{21}F_3N_2O_3$ m/z 369 (M+Na).

Step 3

A solution of tert-butyl N-methyl-N-(2-{[4-(trifluoromethyl)phenyl]formamido}ethyl)carbamate CXIX (0.53 g, 1.44 mmol) in 3 M HCl in EtOAc (20 mL) was stirred for about 2 h. The solvent was evaporated under vacuum to give N-[2-(methylamino)ethyl]-4-(trifluoromethyl)benzamide CXX as white crystals (0.32 g, 1.30 mmol, 90% yield). $^1H$ NMR (DMSO-$d_6$) 2.57 (s, 3H), 3.03-3.06 (m, 2H), 3.57-3.61 (m, 2H), 7.87 (d, J=8 Hz, 2H), 8.12 (d, J=8 Hz, 2H), 8.89 (brs, 2H), 9.06-9.09 (m, 1H); ESIMS found for $C_{11}H_{13}F_3N_2O$ m/z 247 (M+H).

Step 4

A solution of CDMT (0.28 g, 1.6 mmol) in DCM (30 mL) was cooled to 0° C. before adding N-methylmorpholine (0.44 mL, 4 mmol). After 15 min, (2S)-2-{[(tert-butoxy)carbonyl]amino}-4-phenylbutanoic acid CXXI (0.42 g, 1.5 mmol) was added and the solution was stirred for an additional 40 min. After that time, N-[2-(methylamino)ethyl]-4-(trifluoromethyl)benzamide CXX (0.32 g, 1.3 mmol) was added and the mixture stirred at r.t. overnight. The mixture was washed with 1 M HCl (5×), 1 M $K_2CO_3$ (5×), brine and dried over $MgSO_4$. The solvent was evaporated under vacuum and the solid residue was crystallized from EtOAc/hexane to give tert-butyl N-[(1S)-1-[methyl(2-{[4-(trifluoromethyl)phenyl]formamido}ethyl)carbamoyl]-3-phenylpropyl]carbamate CXXII as white solid (0.65 g, 1.23 mmol, 95% yield). $^1H$ NMR (DMSO-$d_6$) 1.34 (s, 9H), 1.66-1.80 (m, 2H), 2.54-2.66 (m, 2H), 2.93 (s, 3H), 3.44-3.52 (m, 2H), 3.74-3.83 (m, 2H), 4.25-4.32 (m, 1H), 6.99-7.14 (m, 7H), 7.74 (d, J=8 Hz, 2H), 7.91 (d, J=8 Hz, 2H), 8.63-8.71 (m, 1H); ESIMS found for $C_{26}H_{32}F_3N_3O_4$ m/z 530 (M+Na).

Step 5

A solution of tert-butyl N-[(1S)-1-[methyl(2-{[4-(trifluoromethyl)phenyl]formamido}ethyl)carbamoyl]-3-phenylpropyl]carbamate CXXII (0.65 g, 1.23 mmol) in 1 M HCl in diethyl ether was stirred overnight. The solvent was evaporated under vacuum to give (2S)-2-amino-N-methyl-4-phenyl-N-(2-{[4-(trifluoromethyl)phenyl]formamido}ethyl)butanamide CXXIII as white crystals (0.46 g, 1.14 mmol, 93% yield). $^1H$ NMR (DMSO-$d_6$) 1.87-2.02 (m, 2H), 2.55-2.74 (m, 2H), 3.00 (s, 3H), 3.44-3.59 (m, 2H), 3.88-3.94 (m, 2H), 4.27 (brs, 1H), 7.18-7.28 (m, 6H), 7.71 (d, J=8 Hz, 2H), 7.95 (d, J=8 Hz, 2H), 8.29 (brs, 3H), 8.86-8.88 (m, 1H); ESIMS found for $C_{21}H_{24}F_3N_3O_2$ m/z 408 (M+H).

Step 6

A solution of CDMT (0.22 g, 1.26 mmol) in DCM (30 mL) was cooled to 0° C. before adding N-methylmorpholine (0.3 mL, 2.62 mmol). After 15 min, (2S)-3-[bis(2-{[(tert-butoxy)carbonyl]amino}ethyl)carbamoyl]-2-{[(tert-butoxy)carbonyl]amino}propanoic acid CXXIV (0.62 g, 1.20 mmol) was added and the solution was stirred for additional 40 min. After that time, (2S)-2-amino-N-methyl-4-phenyl-N-(2-{[4-(trifluoromethyl)phenyl]formamido}ethyl)butanamide CXXIII (0.56 g, 1.26 mmol) was added and the mixture stirred at r.t. overnight. The mixture was washed with 1 M HCl (5×), 1 M $K_2CO_3$ (5×), brine and dried over $MgSO_4$. The solvent was evaporated under vacuum and the residue was purified on a silica gel column (50:1 DCM/methanol) to give tert-butyl N-[(1S)-2-[bis(2-{[(tert-butoxy)carbonyl]amino}ethyl)carbamoyl]-1-{[(1S)-1-[methyl(2-{[4-(trifluoromethyl)phenyl]formamido}ethyl)carbamoyl]-3-phenylpropyl]carbamoyl}ethyl]carbamate as yellow solid (0.78 g, 0.86 mmol, 68% yield). ESIMS found for $C_{44}H_{64}F_3N_7O_{10}$ m/z 908 (M+H).

Step 7

Procedure can be found in examples 1-2. The final compound 34 was isolated as the hydrochloride salt. $^1H$ NMR (DMSO-$d_6$) 2.97 (s, 3H), 2.97-3.18 (m, 6H), 3.18-3.52 (m, 8H), 3.52-3.74 (m, 4H), 4.21-4.38 (m, 1H), 4.53-4.71 (m, 1H), 7.04-7.27 (m, 5H), 7.73 (d, J=8 Hz, 1H), 7.83 (d, J=8 Hz, 1H), 7.97 (d, J=8 Hz, 1H), 8.07 (d, J=8 Hz, 1H), 8.07-8.50 (m, 9H), 8.82 (d, J=8 Hz, 1H), 8.82-8.90 (m, 1H); ESIMS found for $C_{29}H_{40}F_3N_7O_4$ m/z 608 (M+H).

The following compounds were prepared in accordance with the procedure described in the above example 18.

35

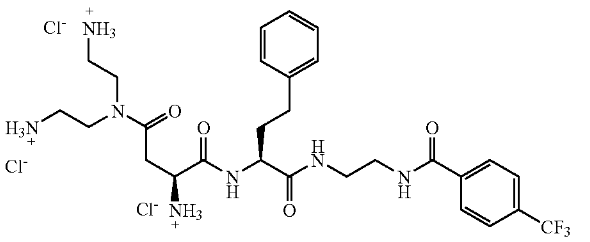

(1S)-2-[bis(2-azaniumylethyl)carbamoyl]-1-{[(1S)-3-phenyl-1-[(2-{[4-(trifluoromethyl)phenyl]formamido}ethyl)carbamoyl]propyl]carbamoyl}ethan-1-aminium trichloride 35

$^1H$ NMR (DMSO-$d_6$) 1.74-2.05 (m, 2H), 2.53-2.69 (m, 2H), 2.91-3.19 (m, 8H), 3.55-3.70 (m, 6H), 4.18 (brs, 1H), 4.32 (brs, 1H), 7.10-7.28 (m, 5H), 7.77 (d, J=8 Hz, 2H), 8.06 (d, J=8 Hz, 2H), 8.16 (brs, 3H), 8.35 (brs, 7H), 8.88 (brs, 2H); $^{19}F$ NMR (DMSO-$d_6$) −60.67 (s, 3F); ESIMS found for $C_{28}H_{38}F_3N_7O_4$ m/z 594 (M+H).

333

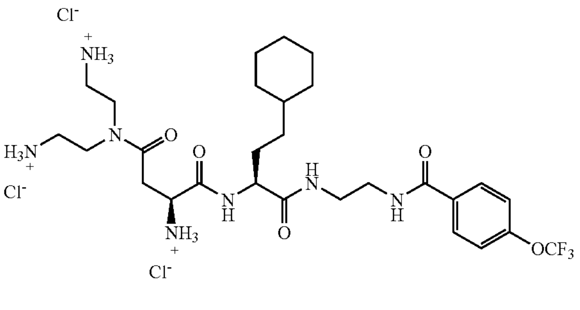

(1S)-2-[bis(2-azaniumylethyl)carbamoyl]-1-{[(1S)-3-cyclohexyl-1-[(2-{[4-(trifluoromethoxy)phenyl]formamido}ethyl)carbamoyl]propyl]carbamoyl}ethan-1-aminium trichloride 333

$^1H$ NMR (MeOD-$d_4$) 0.75-0.90 (m, 2H), 1.17 (brs, 6H), 1.65 (brs, 8H), 3.18-3.38 (m, 9H), 3.38-3.49 (m, 2H), 3.53 (s, 2H), 4.23 (dd, J=5 Hz, J=8 Hz, 1H), 4.41 (t, J=11 Hz, 1H), 7.35 (d, J=9 Hz, 2H), 8.01 (d, J=9 Hz, 2H), $^{19}F$ NMR (MeOD-$d_4$) −58.68 (s); ESIMS found for $C_{28}H_{44}F_3N_7O_5$ m/z 616.6 (M+H).

Synthesis of 3-[(4S)-4-{[(1R)-1-carbamoyl-3-phenylpropyl]carbamoyl}butane-1,2,4-tris(aminium)]quinolin-1-ium tetrachloride 40 is depicted below in scheme 19 and example 19.

Scheme 19

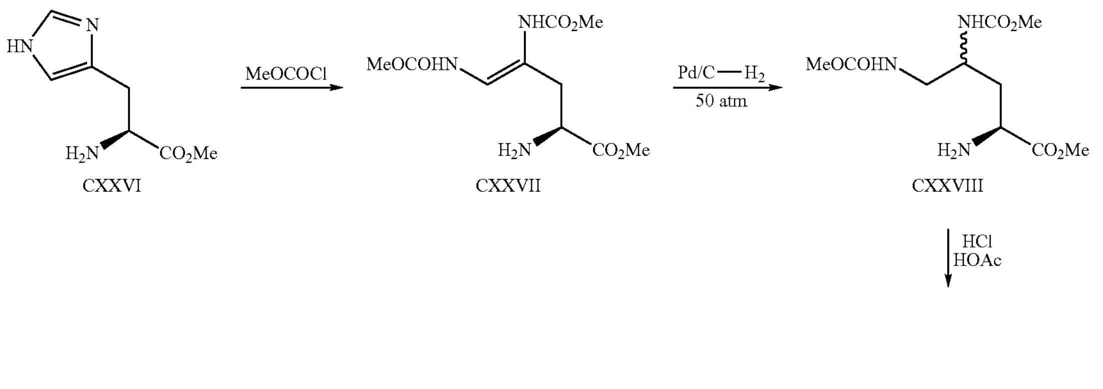

CXXVI CXXVII CXXVIII

-continued

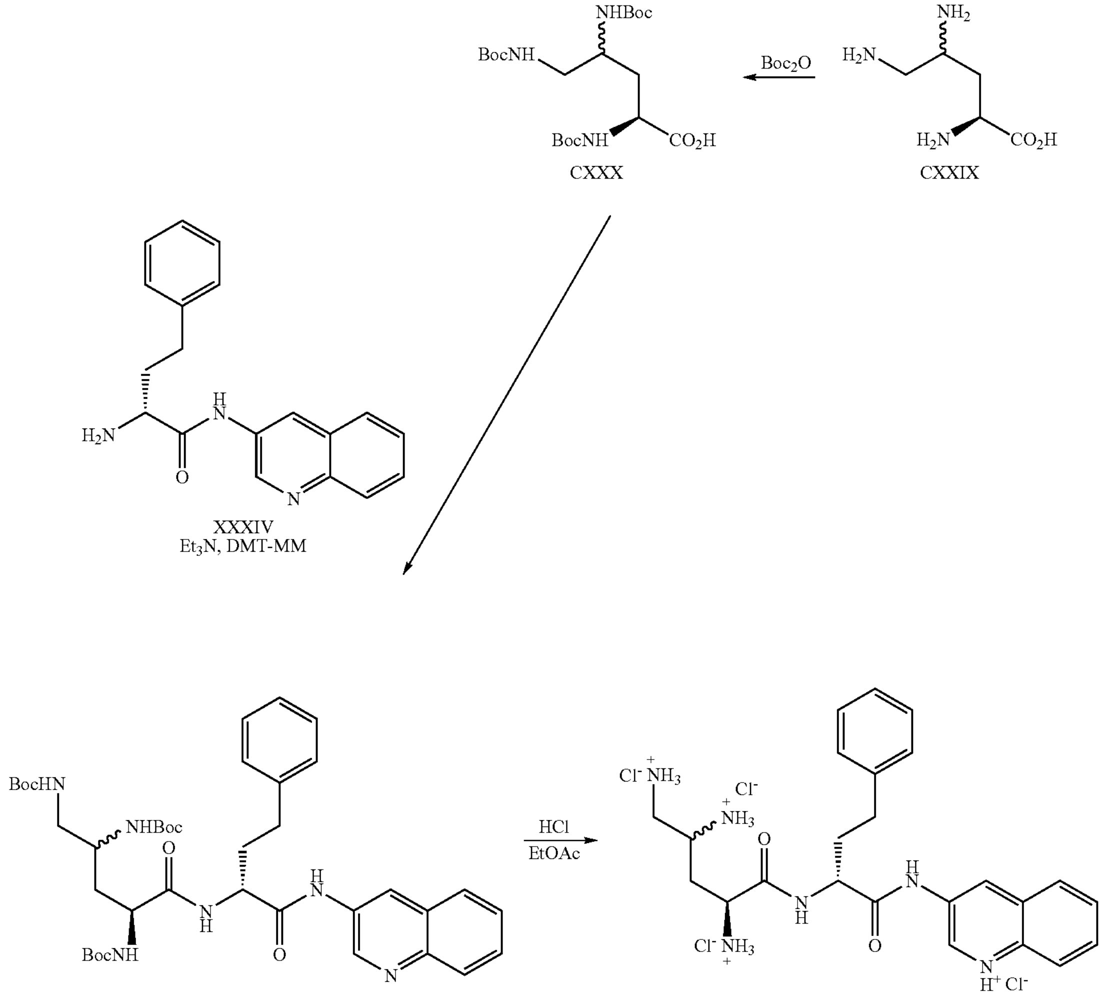

CXXX CXXIX XXXIV CXXXI 40

EXAMPLE 19

Step 1

A solution of histidine methyl ester CXXVI (500 mg, 2.96 mmol) in EtOAc (20 mL) and water (5 mL) was cooled to 0° C. before adding a solution of methyl chloroformate (2.3 mL, 29.6 mmol) in EtOAc (20 mL) and a solution of $NaHCO_3$ (2.5 g, 29.6 mmol) in water (25 mL). After the addition was complete, the mixture was stirred at 0° C. for 2 h and then at r.t. overnight. The organic layer was separated, washed with water, dried over $Na_2SO_4$ and concentrated. The residue was purified on a silica gel column (1:2 hexane:EtOAc) to produce methyl (2S,4Z)-2,4,5-tris[(methoxycarbonyl)amino]pent-4-enoate CXXVII (430 mg, 1.29 mmol, 44% yield). $^1H$ NMR (DMSO-$d_6$) 2.35-2.41 (m, 1H), 2.76-2.80 (m, 1H), 3.57-3.62 (m, 12H), 4.07-4.12 (m, 1H), 6.02 (d, J=10 Hz, 1H), 7.45 (d, J=8 Hz, 1H), 8.15 (brs, 1H), 8.64 (brs, 1H). ESIMS found for $C_{12}H_{19}N_3O_8$ m/z 333 (M+).

Step 2

To a solution of methyl (2S,4Z)-2,4,5-tris[(methoxycarbonyl)amino]pent-4-enoate CXXVII (624 mg, 1.87 mmol) in ethanol (15 mL) was added 10% Pd/C catalyst (60 mg). The mixture was placed in an autoclave and exposed to 50 atm of $H_2$ with stirring at r.t. for 36 h. Reaction mixture was filtered through Celite and concentrated to dryness to give crude methyl (2S)-2,4,5-tris[(methoxycarbonyl)amino]pentanoate CXXVIII (540 mg). ESIMS found for $C_{12}H_{21}N_3O_8$ m/z 358 (M+Na).

Step 3-4

A solution of methyl (2S)-2,4,5-tris[(methoxycarbonyl)amino]pentanoate CXXVIII in acetic acid (3 mL) and conc. HCl (7 mL) and refluxed for 60 h. The reaction mixture was concentrated to dryness giving crude (2S)-2,4,5-triaminopentanoic acid CXXIX as the hydrochloride salt (350 mg). CXXIX was dissolved in DMF (8 mL) before adding TEA (1.3 mL, 9.3 mmol) followed by $Boc_2O$ (1.36 g, 6.54 mmol). The reaction mixture was stirred at r.t. for 48 h. The solvent was evaporated under reduced pressure and the residue was dissolved in water, washed with diethyl ether and acidified with 1 N HCl until pH=2.5. The aqueous phase was further extracted with ethyl acetate. The combined EtOAc was dried over $Na_2SO_4$ and concentrated. The residue was purified on a silica gel column (20:1 EtOAc:MeOH) to give (2S)-2,4,5-tris({[(tert-butoxy)carbonyl]amino}) pentanoic acid CXXX (200 mg, 0.44 mmol, 23% yield). $^1$H NMR (DMSO-$d_6$) 1.38 (s, 27H), 1.84-1.92 (m, 1H), 2.07-2.12 (m, 1H), 2.86-2.98 (m, 2H), 3.99-4.08 (m, 1H), 6.83-6.89 (m, 0.3H 1$^{st}$ diastereoisomer), 6.95-6.98 (m, 0.7 Hz 2$^{nd}$ diastereoisomer), 7.00-7.05 (m, 1H), 7.17 (s, 0.3H), 7.82 (s, 0.7H). ESIMS found for $C_{20}H_{37}N_3O_8$ m/z 470 (M+Na).

Step 5

Procedure can be found in previous examples.

Step 6

Procedure can be found in previous examples. The final compound 40 was isolated as the hydrochloride salt. $^1$H NMR (DMSO-$d_6$) 2.02-2.38 (m, 4H), 2.64-2.80 (m, 2H), 3.24-3.40 (m, 2H), 4.33-4.37 (m, 1H), 4.55-4.58 (m, 1H), 7.17-7.22 (m, 1H), 7.20-7.29 (m, 5H), 7.62-7.67 (m, 1H), 7.71-7.76 (m, 1H), 7.98-8.05 (m, 2H), 8.63 (brs, 6H), 8.79 (brs, 3H), 8.81 (s, 1H), 9.13 (d, J=2 Hz, 1H), 9.47 (d, J=7 Hz, 1H), 10.93 (s, 1H); ESIMS found for $C_{24}H_{30}N_6O_2$ m/z 435 (M+H).

Scheme 20 describes an example for the preparation of a parallel synthesis library of polyamine EPIs. Thus the carboxylic acid CXXXII was coupled using standard methods with a variety of CAP amines CXXXIII to give the polyamine EPI CXXXIV.

Scheme 20

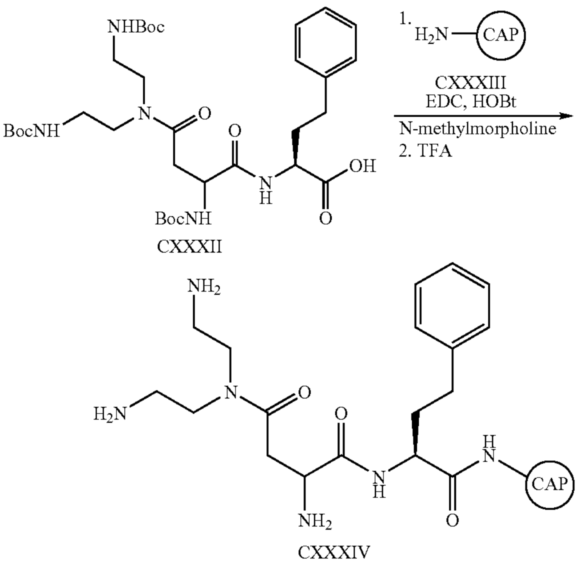

CXXXII

CXXXIV

TABLE 1

The following compounds are prepared in accordance with the procedure described as in the above scheme 20

| Compound # | CAP amine CXXXIII | ESIMS found |
|---|---|---|
| 49 | 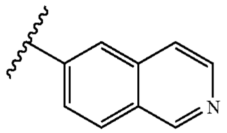 | 506.2 (M + H) |
| 52 | 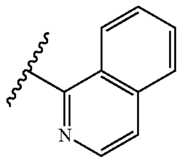 | 506.2 (M + H) |
| 56 | 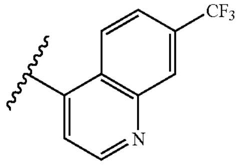 | 574.2 (M + H) |
| 57 | 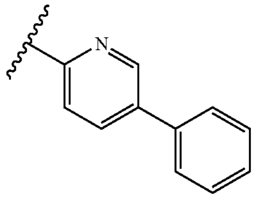 | 532.3 (M + H) |
| 60 | 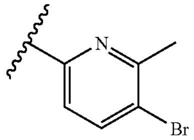 | 548.2 (M + H) |

TABLE 1-continued
The following compounds are prepared in accordance with the procedure described as in the above scheme 20
| Compound # | CAP amine CXXXIII | ESIMS found |
|---|---|---|
| 61 | 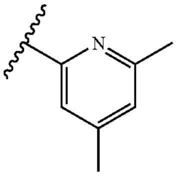 | 506.2 (M + Na) |
| 62 | 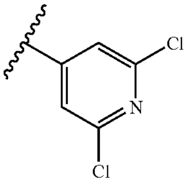 | 524.2 (M + H) |
| 68 | 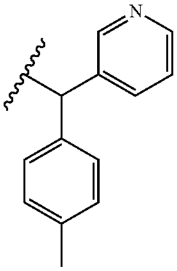 | |
| 69 | 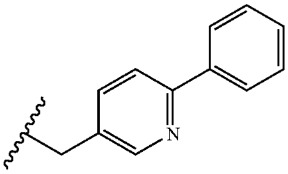 | 546.3 (M + H) |
| 70 | 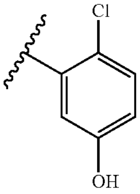 | 505.2 (M + H) |
| 71 | 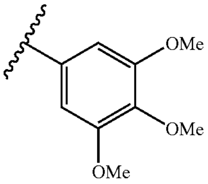 | 545.5 (M + H) |
| 72 | 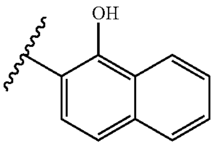 | 521.5 (M + H) |

TABLE 1-continued
The following compounds are prepared in accordance with the procedure described as in the above scheme 20
| Compound # | CAP amine CXXXIII | ESIMS found |
|---|---|---|
| 74 | 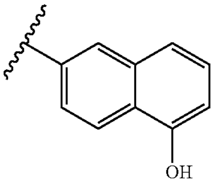 | 521.3 (M + H) |
| 75 | 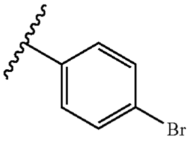 | 533.2 (M + H) |
| 77 | 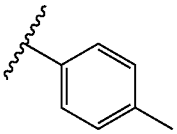 | 469.3 (M + H) |
| 79 | 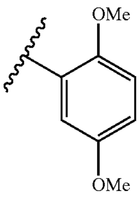 | 515.3 (M + H) |
| 80 | 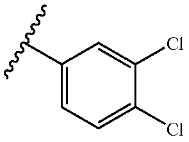 | 523.2 (M + H) |
| 82 | 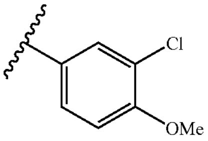 | 519.4 (M + H) |
| 83 | 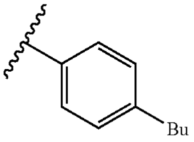 | 511.5 (M + H) |
| 84 | 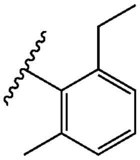 | 497.5 (M + H) |
| 85 | 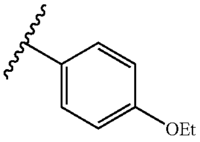 | 499.5 (M + H) |

TABLE 1-continued
The following compounds are prepared in accordance with the procedure described as in the above scheme 20
| Compound # | CAP amine CXXXIII | ESIMS found |
|---|---|---|
| 88 | 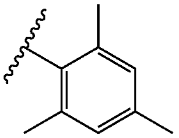 | 497.5 (M + H) |
| 89 | 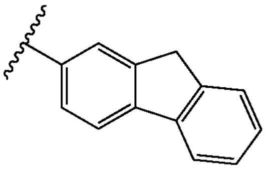 | 543.3 (M + H) |
| 91 | 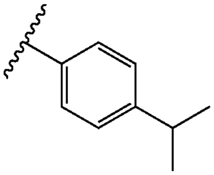 | 497.3 (M + H) |
| 93 | 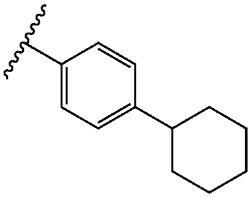 | 537.3 (M + H) |
| 96 | 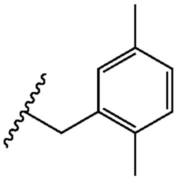 | 497.5 (M + H) |
| 97 | 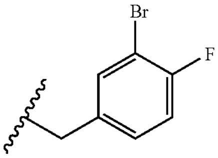 | 565.3 (M + H) |
| 101 | 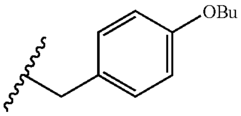 | 541.3 (M + H) |
| 102 | 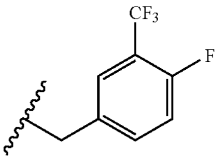 | 555.3 (M + H) |

TABLE 1-continued
The following compounds are prepared in accordance with the procedure described as in the above scheme 20
| Compound # | CAP amine CXXXIII | ESIMS found |
|---|---|---|
| 103 | 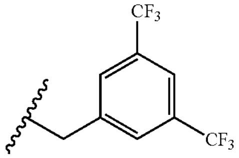 | |
| 106 | 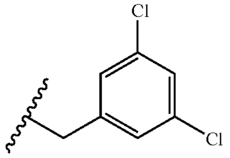 | 537.4 (M + H) |
| 107 | 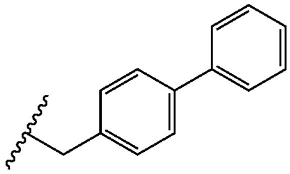 | 545.4 (M + H) |
| 108 | 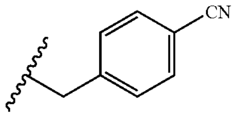 | 494.2 (M + H) |
| 109 | 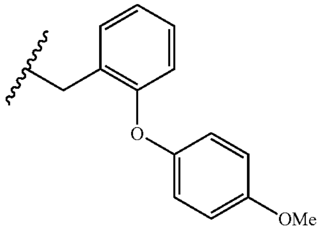 | 591.5 (M + H) |
| 110 | 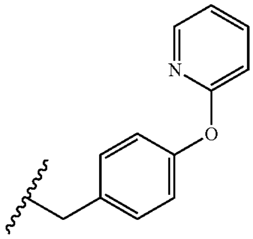 | 562.5 (M + H) |
| 111 | 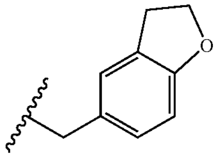 | 511.5 (M + H) |
| 112 | 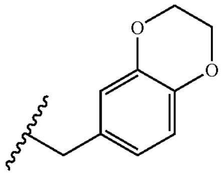 | 527.3 (M + H) |

TABLE 1-continued
The following compounds are prepared in accordance with the procedure described as in the above scheme 20
| Compound # | CAP amine CXXXIII | ESIMS found |
|---|---|---|
| 113 | 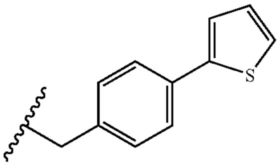 | 551 2 (M + H) |
| 114 | 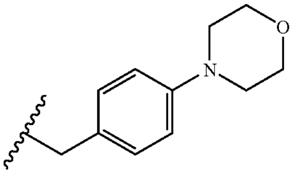 | 554.2 (M + H) |
| 115 | 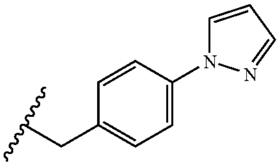 | 535.3 (M + H) |
| 116 | 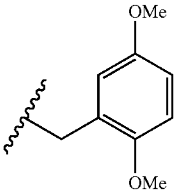 | 529.5 (M + H) |
| 117 | 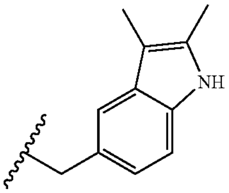 | 536.6 (M + H) |
| 118 | 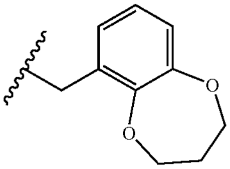 | 541.3 (M + H) |
| 119 | 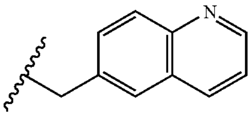 | 260.7 (M + H)/2 |
| 122 | 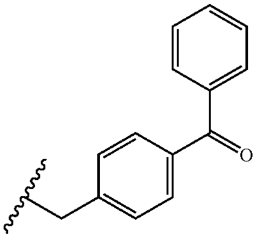 | 573.5 (M + H) |

TABLE 1-continued
The following compounds are prepared in accordance with the procedure described as in the above scheme 20
| Compound # | CAP amine CXXXIII | ESIMS found |
|---|---|---|
| 123 | 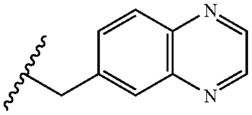 | 521.4 (M + H) |
| 124 | 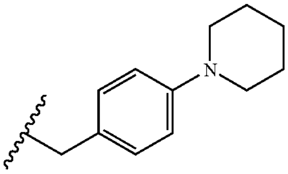 | 552.3 (M + H) |
| 125 | 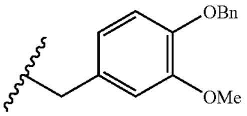 | 605.3 (M + H) |
| 126 | 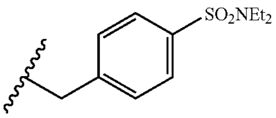 | 604.3 (M + H) |
| 127 | 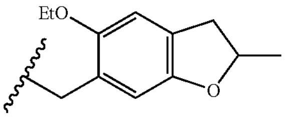 | 569.3 (M + H) |
| 129 | 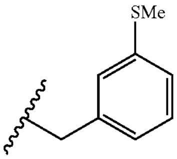 | 515.3 (M + H) |
| 130 | 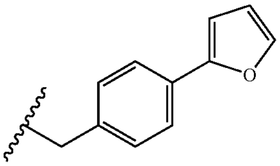 | 535.3 (M + H) |
| 131 | 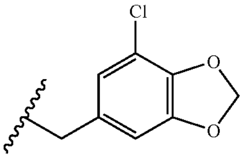 | 547.4 (M + H) |
| 132 | 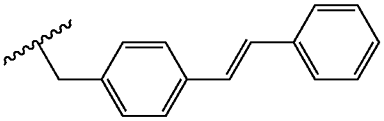 | 571.3 (M + H) |

TABLE 1-continued
| The following compounds are prepared in accordance with the procedure described as in the above scheme 20 | | |
|---|---|---|
| Compound # | CAP amine CXXXIII | ESIMS found |
| 133 | 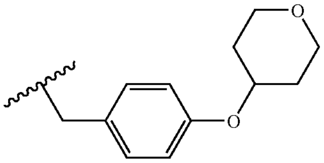 | 569.3 (M + H) |
| 134 | 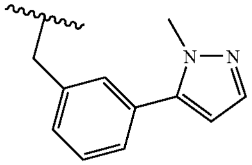 | 549.3 (M + H) |
| 135 | 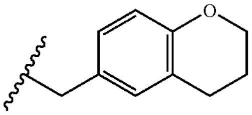 | 525.5 (M + H) |
| 136 | 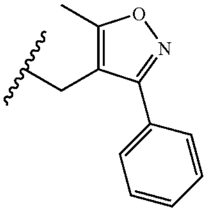 | 550.3 (M + H) |
| 137 | 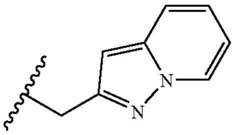 | 509.4 (M + H) |
| 138 | 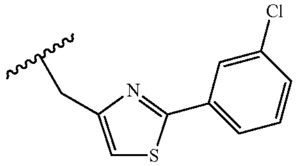 | 586.2 (M + H) |
| 140 | 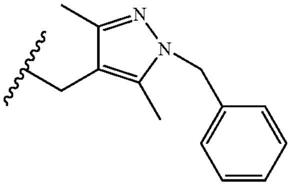 | 577.3 (M + H) |
| 141 | 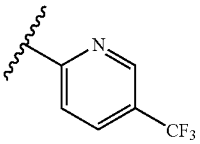 | 524.2 (M + H) |
| 211 | 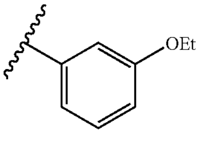 | 499.3 (M + H) |

TABLE 1-continued
| The following compounds are prepared in accordance with the procedure described as in the above scheme 20 | | |
|---|---|---|
| Compound # | CAP amine CXXXIII | ESIMS found |
| 212 | 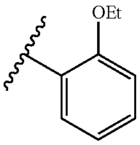 | 499.3 (M + H) |
| 214 | 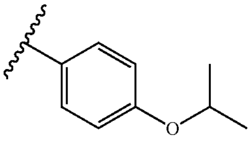 | 513.3 (M + H) |
| 215 | 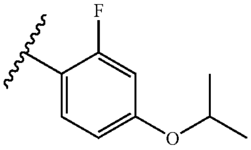 | 531.3 (M + H) |
| 216 | 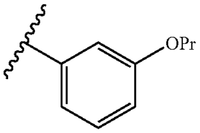 | 513.3 (M + H) |
| 217 | 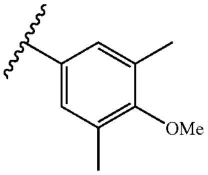 | 513.3 (M + H) |
| 221 | 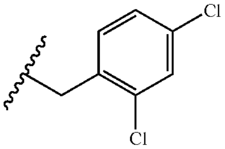 | 537.2 (M + H) |
| 222 | 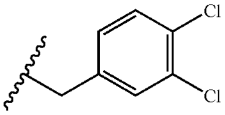 | 537.2 (M + H) |
| 223 | 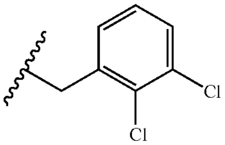 | 537.2 (M + H) |
| 224 | 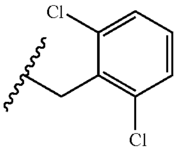 | 537.2 (M + H) |

TABLE 1-continued
| The following compounds are prepared in accordance with the procedure described as in the above scheme 20 | | |
|---|---|---|
| Compound # | CAP amine CXXXIII | ESIMS found |
| 225 | 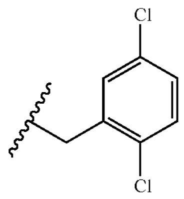 | 537.2 (M + H) |
| 226 | 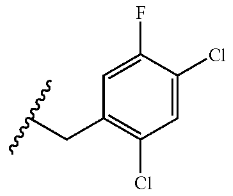 | 552.2 (M + H) |
| 227 | 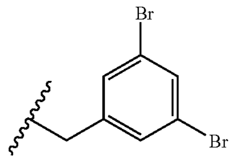 | 627.1 (M + H) |
| 228 | 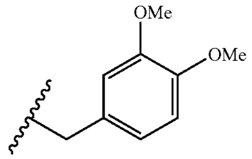 | 529.3 (M + H) |
| 229 | 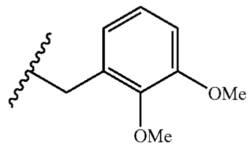 | 529.3 (M + H) |
| 230 | 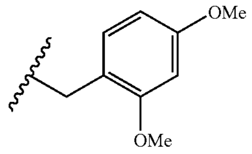 | 529.3 (M + H) |
| 231 | 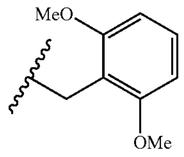 | 529.3 (M + H) |
| 233 | 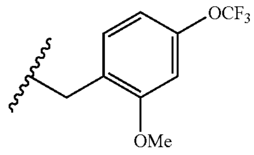 | 583.3 (M + H) |

TABLE 1-continued
| The following compounds are prepared in accordance with the procedure described as in the above scheme 20 | | |
|---|---|---|
| Compound # | CAP amine CXXXIII | ESIMS found |
| 235 | 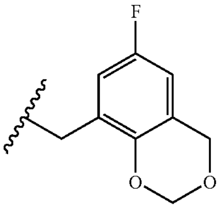 | 545.2 (M + H) |
| 236 | 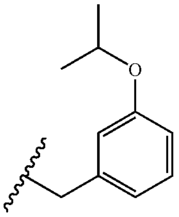 | 527.3 (M + H) |
| 237 | 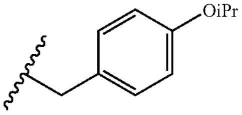 | 527.3 (M + H) |
| 239 | 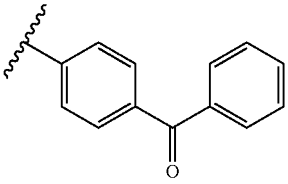 | 559.3 (M + H) |
| 240 | 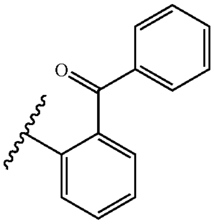 | 559.3 (M + H) |
| 241 | 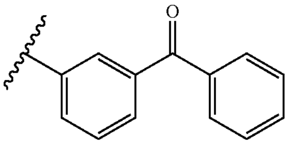 | 559.3 (M + H) |
| 244 | 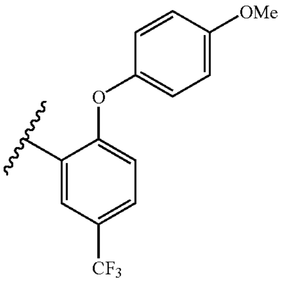 | 645.3 (M + H) |

TABLE 1-continued
| The following compounds are prepared in accordance with the procedure described as in the above scheme 20 | | |
|---|---|---|
| Compound # | CAP amine CXXXIII | ESIMS found |
| 247 | 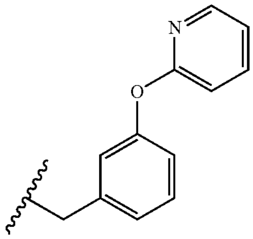 | 562.3 (M + H) |
| 248 | 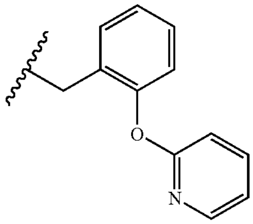 | 562.3 (M + H) |
| 250 | 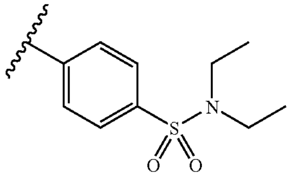 | 590.3 (M + H) |
| 251 | 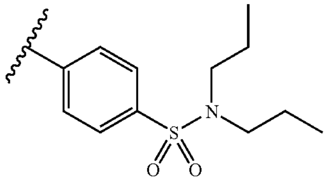 | 618.4 (M + H) |
| 252 | 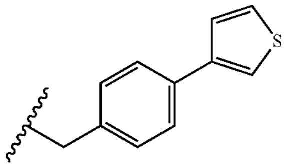 | 551.3 (M + H) |
| 253 | 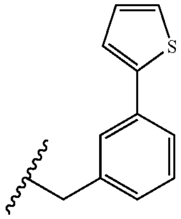 | 551.3 (M + H) |
| 254 | 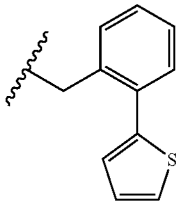 | 551.3 (M + H) |

TABLE 1-continued
| The following compounds are prepared in accordance with the procedure described as in the above scheme 20 | | |
|---|---|---|
| Compound # | CAP amine CXXXIII | ESIMS found |
| 262 | 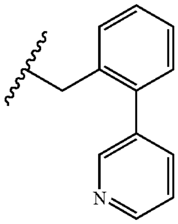 | 546.3 (M + H) |
| 263 | 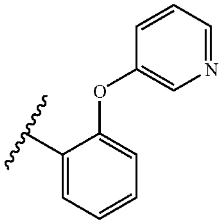 | 548.3 (M + H) |
| 266 | 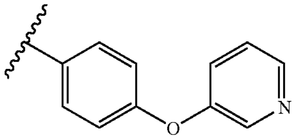 | 548.3 (M + H) |
| 270 | 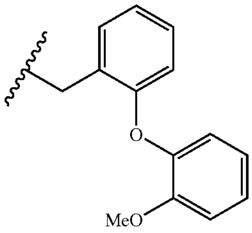 | 591.4 (M + H) |
| 271 | 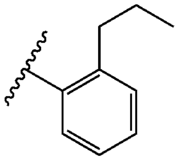 | 497.5 (M + H) |
| 272 | 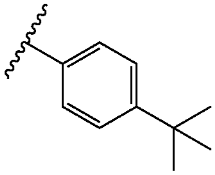 | 511.5 (M + H) |
| 273 | 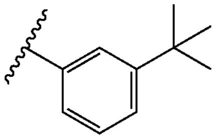 | 511.5 (M + H) |

TABLE 1-continued
The following compounds are prepared in accordance with the procedure described as in the above scheme 20
| Compound # | CAP amine CXXXIII | ESIMS found |
|---|---|---|
| 274 | 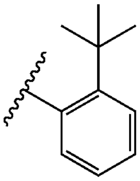 | 511.5 (M + H) |
| 275 | 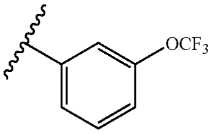 | 539.5 (M + H) |
| 276 | 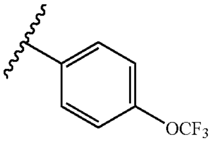 | 539.5 (M + H) |
| 277 | 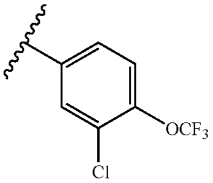 | 573.6 (M + H) |
| 279 | 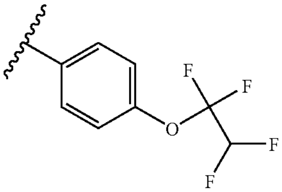 | 571.0 (M + H) |
| 280 | 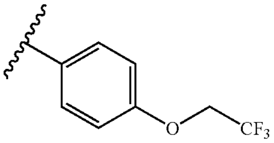 | 554.4 (M + H) |
| 282 | 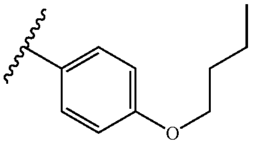 | 527.5 (M + H) |
| 283 | 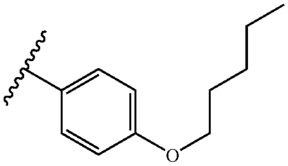 | 541.5 (M + H) |

TABLE 1-continued
| The following compounds are prepared in accordance with the procedure described as in the above scheme 20 | | |
|---|---|---|
| Compound # | CAP amine CXXXIII | ESIMS found |
| 285 | 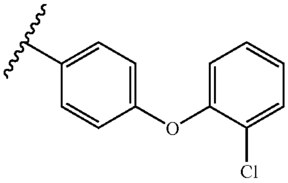 | 581.6 (M + H) |
| 287 | 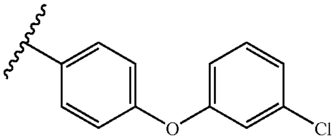 | 581.6 (M + H) |
| 289 | 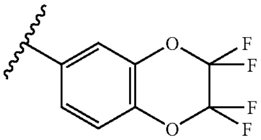 | 585.2 (M + H) |
| 290 | 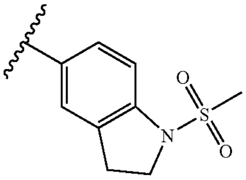 | 574.5 (M + H) |
| 293 | 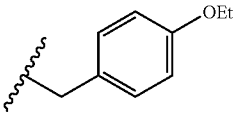 | 513.5 (M + H) |
| 295 | 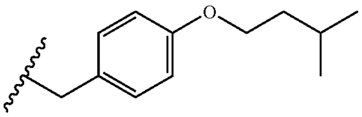 | 555.6 (M + H) |
| 296 | 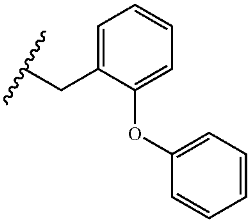 | 561.6 (M + H) |
| 297 | 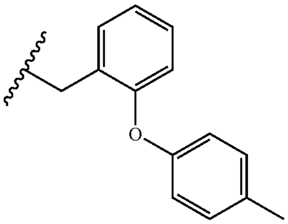 | 575.8 (M + H) |

TABLE 1-continued

| The following compounds are prepared in accordance with the procedure described as in the above scheme 20 | | |
|---|---|---|
| Compound # | CAP amine CXXXIII | ESIMS found |
| 298 | 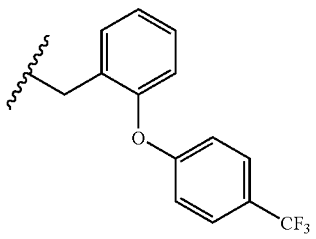 | 629.8 (M + H) |
| 344 | 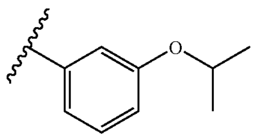 | 513.3 (M + H) |

Scheme 21 below describes a method for the preparation of a parallel synthesis library of polyamine EPIs. The carboxylic acid CXXIV was coupled using standard methods with a variety of amino acids CXXXV, deprotected and then coupled to a variety of CAP amines CXXXIII to give the polyamine EPI CXXXVIII Scheme 21

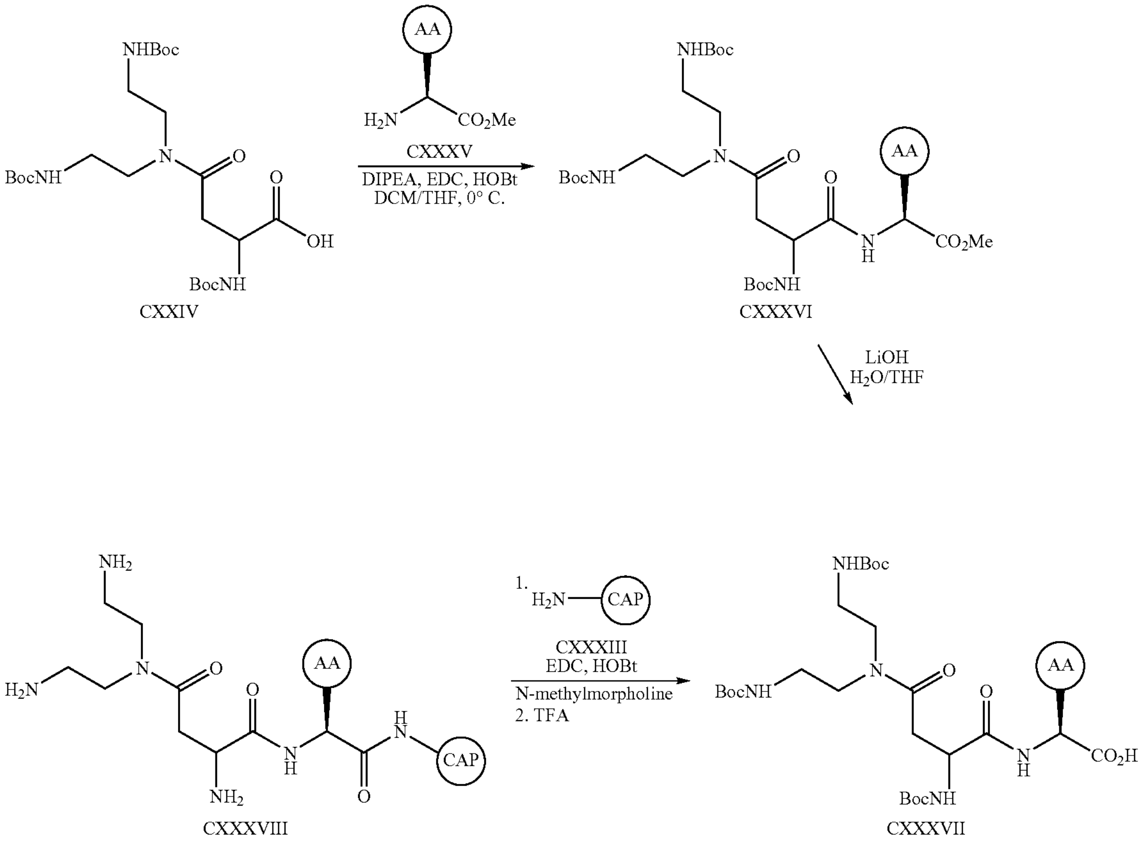

TABLE 2
| The following compounds are prepared in accordance with the procedure described as in the above scheme 21 | | | |
|---|---|---|---|
| Compound # | Central AA CXXXV | CAP amine CXXXIII | ESIMS found |
| 145 | 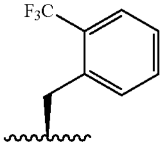 | 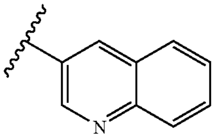 | 280.8 (M + H)/2 |
| 146 | 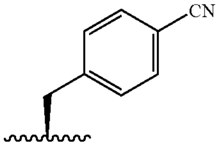 | 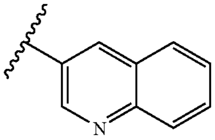 | 517.3 (M + H) |
| 147 | 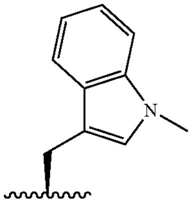 | 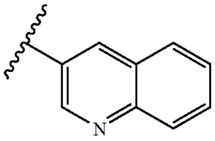 | 545.3 (M + H) |
| 148 | 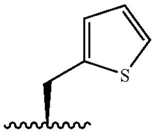 | 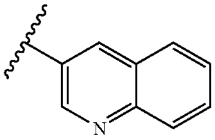 | 498.2 (M + H) |
| 149 | 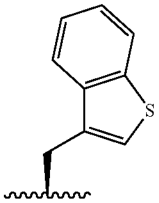 | 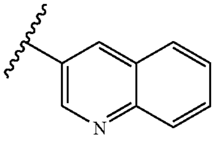 | 548.2 (M + H) |
| 151 | 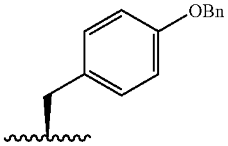 | 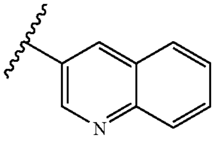 | 598.3 (M + H) |
| 154 | 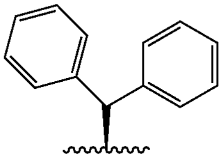 | 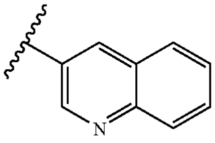 | 568.3 (M + H) |
| 155 | 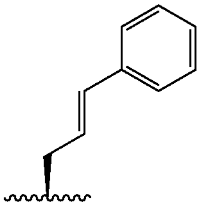 | 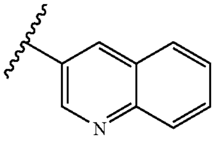 | 518.3 (M + H) |

TABLE 2-continued
The following compounds are prepared in accordance with the procedure described as in the above scheme 21
| Compound # | Central AA CXXXV | CAP amine CXXXIII | ESIMS found |
|---|---|---|---|
| 158 | 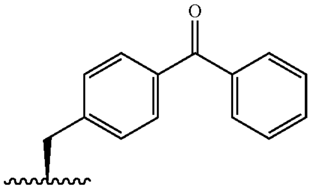 | 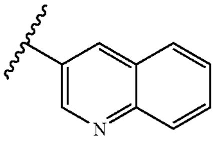 | 596.3 (M + H) |
| 162 | 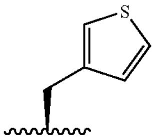 | 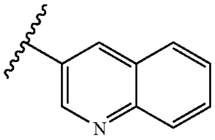 | 498.2 (M + H) |
| 346 | 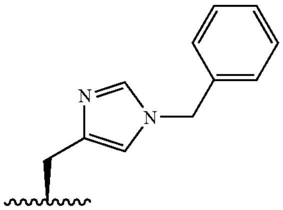 | 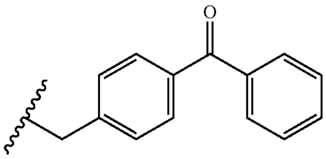 | 639.3 (M + H) |
| 362 | 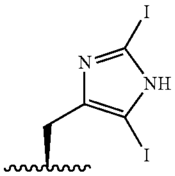 | 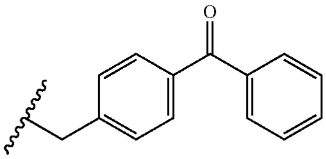 | 801.1 (M + H) |
| 363 | 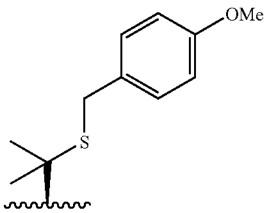 | 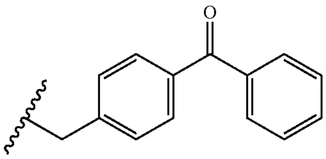 | 663.3 (M + H) |
| 364 | 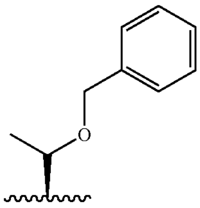 | 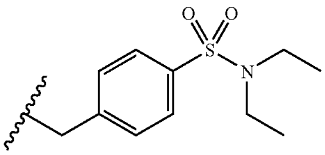 | 634.4 (M + H) |
| 366 | 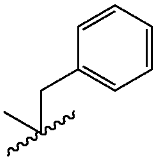 | 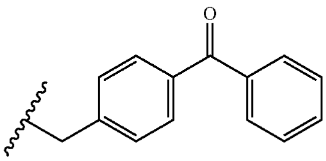 | 573.3 (M + H) |

TABLE 2-continued

| The following compounds are prepared in accordance with the procedure described as in the above scheme 21 | | | |
|---|---|---|---|
| Compound # | Central AA CXXXV | CAP amine CXXXIII | ESIMS found |
| 367 | 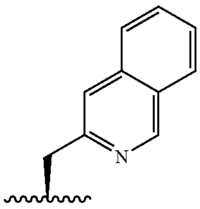 | 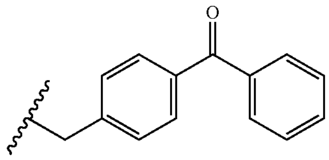 | 610.3 (M + H) |
| 368 | 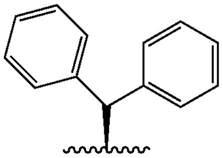 | 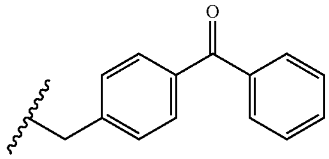 | 635.4 (M + H) |

Synthesis of 3-[(1S)-2-[(2-azaniumylethyl)(3-azaniumylpropyl)carbamoyl]-1-{[(1S)-1-carbamoyl-3-phenylpropyl]carbamoyl}ethan-1-aminium]quinolin-1-ium tetrachloride 168 is depicted below in scheme 22 and example 22.

Scheme 22

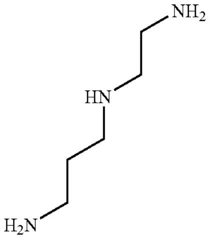

CXXXVIII

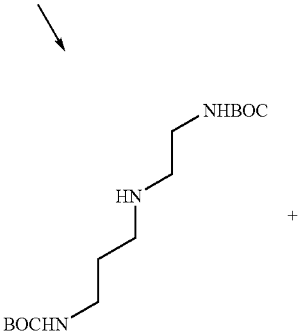

CXXXIX

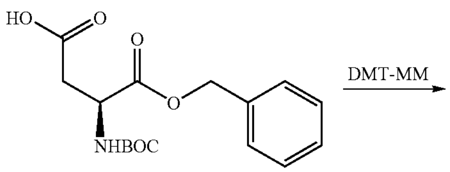

CXL

-continued

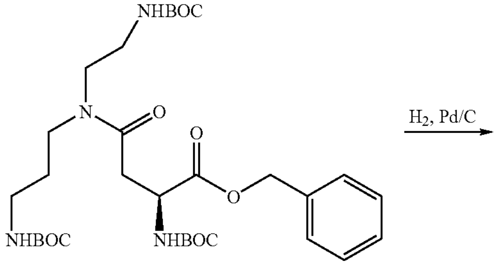

CXLII

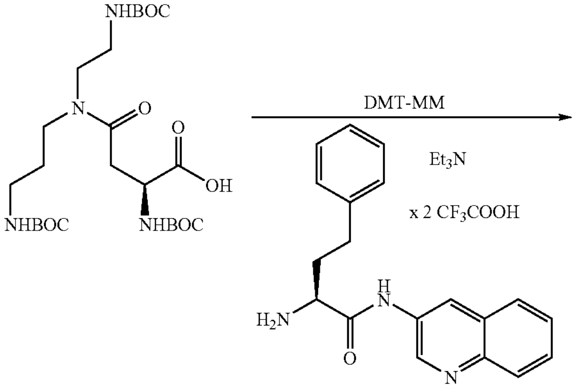

CLXII CXLIII

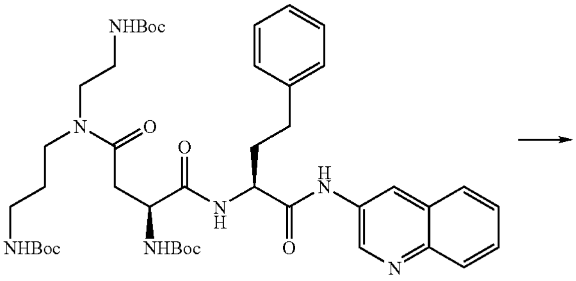

CXLIV

-continued

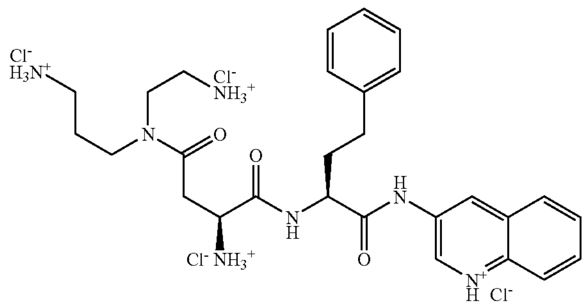

168

EXAMPLE 22

Step 1

Compound CXXXVIII was selectively BOC protected on the primary amine groups to give compound CXXXIX according to the procedure in *Org. Lett.* 2000, 2, 2117. To a solution of compound CXXXIX (523 mg, 1.65 mmol) and compound CXL (485 mg, 1.5 mmol) in DCM (20 mL) was added DMT-MM (500 mg, 1.8 mmol). The mixture was stirred at r.t. overnight. The reaction was washed with water, 1 N HCl, satd. aq. $NaHCO_3$, water and dried over $Na_2SO_4$. The product was purified on a silica gel column (1:1 EtOAc: hexane) to give CXLI (420 mg, 0.67 mmol, 45% yield) ESIMS found for $C_{31}H_{50}N_4O_9$ m/z 623 (M+H).

Step 2

To a solution of compound CXLI (420 mg, 0.67 mmol) in MeOH (30 mL) under argon was added 10% Pd/C catalyst (catalytic amount). The mixture was stirred under an atmosphere of hydrogen at r.t. overnight. The mixture was then filtered through Celite and evaporated to dryness to afford the free acid CXLII (351 mg, 0.66 mmol, 98% yield). ESIMS found for $C_{24}H_{44}N_4O_9$ m/z 533 (M+H).

Step 3

To a solution of compound CXLII (350 mg, 0.66 mmol) in DCM (10 mL) was added DMT-MM (210 mg, 0.75 mmol) and a solution of compound CXLIII (375 mg, 0.70 mmol) in DCM (10 mL) neutralized with $Et_3N$ (0.21 mL, 1.54 mmol). The mixture was stirred at r.t. overnight. The reaction was washed with water and dried over $Na_2SO_4$. The crude product was then purified on silica gel column (50:1 DCM/MeOH) to give CXLIV (400 mg, 0.49 mmol, 74% yield). $^1H$ NMR (DMSO-$d_6$) 1.35 (s, 9H), 1.36 (s, 9H), 1.39 (m, 9H), 1.49-1.56 (m, 1H), 1.60-1.67 (m, 1H), 1.96-2.04 (m, 1H), 2.12-2.22 (m, 1H), 2.60-2.67 (m, 2H), 2.72-2.88 (m, 4H), 2.92-2.96 (m, 2H), 3.04-3.11 (m, 2H), 3.17-3.33 (m, 2H), 4.38-4.43 (m, 2H), 6.73-6.78 (m, 1H), 6.86-6.89 (m, 1H), 6.97-7.01 (m, 1H), 7.16-7.29 (m, 7H), 7.54-7.58 (m, 1H), 7.62-7.67 (m, 1H), 7.90-7.92 (m, 1H), 7.94 (d, J=8 Hz, 1H), 8.38-8.45 (m, 1H), 8.72-8.74 (m, 1H), 9.03-9.05 (m, 1H), 10.15 (d, J=5 Hz, 1H). ESIMS found for $C_{43}H_{61}N_7O_9$ m/z 820 (M+H).

Step 4

Compound CXLIV (395 mg, 0.48 mmol) was treated with 5M HCl/EtOAc (8 mL) at r. t. overnight. Precipitate was filtered, washed with EtOAc and diethyl ether and dried to give 3-[(1S)-2-[(2-azaniumylethyl)(3-azaniumylpropyl)carbamoyl]-1-{[(1S)-1-carbamoyl-3-phenylpropyl]carbamoyl}ethan-1-aminium]quinolin-1-ium tetrachloride 168 (309 mg, 0.46 mmol, 97% yield). $^1H$ NMR (DMSO-$d_6$) 1.85-1.89 (m, 1H), 1.96-2.01 (m, 1H), 2.05-2.24 (m, 2H), 2.68-2.90 (m, 6H), 3.16-3.22 (m, 2H), 3.40-3.55 (m, 4H), 4.41-4.44 (m, 1H), 4.48-4.54 (m, 1H), 7.15-7.20 (m, 1H), 7.28-7.30 (m, 5H), 7.65-7.69 (m, 1H), 7.77-7.78 (m, 1H), 8.05-8.09 (m, 2H), 8.18 (brs, 3H), 8.39 (brs, 3H), 8.47 (brs, 3H), 8.93 (d, J=2 Hz, 1H), 9.22 (d, J=2 Hz, 1H), 11.17 (s, 1H). ESIMS found for $C_{28}H_{37}N_7O_3$ m/z 520 (M+H).

Synthesis of 3-[(1S)-2-{4-[bis(2-azaniumylethyl)azaniumyl]phenyl}-1-{[(1S)-1-carbamoyl-2-[4-(trifluoromethyl)phenyl]ethyl]carbamoyl}ethan-1-aminium]quinolin-1-ium pentachloride 183 is depicted below in scheme 23 and example 23.

Scheme 23

183

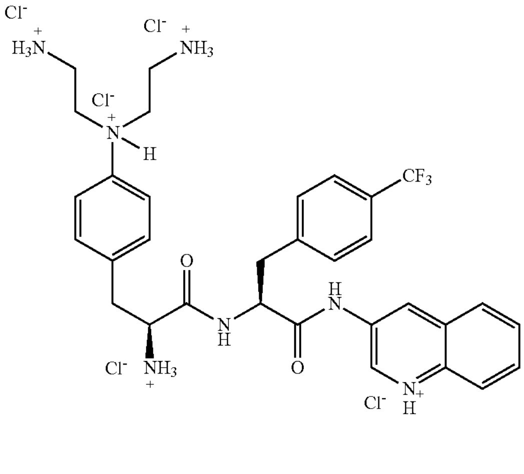

-continued
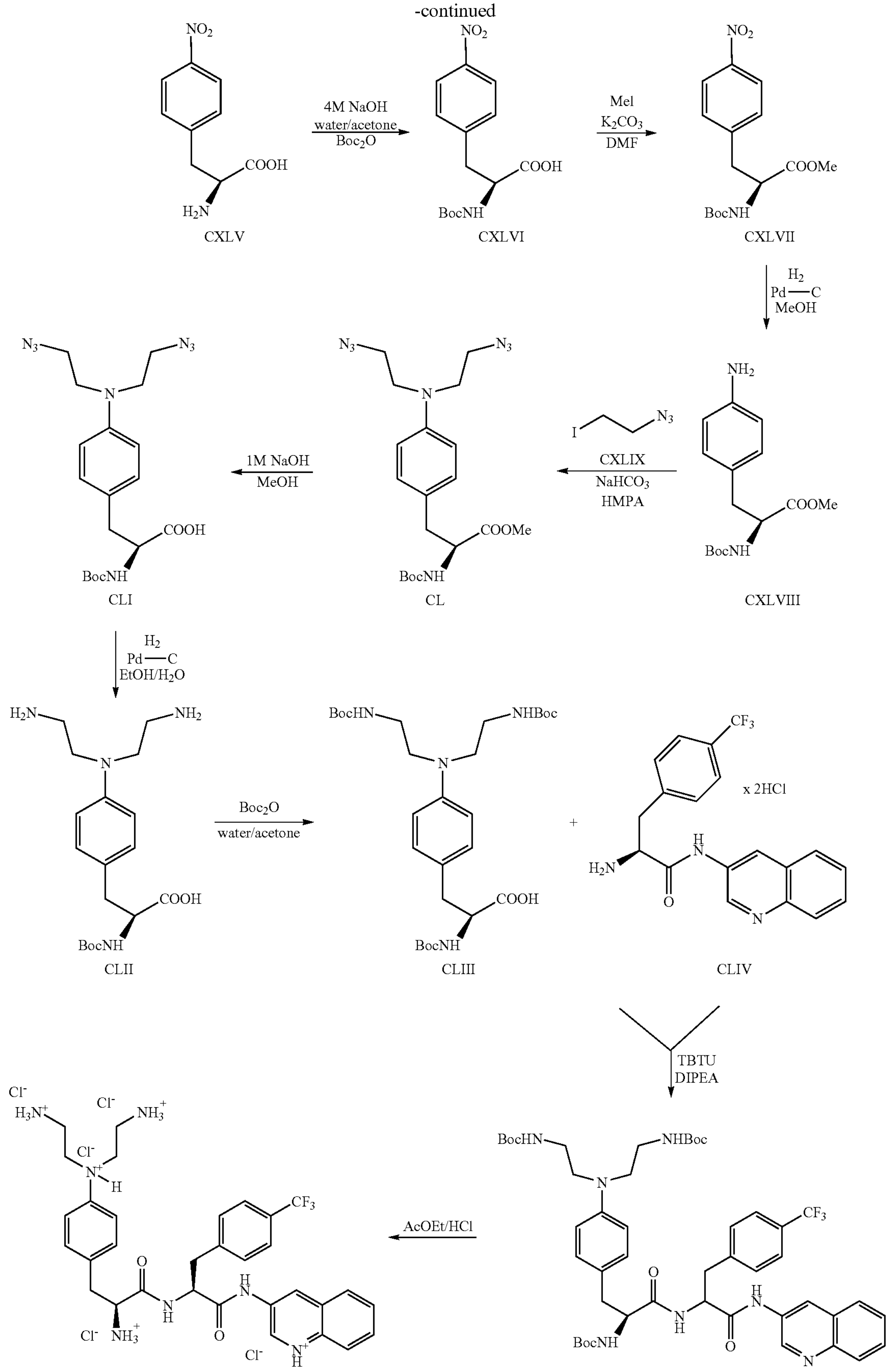
CXLV CXLVI CXLVII
CLI CL CXLVIII
CLII CLIII CLIV
183 CLV

EXAMPLE 23

Step 1

4-nitro-Phe-OH CXLV (745 mg, 3.55 mmol) was dissolved in water (6 mL) and then 5% $NaHCO_3$ aq was added (pH mixture about 10), next solution of $Boc_2O$ (1.94 g, 8.87 mmol) in acetone (4 mL) was added. The reaction mixture was stirred about 2 h and additional portion of 5% aq $NaHCO_3$ was added (to increase pH to 10) and the mixture was stirred overnight at ambient temperature. The acetone was evaporated under vacuum and aqueous residue was washed twice with diethyl ether. The water layer was acidified with 2 M HCl to pH=1, and the mixture was washed four times with EtOAc. The organic layer was washed with brine, dried over anhydrous $MgSO_4$. The solvent was removed under reduced pressure to give CXLVI (969 mg, 3.12 mmol, 89% yield). ESIMS found for $C_{14}H_{18}N_2O_6$ m/z 309.3 (M−H).

Step 2

Methyl iodide (0.21 mL, 3.44 mmol) was added to a solution of CXLVI (969 mg, 3.12 mmol) and $K_2CO_3$ (474 mg, 3.44 mmol) in DMF (5 mL) at r.t and stirred overnight at ambient temperature. EtOAc was then added to the reaction and washed 3×10% $Na_2S_2O_3$ and dried over $MgSO_4$. The solvent was removed under reduced pressure to give CXLVII as a yellow crystalline solid (730 mg, 2.25 mmol, 72% yield). ESIMS found for $C_{15}H_{20}N_2O_6$ m/z 325.3 (M+Na$^+$).

Step 3

To a solution of CXLVII (730 mg, 2.25 mmol) in MeOH (10 mL) under argon was added 10% Pd/C catalyst (catalytic amount). The mixture was stirred under an atmosphere of hydrogen at r.t. overnight. The mixture was then filtered through Celite and evaporated to dryness to give CXLVIII (540 mg, 1.84 mmol, 82% yield). $^1$H NMR ($CDCl_3$) 1.41 (s, 9H), 2.96 (brs, 2H), 3.61 (brs, 2H), 3.70 (s, 3H), 4.46-4.54 (m, 1H), 4.94 (d, J=6 Hz, 1H), 6.61 (d, J=8 Hz, 2H), 6.89 (d, J=7 Hz, 2H); ESIMS found for $C_{15}H_{22}N_2O_4$ m/z 317.3 (M+Na$^+$).

Step 4

To a solution of CXLVIII (540 mg, 1.84 mmol) and CXLIX (1.38 g, 9.18 mmol) in HMPA (5 mL) was added $NaHCO_3$ (617 mg, 7.35 mmol). The reaction mixture was stirred under argon atmosphere at 40° C. for 2 weeks. Then 10% citric acid was poured in the solution, washed twice with diethyl ether, dried over $MgSO_4$. The residue was then purified on a silica gel column (300:1 $CH_2Cl_2$/methanol) to give CL (165 mg, 0.38 mmol, 21% yield). $^1$H NMR ($CDCl_3$) 1.44 (s, 9H), 2.94-3.08 (m, 2H), 3.41-3.53 (m, 4H), 3.54-3.64 (m, 4H), 3.73 (s, 3H), 4.56 (brs, 1H), 4.97 (brs, 1H), 6.67 (d, J=8 Hz, 2H), 7.02 (d, J=8 Hz, 2H); ESIMS found for $C_{19}H_{28}N_8O_4$ m/z 455.6 (M+Na$^+$).

Step 5

To the solution of the ester CL (165 mg, 0.38 mmol) in MeOH (3 mL) 1 M NaOH was added dropwise until pH=11. The mixture was stirred overnight at r.t. before evaporating the MeOH under reduced pressure. The residue was mixed with water and washed with diethyl ether. After acidifying to pH~1 with 2 M HCl, the product was extracted with DCM, dried over $MgSO_4$ and concentrated under vacuum to give acid CLI (157 mg, 0.37 mmol, 98% yield). $^1$H NMR ($CDCl_3$) 1.44 (s, 9H), 2.92-3.19 (m, 2H), 3.48 (t, J=5 Hz, 4H), 3.58 (t, J=5 Hz, 4H), 4.56 (brs, 1H), 4.99 (d, J=7 Hz, 1H), 6.68 (d, J=8 Hz, 2H), 7.10 (d, J=8 Hz, 2H); ESIMS found for $C_{18}H_{26}N_8O_4$ m/z 441.4 (M+Na$^+$).

Step 6

To a solution of acid CLI (157 mg, 0.37 mmol) in EtOH/water (4.5 mL/0.5 mL) under argon 10% Pd/C catalyst was added (catalytic amount). The mixture was stirred under an atmosphere of hydrogen at r.t. overnight. The mixture was then filtered through Celite and evaporated to dryness to give CLII (110 mg, 0.30 mmol, 78.6% yield). ESIMS found for $C_{18}H_{30}N_4O_4$ m/z 367.4 (M+H).

Step 7

The acid CLII (110 mg, 0.30 mmol) was dissolved in water (6 mL) and then 5% $NaHCO_3$ aq was added (pH mixture about 10), next solution of $Boc_2O$ (200 mg, 0.9 mmol) in acetone (4 mL) was added. The reaction mixture was stirred about 2 h and additional portion of 5% $NaHCO_3$ aq was added (to increase pH to 10) and the mixture was stirred overnight at ambient temperature. The acetone was evaporated under vacuum and aqueous residue was washed twice with diethyl ether. The water layer was acidified with 2 M HCl to pH=1 and the mixture was washed four times with EtOAc. The organic layer was washed with brine, dried over anhydrous $MgSO_4$. The solvent was removed under reduced pressure to give CLIII (110 mg, 0.19 mmol, 70% yield). $^1$H NMR (DMSO-$d_6$) 1.32 (s, 9H), 1.36 (s, 18H), 2.57-2.73 (m, 1H), 2.77-2.90 (m, 1H), 2.99 (brs, 4H), 3.24 (brs, 4H), 3.91 (brs, 1H), 6.58-6.69 (m, 2H), 6.88-6.95 (m, 2H), 6.99 (d, J=8 Hz, 2H); ESIMS found for $C_{28}H_{46}N_4O_8$ m/z 589.7 (M+Na$^+$).

Step 8

To the solution of amine compound CLIV (90 mg, 0.21 mmol) in DCM (10 mL) DIPEA (1.1 mL, 0.64 mmol), the acid component CLIII (110 mg 0.19 mmol) and TBTU (70 mg, 0.20 mmol) were added. The mixture was stirred at r.t. overnight. Next the reaction mixture was washed with 1 M $K_2CO_3$, 1 M HCl, brine and dried over $MgSO_4$. The residue was purified on a silica gel column (50:1 $CH_2Cl_2$/methanol) to give CLV (90 mg, 0.1 mmol, 52% yield) as white solid. ESIMS found for $C_{47}H_{60}F_3N_7O_8$ m/z 908.9 (M+H).

Step 9

To a solution of CLV (90 mg, 0.1 mmol) in EtOAc (1 mL) was added HCl (4.5 M solution in EtOAc, 5 mL). The reaction mixture was stirred for 45 min at r.t. before adding diethyl ether (20 mL). The precipitate was filtered and washed with diethyl ether to give 3-[(1S)-2-{4-[bis(2-azaniumylethyl)azaniumyl]phenyl}-1-{[(1S)-1-carbamoyl-2-[4-(trifluoromethyl)phenyl]ethyl]carbamoyl}ethan-1-aminium]quinolin-1-ium pentachloride 183 as a white crystalline solid (38.9 mg, 0.053 mmol, 52% yield). $^1$H NMR (DMSO-$d_6$) 1.21-1.33 (m, 1H), 2.85 (brs, 5H), 3.03-3.22 (m, 2H), 3.28-3.34 (m, 1H), 3.36-3.52 (m, 4H), 4.86 (brs, 1H), 6.83 (d, J=7 Hz, 2H), 7.16 (d, J=8 Hz, 2H), 7.65 (brs, 4H), 7.71-7.85 (m, 2H), 8.05 (brs, 2H), 8.10 (brs, 3H), 8.19 (brs, 6H), 8.86 (brs, 1H), 9.07-9.28 (m, 2H), 11.42 (brs, 1H); ESIMS found for $C_{32}H_{36}F_3N_7O_2$ m/z 608.7 (M+H).

The following compound was prepared in accordance with the procedure described in the above example 23.

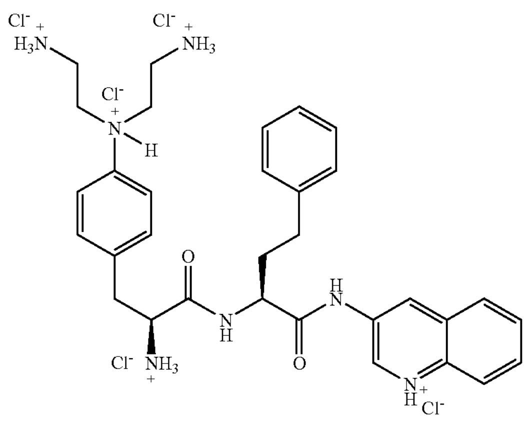

318

3-[(2S)-2-[(1S)-2-{4-[bis(2-azaniumylethyl)azaniumyl]phenyl}-1-formamidoethan-1-aminium]-4-phenylbutanamido]quinolin-1-ium pentachloride 318

$^{1}$H NMR (DMSO-$d_6$) 2.04 (brs, 1H), 2.17 (brs, 1H), 2.68 (brs, 1H), 2.76-2.92 (m, 6H), 3.13-3.21 (m, 1H), 3.45 (brs, 4H), 4.59 (brs, 2H), 6.87 (d, J=8 Hz, 2H), 7.16 (brs, 1H), 7.21 (d, J=8 Hz, 2H), 7.24 (brs, 4H), 7.73 (dd, J=7 Hz, J=7 Hz, 1H), 7.83 (dd, J=8 Hz, J=7 Hz, 1H), 8.09-8.17 (m, 2H), 8.24 (brs, 9H), 8.99 (brs, 1H), 9.24-9.33 (m, 2H), 11.39 (brs, 1H). ESIMS found for $C_{32}H_{39}N_7O_2$ m/z 554.6 (M+H).

Synthesis of 3-({N'-[(2S)-2-azaniumyl-3-[bis(2-azaniumylethyl)carbamoyl]propanoyl]-N-{[4-(trifluoromethyl)phenyl]methyl}hydrazinecarbonyl}amino)quinolin-1-ium tetrachloride 185 is depicted below in scheme 24 and example 24.

Scheme 24

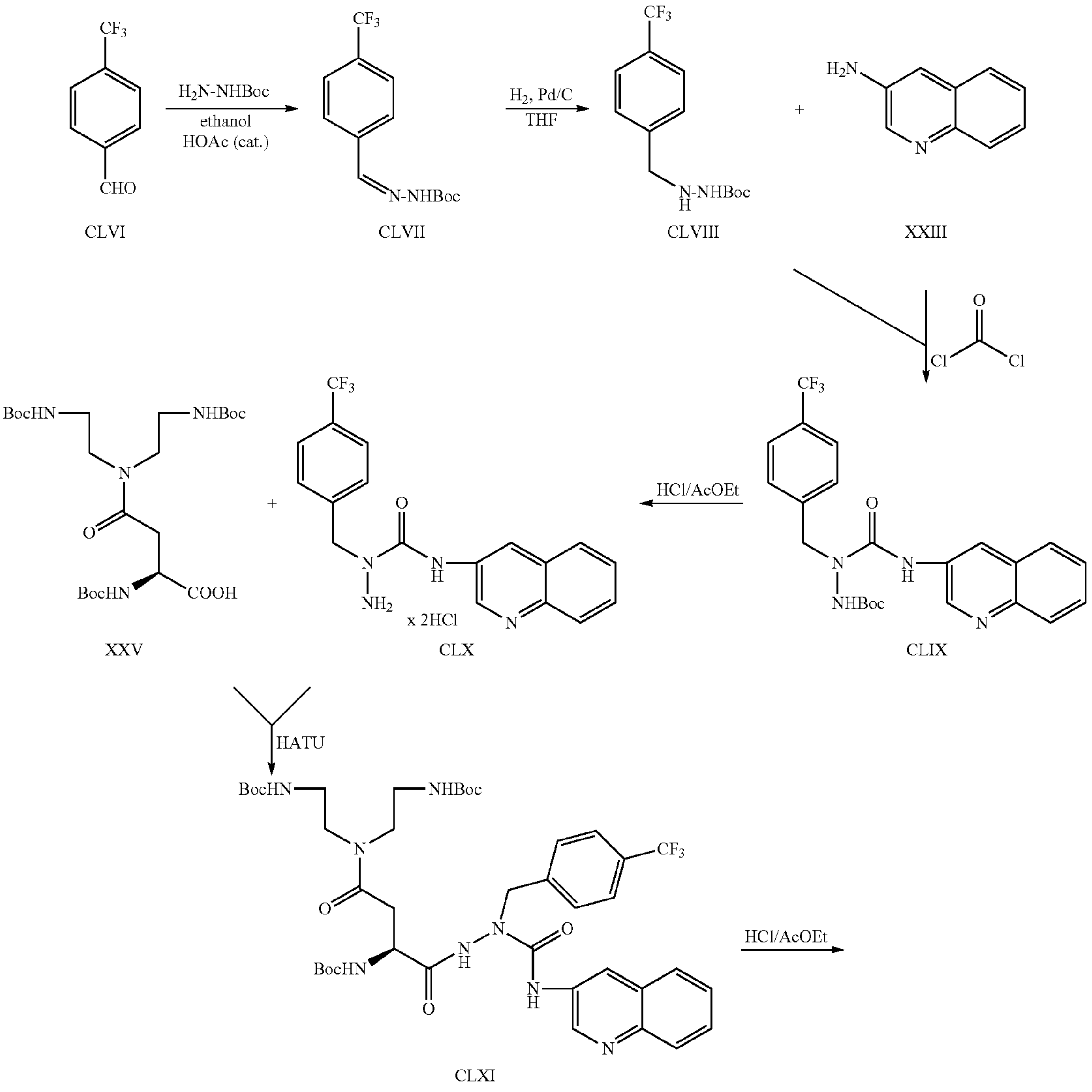

-continued

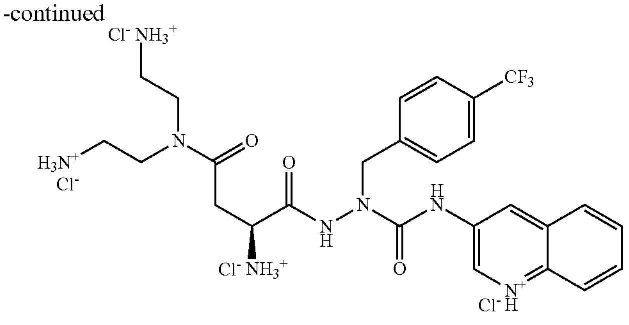

185

EXAMPLE 24

Step 1

4-(Trifluoromethyl)benzaldehyde CLVI (1.35 g, 7.75 mmol) was dissolved in anhydrous ethanol (50 ml) then Boc-hydrazine (1.25 g, 8.85 mmol) and glacial acetic acid (3 drops) were added. The reaction mixture was refluxed overnight. The solvent was removed under reduced pressure to give product CLVII as a yellow solid (2.2 g, 7.63 mmol, 98%). $^{1}$H NMR ($CDCl_3$) 1.52 (s, 9H), 7.56 (d, J=7 Hz, 2H), 7.74 (d, J=8 Hz, 2H), 7.92 (brs, 1H), 8.45 (brs, 1H), ESIMS found for $C_{13}H_{15}F_3N_2O_2$ m/z 289.3 (M+H).

Step 2

To a solution of CLVII (2.2 g, 7.63 mmol) in methanol (50 mL) was added a catalytic amount of palladium on carbon. The mixture was stirred under hydrogen over 45 minutes. When reaction was complete the catalyst was filtered off through a pad of celite and the filtrate was concentrated to dryness under vacuum to give yellow oil CLVIII (1.48 g, 5.10 mmol, 66%). $^{1}$H NMR ($CDCl_3$) 1.47 (s, 9H), 4.06 (s, 2H), 6.16 (brs, 1H), 7.47 (d, J=8 Hz, 2H), 7.59 (d, J=8 Hz, 2H), $^{19}$F NMR ($CDCl_3$) −61.87 (s), ESIMS found for $C_{13}H_{17}F_3N_2O_2$ m/z 291.3 (M+H).

Step 3

The yellow solid of CLVIII (1.48 g, 5.10 mmol) was dissolved in dry toluene (30 mL) then DIPEA (0.87 mL, 5.10 mmol) was added. The mixture was cooled to 0° C. and phosgene 20% in toluene (2.65 mL, 5.10 mmol) was added. The reaction mixture was stirred at r.t. for 4 hours. Solvent was removed in vacuo. Methylene chloride (30 mL), DIPEA (2.62 mL, 15.30 mmol) and 3-aminoquinoline (736 mg, 5.10 mmol) were added to the residue. Reaction was stirred overnight at r.t. The reaction mixture was diluted with $CH_2Cl_2$ and washed with 1M HCl (three times), 1 M NaOH, brine and dried over anhydrous $MgSO_4$. After filtration $MgSO_4$ solvent was removed under reduced pressure. Crude product was purified by flash chromatography using methylene chloride: methanol 700/1-500/1-300/1-200/1 solvents system to give derivative CLIX (330 mg, 0.71 mmol, 14%). ESIMS found for $C_{23}H_{23}F_3N_4O_3$ m/z 461.5 (M+H).

Step 4

Boc-protected compound CLIX (330 mg, 0.71 mmol) was dissolved in ethyl acetate (5 mL) and treated with hydrogen chloride (4.0M solution in ethyl acetate, 5 ml). The reaction mixture was stirred over 45 minutes at r. t. and next ethyl ether was added (about 20 ml). The precipitate was filtered off and washed with ether to give white crystalline solid of CLX (73 mg, 0.16 mmol, 24%). $^{1}$H NMR (DMSO-$d_6$) 4.80 (s, 2H), 7.48-7.58 (m, 2H), 7.60-7.89 (m, 4H), 8.03-8.16 (m, 2H), 9.10 (brs, 1H), 9.41 (brs, 1H), $^{19}$F NMR (DMSO-$d_6$) −60.20 (s), ESIMS found for $C_{18}H_{15}F_3N_4O$ m/z 361.34 (M+H).

Step 5

To the solution of acid XXV (96 mg, 0.18 mmol) in $CH_2Cl_2$ (5 mL) DIPEA (0.1 mL, 0.59 mmol), hydrochloride of amine component CLX (73 mg, 0.16 mmol) and HATU (70 mg, 0.18 mmol) were added. The mixture was stirred at room temperature overnight. Then the reaction mixture was diluted with methylene chloride and washed with 1M $K_2CO_3$, 1M HCl, brine, and dried over $MgSO_4$. Product was purified on silica gel using chloroform/methanol (100:1, 50:1) solvent system to give CLXI (30 mg, 0.034 mmol, 21%), ESIMS found for $C_{41}H_{55}F_3N_8O_9$ m/z 861.9 (M+H).

Step 6

Boc-protected compound CLXI (30 mg, 0.034 mmol) was dissolved in ethyl acetate (2 mL) and treated with hydrogen chloride (4.0M solution in ethyl acetate, 2 ml). The reaction mixture was stirred over 20 minutes at r.t. and ethyl ether was added (about 10 ml). The precipitate was filtered off and washed with ether to give 3-({N'-[(2S)-2-azaniumyl-3-[bis(2-azaniumylethyl)carbamoyl]propanoyl]-N-{[4-(trifluoromethyl)phenyl]methyl}hydrazinecarbonyl}amino)quinolin-1-ium tetrachloride 185, a hygroscopic yellow solid (15 mg, 0.042 mmol, 62%). $^{1}$H NMR (MeOD-$d_4$) 3.13-3.26 (m, 4H), 3.42-3.55 (m, 2H), 3.63-3.90 (m, 6H), 4.53 (brs, 1H), 7.58-7.74 (m, 4H), 7.84-8.09 (m, 2H), 8.13-8.31 (m, 2H), 9.37 (d, J=2 Hz, 1H), 9.69 (d, J=8 Hz, 1H); $^{19}$F NMR (MeOD-$d_4$)-63.29 (s); ESIMS found for $C_{26}H_{31}F_3N_8O_3$ m/z 561.6 (M+H).

Synthesis of 3-[(2S)-2-[(1S)-2-[(2-azaniumylethyl)({2-[(2-azaniumylethyl)azaniumyl]ethyl})carbamoyl]-1-formamidoethan-1-aminium]-4-phenylbutanamido]quinolin-1-ium pentachloride 188 is depicted below in scheme 25 and example 25.

Scheme 25

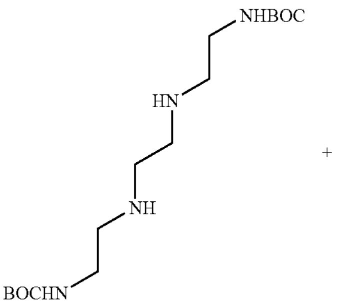

CLXII

-continued

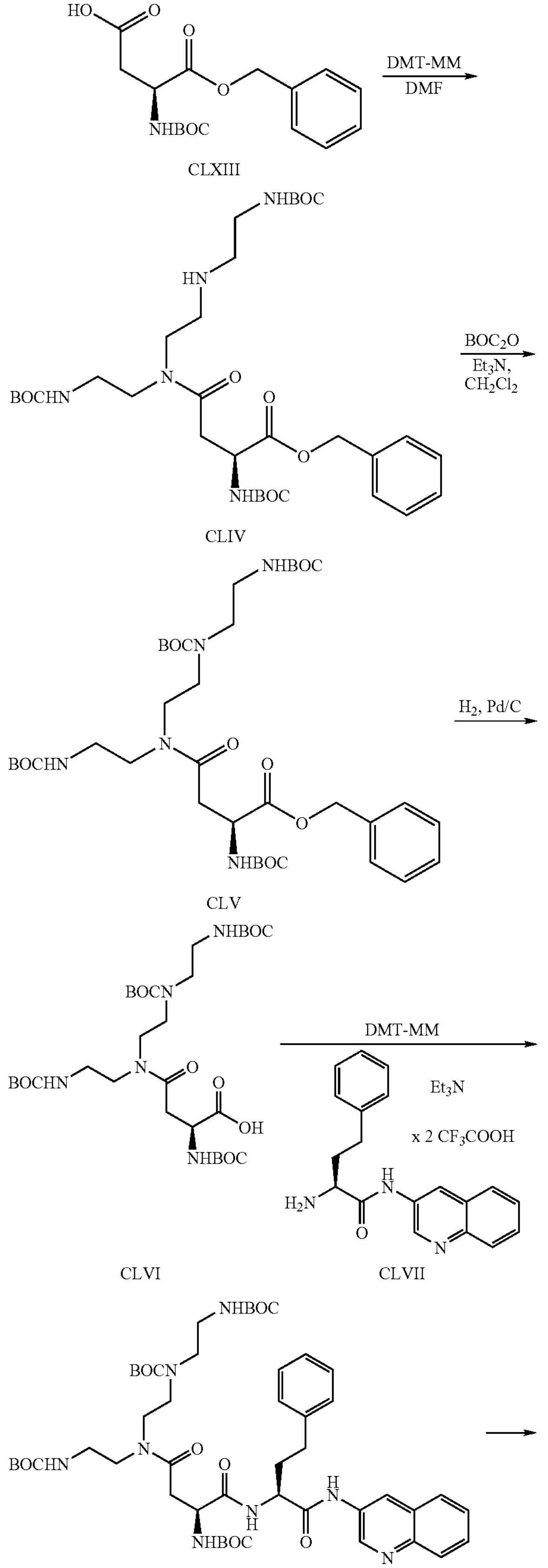

CLXIII

CLIV

CLV

CLVI

CLVII

CLVIII

-continued

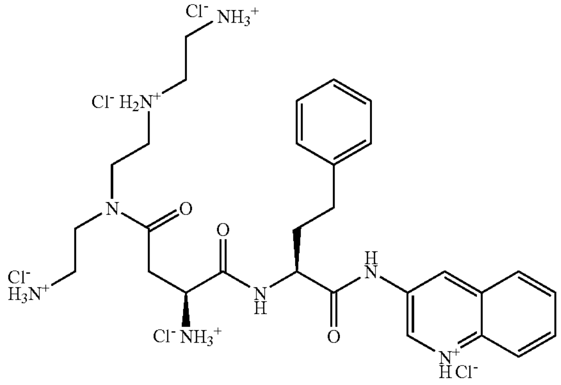

188

EXAMPLE 25

Step 1

Compound CLXIV was prepared by selective BOC protection of the primary groups according to the procedure in in Org. Lett. 2, 2000, 2117. To a solution of compound CLXII (1.10 g, 3.20 mmol) and compound CLXIII (1.00 g, 3.09 mmol) in DMF (15 mL) was added DMT-MM (890 mg, 3.2 mmol). The mixture was stirred at r.t. overnight. DMF was evaporated under reduced pressure. Residue was treated with ethyl acetate, washed with water, 1 N HCl, satd. aq. $NaHCO_3$, water and dried over $Na_2SO_4$. and evaporated to give crude CLXIV (1.54 g, 2.3 mmol, 74% yield). ESIMS found for $C_{32}H_{53}N_5O_9$ m/z 651 (M+H).

Step 2

To a solution of compound CLXIV (1.50 g, 2.3 mmol) in DCM (30 mL) was added diethylamide (1.7 mL, 12 mmol) and $BOC_2O$ (500 mg, 2.4 mmol) and the mixture was stirred at r.t. overnight. The reaction was washed with water and dried over $Na_2SO_4$. The crude product was then purified on silica gel column (EtOAc) to give CLXV (850 mg, 1.13 mmol, 49% yield). ESIMS found for $C_{37}H_{61}N_5O_{11}$ m/z 774 (M+Na).

Step 3

To a solution of compound CLXV (850 mg, 1.13 mmol) in MeOH (50 mL) under argon was added 10% Pd/C catalyst (catalytic amount). The mixture was stirred under an atmosphere of hydrogen overnight at r.t. The mixture was then filtered through Celite and evaporated to dryness to afford the free acid CLXVI (690 mg, 1.04 mmol, 92% yield). ESIMS (negative ions) found for $C_{30}H_{55}N_5O_{11}$ m/z 660 (M−H).

Step 4

To a solution of compound CLXVI (690 mg, 1.04 mmol) in DCM (10 mL) was added DMT-MM (332 mg, 1.20 mmol) and a solution of compound CLXVII (587 mg, 1.10 mmol) in DCM (10 mL) neutralized with $Et_3N$ (0.30 mL, 2.20 mmol). The mixture was stirred at r.t. overnight. The reaction was washed with water and dried over $Na_2SO_4$. The crude product was then purified on silica gel column (2/1 EtOAc/hexane) to give CLXVIII (280 mg, 0.29 mmol, 28% yield). $^1$H NMR (DMSO-$d_6$) 1.34-1.39 (m, 36H), 1.00-1.05 (m, 1H), 1.62-1.68 (m, 1H), 1.96-2.04 (m, 1H), 2.12-2.22 (m, 1H), 2.58-2.63 (m, 2H), 2.75-2.88 (m, 4H), 2.93-2.96 (m, 2H), 3.11-3.15 (m, 4H), 3.15-3.32 (m, 4H), 4.37-4.43 (m, 2H), 6.74-6.78 (m 1H), 6.84-6.90 (m, 1H), 6.96-7.03 (m, 1H), 7.16-7.29 (m, 7H), 7.54-7.58 (m, 1H), 7.62-7.67 (m, 1H), 7.90-7.90 (d, J=8 Hz, 1H), 7.94 (d, J=8 Hz, 1H), 8.32-8.42 (m, 1H), 8.71 (s, 1H), 9.03-9.05 (m, 1H), 10.15-10.20 (m, 1H). ESIMS found for $C_{49}H_{72}N_8O_{11}$ m/z 949 (M+H).

Step 5

Compound CLXVIII (280 mg, 0.29 mmol) was treated with 5M HCl/EtOAc (5 mL) at r. t. overnight. The precipitate was filtered, washed with EtOAc and diethyl ether and dried to give 3-[(2S)-2-[(1S)-2-[(2-azaniumylethyl)({2-[(2-azaniumylethyl)azaniumyl]ethyl})carbamoyl]-1-formamidoethan-1-aminium]-4-phenylbutanamido]quinolin-1-ium pentachloride 188 (190 mg, 0.26 mmol, 90% yield).

$^1$H NMR (DMSO-$d_6$) 2.13-2.18 (m, 2H), 2.70-2.76 (m, 1H), 2.80-2.88 (m, 1H), 3.01-3.05 (m, 1H), 3.13-3.17 (m, 1H), 3.18-3.34 (m, 6H), 3.62-3.81 (m, 4H), 4.44-4.50 (m, 2H), 7.15-7.20 (m, 1H), 7.28-7.30 (m, 5H), 7.65-7.69 (m, 1H), 7.77-7.78- (m, 1H), 8.05-8.09 (m, 3H), 8.33 (brs, 3H), 8.40 (brs, 3H), 8.43 (brs, 3H), 8.95 (d, J=8 Hz, 1H), 9.18-9.25 (m, 2H), 9.54 (brs, 1H), 9.90 (broad s), 9.84 (broad s, 1H), 10.91 (s), 10.98 (s]. MS (ESI) found for $C_{29}H_{40}N_8O_3$ m/z 549 (M+H).

The following compounds were prepared in accordance with the procedure described in the above example 25.

335

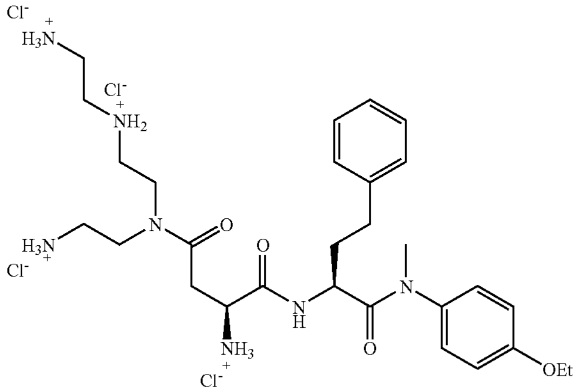

(2-azaniumylethyl)({2-[(1S)-2-[N-(2-azaniumylethyl)formamido]-1-{[(1S)-1-[(4-ethoxyphenyl)(methyl)carbamoyl]-3-phenylpropyl]carbamoyl}ethan-1-aminium]ethyl})azanium tetrachloride 335.

$^1$H NMR (DMSO-$d_6$) 1.34 (t, J=7 Hz, 3H), 1.66-1.85 (m, 2H), 2.18-2.30 (m, 2H), 3.00-3.20 (m, 8H), 3.20-3.30 (m, 7H), 3.51-3.83 (m, 3H), 4.01 (q, J=7 Hz, 2H), 4.16-4.37 (m, 1H), 6.77-7.29 (m, 9H), 8.00-8.56 (brs, 9H), 8.76-8.90 (brs, 2H), 9.42-9.61 (brs, 1H); ESIMS found for $C_{29}H_{45}N_7O_4$ m/z 556.7 (M+H).

336

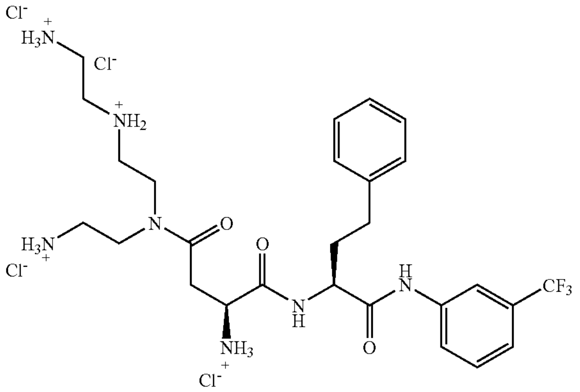

(2-azaniumylethyl)({2-[(1S)-2-[N-(2-azaniumylethyl)formamido]-1-{[(1S)-3-phenyl-1-{[3-(trifluoromethyl)phenyl]carbamoyl}propyl]carbamoyl}ethan-1-aminium]ethyl})azanium tetrachloride 336.

$^{19}$F NMR (DMSO-$d_6$) mixture of diasteroisomers—two signals 6:1; −60.62 (s), −60.68 (s); ESIMS found for $C_{27}H_{38}F_3N_7O_3$ m/z 566.7 (M+H).

3-[(2S)—N,N-bis(2-azaniumylethyl)-N'-[(1S)-1-carbamoyl-2-[4-(trifluoromethyl)phenyl]ethyl]-2-[(1R)-1-formamido-2-hydroxyethan-1-aminium]butanediamide]quinolin-1-ium tetrachloride 327 is depicted below in scheme 26 and example 26.

Scheme 26

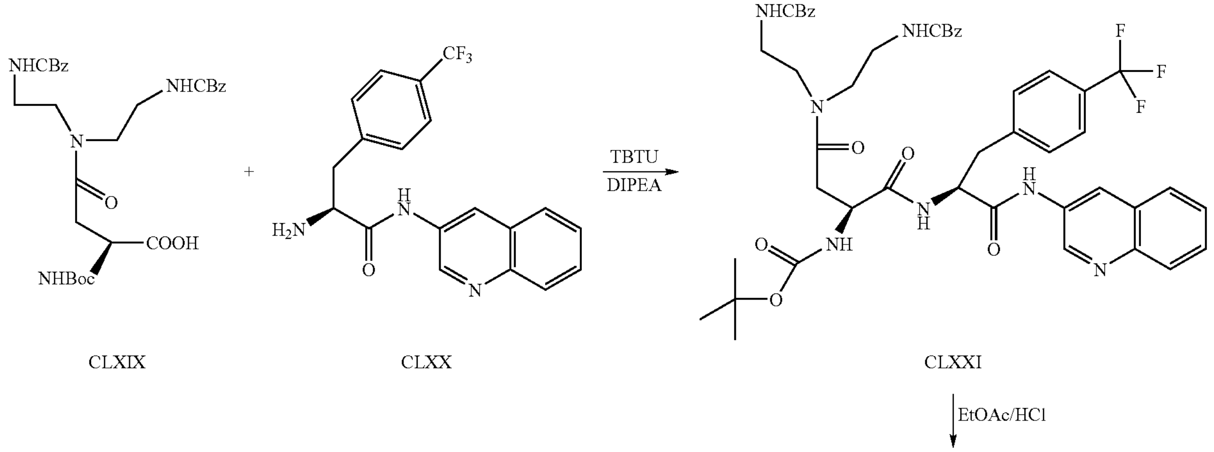

CLXIX CLXX CLXXI

-continued
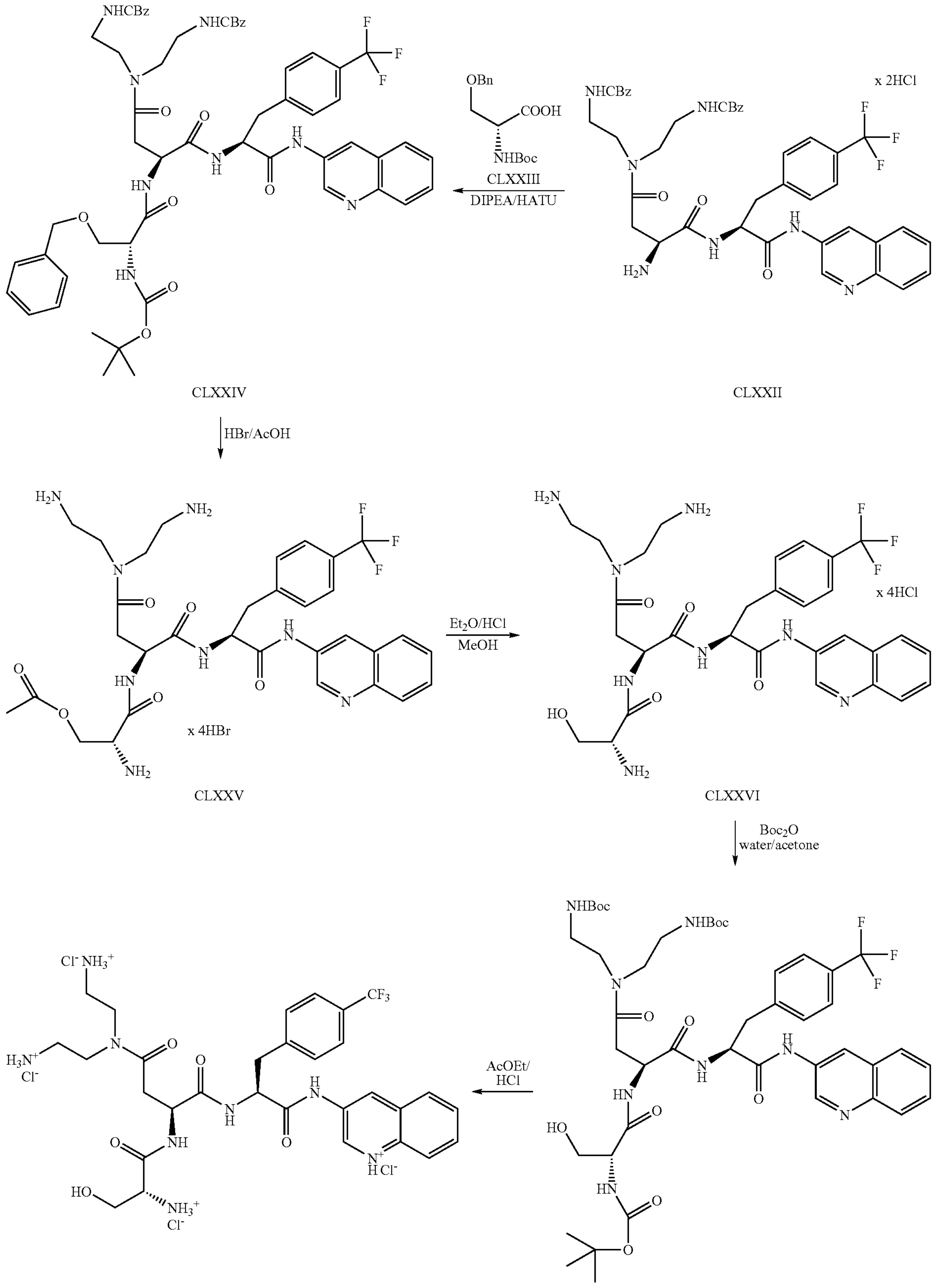
CLXXIV CLXXII
CLXXV CLXXVI
327 CLXXVII

EXAMPLE 26

Step 1

To the solution of CLXX (194 mg, 0.44 mmol) in DCM (10 mL) DIPEA (0.23 mL, 1.35 mmol), acid CLXIX (239 mg 0.41 mmol) and TBTU (140 mg, 0.44 mmol) were added. The mixture was stirred at r.t. overnight. The reaction mixture was washed with 1 M $K_2CO_3$, 1 M HCl, brine and dried over $MgSO_4$ to give CLXXI (350 mg, 0.38 mmol, 93% yield). ESIMS found for $C_{48}H_{52}F_3N_7O_9$ m/z 928.8 (M+H).

Step 2

To a solution of CLXXI (350 mg, 0.38 mmol) in EtOAc (3 mL) was added HCl (4.5 M solution in EtOAc, 10 mL). The reaction mixture was stirred for 30 min at r.t. before adding diethyl ether (20 mL). The precipitate was filtered and washed with diethyl ether to give CLXXII as a white crystalline solid (314 mg, 0.34 mmol, 94% yield). ESIMS found for $C_{43}H_{44}F_3N_7O_7$ m/z 827.8 (M+H).

Step 3

To the solution of Boc-D-Ser(Bn)-OH CLXXIII (93 mg, 0.31 mmol) in DCM (5 mL) DIPEA (0.19 mL, 1.11 mmol), hydrochloride of amine CLXXII (314 mg, 0.34 mmol) and HATU (130 mg, 0.34 mmol) were added. The mixture was stirred at r.t. overnight. The reaction mixture was then washed with 1 M $K_2CO_3$, 1 M HCl, brine and dried over $MgSO_4$. The residue was then purified on a silica gel column (100:1 $CH_2Cl_2$/methanol) to give CLXXIV (220 mg, 0.19 mmol, 63% yield). ESIMS found for $C_{58}H_{63}F_3N_8O_{11}$ m/z 1106.4 (M+H).

Step 4

The derivative CLXXIV (220 mg, 0.19 mmol) was treated with HBr/AcOH (5 mL). The reaction mixture was stirred for 15 min at r.t. before adding diethyl ether (20 mL). The precipitate was filtered and washed with diethyl ether to give CLXXV as a white crystalline solid (110 mg, 0.11 mmol, 55% yield). ESIMS found for $C_{32}H_{39}F_3N_8O_6$ m/z 689.9 (M+H).

Step 5

To a solution of CLXXV (110 mg, 0.11 mmol) in MeOH (1 mL) a few drops of HCl/$Et_2O$ were added. The reaction mixture was stirred for 5 h and then the solvent was evaporated to give CLXXVI (85 mg, 0.11 mmol, 98% yield). ESMIS found for $C_{30}H_{37}F_3N_8O_5$ m/z 647.7 (M+H).

Step 6

The free crude amine CLXXVI (85 mg, 0.11 mmol) was dissolved in water (6 mL), then 5% aqueous $NaHCO_3$ was added (pH mixture about 10), then a solution of $Boc_2O$ (350 mg, 1.6 mmol) in acetone (4 mL) was added. The reaction mixture was stirred about 2 h and additional portion of 5% aqueous $NaHCO_3$ was added (to increase pH to 10) and the mixture was stirred overnight at ambient temperature. The acetone was evaporated under vacuum and aqueous residue was washed twice with diethyl ether and dried over anhydrous $MgSO_4$. The solvent was evaporated. The crude product was purified on a silica gel column (100:1 $CH_2Cl_2$/MeOH) to give CLXXVII as a white crystalline solid (40 mg, 0.04 mmol, 31% yield). ESMIS found for $C_{50}H_{69}F_3N_8O_{13}$ m/z 1048.2 (M+H).

Step 7

To a solution of CLXXVII (40 mg, 0.04 mmol) in EtOAc (5 mL) was added HCl (4.5 M solution in EtOAc, 5 mL). The reaction mixture was stirred for 50 min at r.t. before adding diethyl ether (20 mL). The precipitate was filtered and washed with diethyl ether to give 3-[(2S)—N,N-bis(2-azaniumylethyl)-N'-[(1S)-1-carbamoyl-2-[4-(trifluoromethyl)phenyl]ethyl]-2-[(1R)-1-formamido-2-hydroxyethan-1-aminium]butanediamide]quinolin-1-ium tetrachloride 327 as a white crystalline solid (15 mg, 0.02 mmol, 54.9% yield). $^1$H NMR (MeOD-$d_4$) 1.12-1.24 (m, 2H), 2.86-3.00 (m, 2H), 3.03-3.11 (m, 4H), 3.12-3.15 (m, 2H), 3.55-3.71 (m, 4H), 3.78-3.92 (m, 2H), 3.95-4.04 (m, 1H), 7.47 (d, J=8 Hz, 2H), 7.52 (d, J=7 Hz, 2H), 7.81 (dd, J=7 Hz, J=7 Hz, 1H), 7.94 (dd, J=7 Hz, J=7 Hz, 1H), 8.09 (d, J=9 Hz, 1H), 8.15 (d, J=9 Hz, 1H), 9.07 (brs, 1H), 9.43 (brs, 1H); $^{19}$F (MeOD-$d_4$) −63.22 (s); ESIMS found for $C_{30}H_{37}F_3N_8O_5$ m/z 647.9 (M+H).

The following compounds were prepared in accordance with the procedure described in the above example 26.

329

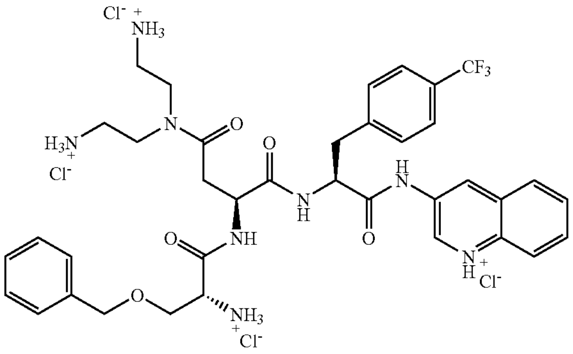

3-[(2S)—N,N-bis(2-azaniumylethyl)-2-[(1R)-2-(benzyloxy)-1-formamidoethan-1-aminium]-N'-[(1S)-1-carbamoyl-2-[4-(trifluoromethyl)phenyl]ethyl]butanediamide]quinolin-1-ium tetrachloride 329

$^1$H (DMSO-$d_6$) 2.86 (d, J=6 Hz, 2H), 2.96 (brs, 2H), 3.03 (brs, 2H), 3.21-3.38 (m, 2H), 3.39-3.50 (m, 1H), 3.59 (brs, 3H), 3.67-3.75 (m, 2H), 4.45-4.59 (m, 2H), 4.60-4.68 (m, 1H), 4.69-4.76 (m, 1H), 7.24-7.31 (m, 1H), 7.33-7.42 (m, 4H), 7.61 (d, J=7 Hz, 2H), 7.66 (d, J=7 Hz, 3H), 7.77 (brs, 1H), 8.09 (brs, 6H), 8.25 (brs, 3H), 8.45 (brs, 3H), 8.67 (d, J=7 Hz, 1H), 8.89 (brs, 1H), 9.20 (brs, 2H), 11.00 (brs, 1H), $^{19}$F NMR (DMSO-$d_6$) −60.02 (s); ESIMS found for $C_{37}H_{43}F_3N_8O_5$ m/z 737.8 (M+H).

331

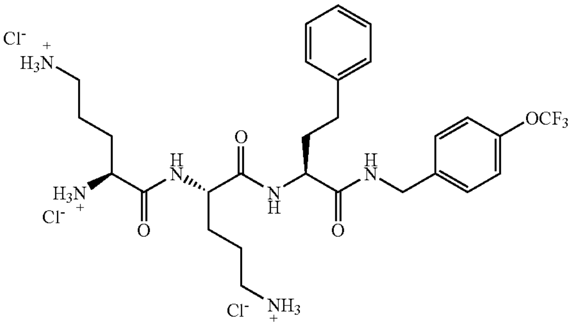

(1S)-1-{[(1S)-4-azaniumyl-1-{[(1S)-3-phenyl-1-({[4-(trifluoromethoxy)phenyl]methyl}carbamoyl)propyl]carbamoyl}butyl]carbamoyl}butane-1,4-bis(aminium) trichloride 331.

$^1$H NMR (DMSO-$d_6$) 1.57-1.98 (m, 12H), 2.33-2.40 (m, 1H), 2.54-2.60 (m, 1H), 2.73-2.88 (m, 4H), 3.92 (brs, 1H), 4.20-4.35 (m, 2H), 4.42 (brs, 1H), 7.09-7.40 (m, 9H), 7.99 (brs, 6H), 8.40 (brs, 3H), 8.62 (t, J=6 Hz, 1H), 8.98 (d, J=8 Hz, 1H); $^{19}$F NMR (DMSO-$d_6$) −56.21 (s); ESIMS found for $C_{28}H_{39}F_3N_6O_4$ m/z 581.6 (M+H).

350

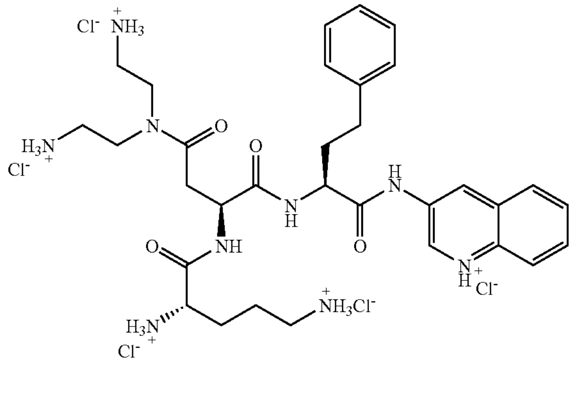

3-[(2S)—N,N-bis(2-azaniumylethyl)-N'-[(1S)-1-carbamoyl-3-phenylpropyl]-2-[(1S)-1-formamidobutane-1,4-bis(aminium)]butanediamide]quinolin-1-ium pentachloride 350

$^{1}$H NMR (DMSO-$d_6$) 1.74-2.12 (m, 4H), 2.83-3.13 (m, 6H), 3.52-3.49 (m, 4H), 3.59-3.56 (m, 4H), 3.95-4.00 (m, 1H), 4.45-4.48 (m, 1H), 4.77-4.80 (m, 1H), 7.14-7.20 (m, 1H), 7.18-7.31 (m, 5H), 7.66 (t, J=8 Hz, 1H), 7.74 (t, J=8 Hz, 1H), 7.97-8.02 (m, 3H), 8.06 (brs, 3H), 8.25 (brs, 3H), 8.31 (brs, 3H), 8.47 (brs, 3H), 8.66 (d, J=7 Hz, 1H), 8.88 (d, J=2 Hz, 1H), 9.17 (s, 1H), 9.18 (d, J=2 Hz, 1H), 10.82 (s, 1H); ESIMS found for $C_{32}H_{45}N_9O_4$ m/z 310 (M+H).

(2S)-4-[bis(2-azaniumylethyl)carbamoyl]-2-{[(1S)-3-phenyl-1-[(quinolin-1-ium-3-yl)-carbamoyl]propyl]carbamoyl}pyrrolidin-1-ium tetrachloride 328 is depicted below in scheme 27 and example 27.

Scheme 27

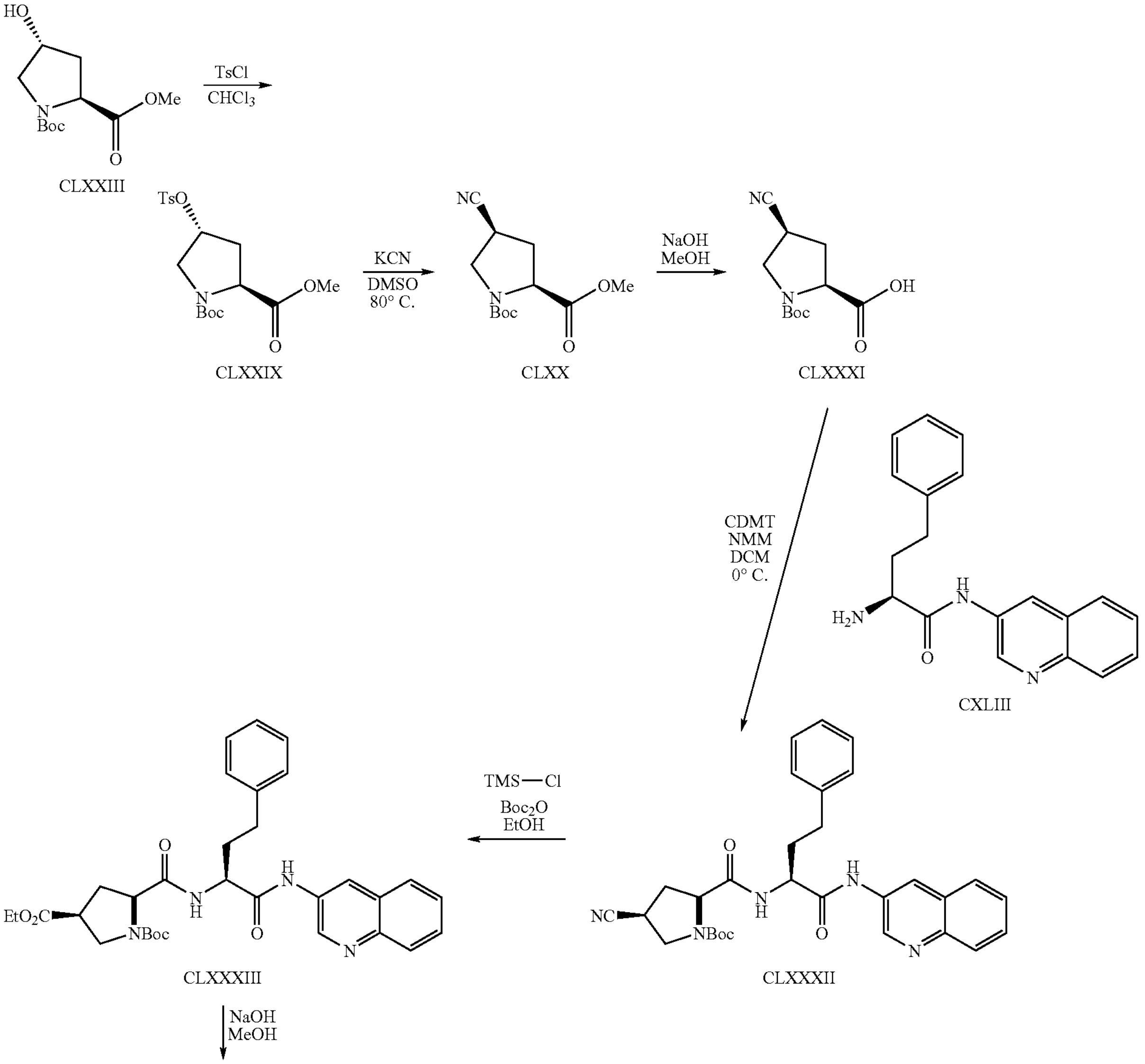

CLXXIII

CLXXIX

CLXX

CLXXXI

CXLIII

CLXXXII

CLXXXIII

-continued

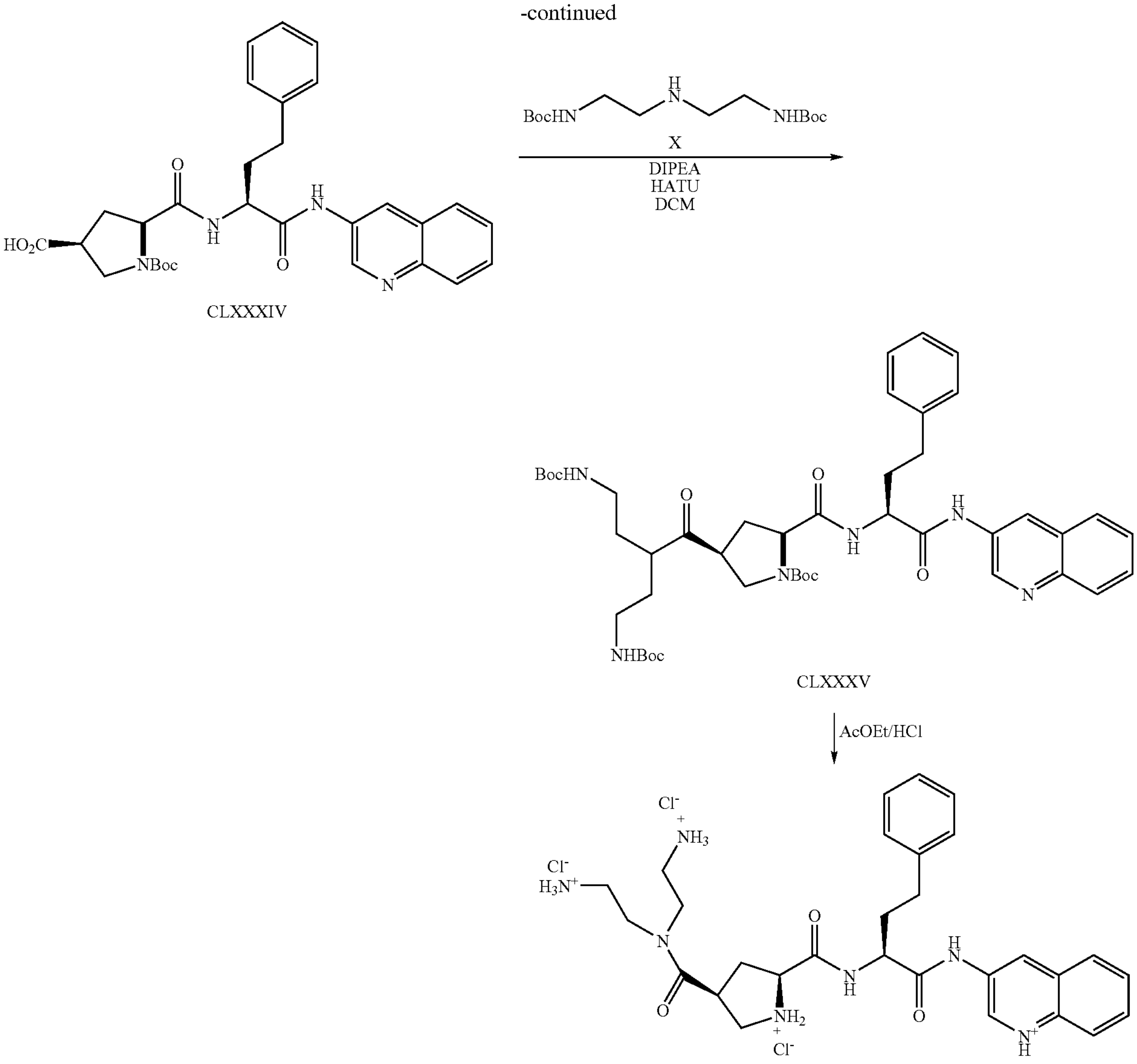

CLXXXIV

CLXXXV

328

EXAMPLE 27

Step 1

Compound CLXXVIII (1.4 g; 5.72 mmol) was dissolved in $CHCl_3$, pyridine (1.5 mL 20.02 mmol) and tosyl chloride (2.2 g 11.44 mmol) were added. The mixture was stirred at r.t. overnight. The reaction mixture was quenched with 1M HCl, then extracted with $CHCl_3$. The organic layer was washed with water, brine and dried over anhydrous $MgSO_4$. The solvent was removed under reduced pressure and the crude product was purified on a silica gel column (10:1, 5:1, 2:1 1:1 hexane/EtOAc) to give almost pure CLXXIX (2.3 g). $^1$H NMR (DMSO-$d_6$): 1.31 (s), 1.33 (s), 2.06-2.16 (m, 1H), 2.32-2.40 (m, 1H), 2.42 (s, 3H), 3.39-3.48 (m, 1H), 3.61 (s), 3.64 (s), 3.98-4.05 (m, 1H), 4.02 (dd, J=8 Hz, J=16 Hz, 1H), 5.03-5.10 (m, 1H), 7.50 (d, J=8 Hz, 2H), 7.82 (d, J=8 Hz, 2H). ESIMS found for $C_{18}H_{25}NO_7S$ m/z 422 (M+Na).

Step 2

Tosylated derivative CLXXIX (2.3 g 5.76 mmol) was dissolved in DMSO, KCN (750 mg, 11.52 mmol) was added and the reaction mixture was refluxed at 80° C. for 5 h. The reaction mixture was cooled at r.t and extracted with tBuOMe. Ether layer was washed with water, brine and dried over anhydrous $MgSO_4$. The solvent was removed under reduced pressure and the crude product was purified on a silica gel column (100:1, 50:1, 10:1, 5:1, 2:1, hexane/EtOAc) to give product CLXXX (500 mg, 1.97 mmol, 34% yield). $^1$H NMR (DMSO-$d_6$): 1.10 (s), 1.17 (s), 1.84-1.93 (m, 1H), 2.39-2.41 (m, 1H), 3.17-3.32 (m, 2H), 3.42 (s), 3.45 (s), 3.49-3.55 (m, 1H), 4.01-4.10 (m, 1H). ESIMS found for $C_{12}H_{18}N_2O_4$ m/z 277 (M+Na).

Step 3

To the solution of CLXXX (500 mg, 1.97 mmol) in MeOH 4M NaOH was added to pH=11. The reaction mixture was stirred for 1.5 h at r.t. before evaporating the MeOH under reduced pressure. The residue was mixed with water and extracted with EtOAc. The organic layer was acidified to pH=2, washed with water, brine and dried over $MgSO_4$, concentrated under vacuum to give crude product CLXXXI (550 mg) that was used in the next step without any additional purification. ESIMS found for $C_{11}H_{16}N_2O_4$ m/z 239 (M−H).

Step 4

To the solution of CDMT (440 mg, 2.29 mmol) in DCM (10 mL) and cooled to 0° C. N-methylmorpholine (0.9 mL, 8 mmol) was added. The mixture was stirred for 10 min before adding crude acid CLXXXI (550 mg, 2.29 mmol). The solution was stirred for 45 min at 0° C., next the amine component CXLIII (870 mg, 2.29 mmol) was added and the reaction mixture was stirred at r.t. overnight. The solution was washed with 1N HCl, 10% $NaHCO_3$, water, brine and dried over anhydrous $MgSO_4$. The crude product was then purified on a silica gel column (100:1, 50:1 $CHCl_3$/MeOH) to give CLXXXII (250 mg, 0.47 mmol, 21% yield). ESIMS found for $C_{30}H_{33}N_5O_4$ m/z 528 (M+H).

Step 5

$(CH_3)_3Si$—Cl (1.1 ml, 8.93 mmol) was dissolved in anhydrous EtOH (2 ml) at 0° C. After 10 min CLXXXII (250 mg, 0.47 mmol, solution in DCM) was added to the mixture that was stirred overnight at r.t. The reaction mixture was quenched with water (20 ml), then 5% $NaHCO_3$ was added until the pH=9. The mixture was extracted with $CH_2Cl_2$. To the organic layer, $Boc_2O$ (200 mg, 0.94 mmol) was added and stirred at r.t. overnight. The solvent was removed under reduced pressure and the crude product was purified on a silica gel column (100:1, 50:1 $CH_2Cl_2$/MeOH) to give product CLXXXIII (160 mg, 0.28 mmol, 59% yield). ESIMS found for $C_{32}H_{38}N_4O_6$ m/z 575 (M+H).

Step 6

To the solution of CLXXXIII (160 mg, 0.28 mmol) in MeOH, 4M NaOH was added until pH=11. The mixture was stirred for 1.5 h at r.t. before evaporating the MeOH under reduced pressure. The residue was mixed with water, acidifying to pH~3 with 2 M HCl, and extracted with EtOAc. The organic layer was washed with water, brine, dried over $MgSO_4$ and concentrated under vacuum to give CLXXXIV (140 mg crude product).

Step 7

To the solution of crude product CLXXXIV (140 mg, 0.29 mmol) and X (106 mg 0.35 mmol) in DCM was added DIPEA (0.06 mL, 0.35 mmol). After 10 min, HATU (133 mg, 0.35 mmol) was added. The reaction mixture was stirred at r.t. overnight. The reaction mixture was then diluted with DCM (20 ml) and washed with 1N HCl, 5% aqueous $NaHCO_3$, water, brine and dried over $MgSO_4$. The residue was then purified on a silica gel column (60:1, 20:1 $CH_2Cl_2$/methanol), to give CLXXXV (140 mg, 0.17 mmol, 58% yield). $^1$H NMR ($CD_3Cl$): 1.40 (s, 9H), 1.42 (s, 9H), 1.46 (s), 1.48 (s), 2.22-2.32 (m, 1H), 2.32-2.42 (m, 1H), 2.61-2.70 (m, 1H), 2.70-2.79 (m, 2H), 2.80-2.92 (m, 1H), 3.18-3.33 (m, 4H), 3.37-3.53 (m, 4H), 3.55-3.68 (m, 2H), 3.80-3.88 (m, 1H), 4.38-4.47 (m, 1H), 4.47-4.55 (m, 1H), 7.11-7.20 (m, 2H), 7.27-7.30 (m, 5H), 7.40-7.46 (m, 1H), 7.53-7.62 (m, 1H), 7.62-7.71 (m, 1H), 7.81 (d, J=7 Hz, 1H), 8.20 (d, J=8 Hz, 1H), 9.04 (brs, 1H), 9.24 (brs, 1H), 9.68 (brs, 1H). ESIMS found for $C_{44}H_{61}N_7O_9$ m/z 833 (M+H).

Step 8

To the derivative CLXXXV (140 mg, 0.17 mmol) HCl (4.5 M solution in EtOAc, 20 mL) was added. The reaction mixture was stirred for 1.5 h at r.t. before adding ethyl ether (20 mL). The precipitate was filtered and washed with ether to give (2S)-4-[bis(2-azaniumylethyl)carbamoyl]-2-{[(1S)-3-phenyl-1-[(quinolin-1-ium-3-yl)carbamoyl]propyl]carbamoyl}pyrrolidin-1-ium tetrachloride 328 (63 mg, 58% yield). $^1$H NMR (DMSO-$d_6$): 2.00-2.03 (m, 1H), 2.11-2.22 (m, 1H), 2.60-2.65 (m, 1H), 2.68-2.71 (m, 2H), 2.78-2.88 (m, 1H), 2.89-2.97 (m, 1H), 3.02-3.13 (m, 1H), 3.31-3.60 (m, 9H), 4.31-4.45 (m, 1H), 4.53-4.62 (m, 1H), 7.18 (t, J=7, 1H), 7.24-7.30 (m, 4H), 7.65 (dd, J=7 Hz, J=7 Hz, 1H), 7.77 (dd, J=7 Hz, J=7 Hz, 1H), 7.95-8.10 (m, 2H), 8.39-8.50 (m, 6H), 8.86 (brs, 3H), 9.13 (brs, 1H), 9.24 (d, J=7 Hz, 1H), 11.13 (brs, 1H). ESIMS found for $C_{29}H_{37}N_7O_{63}$ m/z 532 (M+H).

(1S)-2-[bis(2-azaniumylethyl)carbamoyl]-1-[({[(1S)-3-phenyl-1-({[4-(trifluoromethoxy)phenyl]methyl}carbamoyl)propyl]carbamoyl}methyl)carbamoyl]ethan-1-aminium trichloride 332 is depicted below in scheme 28 and example 28.

Scheme 28

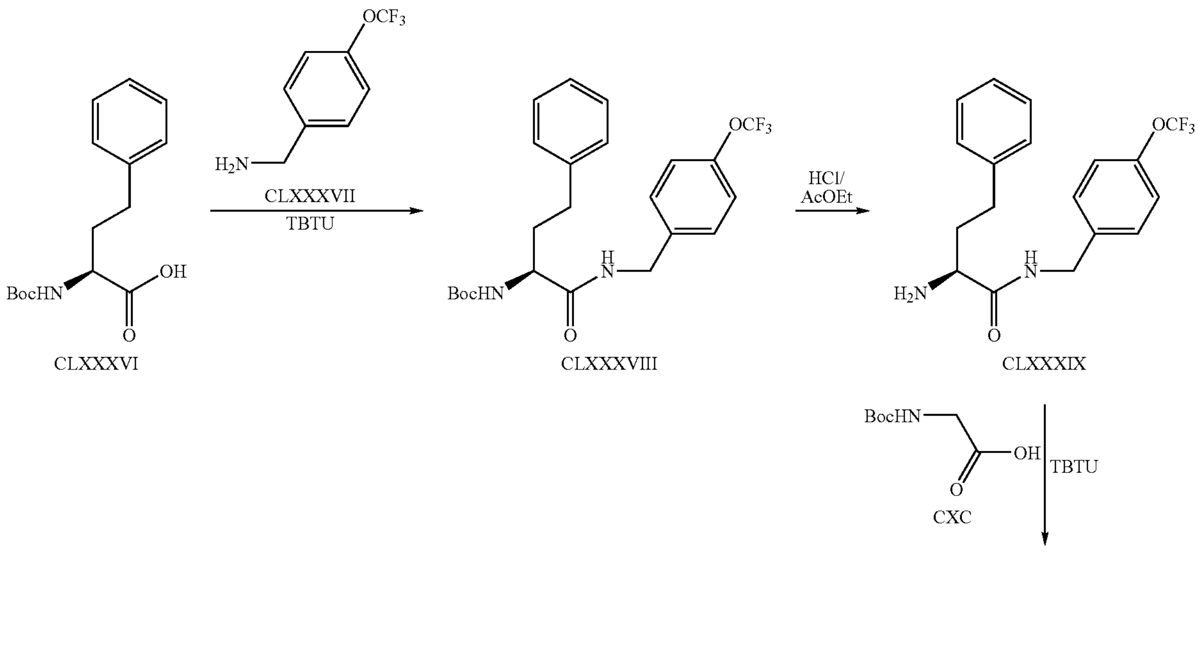

CLXXXVI

CLXXXVIII

CLXXXIX

CXC

-continued

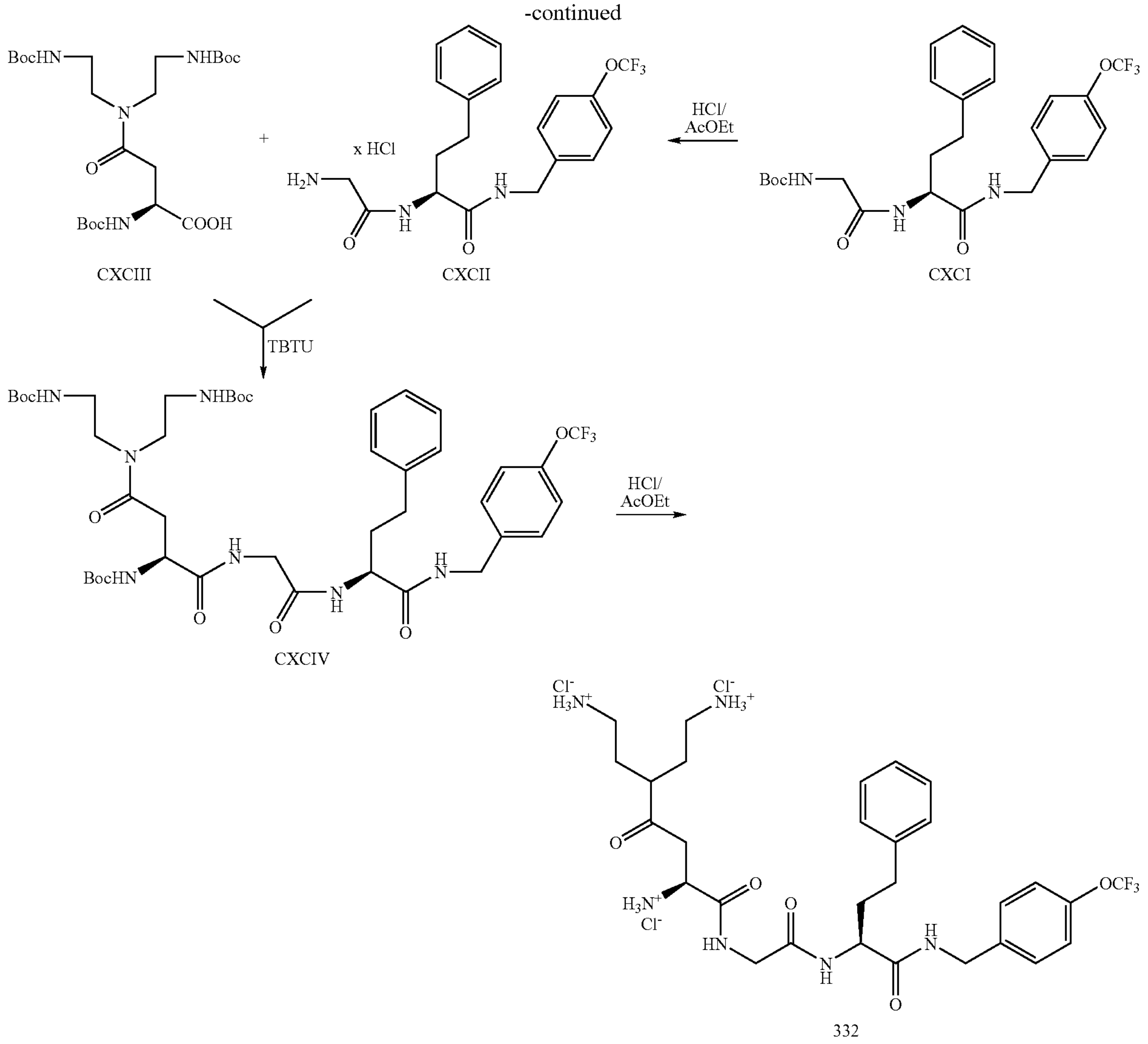

CXCIII CXCII CXCI

CXCIV

332

EXAMPLE 28

Step 1

Boc-L-homoPhe CLXXXVI (470 mg, 1.68 mmol) was dissolved in DCM (15 mL) and 4-(trifluoromethoxy)benzylamine CLXXXVII (321 mg, 1.68 mmol), TBTU (593 mg, 1.84 mmol), DIPEA (0.31 mL, 1.84 mmol) were added. The reaction mixture was stirred overnight at r.t. The reaction was diluted DCM and washed with 1M HCl, 1M $K_2CO_3$, brine and dried over $MgSO_4$. After evaporation of solvent orange oily residue crystallized on air to give product CLXXXVIII as orange solid (692 mg, 1.53 mmol, 91%). $^1$H NMR (DMSO-$d_6$) 1.42 (s, 9H), 1.83-2.07 (m, 1H), 2.09-2.27 (m, 1H), 2.62-2.75 (m, 2H), 4.16 (brs, 1H), 4.41 (d, J=5 Hz, 2H), 5.21 (d, J=8 Hz, 1H), 6.84 (brs, 1H), 7.08-7.19 (m, 4H), 7.22-7.33 (m, 5H); $^{19}$F NMR (DMSO-$d_6$) −57.30 (s); ESIMS found for $C_{23}H_{27}F_3N_2O_4$ m/z 453.4 (M+H).

Step 2

Boc-protected compound CLXXXVIII (692 mg, 1.53 mmol) was dissolved in ethyl acetate (5 mL) and treated with hydrogen chloride (4.0M solution in ethyl acetate, 5 ml). The reaction mixture was stirred over 30 minutes at r.t. and next ethyl ether was added (about 10 ml). The precipitate was filtered off and washed with ethyl ether to give white solid CLXXXIX (505 mg, 1.30 mmol, 85%). $^1$H NMR (DMSO-$d_6$) 1.96-2.13 (m, 2H), 2.47-2.64 (m, 2H), 3.93 (brs, 1H), 4.36 (d, J=5 Hz, 2H), 7.09-7.34 (m, 7H), 7.45 (d, J=8 Hz, 2H), 8.53 (brs, 3H), 9.39 (brs, 1H); $^{19}$F NMR (DMSO-$d_6$) −56.27 (s); ESIMS found for $C_{18}H_{19}F_3N_2O_2$ m/z 353.3 (M+H).

Step 3

Hydrochloride of amine component CLXXXIX (505 mg, 1.30 mmol) was dissolved in DCM (15 mL) and N-Boc-Gly CXC (250 mg, 1.43 mmol), TBTU (459 mg, 1.43 mmol), DIPEA (0.31 mL, 1.84 mmol) were added. The reaction mixture was stirred overnight in r.t. The reaction was diluted with DCM and washed 1M HCl, 1M $K_2CO_3$, brine and dried over $MgSO_4$. After evaporation of solvent the residue was crystallized from ethyl acetate/hexane solvent system to give white solid CXCI (450 mg, 0.88 mmol, 68%). $^1$H NMR (DMSO-$d_6$) 1.41 (s, 9H), 1.92-2.10 9 (m, 1H), 2.13-2.36 (m, 1H), 2.67, (t, J=3 Hz, 2H), 3.71 (d, J=6 Hz, 2H), 4.40 (d, J=6 Hz, 2H), 4.46-4.57 (m, 1H), 5.21 (t, J=5 Hz, 1H), 6.87 (d, J=8 Hz, 1H), 7.07-7.21 (m, 5H), 7.22-7.33 (m, 5H); $^{19}$F NMR (DMSO-$d_6$) −57.27 (s); ESIMS found for $C_{25}H_{30}F_3N_3O_5$ m/z 510.5 (M+H).

Step 4

Boc-protected peptide CXCI (450 mg, 0.88 mmol) was dissolved in ethyl acetate (5 mL) and treated with hydrogen chloride (4.0M solution in ethyl acetate, 5 ml). The reaction mixture was stirred over 30 minutes at r.t. and next ethyl ether was added (about 10 ml). Precipitate was filtered off and washed with ether to give white solid CXCII (283 mg, 0.81 mmol, 92%). ESIMS found for $C_{20}H_{22}F_3N_3O_3$ m/z 410.4 (M+H).

Step 5

Hydrochloride of amine component CXCII (283 mg, 0.81 mmol) was dissolved in DCM (10 mL) and CXCIII (462 mg, 0.89 mmol), TBTU (286 mg, 0.89 mmol), DIPEA (0.39 mL, 2.22 mmol) were added. The reaction mixture was stirred overnight in r.t. The reaction was diluted DCM and washed 1M HCl, 1M $K_2CO_3$, brine and dried over $MgSO_4$. The crude product was purified by flash chromatography using DCM followed by DCM/methanol 100/1-70/1-50/1 solvent system. The solvents were evaporated and solid residue was triturated with ethyl ether to give product CXCIV as a white solid (560 mg, 0.61 mmol, 75%). ESIMS found for $C_{44}H_{64}F_3N_7O_{10}$ m/z 909.4 (M+H).

Step 6

Boc-protected derivative CXCIV (560 mg, 0.61 mmol) was dissolved in ethyl acetate (5 mL) and treated with hydrogen chloride (4.0M solution in ethyl acetate, 5 ml). The reaction mixture was stirred over 30 minutes at r.t. and next ethyl ether was added (about 10 ml). Precipitate was filtered off and washed with ether to give (1S)-2-[bis(2-azaniumylethyl)carbamoyl]-1-[({[(1S)-3-phenyl-1-({[4-(trifluoromethoxy)phenyl]methyl}carbamoyl)propyl]carbamoyl}methyl)carbamoyl]ethan-1-aminium trichloride 332, a white solid (380 mg, 0.49 mmol, 80%). $^1$H NMR (DMSO-$d_6$) 1.89 (brs, 1H), 1.96 (brs, 1H), 2.43-2.51 (m, 1H), 2.54-2.62 (m, 1H), 2.96 (brs, 2H), 3.05 (brs, 2H), 3.11-3.21 (m, 2H), 3.48-3.56 (m, 1H), 3.63 (brs, 3H), 3.75 (dd, J=5 Hz, J=16 Hz, 1H), 3.94 (dd, J=6 Hz, J=16 Hz, 1H), 4.27 (brs, 4H), 7.12-7.18 (m, 3H), 7.24 (d, J=7 Hz, 2H), 7.28 (d, J=7 Hz, 2H), 7.36 (d, J=8 Hz, 2H), 8.14 (brs, 3H), 8.33 (brs, 3H), 8.36 (brs, 4H), 8.67 (t, J=5 Hz, 1H), 8.95 (brs, 1H); $^{19}$F NMR (DMSO-$d_6$) −51.44 (s); ESIMS found for $C_{28}H_{38}F_3N_7O_5$ m/z 610.6 (M+H).

The following compound was prepared in accordance with the procedure described in the above example 28.

348

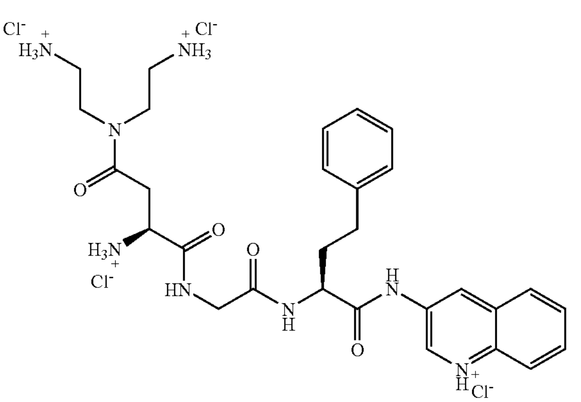

3-[(1S)-2-[bis(2-azaniumylethyl)carbamoyl]-1-[({[(1S)-1-carbamoyl-3-phenylpropyl]carbamoyl}methyl)carbamoyl]ethan-1-aminium]quinolin-1-ium tetrachloride 348

$^1$H NMR (DMSO-$d_6$) 1.96-2.16 (m, 2H), 2.55-2.65 (m, 1H), 2.68-2.77 (m, 1H), 2.94 (d, J=5 Hz, 2H), 2.98-3.07 (m, 2H), 3.08-3.19 (m, 1H), 3.45-3.53 (m, 1H), 3.59 (t, J=7 Hz, 3H), 3.79-3.94 (m, 2H), 4.24 (d, J=5 Hz, 2H), 4.46-4.55 (m, 2H), 7.14 (t, J=7 Hz, 1H), 7.18-7.28 (m, 4H), 7.67 (brs, 1H), 7.77 (brs, 1H), 8.06 (brs, 5H), 8.30 (brs, 6H), 8.58 (d, J=7 Hz, 1H), 8.87-8.97 (m, 2H), 9.26 (d, J=7 Hz, 1H), 11.07 (d, J=14 Hz, 1H); ESIMS found for $C_{29}H_{38}N_8O_4$ m/z 563.6 (M+H).

(2S)-2-[(1S)-1-formamido-2-[(1S)-1-formamidoethane-1,2-bis(aminium)]ethan-1-aminium]-4-phenyl-N-[3-(trifluoromethyl)phenyl]butanamide trichloride 334 is depicted below in scheme 29 and example 29.

Scheme 29

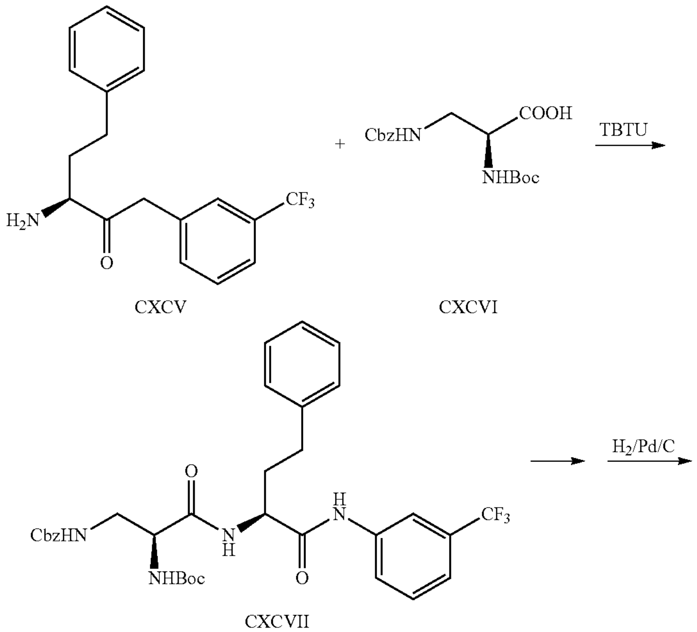

CXCV CXCVI

CXCVII

-continued

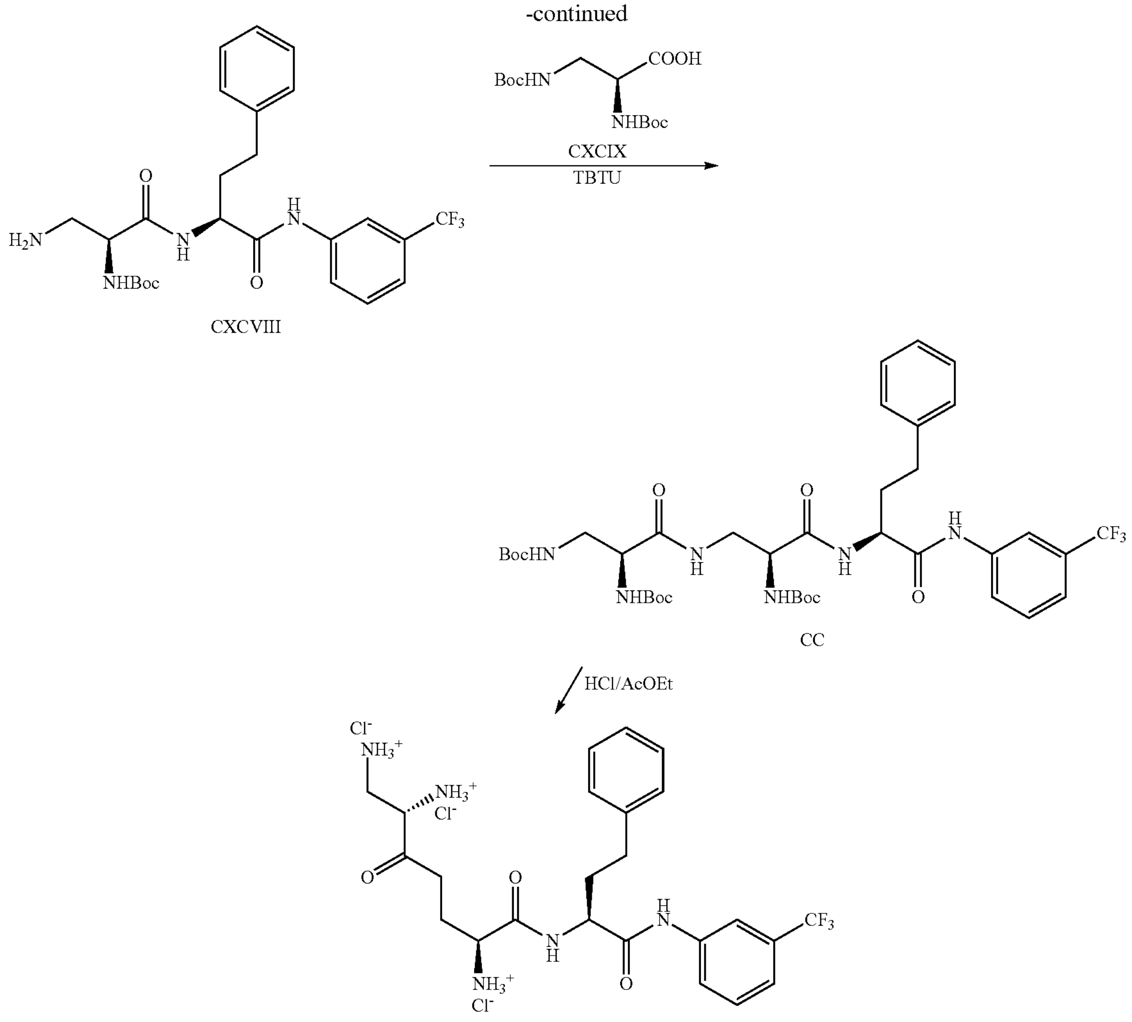

CXCVIII

CC

334

EXAMPLE 29

Step 1

To the solution of CXCVI (0.55 g, 1.62 mmol) in DCM (10 mL) DIPEA (0.31 mL, 1.79 mmol), hydrochloride of amine component CXCV (0.64 g, 1.79 mmol) and TBTU (0.57 g, 1.79 mmol) were added. The mixture was stirred at r.t. overnight. The reaction mixture was then washed with 5% $NaHCO_3$, 1 M HCl, brine and dried over $MgSO_4$. The residue was purified by crystallization from ethyl acetate/hexane to yield CXCVII as a white solid (0.54 mg, 0.84 mmol, 52% yield). $^1$H NMR ($CDCl_3$) 1.46 (brs, 9H), 1.58-1.88 (m, 2H), 1.98-2.48 (m, 2H), 2.73 (t, J=7 Hz, 2H), 3.59 (t, J=6 Hz, 1H), 4.08-4.19 (m, 1H), 4.51-4.68 (m, 1H), 5.08-5.19 (m, 2H), 6.84 (d, J=8 Hz, 1H), 7.11-7.44 (m, 13H), 7.96 (s, 2H), 8.91 (s, 1H); $^{19}$F NMR ($CDCl_3$) −62.07 (s); ESIMS found for $C_{33}H_{37}F_3N_4O_6$ m/z 643.6 (M+H).

Step 2

To a solution of CXCVII (0.54 g, 0.84 mmol) in EtOH/water (20 mL/1 mL) under argon 10% Pd/C catalyst (catalytic amount) was added. The mixture was stirred under an atmosphere of hydrogen at r.t. overnight. The mixture was then filtered through Celite and evaporated to dryness to give CXCVIII as a white crystalline solid (330 mg, 0.65 mmol, 77% yield). $^1$H NMR ($CDCl_3$) 1.43 (s, 9H), 1.99-2.42 (m, 4H), 2.90-3.20 (m, 2H), 4.05-4.16 (m, 1H), 4.47-4.63 (m, 1H), 5.68 (d, J=6 Hz, 1H), 7.11-7.40 (m, 9H), 7.58 (d, J=7 Hz, 1H), 7.73-7.87 (m, 2H), 9.12 (s, 1H); $^{19}$F NMR ($CDCl_3$) −62.08 (s); ESIMS found for $C_{25}H_{31}F_3N_4O_4$ m/z 509.5 (M+H).

Step 3

To the solution of dicyclohexylamine salt of Boc-DAP (Boc)-OH CXCIX in DCM (50 mL) DIPEA (0.12 mL, 0.72 mmol), amine component CXCVIII (330 mg, 0.65 mmol) and TBTU (230 mg, 0.72 mmol) were added. The mixture was stirred at r.t. overnight. The reaction mixture was then washed with 5% $NaHCO_3$, brine and dried over $MgSO_4$. The residue was purified on a silica gel column (200:1 $CHCl_3$/methanol) to yield CC (300 mg, 0.38 mmol, 58% yield). $^1$H NMR (DMSO-$d_6$) 1.17-1.26 (m, 2H), 1.33 (s, 18H), 1.37 (s, 9H), 1.88-2.10 (m, 2H), 2.55-2.75 (m, 2H), 3.10-3.23 (m, 2H), 3.90-4.13 (m, 2H), 4.38 (brs, 1H), 6.53-6.74 (m, 2H), 6.97 (d, J=7 Hz, 1H), 7.14-7.25 (m, 5H), 7.33-7.42 (m, 1H), 7.53 (t, J=8 Hz, 1H), 7.81-7.88 (m, 1H), 7.96 (brs, 1H), 8.06 (s, 1H), 8.28 (d, J=8 Hz, 1H), 10.21 (s, 1H); $^{19}$F NMR (DMSO-$d_6$) −60.74 (s); ESIMS found for $C_{38}H_{53}F_3N_6O_9$ m/z 817.9 (M+Na).

Step 4

To the solution of CC (300 mg, 0.38 mmol) in EtOAc (2 mL) HCl (4.5 M solution in EtOAc, 10 mL) was added. The reaction mixture was stirred for 1 h at r.t. The solvent was evaporated and the residue was washed with 50 mL of hexane to give (2S)-2-[(1S)-1-formamido-2-[(1S)-1-formamidoethane-1,2-bis(aminium)]ethan-1-aminium]-4-phenyl-N-[3-(trifluoromethyl)phenyl]butanamide trichloride 334 as a yellow crystalline solid (70 mg, 0.12 mmol, 31% yield). $^1$H NMR (DMSO-$d_6$) 1.21-1.27 (m, 2H), 1.92-2.25 (m, 2H), 2.56-2.88 (m, 2H), 3.53-3.71 (m, 2H), 4.11-4.16 (m, 1H), 4.18-4.29 (m, 1H), 4.53 (m, 1H), 7.19-7.31 (m, 5H), 7.32-7.46 (m, 1H), 7.54 (t, J=16 Hz, 1H), 7.90-7.97 (d, J=8 Hz, 1H), 8.08 (s, 1H), 8.60 (brs, 9H), 9.07-9.21 (m, 1H), 9.28 (d, J=6 Hz, 1H), 10.82 (s, 1H); $^{19}$F NMR (DMSO-$d_6$) −60.66 (s); ESIMS found for $C_{23}H_{29}F_3N_6O_3$ m/z 495.5 (M+H).

3-[N,N-bis(2-azaniumylethyl)-N'-({[(1S)-1-carbamoyl-3-phenylpropyl]carbamoyl}methyl)pethanediamide]quinolin-1-ium trichloride 347 is depicted below in scheme 30 and example 30.

Scheme 30

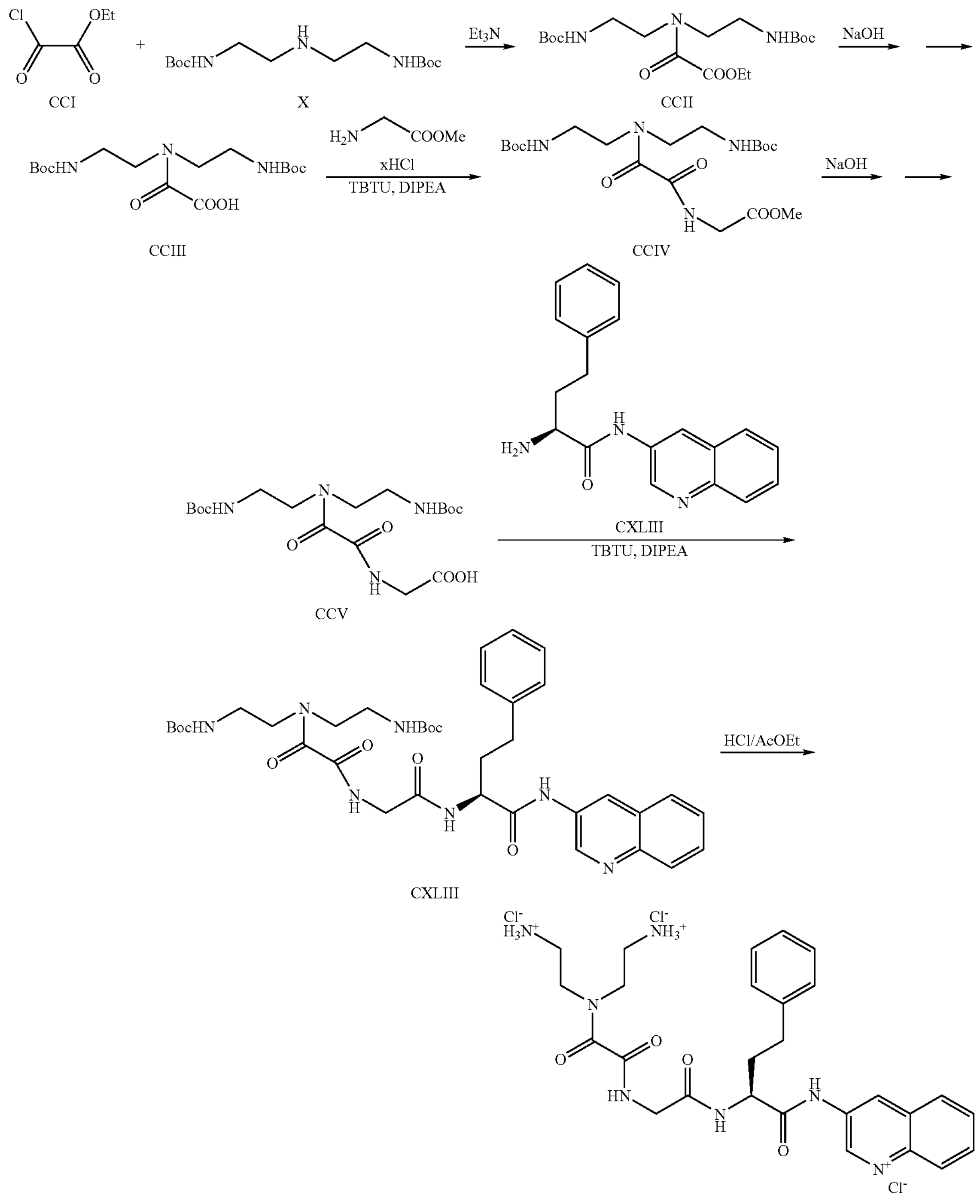

CCI X CCII CCIII CCIV CXLIII CCV CXLIII 347

EXAMPLE 30

Step 1

Ethyl chloroglyoxylate CCI (0.3 mL, 2.75 mmol) was dissolved in DCM (10 mL) and the solution was cooled to 0° C. To this solution amine X (1 g, 3.3 mmol) and $Et_3N$ (0.55 mL, 4.12 mmol) were added, the reaction mixture was stirred at ambient temperature for 4 h. The reaction mixture was washed with 5% $NaHCO_3$, 1 M HCl, brine, dried over $MgSO_4$ and concentrated under vacuum to give CCII (790 mg, 1.96 mmol 60% yield). The crude product was used to the next step without any additional purification. ESIMS found for $C_{18}H_{33}N_3O_7$ m/z 404 (M+H).

Step 2

To the solution of the ester CCII (790 mg, 1.96 mmol) in MeOH (20 mL) 4 M NaOH was added dropwise until pH=13. The mixture was stirred for 1 h at r.t. before evaporating the MeOH under reduced pressure. The residue was mixed with water and washed with ethyl ether. After acidifying to pH~3 with 2 M HCl, the product was extracted with DCM, dried over $MgSO_4$ and concentrated under vacuum to give CCIII (580 mg, 1.54 mmol, 74% yield). The crude product was used to the next reaction step without any purification. $^1$H NMR (DMSO-$d_6$) 1.32 (s, 9H), 1.33 (s, 9H), 3.00-3.09 (m, 4H), 3.21-3.31 (m, 4H), 6.86 (brs, 1H), 6.91 (brs, 1H). ESIMS found for $C_{16}H_{29}N_3O_7$ m/z 374 (M−H).

Step 3

To the solution of CCIII (580 mg, 1.54 mmol) in DCM (10 mL) DIPEA (0.59 mL, 3.34 mmol), hydrochloride of methyl ester of glycine (210 mg 1.69 mmol) and TBTU (540 mg, 1.69 mmol) were added. The mixture was stirred at r.t. overnight. The reaction mixture was then washed with 5% $NaHCO_3$, 1 M HCl, brine and dried over $MgSO_4$. The residue was purified on a silica gel column (50:1 $CHCl_3$/methanol) to give CCIV (350 mg, 0.78 mmol, 51% yield). ESIMS found for $C_{19}H_{34}N_4O_8$ m/z 447 (M+H).

Step 4

To the solution of the ester CCIV (350 mg, 0.78 mmol) in MeOH (10 mL) 4 M NaOH was added dropwise until pH=13. The mixture was stirred for 1 h at r.t. before evaporating the MeOH under reduced pressure. The residue was mixed with water and washed with ether. After acidifying to pH~3 with 2 M HCl, the product was extracted with DCM, dried over $MgSO_4$ and concentrated under vacuum to give CCV (290 mg, 0.67 mmol, 88% yield). The crude product was used to the next reaction step without any purification. ESIMS found for $C_{18}H_{32}N_4O_8$ m/z 431 (M−H).

Step 5

To the solution of acid CCV (290 mg, 0.67 mmol) in DCM (10 mL) DIPEA (0.29 mL, 2.10 mmol), amine component CXLIII (250 mg, 0.66 mmol) and TBTU (210 mg, 0.66 mmol) were added. The mixture was stirred at r.t. overnight. The reaction mixture was then washed with 5% $NaHCO_3$, 1 M HCl, brine and dried over $MgSO_4$. The residue was purified on a silica gel column (50:1 $CH_2Cl_2$/methanol) to yield CCVI (290 mg, 0.40 mmol, 67% yield). $^1$H NMR ($CDCl_3$) 1.38 (s, 9H), 1.40 (s, 9H), 1.57-1.75 (m, 2H), 2.25-2.37 (m, 6H), 2.70-2.81 (m, 2H), 3.62-3.85 (m, 2H), 3.89-4.04 (m, 2H), 4.71 (brs, 1H), 5.26 (brs, 1H), 5.78 (brs, 1H), 7.13-7.22 (m, 5H), 7.47 (brs, 1H), 7.59 (brs, 1H), 7.72 (brs, 2H), 8.00 (brs, 2H), 8.74 (s, 1H), 8.86 (s, 1H), 9.25 (s, 1H). ESIMS found for $C_{37}H_{49}N_7O_8$ m/z 720 (M+H).

Step 6

To the solution of CCVI (290 mg, 0.40 mmol) in EtOAc (5 mL) HCl (4.5 M solution in EtOAc, 10 mL) was added. The reaction mixture was stirred for 35 min at r.t. before adding ethyl ether (20 mL). The precipitate was filtered and washed with ether to give 3-[N,N-bis(2-azaniumylethyl)-N'-({[(1S)-1-carbamoyl-3-phenylpropyl]carbamoyl}methyl)ethanediamide]quinolin-1-ium trichloride 347 as a white crystalline solid (160 mg, 0.25 mmol, 76% yield). $^1$H NMR (DMSO-$d_6$) 2.00-2.17 (m, 2H), 2.62-2.78 (m, 2H), 2.99-3.11 (m, 4H), 3.57-3.60 (m, 2H), 3.70-3.71 (m, 2H), 3.98-4.06 (m, 2H), 4.52-4.59 (m, 1H), 7.16-7.21 (m, 1H), 7.23-7.32 (m, 4H), 7.63 (t, J=15 Hz, 1H), 7.71 (t, J=15 Hz, 1H), 8.02 (brs, 8H), 8.72-8.76 (d, J=8 Hz, 1H), 8.80 (s, 1H), 9.00-9.06 (m, 1H), 9.09 (s, 1H), 10.87 (s, 1H); ESIMS found for $C_{27}H_{33}N_7O_4$ m/z 520 (M+H).

3-[(2S)-2-{[azaniumyl({[bis(2-azaniumylethyl)carbamoyl]methyl}) carbamoyl]amino}-3-[4-(trifluoromethyl)phenyl]propanamido]quinolin-1-ium tetrachloride 349 is depicted below in scheme 31 and example 31.

Scheme 31

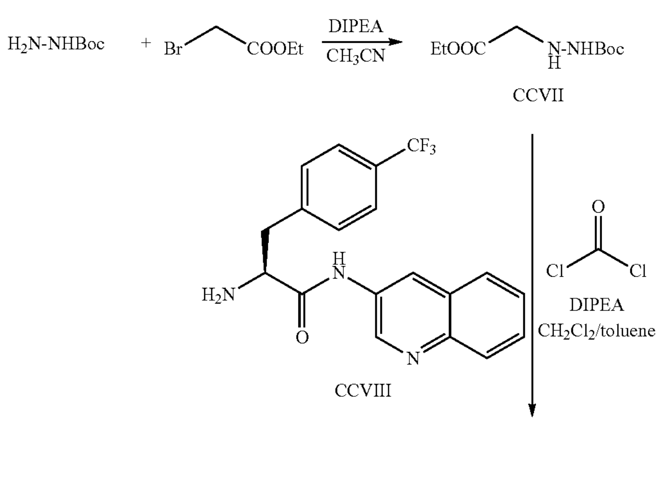

CCVII
CCVIII

-continued

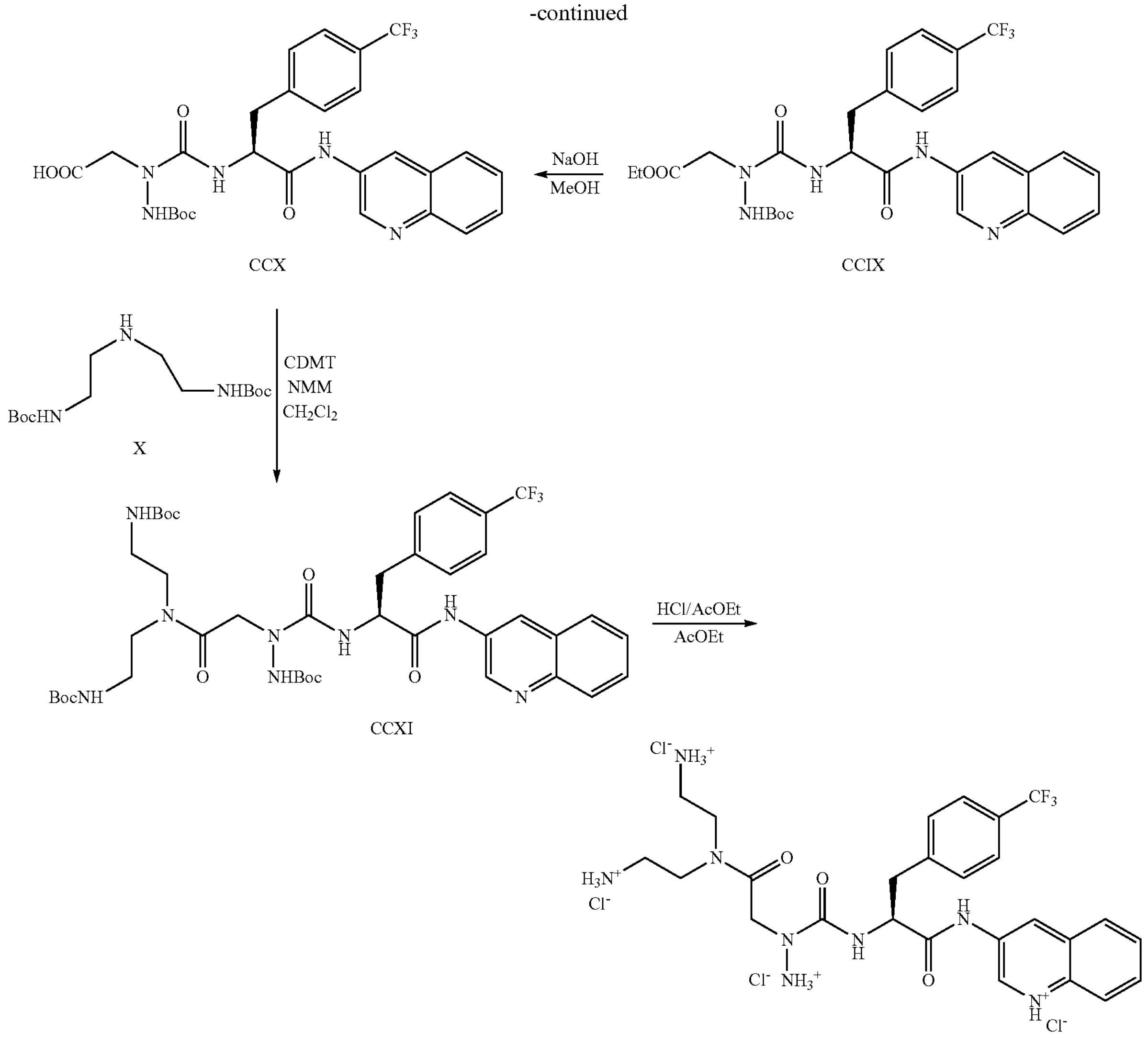

CCX CCIX X CCXI 349

EXAMPLE 31

Step 1

Boc-hydrazine (1.25 g, 9.5 mmol), ethyl bromoacetate (0.21 mL, 1.9 mmol) and DIPEA (0.33 mL, 1.9 mmol) were dissolved in $CH_3CN$ and stirred overnight at r.t. The solvent was removed in vacuo. The residue was distributed between 1N HCl/$CH_2Cl_2$ and the aqueous layer was extracted with methylene chloride. The organic layers were combined, washed with brine, and dried over $MgSO_4$, filtered and concentrated to afford CCVII (0.41 g of crude product), that was used in the next stage without any additional purification. $^1$H NMR ($CDCl_3$) 1.26 (t, J=7 Hz, 3H), 1.43 (s, 9H), 3.36 (s, 2H), 4.18 (q, J=7 Hz, 2H), 6.48 (brs, 1H); ESIMS found for $C_9H_{18}N_2O_4$ m/z 219.3 (M+H).

Step 2

The ester CCVII (0.41 g, 1.88 mmol) was dissolved in dry toluene and DIPEA (0.33 mL, 1.88 mmol) was added. The mixture was cooled to 0° C. and phosgene 20% (1 mL, 1.88 mmol) in toluene was added. Reaction was stirred at r.t. 2 hours. Solvent was removed in vacuo. Methylene chloride, DIPEA (1.64 mL, 9.4 mmol) and hydrochloride of amine component CCVIII (0.82 g, 1.88 mmol) were added to the residue. Reaction was stirred overnight at r.t. $CH_2Cl_2$ was added, mixture was washed with 1M aq. HCl, brine, dried over anhydrous $MgSO_4$. After filtration of $MgSO_4$ solvent was removed under reduced pressure to give 0.75 g of impure product. The crude product was crystallized from MeOH/$Et_2O$ to give white solid of CCIX (0.5 g, 0.83 mmol, 66%). $^1$H NMR ($CDCl_3$) 1.21 (t, J=7, 3H), 1.46 (s), 1.4 (s), 3.48 (q, 2H), 3.56 (brs, 2H), [3.86 (brs), 3.89 (brs) 1H], 4.22 (brs, 1H), [4.9 (brs), 5.26 (brs) 1H], 7.5 (d, J=8 Hz, 2H), 7.58 (d, J=8 Hz, 2H), 7.84 (t, J=8 Hz, 2H), 8.06 (t, 9 Hz, 2H), 8.52 (d, J=8 Hz, 1H), 8.55 (brs, 1H), 9.82 (s, 1H), 10.00 (s, 1H), 11.19 (s, 1H); ESIMS found for $C_{29}H_{32}F_3N_5O_6$ m/z 604.5 (M+H).

Step 3

To the solution of ester CCIX (0.5 g, 0.83 mmol) in MeOH (10 mL) 4M NaOH was added dropwise until pH=11. The mixture was stirred 15 min. and MeOH was evaporated under reduced pressure. The residue was acidifying to pH~3 with 2M HCl. The product was extracted with methylene chloride, dried over $MgSO_4$ and concentrated under vacuum to give 0.47 g of crude product CCX, ESIMS found for $C_{27}H_{28}F_3N_5O_6$ m/z 576.4 (M+H).

Step 4

CDMT (0.16 g, 0.90 mmol) in dry DCM (50 mL) was cooled to 0° C. and N-methylmorpholine (0.1 mL, 0.9 mmol) was added. The mixture was stirred for 15 min before adding acid component CCX (0.47 g, 0.817 mmol). The solution was stirred for 1 hour and hydrochloride of amine X was added and the mixture was stirred overnight. Reaction was washed with 2M HCl, 1M $K_2CO_3$, brine and dried over anhydrous $MgSO_4$. The crude product was purified on a silica gel column ethyl acetate:hexane 1:2 to give white solid of CCXI (155 mg, 0.18 mmol, 22%). $^1H$ NMR ($CDCl_3$) 1.41 (s, 9H), 1.43 (s, 18H), 1.65 (brs, 8H), 3.28 (brs, 2H), 3.37 (brs, 2H), 4.82 (brs, 1H), 5.09 (brs, 1H), 5.95 (brs, 1H), 6.15 (brs, 1H), 6.85 (brs, 1H), 7.38 (d, J=7 Hz, 2H), 7.55 (m, 3H), 7.62 (t, J=7 Hz, 1H), 7.82 (d, J=8 Hz, 1H), 8.04 (d, J=8 Hz, 1H), 8.98 (brs, 3H); ESIMS found for $C_{41}H_{55}F_3N_8O_9$ m/z 861.6 (M+H).

Step 5

To a solution of CCXI (0.15 g, 0.174 mmol) in ethyl acetate (5 mL) was added HCl (4.5M solution in EtOAc, 5 mL). The reaction was stirred for 30 min at r.t. before adding $Et_2O$ (20 mL). The precipitate was filtered off and washed with $Et_2O$ to give 3-[(2S)-2-{[azaniumyl({[bis(2-azaniumylethyl)carbamoyl]methyl}) carbamoyl]amino}-3-[4-(trifluoromethyl) phenyl]propanamido]quinolin-1-ium tetrachloride 349, a white solid (64 mg, 0.095 mmol, 55%). $^1H$ NMR (DMSO-$d_6$) 3.00 (brs, 3H), 3.11 (brs, 2H), 3.22-3.33 (m, 1H), 3.6 (brs, 4H), 4.58-4.71 (m, 1H), 4.85 (brs, 2H), 7.61-7.84 (m, 7H), 8.07 (brs, 6H), 8.11 (brs, 1H), 8.32 (brs, 4H), 8.95 (brs, 1H), 9.21 (brs, 1H), 11.13 (brs, 1H); $^{19}F$ NMR (DMSO-$d_6$) −60.00 (s); ESIMS found for $C_{26}H_{31}F_3N_8O_3$ m/z 561.6 (M+H).

3-[(1S)-2-[bis(2-azaniumylethyl)carbamoyl]-1-{[({[4-(trifluoromethyl)phenyl]methyl}carbamoyl)methyl] carbamoyl}ethan-1-aminium]quinolin-1-ium tetrachloride 357 is depicted below in scheme 32 and example 32.

Scheme 32

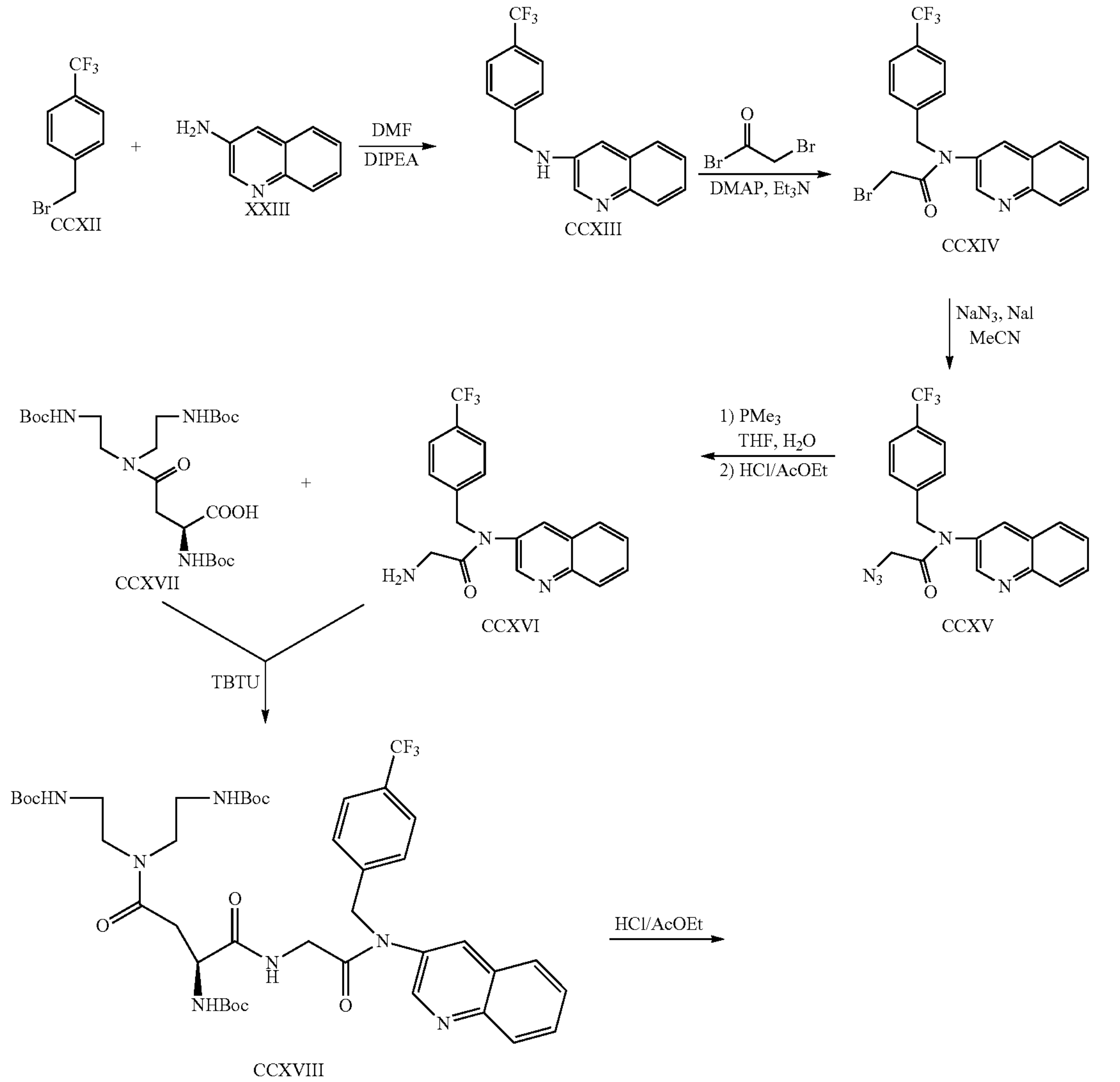

CCXII XXIII CCXIII CCXIV CCXV CCXVI CCXVII CCXVIII

-continued

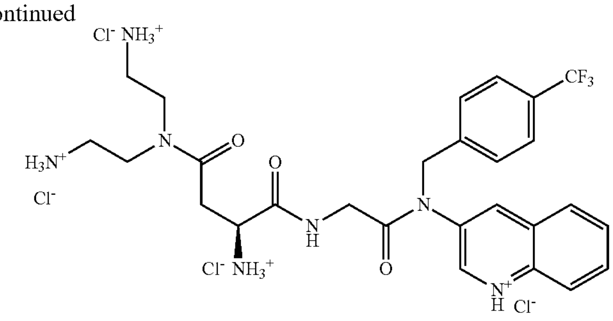

357

EXAMPLE 32

Step 1

3-aminoquinoline XXIII (2.41 g, 16.68 mmol) was dissolved in dry DMF (10 mL) and 4-(trifluoromethyl)benzyl bromide CCXII (1.32 g, 5.56 mmol) and DIPEA (1.06 mL, 6.11 mmol) were added. The reaction mixture was warmed up to 60° C. and stirred over 1 hour. After this time 4-(trifluoromethyl)benzyl bromide wasn't present in reaction so 4-(trifluoromethyl)benzyl bromide (1.16 g, 2.09 mmol) and DIPEA (0.63 mL, 3.06 mmol) were added once again and stirred 1 hour in 60° C. (the reaction mixture was black). The reaction mixture was diluted ethyl acetate and washed with 10% citric acid (three times), 10% $Na_2S_2O_7$ (three times), brine and dried over $MgSO_4$. Product was purified on silica gel using ethyl acetate/hexane 1/5-1/3-1/2-1/1 to give yellow solid CCXIII (1.54 g, 5.09 mmol, 61%). $^1$H NMR (DMSO-$d_6$) 4.50 (d, J=6 Hz, 2H), 6.93-7.07 (m, 2H), 7.24-7.40 (m, 2H), 7.50-7.80 (m, 6H), 8.55 (d, J=3 Hz, 1H); $^{19}$F NMR (DMSO-$d_6$) −60.16 (s); ESIMS found for $C_{17}H_{13}F_3N$ m/z 303.3 (M+H).

Step 2

The amine CCXIII (1.54 g, 5.09 mmol) was dissolved in MeCN (25 mL) and $Et_3N$ (1.40 mL, 10.09 mmol), DMAP (123 mg, 1.01 mmol) and bromoacetyl bromide (0.53 mL, 6.05 mmol) were added. Reaction mixture was refluxed over 1 hour (mixture was black). After this time substrate (CCXIII) was present in reaction so $Et_3N$ (1.40 mL, 10.09 mmol) and bromoacetyl bromide (0.53 mL, 6.05 mmol) were added and refluxed for an additional hour. The solvent was removed under reduced pressure. The residue was suspended in ethyl acetate and filtered off through a pad of celite. The filtrate was washed 1 M HCl, brine and dried over $MgSO_4$. Product was purified on silica gel using ethyl acetate/hexane 1/5-1/3-1/2-1/1 to give yellow solid CCXIV (0.69 g, 1.64 mmol, 32%). ESIMS found for $C_{19}H_{14}BrF_3N_2O$ m/z 424.2 (M+H).

Step 3

The derivative CCXIV (0.69 g, 1.64 mmol) was dissolved in MeCN (20 mL) and $NaN_3$ (113 mg, 1.97 mmol), NaI (25 mg, 0.16 mmol) were added and the mixture was refluxed for 1 hour. The solvent was removed under reduced pressure. The residue was dissolved in ethyl acetate and washed with water, 1M HCl, brine, and dried over $MgSO_4$. The solvent was removed under reduced pressure to give a black oil. The crude product was purified on silica gel using chloroform and a chloroform/methanol 500/1-300/1 solvent system to give CCXV (415 mg, 1.07 mmol, 65%) as light brown oil. $^1$H NMR ($CDCl_3$) 3.67 (s, 2H), 5.07 (s, 2H), 7.37 (d, J=8 Hz, 2H), 7.58 (d, J=8 Hz, 2H), 7.67 (d, J=7 Hz, 1H), 7-75-7-86 (m, 3H), 8.16 (d, J=8 Hz, 1H), 8.58 (d, J=2 Hz, 1H); $^{19}$F NMR ($CDCl_3$) −61.98 (s); ESIMS found for $C_{19}H_{14}F_3N_5O$ m/z 385.3 (M+H).

Step 4

The azide CCXV (415 mg, 1.07 mmol) was dissolved in $THF/H_2O$ (9 mL/1 mL), then trimethylphosphine (5.40 ml 1 M solution in THF, 5.40 mmol) was added. The reaction mixture was stirred overnight in r.t. The solvents were removed under reduced pressure. The residue was dissolved in methyl chloride, washed with brine and dried over $MgSO_4$. The solvent was removed under reduced pressure to give yellow oil. The oil was dissolved in ethyl acetate (5 mL) and treated with hydrogen chloride (4.0M solution in ethyl acetate, 5 ml). The reaction mixture was stirred over 20 minutes at r.t. and next ethyl ether was added (about 20 ml). The precipitate (highly hygroscopic) was filtered off and washed with ether to give light yellow crystalline solid of CCXVI (410 mg, 0.94 mmol, 88%). $^1$H NMR (DMSO-$d_6$) 3.60 (brs, 2H), 5.14 (s, 2H), 7.52 (d, J=7 Hz, 2H), 7.67 (d, J=8 Hz, 2H), 7.74 (brs, 1H), 7.80-7.93 (m, 1H), 8.00 (d, J=7 Hz, 1H), 8.10 (d, J=7 Hz, 1H), 8.32 (brs, 3H), 8.56 (s, 1H), 8.92 (d, J=2 Hz, 1H); $^{19}$F NMR (DMSO-$d_6$) −60.29 (s); ESIMS found for $C_{19}H_{16}F_3N_3O$ m/z 359.3 (M+H).

Step 5

The hydrochloride of amine CCXVI (400 mg, 0.93 mmol) was dissolved in DCM (15 mL) and the acid component CCXVII (480 mg, 0.93 mmol), TBTU (328 mg, 1.02 mmol), DIPEA (0.57 mL, 3.25 mmol) were added. The reaction mixture was stirred overnight in r.t. The reaction was diluted DCM and washed 1M HCl, 1M $K_2CO_3$, brine and dried over $MgSO_4$. The crude product was purified on silica gel using chloroform then a chloroform/methanol 100/1-50/1 solvent system to afford CCXVIII (780 mg, 0.90 mmol, 96%). $^1$H NMR ($CDCl_3$) 1.39 (s, 9H), 1.42 (s, 9H), 1.47 (s, 9H), 3.04-3.19 (m, 2H), 3.20-3.42 (m, 7H), 3.44-3.66 (m, 3H), 3.83-4.01 (m, 1H), 4.59-4.73 (m, 1H), 5.03 (d, J=3 Hz, 2H), 5.39 (brs, 1H), 5.51 (brs, 1H), 6.13 (brs, 1H), 7.33 (d, J=8 Hz, 2H), 7.56 (d, J=8 Hz, 2H), 7.62-7.68 (m, 1H), 7.72-7.89 (m, 3H), 8.15 (d, J=8 Hz, 1H), 8.60 (brs, 1H); $^{19}$F NMR ($CDCl_3$) −61.97 (s); ESIMS found for $C_{42}H_{56}F_3N_7O_9$ m/z 860.6 (M+H).

Step 6

The Boc-protected compound CCXVIII (750 mg, 0.87 mmol) was dissolved in ethyl acetate (5 mL) and treated with hydrogen chloride (4.0M solution in ethyl acetate, 5 ml). The reaction mixture was stirred over 30 minutes at r.t. and next ethyl ether was added (about 10 ml). Precipitate was filtered off and washed with ethyl ether to give yellow solid. The solid was crystallized from methanol/ether solvent system to give 3-[(1S)-2-[bis(2-azaniumylethyl)carbamoyl]-1-{[({[4-(trifluoromethyl)phenyl]methyl}carbamoyl)methyl]carbamoyl}ethan-1-aminium]quinolin-1-ium tetrachloride 357, a light yellow hygroscopic solid (350 mg, 0.50 mmol, 58%). $^1$H NMR (DMSO-$d_6$) 2.92-3.00 (m, 2H), 3.01-3.12 (m, 4H), 3.48-3.56 (m, 1H), 3.58-3.66 (m, 3H), 3.80 (brs, 2H), 4.24 (brs, 1H), 5.07-5.15 (m, 2H), 7.52 (brs, 2H), 7.65-7.75 (m, 3H), 7.88 (t, J=5 Hz, 1H), 8.03 (brs, 1H), 8.11 (s, 1H), 8.12 (brs, 3H), 8.29 (brs, 3H), 8.37 (brs, 3H), 8.56 (s, 1H), 8.91 (brs, 1H), 8.95 (s, 1H); $^{19}$F NMR (DMSO-$d_6$) −60.26 (s); ESIMS found for $C_{27}H_{32}F_3N_7O_3$ m/z 560.6 (M+H).

The following compound was prepared in accordance with the procedure described in the above example 32.

355

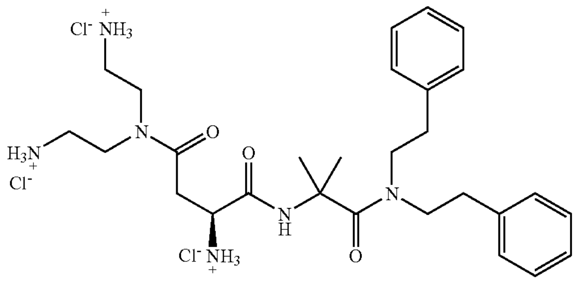

(1S)-2-[bis(2-azaniumylethyl)carbamoyl]-1-({1-[bis(2-phenylethyl)carbamoyl]-1-methylethyl}carbamoyl)ethan-1-aminium trichloride 355

$^1$H NMR (DMSO-$d_6$) 1.38 (s, 3H), 1.40 (s, 3H), 2.66-2.84 (m, 2H), 2.89-3.19 (m, 8H), 3.37-3.74 (m, 8H), 4.12 (brs, 1H), 7.16-7.35 (m, 10H), 8.07 (brs, 3H), 8.24 (brs, 3H), 8.33 (brs, 3H), 9.07 (s, 1H); ESIMS found for $C_{28}H_{42}N_6O_3$ m/z 511.6 (M+H).

3-{N-[(2S)-2-azaniumyl-2-{[(1S)-1-carbamoyl-3-phenylpropyl]carbamoyl}ethyl]-N',N'-bis(2-azaniumylethyl)ethanediamide}quinolin-1-ium tetrachloride 365 is depicted below in scheme 33 and example 33.

Scheme 33

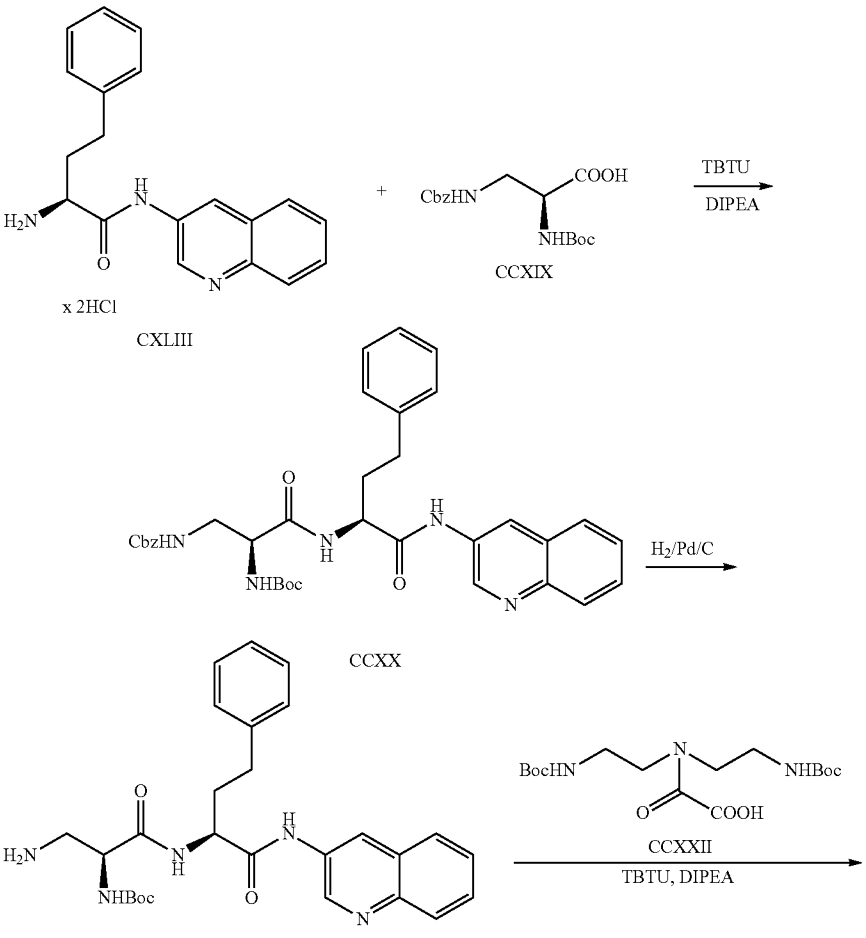

x 2HCl

CXLIII

CCXIX

CCXX

CCXXII

CCXXI

-continued

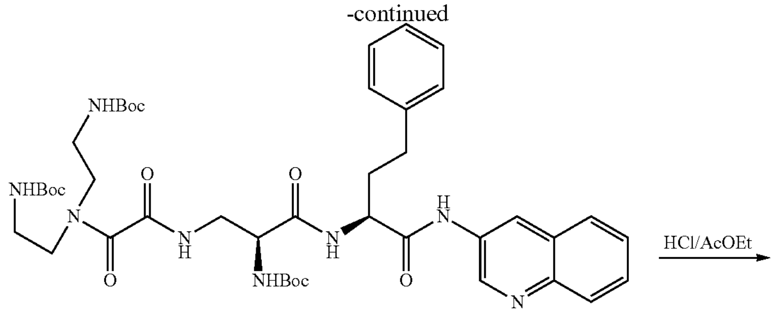

CCXXIII

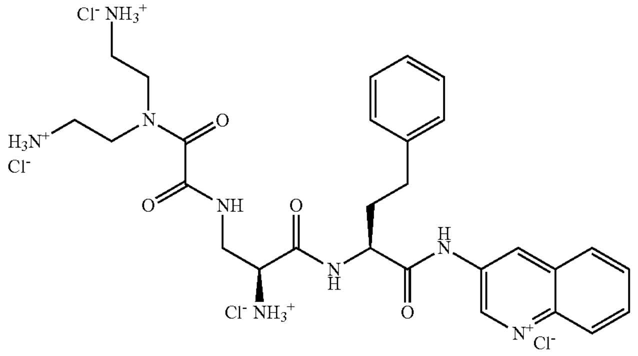

365

EXAMPLE 33

Step 1

To the solution of acid CCXIX (240 mg, 0.71 mmol) in DCM (20 mL) DIPEA (0.37 mL, 2.13 mmol), amine component CXLIII (290 mg, 0.77 mmol) and TBTU (247 mg, 0.77 mmol) were added. The mixture was stirred at r.t. overnight. The reaction mixture was then washed with 1 M HCl, 5% $NaHCO_3$, brine and dried over $MgSO_4$. The residue was purified on a silica gel column (50:1 $CH_2Cl_2$/methanol) to give CCXX (350 mg, 0.56 mmol, 80% yield). $^1$H NMR ($CDCl_3$) 1.47 (s, 9H), 1.72 (s, 2H), 1.97-2.53 (m, 2H), 2.68-2.83 (t, J=15 Hz, 2H), 3.62 (t, J=11 Hz, 2H), 4.21 (brs, 1H), 4.65 (brs, 1H), 5.12 (brs, 2H), 5.53 (brs, 1H), 6.22 (brs, 1H), 6.91 (d, J=8 Hz, 2H), 7.16-7.24 (m, 2H), 7.25-7.28 (m, 4H), 7.48-7.70 (m, 2H), 7.75-7.80 (m, 1H), 8.00-8.06 (m, 2H), 8.81 (brs, 1H), 8.97 (brs, 1H), 9.12 (brs, 1H); ESIMS found for $C_{35}H_{39}N_5O_6$ m/z 626 (M+H).

Step 2

To a solution of CCXX (350 mg, 0.56 mmol) in EtOH/water (15 mL/2 mL) under argon 10% Pd/C catalyst (catalytic amount) was added. The mixture was stirred under an atmosphere of hydrogen at r.t. for 1.5 h. The mixture was then filtered through Celite and evaporated to dryness. The residue was purified on a silica gel column (50:1 $CH_2Cl_2$/methanol) to give CCXXI as a yellow oil (120 mg, 0.24 mmol, 45% yield). ESIMS found for $C_{27}H_{33}N_5O_4$ m/z 492 (M+H).

Step 3

To the solution of the acid component CCXXII (100 mg 0.27 mmol) in DCM (15 mL) DIPEA (0.023 mL, 0.27 mmol), hydrochloride of amine component CCXXI (120 mg, 0.24 mmol) and TBTU (86 mg, 0.27 mmol) were added. The mixture was stirred at r.t. overnight. The reaction mixture was then washed with 1 M HCl, 5% $NaHCO_3$, brine and dried over $MgSO_4$. The residue was purified on a silica gel column (50:1 $CH_2Cl_2$/methanol) to give CCXXIII (135 mg, 0.16 mmol, 64% yield) as a pale yellow crystalline solid. $^1$H NMR ($CDCl_3$) 1.40 (s, 9H), 1.41 (s, 9H), 1.44 (s, 9H), 2.00-2.19 (m, 6H), 2.75 (brs, 2H), 3.20-3.40 (m, 5H), 3.50-3.67 (m, 4H), 4.31 (brs, 1H), 4.67 (brs, 1H), 7.18 (s, 5H), 7.37 (brs, 1H), 7.52 (brs, 2H), 7.61 (brs, 1H), 7.78 (brs, 2H), 8.02 (brs, 1H), 8.83 (brs, 1H), 8.92 (brs, 1H). ESIMS found for $C_{43}H_{60}N_8O_{10}$ m/z 849 (M+H).

Step 4

To a solution of CCXXIII (135 mg, 0.16 mmol) in EtOAc (5 mL) HCl (4.5 M solution in EtOAc, 5 mL) was added. The reaction mixture was stirred for 45 min at r.t. before adding ethyl ether (20 mL). The precipitate was filtered and washed with ether to give 3-{N-[(2S)-2-azaniumyl-2-{[(1S)-1-carbamoyl-3-phenylpropyl]carbamoyl}ethyl]-N',N'-bis(2-azaniumylethyl)ethanediamide}quinolin-1-ium tetrachloride 365 as a white crystalline solid (43 mg, 0.13 mmol, 53% yield). $^1$H NMR (DMSO-$d_6$) 2.00-2.19 (m, 2H), 2.63-2.87 (m, 2H), 2.96-3.16 (m, 4H), 3.35-3.39 (m, 1H), 3.56-3.71 (m, 6H), 4.31 (m, 1H), 4.60 (m, 1H), 7.15-7.19 (m, 1H), 7.25-7.30 (m, 3H), 7.66 (t, J=15 Hz, 1H), 7.74 (t, J=15 Hz, 1H), 8.05 (t, J=16 Hz, 2H), 8.10 (brs, 6H), 8.57 (brs, 3H), 8.84 (s, 1H), 9.11-9.14 (m, 1H), 9.15 (s, 1H), 9.34 (s, 1H), 11.11 (s, 1H). ESIMS found for $C_{28}H_{36}N_8O_4$ m/z 549 (M+H).

(3S)-1-[(3S)-3-azaniumyl-3-{[(1S)-3-phenyl-1-{[3-(trifluoromethyl)phenyl]carbamoyl}propyl]carbamoyl}propyl]-1λ$^4$-pyrrolidin-3-aminium trihydrochloride is depicted below in scheme 34.
Scheme 34
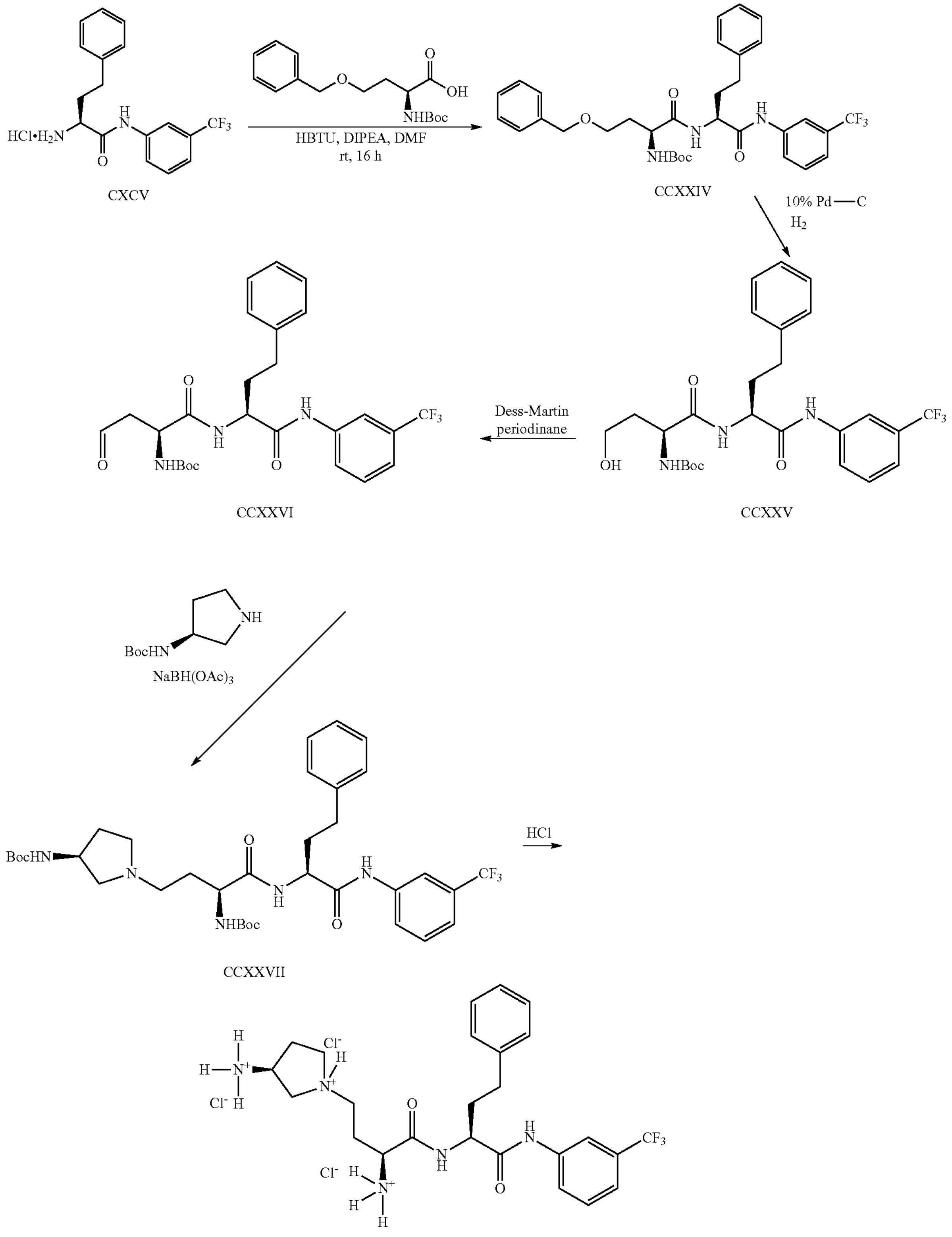

EXAMPLE 34

Step 1

To a solution of CXCV (0.61 g; 1.7 mmol), (S)-4-(benzyloxy)-2-(tert-butoxycarbonylamino)butanoic acid (0.5 g; 1.6 mmol), and HBTU (0.76 g; 2.0 mmol) in DMF (6.5 mL) was added DIPEA (0.67 mL; 4.0 mmol). The mixture was stirred at room temperature overnight. The resulting solution was added $H_2O$ (20 mL) and extracted with ethyl acetate (20 mL). The organic layer was washed with $H_2O$ (20 mL), 1N HCl (20 mL), saturated $NaHCO_3$ (20 mL), and brine (20 mL). The solution was dried over $MgSO_4$ and concentrated to afford a yellow solid. tert-Butyl (S)-4-(benzyloxy)-1-oxo-1-((S)-1-oxo-4-phenyl-1-(3-(trifluoromethyl)phenylamino)butan-2-ylamino)butan-2-ylcarbamate CCXXIV (0.99 g; 1.6 mmol; 100% yield). ESIMS found for $C_{33}H_{38}F_3N_3NaO_5$ m/z 636 $(M+Na)^+$.

Step 2

To a solution of CCXXIV (0.99 g, 1.6 mmol) in methanol (5 mL) was charged with 10% Pd—C (100 mg). The mixture was stirred over under $H_2$ (balloon pressure) at room temperature overnight. The resulting mixture was filtered through a pad of Celite. The crude mixture was purified on a silica gel column (100% hexanes→50:50 hexanes:ethyl acetate) to afford a white solid. tert-Butyl (S)-4-hydroxy-1-oxo-1-((S)-1-oxo-4-phenyl-1-(3-(trifluoromethyl)phenylamino)butan-2-ylamino)butan-2-ylcarbamate CCXXV (0.82 g; 1.6 mmol; 98% yield). ESIMS found for $C_{26}H_{32}F_3N_3NaO_5$ m/z 546 $(M+Na)^+$.

Step 3

To a solution of CCXXV (0.66 g, 1.3 mmol) in $CH_2Cl_2$ (12 mL) cooled in an ice/water bath was added Dess-Martin periodinane (0.8 g, 1.9 mmol) in one portion. After 1 h, the mixture was added a solution of $Na_2S_2O_3$ (2.3 g) in $H_2O$ (13.5 mL) and saturated $NaHCO_3$ (13.5 mL). The mixture was stirred for 10 min and extracted with ethyl acetate (3×25 mL). The organic extractions were combined, washed with brine, and dried over MgSO4 to afford a white foam. tert-Butyl (S)-1,4-dioxo-1-((S)-1-oxo-4-phenyl-1-(3-(trifluoromethyl)phenylamino)butan-2-ylamino)butan-2-ylcarbamate CCXXVI (0.65 g; 1.2 mmol; 99%). ESIMS found for $C_{26}H_{30}F_3N_3NaO_5$ m/z 544 $(M+Na)^+$.

Step 4

To a solution of CCXXVI (0.1 g, 0.2 mmol) and (S)-tert-butyl pyrrolidin-3-ylcarbamate (0.04 g, 0.2 mmol) in THF (2 mL) was added $NaBH(OAc)_3$ (0.057 g, 0.27 mmol). The mixture was stirred at room temperature for 3 h. The resulting mixture was added saturated $NaHCO_3$ (5 mL), extracted with ethyl acetate (5 mL) and dried over $MgSO_4$. The crude mixture was purified on a silica gel column (100% $CH_2Cl_2$→95:5 $CH_2Cl_2$:methanol) to afford a white solid. CCXXVII (0.076 g; 0.11 mmol; 58% yield). ESIMS found for $C_{35}H_{48}F_3N_5O_6$ m/z 692 $(M+H)^+$.

Step 5

To a solution of CCXXVII (0.066 g, 0.099 mmol) in methanol (2 mL) was added a solution of 4 M HCl in 1,4-dioxane (0.5 mL). The mixture was stirred at 50° C. for 1 h and concentrated. The resulting solid was added $Et_2O$ (5 mL) and concentrated to afford a white solid. (3S)-1-[(3S)-3-azaniumyl-3-{[(1S)-3-phenyl-1-{[3-(trifluoromethyl)phenyl]carbamoyl}propyl]carbamoyl}propyl]-1λ$^4$-pyrrolidin-3-aminium trihydrochloride 373 (0.059 g; 0.1 mmol; 100% yield). ESIMS found for $C_{25}H_{32}F_3N_5O_2$ m/z 492 (M+H). $^1H$ NMR ($CD_3OD$, 500 MHz) 2.16-2.19 (m, 2H), 2.30-2.35 (m, 2H), 2.44-2.46 (m, 1H), 2.75-2.81 (m, 2H), 2.89-2.91 (m, 1H), 3.30-3.31 (m, 1H), 3.56-3.59 (m, 1H), 3.65-3.66 (m, 1H), 3.70-3.74 (m, 2H), 4.01-4.05 (br s, 1H), 4.18-4.28 (br s, 1H), 4.40-4.42 (br s, 1H), 4.52-4.55 (dd, J=8.7, 5.2 Hz, 1H), 7.16-7.19 (m, 1H), 7.27-7.29 (m, 4H), 7.40 (d, J=7.7 Hz, 1H), 7.51 (t, J=8.0 Hz, 1H), 7.72 (d, J=8.2 Hz, 1H), 8.00 (s, 1H). $^{19}F$ NMR ($CD_3OD$, 500 MHz) 60.94 (s).

The following compounds have been prepared (or, in the case of compounds 376, is to be prepared) in accordance with the procedure described in the above Example 34.

374

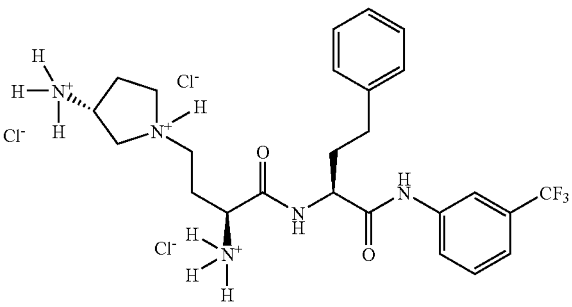

(3R)-1-[(3S)-3-azaniumyl-3-{[(1S)-3-phenyl-1-{[3-(trifluoromethyl)phenyl]carbamoyl}propyl]carbamoyl}propyl]-1λ$^4$-pyrrolidin-3-aminium trihydrochloride.

Step 1

To a solution of CCXXVI (0.1 g, 0.2 mmol) and (R)-tert-butyl pyrrolidin-3-ylcarbamate (0.04 g, 0.2 mmol) in THF (2 mL) was added $NaBH(OAc)_3$ (0.057 g, 0.27 mmol). The mixture was stirred at room temperature for 3 h. The resulting mixture was added saturated $NaHCO_3$ (5 mL), extracted with ethyl acetate (5 mL) and dried over $MgSO_4$. The crude mixture was purified on a silica gel column (100% $CH_2Cl_2$→95:5 $CH_2Cl_2$:methanol) to afford a white solid. CCXXVIII (0.059 g; 0.09 mmol; 44% yield). ESIMS found for $C_{35}H_{48}F_3N_5O_6$ m/z 692 $(M+H)^+$.

Step 2

To a solution of CCXXVIII (0.053 g, 0.077 mmol) in methanol (2 mL) was added a solution of 4 M HCl in 1,4-dioxane (0.5 mL). The mixture was stirred at 50° C. for 1 h and concentrated. The resulting solid was added $Et_2O$ (5 mL) and concentrated to afford a white solid. (3R)-1-[(3S)-3-azaniumyl-3-{[(1S)-3-phenyl-1-{[3-(trifluoromethyl)phenyl]carbamoyl}propyl]carbamoyl}propyl]-1λ$^4$-pyrrolidin-3-aminium trihydrochloride 374 (0.037 g; 0.077 mmol; 100% yield). ESIMS found for $C_{25}H_{32}F_3N_5O_2$ m/z 492 (M+H). $^1H$ NMR ($CD_3OD$, 500 MHz) 2.16-2.21 (m, 2H), 2.30-2.36 (m, 2H), 2.43-2.47 (m, 1H), 2.76-2.79 (m, 2H), 2.88-2.92 (m, 1H), 3.55-3.74 (m, 5H), 4.10-4.30 (br s, 2H), 4.39-4.20 (dd, J=8.4, 5.4 Hz, 1H), 4.52-4.55 (dd, J=9.0, 5.0 Hz, 1H), 7.16-7.19 (m, 1H), 7.23-7.28 (m, 4H), 7.40 (d, J=7.8 Hz, 1H), 7.51 (t, J=8.0 Hz, 1H), 7.72 (d, J=8.3 Hz, 1H), 8.00 (s, 1H). $^{19}F$ NMR ($CD_3OD$, 500 MHz) 3.89 (s).

The following compound was prepared in accordance with the procedure described in the above example 34.

375

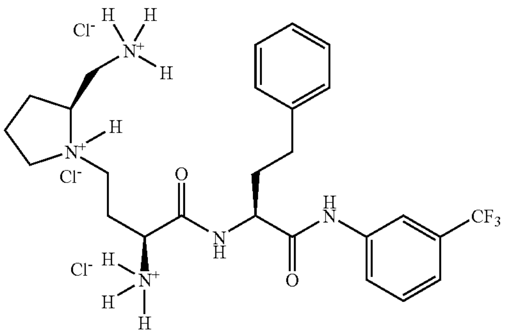

[(2S)-1-[(3S)-3-azaniumyl-3-{[(1S)-3-phenyl-1-{[3-(trifluoromethyl)phenyl]carbamoyl}propyl]carbamoyl}propyl]-1λ$^4$-pyrrolidin-2-yl]methanaminium trihydrochloride.

Step 1

To a solution of CCXXVI (0.1 g, 0.2 mmol) and (S)—N-Boc-aminomethylpyrrolidine (0.04 g, 0.2 mmol) in THF (2 mL) was added $NaBH(OAc)_3$ (0.057 g, 0.27 mmol). The mixture was stirred at room temperature for 3 h. The resulting mixture was added saturated $NaHCO_3$ (5 mL), extracted with ethyl acetate (5 mL) and dried over $MgSO_4$. The crude mixture was purified on a silica gel column (100% $CH_2Cl_2$→95:5 $CH_2Cl_2$:methanol) to afford a white solid. CCXXIX (0.072 g; 0.1 mmol; 53% yield). ESIMS found for $C_{36}H_{50}F_3N_5NaO_6$ m/z 728 $(M+Na)^+$.

Step 2

To a solution of CCXXIX (0.062 g, 0.088 mmol) in methanol (2 mL) was added a solution of 4 M HCl in 1,4-dioxane (0.5 mL). The mixture was stirred at 50° C. for 1 h and concentrated. The resulting solid was added $Et_2O$ (5 mL) and concentrated to afford a white solid. (S)-2-Amino-4-((S)-2-(aminomethyl)pyrrolidin-1-yl)-N—((S)-1-oxo-4-phenyl-1-(3-(trifluoromethyl)phenylamino)butan-2-yl)butanamide trihydrochloride 375 (0.037 g; 0.06 mmol; 70% yield). ESIMS found for $C_{27}H_{34}F_3N_5O_2$ m/z 506 (M+H). $^1H$ NMR ($CD_3OD$, 500 MHz) 1.99-2.03 (m, 1H), 2.20-2.25 (m, 2H), 2.45-2.50 (m, 3H), 2.75-2.81 (m, 1H), 2.90-2.94 (m, 1H), 3.38-3.42 (m, 4H), 3.75-3.85 (m, 4H), 3.92-3.98 (m, 1H), 4.35 (br s, 1H), 4.50 (t, J=5.8 Hz, 1H), 7.18 (br s, 1H), 7.23-7.28 (m, 4H), 7.41 (d, J=7.4 Hz, 1H), 7.52 (t, J=8.1 Hz, 1H), 7.73 (d, J=7.8 Hz, 1H), 8.01 (s, 1H). $^{19}F$ NMR ($CD_3OD$, 500 MHz) 63.83 (s).

376

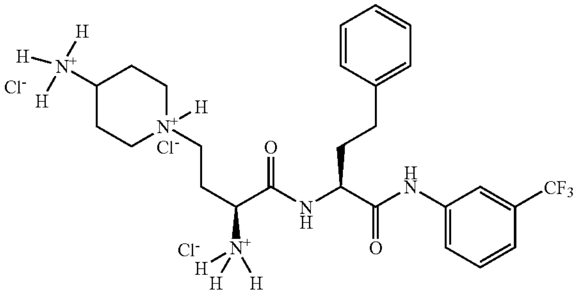

1-[(3S)-3-azaniumyl-3-{[(1S)-3-phenyl-1-{[3-(trifluoromethyl)phenyl]carbamoyl}propyl]carbamoyl}propyl]-1λ$^4$-piperidin-4-aminium trihydrochloride.

Compounds 377-438 shown in Table 3 were assembled according to the general Scheme 35. A general description of the steps appears below the scheme.

Scheme 35

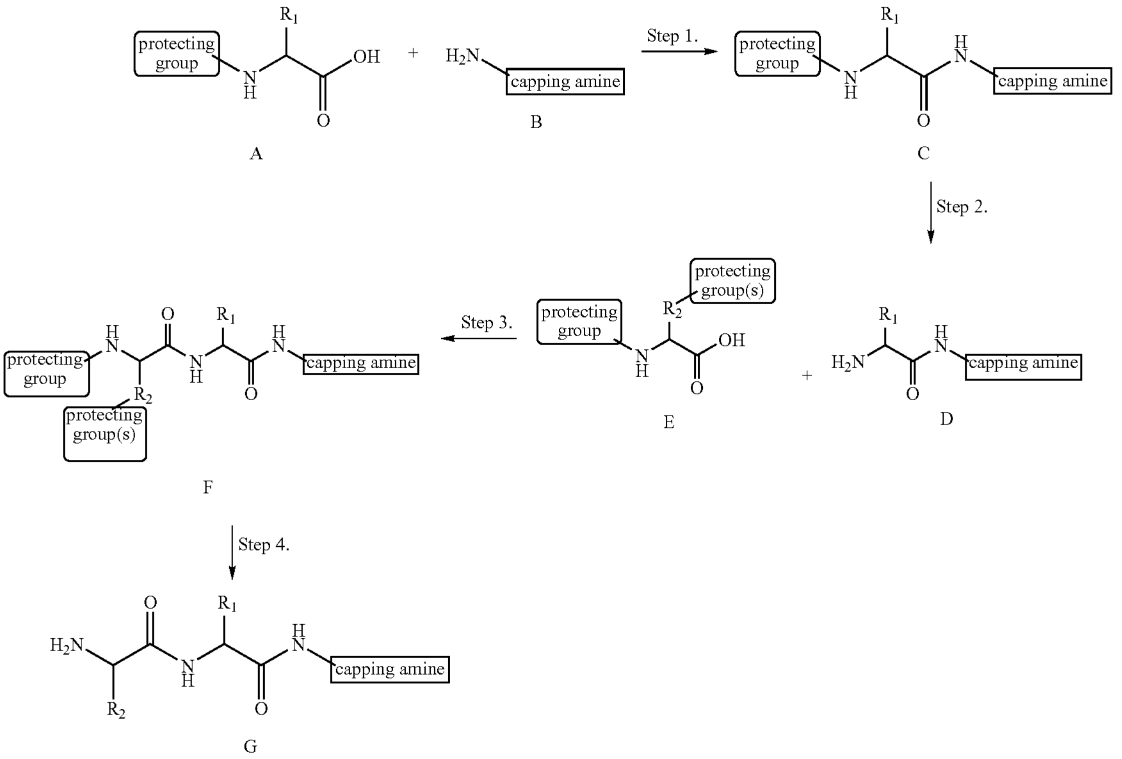

Step 1. Capping amine intermediate B was attached using one of coupling procedures A1-A4 (described below) to a protected central amino acid intermediate to form corresponding amide bond containing intermediate C.

Step 2. The amine functionality of the obtained intermediate C was unmasked by removal of protecting group producing intermediate D using one of the deprotection methods described below.

Step 3. Acid intermediate E containing masked polybasic functionalities was attached using one of coupling procedures A1-A4 to intermediate D producing fully protected intermediate F.

Step 4. Fully assembled intermediate F was deprotected in order to produce final inhibitor compounds G using one of the deprotection methods described below.

$R_1$ in Scheme 35 refers to the side chain in the central amino acid structure in the structures of Formulae I, II, and IV depicted herein. $R_2$ refers to the polybasic moiety on the N-terminal amino acid structure in the structures of Formulae I, II, and IV depicted herein. In some cases additional steps were required when different protecting groups were present which required different deprotecting conditions.

Amide coupling procedures in Scheme 35:

General Procedure $A_1$: preparation of amides using chlorodimethoxytriazine (CDMT)

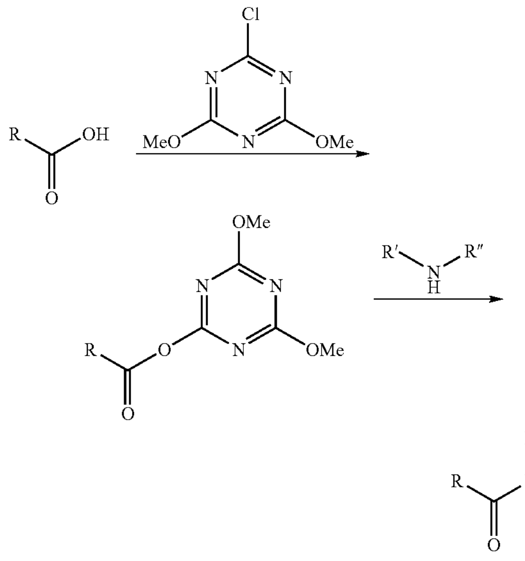

CDMT (1.1 eq) was dissolved in dichloromethane (5 mL/mmol), the solution was cooled to 0° C. and N-methylmorpholine (1.1 eq) was added. After 10 min protected amino acid (1 eq) was added and the solution was stirred for additional 40 min. After that time the amine component was added and the mixture stirred at ambient temperature overnight. The solution was filtered and the filtrate washed twice with 1M aqueous NaOH, twice with 2M aqueous HCl (caution: only when basic groups were not present in the molecule), brine and dried over anhydrous $MgSO_4$. The solvent was evaporated and product crystallized from ethyl acetate/hexane solvent system or purified by column chromatography.

General Procedure $A_2$: preparation of amides using O-(7-azabenzotriazol-1-yl)-1,1,3,3-tetramethyluronium hexafluorophosphate (HATU)

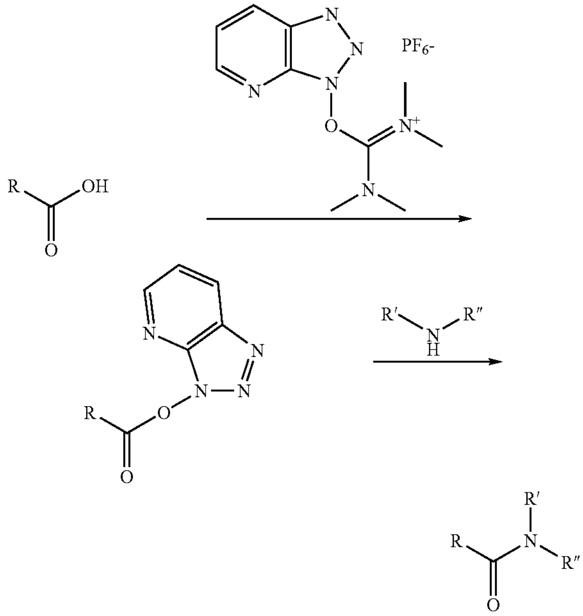

Protected amino acid (1 eq) was dissolved in DCM and diisopropylethylamine (1 eq) was added at ambient temperature followed by addition of amine to be coupled (1 eq) and HATU (1.05 eq). The reaction mixture was stirred overnight, diluted with methylene chloride and washed twice with 1M aqueous NaOH, twice with 2M aqueous HCl (caution: only when basic groups were not present in the molecule), brine and dried over anhydrous $MgSO_4$. The solvent was evaporated and product crystallized from ethyl acetate/hexane solvent system or purified by column chromatography.

General Procedure $A_3$: preparation of amides using O-(Benzotriazol-1-yl)-N,N,N',N'-tetramethyluronium tetrafluoroborate (TBTU)

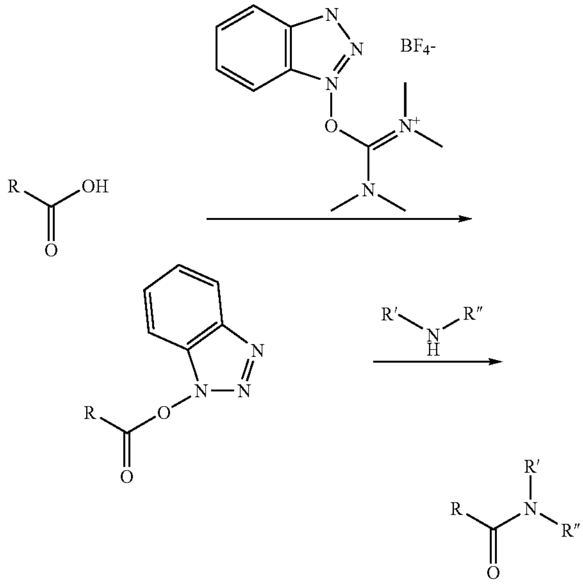

Protected amino acid (1 eq) was dissolved in DCM and diisopropylethylamine (1 eq) was added at ambient temperature followed by addition of amine to be coupled (1 eq) and TBTU (1.05 eq). The reaction mixture was stirred overnight, diluted with methylene chloride and washed twice with 1M aqueous NaOH, twice with 2M aqueous HCl (caution: only when basic groups were not present in the molecule), brine and dried over anhydrous $MgSO_4$. The solvent was evaporated and product crystallized from ethyl acetate/hexane solvent system or purified by column chromatography.

General Procedure $A_4$: Preparation of amides using O-(Benzotriazol-1-yl)-N,N,N',N'-tetramethyluronium hexafluorophosphate (HBTU) as a coupling reagent.

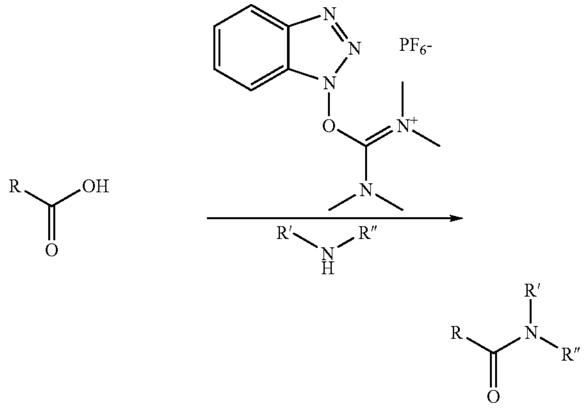

To a solution of protected amino acid (1.0 eq), amine (1.0 eq) and HBTU (1.3 eq) in DCM/DMF was added diisopropylethylamine (1.5 eq). The reaction mixture was stirred at r.t. for 2 to 5 h, then poured into water. The resulting mixture was extracted with EtOAc and the combined organic layers washed with brine. The organic layer was dried over anhydrous $MgSO_4$, filtered and concentrated. The residue was purified by flash chromatography on silica gel using ethyl acetate/hexanes or methanol/dichloromethane as an elution solvent.

N-Boc Deprotection procedures in Scheme 35:

General Procedure B: Boc deprotection using 3.5 M HCl in ethyl acetate.

Boc-protected peptide (1 eq) was dissolved in ethyl acetate and treated with hydrogen chloride (3.5M solution in ethyl acetate). The reaction mixture was stirred at ambient temperature and monitored by TLC (chloroform/methanol 3:1). When substrate was no longer detected the product was filtered off and washed with ether General Procedure $B_1$: Boc deprotection using 4N HCl in dioxane.

To Boc-protected peptide (1.0 equiv.) was treated with hydrogen chloride (4 M solution in dioxane, ≧15 eq). The reaction mixture was stirred at r.t. and monitored by LC-MS (~3-15 h). The reaction mixture was concentrated, triturated in ether and the solid filtered to afford the product as an HCl salt.

General Procedure $B_2$: Boc protection using 4N HCl in dioxane with added co-solvent.

Boc-protected peptide (1.0 eq) was dissolved in minimum amount of MeOH or EtOAc and treated with hydrogen chloride (4 M solution in dioxane, ≧15 eq). The reaction mixture was stirred at r.t. and monitored by LC-MS (~3-15 h). The reaction mixture was concentrated, triturated in ether, and the solid filtered to afford the product as an HCl salt.

General Procedure $B_3$: Boc deprotection using 4 N HCl in dioxane with added co-solvent and heated to 60° C.

Boc-protected peptide (1.0 eq) was dissolved in minimum amount of MeOH or EtOAc and treated with hydrogen chloride (4 M solution in dioxane, ≧15 eq). The reaction mixture was stirred at 60° C. and monitored by LC-MS (~1-3 h). The reaction mixture was concentrated, triturated in ether, and the solid filtered to afford the product as an HCl salt.

EXAMPLE 35

Preparation of Compound 377

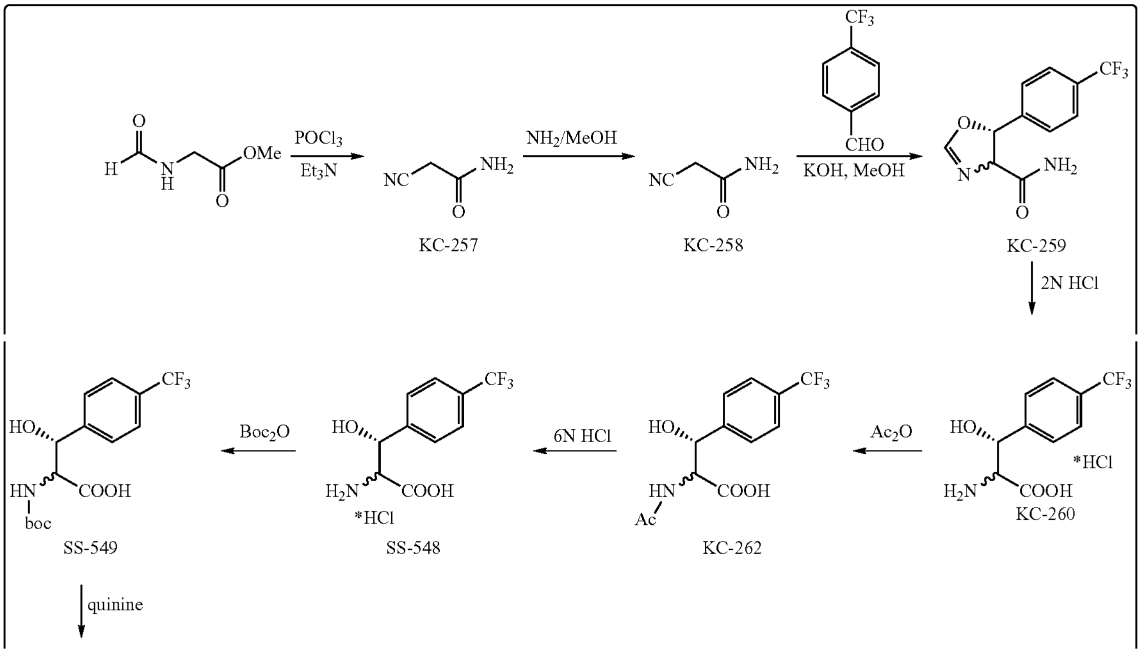

KC-257
KC-258
KC-259
KC-260
KC-262
SS-548
SS-549

-continued
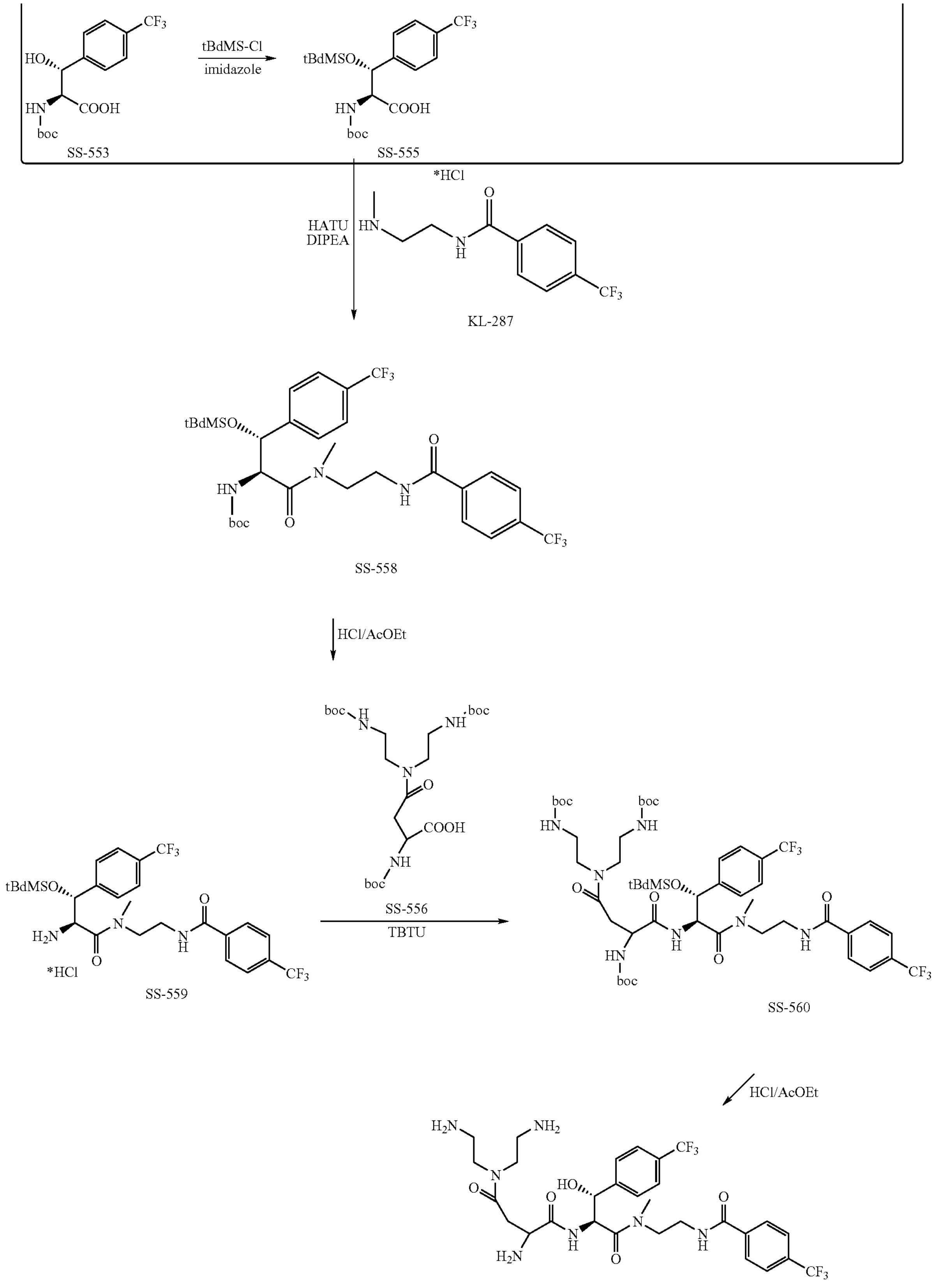
377

Step 1 (KC-257)

N-formylglycine methyl ester (27.5 g, 235 mmol) was dissolved in DCM and $Et_3N$ (81.3 mL, 587 mmol) was added. The reaction mixture was cooled to 0° C. and $POCl_3$ (21.6 mL, 235 mmol) was added dropwise and stirred for 1 h at these conditions. The reaction mixture was warmed to r.t. and saturated aqueous solution of $Na_2SO_3$ was added dropwise, after 30 min. phases were separated and water layer was washed with $CH_2Cl_2$. Combined organic layers were washed with brine, dried over $MgSO_4$ and concentrated under vacuum to give KC-257 (30 g) as dark brown oil. The crude product was used to the next step without any purification.

Step 2 (KC-258)

To crude ester KC-257, 6.7M solution of $NH_3$ in MeOH was added (70 mL, 470 mmol) and was stirred at r.t. overnight. After that time excess of ammonia and MeOH were evaporated under reduced pressure. The crude residue was dissolved in MeOH and stirred with charcoal at 50° C. for 2 h. Next, charcoal was filtered off through Celite and the filtrate was concentrated to dryness under vacuum to give a white solid of amide KC-258 (25 g). The crude product was used to the next step without any purification.

Step 3 (KC-259)

To the cooled (about 10° C.) solution of KOH (13.2 g, 235 mmol) in MeOH (50 mL) solution of amide KC-258 in MeOH (60 mL) was added dropwise to keep temperature 10-15° C., next solution of p-$CF_3$-benzaldehyde (40.9 g, 235 mmol) in MeOH (50 mL) resulting mixture was stirred for additional 2 h. When the substrate was invisible on TLC the reaction mixture was cooled to −20° C.; the precipitated white solid was filtered off to give crude oxazoline KC-259 (62 g). The crude product was used to the next step without any purification.

Step 4 (KC-260)

To KC-259, aqueous 2N HCl was added and all was refluxed for 20 h. Then charcoal was added and refluxed for next 1 h. The charcoal was filtered off through Celite, the filtrate was concentrate to ⅓ volume under vacuum and acidic solution of product KC-260 was used for the next step without any purification.

Step 5 (KC-262)

To acidic solution of amino acid KC-260 (4N NaOH aq. was added (pH mixture about 10) and solution was cooled to 5° C., then acetic anhydride (44.4 mL, 470 mmol) was added dropwise. The reaction mixture was stirred about 30 min, then all was acidified with 2N HCl to pH=2. The precipitated solid was filtered off to give a white crystalline product KC-262 (48 g), with was purified by refluxing in AcOEt/MeOH (100:1, 40 mL). Then all was cooled to r.t. and the crystallized product was filtered off to give a white solid KC-262 (45 g, 155 mmol, 66%)

Step 6 (SS-548)

Acetylated amino acid KC-262 (45 g, 155 mmol) was dissolved in 6 HCl (300 mL) and refluxed 2 h, progress of reaction was monitored by LCMS, when substrate wasn't observed, all was used to the next stage.

Step 7 (SS-549)

Amino acid SS-548 obtained above was treated with 4M NaOH (600 mL) to pH~9.5 and $Boc_2O$ (43.7 g, 200 mmol) in acetone (600 mL mL) was added in portions. The mixture was stirred at r.t. overnight. Reaction mixture was washed with $Et_2O$, acidified 2N HCl to pH~2 and product was extracted with AcOEt. Organic layer was washed with brine and dried over $MgSO_4$. $MgSO_4$ was filtered off, solvent was removed in vacuum to give Boc-protected amino acid SS-549 (35 g, 100 mmol, 65%) as a white solid.

Step 8 (SS-553)

Boc-protected amino acid SS-549 (35 g, 100 mmol) was dissolved in $Et_2O$ (600 mL) and quinine (34 g, 100 mmol) was added in portions. All was dissolved and the mixture was stirred at r.t. After 15 minutes a white solid (salt of L-enantiomer) precipitated. After additional 30 minutes solid was filtered off and washed with $Et_2O$. Next obtained salt was taken into AcOEt/aq $KHSO_4$. Organic layer was washed with aq $KHSO_4$, brine and dried over $MgSO_4$. $MgSO_4$ was filtered off, solvent was removed in vacuum to give optically pure (de>99% by Marfey's test) Boc-protected L-enantiomer SS-553 (12 g, 34 mmol, 68%).

Step 9

Boc-protected L-enantiomer SS-553 (12 g, 34 mmol) was dissolved in DMF and imidazole (11.5 g, 169 mmol) was added. The mixture was stirred at r.t. and t-butyldimethylsilyl chloride (7.7 g, 51 mmol) was added in portions. Reaction was stirred at r.t. overnight next acidified to pH~2 and extracted with DCM (200 mL). Organic layers were evaporated, residue was taken into diethyl ether/10% aq $Na_2S_2O_3$. Organic layer was thoroughly washed with 10% aq. $Na_2S_2O_3$, brine and dried over $MgSO_4$. $MgSO_4$ was filtered off, solvent was removed in vacuum to give crude SS-555 (16.4 g) that was purified by flash chromatography on silica gel (DCM: MeOH 200:1) to give pure SS-555 (14.8 g, 32 mol, 94%) as a white solid.

Step 10 (SS-558)

To the solution of acid SS-555 (14.8 g, 32 mmol) in DCM (100 mL) diisopropylethylamine (12.2 mL, 70 mmol), hydrochloride of amine KL-287 (9.5 g, 33.5 mmol) and HATU (13.3 g, 35 mmol) were added. The mixture was stirred at r.t. overnight. The reaction mixture was then washed with 1M $K_2CO_3$, 2N HCl, brine and dried over $MgSO_4$. $MgSO_4$ was filtered off, solvent was evaporated to dryness to give crude product as a white foam SS-558 (21.5 g, 31 mmol, 97%), that was used in the next step without any additional purification.

Step 11 (SS-559)

Intermediate SS-558 (21.5 g, 31 mmol) was dissolved in AcOEt and treated with HCl (5.5M solution in EtOAc, 200 mL), the reaction mixture was stirred ~10 minutes at r.t. then evaporated to dryness to give hydrochloride SS-559 (18.4 g, 29 mmol, 93.5%).

Step 12 (SS-560k)

To the solution of protected acid SS-556 (15.2 g, 29 mmol) in DCM (100 mL) DIPEA (12.8 mL, 73 mmol), hydrochloride of amine SS-559 (18.4 g, 29 mmol) and TBTU (11.3 g, 35 mmol) were added. The reaction mixture was stirred at r.t. for 2 h. The reaction mixture was then washed with 1M $K_2CO_3$, 2N HCl, brine and dried over $MgSO_4$. $MgSO_4$ was filtered off, solvent was evaporated to dryness to give crude product (30.6 g). The crude product was purified on a silica gel column (100:1 $CH_2Cl_2$/methanol) to give pure peptide SS-560k (12 g, 11 mmol, 38%).

Step 13 Compound 377

To the solution of protected peptide SS-560 (12 g, 11 mmol) in AcOEt (50 mL) solution of HCl (5.5 M solution in AcOEt, 100 mL) was added. The reaction mixture was stirred for 6 h at r.t. and evaporated to dryness. $Et_2O$ was added and the solid was filtered off and washed with diethyl ether and ethyl acetate to give 8.4 g of as a off-white crystalline solid. Solid was dissolved in MeOH, charcoal was added and the mixture was heated at 45° C. for 1 h. Charcoal was filtered off thought Celite. Filtrate was evaporated to dryness to give final hydrochloride of compound 377 (6.6 g, 8.4 mmol, 76%) as white solid.

EXAMPLE 36

Preparation of Compound 400

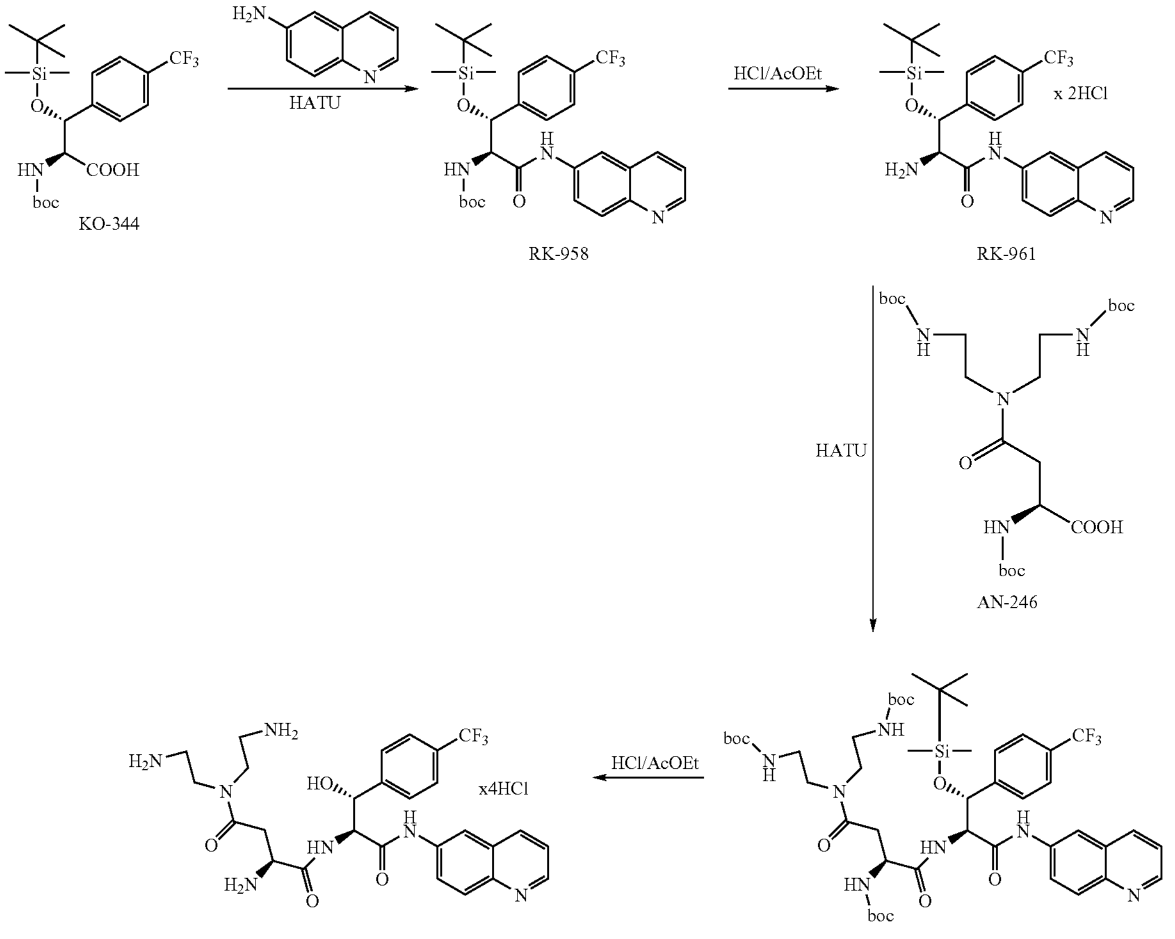

KO-344

RK-958

RK-961

AN-246

400

RK-962

Step 1 (RK-958)

Acid KO-344 (20.00 g, 43.0 mmol) and 6-aminoquinoline (6.84 g, 47.0 mmol) were dissolved in DCM (250 mL) next DIPEA (9 mL, 51.6 mmol) and HATU (17.82 g, 47.0 mmol) were added and all was stirred in r.t. over 4 hours. The reaction mixture was diluted with DCM and washed with 1MHCl (2×), 1 M NaOH, brine and dried over anhydrous $MgSO_4$. The solvent was removed in vacuum. Crude product was purified by flash chromatography using DCM/MeOH 500/1-300/1-200/1 solvent system to give pure product as a white foam (20.25 g, 34.3 mmol, 80%).

Step 2 (RK-961)

RK-958 (20.0 g, 33.9 mmol) was dissolved in AcOEt (30 mL) and treated with 4M HCl/AcOEt (150 mL) and stirred over 10 minutes at r.t. The solvent was removed in vacuum and crude residue was triturated with $Et_2O$ to give a white solid (18.2 g, HPLC: 86% desired product with tBdMS group and 14% of fully deprotected product)

Step 3 (RK-962)

Amine RK-961 (17.80 g, 31.6 mmol) and acid AN-246 (18.05 g, 34.8 mmol) were dissolved in DCM (150 mL), then DIPEA (19.12 mL, 109.7 mmol) and HATU (13.19 g, 34.8 mmol) were added. The reaction mixture was stirred at r.t. overnight. The reaction mixture was diluted with DCM and washed with 1MHCl (2×), 1 M NaOH, brine and dried over anhydrous $MgSO_4$. The solvent removed in vacuum. Crude product was purified by flash chromatography using DCM/MeOH 500/1-300/1-200/1-100/1 solvent system to give pure product as white foam (22.80 g, 23.0 mmol, 73%)

Step 4

The peptide RK-962 (22.5 g, 22.7 mmol) was dissolved in MeOH (50 mL) and treated with 4M HCl/AcOEt (150 mL) and stirred over 5 hours at r.t. The solvent was removed in vacuum and oily residue was triturated with $Et_2O$ to give a yellow solid. The solid was dissolved in MeOH (300 mL) then charcoal (3 g) was added and all was stirred over 30 minutes at 50° C., charcoal was filtered off thought Celite, and the solvent was removed in vacuum. Residue triturated with $Et_2O$ to give off-white solid of compound 400 (12.8 g, 17.7 mmol, 78%)

Preparations of Capping Amines for Compounds 377-474

EXAMPLE 37

Capping Amine for Compound 377

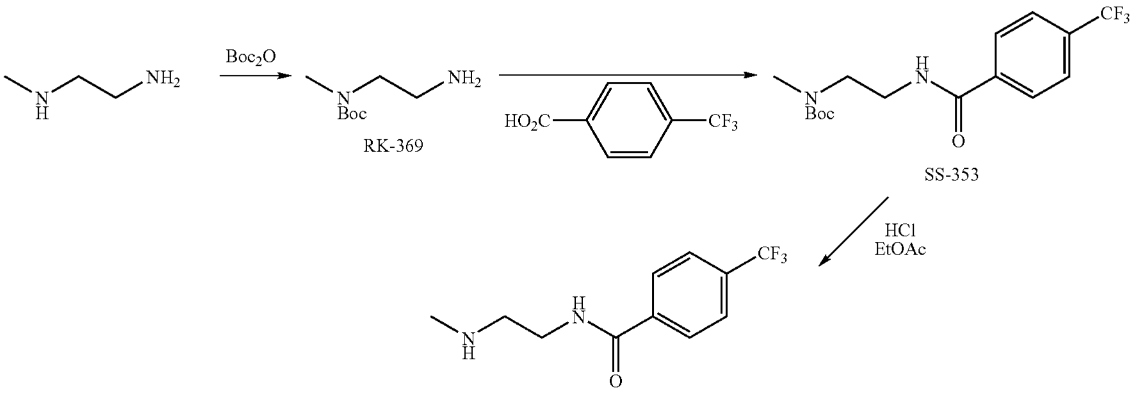

RK-369

SS-353

SS-355

Step 1 RK-369

N-methylethylenediamine (5.05 g, 68 mmol) was dissolved in dry DCM (50 mL), cooled to −30° C. and $Et_3N$ (11.33 mL, 81.7 mmol) was added. Solution of $Boc_2O$ (11.9 g, 54.5 mmol) in DCM (80 mL) was added very slowly dropwise during 2 h at −30° C. Reaction was stirred at r.t. for about 1 h and washed with 2N HCl. Water layers were combined and alkalized to pH 9-10. Product was extracted with DCM. Organic layers were combined, washed with brine and dried over $MgSO_4$. $MgSO_4$ was filtered off, solvent was evaporated to dryness to give pure RK-369 as yellow oil (3.6 g, 20.7 mmol, 30%)

Step 2 SS-353

Amine SS-369 (0.66 g, 3.79 mmol) and 4-(trifluoromethyl)benzoic acid (0.6 g, 3.16 mmol) were dissolved in DCM (10 mL) next TBTU (1.11 g, 3.47 mmol) and DIPEA (0.66 mL, 3.79 mmol) were added. The reaction mixture was stirred at r.t. 2 h and washed with 2N HCl, 1M $K_2CO_3$, brine, dried over $MgSO_4$. $MgSO_4$ was filtered and solvent was evaporated to dryness to give impure SS-353 (1.2 g of white solid). Product was crystallized with ethyl acetate/hexane to give pure SS-353 (0.8 g, 2.3 mmol, 73%) as a white solid.

Step 3 SS-355

SS-353 (0.8 g, 2.3 mmol) was dissolved in AcOEt (5 mL) and solution of HCl (3M in AcOEt) (5 mL) was added. After 20 minutes the reaction mixture was evaporated to dryness, $Et_2O$ was added, white solid precipitated, was filtered off, washed with $Et_2O$ to give pure SS-355 (0.6 g, 2.12 mmol, 92%).

EXAMPLE 38

Capping Amine for Compound 378

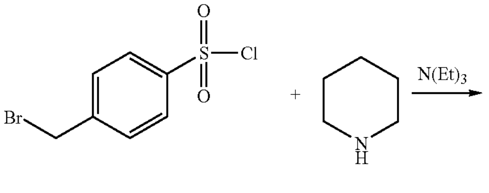

-continued

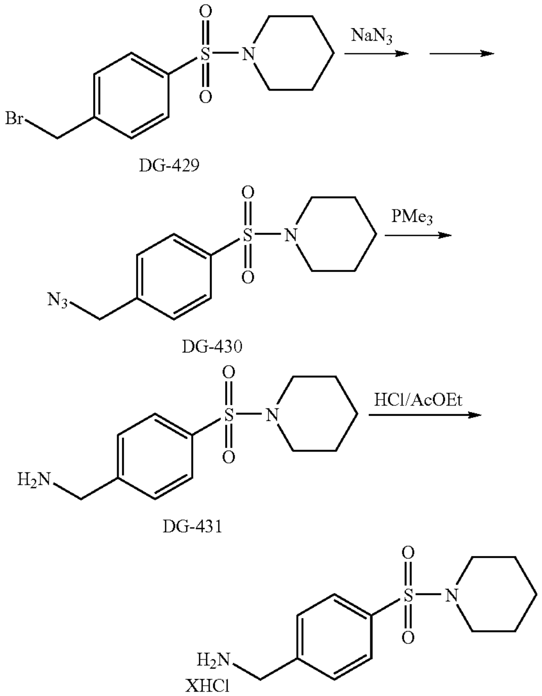

DG-429

DG-430

DG-431

DG-431HCl

Step 1 DG-429

To a solution of 4-bromomethyl-benzenesulfonyl chloride (2 g, 7.40 mmol) in dichloromethane (35 mL) cooled to 0° C. piperidine (0.73 mL, 7.40 mmol) was added. Next to the reaction mixture solution of triethylamine (1.03 mL, 7.40 mmol) in dichloromethane (5 mL) was added dropwise for one hour. After the addition was complete the reaction mixture was washed thoroughly with 1 M HCl, brine, dried over MgSO4, filtered, concentrated to dryness. The crude product was recrystallized from DCM/diethyl ether to give DG-429 as a white crystalline solid (2.15 g, 6.76 mmol, 91% yield).

Step 2 DG-430

To a suspension of DG-429 (2.15 g, 6.76 mmol) in methanol (35 mL) sodium azide (0.88 g, 13.50 mmol) was added and the reaction mixture was heated to 50-60° C. and stirred overnight. After removal of the solvent, the residue was dissolved in dichloromethane and inorganic solid was filtered off. The filtrate was concentrated to dryness. The crude product was recrystallized from ethyl acetate/hexane to give DG-430 as a white crystalline solid (1.60 g, 5.70 mmol, 86% yield).

Step 3 DG-431

To a solution of DG-430 (1.60 g, 5.70 mmol) in THF/water mixture (9:1, mL) cooled to 0° C. trimethylphospine (1M in THF, 17 mL, 17.00 mmol) was added dropwise for 2 h. After addition was complete the reaction mixture was stirred overnight at r.t. After removal of the solvent, the residue was dissolved in diethyl ether and inorganic solid was filtered off. The filtrate was concentrated to dryness to give DG-431 as yellow oil (1.7 g of crude product). The crude product was used to the next reaction step without further purification.

Step 4 DG-431

To a solution of DG-431 (1.7 g of crude product) in ethyl acetate (8 mL) was poured 4.5M solution of HCl in AcOEt (20 mL). The reaction mixture was stirred for 30 min at r.t. Excess of hydrogen chloride was removed under reduced pressure and the residue was treated with diethyl ether (20 mL). The white precipitate was filtered off and washed with diethyl ether to give DG-431HCl as a white crystalline solid (1.50 g, 5.16 mmol, 90% yield).

EXAMPLE 39

Capping Amine for Compound 380

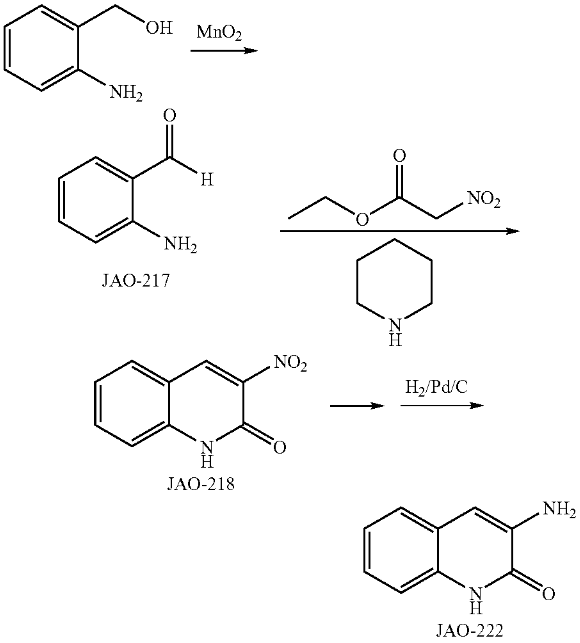

Step 1 JAO-217

A solution of 2-amino-benzylalcohol (4.70 g, 38.13 mmol) in dry dichloromethane (95 mL) was added to a suspension of manganese dioxide (13.26 g, 152 mmol) in dry dichloromethane (95 mL) at r.t. under argon. The reaction mixture was stirred overnight at r.t. The reaction mixture was then filtered through Celite and concentrated to dryness to give JAO-217 as a orange oil (4.67 g of crude product). The crude product was used to the next reaction step without further purification.

Step 2 JAO-218

A solution of JAO-217 obtained above in dry xylene (31 mL) was treated with ethyl nitroacetate (4.22 mL, 38.13 mmol) and piperidine (2.69 mL, 45.76 mL) at r.t. under argon. The reaction mixture was refluxed for 1 h and the yellow precipitate was filtered off and washed with diethyl ether to give JAO-218 as a yellow crystalline solid (5.8 g, 30.5 mmol, 80% yield).

Step 3 JAO-222

To a solution of JAO-218 (5.8 g, 30.5 mmol) in methanol (900 mL) under argon was added 10% Pd/C catalyst (catalytic amount). The reaction mixture was stirred under 1 atmosphere of hydrogen for 2 h. The reaction mixture was then filtered through Celite and evaporated to dryness. The residue was purified on a silica gel column (500:1 $CH_2Cl_2$/methanol) to give JAO-222 as a slightly orange crystalline solid (2.85 g, 17.80 mmol, 58% yield).

EXAMPLE 40

Capping Amine for Compound 381

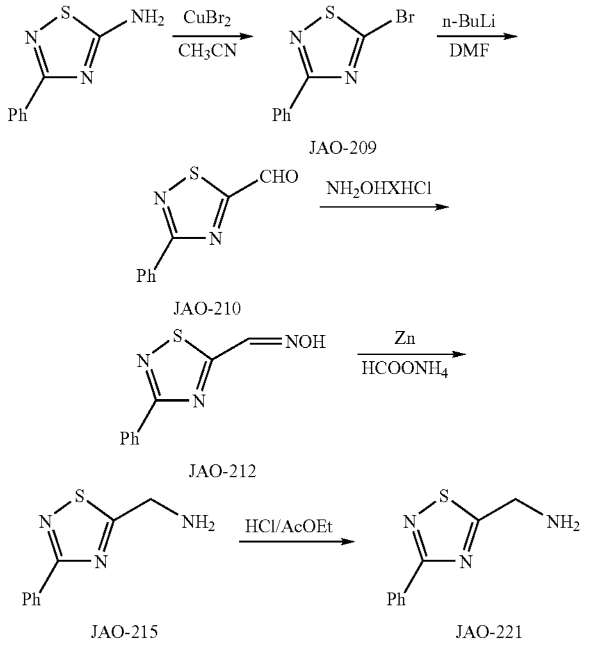

Step 1 JAO-209

To the solution of phenyl-1,2,4-thiodiazol-5-amine (6.71 g, 0.38 mol) in dry acetonitrile (300 mL) anhydrous CuBr2 (12.72 g, 0.57 mol) and isoamyl nitrite (5.32 g, 0.45 mol) were added. The reaction mixture was stirred overnight at r.t. The reaction mixture was slowly poured into ice-cold aqueous bath. The aqueous phase was extracted thoroughly with DCM. The organic extracts were combined washed with brine and dried over MgSO4, filtered and concentrated to dryness. The crude product was purified on a silica gel column (CH2Cl2) to give JAO-209 (6.25 g, 68% yield).

Step 2 JAO-210

A solution of n-BuLi (2.5M in hexane, 12.4 mL) was added dropwise under argon to diethyl ether (26 mL) previously cooled to −78° C. Next a solution of JAO-209 (6.25 g, 0.026 mol) in dry diethyl ether (52 mL) was added dropwise. The reaction mixture was stirred at −70° C. for 30 min before adding DMF (3.12 mL). The reaction mixture was stirred for 3 h from −70° C. to −40° C. Then it was cooled again to −78° C. and carefully quenched with dropwise addition of aqueous solution of HCl (1:2, 20 mL). The yellow precipitate was filtered and washed with hexane to give JAO-210 (4.70 g, 0.025 mol, 95% yield)

Step 3 JAO-212

To the solution of JAO-210 (4.70 g, 0.025 mol) in methanol (50 mL) hydroxylamine hydrochloride (2.00 g, 0.030 mol) was added. The reaction mixture was heated to reflux for 2 h. The reaction mixture was allowed to cool down to r.t. and the white precipitate was filtered. The crude product was recrystallized from hot methanol to give JAO-212 as a white crystalline solid (4.06 g, 0.02 mol, 80% yield).

Step 4 JAO-215

To the solution of JAO-212 (4.06 g, 0.02 mol) in methanol (416 mL) ammonium formate (16.47 g, 0.26 mol) and Zn (16.42 g, 0.25 mol) were added. The reaction mixture was refluxed for 2.5 h. Next the reaction mixture was filtered through Celite. After removal of the solvent, the residue was dissolved in diethyl ether and washed with 5% NaHCO3, dried over MgSO4, filtered, concentrated to dryness The residue was purified on a silica gel column (500:1 CH2Cl2/methanol) to give JAO-215 (2.57 g, 0.013 mol, 68% yield).

Step 5 JAO-221

To the slightly red solid JAO-215 (2.57 g, 0.013 mol) was poured 4.5M solution of HCl in AcOEt (15 mL). The reaction mixture was stirred for 20 min at r.t. before adding diethyl ether (25 mL). The precipitate was filtered and washed with diethyl ether to give JAO-221 as a slightly red crystalline solid (2.16 g, 71% yield).

EXAMPLE 41

Capping Amine for Compound 382

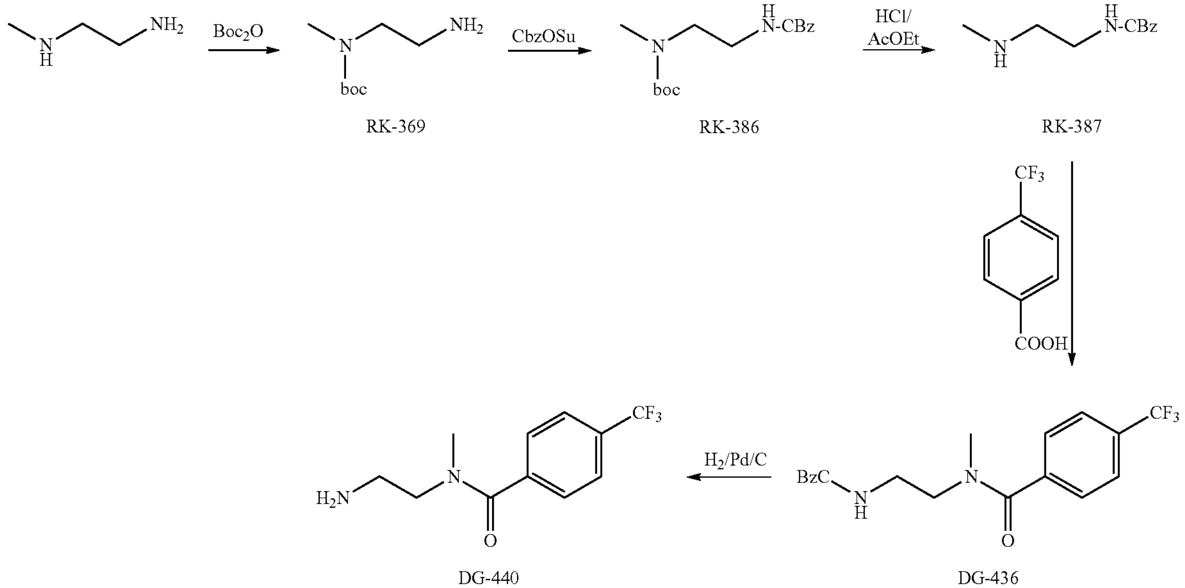

RK-369 RK-386 RK-387

DG-440 DG-436

Step 1 RK-369

N-(2-aminoethyl)-N-methylamine (1.34 mL, 15.33 mmol) was dissolved in DCM (20 mL), cooled to −30° C. and $Et_3N$ (0.90 mL, 6.69 mmol). To the mixture solution of $Boc_2O$ (1.18 g, 5.41 mmol) in DCM (10 mL) was added dropwise at −30° C. Cooling bath was removed and reaction mixture was stirred over 20 minutes at r.t. White precipitate was filtered off and the filtrate concentrated in vacuum yielding the oily residue which was purified by flash chromatography using DCM to give RK-369 as a light yellow oil (0.80 g, 4.68 mmol, 86%)

Step 2 RK-386

RK-369 (0.80 g, 4.68 mmol) was dissolved in DCM (20 mL) then CBzOSu (1.28 g, 5.15 mmol), $Et_3N$ (0.71 mL, 5.15 mmol) were added and mixed at r.t. for 2 h. The solution was diluted with DCM and washed with 1M HCl, brine and dried over $MgSO_4$. The solvent removed in vacuum and oily residue was crystallized from AcOEt/hexane solvent system to give RK-386 as a white solid (1.33 g, 4.31 mmol, 92%)

Step 3 RK-387

RK-386 (1.33 g, 4.31 mmol) was treated with 3.5M HCl/AcOEt (20 mL) and mixed at r.t. for 20 minutes next $Et_2O$ (50 mL) was added and filtered off to give RK-387 as a white solid (1.00 g, 4.08 mmol, 95%)

Step 4 RK-436

4-trifluoromethylbenzoic acid (0.85 g, 4.47 mmol), amine RK-387 (1.00 g, 4.08 mmol) were dissolved in DCM then DIPEA (1.54 mL, 9.83 mmol) and HATU (1.70 g, 4.48 mmol) were added and reaction mixture stirred overnight at r.t. The mixture was diluted with DCM and washed with 1M HCl, 1M NaOH, brine and dried over $MgSO_4$. The solvent removed in vacuum and crude product was purified by crystallization using DCM/ether as solvents to give DG-436 as a white solid (1.40 g, 3.68 mmol, 89%)

Step 5 RK-440

Cbz-protected amine DG-436 (1.40 g, 3.68 mmol) was dissolved in a mixture of ethanol/water (18 mL/2 mL), Pd/C (catalytic amount) was added and reaction mixture was stirred at r.t. for 2 h under hydrogen. Catalyst was filtered off through Celite pad and filtrate concentrated in vacuum to give DG-440 as light yellow oil (0.70 g, 2.84 mmol, 78%)

EXAMPLE 42

Capping Amine for Compound 383

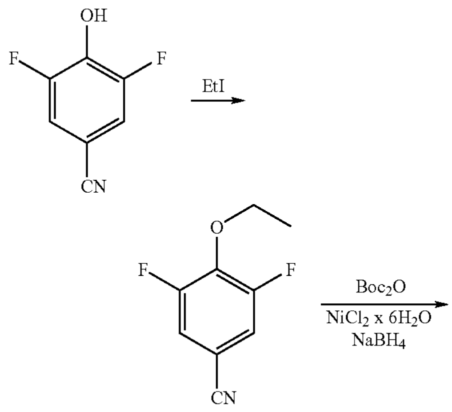

SS-526

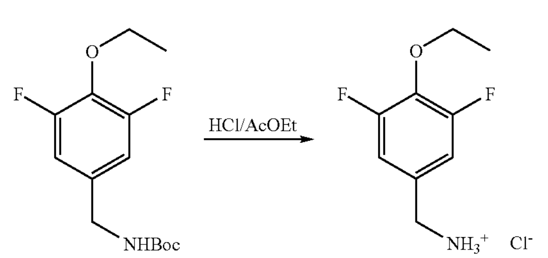

SS-527 SS-534

Step 1 SS-526

3,5-difluoro-4-hydroxybenzonitrile (1.5 g, 9.7 mmol) was dissolved in DMF (30 mL) and $K_2CO_3$ (1.6 g, 11.6 mmol) was added. Iodoethane (0.94 mL, 11.6 mmol) was added dropwise and the mixture was stirred at r.t. Overnight, taken into ethyl acetate/water. Organic layer was washed with 10% $Na_2S_2O_3$ (×5), brine and dried over $MgSO_4$. $MgSO_4$ was filtered off, solvent was removed in vacuum to give SS-526 (1.67 g, 9.12 mmol, 94%) of white solid.

Step 2 SS-527

To a suspension of SS-526 (1.67 g, 9.12 mmol) in MeOH (30 mL) cooled to −20° C., $Boc_2O$ (4 g, 18.24 mmol), $NiCl_2$× $6H_2O$ (0.22 g, 0.912 mmol) were added. $NaBH_4$ (2.41 g, 63.8 mmol) was added slowly by portions about 1 h (color of the mixture was changed to black). The mixture was stirred overnight (temp. −20° C. to r.t.) and taken into AcOEt/2N HCl. Organic layer was washed with 2N HCl, brine and dried over $MgSO_4$. $MgSO_4$ was filtered off, solvent was removed to give crude SS-527 (yellow oil). Crystallization with AcOEt/hexane gave pure SS-527 (1.1 g, 3.83 mmol, 42%).

Step 3 SS-534

SS-527 (1.1 g, 3.83 mmol) was dissolved in AcOEt and HCl (5.1M in AcOEt) was added and the mixture was stirred at r.t. 1 h. $Et_2O$ was added and product was precipitated, filtered off, washed with $Et_2O$ and dried to give SS-534 (0.82 g, 3.67 mmol, 96%).

EXAMPLE 43

Capping Amine for Compound 384

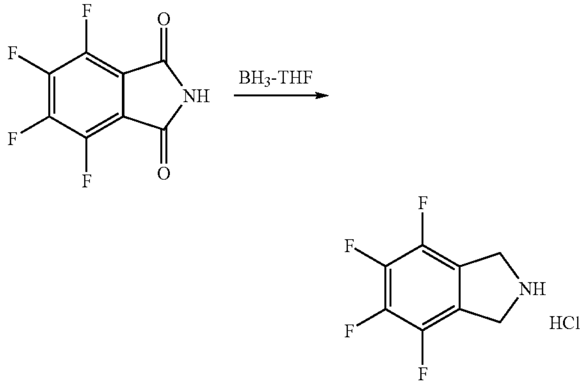

AJ-441

Step 1

To tetrafluorophthalimide (0.5 g, 2.43 mmol) in THF was added dropwise $BH_3$-THF (1M in THF) (7 mL, 7.05 mmol). Resulting mixture was stirred overnight and refluxed. When no substrate no detected, the mixture was cooled to 0° C. and to this was added 10 mL of methanol and 8 mL of HCl (6M)

Resulting mixture was stirred and refluxed for 3 hours. Upon cooling to r.t. the organic solvent was removed in vacuum, the mixture was diluted with water and was extracted with dichloromethane. The aqueous layer was basified to pH=12 or above by the addition of 4M NaOH, extracted with dichloromethane, dried over $MgSO_4$ and evaporated. To this crude product was added 20 mL of diethyl ether/HCl, stirred for 15 minutes and filtered to give pure product AJ-441 (0.220 g, 40%) as brown precipitate.

EXAMPLE 44

Capping Amine for Compounds 385/386

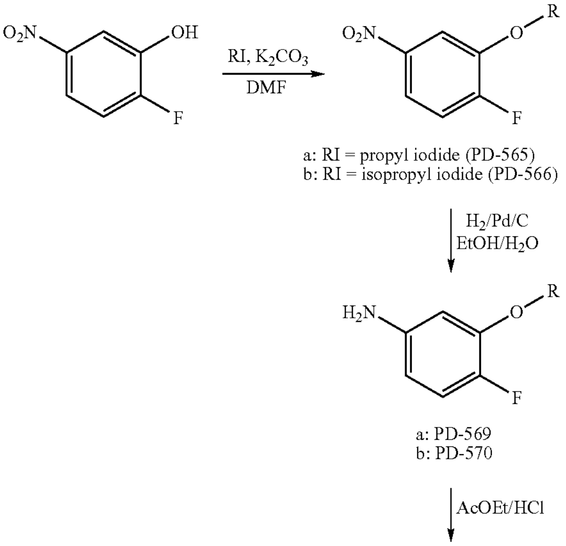

-continued

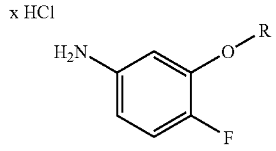

a: PD-569
b: PD-570

Step 1

To the solution of 2-fluoro-5-nitrophenol (1 g, 6.36 mmol) in DMF (20 mL) $K_2CO_3$ (2.63 g, 19.08 mmol) and propyl iodide (0.93 mL, 9.54 mmol) were added. The reaction mixture was stirred for 5.5 h at 60° C. Next the reaction mixture was stirred overnight at ambient temperature. Reaction mixture was diluted with water and was washed thoroughly with DCM. Next organic layer was washed with $Na_2S_2O_3$ and brine, dried over anhydrous $MgSO_4$. $MgSO_4$ was filtered off and solvent was removed under reduced pressure to give PD-565 as a brown oil (1.08 g, 5.42 mmol, 85.7% yield).

Step 2

To the solution of PD-565 (1.05 g, 5.27 mmol) in EtOH/water (10 mL/1 mL) under argon was added 10% Pd/C catalyst (catalytic amount). The mixture was stirred under an atmosphere of hydrogen for 4 days at 35° C. When reaction was completed the catalyst was filtered through a pad of Celite and solvent was evaporated to dryness to give a brown oil. (800 mg, 4.72 mmol, 89.8% yield).

Product was purified by treatment with AcOEt/HCl (4.5 solution in AcOEt, 7 mL). Reaction mixture was stirred for 1 h. The precipitate was filtered and washed with diethyl ether to give PD-569 as a light brown solid (720 mg, 3.5 mmol, 66.6% yield).

Capping amine PD-570 was prepared in analogous fashion using isopropyl iodide.

EXAMPLE 45

Capping Amine for Compound 387

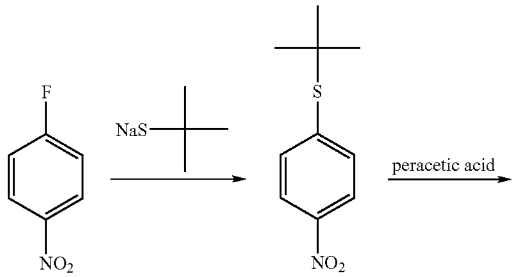

KO-301

-continued

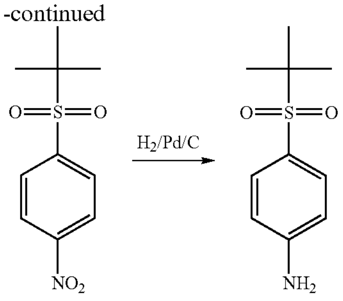

KO-305 KO-306

Step 1 (KO-301)

Mixture of 1-Fluoro-4-nitrobenzene (2.5 g, 1.88 mL, 17.72 mmol) and sodium t-butylthiolate (3.18 g, 28.35 mmol) was stirred for 1 h at r.t. The mixture was poured into brine and extracted thoroughly with $Et_2O$. Organic layer was washed with brine and dried over $MgSO_4$. $MgSO_4$ was filtered off, solvent was evaporated to dryness to give 4 g of crude product. The residue was purified on a silica gel column (1:20 AcOEt/hexane) to give (3.25 g, 15.38 mmol, yield 87%) as a yellow solid.

Step 2 (KO-305)

KO-301 (2.1 g, 9.94 mmol) was dissolved in ethyl acetate and peracetic acid was added dropwise. After 10 minutes the reaction mixture was concentrated to dryness to give (2.41 g, 9.90 mmol yield 100%) of pure product.

Step 3 (KO-306)

To the solution of KO-305 (2.41 g, 9.90 mmol) in EtOH/water (30/3 mL) under argon was added 10% Pd/C catalyst (catalytic amount). The reaction mixture was stirred under an atmosphere of hydrogen at r.t. for 2 h. The reaction mixture was then filtered through Celite and evaporated to dryness. Diethyl ether was added and white solid was filtered off to give (1.82 g, 8.53 mmol, yield 86%)

EXAMPLE 46

Capping Amine for Compound 388

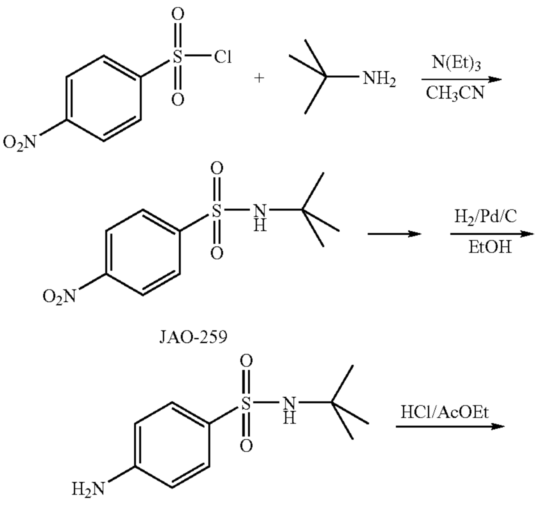

JAO-259

JAO-267

-continued

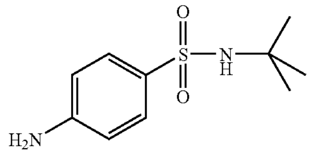

JAO-270

Step 1 JAO-259

To the solution of tert-Butylamine (1.4 mL, 13.42 mmol) in acetonitrile (32 mL) triethylamine (2.23 mL, 16.11 mmol) was added and the content of the flask was cooled to 0° C. Next to the reaction mixture 4-nitrobenzenesulfonyl chloride (2.38 g, 10.74 mmol) was added. The reaction mixture was stirred overnight at ambient temperature. The reaction mixture was concentrated to dryness and the residue was dissolved in DCM and washed with 1 M HCl, brine and dried over MgSO4, filtered and concentrated to dryness. The crude product was recrystallized from DCM/hexane to give JAO-259 as a slightly orange crystalline solid (2.48 g, 9.60 mmol, 89% yield).

Step 2 JAO-267

To a solution of JAO-259 (2.48 g, 9.60 mmol) in anhydrous EtOH (50 mL) under argon was added 10% Pd/C catalyst (catalytic amount). The reaction mixture was stirred under an atmosphere of hydrogen at r.t. for 6 h. The reaction mixture was then filtered through Celite and evaporated to dryness to give JAO-267 as a orange crystalline solid (1.86 g, 8.15 mmol, 85% yield).

Step 3 JAO-270

To the solution of JAO-267 (1.86 g, 8.15 mmol) was poured 4.5M solution of HCl in AcOEt (30 mL). The reaction mixture was stirred for 10 min at r.t. before adding diethyl ether (40 mL). The precipitate was filtered and washed with diethyl ether to give JAO-270 as a white crystalline solid (2.13 g, 8.04 mmol, 99% yield).

EXAMPLE 47

Capping Amine for Compounds 389/393/395

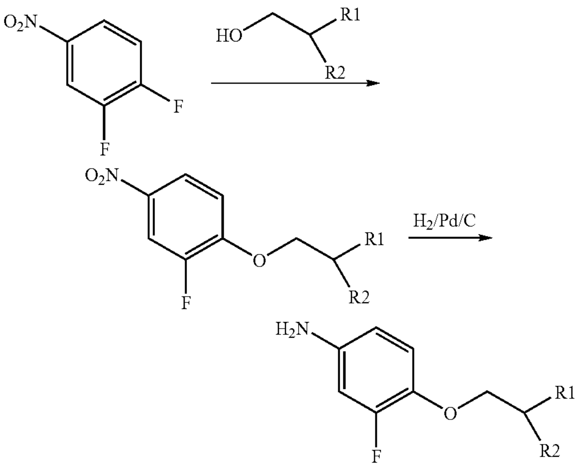

-continued

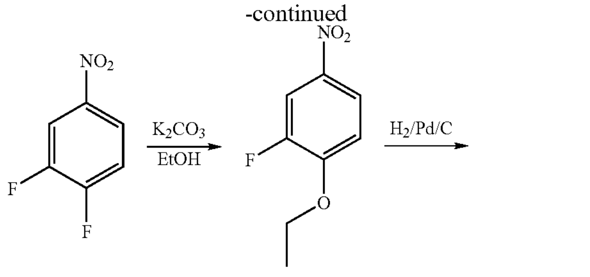

SS-500

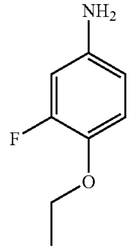

SS-507

R1 = R2 = H
R1 = R2 = F
R1 = H, R2 = F

Step 1 SS-500

3,4-difluorobenzene (2 g, 12.6 mmol) was dissolved in absolute EtOH and $K_2CO_3$ (7 g, 50.3 mmol) was added and the mixture was stirred at r.t. 3 days next taken into ethyl acetate/water. Water layer was extracted with ethyl acetate Organic layers were combined, washed with brine and dried over $MgSO_4$. $MgSO_4$ was filtered off, solvent was removed in vacuum to give pure SS-500 as a yellow solid (2.3 g, 12.4 mmol, 99%).

Step 2 SS-507

Nitro compound SS-500 was dissolved in hot EtOH/water and Pd/C was slowly added. Air was removed and the mixture was stirred overnight under $H_2$ at 40° C. Pd/C was filtered off through Celite, filtrate was evaporated to dryness to give SS-507 as a dark red oil (1.9 g, 12.2 mmol, 98%).

Capping amines for compounds 389/395 were prepared in analogous fashion using 2,2-difluoroethanol and 2-fluoroethanol respectively

EXAMPLE 48

Capping Amine for Compound 390

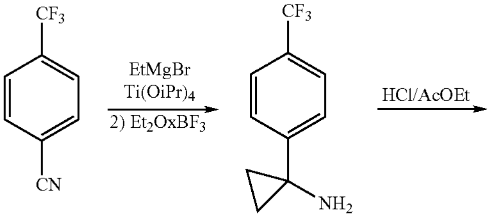

RK-898

-continued

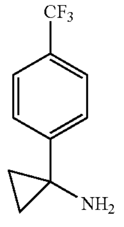

x HCl

RK-898 xHCl

RK-898

To the solution of nitrile (5.00 g, 29.22 mmol) and Ti $(OPr)_4$ (9.57 mL, 32.14 mmol) in ether (4 mL/mmol) ethylmagnesium bromide (19.5 mL, 58.4 mmol) was added dropwise at −70° C. under argon. The reaction mixture was stirred 10 minutes at −70° C. then the solution was warmed to ambient temperature and stirred over 2 hours at r.t., next the solution was re-cooled to 0° C.; $BF_3$x $Et_2O$ was added dropwise and stirred over 1 hour at r.t. After this period to the mixture 1 M HCl (100 mL) was carefully added and phases separated. The aqueous layer was washed twice with $Et_2O$. All organic layers were combined, dried over anhydrous $MgSO_4$ and concentrated in vacuum to give yellow oil which was treated with 4M HCl/AcOEt (50 mL) and stirred over 20 minutes at r.t. The solvent was removed in vacuum and residue triturated with $Et_2O$ to give white crystal (2.73 g, 11.48 mmol, 40%)

EXAMPLE 49

Capping Amine for Compound 391

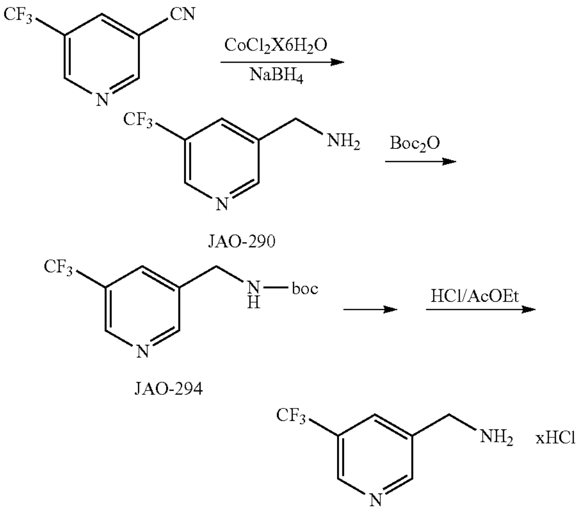

JAO-290

JAO-294

JAO-298

Step 1 JAO-290

To the solution of 5-(trifluoromethyl)nicotinonitrile (400 mg, 2.32 mmol) in methanol (16 mL) $COCl_2x_6H_2O$ (1.1 g, 4.65 mmol) was added and the content of the flask was cooled to 0° C. The reaction mixture was stirred for 20 min before adding $NaBH_4$. The reaction mixture was stirred overnight at ambient temperature. The reaction mixture was concentrated to dryness and dissolved in 2M HCl. The aqueous layer was washed with ethyl acetate. To the aqueous layer EDTA (2.6 g, 6.97 mmol) in 4M NaOH (aq) was added and it was stirred for 2 h. Crude product JAO-290 was temporarily protected with Boc groups in next reaction step in order to facilitate the process of isolation and purification.

Step 2 JAO-294

To the reaction mixture JAO-290 (pH mixture about 10) solution of Boc2O (590 mg, 2.72 mmol) in acetone (30 mL) was added. The reaction mixture was stirred for 2 days at ambient temperature. The acetone was evaporated under vacuum and aqueous residue was washed twice with diethyl ether. The organic extracts were combined washed with brine and dried over MgSO4, filtered and concentrated to dryness. The crude product was purified on a silica gel column (500:1 CH2Cl2/methanol) to give JAO-298 (240 mg, 0.87 mmol, 38% yield).

Step 3 JAO-298

To the solution of JAO-294 (240 mg, 0.87 mmol) was poured 4.5M solution of HCl in AcOEt (3 mL). The reaction mixture was stirred for 10 min at r.t. before adding diethyl ether (9 mL). The precipitate was filtered and washed with diethyl ether to give JAO-298 as a rose crystalline solid (100 mg, 0.47 mmol, 55% yield).

EXAMPLE 50

Capping Amine for Compounds 392, 416, and 419

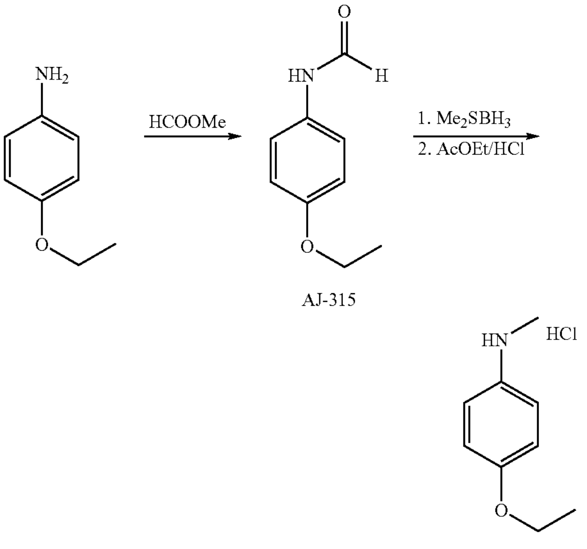

AJ-315

AJ-322

Step 1

To 4-Ethoxyaniline (5 g, 36.4 mmol) was added HCOOMe (130 mL). This reaction mixture was refluxed for 3 days. After this time mixture was evaporated in vacuum and to this was added hexane to give crude product AJ-315, which was purified by recrystallization with ethyl acetate/hexane. Product AJ-315 (4.8 g, yield=80%) was obtained as a grey precipitate.

Step 2

To the solution of AJ-315 (4.8 g, 29.05 mmol) in THF (100 mL) $Me_2S$x$BH_3$ (5.5 mL, 58.1 mmol) was added dropwise, next the reaction mixture was refluxed for 1 hour. The residue was quenched with water, THF was removed in vacuum, residue was taken between AcOEt/water and product was extracted thoroughly with AcOEt. Organic layer was dried over $MgSO_4$. After filtration of $MgSO_4$ solvent was concentrated under vacuum. Next to this mixture 50 ml AcOEt/HCl (3M) was added and the reaction mixture was stirred for 1 hour at rt. Reaction mixture was evaporated and treated with diethyl ether, pure product AJ-322 (yield 73%) precipitated as a white solid.

Capping amine for compounds 416 and 419 were prepared in analogous fashion from corresponding primary amines.

EXAMPLE 51

Capping Amine for Compound 394

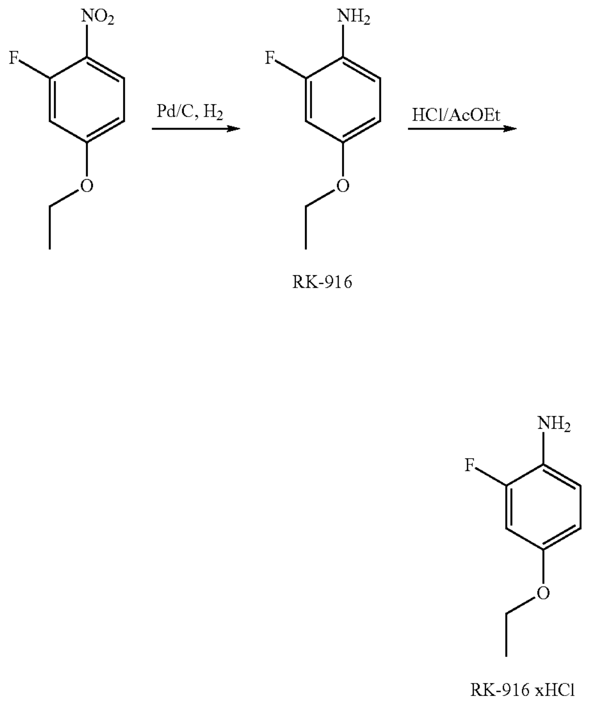

RK-916

RK-916 xHCl

RK-916

4-Ethoxy-2-fluoronitrobenzene (0.50 g, 2.70 mmol) was dissolved in EtOH (10 mL), then catalytic amount of palladium on carbon was added and reaction mixture was stirred overnight at r.t. under hydrogen. The catalyst was filtered of through a pad of Celite and the filtrate was concentrated in vacuum to give red, viscous oil. The oily residue was treated witch 4M HCl/AcOEt (8 mL) and stirred over 5 minutes at r.t. The solvent removed in vacuum to give light red solid. Crude product was triturated thoroughly with $Et_2O$ to produce white solid (0.45 g, 2.34 mmol, 87%)

EXAMPLE 52

Capping Amine for Compound 413

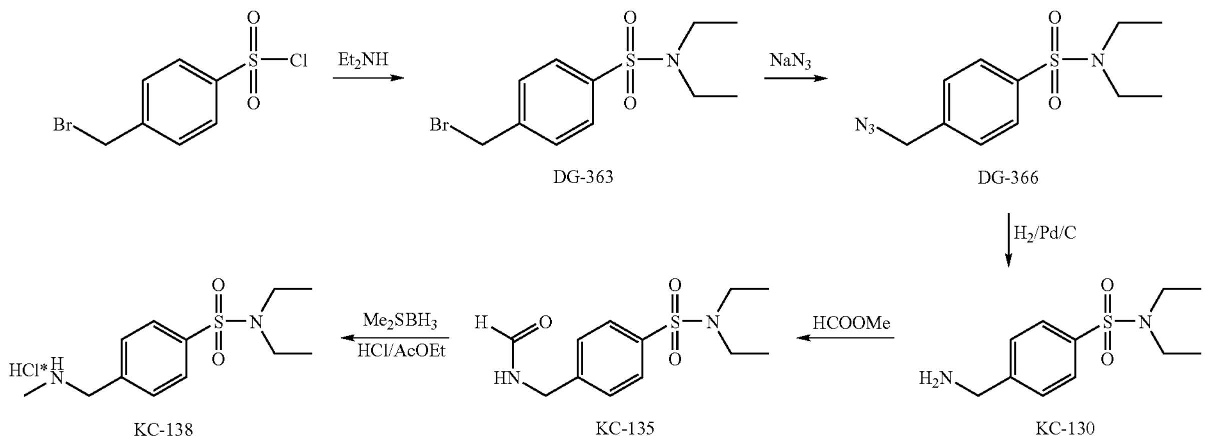

DG-363

DG-366

KC-138

KC-135

KC-130

Step 1

4-(Bromomethyl)benzenesulfonyl chloride (1 g, 3.77 mmol) was dissolved in DCM (20 mL), triethylamine (0.51 mL, 3.7 mmol) was added and the reaction mixture was cooled to 0° C. Next diethylamine (0.38 mL, 3.77 mmol) was added dropwise, the reaction mixture was stirred at 0° C. for 2 h, next overnight at r.t. Solvent was removed under reduced pressure to give substituted benzyl bromide DG-363 (912 mg, 2.98 mmol, 79%) as a light yellow solid. The crude product was used to the next step without any additional purification.

Step 2

The substituted benzyl bromide DG-363 (912 mg, 2.98 mmol) was dissolved in MeOH (6 mL) and sodium azide (380 mg, 5.96 mmol) was added. The reaction mixture was stirred at 50° C. overnight. Solvent was removed under reduced pressure to give azide DG-366 (687 mg, 2.56 mmol, 86%) as a yellow solid. The crude product was used to the next step without any additional purification.

Step 3

To the solution of azide DG-366 (687 mg, 2.56 mmol) in EtOH/water (50 mL/5 mL) under argon Pd/C catalyst (catalytical amount) was added. The mixture was stirred under an atmosphere of hydrogen at 50° C. overnight. The mixture was then filtered through Celite and evaporated to dryness. The residue was purified on a silica gel column (150:1 $CH_2Cl_2$/methanol) to give amine KC-130 as a yellow solid (310 mg, 1.28 mmol, 50% yield).

Step 4

Pure amine KC-130 (310 mg, 1.28 mmol) was suspended in methyl formate (30 mL) and all was stirred at 40° C. for 5 h. TLC was showed no substrates, solvent was removed in vacuum to give formylated amine KC 135 (500 mg) as a light yellow oil. The crude product was used to the next reaction step without any purification.

Step 5

Crude formylated amine KC 135 was dissolved in THF (50 mL) and $Me_2S \times BH_3$ (0.25 mL, 2.56 mmol) was added dropwise. The reaction mixture was stirred at r.t. overnight. Next the reaction was quenched by slowly addition of water (10 mL). Next THF was removed in vacuum. Residue was taken between AcOEt/water and product was extracted with ethyl acetate. Organic layers was combined, washed with brine and dried over $MgSO_4$. After filtration of $MgSO_4$ solvent was removed and crude residue was treated with HCl saturated in ethyl acetate (4.0M, 20 mL). All was stirred at r.t. for 3 h and next ethyl ether was added (about 70 mL). Precipitate was filtered off and washed with ether to give product pure KC-138 as an off-white solid (329 g, 1.27 mmol, 99%).

EXAMPLE 53

Capping Amine for Compound 418

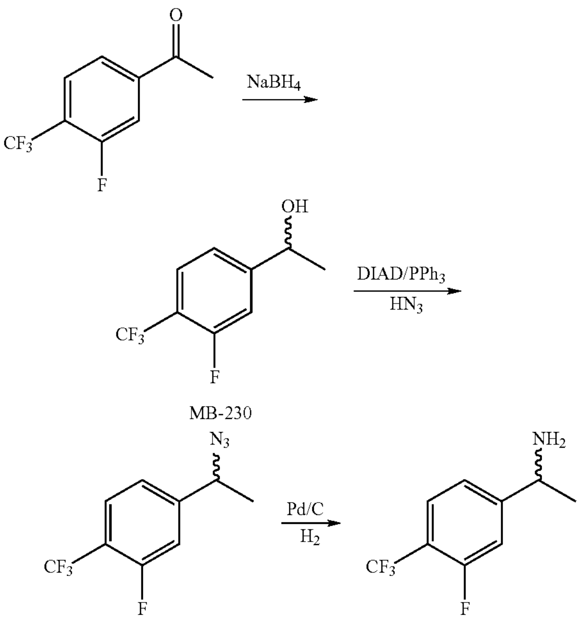

MB-230

MB-234

MB-235

Step 1

4-Fluoro-3-(trifluoromethyl)-acetophenone (700 mg, 3.39 mmol) was dissolved in methanol (10 mL) and cooled to 0° C. then $NaBH_4$ (141 mg, 3.73 mmol) was added and the mixture stirred overnight at r.t. The solvent removed in vacuum and residue treated with DCM, filtered through Celite and filtrate concentrated in vacuum to give oil MB-230 (635 mg, 3.07 mmol, 90%)

Step 2

Triphenylphosphine (965 mg, 3.68 mmol) was suspended in DCM (15 mL) and cooled to −5° C. then DIAD (0.725 mL, 3.68 mmol) was added dropwise. After 15 minutes $HN_3$ (1.84 mL, 3.68 mmol, 2M in toluene) was added in the same manner and stirred at −5° C. for 15 minutes. Next solution of MB-231 (635 mg, 3.07 mmol) in DCM (5 mL) was added dropwise and stirred over 1 hour. The solvent was removed in vacuum and residue was treated with $Et_2O$, filtered and filtrate concentrated in vacuum. Crude product MB-234 was used in the next step.

Step 3

The residue from MB-234 was dissolved in EtOH/water (15 ml/2 mL) solvent system under argon atmosphere. The palladium catalyst (10% on activated carbon, catalytic amount) was added and argon was displaced with hydrogen introduced from the balloon. The mixture was stirred overnight in r.t. The catalyst was filtered off through Celite and solvents removed in vacuum. Crude product was purified by flash chromatography using DCM/MeOH 400/1 as solvent to give 300 mg pure product MB-235.

EXAMPLE 54

Capping Amine for Compound 420

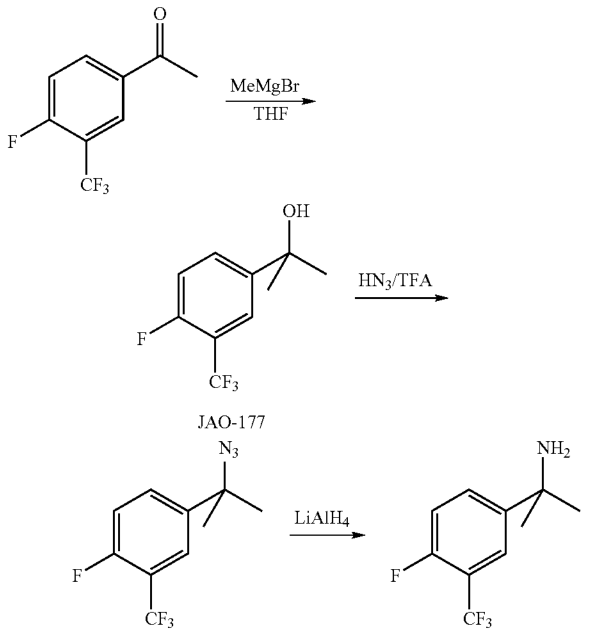

JAO-177

JAO-178

JAO-180

Step 1 JAO-177

A solution of 4-Fluoro-3-(trifluoromethyl)acetophenone (500 mg, 2.43 mmol) in dry THF (1.2 mL) was added dropwise under argon to the solution of methyl magnesium bromide (3M in diethyl ether, 0.97 mL, 2.91 mmol) at a such rate that gentle refluxing was maintained. After the addition was complete the reaction mixture was stirred at ambient temperature for 1 hour. The solvent was evaporated and the residue was poured into ice-cold aqueous saturated ammonium chloride. The aqueous phase was extracted thoroughly with ethyl acetate. The organic extracts were combined washed with brine and dried over MgSO4, filtered and concentrated to dryness to give JAO-177 (530 mg of crude product) as a colorless liquid. The crude product was used to the next reaction step without further purification.

Step 2 JAO-178

Hydrazoic acid (2M in toluene, 1.69 mL, 3.37 mmol) was added to the solution of JAO-177 (theoretical amount: 500 mg, 2.25 mmol) in chloroform (3 mL) and the content of the flask was cooled to −5° C. The mixture of trifluoroacetic acid (0.43 mL, 5.63 mmol) with chloroform (0.43 mL) was added dropwise at such rate to keep the internal temperature below −5° C. After the addition was complete, the reaction mixture was allowed to warm to ambient temperature and stirred overnight. The reaction mixture was poured into 2M NaOH and aqueous phase was extracted thoroughly with chloroform. The organic extracts were combined washed with brine and dried over MgSO4, filtered and concentrated to give JAO-178 (710 mg of crude product) as a colorless liquid. The crude product was used to the next reaction step without further purification.

Step 3 JAO-180

JAO-178 (theoretical amount: 560 mg, 2.26 mmol) diluted with dry diethyl ether (2 mL) was added dropwise over one hour to the suspension of lithium aluminum hydride (90 mg, 2.38 mmol) in dry diethyl ether (4 mL) cooled previously to 0° C. After the addition was complete the reaction mixture was stirred at 0-10° C. for two hours and carefully quenched with dropwise addition of 2M HCl until pH=2 was obtained. The aqueous phase was separated and washed with ethyl acetate. The organic extracts were combined washed with brine and dried over MgSO4, filtered and concentrated to dryness to give JAO-180 (600 mg of crude product) as a white solid. The crude product was used to the next reaction step without further purification.

EXAMPLE 55

Capping Amine for Compound 421

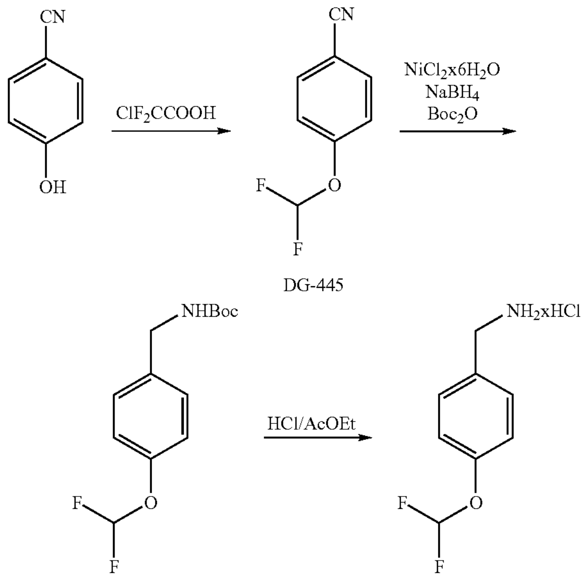

DG-445

DG-450 RK-896

Step 1

To the stirred solution of 4-cyanophenol (2 g, 16.8 mmol) and $K_2CO_3$ (7 g, 50.4 mmol) in dry DMF (10 mL) chlorodifluoroacetic acid was added (2.13 mL, 25.2 mmol). The reaction mixture was stirred at 60° C. for 3 h. After that time substrate was not present, so reaction mixture was diluted with DCM, washed with 1MHCl (2×), 1MNaOH (2×), 10% $Na_2S_2O_3$ (3×), brine and dried over anhydrous $MgSO_4$. After filtration of $MgSO_4$ solvent was removed under reduced pressure. The crude product (light brown oil) was dissolved in MeOH and stirred with charcoal at 50° C. for 30 min., after filtration through Celite solvent was removed under reduced pressure, product DG-445—light yellow solid 1.62 g, 9.6 mmol yield 57%) was used for the next step without any additional purification.

Step 2

Solution of compound DG-445 (1.62 g, 9.6 mmol) in methanol (80 mL) was cooled to −10° C. next $Boc_2O$ (4.2 g, 19.2 mmol) and $NiCl_2 x 6H_2O$ (0.23 g, 0.96 mmol) were added. To the cooled reaction mixture $NaBH_4$ (2.54 g, 67.2 mmol) was added portionwise during about 2 h. After addition of all $NaBH_4$ the reaction mixture was stirred overnight at r.t. Methanol was removed under reduced pressure, the residue was dissolved in DCM and washed with 1M HCl (2×) brine and dried over anhydrous $MgSO_4$. After filtration of $MgSO_4$ solvent was removed under reduced pressure. The crude product light yellow oil was purified by column chromatography DCM to give pure product DG-450 (1.4 g, 5.12 mmol, yield 53.8%) as a colorless oil.

Step 3

Boc protected amine DG-450 (1.4 g, 5.12 mmol) was dissolved in AcOEt and treated with solution of HCl in AcOEt (3.5M, 15 mL). The reaction mixture was stirred at r.t. for 20 minutes and treated with $Et_2O$, white solid precipitated, was filtered off to give pure amine RK-896 (1 g, 4.77 mmol, yield 93%).

EXAMPLE 56

Capping Amine for Compound 422

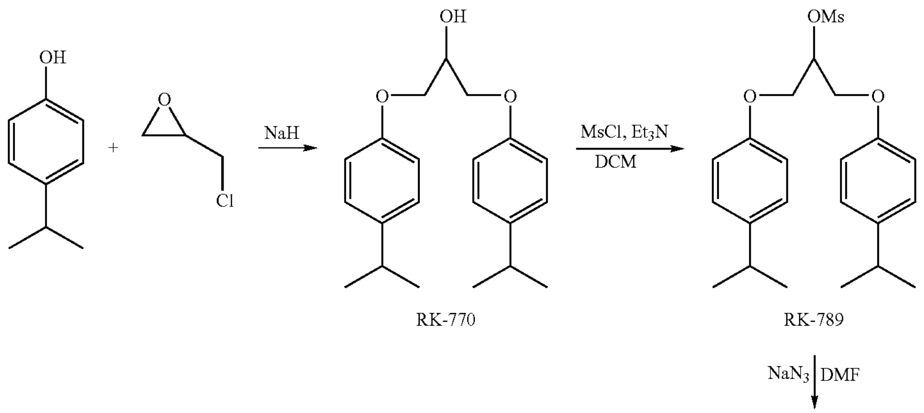

RK-770 RK-789

-continued

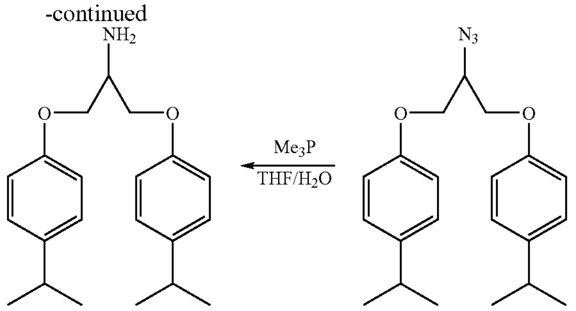

RK-791 RK-790

Step 1

NaH (1.30 g, 32.3 mmol) was suspended in anhydrous THF (20 mL) under argon then solution of 4-isopropylphenol (4.00 g, 29.4 mmol) in anhydrous THF (10 mL) was added dropwise. The reaction mixture was stirred over 1 hour in r.t., then a solution of epichlorohydrin (1.10 mL, 14.7 mmol) in anhydrous THF (10 mL) was added dropwise. The reaction mixture was stirred for 5 days at 50° C., then diluted with AcOEt (20 mL) and washed with water. Organic layer was dried over anhydrous $MgSO_4$, filtered and solvent removed in vacuum. Crude product was purified by flash chromatography using DCM as solvent to give yellow oil (3.68 g, 60% purity in LC/MS). This product was used to next step.

Step 2

RK-770 was dissolved in DCM then $Et_3N$ was added. The reaction mixture was cooled to 0° C. and methanesulfonyl chloride was added. The mixture was stirred over 10 minutes at 0° C. next 40 minutes at r.t. The solution was next washed with 0.5M HCl, brine and dried over anhydrous $MgSO_4$. The solvent removed in vacuum to give orange oil which crystallized (2.4 g). Crude product was used for the next step.

Step 3

RK-789 (2.30 g) was dissolved in DMF (30 mL) then $NaN_3$ was added and stirred overnight at 50° C.-60° C. The mixture diluted with DCM and washed with 10% solution of $Na_2S_2O_7$ in water (×3), dried over anhydrous $MgSO_4$. The solvent removed in vacuum to give yellow oil. Crude product was purified by flash chromatography using hexane/ethyl acetate 200/1-150/1-100/1 solvent system to give colorless oil (1.08 g)

Step 4

RK-790 (1.08 g, 3.0 mmol) was dissolved in THF/water (9 mL/1 mL) solvent system then 1M solution of $Me_3P$ in THF (12.22 mL, 12.2 mmol) was added and stirred overnight at r.t. The solvents were removed in vacuum to give white oil. The oily residue was dissolved in $Et_2O$ and dried over anhydrous $MgSO_4$. The solvent removed in vacuum and crude product was purified by flash chromatography using DCM next MeOH as solvents to give colorless, viscous oil (0.92 g, 2.80 mmol, 93%)

EXAMPLE 57

Capping Amine for 433

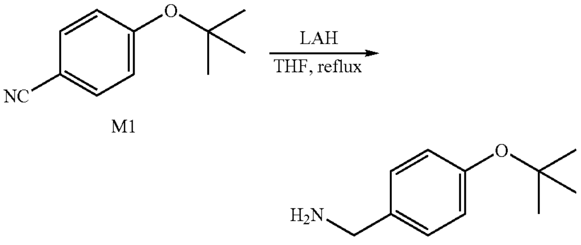

M1

M2

To a suspension of lithium aluminum hydride (LAH) (0.25 g, 6.6 mmol) in THF (8 mL) under argon was added 4-tert-butoxybenzonitrile (Ml, 1.0 g, 5.7 mmol). The mixture was heated at reflux for 4 h and allowed to cool to ambient temperature. Reaction was quenched with sequential addition of water (0.2 mL), 4M NaOH (0.2 mL) and water (0.6 mL). The residue was filtered, washed twice with diethyl ether and the filtrate concentrated. Water (15 mL) was added to the residue and the pH adjusted to ~3 with 1M HCl. The aqueous layer was then washed with diethyl ether and the pH of the aqueous layer adjusted to ~9 with 4M NaOH. The resulting aqueous layer was then extracted with EtOAc and the organic layer washed with brine. The organic layer was dried over anhydrous $MgSO_4$, filtered and the filtrate concentrated to afford M2 (0.85 g, 83%) as colorless oil.

EXAMPLE 58

Capping Amine for 435

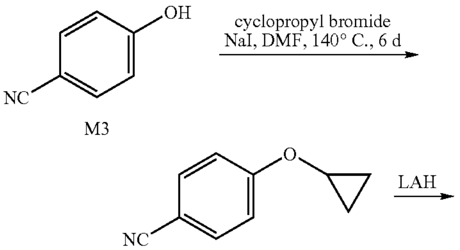

M3

M4

-continued

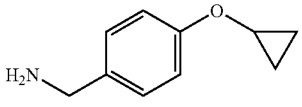

M5

Step 1 M4

To a reaction tube was charged with 4-hydroxybenzonitrile (M3, 0.5 g, 4.2 mmol), cyclopropyl bromide (0.5 mL, 6.3 mmol), NaI (0.63 g, 4.2 mmol), $Cs_2CO_3$ (2.1 g, 6.5 mmol) and DMF (8 mL). The tube was sealed and heated at 140° C. for 6 d. The reaction was cooled to RT and poured into water (10 mL). The mixture was extracted with EtOAc (2×15 mL) and the organic layers washed with brine. The organic layer was dried over anhydrous $MgSO_4$, filtered and the filtrate concentrated. The residue was purified by flash chromatography on silica gel (Hexanes to 25% EtOAc/Hexanes) to afford M4 (0.38 g, 57%) as a colorless oil.

Step 2 M5

To a suspension of LAH (0.13 g, 3.4 mmol) in THF (5 mL) under argon was added M4 (0.43 g, 2.7 mmol). The mixture was heated at reflux for 5 h and then cooled to r.t. Reaction was quenched with sequential addition of water (0.1 mL), 4M NaOH (0.1 mL) and water (0.3 mL). The residue was filtered, washed twice with diethyl ether and the filtrate concentrated. Water (10 mL) was added to the residue and the pH adjusted to ~3 with 1M HCl. The aqueous layer was then washed with diethyl ether and the pH of the aqueous layer adjusted to ~9 with 4M NaOH. The resulting aqueous layer was then extracted with EtOAc and the organic layer washed with brine. The organic layer was dried over anhydrous $MgSO_4$, filtered and the filtrate concentrated to afford M5 (0.38 g, 86%) as colorless oil.

TABLE 3

The following compounds were prepared in accordance with Scheme 35 in a manner analogous to the specific examples described in Examples 35-58. The coupling and deprotection methods used are identified next to the relevant intermediate or final structure. A description of these methods appears after Scheme 35.

| Compound | Inhibitor structure (deprotection procedure B-B3) | | Protected N-terminal acid structure (coupling procedure A1-A3) | |
|---|---|---|---|---|
| 377 | 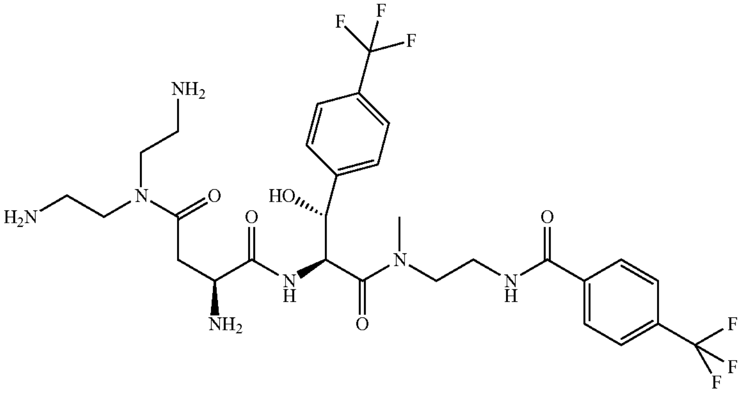 | B | 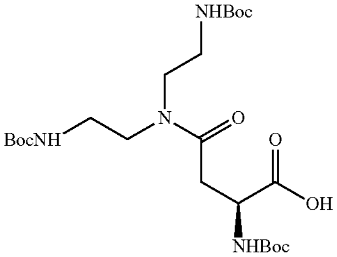 | A3 |
| 378 | 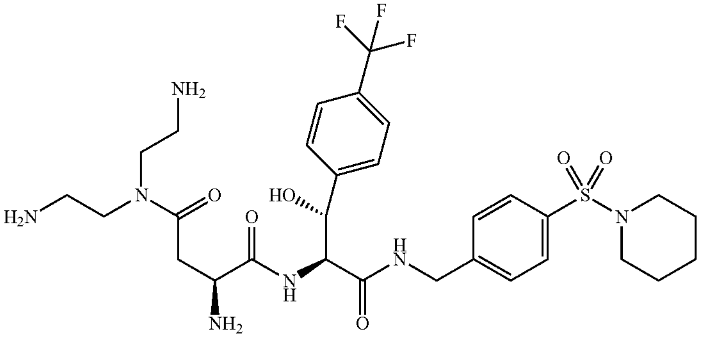 | B | 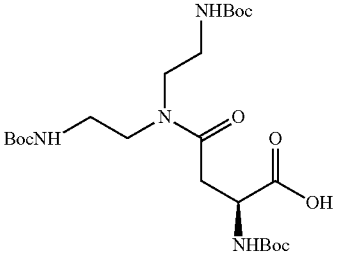 | A3 |

TABLE 3-continued
| | | | | |
|---|---|---|---|---|
| 379 | 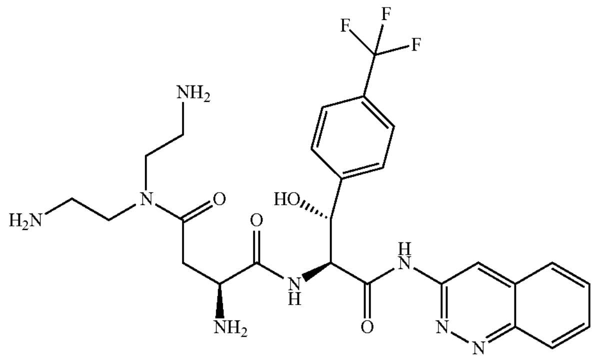 | B | 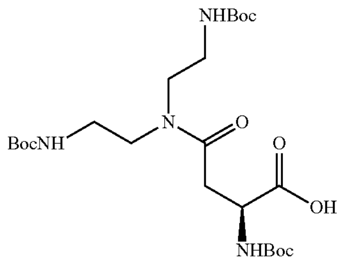 | A3 |
| 380 | 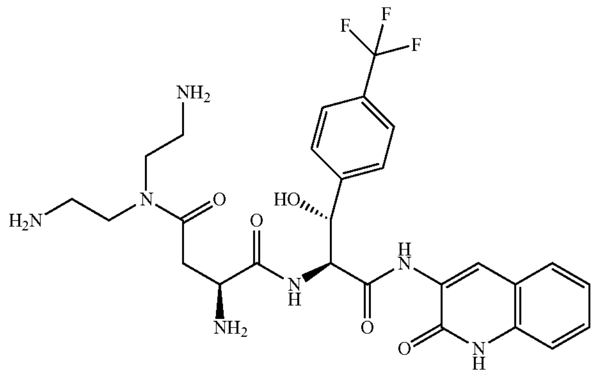 | B | 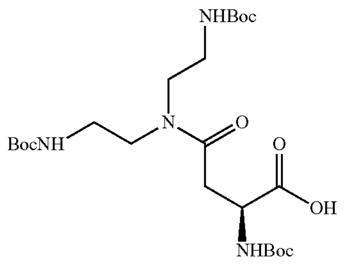 | A3 |
| 381 | 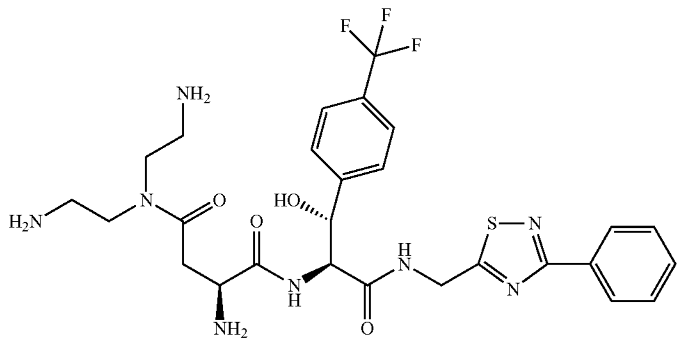 | B | 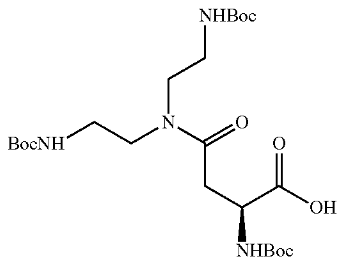 | A3 |

TABLE 3-continued
| | | | | |
|---|---|---|---|---|
| 382 | 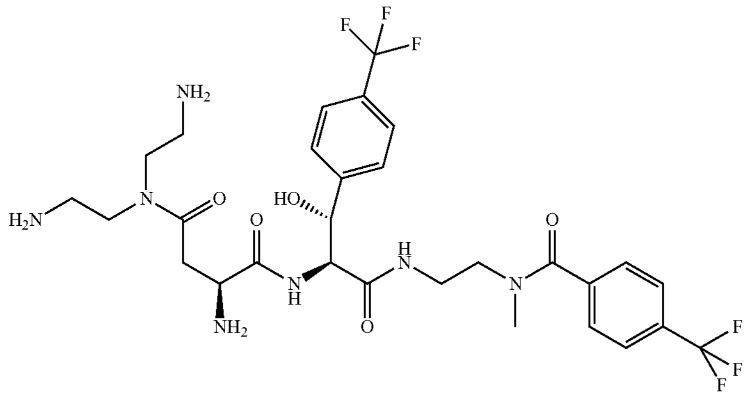 | B | 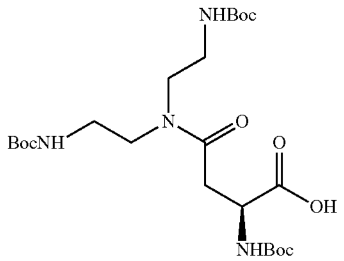 | A3 |
| 383 | 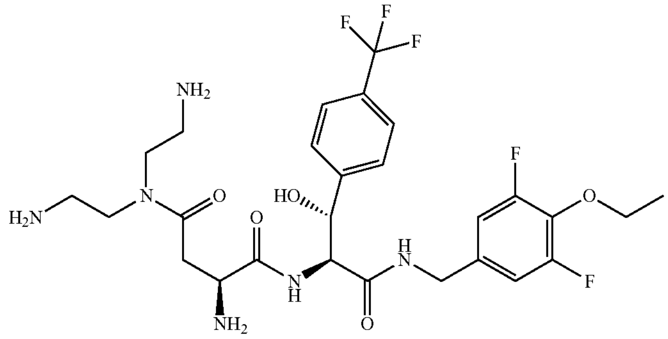 | B | 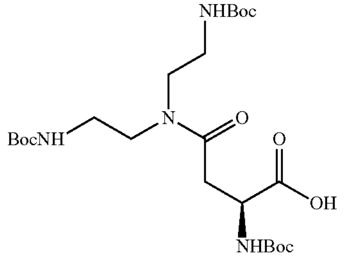 | A3 |
| 384 | 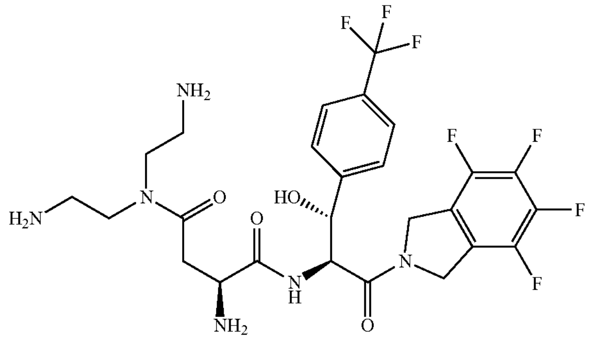 | B | 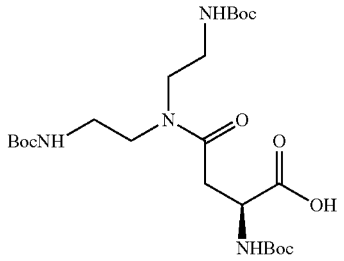 | A3 |

TABLE 3-continued
| | | | | |
|---|---|---|---|---|
| 385 | 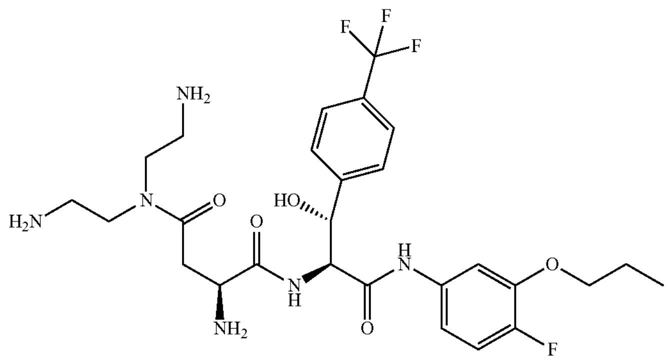 | B | 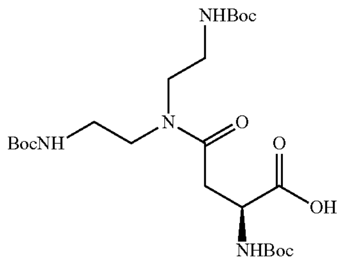 | A3 |
| 386 | 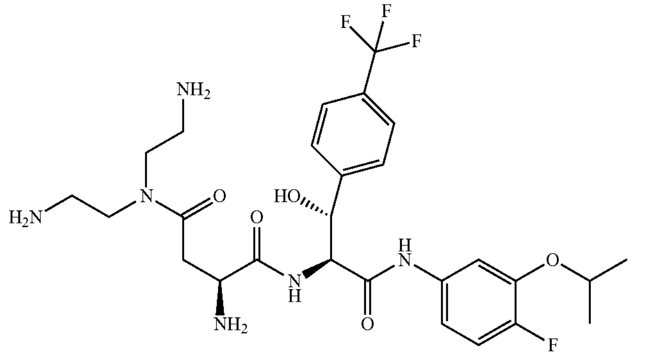 | B | 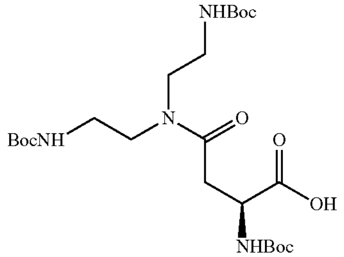 | A3 |

TABLE 3-continued
| | | | | |
|---|---|---|---|---|
| 387 | 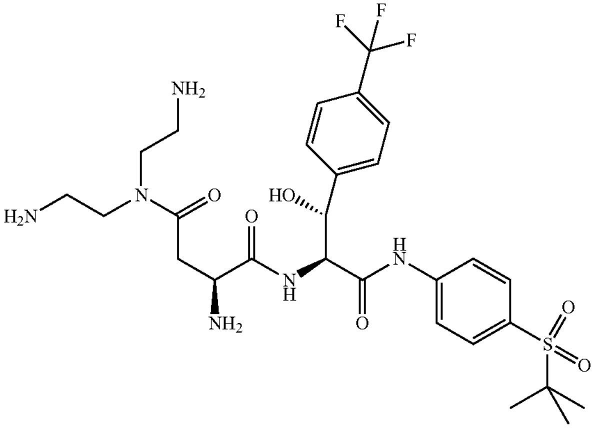 | B | 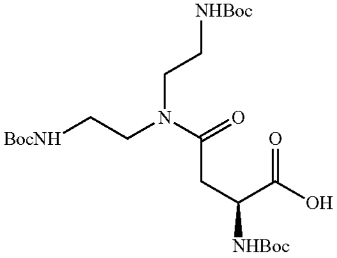 | A3 |
| 388 | 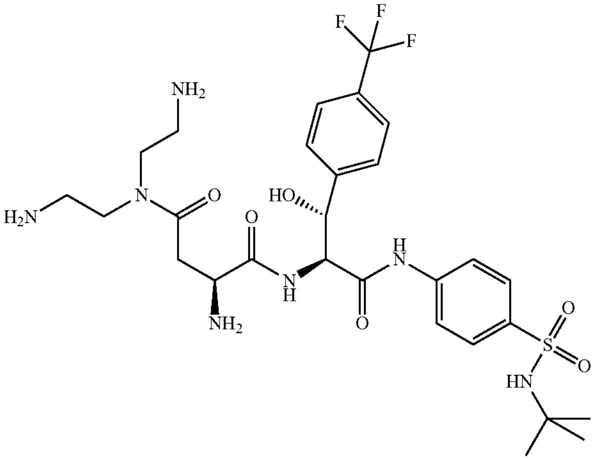 | B | 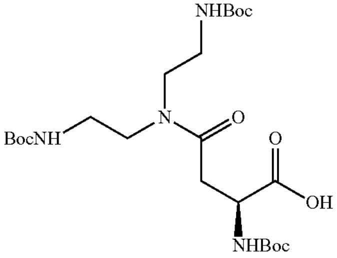 | A3 |

TABLE 3-continued
| | | | | |
|---|---|---|---|---|
| 389 | 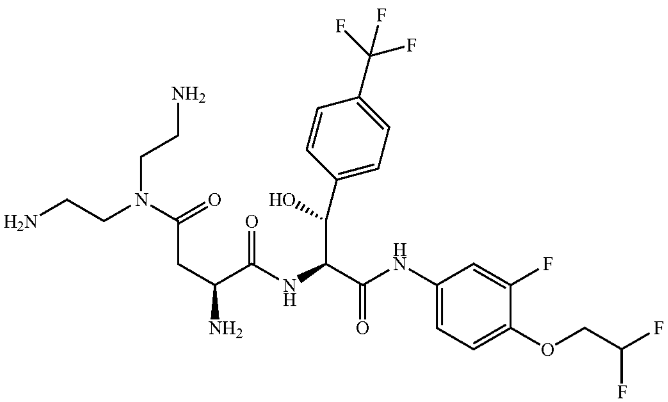 | B | 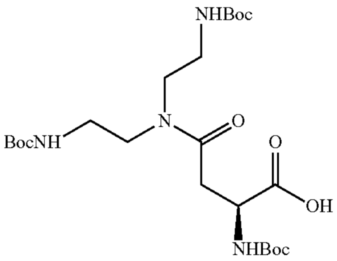 | A3 |
| 390 | 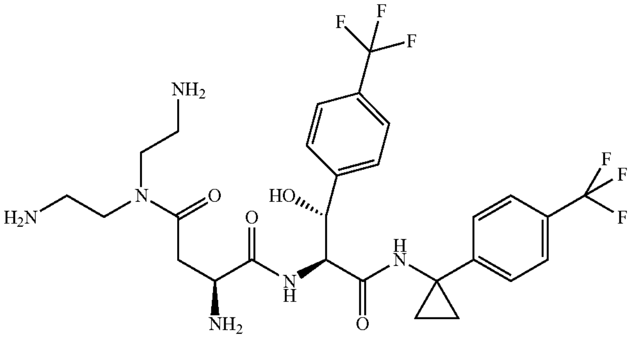 | B | 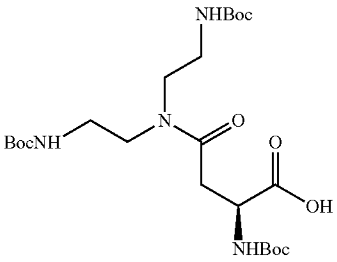 | A3 |
| 391 | 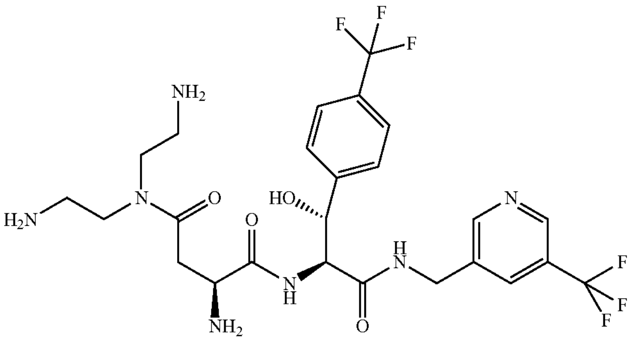 | B | 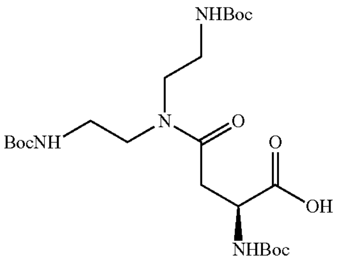 | A3 |

TABLE 3-continued
| | | | | |
|---|---|---|---|---|
| 392 | 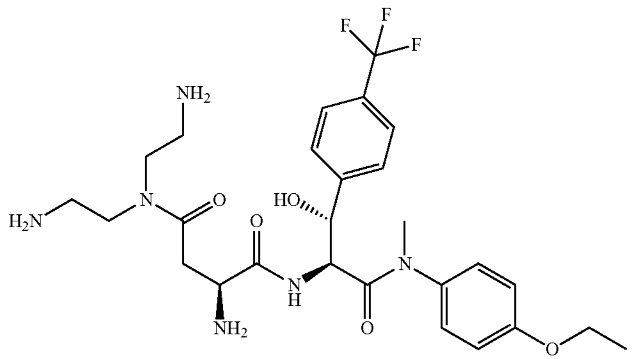 | B | 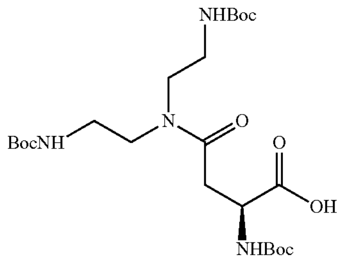 | A3 |
| 393 | 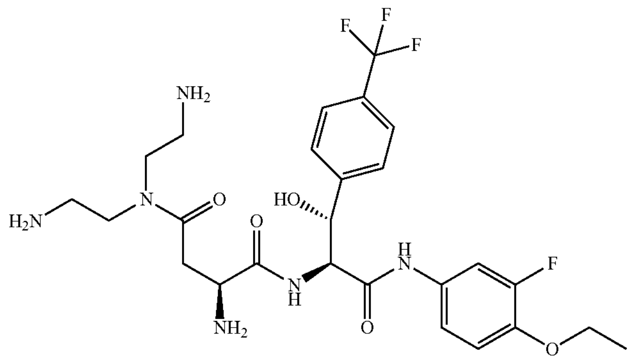 | B | 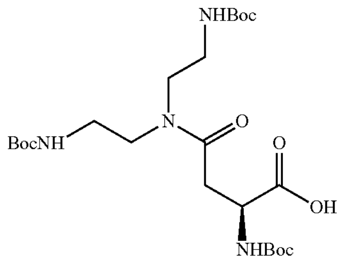 | A3 |
| 394 | 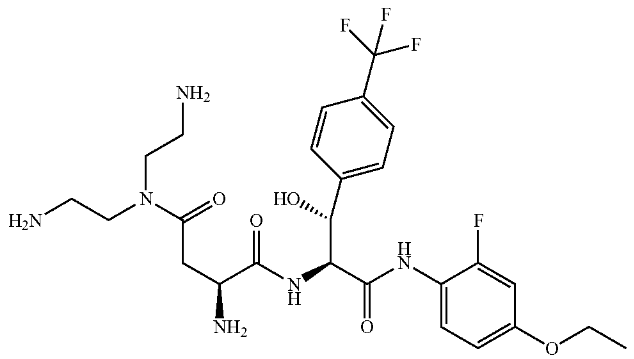 | B | 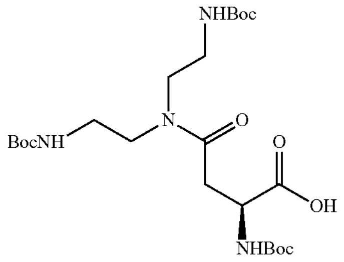 | A3 |

TABLE 3-continued
| | | | | |
|---|---|---|---|---|
| 395 | 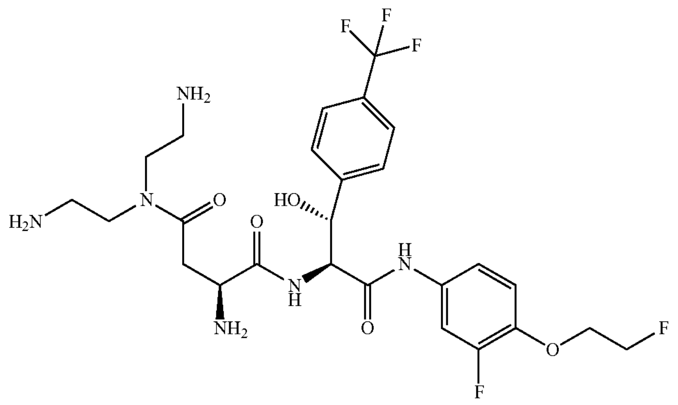 | B | 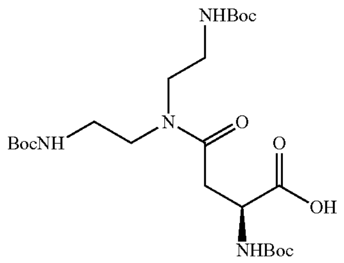 | A3 |
| 396 | 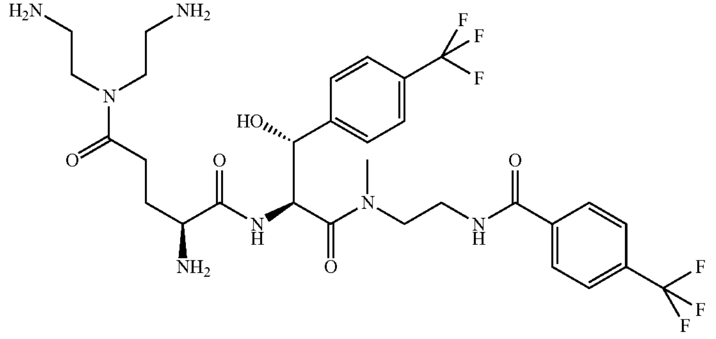 | B | 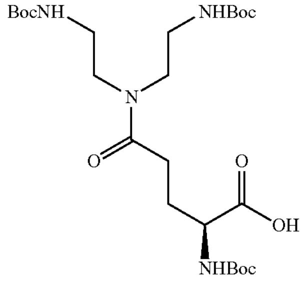 | A3 |
| 397 | 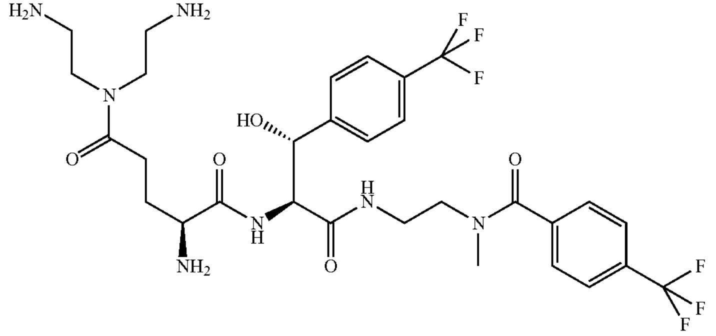 | B | 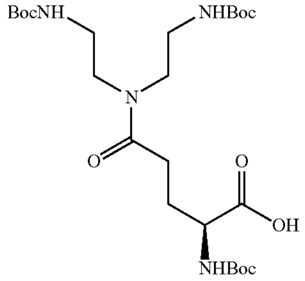 | A3 |

TABLE 3-continued
| | | | | |
|---|---|---|---|---|
| 398 | 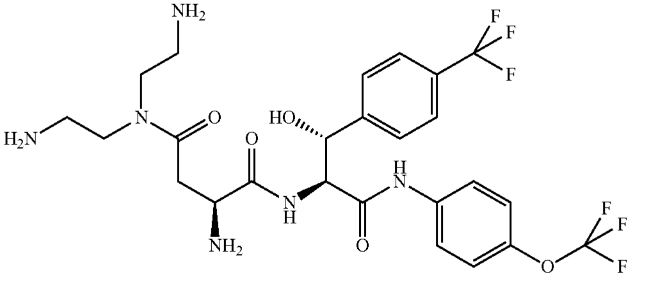 | B | 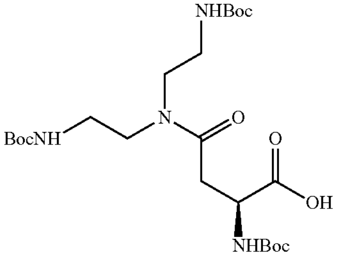 | A3 |
| 399 | 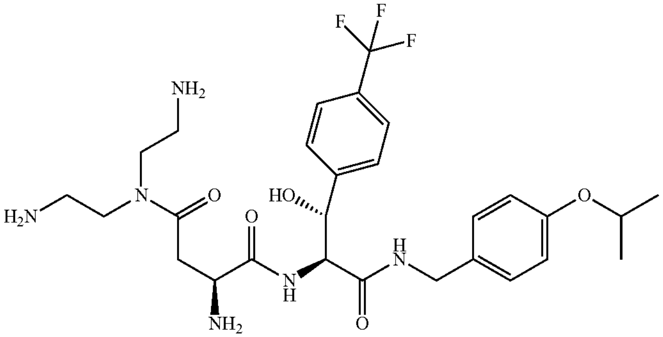 | B | 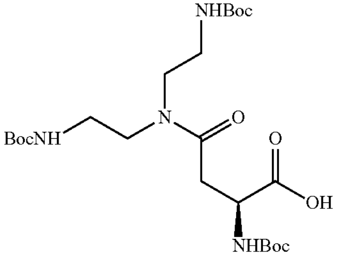 | A3 |
| 400 | 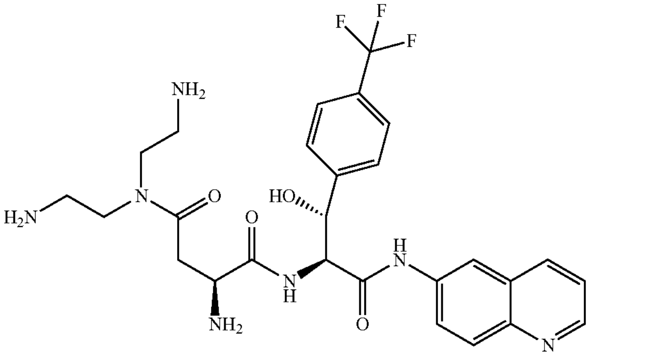 | B | 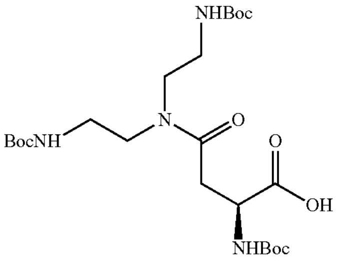 | A3 |

TABLE 3-continued
| | | | | |
|---|---|---|---|---|
| 401 | 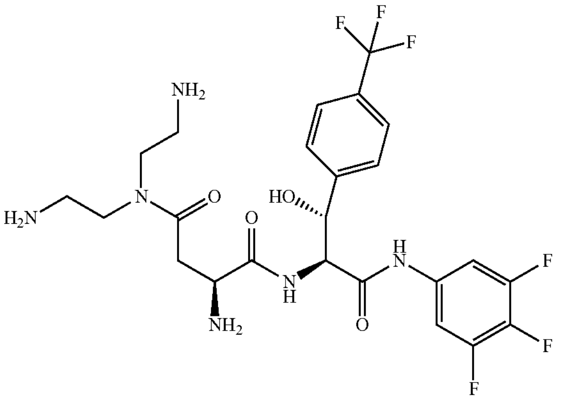 | B | 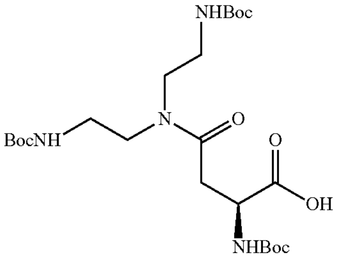 | A3 |
| 402 | 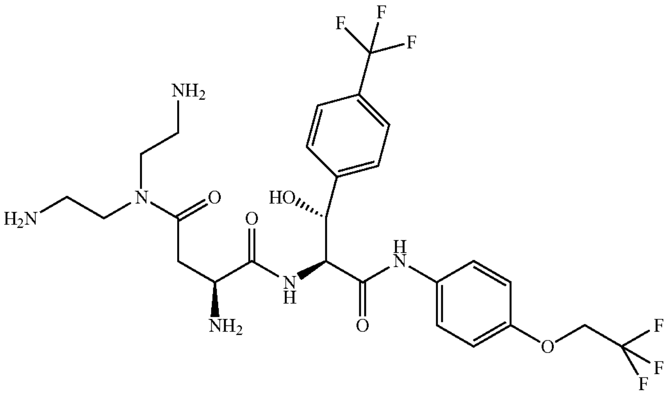 | B | 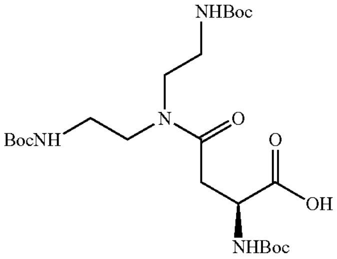 | A3 |

TABLE 3-continued
| | | | | |
|---|---|---|---|---|
| 403 | 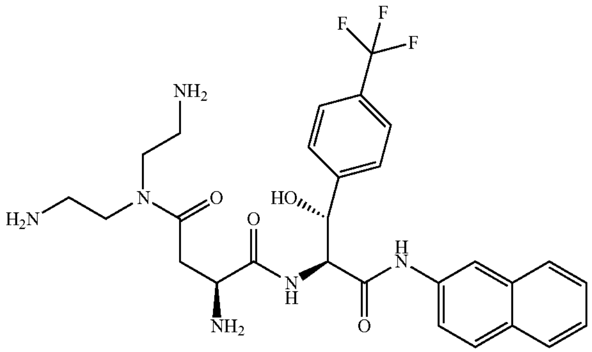 | B | 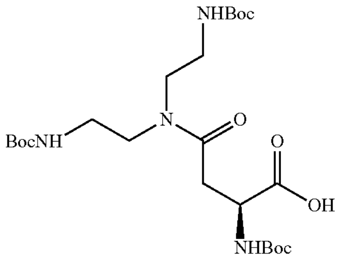 | A3 |
| 404 | 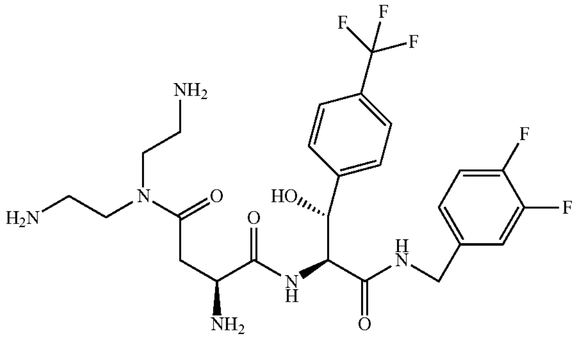 | B | 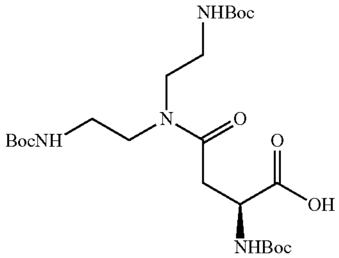 | A3 |
| 405 | 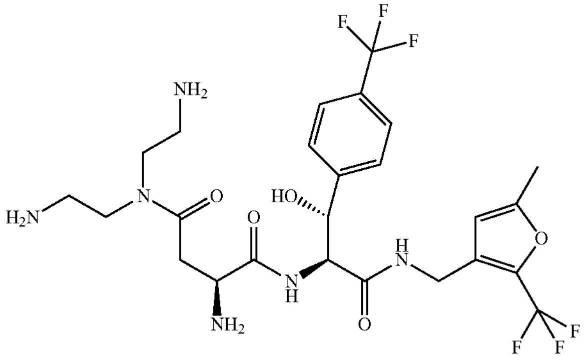 | B | 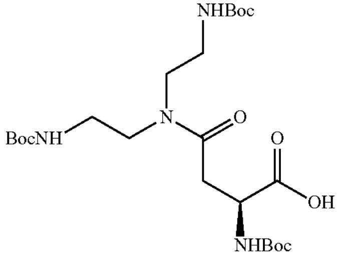 | A3 |

TABLE 3-continued
| | | | | |
|---|---|---|---|---|
| 406 | 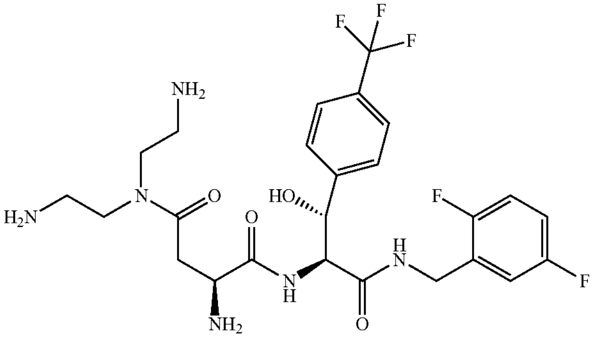 | B | 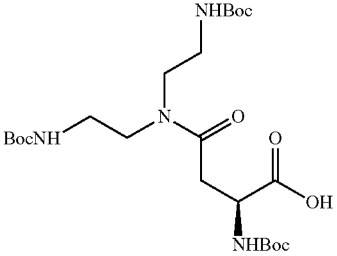 | A3 |
| 407 | 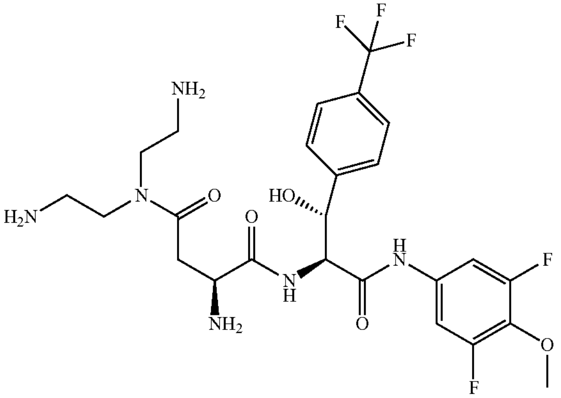 | B | 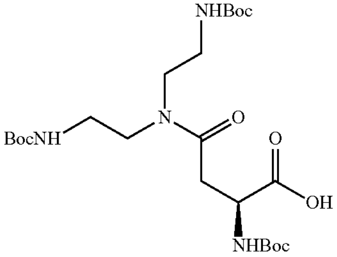 | A3 |

TABLE 3-continued
| | | | | |
|---|---|---|---|---|
| 408 | 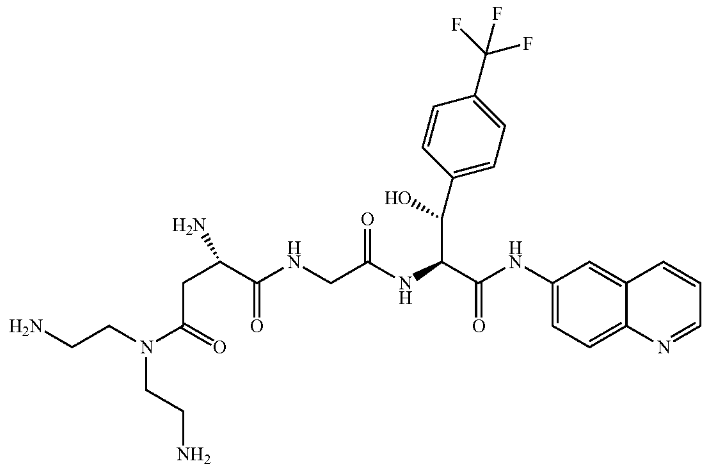 | B | 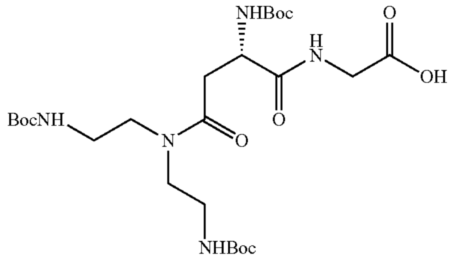 | A3 |
| 409 | 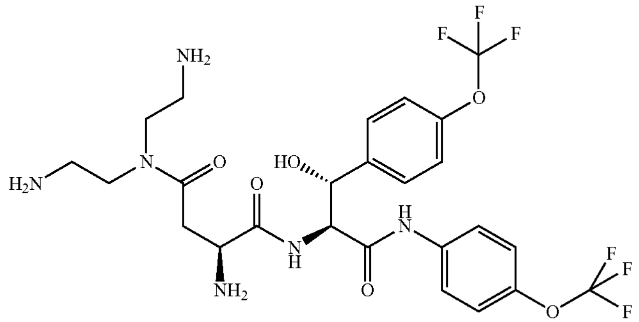 | B | 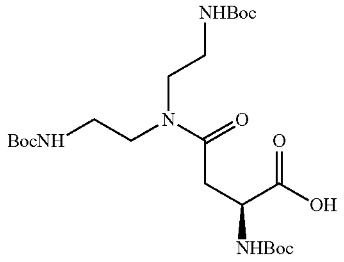 | A3 |
| 410 | 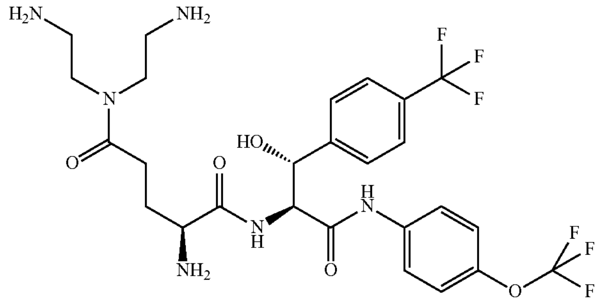 | B | 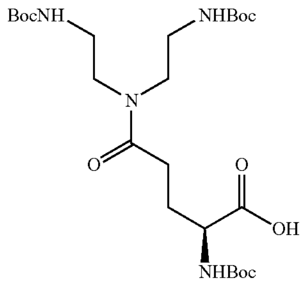 | A3 |

TABLE 3-continued
| | | | | |
|---|---|---|---|---|
| 411 | 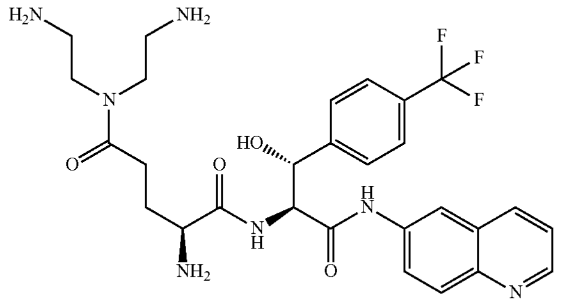 | B | 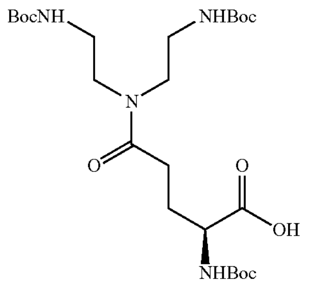 | A2 |
| 412 | 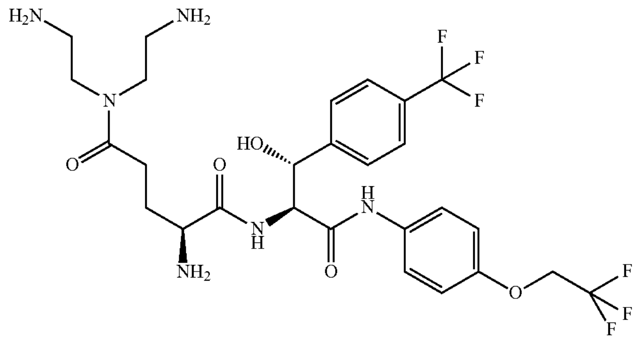 | B | 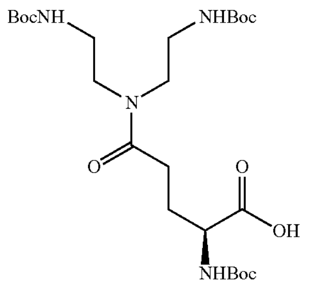 | A3 |
| 413 | 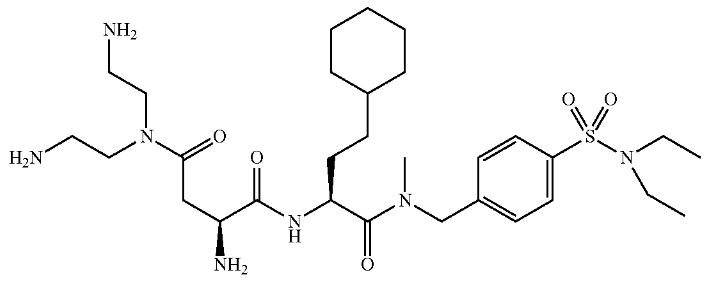 | B | 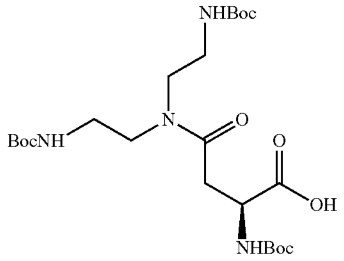 | A2 |

TABLE 3-continued
| | | | | |
|---|---|---|---|---|
| 414 | 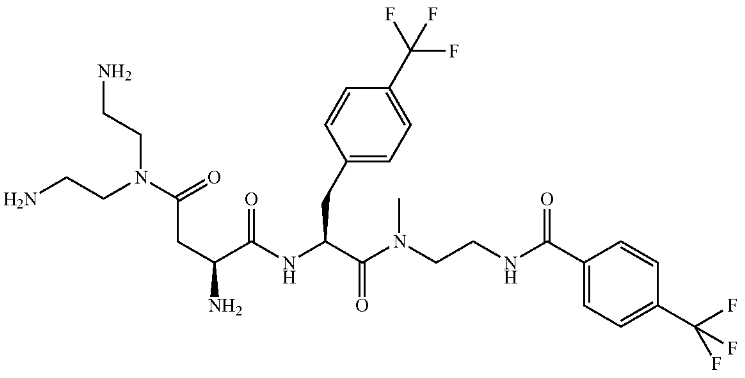 | B | 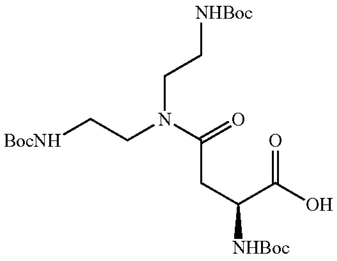 | A3 |
| 415 | 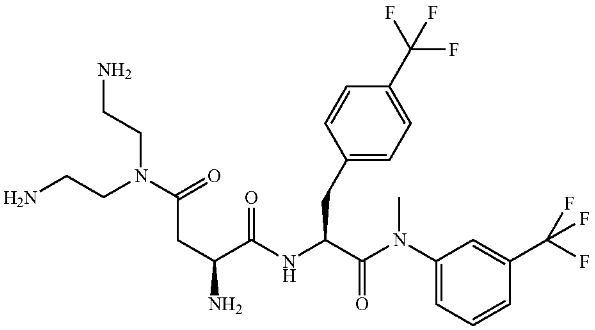 | B | 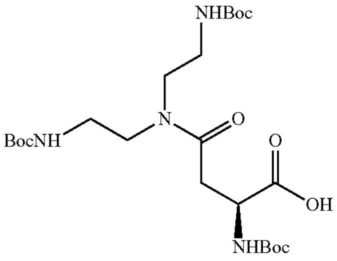 | A1 |
| 416 | 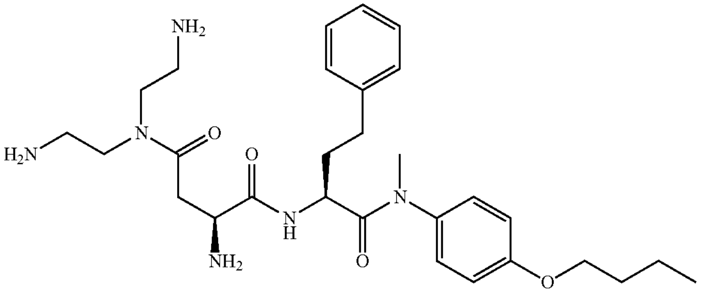 | B | 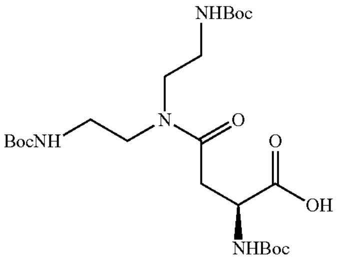 | A3 |

TABLE 3-continued
| | | | | |
|---|---|---|---|---|
| 417 | 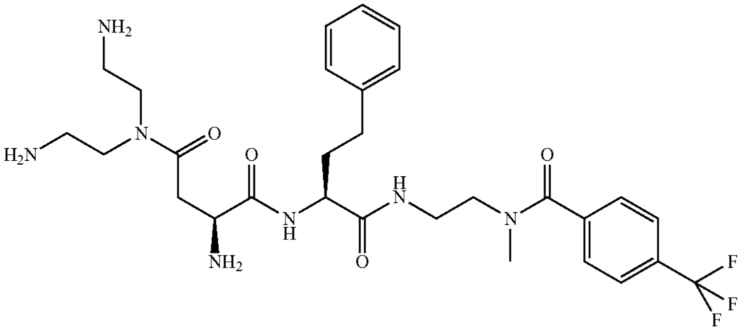 | B | 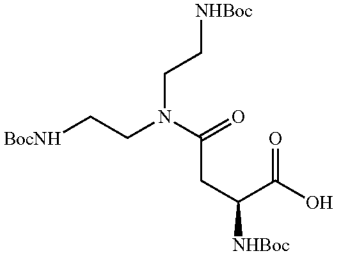 | A3 |
| 418 | 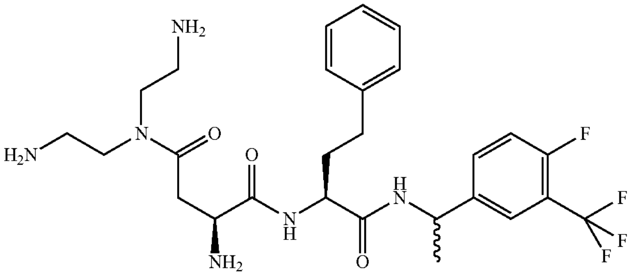 | B | 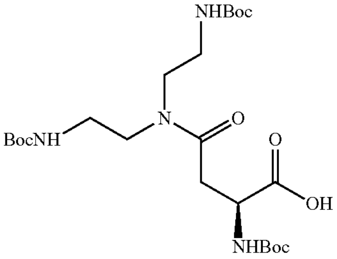 | A3 |
| 419 | 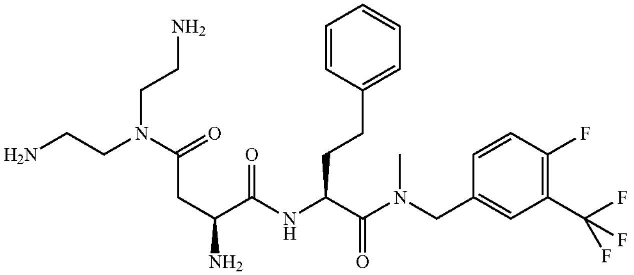 | B | 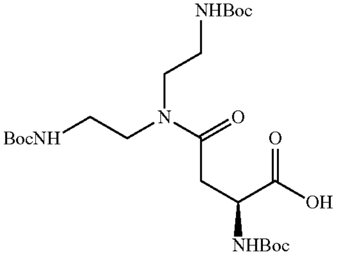 | A3 |

TABLE 3-continued
| | | | | |
|---|---|---|---|---|
| 420 | 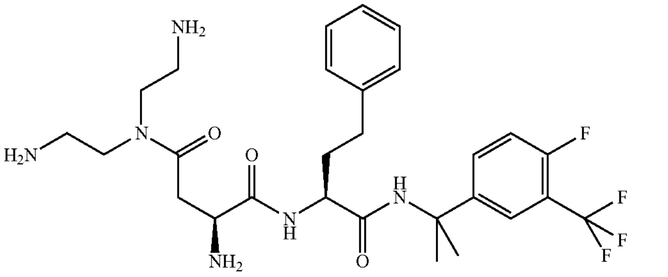 | B | 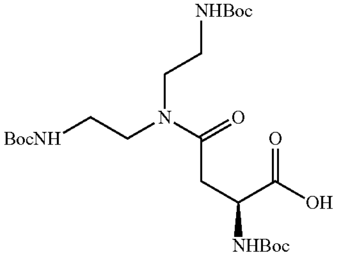 | A3 |
| 421 | 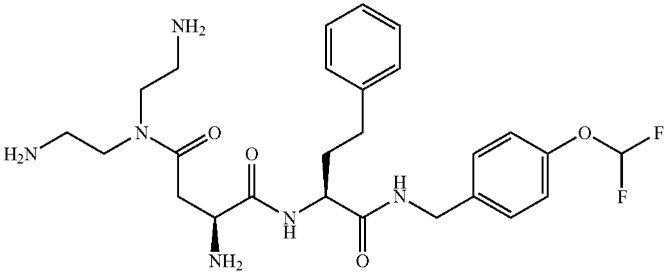 | B | 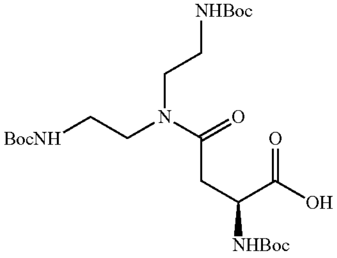 | A3 |
| 422 | 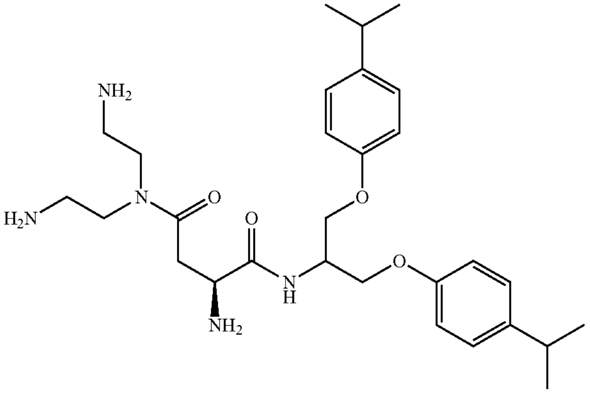 | B | 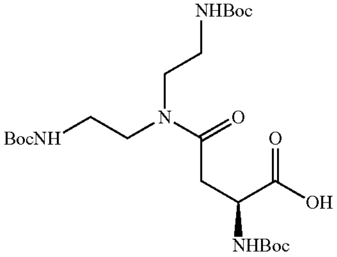 | A3 |

TABLE 3-continued
| | | | | |
|---|---|---|---|---|
| 423 | 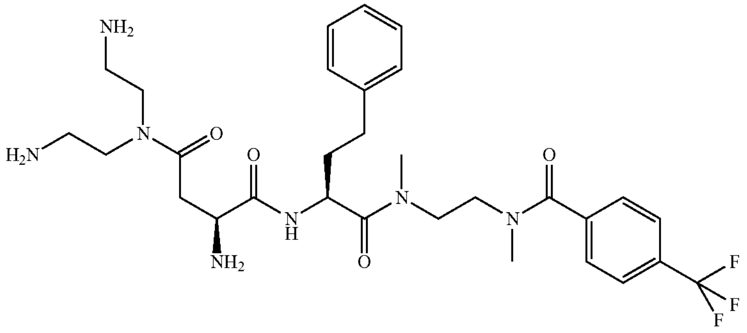 | B | 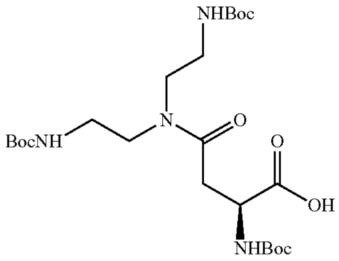 | A3 |
| 424 | 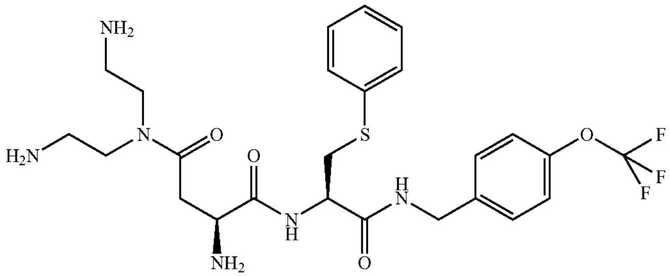 | B | 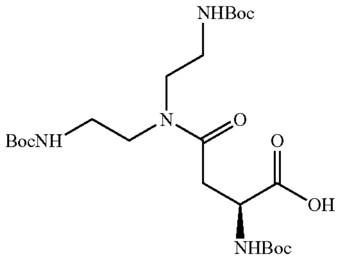 | A3 |
| 425 | 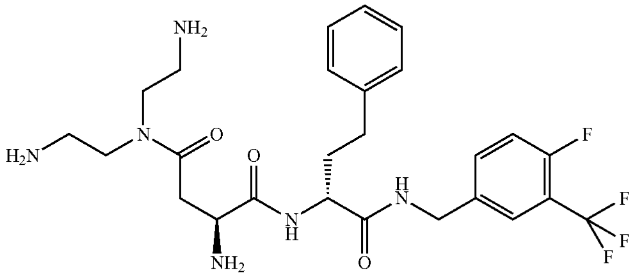 | B | 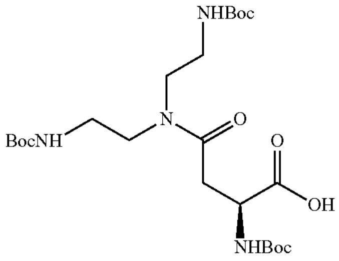 | A3 |

TABLE 3-continued
| | | | | |
|---|---|---|---|---|
| 426 | 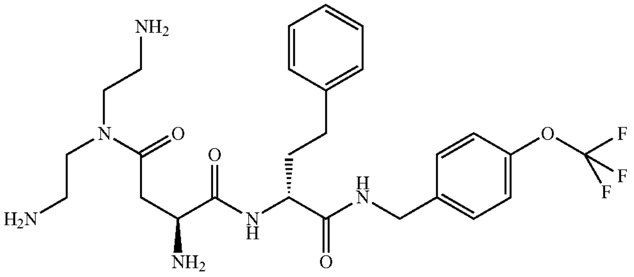 | B | 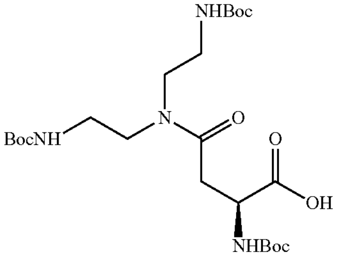 | A3 |
| 427 | 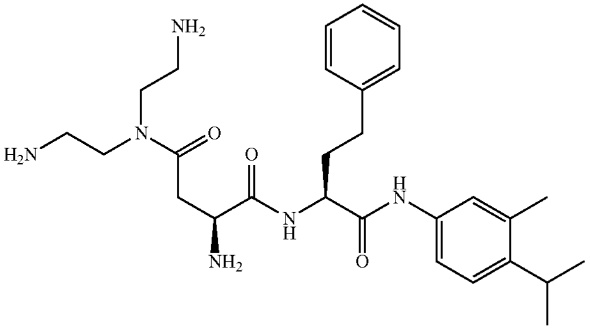 | B | 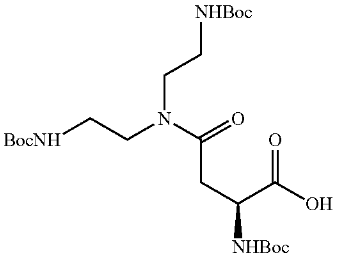 | A3 |
| 428 | 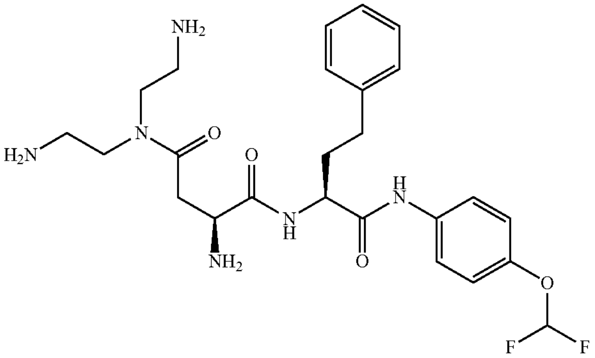 | B | 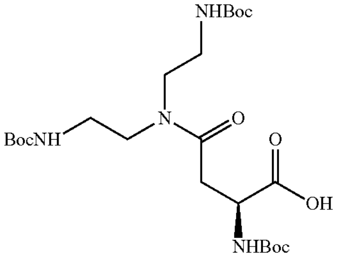 | A3 |

TABLE 3-continued
| | | | | |
|---|---|---|---|---|
| 429 | 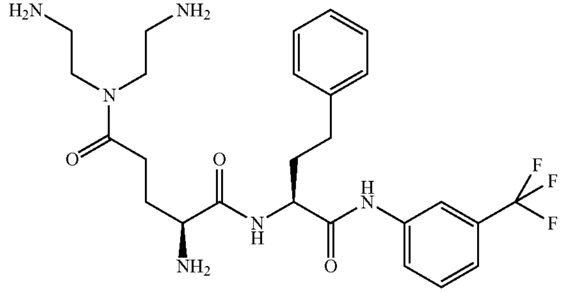 | B | 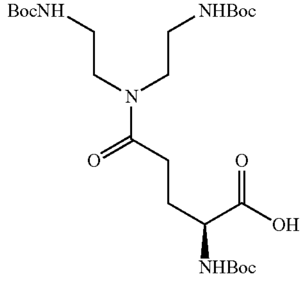 | A3 |
| 430 | 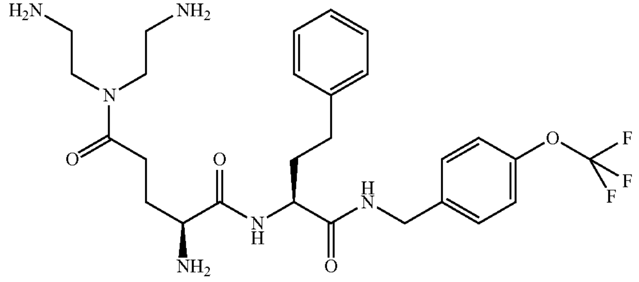 | B | 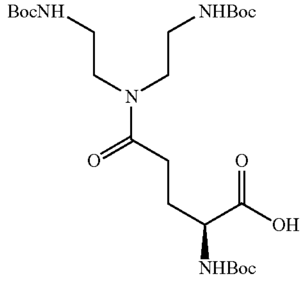 | A3 |
| 431 | 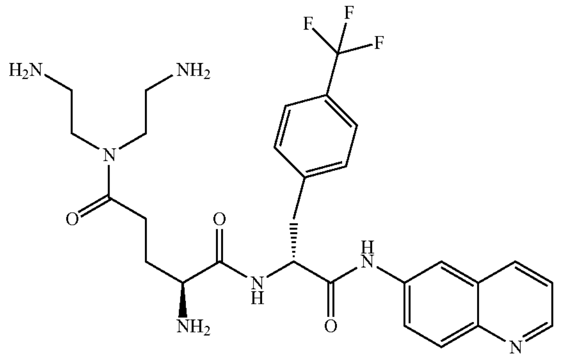 | B | 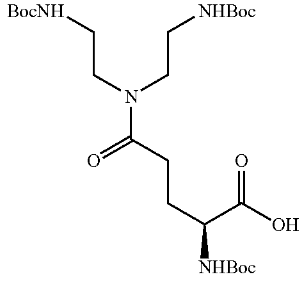 | A3 |

TABLE 3-continued
| | | | | |
|---|---|---|---|---|
| 432 | 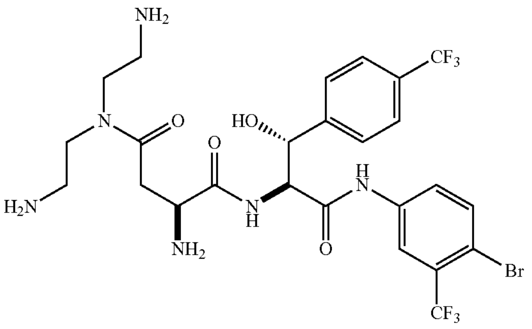 | B2 | 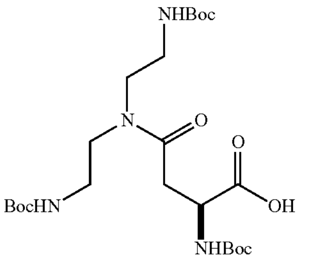 | A2 |
| 433 | 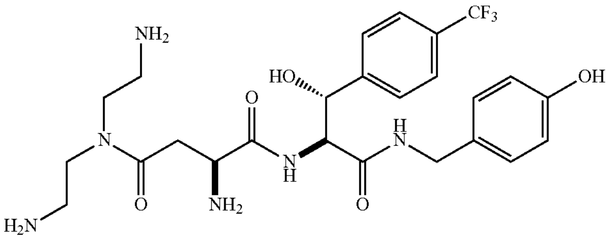 | B3* | 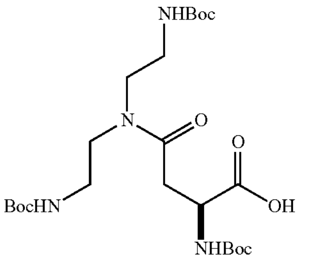 | A2 |
| 434 | 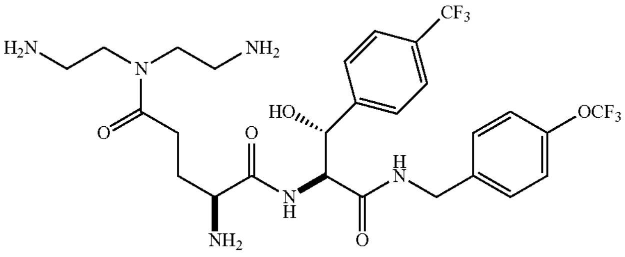 | B2 | 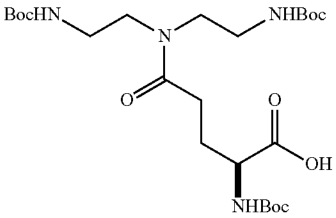 | A2 |
*Concomitant removal of t-butyl ether during B3 conditions TABLE 3-continued
| | | | | |
|---|---|---|---|---|
| 435 | 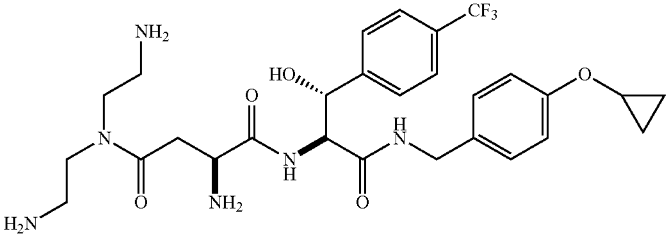 | B2 | 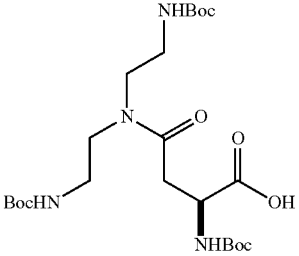 | A2 |
| 436 | 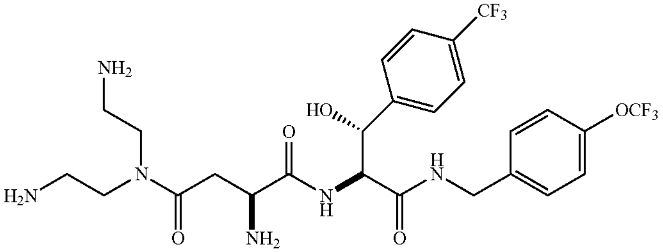 | B1 | 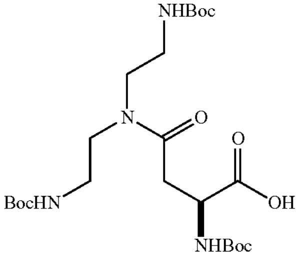 | A2 |
| 437 | 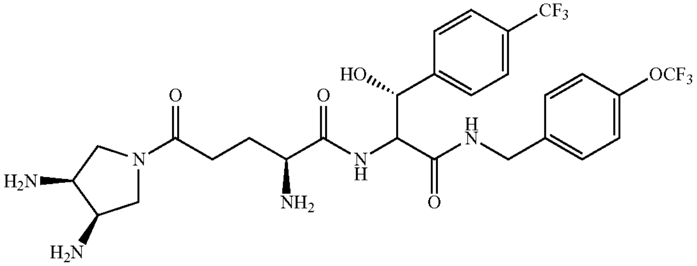 | B2 | 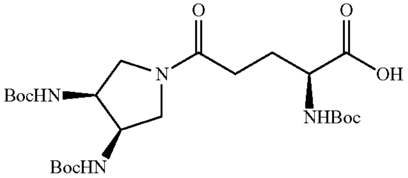 | A2 |
| 438 | 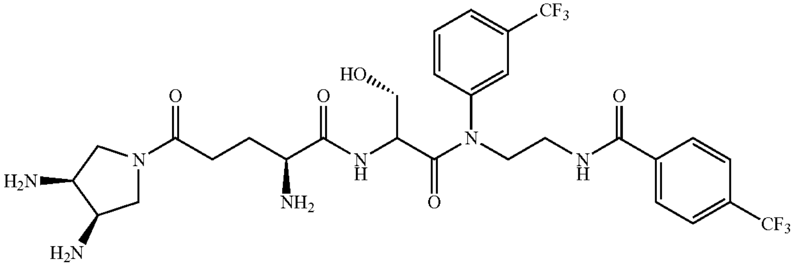 | B2 | 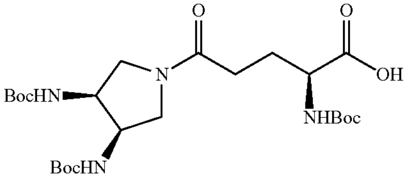 | A2 |

TABLE 3-continued
| Compound | Protected central acid structure (coupling procedure A1-A3) | Capping amine structure | Ret. Time Min. (method) | MS m/e |
|---|---|---|---|---|
| 377 | 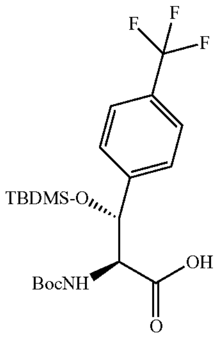 | A2 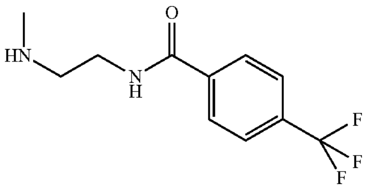 | 2.58 (H1) | 678 |
| 378 | 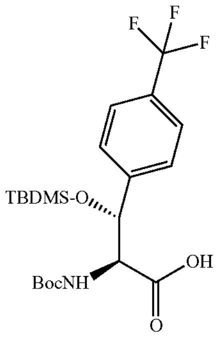 | A3 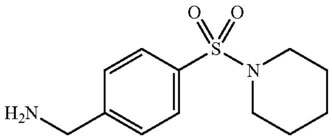 | 0.51 (H1) | 686 |
| 379 | 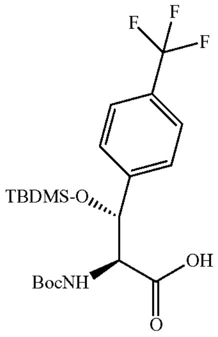 | A2 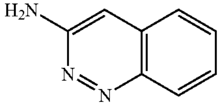 | 0.63 (H1) | 577 |

TABLE 3-continued
| | | | | |
|---|---|---|---|---|
| 380 | 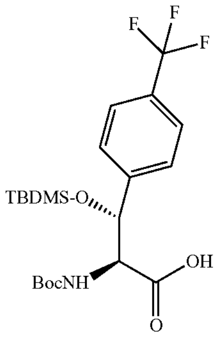 | A1 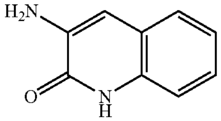 | 0.68 (H1) | 592 |
| 381 | 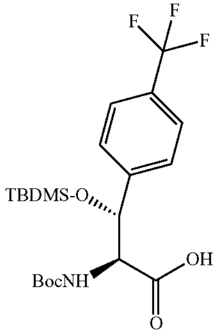 | A3 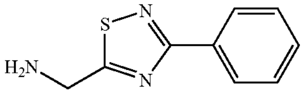 | 0.79 (H1) | 623 |
| 382 | 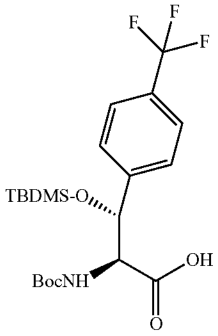 | A3 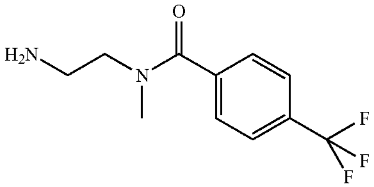 | 2.42 (H1) | 678 |

TABLE 3-continued
| | | | | | |
|---|---|---|---|---|---|
| 383 | 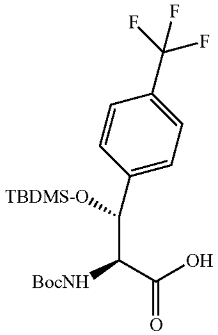 | A3 | 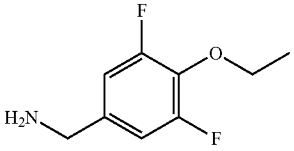 | 0.68 (H1) | 619 |
| 384 | 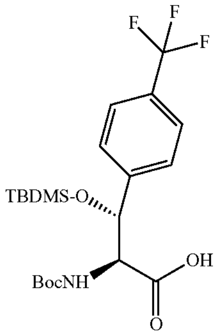 | A2 | 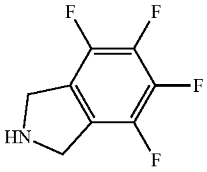 | 1.61 (H1) | 623 |
| 385 | 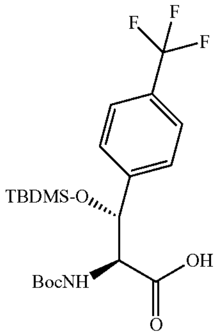 | A1 | 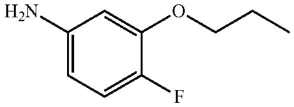 | 2.13 (H1) | 601 |

TABLE 3-continued
| | | | | |
|---|---|---|---|---|
| 386 | 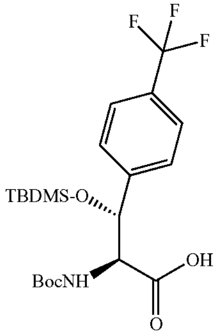 | A1 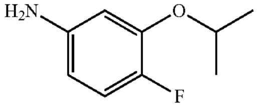 | 0.65 (H1) | 601 |
| 387 | 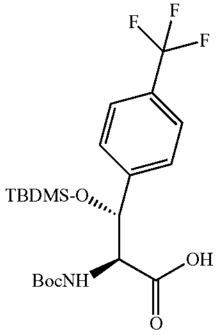 | A1 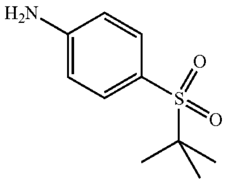 | 0.68 (H1) | 645 |
| 388 | 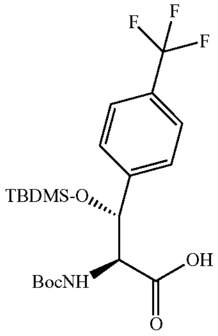 | A1 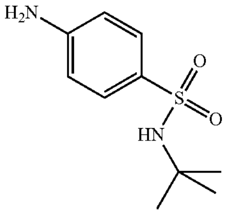 | 0.65 (H1) | 660 |

TABLE 3-continued
| | | | | | |
|---|---|---|---|---|---|
| 389 | 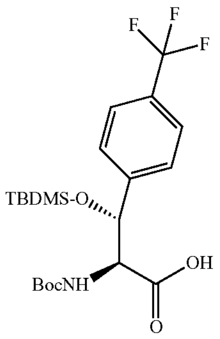 | A1 | 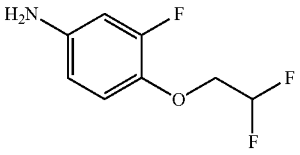 | 0.68 (H1) | 623 |
| 390 | 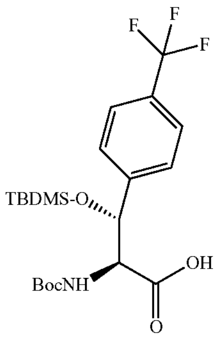 | A1 | 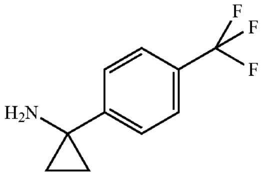 | 2.32 (H1) | 633 |
| 391 | 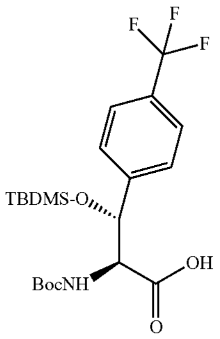 | A3 | 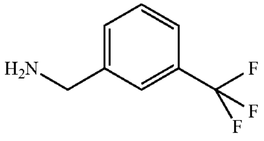 | 0.65 (H1) | 608 |

TABLE 3-continued
| | | | | | |
|---|---|---|---|---|---|
| 392 | 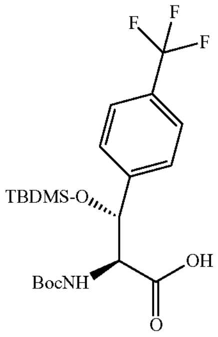 | A2 | 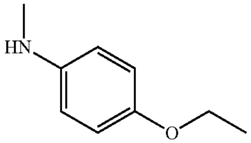 | 0.65 (H1) | 583 |
| 393 | 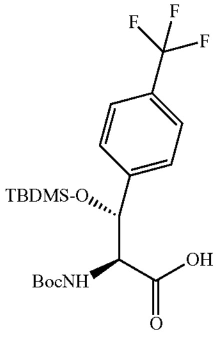 | A1 | 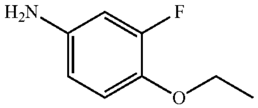 | 0.64 (H1) | 587 |
| 394 | 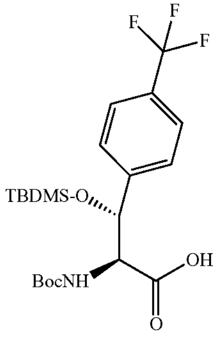 | A1 | 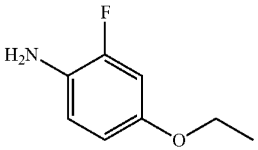 | 0.65 (H1) | 587 |

TABLE 3-continued
| | | | | | |
|---|---|---|---|---|---|
| 395 | 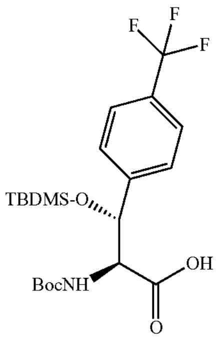 | A2 | 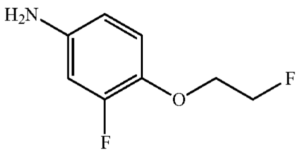 | 2.26 (H1) | 605 |
| 396 | 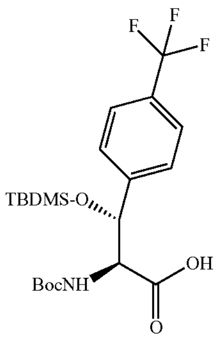 | A2 | 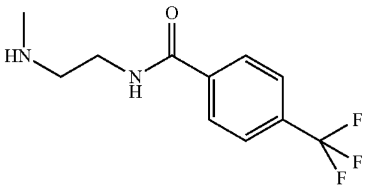 | 1.22 (H1) | 692 |
| 397 | 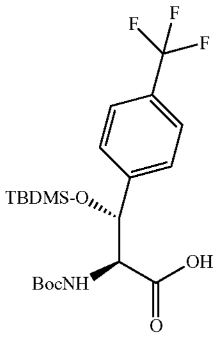 | A2 | 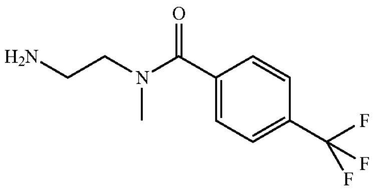 | 2.45 (H1) | 692 |

TABLE 3-continued
| | | | | | |
|---|---|---|---|---|---|
| 398 | 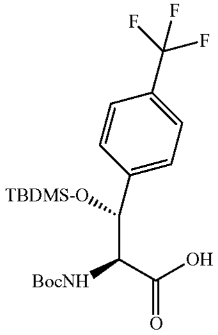 | A1 | 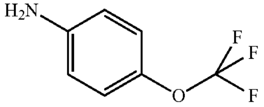 | 0.70 (H1) | 609 |
| 399 | 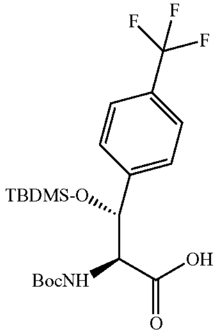 | A3 | 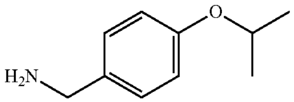 | 2.57 (H1) | 597 |
| 400 | 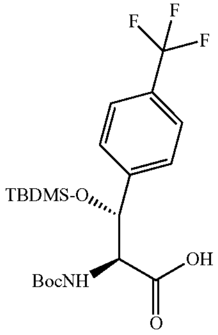 | A1 | 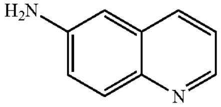 | 0.53 (H1) | 576 |

TABLE 3-continued
| | | | | |
|---|---|---|---|---|
| 401 | 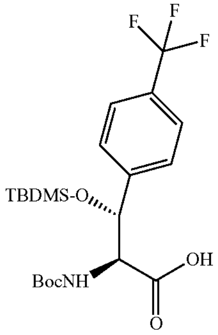 | A1 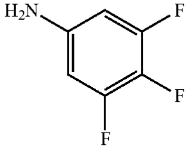 | 2.06 (H1) | 579 |
| 402 | 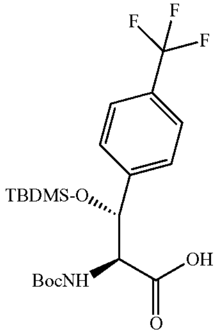 | A1 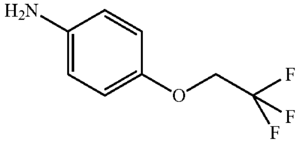 | 2.70 (H1) | 623 |
| 403 | 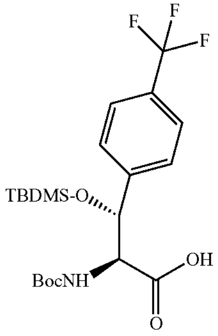 | A1 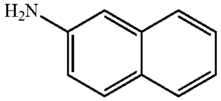 | 2.68 (H1) | 575 |

TABLE 3-continued
| | | | | | |
|---|---|---|---|---|---|
| 404 | 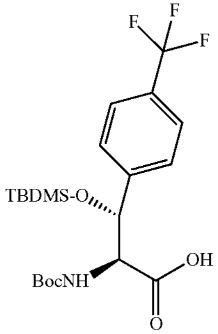 | A3 | 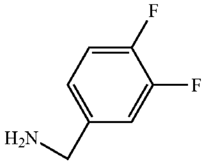 | 0.65 (H1) | 575 |
| 405 | 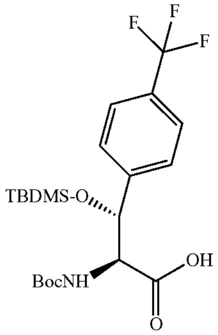 | A3 | 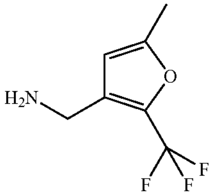 | 0.65 (H1) | 611 |
| 406 | 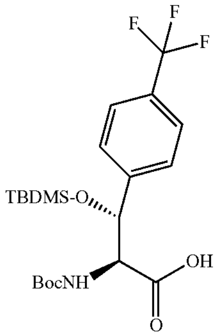 | A3 | 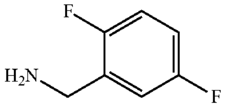 | 0.65 (H1) | 575 |

TABLE 3-continued
| | | | | | |
|---|---|---|---|---|---|
| 407 | 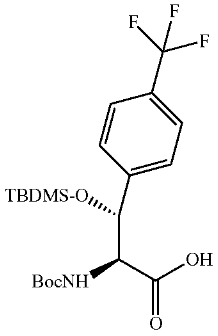 | A1 | 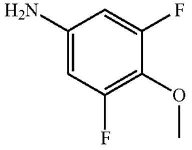 | 0.66 (H1) | 591 |
| 408 | 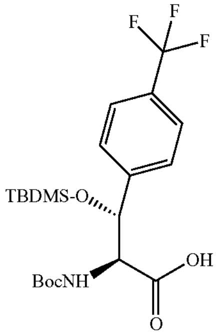 | A2 | 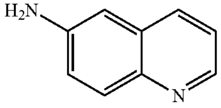 | 1.84 (H1) | 634 |
| 409 | 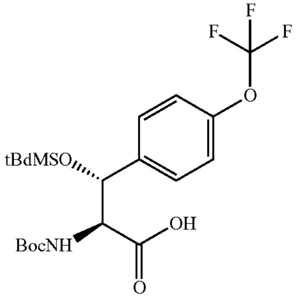 | A1 | 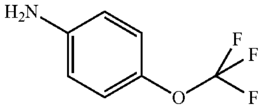 | 2.56 (H1) | 625 |

TABLE 3-continued
| | | | | | |
|---|---|---|---|---|---|
| 410 | 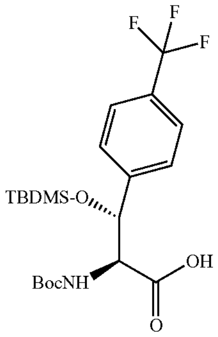 | A1 | 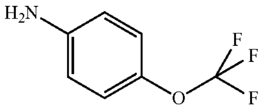 | 0.70 (H1) | 623 |
| 411 | 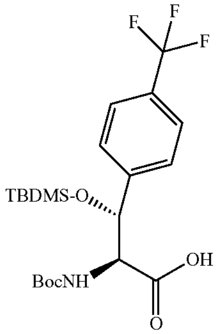 | A1 | 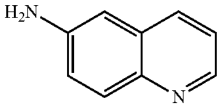 | 1.97 (H1) | 590 |
| 412 | 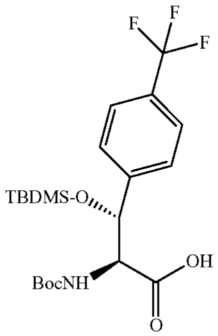 | A1 | 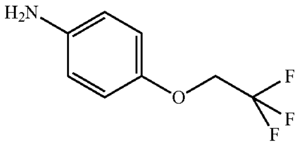 | 0.67 (H1) | 637 |

TABLE 3-continued
| | | | | |
|---|---|---|---|---|
| 413 | 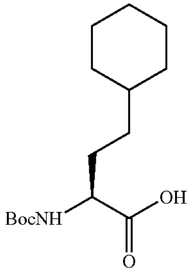 | A1 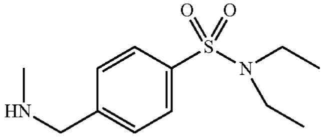 | 3.38 (H1) | 625 |
| 414 | 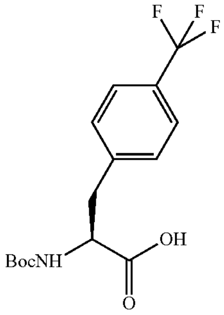 | A2 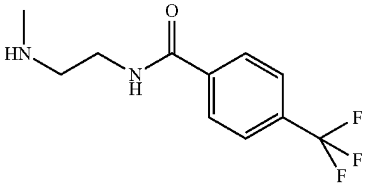 | 3.03 (H1) | 662 |
| 415 | 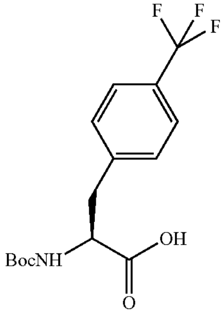 | A2 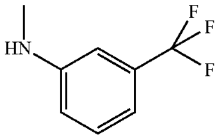 | 0.79 (H1) | 591 |

TABLE 3-continued
| | | | | | |
|---|---|---|---|---|---|
| 416 | 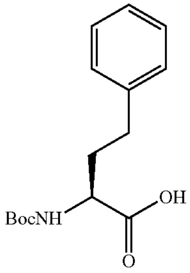 | A2 | 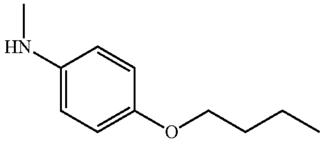 | 2.76 (H1) | 541 |
| 417 | 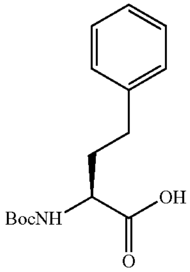 | A3 | 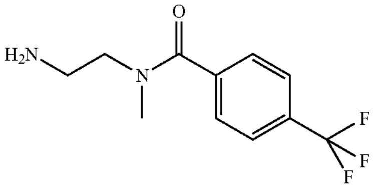 | 2.83 (H1) | 608 |
| 418 | 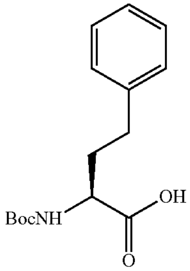 | A3 | 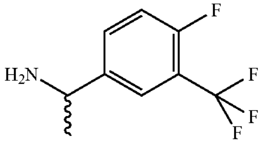 | 0.81 (H1) | 569 |

TABLE 3-continued
| | | | | | |
|---|---|---|---|---|---|
| 419 | 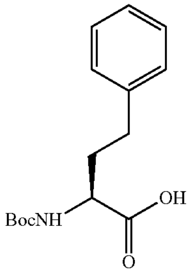 | A2 | 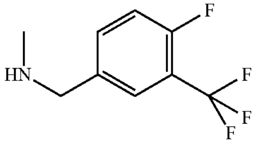 | 3.03 (H1) | 569 |
| 420 | 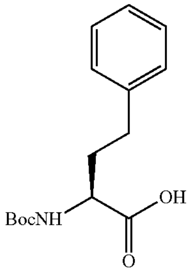 | A3 | 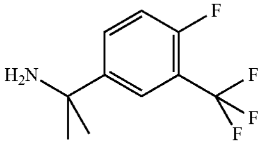 | 0.86 (H1) | 583 |
| 421 | 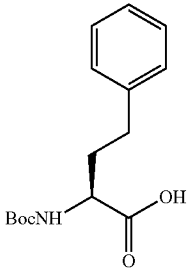 | A3 | 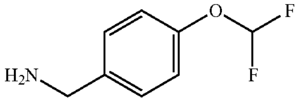 | 0.64 (H1) | 535 |

TABLE 3-continued
| | | | | |
|---|---|---|---|---|
| 422 | — | — 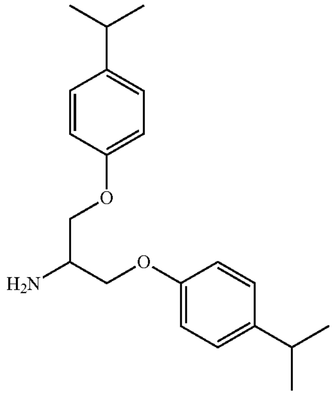 | 3.61 (H1) | 528 |
| 423 | 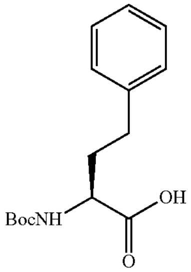 | A2 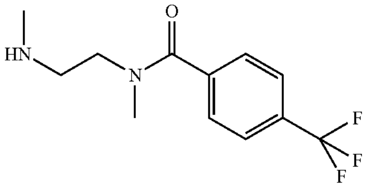 | 2.87 (H1) | 622 |
| 424 | 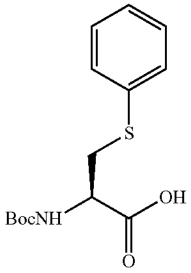 | A3 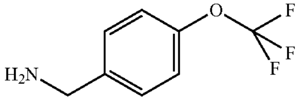 | 2.82 (H1) | 571 |

TABLE 3-continued
| | | | | | |
|---|---|---|---|---|---|
| 425 | 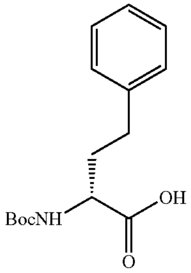 | A3 | 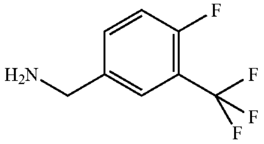 | 0.92 (H1) | 567 |
| 426 | 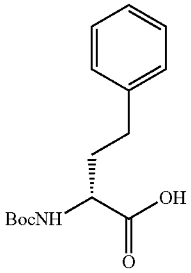 | A3 | 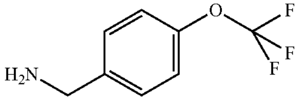 | 2.97 (H1) | 553 |
| 427 | 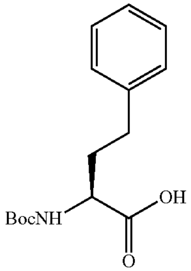 | A3 | 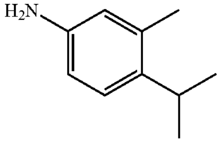 | 0.84 (H1) | 511 |

TABLE 3-continued
| | | | | | |
|---|---|---|---|---|---|
| 428 | 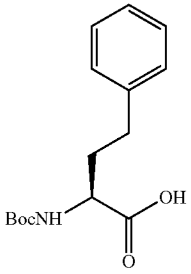 | A1 | 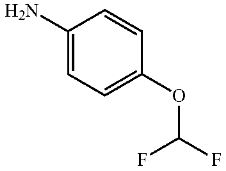 | 0.68 (H1) | 521 |
| 429 | 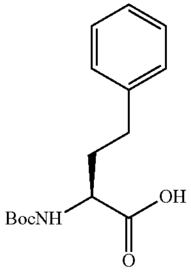 | A1 | 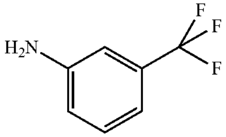 | 2.18 (H1) | 537 |
| 430 | 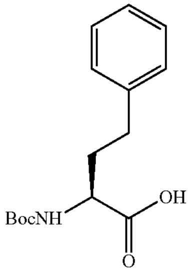 | A3 | 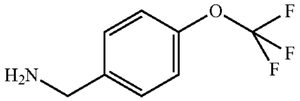 | 0.64 (H1) | 567 |

TABLE 3-continued
| | | | | | |
|---|---|---|---|---|---|
| 431 | 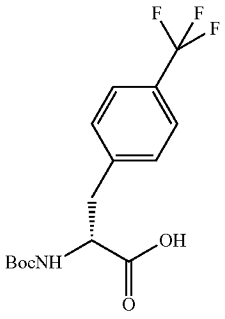 | A1 | 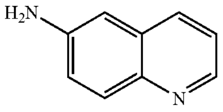 | 0.64 (H1) | 574 |
| 432 | 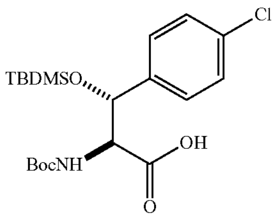 | A1 | 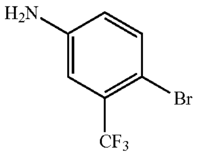 | 7.53 (H2) | 671 |
| 433 | 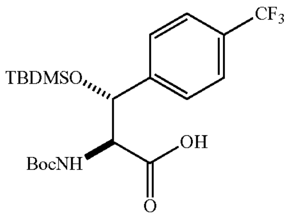 | A2 | 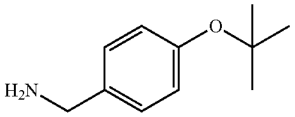 | 3.49 (H2) | 555 |
| 434 | 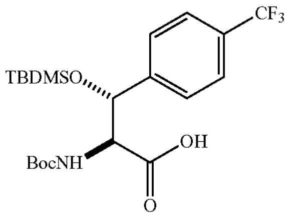 | A3 | 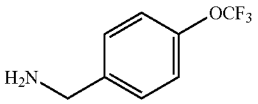 | 7.16 (H2) | 637 |

TABLE 3-continued
| | | | | | |
|---|---|---|---|---|---|
| 435 | 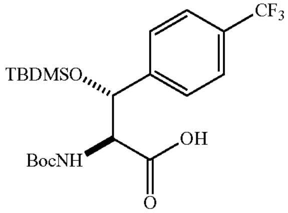 | A2 | 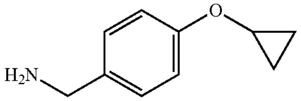 | 5.37 (H3) | 595 |
| 436 | 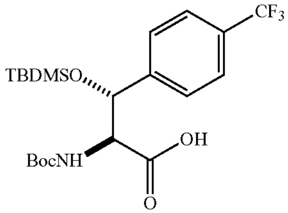 | A4 | 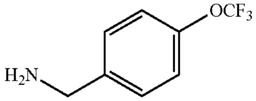 | 7.12 (H2) | 623 |
| 437 | 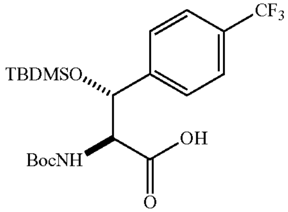 | A3 | 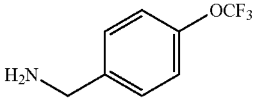 | 7.3 (H2) | 635 |
| 438 | 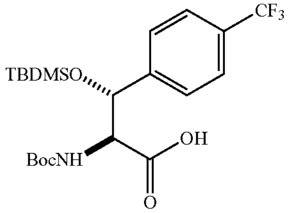 | A2 | 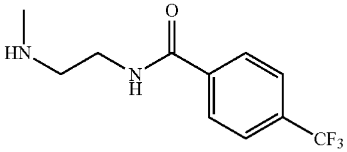 | 6.6 (H2) | 690 |

Compounds 439-444 shown in Table 4 were assembled according to the general Scheme 36. A general description of the steps appears below the scheme.
Scheme 36
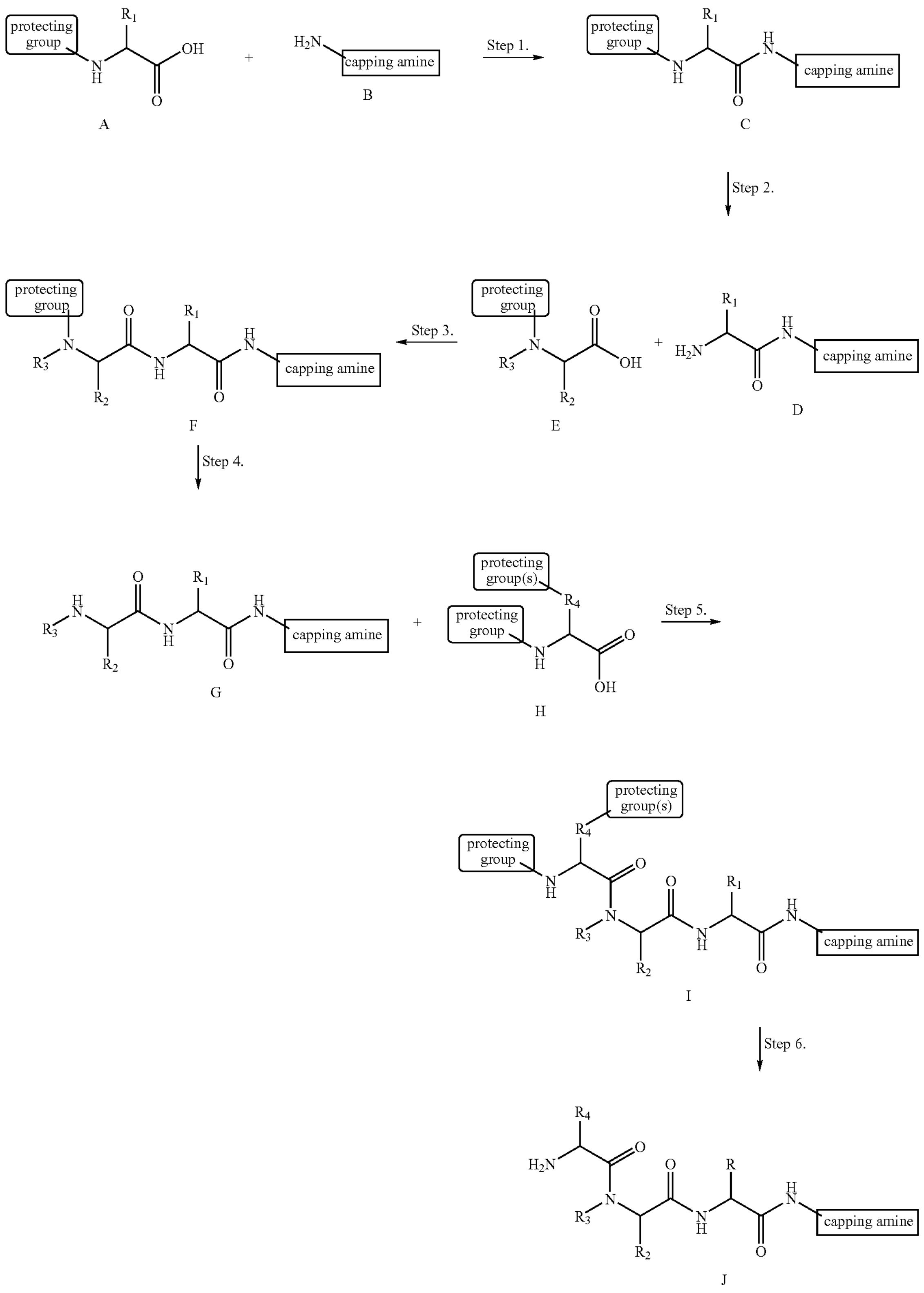

Step 1. Capping amine intermediate B was attached using one of coupling procedures A1-A4 (described above for Scheme 35) to a protected central amino acid intermediate A to form corresponding amide bond containing intermediate C.

Step 2. The amine functionality of the obtained intermediate C was unmasked by removal of protecting group producing intermediate D using one of the deprotection methods described above for Scheme 35.

Step 3. Acid intermediate E containing masked basic functionalities was attached using one of coupling procedures A1-A4 to intermediate D producing protected intermediate F.

Step 4. Intermediate F was deprotected in order to produce intermediate compounds G using one of the deprotection methods described above for Scheme 35 (for compound 439 and related compounds, amines present in $R_2$ are also unmasked at this stage).

Step 5. Acid intermediate H containing masked basic functionalities was attached using one of coupling procedures A1-A4 to intermediate G producing protected intermediate I (for compound 439 and related compounds, amines present in $R_2$ were also acylated with N-protected glycine at this stage. No protecting groups were present at $R_4$ ($R_4$=H)).

Step 6. Fully assembled intermediate I was deprotected in order to produce final inhibitor compounds J using one of the deprotection methods described above for Scheme 35.

$R_1$ in Scheme 36 refers to the side chain in the central amino acid structure in the structures of Formulae I, II, and IV depicted herein. $R_2$ refers to either the polybasic moiety on the N-terminal amino acid structure in the structures of Formulae I, II, and IV depicted herein (e.g., Compound 439) or a side chain on an additional central amino acid structure (e.g., Compounds 440-444). $R_3$ refers to hydrogen (e.g., Compounds 439-441) or a side chain on an additional central amino acid structure (e.g., Compounds 442-444). $R_2$ and $R_3$ may together form a ring (e.g., Compounds 442-444). $R_4$ refers to either the polybasic moiety on the N-terminal amino acid structure (e.g., Compounds 440-444) or hydrogen (e.g., Compound 439). In some cases additional steps were required when different protecting groups were present which required different deprotecting conditions.

TABLE 4

The following compounds were prepared in accordance with Scheme 36. The coupling and deprotection methods used are identified next to the relevant intermediate or final structure. A description of these methods appears after Scheme 35.

| Compound | Inhibitor structure (deprotection procedure B-B3) | | Protected N-terminal acid structure (coupling procedure A1-A3) | |
|---|---|---|---|---|
| 439 | 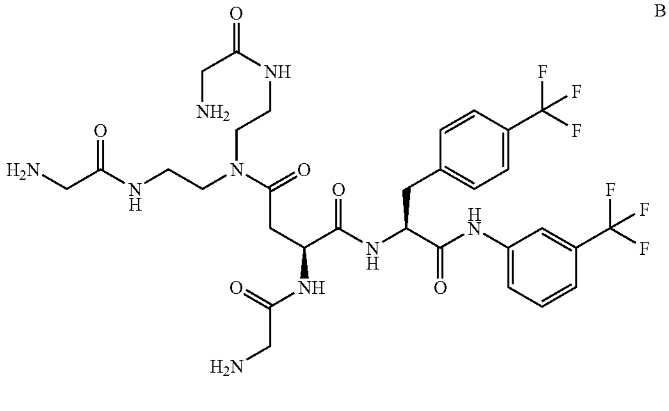 | B | 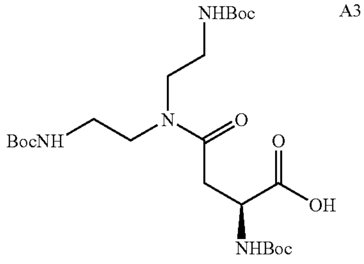 | A3 |
| 440 | 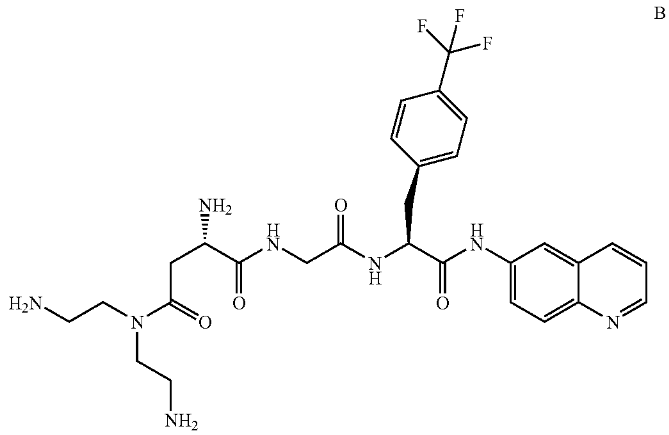 | B | 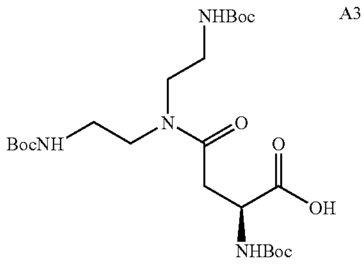 | A3 |

TABLE 4-continued
The following compounds were prepared in accordance with Scheme 36. The coupling and deprotection methods used are identified next to the relevant intermediate or final structure. A description of these methods appears after Scheme 35.
| | | | | |
|---|---|---|---|---|
| 441 | 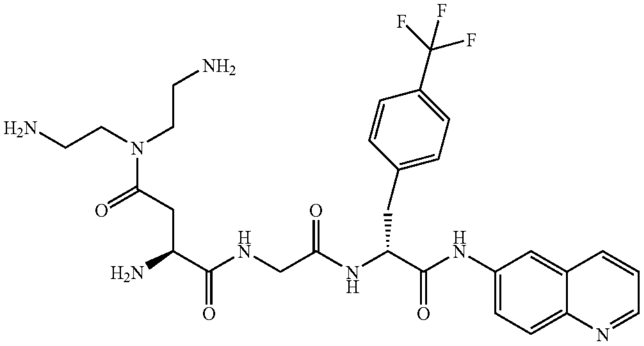 | B | 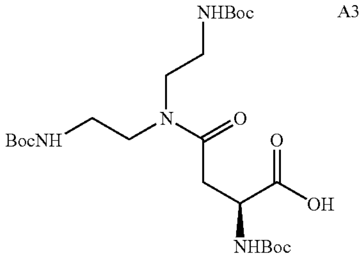 | A3 |
| 442 | 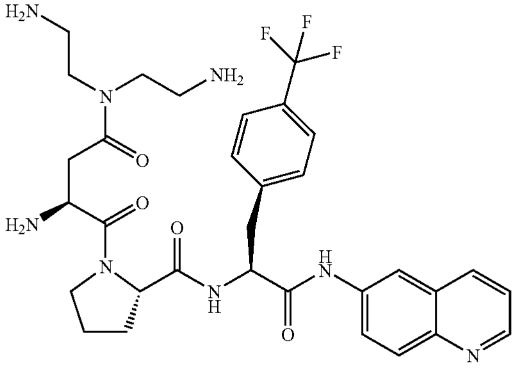 | B | 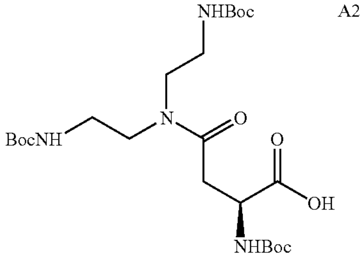 | A2 |
| 443 | 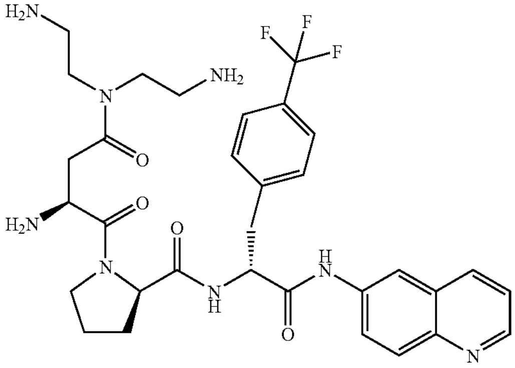 | B | 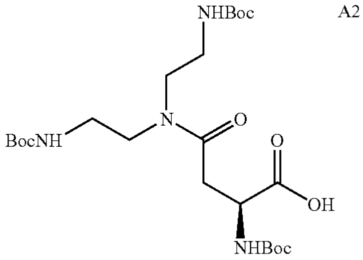 | A2 |
| 444 | 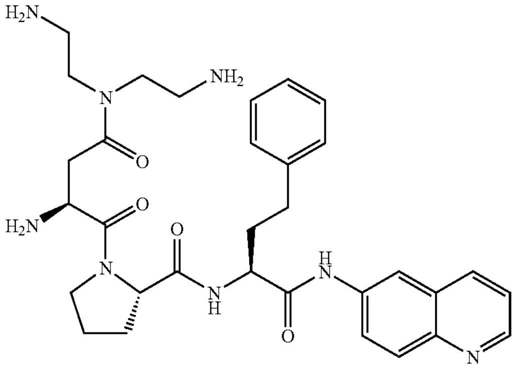 | B | 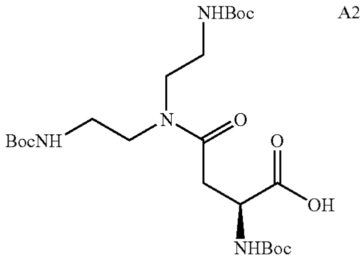 | A2 |

TABLE 4-continued

The following compounds were prepared in accordance with Scheme 36. The coupling and deprotection methods used are identified next to the relevant intermediate or final structure. A description of these methods appears after Scheme 35.

| Compound | Protected central acid structure (coupling procedure A1-A3) | | Capping amine structure | Ret. Time Min. (method) | MS m/e |
|---|---|---|---|---|---|
| 439 | 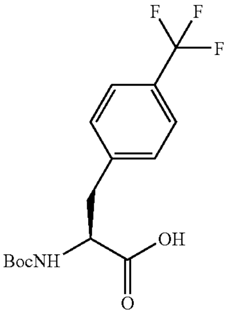 | A1 | 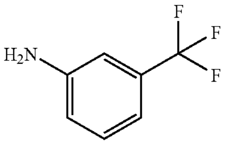 | 3.03 (H1) | 748 |
| 440 | 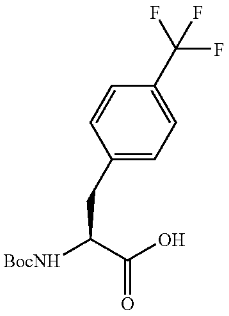 | A1 | 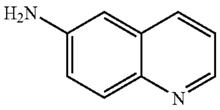 | 0.65 (H1) | 617 |
| 441 | 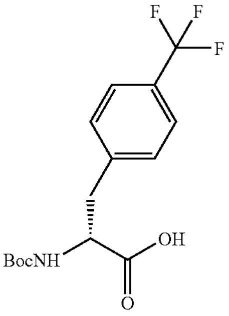 | A2 | 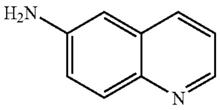 | 2.05 (H1) | 617 |
| 442 | 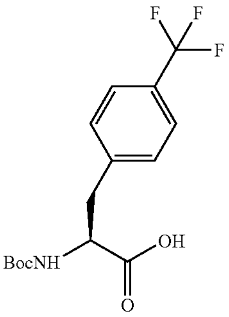 | A1 | 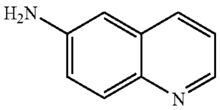 | 0.73 (H1) | 657 |

TABLE 4-continued

The following compounds were prepared in accordance with Scheme 36. The coupling and deprotection methods used are identified next to the relevant intermediate or final structure. A description of these methods appears after Scheme 35.

| | | | | | |
|---|---|---|---|---|---|
| 443 | 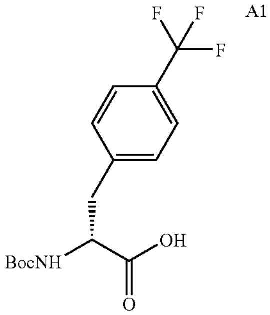 | A1 | 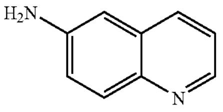 | 2.04 (H1) | 657 |
| 444 | 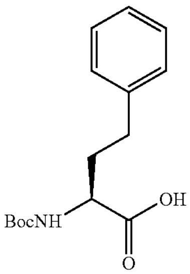 | A1 | 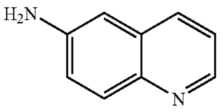 | 1.61 (H1) | 604 |

EXAMPLE 59

Preparation of Intermediate E1

Scheme E1

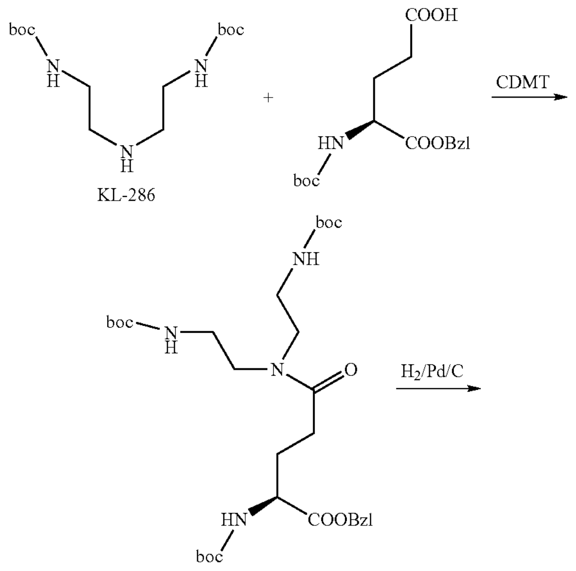

KL-286

SS-562

-continued

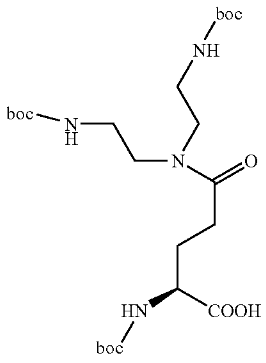

SS-564

SS-562 (36 g, 57.8 mmol) was dissolved in EtOH/water and Pd/C was slowly added. Air was removed and the mixture was stirred overnight under $H_2$ at r.t. Catalyst was filtered off through Celite, filtrate was evaporated to dryness to give SS-564 as white foam (30.6 g, 57.8 mmol, 100%).

EXAMPLE 60

Preparation of Compound 446

Scheme E2

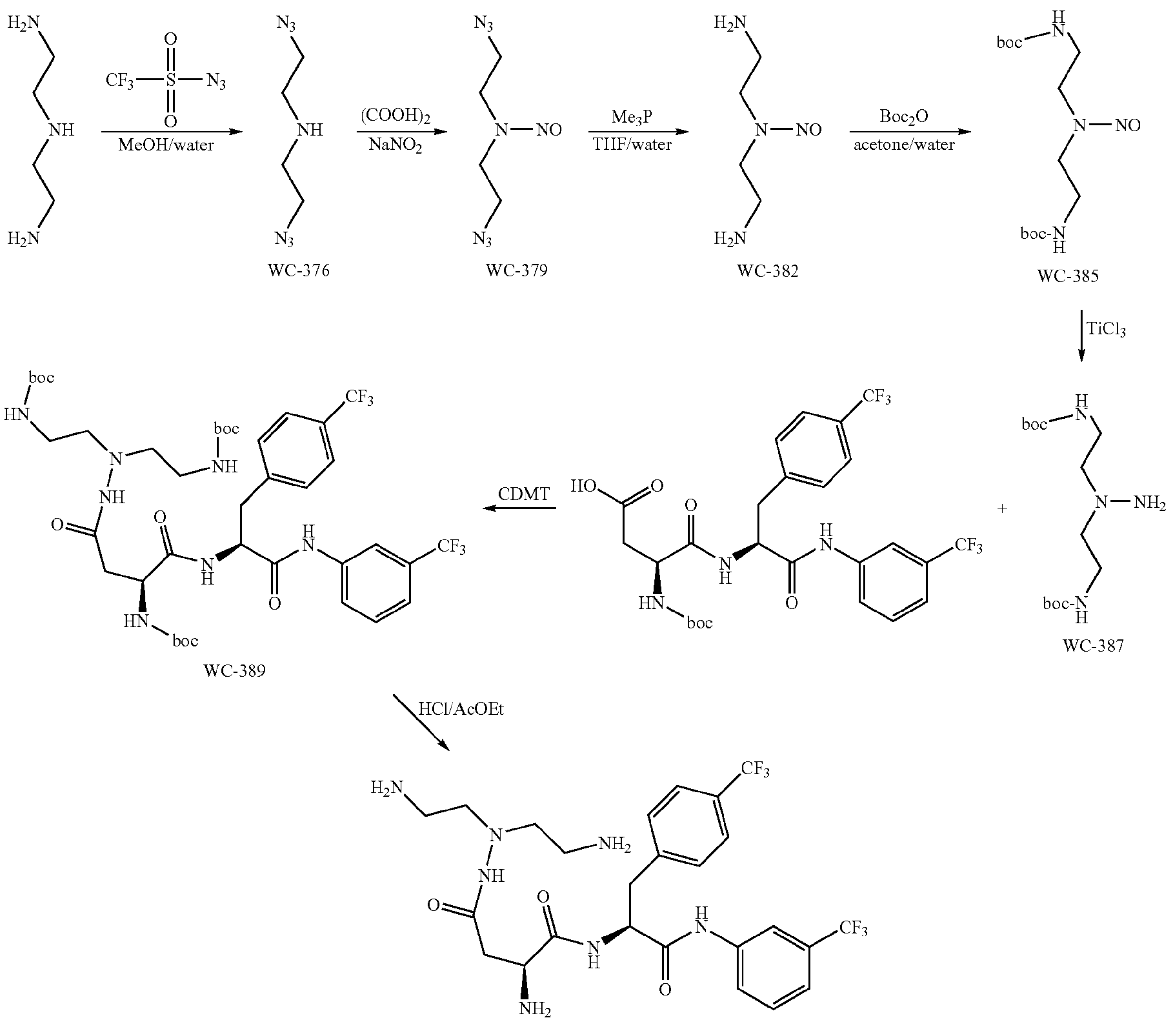

446

Step 1 (WC-379)

A suspension of sodium nitrite (13.4 g; 0.194 mol), oxalic acid dihydrate (24.4 g; 0.194 mol) and N,N-bis(2-azidoethyl) amine WC-376 (15 g; 0.097 mol) in dichloromethane (300 mL) was stirred vigorously at ambient temperature for 2.5 h. The progress of the reaction was followed by TLC (hexane/ethyl acetate 5/1). To the reaction mixture silica gel (20 g) and hexane (200 mL) were added, the solids were removed by filtration and were washed with mixture hexane/dichloromethane (1:1 vol/vol; 200 mL). Solvents were evaporated and the N-nitroso compounds WC-379 was obtained (15 g; 0.081 mol; 84% yield).

Step 2 (WC-382)

N,N-bis(2-azidoethyl)-N-nitrosoamine WC-379 (15 g; 0.081 mol) was dissolved in dry THF and trimethylphosphine (1M solution in THF; excess) was slowly added (caution: exothermic reaction) with cooling the reaction mixture in cold water bath. The solution of $Me_3P$ was added until foaming stopped. Stirring was continued overnight. After this time, the solution was evaporated and crude product WC-382 (12 g; quantitative yield) was used for next step.

Step 3 (WC-385)

The crude compound WC-382 (0.081 mol) was dissolved in acetone (160 mL) and 1M solution of sodium hydrogen carbonate in water was added until pH~9-10 was achieved. Next, $Boc_2O$ (53 g; 0.243 mol) was added in portions. After 3 h, acetone was evaporated and aqueous solution was extracted thoroughly with ethyl acetate. Combined organic layers were dried over magnesium sulphate anhydrous and then solvent was evaporated. Crude product was purified on column chromatography using gradient hexane/ethyl acetate from 10/1 to 2/1 (vol/vol). Pure product WC-385 was obtained (23.66 g; 0.071 mol; 88% yield).

Step 4 (WC-387)

The substrate WC-385 (2 g; 6.02 mmol) was dissolved in methanol (15 mL) and solution of titanium (III) chloride (3.7 g; 24.07 mmol) in 20 mL of water was added. After 1.5 h the reaction mixture was cooled in ice/water bath and potassium hydroxide (12 g) was added in portions for 40 minutes. The stirring was continued for additional 1 h at ambient temperature and after filtered. The filtrate was evaporated and after short, flash column chromatography (chloroform/methanol) crude product WC-387 (0.85 g) was obtained and without further purifications it was used for next step.

EXAMPLE 61

Preparation of Compound 447

Scheme E3

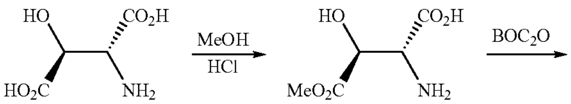

JPO-135 AJ-368

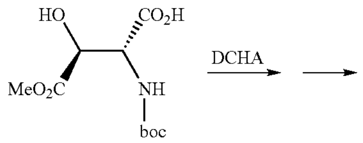

AJ-371

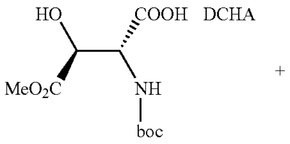

AJ-373

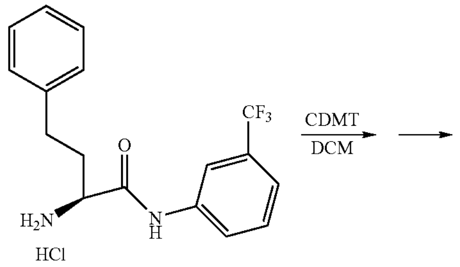

JAO-123

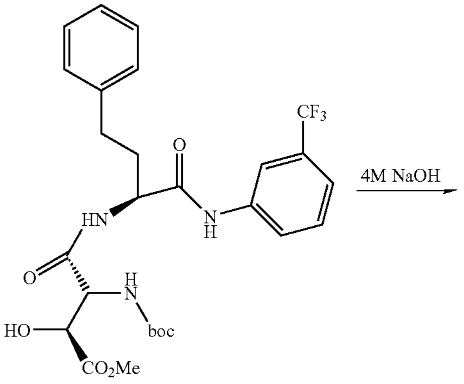

AJ-374

-continued

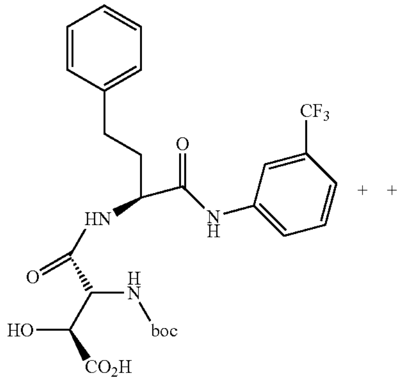

AJ-376

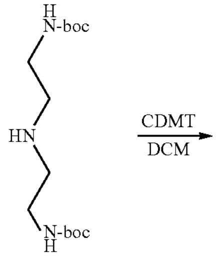

KL-201

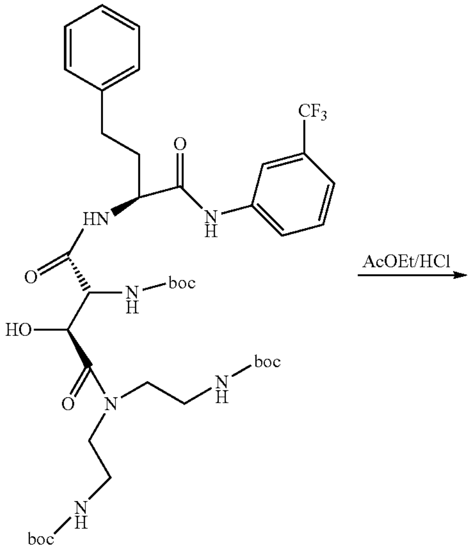

AJ-386

-continued

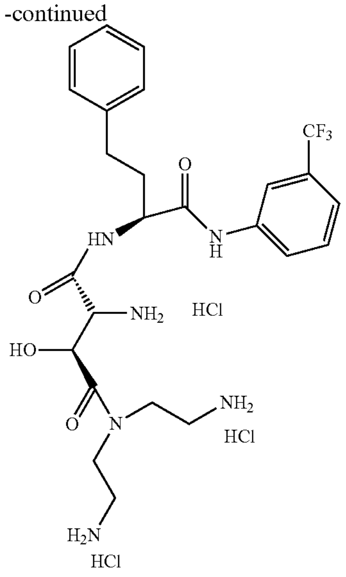

447

Step 1

To JPO-135 (2.2 g, 12 mmol) in solution: methanol (35 mL)/HCl conc., 2.2 mL) was stirred and refluxed for 4 hours. When no substrate was detected, reaction was evaporated to dryness. Product AJ-368 (2.4 g, yield 98%) was obtained as white precipitate.

Step 2

To AJ-368 (2.4 g, 12 mmol) in mixture: $CH_2Cl_2$ (10 mL)/DMF (20 mL) was added $Et_3N$ (4.1 mL, 29 mmol), this reaction was cooled to −5° C. and to this was added slowly $Boc_2O$ in DCM. This reaction mixture was stirred overnight at r.t. Next DCM was evaporated, 1M HCl was added to the residue, and extracted with ethyl acetate. Organic layer was dried over $MgSO_4$, filtered and evaporated in vacuum to give (2.2 g, yield 71%) of crude compound AJ-371. The product was used to the next step without any additional purification.

Step 3

To AJ-371 (2.2 g, in 1.8 ml diethyl ether was added dicyclohexylamine (1.66 mL, 8.36 mmol) in diethyl ether. Reaction was stirred overnight, precipitate was filtered and washed with hexane to give compound AJ-373 (3.5 g, yield 83%) as white solid.

Step 4

CDMT (0.8 g, 4.5 mmol) was dissolved in DCM, the solution was cooled to 0° C. and N-methylmorpholine (1.1 mL, 10 mmol) was added. After 10 minutes compound AJ-373 (1.9 g, 4.2 mmol) was added and the solution was stirred for additional 40 minutes. After that time the amine JAO-123 (1.5 g, 4.2 mmol) was added, and the mixture was stirred at ambient temperature overnight.

Next, reaction mixture was washed with water, 1M HCl, dried over $MgSO_4$, filtered and evaporated in vacuum to give product AJ-374 which was purified by column chromatography in ($CHCl_3$:MeOH, 400:1). Pure product AJ-374 (0.3 g, yield 13%) was obtained as white precipitate.

Step 5

Compound AJ-374 (0.3 g, 0.53 mmol) was dissolved in 0.03 ml of MeOH, and to this mixture was added 1 ml 4M NaOH. Reaction mixture was stirred at r.t. as long as no substrate was detected. Next reaction mixture was evaporated (from MeOH). To this was added 2M HCl to pH=2 and extracted with ethyl acetate. Organic layer was dried over $MgSO_4$, filtered and concentrated in vacuum to give product AJ-376 (0.28 g, yield 95%) as yellow precipitate.

Step 6

CDMT (0.1 g, 0.55 mmol) was dissolved in DCM, the solution was cooled to 0° C. and N-methylmorpholine (0.17 mL, 1.53 mmol) was added. After 10 minutes compound AJ-376 (0.28 g, 0.51 mmol) was added and the solution was stirred for additional 40 minutes. After that time the amine KL-201 (0.16 g, 0.51 mmol) was added, and the mixture was stirred at ambient temperature overnight.

Next reaction mixture was washed with water, 1M HCl, dried over $MgSO_4$, filtered and evaporated in vacuum to give product AJ-386 which was purified by column chromatography in ($CHCl_3$:MeOH, 700:1). Pure product AJ-386 (0.08 g, yield 18%) was obtained as white precipitate.

Step 7

To compound AJ-386 (0.08 g, 0.0953) was added AcOEt/HCl and stirred until no substrate was detected. Reaction mixture was evaporated in vacuum and to this was added diethyl ether and filtered. Crude compound AJ-390 was purified by HPLC chromatography to give product AJ-390 (10 mg, yield 20%) as pale brown precipitate.

EXAMPLE 62

Preparation of Compound 448

Scheme E4

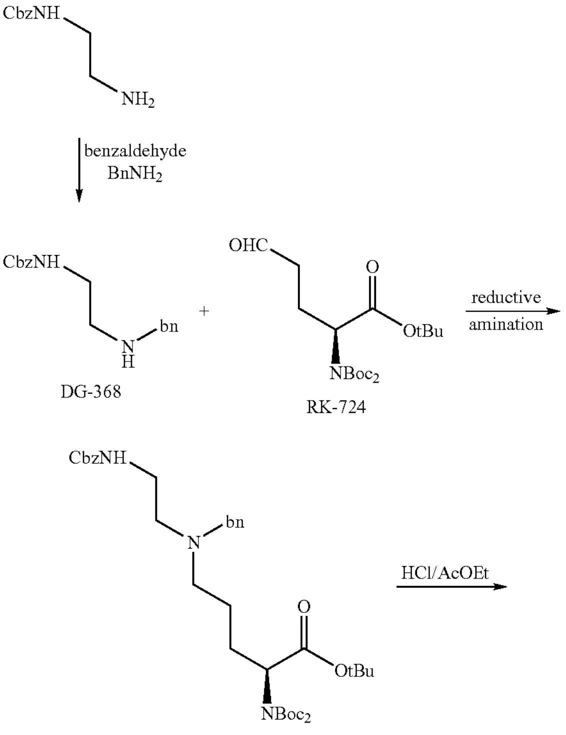

DG-368

RK-724

DG-374

-continued

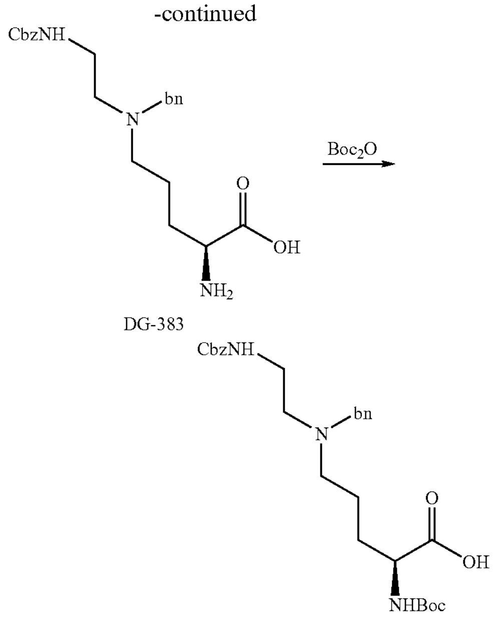

DG-383
DG-387

Step 1 DG-368

Benzyl-2-aminoethylcarbamate (5.00 g, 26.0 mmol) was dissolved in DCM (130 mL), cooled to 0° C. then benzaldehyde (2.47 mL, 24.0 mmol) and glacial acetic acid (7.37 mL, 129.0 mmol) were added and stirred at 0° C. for 1 h. NaBH(OAc)$_3$ (8.20 g, 39.0 mmol) was added portionwise and stirred overnight at r.t. The solution was washed with 1M HCl, brine and organic fraction was dried over MgSO4. The solvent removed in vacuum to give white solid (5.30 g, 18.63 mmol, 72%)

Step 2 DG-374

(5.16 g, 18.20 mmol) was dissolved in DCM (50 mL), cooled to 0° C. then RK-724 (6.40 g, 16.50 mmol) and glacial acetic acid (4.70 mL, 82.60 mmol) were added and stirred at 0° C. for 1 h. NaBH(OAc)$_3$ (5.25 g, 24.80 mmol) was added portionwise and stirred overnight at r.t. The solution was washed with 1M HCl, brine and organic fraction was dried over MgSO4. The solvent removed in vacuum to give white solid (6.50 g, 9.91 mmol, 60%)

Step 3 DG-387 t-Butyl ester DG-374 (6.50 g, 9.91 mmol) was dissolved in AcOEt (20 mL) and treated with 3.5M HCl (50 mL). The reaction mixture was stirred at r.t. for 3 h then solvent removed in vacuum. Crude product was used to next step.

DG-383 was dissolved in 2M NaOH until pH was about 11; next solution of Boc$_2$O (2.37 g, 10.90 mmol) in acetone (20 mL) was added dropwise and stirred overnight at r.t. Acetone was removed in vacuum and residue was acidified with 2M HCl to pH~2. The solution was thoroughly washed with DCM. The organic fractions were washed with brine and dried over MgSO4. The solvent removed in vacuum and crude product was purified by flash chromatography using DCM/MeOH 200/1-100/1-50/1-20/1-10/1 solvent system to give DG-387 as a white foam (1.91 g, 3.82 mmol, 39% (two steps))

EXAMPLE 63

Preparation of Compound 449

Scheme E5

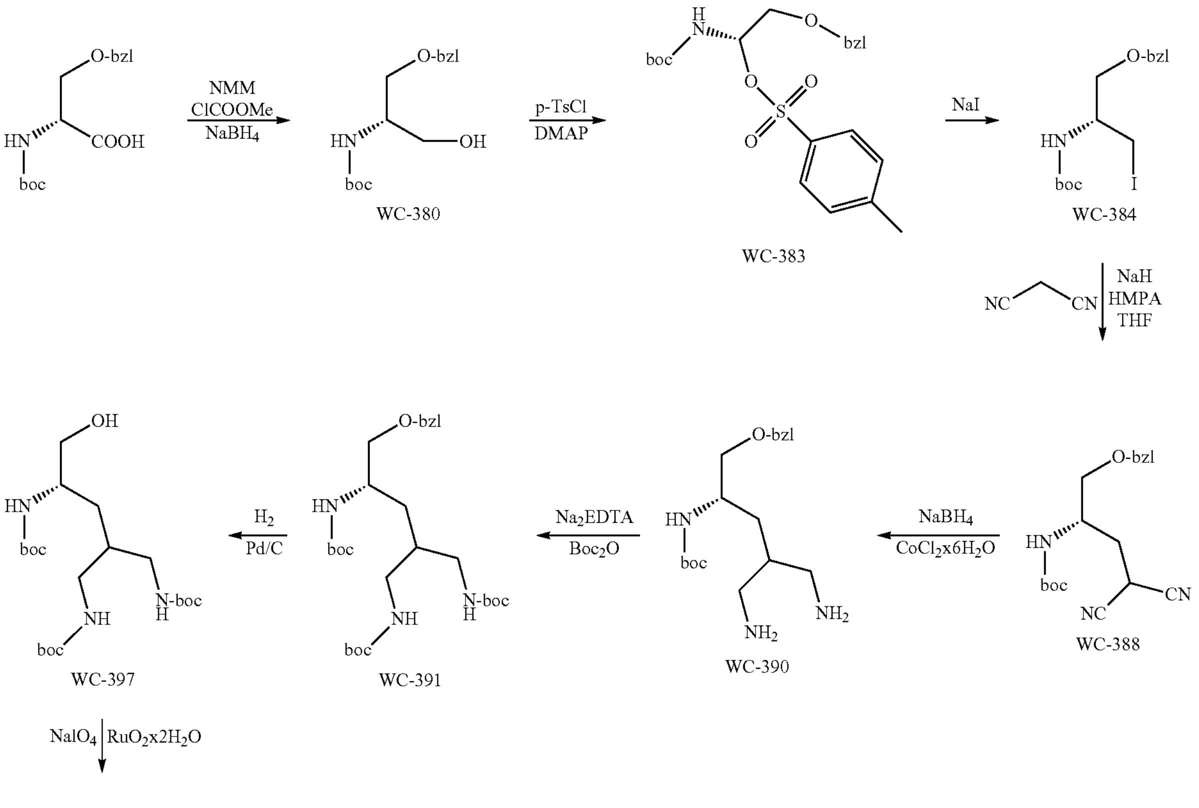

-continued

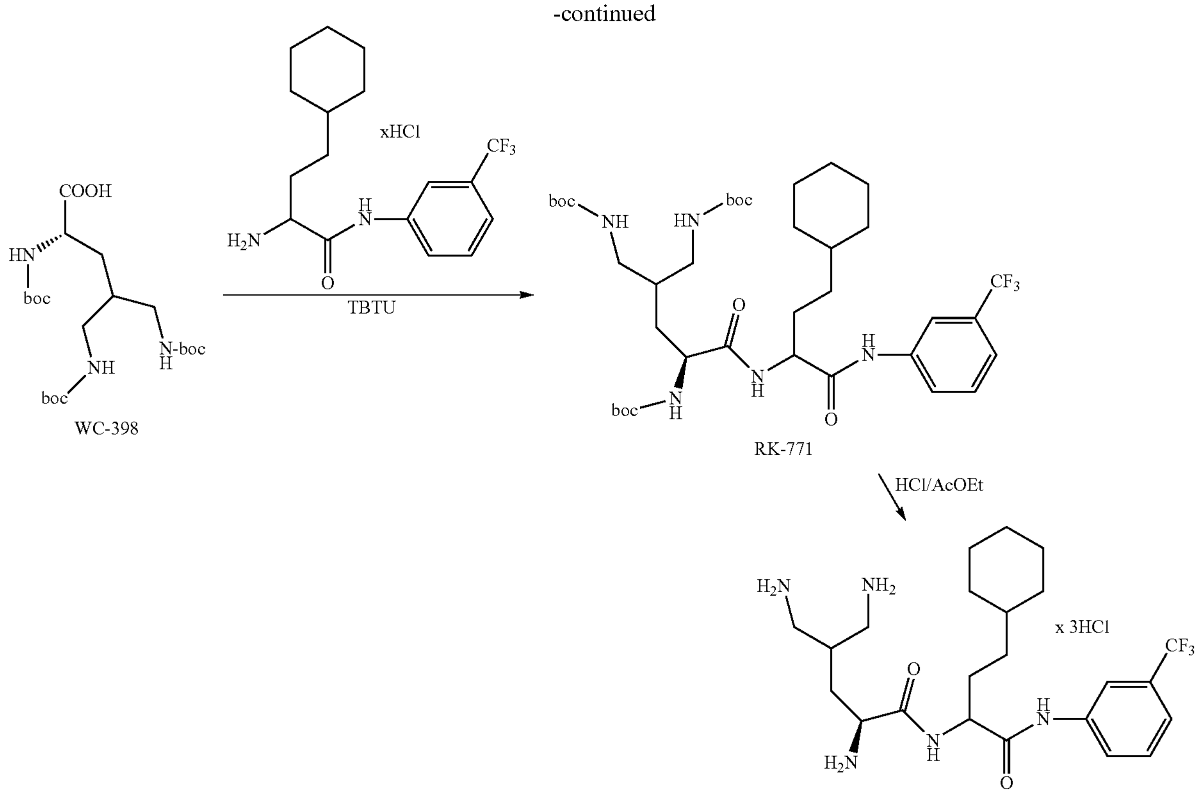

WC-398

RK-771

449

Step 1 WC-380

Boc-D-Ser (Bzl)-OH (1.15 g, 3.89 mmol) was dissolved in THF (10 mL) then N-methylmorpholine (0.47 mL, 4.27 mmol) was added and cooled to −20° C. To the mixture methyl chloroformate (0.33 mL, 4.27 mmol) was added dropwise and stirred at −10° C. for 20 minutes. After this time the solution was filtered and filtrate added dropwise to the solution of $NaBH_4$ (0.37 g, 9.72 mmol) in water (10 mL) at 0° C. then stirred overnight at r.t. After night layers was separated and aqueous fraction was washed witch AcOEt (×2). All organic fractions were connected and washed with 1M NaOH, dried over $MgSO_4$, filtered and solvent removed in vacuum to give white foam (1.06 g, 3.76 mmol, 92%)

Step 2 WC-383

WC-380 (1.06 g, 3.76 mmol) was dissolved in DCM (10 mL), cooled to 0° C. then DMAP (46 mg, 0.37 mmol) and TosCl (1.07 g, 5.64 mmol) were added and mixed at 0° C. for 30 minutes. Next to the mixture solution of $Et_3N$ (0.78 mL, 5.64 mmol) in DCM (3 mL) was added and stirred for 1.5 h at r.t. The reaction mixture was diluted with DCM and washed with water (×2), 1M HCl (×2), brine, filtered and solvent removed in vacuum. Crude product was purified by flash chromatography using hexane/AcOEt 20/1-15/1-10/1-5/1 solvent system to give viscous colorless oil (1.13 g, 2.60 mmol, 69%)

Step 3 WC-384

WC-383 (1.13 g, 2.60 mmol) was dissolved in anhydrous acetone (25 mL) then NaI (3.89 g, 26.00 mmol) was added and stirred at r.t. for 2 days. The reaction mixture was filtered and filtrate concentrated in vacuum. Oily residue was triturated with $Et_2O$, filtered once again and filtrate washed with 10% $Na_2S_2O_7$. The solution dried over $MgSO_4$, filtered and solvent removed in vacuum to give light oil mol, (407 mg, 1.04 mmol, 40%) with crystallized on standing.

Step 4 WC-388

Malononitrile (1.10 mmol, 72 mg) was dissolved under argon in THF/HMPA (6 mL/4 mL) solvent system and NaH (60% in mineral oil 1.09 mmol, 42 mg) was added. The reaction mixture was mixed at r.t. for 30 minutes next a solution of WC-384 (407 mg, 1.04 mmol) in anhydrous THF (10 mL) was added and stirred overnight at r.t. under argon. The reaction was quenched with 1M $NH_4Cl$ and extracted thoroughly with $Et_{20}$. All organic layers were washed with 1M $NH_4Cl$ and brine, dried over $MgSO_4$, filtered and solvent removed in vacuum. The crude product was purified by flash chromatography using hexane/ethyl acetate 10/1-5/1-2/1 solvent system to give 207 mg, 0.63 mmol, 60% expected product.

Step 5 WC-390

WC-388 (204 mg, 0.62 mmol) was dissolved in THF (6 mL) and cobalt (II) chloride hexahydrate (737 mg, 3.10 mmol) was added in one portion. The mixture cooled to −10° C. and $NaBH_4$ was added portionwise. Next the stirring was continued in these conditions for 15 minutes and 1 hour at r.t. The crude mixture was used to next step (WC-391)

Step 6 WC-391

To the mixture (WC-390) 1M NaOH was added to pH=10 then $Boc_2O$ (406 mg, 1.86 mmol) and EDTA $Na_2 \times 2H_2O$ (1.15 g, 3.10 mmol) were added and mixed overnight at r.t. The mixture was filtered through Celite and filtrate concentrated in vacuum. The residue was dissolved in DCM and washed with 0.5 M HCl, dried over $MgSO_4$, filtered and solvent removed in vacuum. Crude product was purified by flash chromatography using hexane/ethyl acetate 20/1-15/1-10/1-5/1 solvent system to give white foam (134 mg, 0.25 mmol, 40% after two steps)

Step 7 WC-397

WC-391 (134 mg, 0.25 mmol) was dissolved in methanol (5 mL) then 10% Pd/C (catalytic amount) was added and reaction mixture stirred overnight at r.t. under hydrogen atmosphere. The mixture was filtered through Celite and filtrate concentrated in vacuum. Crude product was purified by flash chromatography using hexane/ethyl acetate 5/1-3/1-1/1 solvent system to give white foam (78 mg, 0.174 mmol, 70%)

Step 8 WC-398

WC-397 (78 mg, 0.174 mmol) was dissolved in acetone/water (2 mL/1.2 mL) solvent system then $NaIO_4$ (372 mg, 1.74 mmol) and $Ru_2O{\times}H_2O$ were added and mixed at r.t. for 2 hours. To the mixture iPr—OH (2 mL) was added and mixed for 30 minutes then the mixture was filtered through Celite. The filtrate concentrated in vacuum and residue purified by flash chromatography using $CHCl_3$/MeOH 150/1-100/1-50/1 solvent system, followed by second flash chromatography using ethyl acetate solvent, hexane/ethyl acetate 5/1-2/1 as solvent system to give white foam (30 mg, 0.066 mmol, 28%)

EXAMPLE 64

Preparation of Compound 450 chromatography (silica gel, DCM:MeOH 500:1, 250:1), to give 2.6 g of product as a colorless oil.

EXAMPLE 65

Preparation of Compound 451

Scheme E7

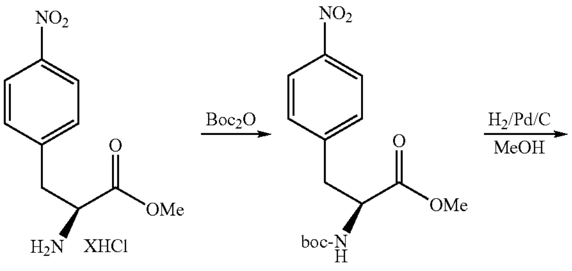

JAO-126

Scheme E6

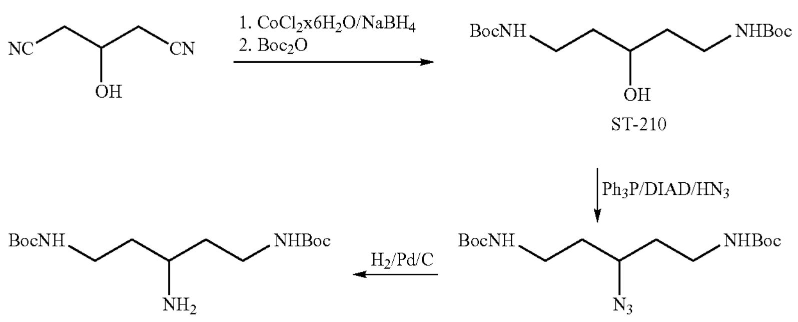

ST-210

KC-174

KC-168

Step 1 ST-210

3-hydroxypentanedinitrile was dissolved in MeOH, added $COCl_2{\times}6H_2O$, next the reaction mixture was cooled to 0° C. After several minutes was added slowly $NaBH_4$. The reaction mixture was stirred for 30 min at 0° C., next the mixture allowed to warm up to r.t., stirred overnight. The solvent was evaporated; to the residue was added water and 2N HCl, filtered through for Celite. The filtrate was washed with AcOEt. To the aqueous layer was added EDTA and alkalized to pH=10, the mixture was stirred for 1 h at r.t., next added $Boc_2O$ (dissolved in acetone). The reaction mixture was stirred at r.t. overnight. The acetone was evaporated, residue extracted with AcOEt, organic layer washed with water, brine and dried over $MgSO_4$. Crude product was purified by silica gel column (hexane/AcOEt 60; 1, 10:1, 5:1, 2:1, 1:1), to give product as colorless oil which was crystallized from hexane/AcOEt to produce 4 g of white solid.

Step 2 KC-168

$Ph_3P$ was dissolved in dry DCM, the mixture cooled to −20° C., added DIAD, stirred for 30 min at −20° C. Next to the mixture was added $HN_3$, after 30 min added ST-210 (dissolved in DCM). The reaction mixture was stirred at −20° C. for 1 h, next allowed to warm to r.t. The reaction was monitored by TLC (9:1 chloroform:methanol). The solvent was evaporated ant the resulting residue was purified by flash -continued

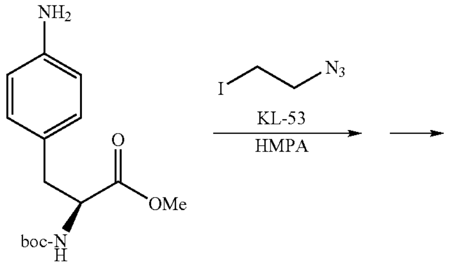

JAO-129

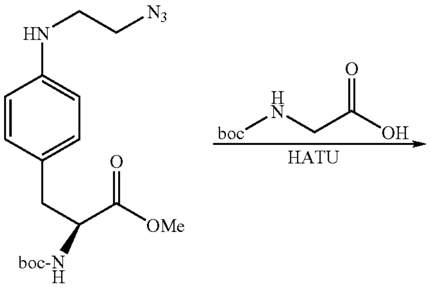

JAO-134

-continued

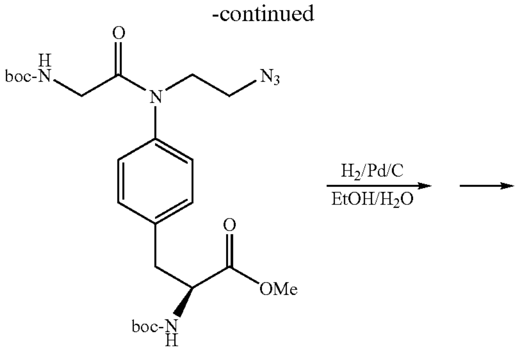

JAO-144

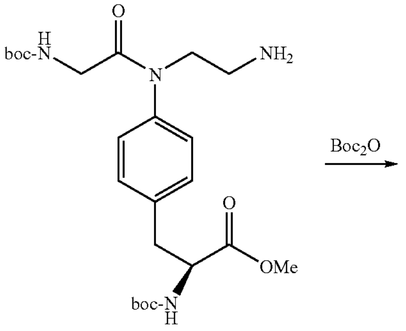

JAO-146

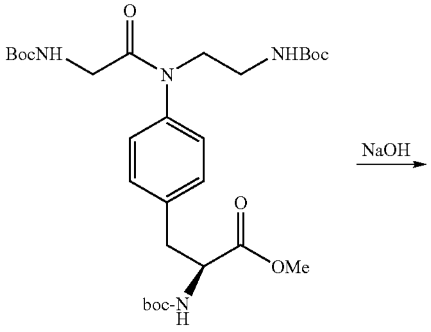

KO-203

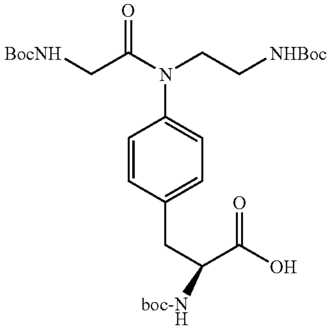

KO-207

Step 1 JAO-126

L-4-nitrophenylalanine methyl ester hydrochloride (1.87 g, 7.17 mmol) was suspended in dry dichloromethane (100 mL) and cooled to 0° C. To this suspension triethyl amine (2.49 mL, 17.93 mmol) was added followed by Boc2O (1.88 g, 8.61 mmol) addition. The reaction mixture was stirred overnight at r.t. The reaction mixture was washed thoroughly with 1 M HCl, brine and dried over MgSO4, filtered and concentrated to dryness to give JAO-126 as a slightly yellow crystalline solid (2.30 g, 7.14 mmol, 99% yield).

Step 2 JAO-129

To a solution of JAO-126 (2.30 g, 7.14 mmol) in methanol (15 mL) catalytic amount of 10% Pd/C was added. The reaction mixture was stirred overnight under 1 atmosphere of hydrogen. Next the reaction mixture was filtered through Celite and evaporated to dryness. The oily residue was purified on a silica gel column (500:1 CH2C12/methanol) to give JAO-129 as a orange crystalline solid (2.30 g, 7.14 mmol, 64% yield).

Step 3 JAO-134

To JAO-129 (1.37 g, 4.68 mmol) under argon NaHCO3 (790 mg, 9.36 mmol), KL-53 (1.40 g, 9.36 mmol) and HMPA (14 mL) were added. The reaction mixture was stirred overnight at ambient temperature. To the reaction mixture aqueous solution of citric acid was poured and it was washed thoroughly with diethyl ether. The organic extracts were combined and washed with brine and dried over MgSO4, filtered and concentrated. The oily residue was purified on a silica gel column (CH2C12) to give JAO-134 as a slightly orange crystalline solid (1.18 g, 3.25 mmol, 69% yield).

Step 4 JAO-144

To a solution of JAO-134 (1.18 g, 3.25 mmol) in DCM (17 mL) DIPEA (0.59 mL, 3.58 mmol), N-Boc-glycine (570 mg, 3.25 mmol) and HATU (1.36 g, 3.58 mmol) were added. The mixture was stirred at r.t. overnight. The reaction mixture was then washed with 5% NaHCO3, 1 M HCl, brine and dried over MgSO4, filtered and concentrated to dryness. The crude product was dissolved in methanol and stirred with charcoal at 40° C. for 3 h. Next it was filtered through Celite and evaporated to dryness to give JAO-144 as a slightly orange crystalline solid (1.56 g, 2.99 mmol, 92% yield).

Step 5 JAO-146

To a solution of JAO-144 (1.56 g, 2.99 mmol) in ethanol with 10% water (25 mL) catalytic amount of 10% Pd/C was added. The reaction mixture was stirred under 1 atmosphere of hydrogen for 5 h at r.t. Next the reaction mixture was filtered through Celite and concentrated. The oily residue was purified on a silica gel column (150:1 CH2C12/methanol) to give JAO-146 as a white crystalline solid (0.58 g, 1.17 mmol, 39% yield).

Step 6 KO-203

JAO-146 (0.58 g, 1.17 mmol) was suspended in dry dichloromethane (10 mL) cooled to 0° C. To this suspension triethyl amine (0.165 mL, 1.17 mmol) was added followed by $Boc_2O$ (0.256 g, 1.17 mmol) addition. The reaction mixture was stirred overnight at r.t. The reaction mixture was washed thoroughly with 1 M HCl, brine and dried over $MgSO_4$, filtered and concentrated to dryness. The residue was purified on a silica gel column ($CH_2Cl_2$/MeOH 150:1) to give KO-203 (220 mg, 0.37 mmol, 31% yield).

Step 7 KO-207

To the solution of KO-203 (220 mg, 0.37 mmol) in MeOH (5 mL) 4 M NaOH was added dropwise until pH=13. The mixture was stirred for 1 h at r.t. before evaporating the MeOH under reduced pressure. The residue was mixed with water and washed with ethyl ether. After acidifying the aqueous layer to pH~3 with 2 M HCl, the product was extracted with DCM, dried over $MgSO_4$ and concentrated under vacuum to give KO-207 (140 mg, 0.24 mmol, 67% yield).

EXAMPLE 66

Preparation of Compound 452

Scheme E8

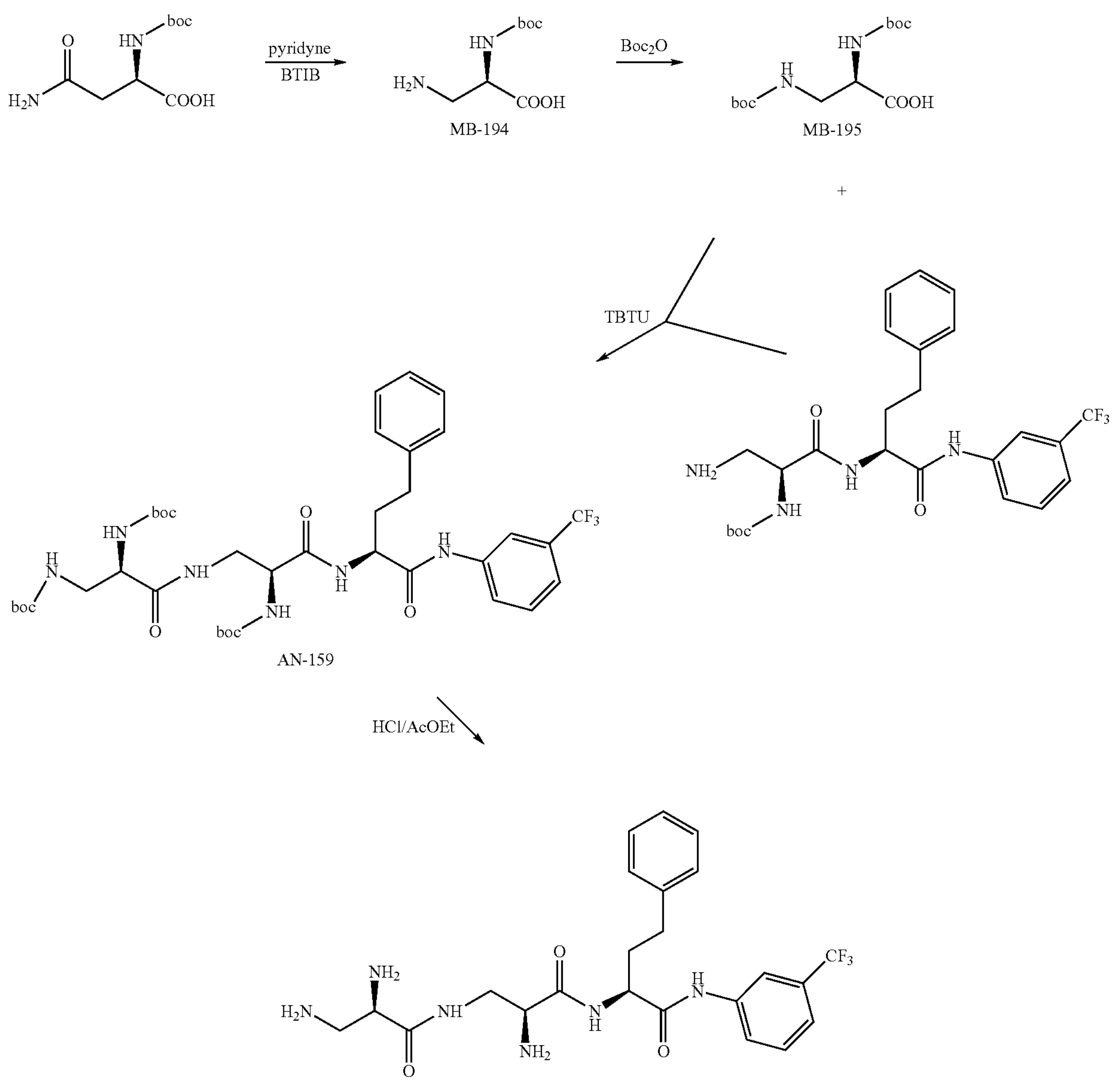

452

Step 1 MB-194

To the solution of Boc-D-Asn (3.00 g, 12.92 mmol) in DMF/water mixture (18 mL/7 mL) pyridine (2.08 mL, 25.80 mmol) and bis (trifluoroacetoxy)iodobenzene were added. The reaction mixture was stirred overnight at r.t. Crude product MB-194 was used in next reaction step without any further purification.

Step 2 MB-195

The reaction mixture MB-194 was alkalized to pH~9 using 1M NaOH. Next to the reaction mixture a solution of Boc$_2$O (4.23 g, 19.40 mmol) in acetone was added. The reaction mixture was stirred overnight at ambient temperature. The acetone was evaporated under vacuum and aqueous residue was washed twice with diethyl ether. The aqueous layer was acidified with 2M HCl to pH~2 and washed twice with ethyl acetate. The organic extracts were combined washed thoroughly with $Na_2S_2O_3$, brine and dried over $MgSO_4$, filtered and concentrated to dryness. The crude product was purified on a silica gel column (200:1 $CH_2Cl_2$/methanol) to give MB-195 (430 mg, 1.41 mmol, 11% yield).

EXAMPLE 67

Preparation of Compound 453

Compound 453 was prepared using standard coupling procedures according to the following scheme Scheme E9
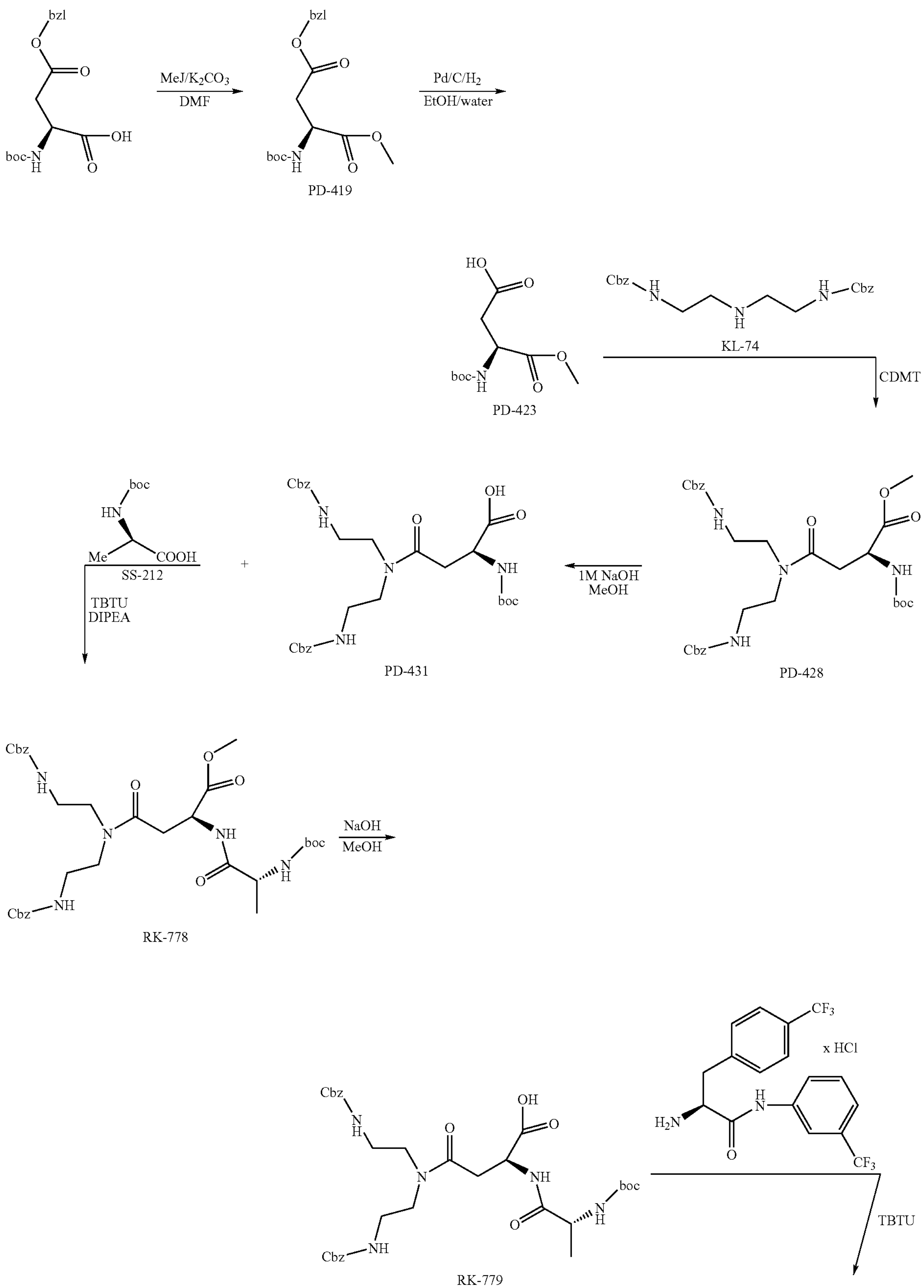

-continued
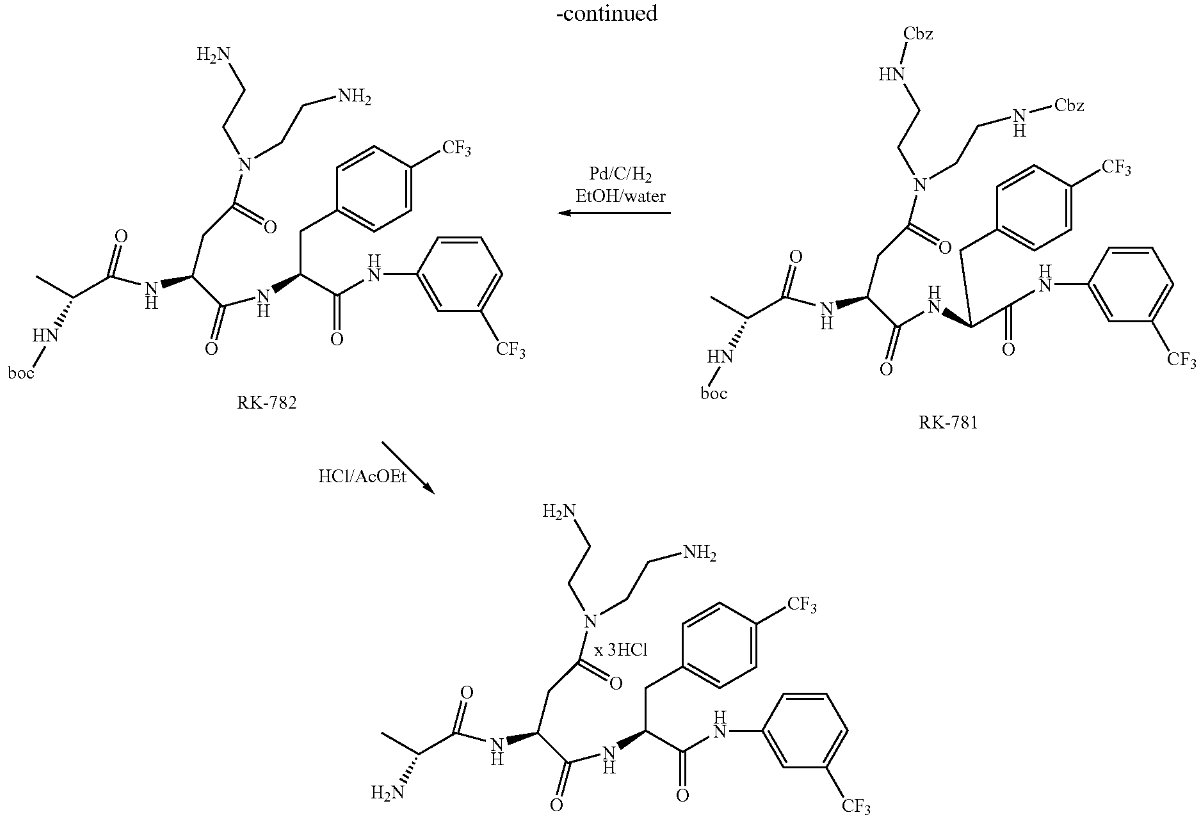
RK-782
RK-781
453
EXAMPLE 68
Preparation of Compound 454
Scheme E10
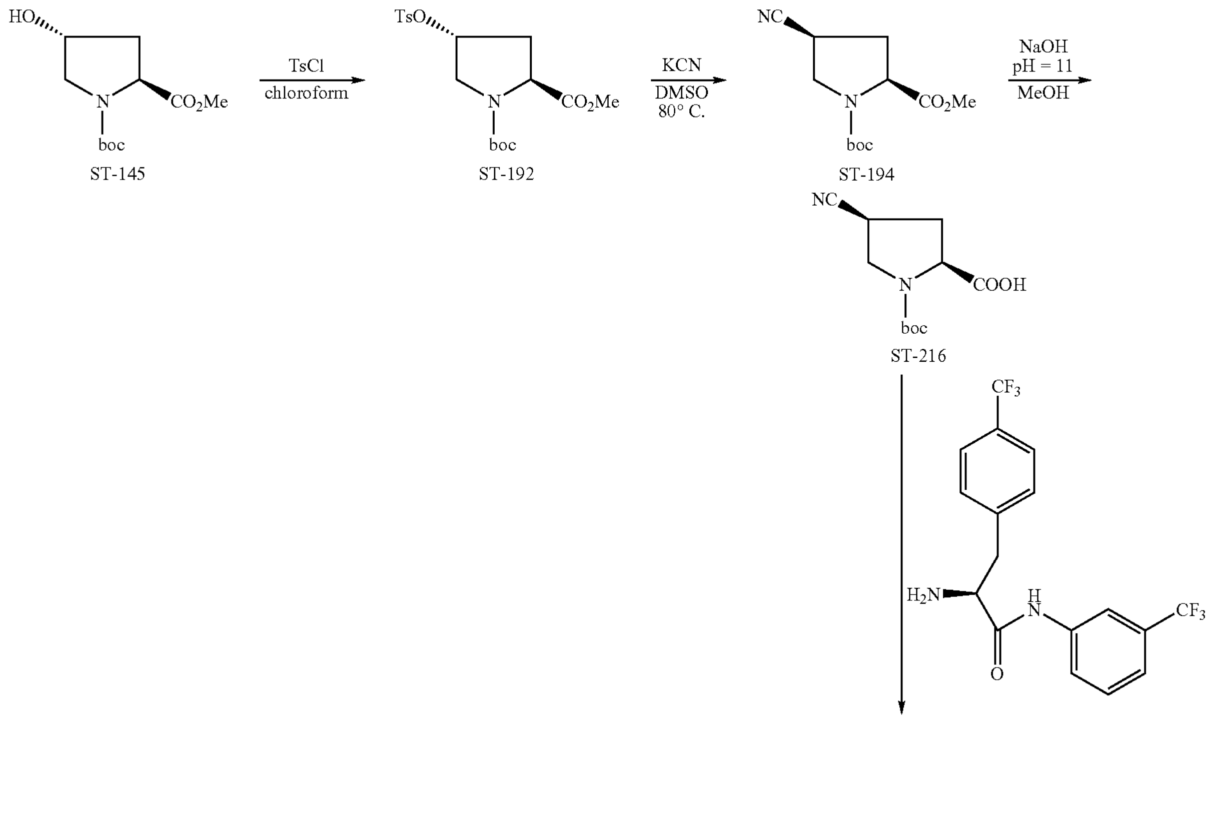
ST-145
ST-192
ST-194
ST-216

-continued

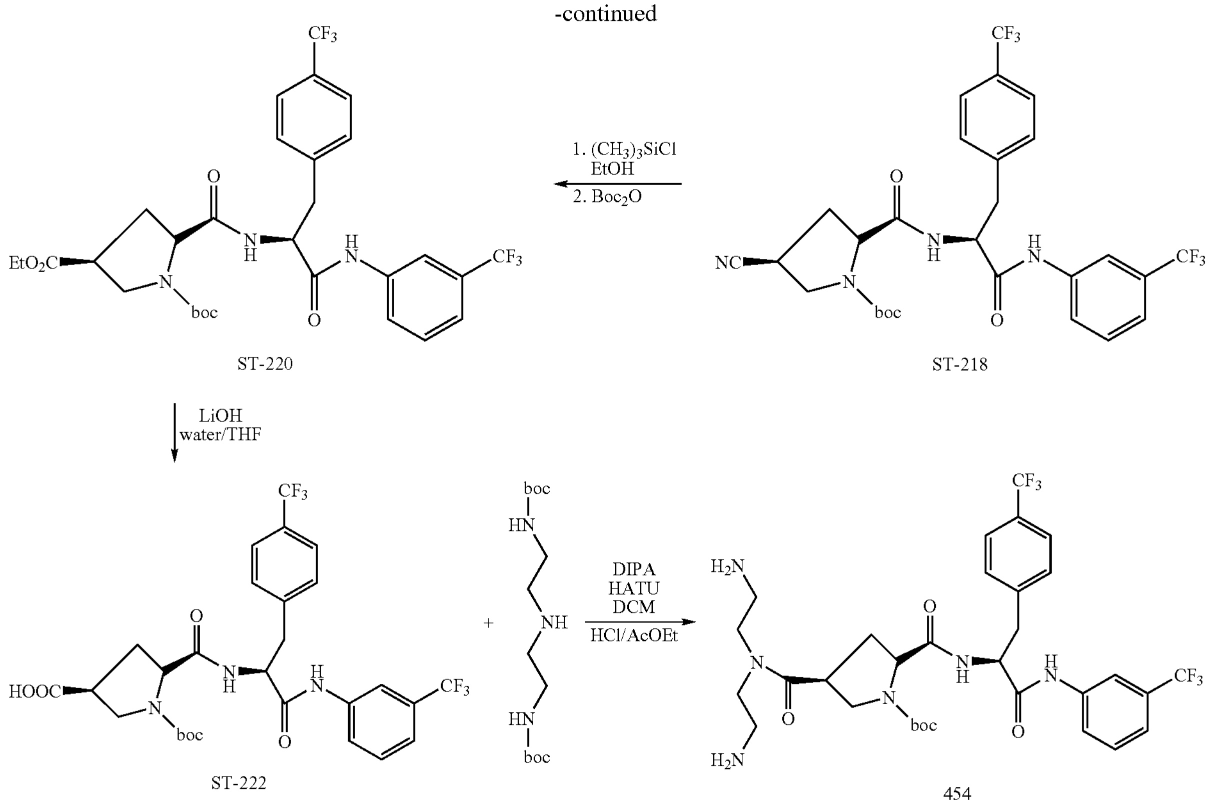

ST-218

ST-220

ST-222

454

Step 1

To compound ST-145 (1.5 g 6.1 mmol) dissolved in chloroform, was added pyridine (1.6 mL, 21.4 mmol) and TsCl (2.3 g 12.2 mmol). The mixture was stirred overnight at r.t., monitored by TLC (chloroform:methanol 9:1 visualization: ninhidrin and heating). To the reaction mixture was added 1M HCl (80 mL), then it was extracted with chloroform. Next organic phase was washed with 1M HCl, brine, dried over $MgSO_4$ and concentrated under vacuum to give colorless oil. The product was purified by flash column chromatography (silica gel, hexane, hexane:AcOEt 10:1, 5:1, 2:1, 1:1) to give 2.5 g of product ST-192 as colorless oil.

Step 2 ST-194

Compound ST-192 (2.3 g, 5.9 mmol) was dissolved in DMSO (40 mL), added KCN (0.7 g, 11.8 mmol) The mixture was refluxed at 80° C., 5 h, next cooled at r.t. and stirred overnight, (monitored by TLC chloroform:methanol 9:1 visualization:ninhidrin and heating). The mixture was diluted with t-BuOMe, and washed with water, brine. Organic phase was dried over $MgSO_4$ and concentrated under vacuum colorless yielding 3 g of oil. The product was purified by flash column chromatography (silica gel, hexane, hexane:AcOEt 50:1, 10:1, 5:1, 2:1, 1:1) to give 500 mg (34%) of white solid Step 3 ST-216

ST-194 (487 mg 1.9 mmol) was dissolved in MeOH (30 mL), the mixture alkalized to pH=11 with 4N NaOH. The reaction mixture was stirred at r.t. and monitored by TLC (chloroform:methanol: acetic acid 90:10:2 visualization:ninhidrin and heating). The solvent was evaporated, residue diluted with water, and acidified to pH=1-2, extracted with AcOEt. Organic layer was washed with brine and dried over $MgSO_4$. The solvent was evaporated, to give colorless oil which was used without purification for the next step.

Step 4 ST-218

CDMT (364 mg, 2.07 mmol) was dissolved in dry DCM, the mixture cooled to 0° C., added N-methylmorpholine (0.5 mL, 4.7 mmol). After 10 min was added ST-216 (451 mg, 1.88 mmol), after 45 min added PD-438 (745 mg, 1.88 mmol). Next the reaction mixture was allowed to warm up to r.t. and stirred overnight, (monitored by TLC; chloroform: methanol 9:1 visualization:ninhidrin and heating). The reaction mixture was diluted DCM, washed with 10% citric acid, 5% $NaHCO_3$, brine and dried over $MgSO_4$. The product was purified by flash column chromatography (silica gel, hexane, hexane:AcOEt 60:1, 20:1, 10:1, 5:1, 3:1) to give 620 mg of product ST-218 (55%)

Steps ST-220

Trimethylsilyl chloride (2.5 mL) was dissolved in EtOH (5 mL) (anhydride) at 0° C., to the mixture added ST-218 (620 mg) (dissolved in dry DCM 15 mL). The reaction mixture was allowed to warm up to r.t. and stirred overnight, monitored by TLC (chloroform:methanol 9:1 visualization:ninhidrin and heating). The reaction was quenched water, next alkalized 5% $Na_2CO_3$ to pH 9-10 and extracted with DCM. To organic layer was added $Boc_2O$ (300 mg), stirred at r.t. When the reaction was completed, concentrated under vacuum, crude product 1.65 g ST-220 used to next step ST-222.

Step 6 ST-222

Compound ST-220 (1.65 g, 642 mg, 1.04 mmol) was dissolved in THF (20 mL), cooled to 0° C., added LiOH (44 mg, 1.04 mmol) (dissolved in water 10 mL). The reaction mixture was allowed to warm up to r.t. and stirred. When the reaction was completed, concentrated under vacuum, producing crude product ST-222 as orange oil 540 mg, which was used for the next step Step 7 ST-225

Compound ST-222 (540 mg, 0.87 mmol) was dissolved in dry DCM, added KL-86 (318 mg, 1.05 mmol) and DIPA (0.2 mL, 1.05 mmol). After several minutes to the reaction mixture was added HATU (398 mg, 1.05 mmol), stirred over night at r.t., monitored by TLC (chloroform:methanol 9:1 visualization:ninhidrin and heating). The reaction mixture was diluted DCM, washed with 10% citric acid, 5% $NaHCO_3$, brine, dried over $MgSO_4$ and concentrated under vacuum. The product was purified by flash column chromatography (silica gel, hexane, hexane:AcOEt 20:1, 10:1, 5:1, 2:1, 1:1) to give 200 mg (25%) of ST-225.

Step 8 Compound 454

Compound ST-225 (150 mg, 0.17 mmol) was treated with AcOEt/HCl 4M (30 mL), the reaction mixture was stirred for 1.5 h at r.t. After this time the solvent was evaporated, residue treated with ether. The precipitate was filtered off, to give 40 mg (33%) of compound 454.

EXAMPLE 69

Preparation of Compound 455

Scheme E11

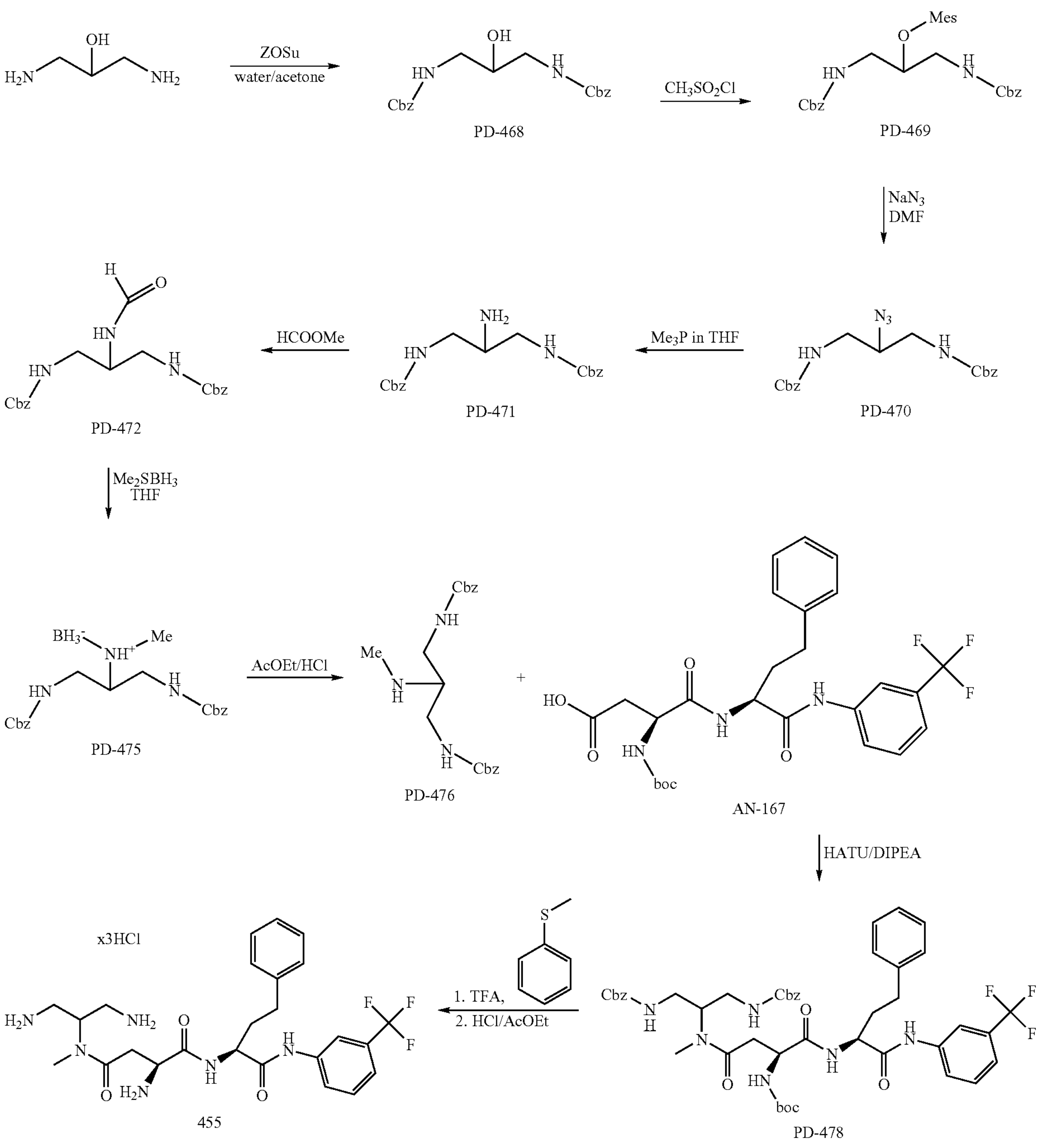

PD-468 PD-469 PD-470 PD-471 PD-472 PD-475 PD-476 AN-167 PD-478 455

Step 1PD-468

1,3-diamino-2-hydroksypropane (0.67 g, 7.44 mmol) was dissolved in water (15 mL) and then 5% $NaHCO_3$ aq was added followed by addition of solution of CBzOSu (3.7 g, 14.88 mmol) in acetone (10 mL). The reaction mixture was stirred about 2 h and additional portion of 5% $NaHCO_3$ aq was added (to increase to adjust pH to 10) and the mixture was stirred for 4 h at ambient temperature. The reaction mixture was filtered to give PD-468 as a white solid (2.3 g, 6.42 mmol, 86% yield).

Step 2 PD-469

To the solution of PD-468 (2.3 g, 6.42 mmol) in DCM (30 mL) was added TEA (1.42 mL, 10.27 mmol). Next the reaction mixture was cooled 0° C. and mesyl chloride was added dropwise (0.79 mL, 10.27 mmol). The reaction mixture was stirred at ambient temperature for 4 h. The reaction mixture was washed with 1M HCl (×3), 5% $NaHCO_3$ (×3), brine and dried over $MgSO_4$. Solvent was removed under reduced pressure to give PD-469 (2.7 g, 6.19 mmol, 96.7% yield).

Step 3 PD-470

To the solution of PD-469 (2.7 g, 6.2 mmol) in DMF (10 mL) $NaN_3$ was added. The reaction mixture was refluxed overnight. Reaction mixture was diluted with water and was washed thoroughly with DCM. Next organic layer was washed with $Na_2S_2O_3$ and brine, dried over anhydrous $MgSO_4$. Solvent was evaporated to dryness to give PD-470 (2 g, 5.2 mmol, 84.3% yield).

Step 4 PD-471

PD-470 (2 g, 5.2 mmol) was dissolved in THF/water (4 mL/0.4 mL) and $Me_3P$ was added. The reaction mixture was stirred overnight at ambient temperature. The solvent was evaporated under vacuum to dryness to give crude PD-471 (2.18 g, 6.09 mmol).

Step 5 PD-472

PD-471 (2.18 g, 6.09 mmol) was suspended in methyl formate (20 mL). The reaction mixture was stirred for 3 days at 40° C.). Next the reaction mixture was filtered to produce white solid PD-472 (1.31 g, 3.39 mmol, 56.9% yield).

Step 6 PD-475

PD-472 (1.31 g, 3.39 mmol) was dissolved in THF (10 mL) and $Me_2S{\times}BH_3$ (0.8 mL, 8.49 mmol) was added. The reaction mixture was stirred overnight at ambient temperature. The reaction was quenched by addition dropwise addition of water. Then THF was evaporated under vacuum. The water layer was extracted with AcOEt and the extract was dried over $MgSO_4$. Solvent was evaporated to give PD-475 (1.27 g, 3.29 mmol, 97.6% yield).

Step 7 PD-476

PD-475 (1.27 g, 3.29 mmol) was dissolved in ethyl acetate (2 mL) and treated with hydrogen chloride (4.0M solution in ethyl acetate, 10 mL). The reaction mixture was stirred over 20 minutes at ambient temperature and next ethyl ether was added (about 20 mL). Precipitate was filtered off and washed with ether to give white crystalline solid PD-476 (1.21 g, 2.96 mmol, 90% yield).

EXAMPLE 70

Preparation of Compound 456

Scheme E12

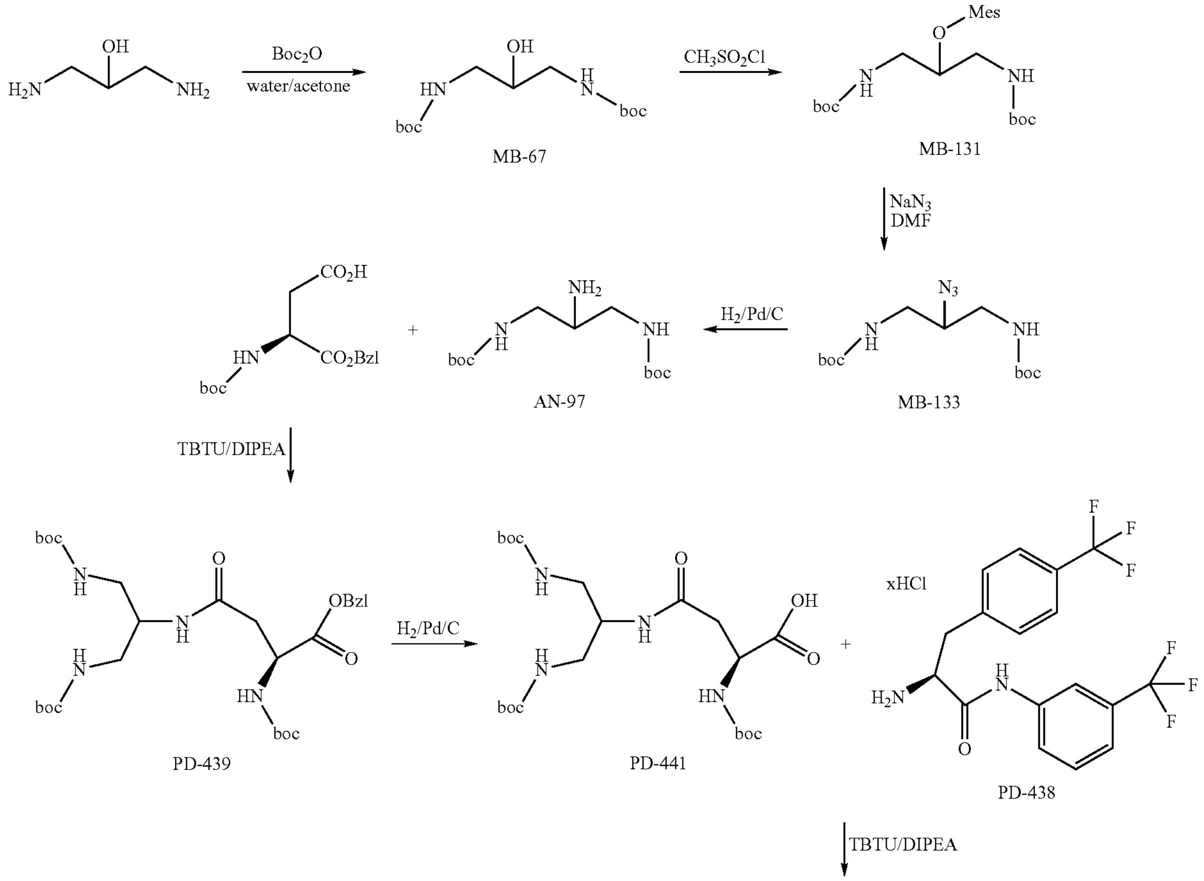

MB-67

MB-131

AN-97

MB-133

PD-439

PD-441

PD-438

-continued

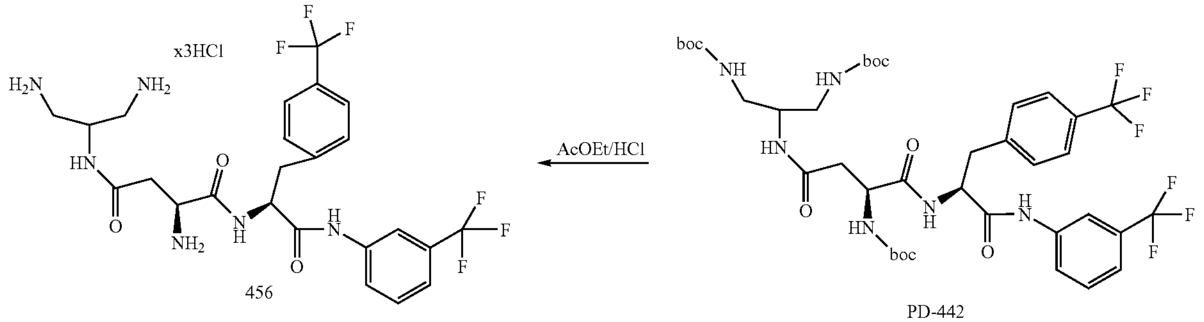

x3HCl 456 PD-442

Step 1 MB-67

1,3-diamino-2-hydroksypropane (110 mg, 1.23 mmol) was dissolved in water (10 mL) and then 5% $Na_2CO_3$ aq was added (pH mixture about 10), next solution of $Boc_2O$ (1.07 g, 4.92 mol) in acetone (4 mL) was added. The reaction mixture was stirred about 2 h and additional portion of 5% $Na_2CO_3$ aq was added (to adjust pH to 10) and the mixture was stirred overnight at ambient temperature. Acetone was evaporated under vacuum and aqueous residue was washed twice with diethyl ether. Water layer was acidified with 2M HCl to pH1 and the mixture was washed thoroughly with AcOEt. The organic layer was washed with brine and dried over $MgSO_4$. $MgSO_4$ was filtered off and solvent was removed under reduced pressure. Product was purified on silica gel using chloroform/methanol, (50:1) solvent system to give MB-67 (224 mg, 0.77 mmol, 62% yield).

Step 2 MB-131

To MB-67 (224 mg, 0.77 mmol) dissolved in DCM (10 mL) TEA (0.09 mL, 1.23 mmol) was added. Reaction mixture was cooled to 0° C. and mesyl chloride was added (0.095 mL, 1.23 mmol). The reaction mixture was stirred 1 h at ambient temperature. Organic phase was washed with 1M HCl, 5% NaHCO3, brine, dried over MgSO4 and concentrated to give MB-131 (285 mg, 0.77 mmol, 100% yield).

Step 3 MB-133

To the solution of MB-131 (285 mg, 0.77 mmol) in DMF (10 mL) NaN3 (100 mg, 1.54 mmol) was added. Reaction mixture was heated overnight. Reaction mixture was diluted with water and was washed thoroughly with DCM. Next organic layer was washed with $Na_2$S2O3 (to remove residue of DMF) and brine, dried over anhydrous MgSO4. Solvent was evaporated to dryness to give MB-133 (189 mg, 0.6 mmol, 75% yield).

Step 4 AN-97

To the solution of MB-133 (189 mg, 0.634 mmol) in EtOH/water (5 mL/0.5 mL) under argon was added 10% Pd/C catalyst (catalytic amount). The mixture was stirred under 1 atmosphere of hydrogen at ambient temperature (6 h). The mixture was filtered through Celite and evaporated to dryness to give AN-97 (165 mg, 0.570 mmol, 90% yield).

Step 5 PD-439

To the solution of Boc-AspOBzl (200 mg, 0.625 mmol) in methylene chloride (7 mL) DIPEA (0.11 mL, 0.625 mmol), hydrochloride of amine AN-97 (165 mg, 0.57 mmol) and TBTU (200 mg, 0.625 mmol) were added. The mixture was stirred at r.t. overnight. Then the reaction mixture was diluted with methylene chloride and washed with 1M $K_2CO_3$, 1M HCl, brine and dried over $MgSO_4$. Product was crystallized from DCM:hexane to give PD-439 (255 mg, 0.428 mmol, 75% yield).

Step 6 PD-441

To the solution of PD-439 (255 mg, 0.428 mmol) in EtOH/water (15 mL/1.5 mL) was added 10% Pd/C catalyst. The mixture was stirred under 1 atmosphere of hydrogen at ambient temperature (6 h). The mixture was filtered through Celite and evaporated to dryness to give PD-441 (200 mg, 0.396 mmol, 93% yield).

EXAMPLE 71

Preparation of Compound 457

Scheme E13

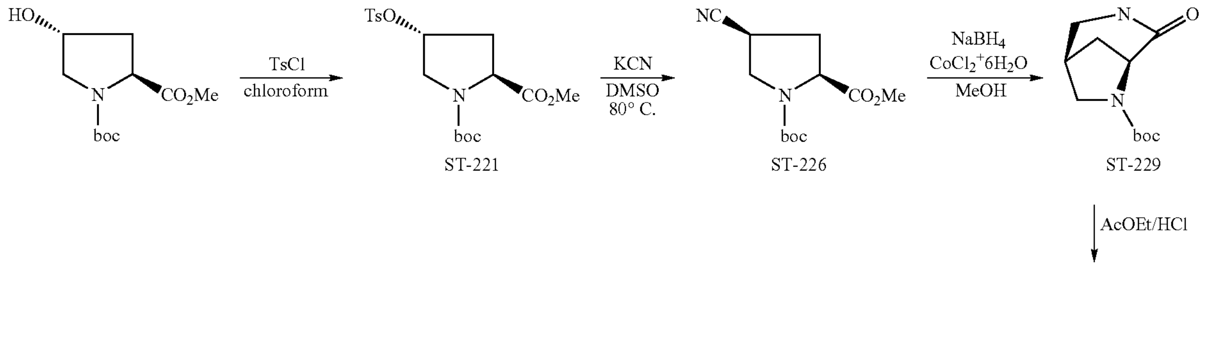

ST-221 ST-226 ST-229

-continued

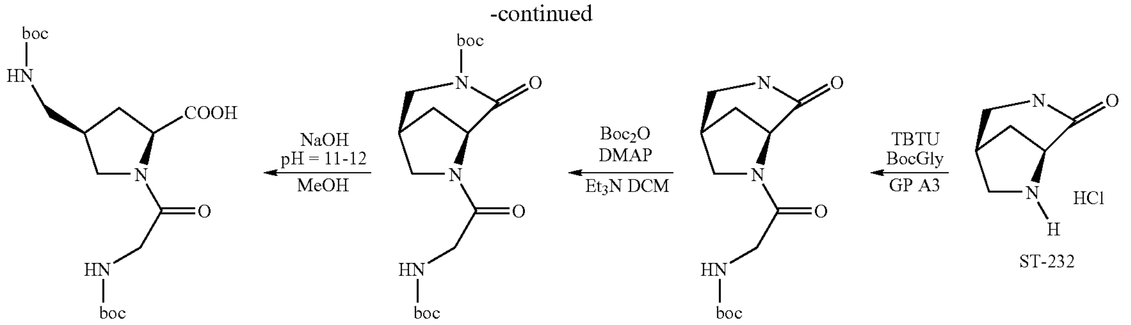

ST-236 ST-234 ST-233 ST-232

Step 1 ST-221

To compound ST-145 (10 g 41 mmol) dissolved in chloroform (200 mL), was added pyridine (11 mL, 143 mmol) and tosyl chloride (15.5 g, 82 mmol). The mixture was stirred overnight at the r.t., monitored by TLC (chloroform:methanol 9:1 visualization: ninhidrin and heating). To the reaction mixture was added 1M HCl (80 mL), then extracted with chloroform. Next organic phase was washed with 1M HCl, brine, dried over $MgSO_4$ and concentrated under vacuum to give colorless oil. The product was purified by flash column chromatography (silica gel, hexane, hexane:AcOEt 10:1, 5:1, 2:1, 1:1) to give 14 g of product ST-221 (86%) as colorless oil.

Step 2. ST-226

Compound ST-221 (13.4 g, 34 mmol) was dissolved in DMSO (100 mL), added KCN (4.4 g 67 mmol) The mixture was refluxed at 80° C., 5 h, next cooled at r.t. and stirred overnight, monitored by TLC (chloroform:methanol 9:1 visualization:ninhidrin and heating). The mixture was diluted tBuOMe, and washed with water, brine. Organic phase was dried over $MgSO_4$ and under vacuum to give colorless oil. The product was purified by flash column chromatography (silica gel, hexane, hexane:AcOEt 50:1, 10:1, 5:1, 2:1, 1:1) to give 2.0 g (24%) white solid.

Step 3. ST-229

Compound ST-226 (1.9 g, 7.84 mmol) was dissolved in MeOH 30 added $CoCl_2 \times 6H_2O$ (7.1 g 30 mmol). The reaction mixture was stirred and cooled to 0° C., added $NaBH_4$ (2.8 g, 74.8 mmol) (slowly) at 0° C. Next the reaction mixture was allowed to warm up to r.t., stirred overnight. The solvent was evaporated, to residue added 70 mL water and 70 mL 2N HCl. The mixture was filtered through Celite. To the water layer was added EDTA (16.7 g 45 mmol), and stirred for 1 h. The water layer was acidified to pH=2-3, next extracted with AcOEt. Organic layer was washed brine and dried over $MgSO_4$. The solvent was evaporated to give colorless oil. The product was purified by flash column chromatography (silica gel, hexane, hexane:AcOEt 60:1, 10:1, 5:1) to give white solid which after crystallization from AcOEt/hexane yielded 520 mg (31%) of ST-229

Step 4. ST-232

Compound ST-229 (250 mg, 1.11 mmol) was treated with AcOEt/HCl 4M 20 mL, stirred at r.t. for 1 h. The precipitate formed was filtered off to give 200 mg of white solid ST-232.

Step 5. ST-233

N-Boc-Gly (300 mg, 1.43 mmol) was dissolved in DCM 30 mL, next added DIPA (1 mL, 5 mmol), after several minutes added ST-232 (180 mg, 1.43 mmol), after 10 min added TBTU (550 mg, 1.71 mmol). The reaction mixture was stirred at r.t. for 1.5 h, next diluted DCM and washed with 1N HCl, 5% $NaHCO_3$, brine and dried over $MgSO_4$. The solvent was evaporated, and the product was purified by flash column chromatography (silica gel, DCM:MeOH 60:1 50:1 20:1), to give 200 mg (49%) of ST-233 as colorless oil.

Step 6. ST-234

Compound ST-233 (200 mg, 0.71 mmol) was dissolved in DCM, added $Et_3N$ (0.13 mL) after several minutes added $Boc_2O$ (231 mg) and DMAP (112 mg). The reaction mixture was stirred at r.t. overnight. The reaction mixture was diluted DCM and washed 1N HCl, 5% $NaHCO_3$, brine and dried over $MgSO_4$. The solvent was evaporated, residue crystallized from AcOEt/hexane, to give 200 mg (73%) of ST-234 as white solid.

Step 7. ST-236

Compound ST-234 (120 mg, 0.31 mmol) was dissolved in MeOH, and added 10 mL 4N NaOH. The reaction mixture was stirred at r.t. overnight. The solvent was evaporated, residue diluted water and washed AcOEt, next water layer acidified to pH=2-3 and extracted with DCM, organic layer washed with brine, dried over $MgSO_4$. The solvent was evaporated, to give 100 mg (80%) of ST-236 as oil.

EXAMPLE 72

Preparation of Compound 458

Scheme E14

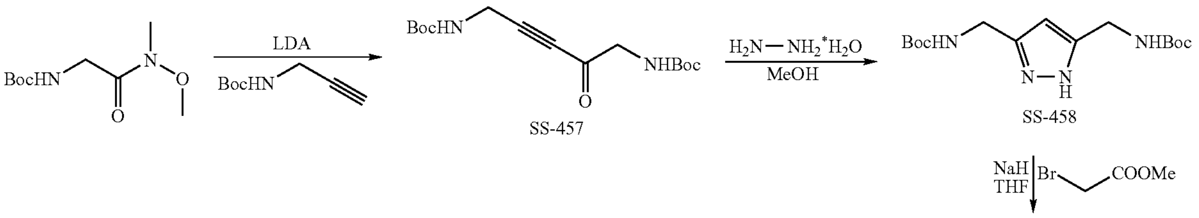

SS-457 SS-458

-continued

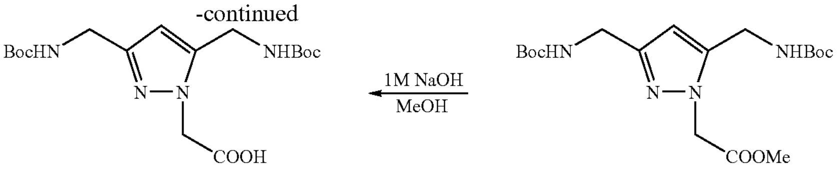

SS-470 SS-465

Step 1 SS-457

Diisopropylamine (6 mL, 42.5 mmol) was dissolved in dry THF and cooled to −30° C. BuLi 2.5M in hexane (17.4 mL, 43.5 mmol) was added at −30° C. dropwise and the mixture was stirred 30 min. Boc-propalgylamine (3 g, 19 mmol) in 5 mL THF was added dropwise at −30° C. and stirred 1 h. Weinreb amide (2.11 g, 9.7 mmol) in 5 mL THF was added dropwise and cooling bath was removed. After 0.5 h reaction was quenched with 2N HCl (70 mL) in one portion. Product was extracted with ethyl acetate. Organic extracts were combined, washed with brine and dried over $MgSO_4$. $MgSO_4$ was filtered off, solvent was removed in vacuum to give SS-457 (5.6 g of orange oil). Crude product was used in the next stage (unstable during attempted silica gel column purification).

Step 2 SS-458

Crude SS-457 obtained above was dissolved in MeOH (100 mL) and hydrazine monohydrate (hydrazine~65%) (1.7 mL) and stirred at r.t. 1 h. MeOH was removed, residue was taken into water/ethyl acetate. Organic layer was washed with 2N HCl, brine and dried over $MgSO_4$. $MgSO_4$ was filtered off, solvent was removed under vacuum to give 5.07 g of impure SS-458. Flash chromatography on silica gel (ethyl acetate:hexane 1:1) produced pure SS-458 (2.08 g, 6.37 mmol, 66%).

Step 3 SS-465

SS-458 (0.76 g, 2.33 mmol) was dissolved in dry THF (20 mL) under Ar. NaH (0.27 g, 7 mmol) was added slowly and the mixture was stirred at r.t. 1 h. Methyl bromoacetate (0.21 mL, 2.33 mmol) in 20 mL THF was added dropwise very slowly (about 2 h) and the mixture was stirred at r.t. overnight. The mixture was taken into $CH_2Cl_2$/saturated $NH_4Cl$. Water layer was extracted with $CH_2Cl_2$. Organic layers were combined, washed with brine and dried over $MgSO_4$. $MgSO_4$ was filtered off, solvent was removed in vacuum to give 0.6 g impure product which was purified by silica gel flash chromatography (DCM:MeOH 200:1). Yield 0.24 g, 0.6 mmol, 26% of SS-465.

Step 4 SS-470

SS-465 (0.24 g, 0.6 mmol) was dissolved in MeOH (3 mL) 1M NaOH was added to pH~10 and the mixture was stirred 1 h at r.t. The mixture was washed with DCM, water layer was acidified to pH ~2 and product was extracted with DCM. Organic layers were combined, washed with brine and dried over $MgSO_4$. $MgSO_4$ was filtered off, solvent was removed to give SS-470 as white foam (0.17 g, 0.44 mmol, 74%).

EXAMPLE 73

Preparation of Compound 459

Scheme E16

Compound 459 was prepared using standard coupling procedures according to the following scheme:

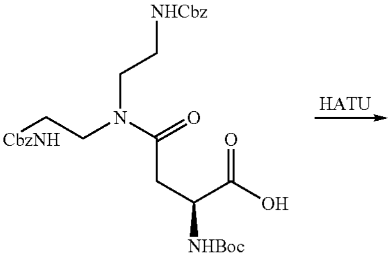

PD-431

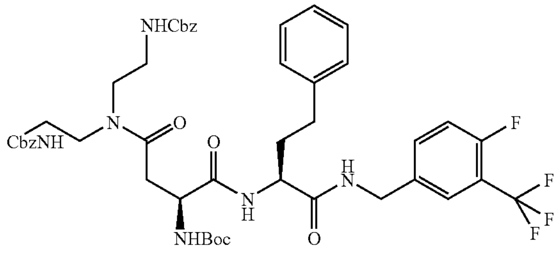

AN-190

HCl/AcOEt

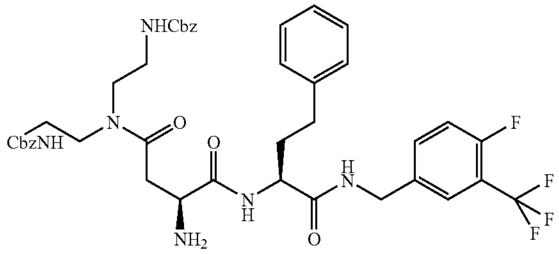

AN-193

TBTU

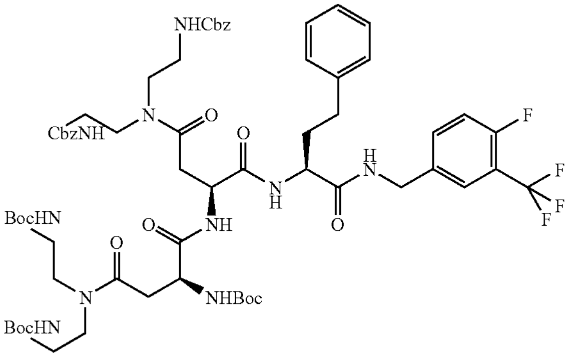

AN-194

1. TFA, PhSMe
2. HCl/AcOEt

-continued

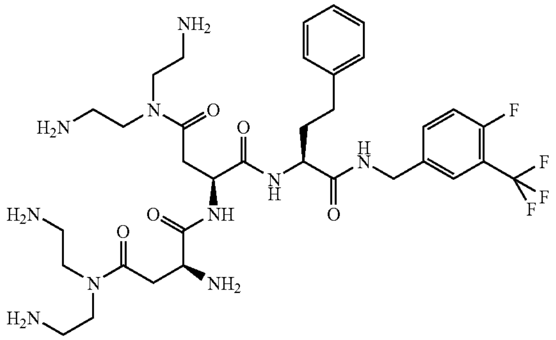

459

EXAMPLE 74

Preparation of Compound 460

Scheme E17

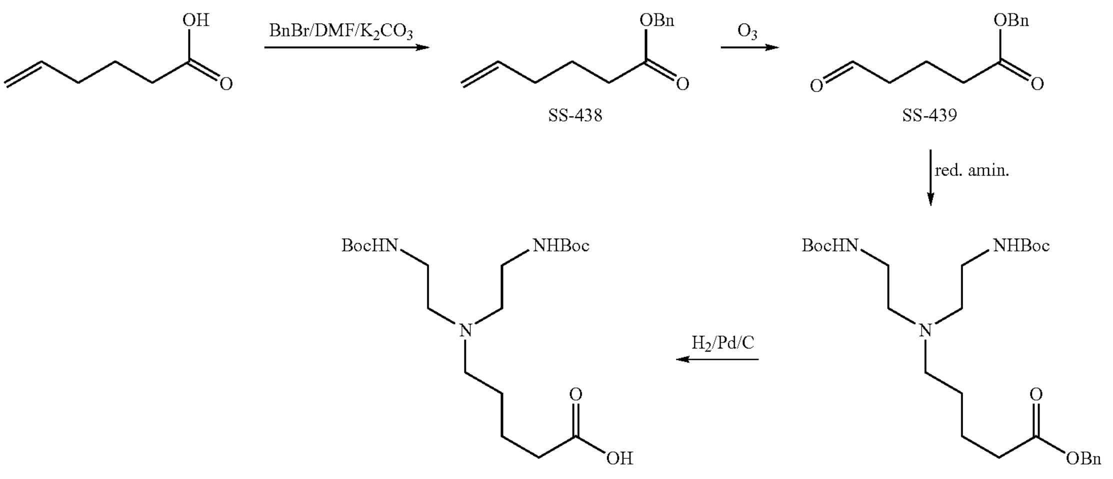

Step 1 SS-438

5-hexenoic acid (5 g; 44 mmol) was dissolved in dry DMF, benzyl bromide (5.2 mL; 44 mmol) and $K_2CO_3$ (7.3 g; 52.6 mmol) were added. The reaction mixture was stirred at r.t. for overnight. The mixture was taken into DCM/1M $K_2CO_3$. Organic layer was washed with 10% $Na_2SO_3$, brine, dried over $MgSO_4$. During evaporation product partially co-evaporated with solvents. Recovery of lost material was performed by partitioning the condensate between water and ether. After careful removal of solvents SS-438 6. 3 g (yield 70%) was obtained which was used for the next step without purification.

Step 2 ST-439

SS-438 (5.5 g; 27 mmol) was dissolved in DCM (ca 50 mL) cooled to −78° C. and $O_3$ (ca 1% on $O_2$; was bubbled until faint blue color persisted (ca 5 min), then the mixture was purged with $N_2$ for about 10 minutes until the color was gone, dimethyl-sulfide (2.5 eq) was added. Reaction mixture was allowed to warm up to r.t. and then stirred for 1 h at r.t. Reaction mixture was evaporated, and chromatographed in hexane/AcOEt producing 5.3 g of ST-439 (95% yield).

Step 3 ST-254

T-butyl 2,2'-azanediylbis(ethane-2,1-diyl)dicarbamate (7.8 g 25.7 mmol) was dissolved in dry DCM, acetic acid (7.3 mL; 128.5 mmol) was added cooled to 0° C. After 15 minutes to the reaction mixture was added SS-439 (5.3 g; 25.7 mmol). The reaction mixture was stirred for 1 h at 0° C., next was added $NaBH(AcO)_3$ and was allowed to warm up to r.t. After overnight stirring the reaction mixture was washed with 10% $NaHCO_3$, brine, dried over $MgSO_4$ and evaporated to oily residue. The crude product was purified by flash chromatography (silica gel, hexane/AcOEt 10:1, 6:1, 5:1, 2:1), to give 3.5 g (yield 28%)

Step 4 ST-258

ST-254 (3 g; 6.09 mmol) was dissolved in MeOH/water 3/2, added catalytic amount of Pd/C and hydrogenated at 1 atm. Hydrogen overnight at r.t. Pd/C was filtered off, the filtrate concentrated, to give colorless oil 1.3 g (yield 52%).

EXAMPLE 75

Preparation of Compound 461

Scheme E18

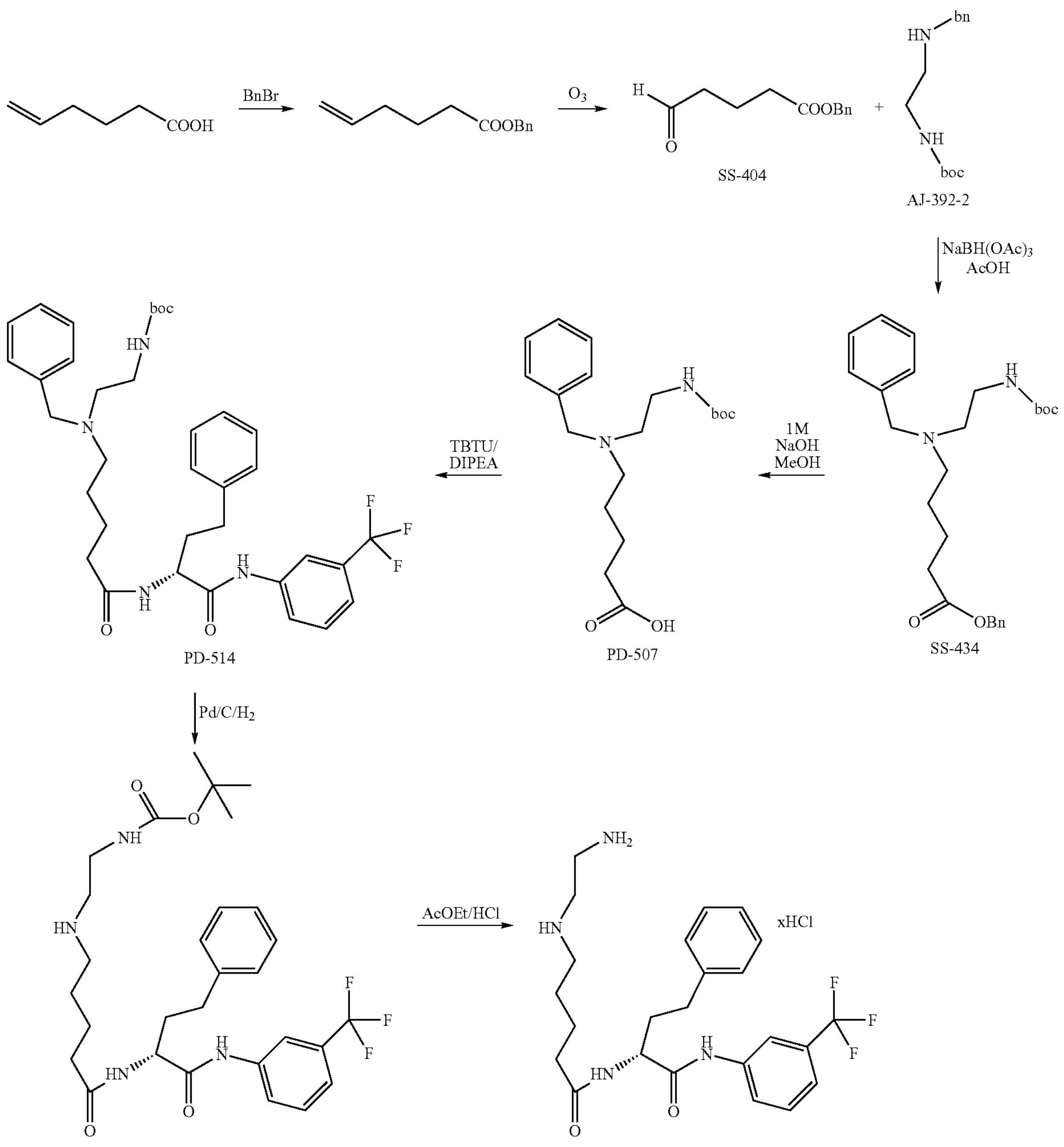

SS-404
AJ-392-2
SS-434
PD-507
PD-514
PD-518
461

Step SS-404

To the 5-hexenoic acid (416 mg, 3.65 mmol) was dissolved in DMF (20 mL) was added $NaHCO_3$ (337 mg, 4.01 mmol). Next benzyl bromide (0.41 mL, 3.46 mmol) was added dropwise. The reaction mixture was stirred overnight. Reaction mixture was diluted with water and was washed thoroughly with AcOEt. Next organic layer was washed with aqueous $Na_2S_2O_3$ and brine, dried over anhydrous $MgSO_4$. Solvent was removed under vacuum to give crude benzyl ester (527 mg, 2.56 mmol, 70.7% yield). Subsequently it was dissolved in DCM (ca 50 mL) cooled to −78° C. and ozone was bubbled until faint blue color (ca 5 min), then reaction mixture was purged with nitrogen until color was gone (~10 min.), dimethyl sulfide (7.5 mM) was added. Reaction mixture was allowed to warm up to r.t. and additionally stirred for 1 h at r.t. Reaction mixture evaporated, and chromatographed hexane/EtOAc to produce aldehyde SS-404 (95% yield).

Step 2 SS-434

AJ-392-2 (640 mg, 2.56 mmol) was dissolved in $CH_2Cl_2$ (10 mL) and AcOH (0.73 mL, 12.8 mmol) was added. The reaction mixture was cooled to 0° C. and SS-404. (527 mg, 2.56 mmol) was added. The mixture was stirred 1 h at 0° C. and then NaBH(OAc)3 (813 mg, 3.84 mmol) was added. The mixture was stirred at ambient temperature overnight. The reaction mixture was washed with water, 1MHCl, brine and dried over MgSO4. The solvent was evaporated. Product was purified on silica gel column using DCM:MeOH (150:1) solvent system to give SS-434 (580 mg, 1.31 mmol, 51% yield).

Step 3 PD-507

To the solution of SS-434 (580 mg, 1.31 mmol) in MeOH (3 mL) 1 M NaOH was added dropwise until pH=10. The mixture was stirred for 2 h at r.t. before evaporating the MeOH under reduced pressure. The residue was mixed with water and washed with ether. After acidifying to pH~3 with 2 M HCl, the product was extracted with AcOEt, dried over MgSO4. MgSO4 was filtered off and solvent was concentrated under vacuum to give PD-507 (460 mg, 1.31 mmol, 100% yield).

EXAMPLE 76

Preparation of Compound 462

Step 1 SS-335

To the solution of cumaric acid (487 mg, 2.97 mmol) in DCM (10 mL) DIPEA (1.29 mL, 7.42 mmol) SS-334 (680 mg, 2.97 mmol) and TBTU (1.04 g, 3.26 mmol) were added. The mixture was stirred at r.t. overnight. The reaction mixture was then washed with 5% NaHCO3, 1 M HCl, brine and dried over MgSO4. Solvent was removed under vacuum to give SS-335 (790 mg, 2.34 mmol, 78% yield).

Step 2 SS-340

SS-335 (790 mg, 2.34 mmol) was dissolved in $NH_3$/MeOH (3M) and the reaction mixture was stirred 2 days at ambient temperature. Solvent was evaporated to dryness to give SS-340 (820 mg, 2.53 mmol, 93% yield).

Step 3 PD-451

SS-340 (820 mg, 2.53 mmol) was dissolved in a mixture of DMF/water (30 mL/12 mL). Then were added pyridine (0.45 mL, 5.57 mmol) and bis(trifluoroacetoxy)-iodobenzene (1.6 g, 3.79 mmol). The reaction mixture was stirred at ambient temperature overnight. Reaction mixture was diluted with water and was washed thoroughly with AcOEt. Next organic layer was washed with $Na_2S_2O_3$ and brine, dried over anhydrous $MgSO_4$. Solvent was removed under vacuum. Product was purified on silica gel column (DCM:MeOH:TEA; 300:1:0.5) to give PD-451 (480 mg, 1.62 mmol, 64.8% yield).

Scheme F

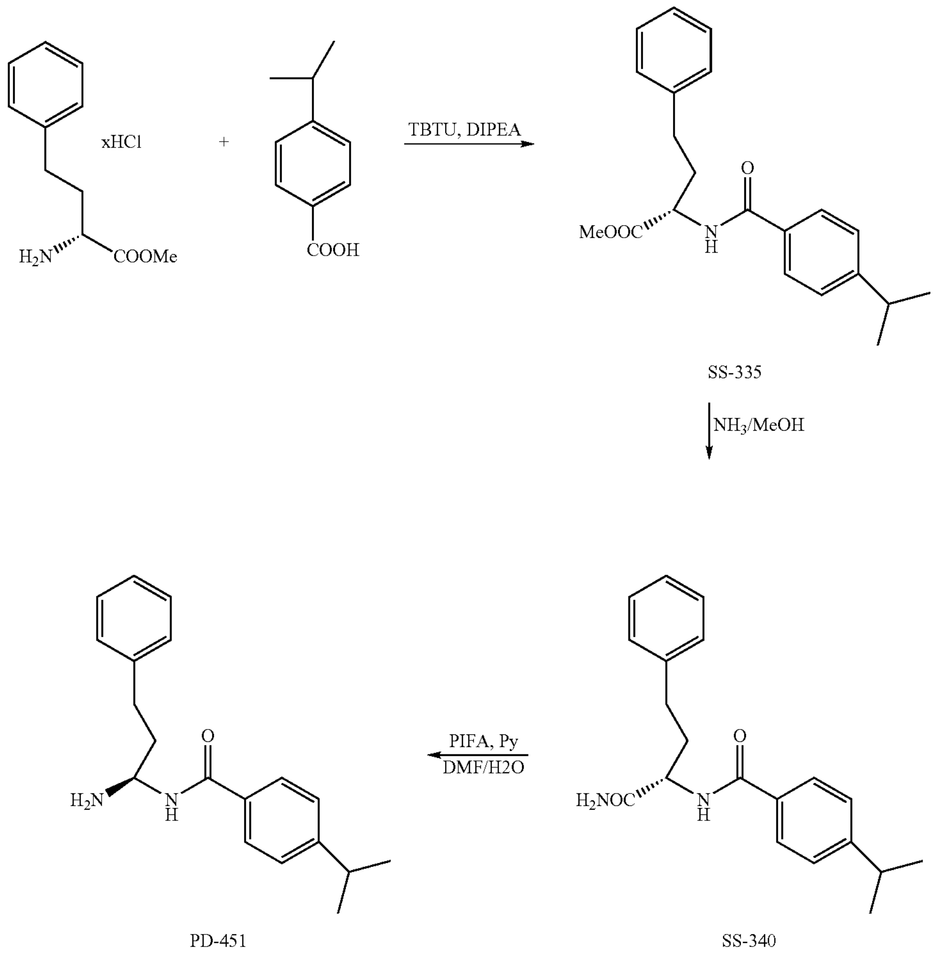

EXAMPLE 77
Preparation of Compound 463
Scheme G
Compound 463 was prepared using standard coupling procedures according to the following scheme
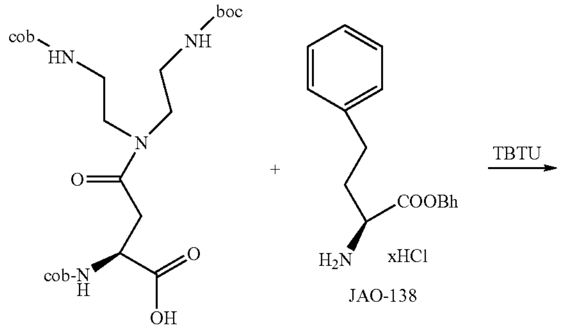
KC-117
JAO-138
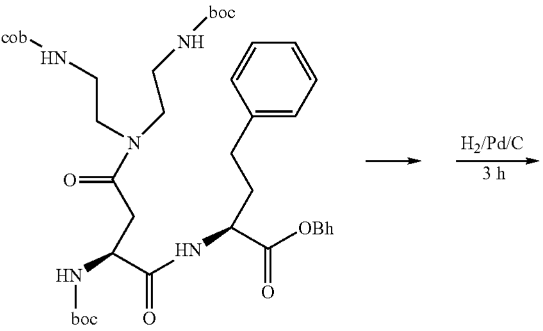
JAO-140
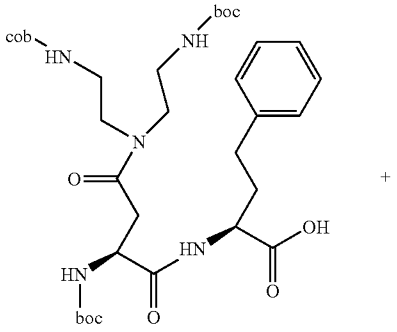
JAO-141
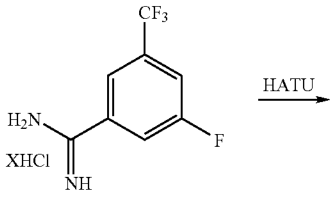
trade
-continued
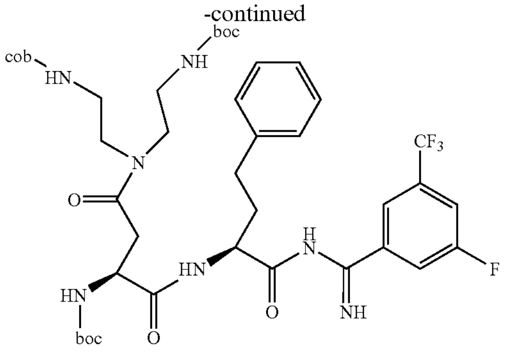
JAO-155
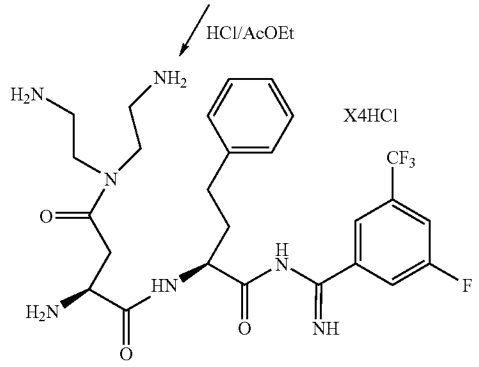
463
EXAMPLE 78
Protected N-Terminal Acids for 437 and 438
M6
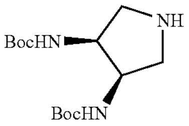
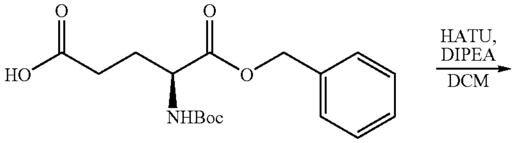
M7
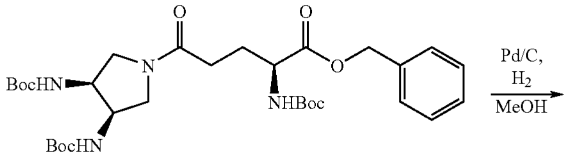
M8
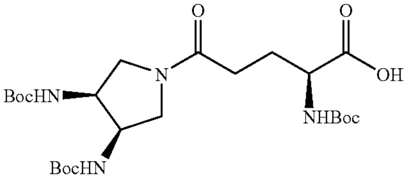
M9

Step 1: To a solution of M6 (0.50 g, 1.7 mmol), M7 (0.60 g, 1.8 mmol) and HATU (0.80 g, 2.1 mmol) in DCM (10 mL) was added diisopropylethylamine (0.55 mL, 3.3 mmol). The reaction mixture was stirred at RT for 3 h and then poured into water. The resulting mixture was extracted with EtOAc (2×20 mL) and the combined organic layers washed with brine. The organic layer was dried over anhydrous $MgSO_4$, filtered and the filtrate concentrated. The residue was purified by flash chromatography on silica gel (Hexanes to 80% EtOAc/Hexanes) to afford M8 (0.81 g, 79%) as a white foam.

Step 2: A solution of M8 (0.8 g, 1.3 mmol) in MeOH (15 mL) was flushed with argon and then added with Pd/C (20% by weight). The reaction was evacuated under house vacuum and refilled with hydrogen from hydrogen balloon. The mixture was stirred at RT for 7 h and filtered through a syringe filter. The filtrate was concentrated to afford M9 (0.67 g, 98%) as a white solid, which was used in the next step without purification.

EXAMPLE 79

Preparation of Compound 464

Scheme M5

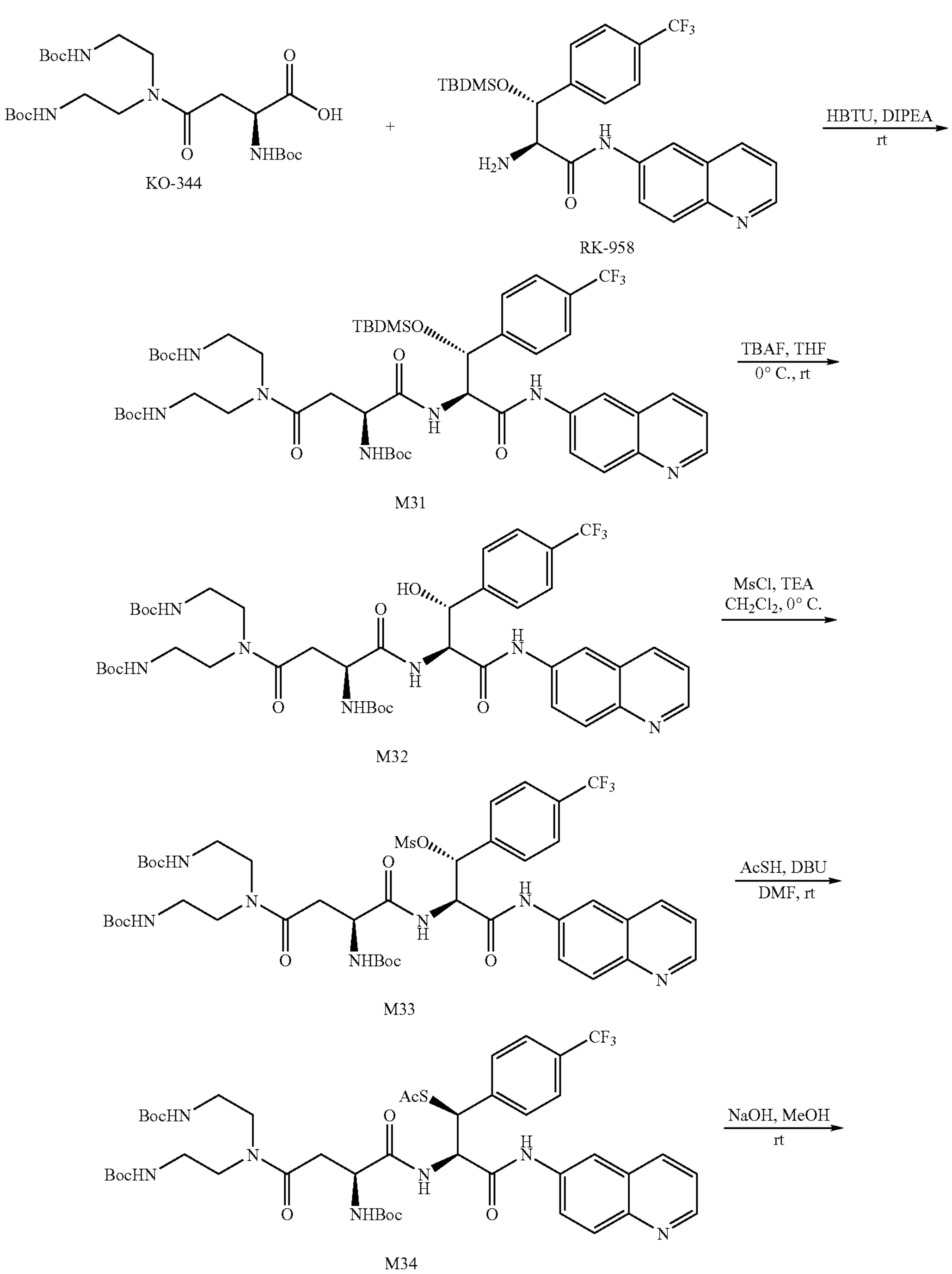

-continued

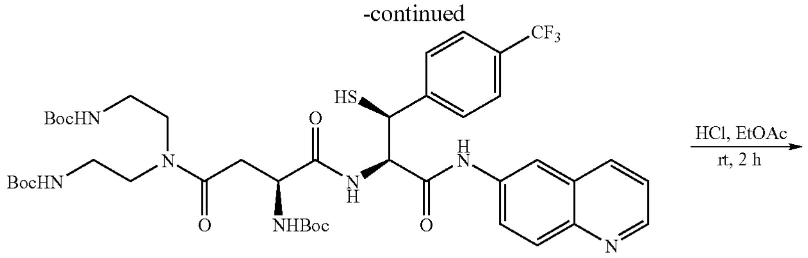

M35

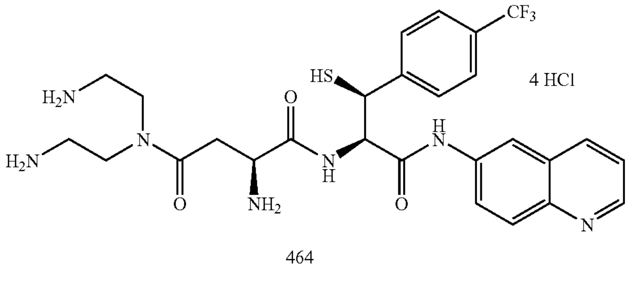

464

Step 1: Compound M31 was prepared from compound KO-344 and RK-958 according to General Procedure A4.

Step 2: To a solution of M31 (0.89 g, 0.9 mmol) in THF (10 mL) at 0° C. was added a solution of 1M tetrabutylammonium fluoride in THF (1.8 mL, 1.8 mmol). The mixture was warmed to r.t. and stirred for 3 h. The resulting mixture was concentrated and purified on a silica gel column (100% $CH_2Cl_2$→95:5 $CH_2Cl_2$:methanol) to afford M32, a white solid (0.69 g; 0.8 mmol; 87% yield). ESIMS found for $C_{42}H_{57}F_3N_7O_{10}$ m/z 876 (M+H).

Step 3: To a solution of M32 (0.2 g, 0.2 mmol) in $CH_2Cl_2$ (0.7 mL) at 0° C. was triethylamine (72 μL, 0.5 mmol). To this solution methanesulfonyl chloride (20 μL, 0.3 mmol) was added. The mixture was stirred for 45 min at 0° C. and added cold 1N HCl (1 mL). The resulting mixture was extracted with $CH_2Cl_2$ (5 mL). The organic layer was washed with saturated $NaHCO_3$, brine, dried over $MgSO_4$, and concentrated to afford M33, a yellow solid (0.19 g; 0.2 mmol; 85% yield). ESIMS found for $C_{43}H_{59}F_3N_7O_{12}S$, m/z 954 (M+H).

Step 4: To a solution of 1,8-diazabicyclo[5.4.0]undec-7-ene (0.12 g, 0.8 mmol) in DMF (0.5 mL) was added thioacetic acid (82 μL, 1.1 mmol). A solution of M33 (0.2 g, 0.2 mmol) in DMF (1 mL) was added. The reaction mixture was stirred for 3 d at r.t. The resulting mixture was added saturated water (1 mL), extracted with $CH_2Cl_2$ (5 mL) and dried over $MgSO_4$. The crude mixture was purified on a silica gel column (100% hexanes→0:100 hexanes:EtOAc) to afford M34, a brown solid (0.15 g; 0.1 mmol; 71% yield). ESIMS found for $C_{44}H_{59}F_3N_7O_{10}S$ m/z 834 (M+H).

Step 5: To a solution of M34 (0.15 g, 0.16 mmol) in MeOH (1 mL) was added 1 M NaOH in MeOH (0.16 mL). The mixture was stirred at r.t. for 10 min. The resulting mixture was added 1 N HCl (1 mL), extracted with $CH_2Cl_2$ (5 mL) and dried over $MgSO_4$. The crude mixture was purified on a silica gel column (100% $CH_2Cl_2$→95:5 MeOH:$CH_2Cl_2$) to afford M35, a yellow solid (0.084 g; 0.09 mmol; 59% yield). ESIMS found for $C_{44}H_{59}F_3N_7O_{10}S$ m/z 892 (M+H).

Step 6: A solution of 4 M HCl in EtOAc (3 mL) was added to M35 (0.054 g, 0.06 mmol). The mixture was stirred for 2 h at r.t. The resulting mixture was concentrated to afford 464 (0.043 g; 0.06 mmol; 100% yield). ESIMS found for $C_{27}H_{33}F_3N_7O_3S$ m/z 592 (M+H).

EXAMPLE 80

Preparation of Compound 465

Scheme M6

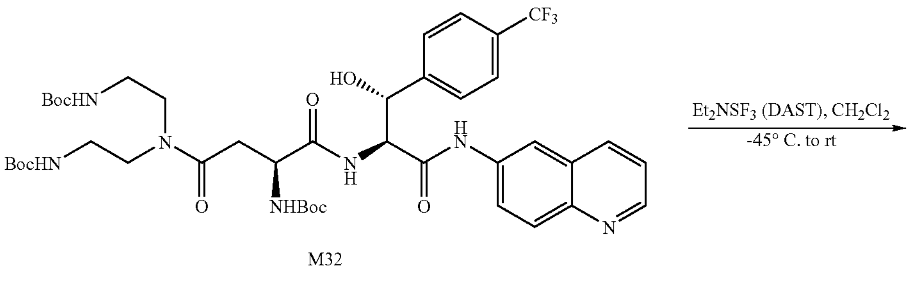

M32

-continued

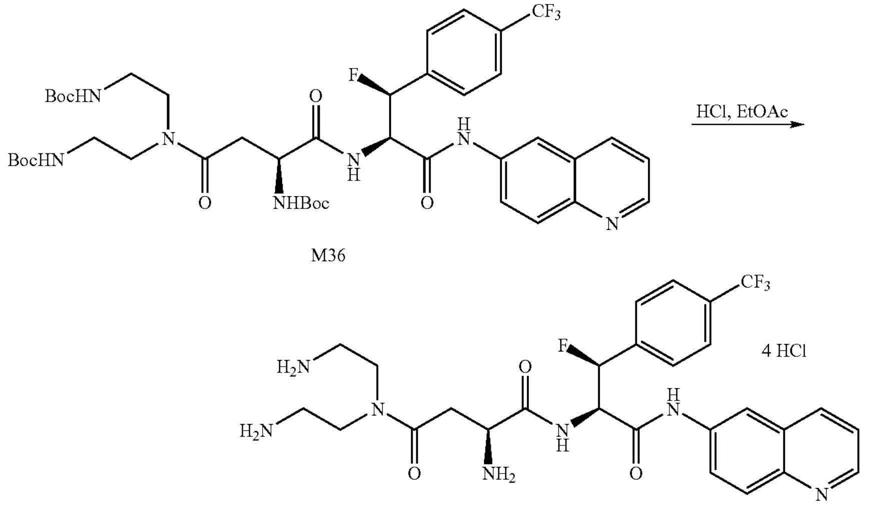

M36

465

Step 1: To a solution of 32 (0.25 g, 0.29 mmol) in $CH_2Cl_2$ (5 mL) at −45° C. was added diethylaminosulfur trifluoride (57 μL, 0.43 mmol). The mixture was stirred at −45° C. for 10 min, warmed to r.t., stirred for additional 30 min. The resulting mixture was added saturated $NaHCO_3$ (5 mL), extracted with ethyl acetate (20 mL) and dried over $MgSO_4$. The crude mixture was purified on a silica gel column (100% $Et_2$→95:5 Et2O:$CH_3CN$) to afford M36, a white solid (0.12 g; 0.1 mmol; 46% yield). ESIMS found for $C_{42}H_{56}F_4N_7O_9$ m/z 878 (M+H).

Step 2: A solution of 4 M HCl in EtOAc (5 mL) was added to M36 (0.13 g, 0.13 mmol). The mixture was stirred overnight at r.t. The resulting mixture was concentrated to afford 465 (0.082 g; 0.12 mmol; 89% yield). ESIMS found for $C_{23}H_{31}F_4N_7O_2$ m/z 578 (M+H).

Scheme M7

EXAMPLE 81

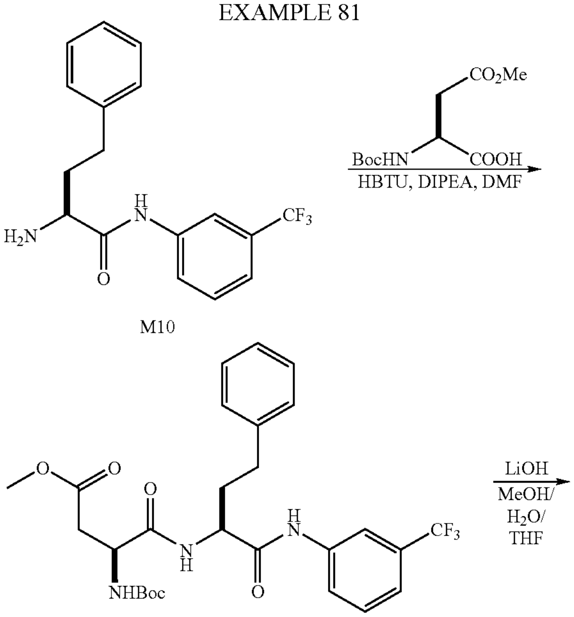

M10

M37

-continued

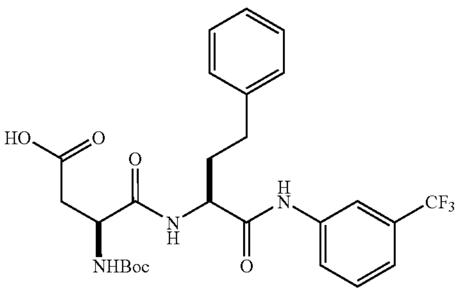

M38

Synthesis of Acid M38.

Step 1: To a solution of M10 (1.0 g, 2.8 mmol), Boc-Asp (OMe)-OH (0.80 g, 3.2 mmol) and HBTU (1.2 g, 3.2 mmol) in DMF (15 mL) was added diisopropylethylamine (1.5 mL, 9.1 mmol). The reaction mixture was stirred at RT for 2.5 h and then diluted with EtOAc (20 mL). The resulting mixture was washed with water, 1 M aq. HCl, saturated $NaHCO_3$ solution and brine in that order. The organic layer was separated, dried over anhydrous $MgSO_4$, filtered and the filtrate concentrated. The residue was triturated in diethyl ether/Hexanes (2/1) and the resulting solid filtered to afford M37 (1.24 g, 81%) as an off white solid.

Step 2: To a solution of M37 (0.47 g, 0.85 mmol) in a mixture of MeOH/water/THF (1/1/1, 15 mL) was added LiOH (80 mg, 3.3 mmol). The mixture was stirred at RT for 1.5 h and the reaction poured into 1 M HCl solution. The resulting mixture was extracted with EtOAc and the organic layer separated and washed with brine. The organic layer was dried over anhydrous $MgSO_4$, filtered and the filtrate concentrated. The residue was triturated in Hexanes and the resulting solid filtered to afford M38 (0.41 g, 90%) as an off white solid.

EXAMPLE 82
Preparation of Compounds 466-469
Scheme M8
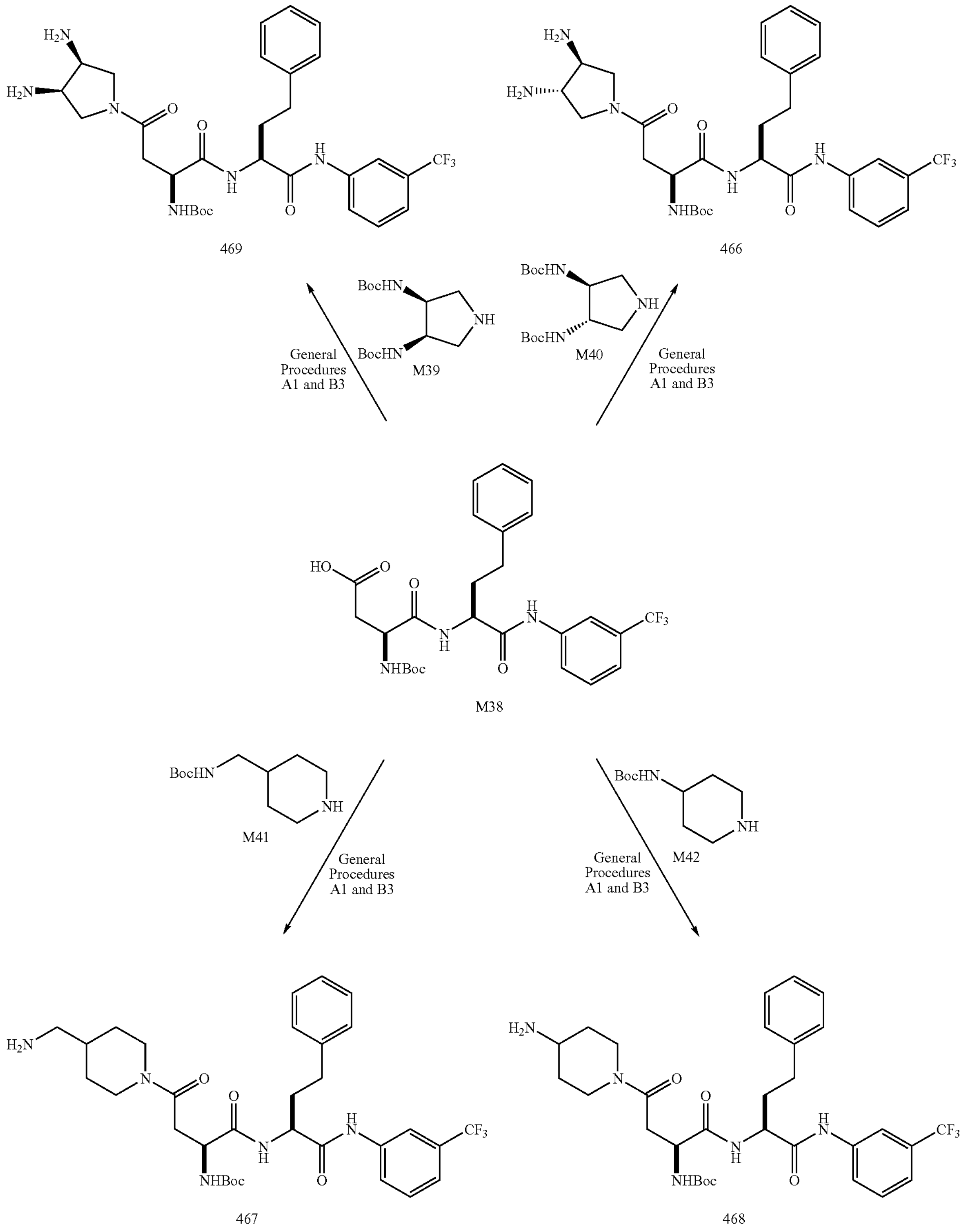

Synthesis of Final Inhibitor Compounds.

Synthesis of 466. Compound 466 was prepared from compound M38 and M40 by sequential treatment of General Procedures A1 and B3.

Synthesis of 467. Compound 467 was prepared from compound M38 and M41 by sequential treatment of General Procedures A1 and B3.

Synthesis of 468. Compound 468 was prepared from compound M38 and M42 by sequential treatment of General Procedures A1 and B3.

Synthesis of 469. Compound 469 was prepared from compound M38 and M39 by sequential treatment of General Procedures A1 and B3.

TABLE 5

The following compounds were prepared in accordance with the specific examples described in Examples 59-82. The coupling and deprotection methods used are identified next to the relevant intermediate or final structure. A description of these methods appears after Scheme 35.

| Compound | Inhibitor structure (deprotection procedure B-B3) | | Protected N-terminal acid structure (coupling procedure A1-A3) | |
|---|---|---|---|---|
| 445 | 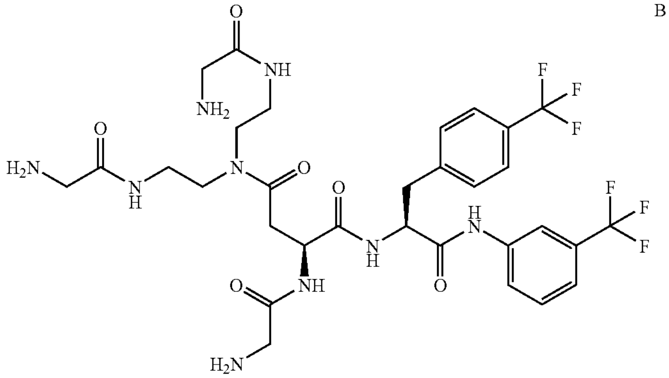 | B | 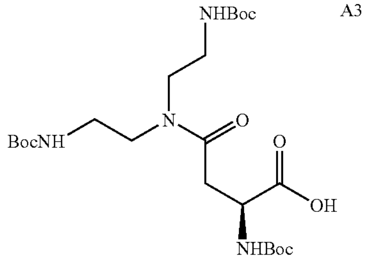 | A3 |
| 446 | 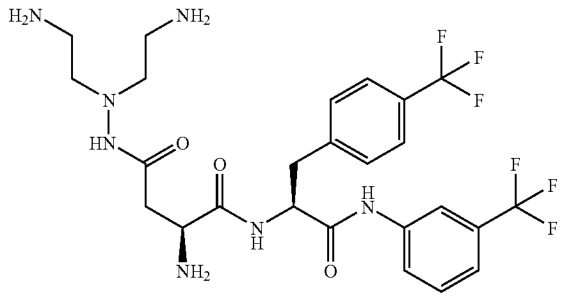 | B | 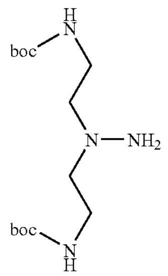 See scheme E2 | A1 |
| 447 | 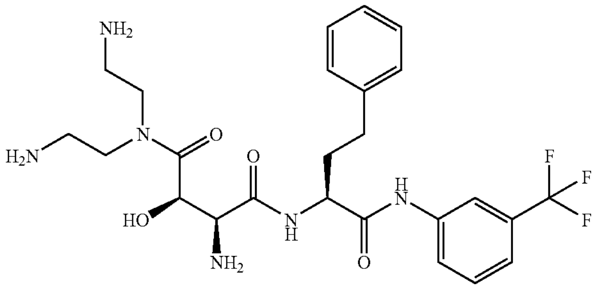 | B | See scheme E3 | A1 |
| 448 | 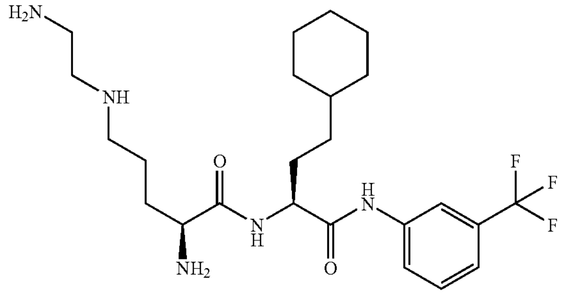 | B | 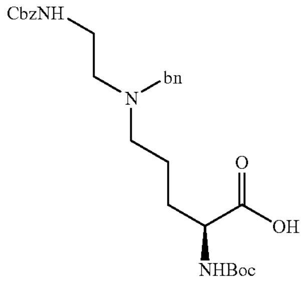 See scheme E4 | A3 |

TABLE 5-continued
The following compounds were prepared in accordance with the specific examples described in Examples 59-82. The coupling and deprotection methods used are identified next to the relevant intermediate or final structure. A description of these methods appears after Scheme 35.
| | | | | |
|---|---|---|---|---|
| 449 | 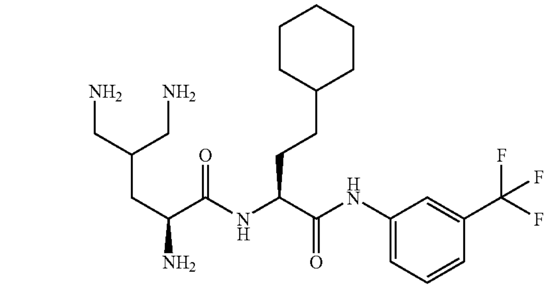 | B | 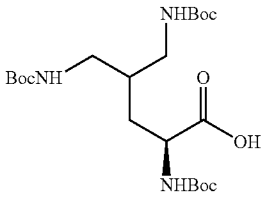 See scheme E5 | A3 |
| 450 | 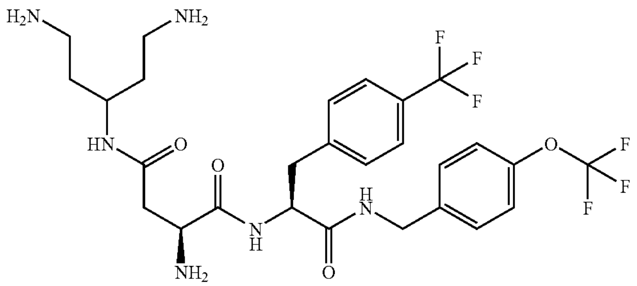 | B | 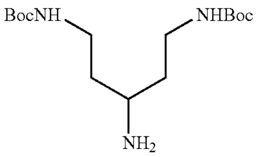 See scheme E6 | A3 |
| 451 | 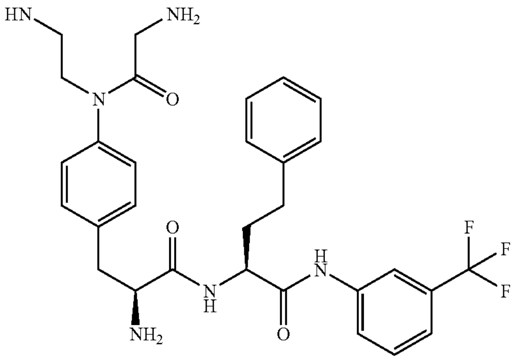 | B | 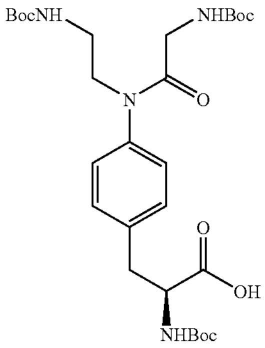 See scheme E7 | A3 |
| 452 | 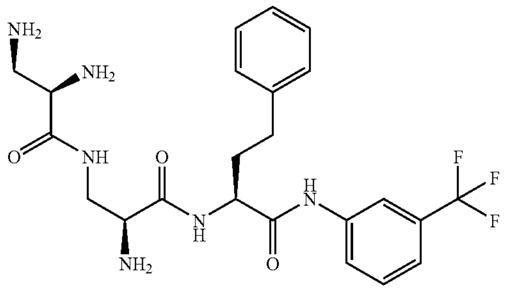 | B | 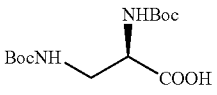 See scheme E8 | A3 |

TABLE 5-continued

The following compounds were prepared in accordance with the specific examples described in Examples 59-82.
The coupling and deprotection methods used are identified next to the relevant intermediate or final structure.
A description of these methods appears after Scheme 35.

| | | | | |
|---|---|---|---|---|
| 453 | 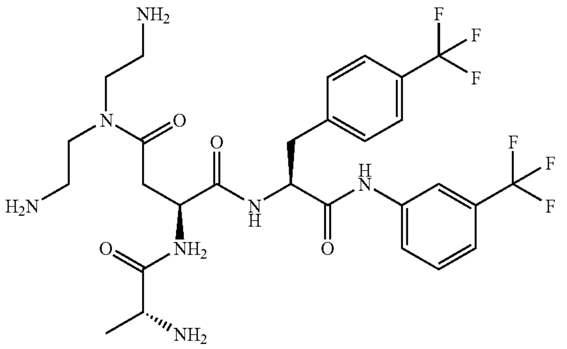 | B | 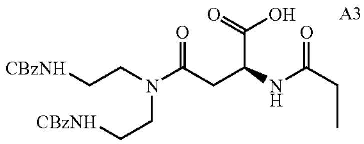<br>See scheme E9 | A3 |
| 454 | 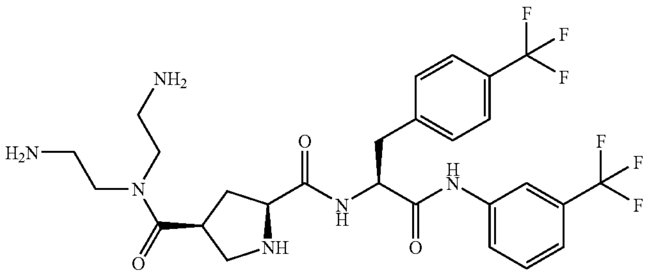 | B | 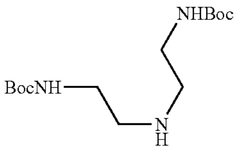<br>See scheme E10 | A2 |
| 455 | 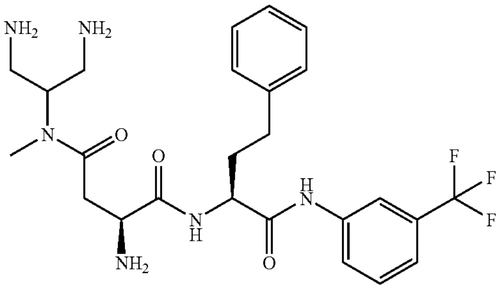 | B | 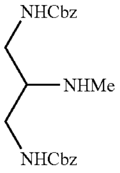<br>See scheme E11 | A2 |
| 456 | 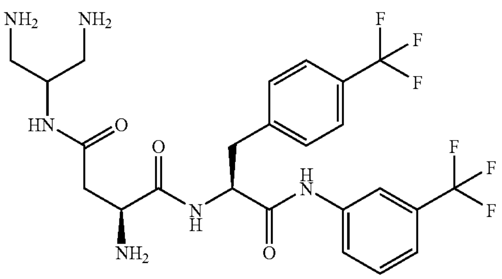 | B | 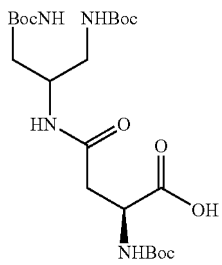<br>See scheme E12 | A3 |

TABLE 5-continued
| The following compounds were prepared in accordance with the specific examples described in Examples 59-82. The coupling and deprotection methods used are identified next to the relevant intermediate or final structure. A description of these methods appears after Scheme 35. | | | | |
|---|---|---|---|---|
| 457 | 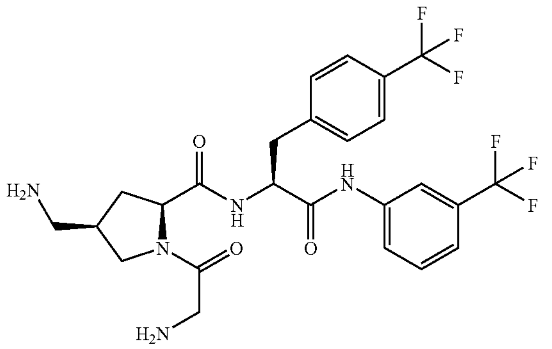 | B | 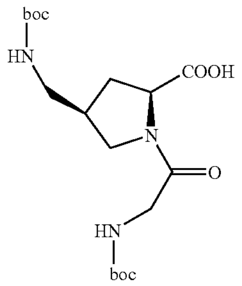 See scheme E13 | A3 |
| 458 | 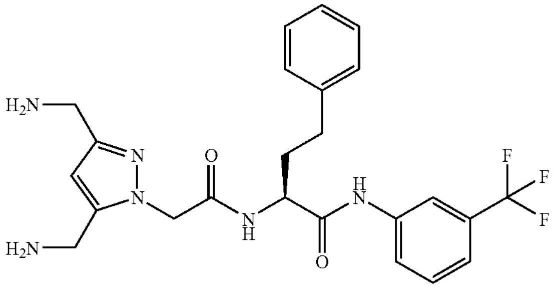 | B | 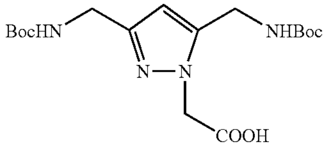 See scheme E14 | A3 |
| 459 | 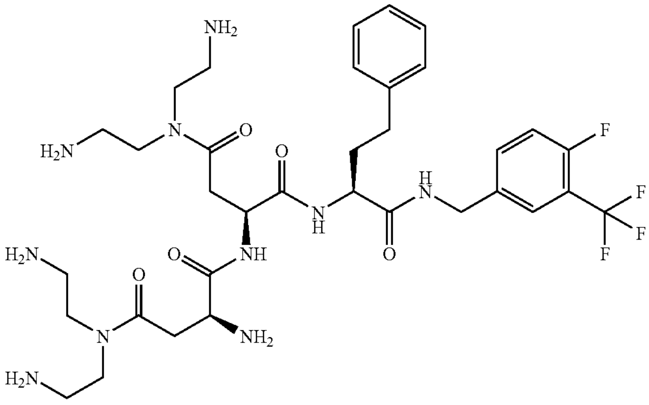 | B | 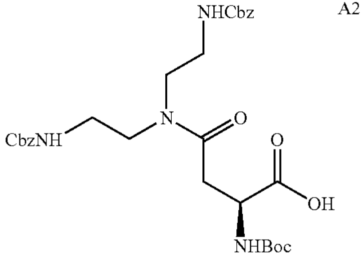 See scheme E16 | A2 |
| 460 | 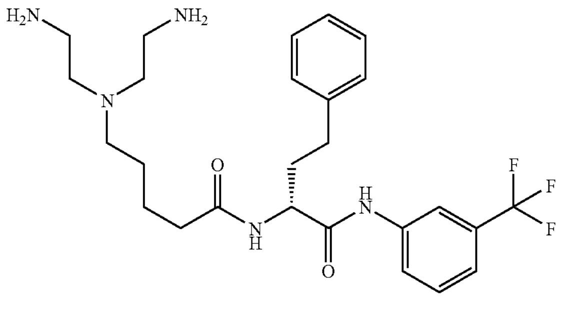 | B | 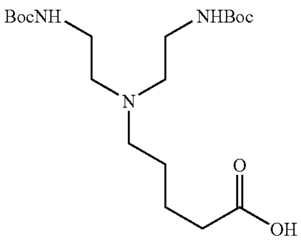 See scheme E17 | A3 |

TABLE 5-continued
The following compounds were prepared in accordance with the specific examples described in Examples 59-82.
The coupling and deprotection methods used are identified next to the relevant intermediate or final structure.
A description of these methods appears after Scheme 35.
| | | | | |
|---|---|---|---|---|
| 461 | 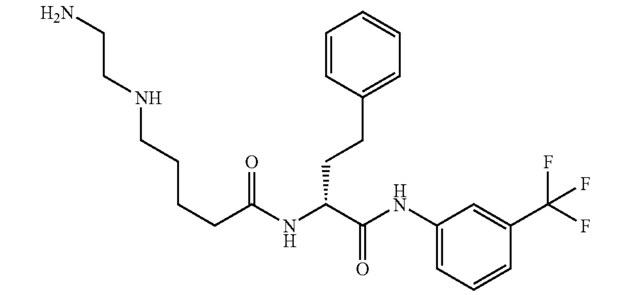 | B | 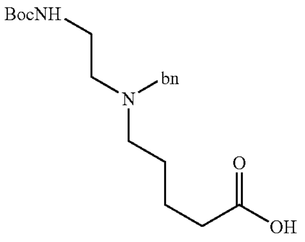 See scheme E18 | A3 |
| 462 | 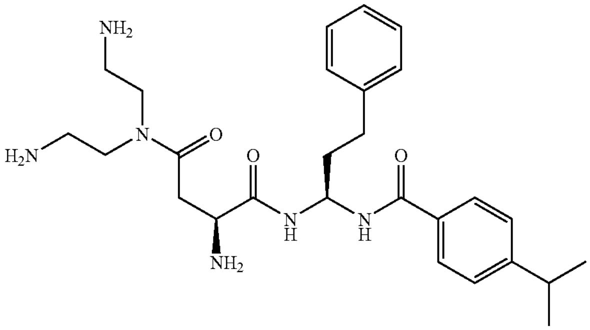 | B | 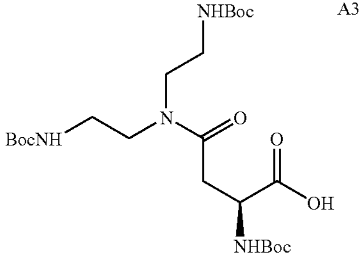 See scheme F | A3 |
| 463 | 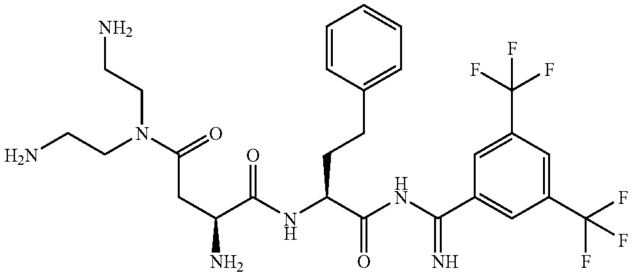 | B | 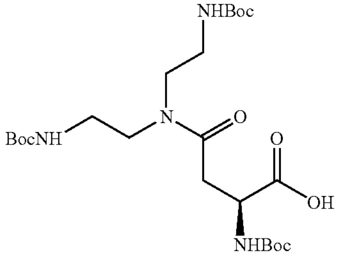 See scheme G | |
| 464 | 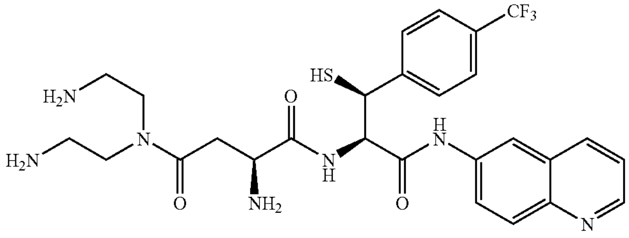 | | See Scheme M5 | |
| 465 | 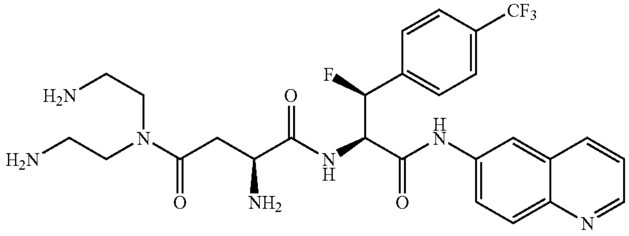 | | See Scheme M6 | |

TABLE 5-continued

The following compounds were prepared in accordance with the specific examples described in Examples 59-82. The coupling and deprotection methods used are identified next to the relevant intermediate or final structure. A description of these methods appears after Scheme 35.

| | | | | |
|---|---|---|---|---|
| 466 | 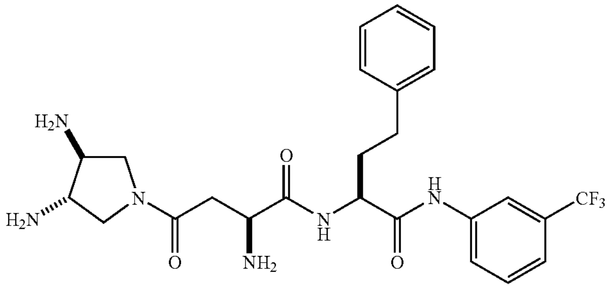 | B3 | 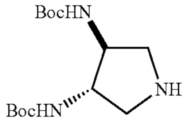 See Schemes M7 and M8 | A1 |
| 467 | 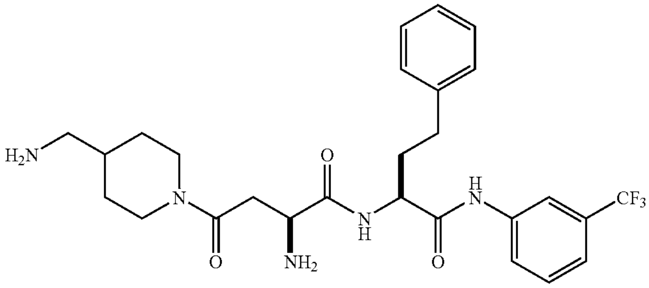 | B3 | 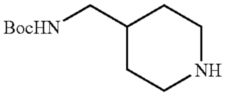 See Schemes M7 and M8 | A1 |
| 468 | 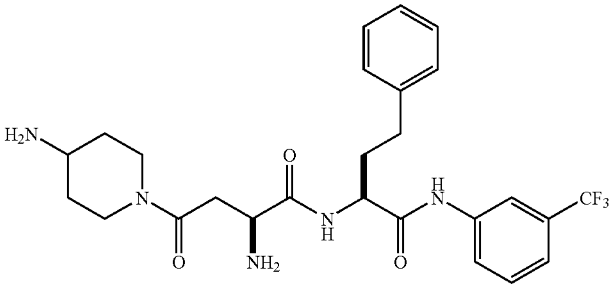 | B3 | 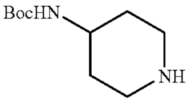 See Schemes M7 and M8 | A1 |
| 469 | 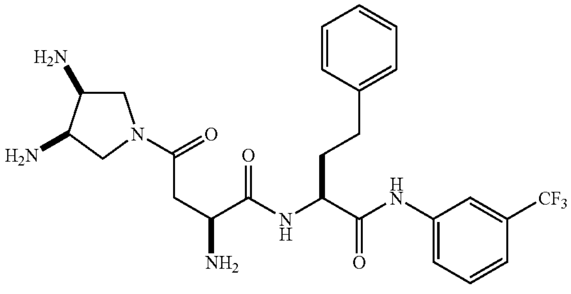 | B3 | 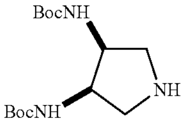 See Schemes M7 and M8 | A1 |

TABLE 5-continued

The following compounds were prepared in accordance with the specific examples described in Examples 59-82. The coupling and deprotection methods used are identified next to the relevant intermediate or final structure. A description of these methods appears after Scheme 35.

| Compound | Protected central acid structure (coupling procedure A1-A3) | Capping amine structure | Ret. Time Min. (method) | MS m/e |
|---|---|---|---|---|
| 445 | 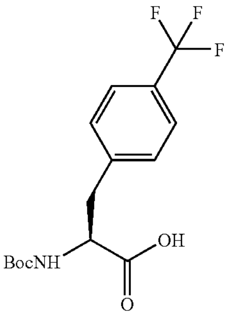 A1 | 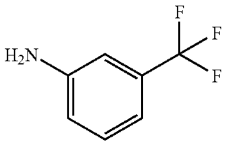 | 3.03 (H1) | 748 |
| 446 | 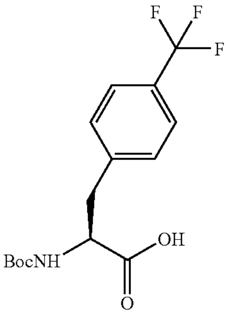 A1 | 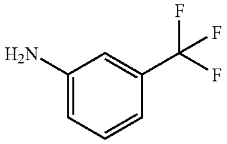 | 3.15 (H1) | 592 |
| 447 | 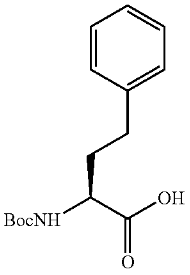 A1 | 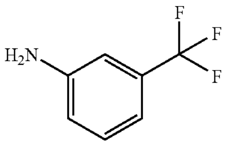 | 0.68 (H1) | 539 |
| 448 | 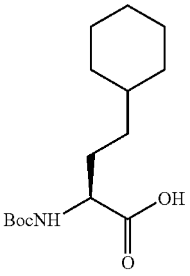 A1 | 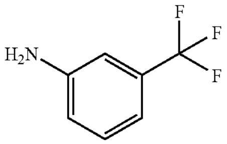 | 1.20 (H1) | 486 |
| 449 | 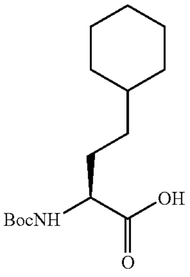 A1 | 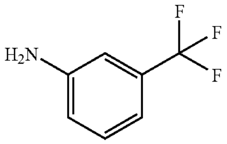 | 3.25 (H1) | 472 |

TABLE 5-continued
The following compounds were prepared in accordance with the specific examples described in Examples 59-82. The coupling and deprotection methods used are identified next to the relevant intermediate or final structure. A description of these methods appears after Scheme 35.
| | | | | | |
|---|---|---|---|---|---|
| 450 | 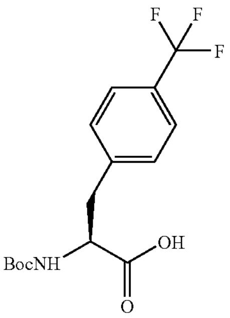 | A3 | 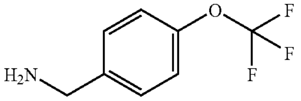 | 1.34 (H1) | 621 |
| 451 | 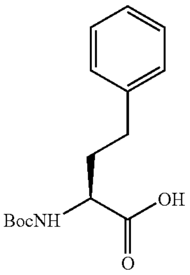 | A1 | 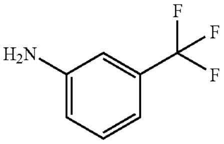 | 2.35 (H1) | 585 |
| 452 | 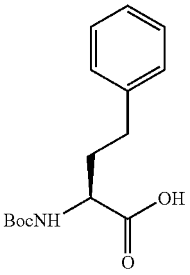 | A1 | 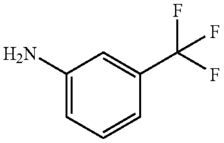 | 3.27 (H1) | 495 |
| 453 | 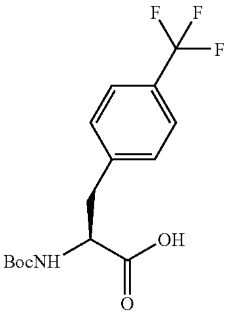 | A1 | 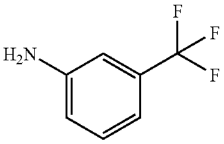 | 2.60 (H1) | 648 |
| 454 | 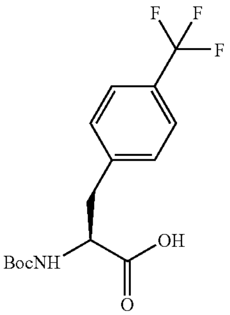 | A1 | 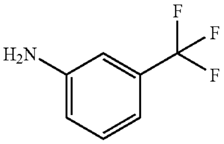 | 3.21 (H1) | 603 |

TABLE 5-continued
The following compounds were prepared in accordance with the specific examples described in Examples 59-82.
The coupling and deprotection methods used are identified next to the relevant intermediate or final structure.
A description of these methods appears after Scheme 35.
| | | | | | |
|---|---|---|---|---|---|
| 455 | 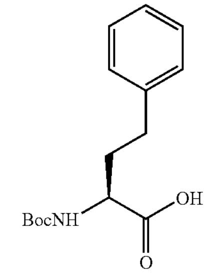 | A1 | 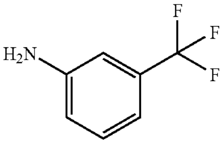 | 0.76 (H1) | 523 |
| 456 | 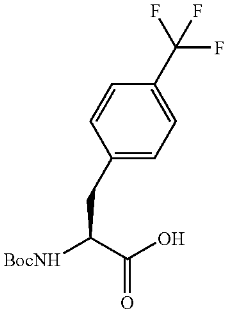 | A1 | 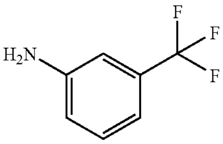 | 2.93 (H1) | 563 |
| 457 | 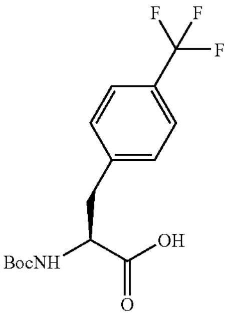 | A1 | 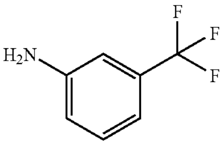 | 3.75 (H1) | 560 |
| 458 | 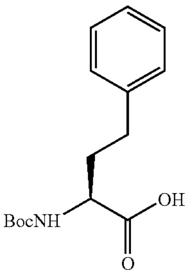 | A1 | 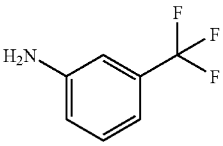 | 3.36 (H1) | 489 |
| 459 | 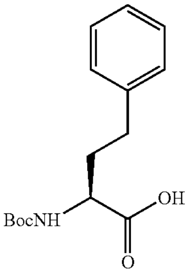 | A3 | 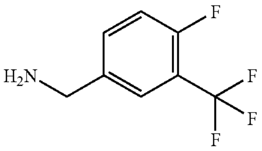 | 0.98 (H1) | 755 |

TABLE 5-continued
The following compounds were prepared in accordance with the specific examples described in Examples 59-82.
The coupling and deprotection methods used are identified next to the relevant intermediate or final structure.
A description of these methods appears after Scheme 35.
| | | | | | |
|---|---|---|---|---|---|
| 460 | 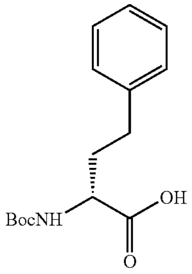 | A1 | 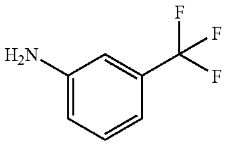 | 2.68 (H1) | 508 |
| 461 | 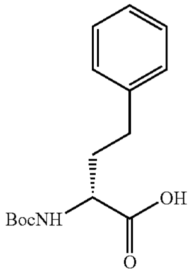 | A1 | 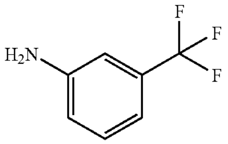 | 2.76 (H1) | 465 |
| 462 | | | | 1.37 (H1) | 497 |
| 463 | 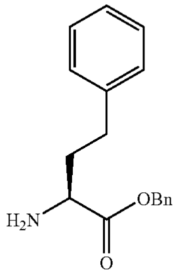 | | 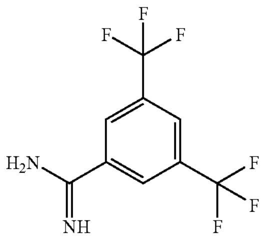 | 2.92(H1) | 618 |
| 464 | | | | 3.89 (H2) | 592 |
| 465 | | | | 3.31 (H2) | 578 |
| 466 | 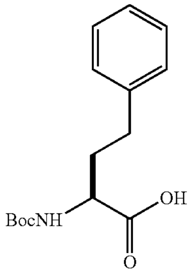 | A1 | 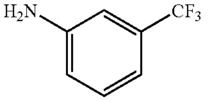 | 6.5 (H2) | 521 |
| 467 | 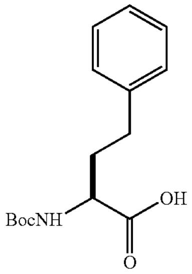 | A1 | 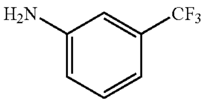 | 7.44 (H2) | 534 |

TABLE 5-continued

The following compounds were prepared in accordance with the specific examples described in Examples 59-82. The coupling and deprotection methods used are identified next to the relevant intermediate or final structure. A description of these methods appears after Scheme 35.

| | | | | | |
|---|---|---|---|---|---|
| 468 | 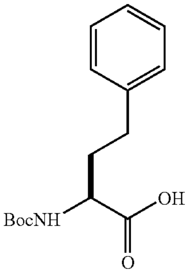 | A1 | 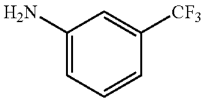 | 7.41 (H2) | 520 |
| 469 | 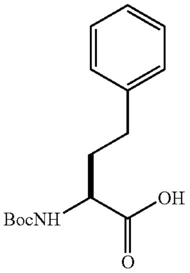 | A1 | 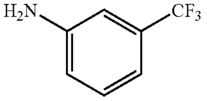 | 6.5 (H2) | 521 |

Chromatographic Methods for Compounds in Tables 3-5

Method H1: Analytical HPLC conditions for analysis of final compounds. The compounds were analyzed on an Nucleosil-100-C18 (250×4 mm), at a flow rate of 1 mL/min at 40° C. using a gradient from 10% acetonitrile in water (plus 0.1% trifluoroacetic acid) to 90% acetonitrile in water (plus 0.1% trifluoroacetic acid) over a gradient of 25 minutes.

Method H2: Analytical HPLC conditions for analysis of final compounds. The compounds were analyzed on an Agilent Eclipse Plus C18 (15 cm×4.6 mm), at a flow rate of 1.2 mL/min at 40° C. using a gradient from 20% acetonitrile in water (plus 0.1% trifluoracetic acid) to 50% acetonitrile in water (plus 0.1% trifluoroacetic acid) over a gradient of 9 min.

Method H3: Analytical HPLC conditions for analysis of final compounds. The compounds were analyzed on an Agilent Eclipse Plus C18 (15 cm×4.6 mm), at a flow rate of 1.2 mL/min at 40° C. using a gradient from 25% acetonitrile in water (plus 0.1% trifluoracetic acid) to 50% acetonitrile in water (plus 0.1% trifluoroacetic acid) over a gradient of 9 min.

Methods of Treatment

Some embodiments include a method of inhibiting a bacterial efflux pump comprising administering to a subject infected with bacteria, a compound according to any of the structures described above. Other embodiments include a method of treating or preventing a bacterial infection comprising administering to a subject infected with bacteria or subject to infection with bacteria, a compound according to any of the structures described above in combination with another anti-bacterial agent.

Microbial Species

The microbial species to be inhibited through the use of efflux pump inhibitors, such as the above-described EPIs, can be from other bacterial groups or species, such as one of the following: *Pseudomonas aeruginosa, Pseudomonas fluorescens, Pseudomonas acidovorans, Pseudomonas alcahgenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus.*

A particularly appropriate example of a microbe appropriate for the use of an efflux pump inhibitor of the preferred embodiments is a pathogenic bacterial species, *Pseudomonas*

*aeruginosa*, which is intrinsically resistant to many of the commonly used antibacterial agents. Exposing this bacterium to an efflux pump inhibitor can significantly slow the export of an antibacterial agent from the interior of the cell or the export of siderophores. Therefore, if another antibacterial agent is administered in conjunction with the efflux pump inhibitor of preferred embodiments, the antibacterial agent, which would otherwise be maintained at a very low intracellular concentration by the export process, can accumulate to a concentration, which will inhibit the growth of the bacterial cells. This growth inhibition can be due to either bacteriostatic or bactericidal activity, depending on the specific antibacterial agent used. While *P. aeruginosa* is an example of an appropriate bacterium, other bacterial and microbial species may contain similar broad substrate pumps, which actively export a variety of antimicrobial agents, and thus can also be appropriate targets.

Antimicrobial Agents

In particular embodiments various antibacterial agents can be used in combination with the efflux pump inhibitors described herein. These include quinolones, tetracyclines, glycopeptides, aminoglycosides, β-lactams, rifamycins, macrolides/ketolides, oxazolidinones, coumermycins, and chloramphenicol. In particular embodiments, an antibiotic of the above classes can be, for example, one of the following.

Beta-Lactam Antibiotics

Beta-lactam antibiotics include, but are not limited to, imipenem, meropenem, biapenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefmetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, and LY206763.

Macrolides

Macrolides include, but are not limited to, azithromycin, clarithromycin, erythromycin, oleandomycin, rokitamycin, rosaramicin, roxithromycin, and troleandomycin.

Ketolides

Ketolides include, but are not limited to, telithromycin and cethrimycin.

Quinolones

Quinolones include, but are not limited to, amifloxacin, cinoxacin, ciprofloxacin, enoxacin, fleroxacin, flumequine, lomefloxacin, nalidixic acid, norfloxacin, ofloxacin, levofloxacin, oxolinic acid, pefloxacin, rosoxacin, temafloxacin, tosufloxacin, sparfloxacin, clinafloxacin, moxifloxacin; gemifloxacin; garenofloxacin; PD131628, PD138312, PD140248, Q-35, AM-1155, NM394, T-3761, rufloxacin, OPC-17116, DU-6859a (see, e.g., Sato, K. et al., 1992, Antimicrob Agents Chemother. 37:1491-98), and DV-7751a (see, e.g., Tanaka, M. et al., 1992, Antimicrob. Agents Chemother. 37:2212-18).

Tetracyclines, Glycylcyclines and Oxazolidinones

Tetracyclines, glycylcyclines, and oxazolidinones include, but are not limited to, chlortetracycline, demeclocycline, doxycycline, lymecycline, methacycline, minocycline, oxytetracycline, tetracycline, tigecycline, linezolide, and eperozolid.

Aminoglycosides

Aminoglycosides include, but are not limited to amikacin, arbekacin, butirosin, dibekacin, fortimicins, gentamicin, kanamycin, meomycin, netilmicin, ribostamycin, sisomicin, spectinomycin, streptomycin, and tobramycin.

Lincosamides

Lincosamides include, but are not limited to, clindamycin and lincomycin.

Efflux pumps export substrate molecules from the cytoplasm in an energy-dependent manner, and the exported substrate molecules can include antibacterial agents. Such efflux pump inhibitors are useful, for example, for treating microbial infections by reducing the export of a co-administered antimicrobial agent or by preventing the export of a compound synthesized by microbes (e.g., bacteria) to allow or improve their growth. While the endogenous substrates of efflux pumps are not yet identified, there are some indications that efflux pumps may be important for bacterial virulence. Thus, also disclosed herein are compositions that include such efflux pump inhibitors and methods for treating microbial infections using those compositions.

In some embodiments, a method is provided for treating a microbial infection in an animal, specifically including in a mammal, by treating an animal suffering from such an infection with an antimicrobial agent and an efflux pump inhibitor, which increase the susceptibility of the microbe for that antimicrobial agent. Such efflux pump inhibitors can be selected from any of the compounds generically or specifically described herein. In this way a microbe involved in the infection can be treated using the antimicrobial agent in smaller quantities, or can be treated with an antimicrobial agent, which is not therapeutically effective when used in the absence of the efflux pump inhibitor. Thus, this method of treatment is especially appropriate for the treatment of infections involving microbial strains that are difficult to treat using an antimicrobial agent alone due to a need for high dosage levels (which can cause undesirable side effects), or due to lack of any clinically effective antimicrobial agents. However, it is also appropriate for treating infections involving microbes that are susceptible to particular antimicrobial agents as a way to reduce the dosage of those particular agents. This can reduce the risk of side effects. It is also appropriate for treating infections involving microbes that are susceptible to particular antimicrobial agents as a way of reducing the frequency of selection of resistant microbes. In particular embodiments the microbe is a bacterium, which may, for example, be from any of the groups or species indicated above.

In some embodiments, a method is provided for prophylactic treatment of a mammal. In this method, an antimicrobial agent and an efflux pump inhibitor is administered to a mammal at risk of a microbial infection, e.g., a bacterial infection. The efflux pump inhibitor can be selected from any of the compounds generically or specifically described herein.

In some embodiments, a method is provided for enhancing the antimicrobial activity of an antimicrobial agent against a microbe, in which such a microbe is contacted with an efflux pump inhibitor, and an antibacterial agent. The efflux pump inhibitor can be selected from any of the compounds generically or specifically described herein. Thus, this method makes an antimicrobial agent more effective against a cell, which expresses an efflux pump when the cell is treated with the combination of an antimicrobial agent and an efflux pump inhibitor. In particular embodiments the microbe is a bacterium or a fungus, such as any of those indicated above; the antibacterial agent can be selected from a number of structural classes of antibiotics including, e.g., beta-lactams, glycopeptides, aminoglycosides, quinolones, oxazolidinones, tetracyclines, rifamycins, coumermycins, macrolides, and chloramphenicol. In particular embodiments an antibiotic of the above classes can be as stated above.

In other embodiments, a method is provided for suppressing growth of a microbe, e.g., a bacterium, expressing an efflux pump, e.g., a non-tetracycline-specific efflux pump. As illustrated by the case where the microbe is a bacterium, the method involves contacting that bacterium with an efflux pump inhibitor, in the presence of a concentration of antibacterial agent below the MIC of the bacterium. The efflux pump inhibitor can be selected from any of the compounds generically or specifically described herein. This method is useful, for example, to prevent or cure contamination of a cell culture by a bacterium possessing an efflux pump. However, it applies to any situation where such growth suppression is desirable.

In some embodiments, any of the compounds generically or specifically described herein may be administered as an efflux pump inhibitor either alone or, more preferably, in conjunction with another therapeutic agent. In some embodiments, any of the compounds generically or specifically described herein may be administered as an efflux pump inhibitor in conjunction with any of the antibacterial agents specifically or generically described herein, as well as with any other antibacterial agent useful against the species of bacterium to be treated, when such bacteria do not utilize an efflux pump resistance mechanism. In some embodiments, the antibacterial agents are administered at their usual recommended dosages. In other embodiments, the antibacterial agents are administered at reduced dosages, as determined by a physician. For all conventional antibacterials on the market, and many in clinical development, dosage ranges and preferred routes of administration are well established, and those dosages and routes can be used in conjunction with the efflux pump inhibitors of the preferred embodiments. Reduced dosages of the antibacterials are contemplated due to the increased efficacy of the antibacterial when combined with an efflux pump inhibitor.

Potential efflux pump inhibitor compounds can be tested for their ability to inhibit multi-drug resistance efflux pumps of various microbes using the methods described herein as well as those known in the art. For example, treatment of *P. aeruginosa* with a test compound allows obtaining one or more of the following biological effects:

1) *P. aeruginosa* strains will become susceptible to antibiotics that could not be used for treatment of pseudomonad infections, or become more susceptible to antibiotics, which do inhibit pseudomonal growth.
2) *P. aeruginosa* strains will become more susceptible to antibiotics currently used for treatment of pseudomonad infections.
3) Inhibition of the pump will result in a decreased frequency of resistance development to antibiotic, which is a substrate of the pump.

Obtaining even one of these effects provides a potential therapeutic treatment for infections by this bacterium. Also, similar pumps are found in other microorganisms. Some or all of the above effects can also be obtained with those microbes, and they are therefore also appropriate targets for detecting or using efflux pump inhibitors.

Administration

The efflux pump inhibitors are administered at a therapeutically effective dosage, e.g., a dosage sufficient to provide treatment for the disease states previously described. While human dosage levels have yet to be optimized for the compounds of the preferred embodiments, generally, a daily dose for most of the inhibitors described herein is from about 0.05 mg/kg or less to about 100 mg/kg or more of body weight, preferably from about 0.10 mg/kg to 10.0 mg/kg of body weight, and most preferably from about 0.15 mg/kg to 1.0 mg/kg of body weight. Thus, for administration to a 70 kg person, the dosage range would be about 3.5 mg per day or less to about 7000 mg per day or more, preferably from about 7.0 mg per day to 700.0 mg per day, and most preferably from about 10.0 mg per day to 100.0 mg per day. The amount of active compound administered will, of course, be dependent on the subject and disease state being treated, the severity of the affliction, the manner and schedule of administration and the judgment of the prescribing physician; for example, a likely dose range for oral administration can be from about 70 mg per day to 700 mg per day, whereas for intravenous administration a likely dose range can be from about 700 mg per day to 7000 mg per day, the active agents being selected for longer or shorter plasma half-lives, respectively. Screening techniques described herein for the compounds of preferred embodiments can be used with other efflux pump inhibitors described herein to establish the efficacy of those inhibitors in comparison to reference compounds, and the dosage of the inhibitor can thus be adjusted to achieve an equipotent dose to the dosages of reference compound.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administration are customary in treating the indication.

Pharmaceutically acceptable compositions include solid, semi-solid, liquid and aerosol dosage forms, such as, e.g., tablets, capsules, powders, liquids, suspensions, suppositories, aerosols or the like. The compounds can also be administered in sustained or controlled release dosage forms, including depot injections, osmotic pumps, pills, transdermal (including electrotransport) patches, and the like, for prolonged and/or timed, pulsed administration at a predetermined rate. Preferably, the compositions are provided in unit dosage forms suitable for single administration of a precise dose.

The compounds can be administered either alone or more typically in combination with a conventional pharmaceutical carrier, excipient or the like (e.g., mannitol, lactose, starch, magnesium stearate, sodium saccharine, talcum, cellulose, sodium croscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical formulation will contain about 0.005% to 95%, preferably about 0.5% to 50% by weight of a compound of the preferred embodiments. Actual methods of preparing such dosage forms are known, or will be apparent, to those skilled in this art; for example, see Remington's Pharmaceutical Sciences, Mack Publishing Company, Easton, Pa.

In addition, the compounds can be co-administered with, and the pharmaceutical compositions can include, other medicinal agents, pharmaceutical agents, adjuvants, and the like. Suitable additional active agents include, for example, antimicrobial agents as described above. When used, other active agents may be administered before, concurrently, or after administration of an efflux pump inhibitor of the preferred embodiments. In some embodiments, an efflux pump inhibitor is co-administered with one or more other antimicrobial agents. By "co-administer" it is meant that the efflux pump inhibitors are administered to a patient such that the present compounds as well as the co-administered compound may be found in the patient's bloodstream at the same time, regardless of when the compounds are actually administered, including simultaneously. In one advantageous embodiment, the pharmacokinetics of the efflux pump inhibitors and the co-administered antimicrobial agent are substantially the same.

Thus, in the preferred embodiments, an efflux pump inhibitor compound as set forth herein can be administered through a first route of administration, and the antimicrobial agent can be administered through a second route. Thus, for example, an efflux pump inhibitor can be administered via a pulmonary route, e.g., through a nebulizer, atomizer, mister, aerosol, dry powder inhaler, or other suitable device or technique, and the antimicrobial can be administered via the same or a different route, e.g., orally, parenterally, intramuscularly, intraperitoneally, intratracheally, intravenously, subcutaneously, transdermally, or as a rectal or vaginal suppository. The blood levels of drugs are affected by the route of administration. Thus, in one preferred embodiment, when the efflux pump inhibitor is administered by a first route, and the antibiotic or antimicrobial through a second route, the dosages or dosage forms are adjusted, as appropriate, to match the pharmcokinetic profiles of each drug. This may also be done when both drugs are administered by the same route. In either event, conventional techniques, including controlled release formulations, timing of administration, use of pumps and depots, and/or use of biodegradable or bioerodible carriers can be used to match the pharmacokinetic of the two active moieties.

In one preferred embodiment, the compositions will take the form of a unit dosage form such as a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule. Unit dosage forms in which the two active ingredients (inhibitor and antimicrobial) are physically separated are also contemplated; e.g., capsules with granules of each drug; two-layer tablets; two-compartment gel caps, etc.

Liquid pharmaceutically administrable compositions can, for example, be prepared by dissolving, dispersing, etc. an active compound as defined above and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid, which will be subsequently diluted to the above percentages. In some embodiments, the composition will comprise 0.2-2% of the active agent in solution.

Efflux pump inhibitors (EPIs) as described herein, including any of the compounds generically or specifically described herein, can also be administered to the respiratory tract as an aerosol. For the purposes of delivery to the respiratory tract, any of the inhaler designs known in the art may be used. In some embodiments, a metered dose inhaler (MDI) is used. A typical MDI for use with the EPIs described herein comprises the EPI compound suspended or dissolved in a pressurized liquid propellant, with or without other excipients. When the MDI inhaler is activated, a metered amount of the propellant is released and rapidly evaporates due to the sudden reduction in pressure. The process causes an aerosol cloud of drug particles to be released that can be inhaled by the patient.

Solid compositions can be provided in various different types of dosage forms, depending on the physicochemical properties of the drug, the desired dissolution rate, cost considerations, and other criteria. In one of the embodiments, the solid composition is a single unit. This implies that one unit dose of the drug is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In a preferred embodiment, the solid composition is a highly porous lyophilized form. Such lyophilizates, sometimes also called wafers or lyophilized tablets, are particularly useful for their rapid disintegration, which also enables the rapid dissolution of the active compound.

On the other hand, for some applications the solid composition may also be formed as a multiple unit dosage form as defined above. Examples of multiple units are powders, granules, microparticles, pellets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution.

Another type of multiparticulate system which is also capable of achieving rapid drug dissolution is that of powders, granules, or pellets from water-soluble excipients which are coated with the drug, so that the drug is located at the outer surface of the individual particles. In this type of system, the water-soluble low molecular weight excipient is useful for preparing the cores of such coated particles, which can be subsequently coated with a coating composition comprising the drug and, preferably, one or more additional excipients, such as a binder, a pore former, a saccharide, a sugar alcohol, a film-forming polymer, a plasticizer, or other excipients used in pharmaceutical coating compositions.

For purposes of co-administration of an EPI as described herein and another anti-bacterial compound, the EPI can be administered by the same route as the other anti-bacterial compound, either simultaneously or sequentially. In some embodiments, the EPI and other anti-bacterial compound or compounds are both administered intravenously (i.v.), either mixed in a fixed drug formulation or present in separate formulations. In other embodiments, the EPI and other anti-bacterial compound or compounds are both administered orally, either in the same fixed formulation or in separate formulations. In still other embodiments, the EPI and other anti-bacterial compound or compounds are both administered intramuscularly (i.m.), again either mixed in a fixed drug formulation or present in separate formulations.

In some embodiments, the EPI and other anti-bacterial compound to be co-administered are administered by separate routes. For example, the EPI may be administered by inhalation while the other anti-bacterial compound is administered i.v., i.m., or orally. Any other possible combination of separate route administration is also contemplated.

The preferred embodiments also include any of the novel compounds disclosed herein per se, as well as any of the efflux pump inhibitors disclosed herein in unit dosage forms combined with or for co-administration with an antimicrobial, as well as methods of treating an animate or inanimate subject or object with those efflux pump inhibitors, preferably in combination with an antimicrobial. Metered dose inhalers or other delivery devices containing both an efflux pump inhibitor as described herein as well as an antimicrobial are also preferred embodiments

BIOLOGICAL EXAMPLES

EPI activity is defined as concentration of an EPI compound that is necessary to achieve ½ of a maximum theoretical effect in increase of antibiotic susceptibility due to efflux inhibition. The maximum theoretical effect, $E_{max}$, is defined as a ratio of antibacterial activity of antibiotics (minimal inhibitory concentration, MIC) of pump overexpressing vs. pump lacking strains. Levofloxacin was used as a test antibiotic to assess the EPI activity in *P. aeruginosa*. The strain PAM1723, overexpressing the MexABOprM efflux pump was used as a test strain. Levofloxacin MIC of this strain is 1 μg/ml vs. 0.015 μg/ml for the strain PAM1626 which lacks efflux, resulting in $E_{max}$=64. Thus, EPI activity that is assessed in *P. aeruginosa*, is a concentration of an EPI compound that is necessary to increase susceptibility to levofloxacin of PAM1723 eightfold. Azithromycin was used as test antibiotic to assess the EPI activity in *Klebsiella pneumoniae*. The strain KPM1004 overexpressing the AcrABTolC efflux pump was used as a test strain. Azithromycin MIC of this strain is 32 μg/ml vs 0.125 μg/ml for the strain KPM1007 which lacks efflux, resulting in $E_{max}$=256. Thus, EPI activity, that is assessed in *K. pneumoniae*, is a concentration of an EPI compound that is necessary to increase susceptibility to azithromicin of KPM1004 sixteen fold.

The EPI activity of the test compounds was assessed by the checkerboard assay (Antimicrobial Combinations, Antibiotics in Laboratory Medicine, Ed. Victor Lorian, M.D., Fourth edition, 1996, pp 333338, which is incorporated herein by reference in its entirety) using a broth microdilution method performed as recommended by the NCCLS (National Committee for Clinical Laboratory Standards (NCCLS), 1997, Methods for Dilution of Antimicrobial Susceptibility Tests for Bacteria That Grow Aerobically, Fourth Edition; Approved Standard. NCCLS Document M7A4, Vol 17 No. 2, which is incorporated herein by reference in its entirety). In this assay, multiple dilutions of two drugs, namely an EPI and antibiotics (levofloxacin or azithromycin), were tested, alone and in combination, at concentrations equal to, above and below their respective minimal inhibitory concentrations (MICs). All EPI compounds were readily soluble in water and stock solutions were prepared at a final concentration of 10 mg/ml. Stock solutions were further diluted, according to the needs of the particular assay, in Mueller Hinton Broth (MHB). Stock solution was stored at −80° C. The checkerboard assay was performed in microtiter plates. Levofloxacin or azithromycin were diluted in the axis, each column containing a single concentration of antibiotic (levofloxacin or azithromycin). EPIs were diluted in the axis, each row containing a single concentration of an EPI. The result of these manipulations was that each well of the microtiter plate contained a unique combination of concentrations of the two agents. The assay was performed in MHB with a final bacterial (PAM1723 or PAM1004) inoculum of 5 times $10^5$ CFU/ml (from an early log phase culture). Microtiter plates were incubated during 20 h at 35° C. and were read using a microtiter plate reader (Molecular Devices) at 650 nm as well as visual observation using a microtiter plate reading mirror. The MIC (here referred to as MPC; see infra) was defined as the lowest concentration of antibiotics, within the combination, at which the visible growth of the organism was completely inhibited.

Biological Example 1

Potentiation of levofloxacine ($MPC_8$) by Polybasic Efflux Pump Inhibitors

TABLE 6

| Compound | $MPC_8$ (μg/mL) (Levofloxacin, PAM1723) | $MPC_{16}$ (μg/mL) Azithromycin, KPM1004) | Compound | $MPC_8$ (μg/mL) (Levofloxacin, PAM1723) | $MPC_{16}$ (μg/mL) Azithromycin, KPM1004) |
|---|---|---|---|---|---|
| 1 | 0.3 | 0.6 | 49 | 5 | 5 |
| 2 | 1.25 | 2.5 | 56 | 1.25 | — |
| 3 | 1.25 | 1.25 | 57 | 1.25 | — |
| 4 | 1.25 | 1.25 | 67 | >10 | 2.5 |
| 5 | 0.6 | — | 77 | 5 | 2.5 |
| 6 | 2.5 | 1.25 | 83 | 0.63 | — |
| 8 | 1.25 | 2.5 | 85 | 5 | 2.5 |
| 10 | 0.6 | 1.25 | 87 | 5 | 0.63 |
| 12 | 1.25 | 1.25 | 88 | 10 | 5 |
| 11 | 2.5 | — | 90 | 1.25 | 0.60 |
| 13 | 1.25 | — | 91 | 0.60 | 0.30 |
| 14 | 2.5 | — | 95 | 2.5 | 1.25 |
| 15 | 5 | 2.5 | 96 | 10 | 2.5 |
| 17 | 2.5 | 2.5 | 102 | 5 | 1.25 |
| 19 | 10 | 10 | 107 | 2.5 | — |
| 20 | 10 | — | 109 | 2.5 | 0.60 |

TABLE 6-continued

| Compound | $MPC_8$ (μg/mL) (Levofloxacin, PAM1723) | $MPC_{16}$ (μg/mL) Azithromycin, KPM1004) | Compound | $MPC_8$ (μg/mL) (Levofloxacin, PAM1723) | $MPC_{16}$ (μg/mL) Azithromycin, KPM1004) |
|---|---|---|---|---|---|
| 21 | 2.5 | — | 110 | 5 | 5 |
| 22 | 0.3 | — | 115 | 5 | 10 |
| 23 | 1.25 | 5 | 122 | 2.5 | 10 |
| 24 | 0.6 | 1.25 | 133 | 5 | 10 |
| 25 | 0.3 | 0.6 | 138 | 2.5 | — |
| 27 | 0.6 | — | 169 | 1.25 | 1.25 |
| 28 | 1.25 | 1.25 | 188 | 0.6 | 1.25 |
| 30 | 2.5 | 5 | 214 | 2.5 | 1.25 |
| 31 | 0.3 | — | 215 | 2.5 | 2.5 |
| 32 | 1.25 | — | 224 | >10 | 2.5 |
| 33 | 2.5 | 5.0 | 233 | 1.25 | 0.60 |
| 38 | 0.3 | — | 237 | 2.5 | 2.5 |
| 39 | 10 | — | 271 | 5 | 2.5 |
| 40 | 20 | 10 | 327 | 1.25 | 1.25 |
| 41 | 5 | 10 | 331 | >10 | 2.5 |
| 42 | 0.3 | — | 345 | 2.5 | 1.25 |
| 43 | 0.6 | — | 348 | 2.5 | 2.5 |
| 44 | 0.6 | — | 352 | 1.25 | — |
| 45 | 0.6 | — | 354 | 0.6 | 0.60 |
| 46 | 0.6 | 1.25 | 357 | 1.25 | 1.25 |
| 47 | 0.6 | — | 359 | 0.60 | 1.25 |
| 48 | 1.25 | — | 361 | 1.25 | 0.31 |
| 377 | 1.25 | 1.25 | 381 | 0.6 | 2.5 |
| 382 | 1.25 | 1.25 | 379 | 5 | 2.5 |
| 383 | 1.25 | 5 | 384 | 1.25 | 1.25 |
| 385 | 1.25 | 0.6 | 386 | 10 | 0.6 |
| 388 | 1.25 | 1.25 | 389 | 0.6 | 1.25 |
| 390 | 10 | 1.25 | 391 | >10 | 5 |
| 392 | 1.25 | 1.25 | 395 | 2.5 | 2.5 |
| 398 | 0.6 | 0.6 | 399 | 0.6 | 2.5 |
| 400 | 1.25 | 2.5 | 401 | 0.6 | 0.6 |
| 402 | 0.6 | 1.25 | 403 | 1.25 | 0.6 |
| 408 | 2.5 | 5 | 411 | 1.25 | 2.5 |
| 412 | 0.6 | 1.25 | 431 | 0.6 | 1.25 |
| 415 | 1.25 | 0.6 | 422 | 2.5 | 1.25 |
| 424 | 2.5 | 1.25 | 421 | 5 | 2.5 |
| 441 | 0.6 | 2.5 | 442 | 2.5 | 5 |
| 440 | 1.25 | 2.5 | 443 | 5 | 5 |
| 444 | >10 | >10 | 430 | 10 | 1.25 |
| 446 | 0.6 | 1.25 | 450 | 1.25 | 2.5 |
| 449 | 1.25 | 0.63 | 451 | 1.25 | 1.25 |
| 454 | 0.63 | 1.25 | 457 | 2.5 | 1.25 |
| 435 | 0.6 | 5 | 436 | 1.25 | 1.25 |
| 437 | 5 | 5 | 464 | 10 | 5 |
| 465 | 2.5 | 10 | | | |

In the experiment depicted in Table 6, above, levofloxacin potentiation activities of selected inhibitors for *P. aeruginosa* are reported as Minimum Potentiating Concentration $MPC_8$ values. These values correspond to the lowest concentration of the inhibitor required to achieve antibacterial activity in combination with the concentration of levofloxacin equal to ⅛ of the levofloxacin concentration required to achieve the same antibacterial effect alone (MIC of levofloxacin). Azithromycin potentiation activities of selected inhibitors for *K. pneumoniae* are reported as $MPC_{16}$ values. These values correspond to the lowest concentration of the inhibitor required to achieve antibacterial activity in combination with the concentration of azithromycin equal to 1/16 of the azithromycin concentration required to achieve the same antibacterial effect alone (MIC of azithromycin).

Biological Example 2

Pharmacokinetics of Polybasic Efflux Pump Inhibitors in Rats after IV Infusion

TABLE 7

| Compound | Dose (mg/kg) | Clearance[a] (L/h/kg) | C max (μg/mL) |
|---|---|---|---|
| 2 | 5 | 13.0 | 2.25 |
| 3 | 20 | 1.2 | 27.8 |
| 8 | 20 | 9.20 | 19.5 |
| 28 | 10 | 14.15 | 3.62 |
| 30 | 10 | 3.36 | 7.61 |
| 31 | 10 | 1.80 | 21.9 |
| 33 | 10 | 6.32 | 3.98 |
| 41 | 10 | 2.72 | 8.1 |
| 44 | 2 | 1.48 | 2.68 |

TABLE 7-continued

| Compound | Dose (mg/kg) | Clearance[a] (L/h/kg) | C max (µg/mL) |
|---|---|---|---|
| 46 | 2 | 0.81 | 4.0 |
| 47 | 5 | 1.70 | 8.1 |
| 48 | 5 | 1.56 | 7.2 |
| 49 | 2.6 | 4.21 | 2.39 |
| 67 | 5 | 3.1 | 2.98 |
| 77 | 5 | 3.79 | 2.96 |
| 85 | 20 | 3.0 | 13.86 |
| 87 | 5 | 3.86 | 10.97 |
| 88 | 2.8 | 1.68 | 2.5 |
| 90 | 1.5 | 6.17 | 1.22 |
| 91 | 4.5 | 5.89 | 2.67 |
| 95 | 1.2 | 1.81 | 1.75 |
| 96 | 5 | 3.11 | 3.85 |
| 102 | 5 | 2.58 | 5.05 |
| 110 | 5 | 5.47 | 1.89 |
| 115 | 5 | 3.47 | 2.65 |
| 133 | 5 | 5.30 | 1.27 |
| 169 | 20 | 1.88 | 22.86 |
| 214 | 2.5 | 5.53 | 1.54 |
| 215 | 1.5 | 5.60 | 0.69 |
| 224 | 2.5 | 3.97 | 1.59 |
| 233 | 5 | 7.1 | 4.92 |
| 237 | 2.5 | 4.25 | 1.26 |
| 271 | 1.0 | 4.71 | 0.34 |
| 348 | 5 | 19.7 | 2.20 |
| 352 | 4.7 | 10.6 | 2.44 |
| 357 | 2.5 | 8.69 | 0.66 |
| 359 | 5 | 2.89 | 5.03 |

[a]free drug clearance

In the experiment depicted in Table 7, above, rat serum pharmacokinetics of selected inhibitor compounds was evaluated after 1.5-hour IV infusion of 1.5 ml solution of corresponding efflux pump inhibitor in 0.9% saline. Depending on the concentration used the total infused dose was 2, 5, 10 or 20 mg/kg. A two-compartment model was used to fit the data and calculate PK parameters. Compounds 2, 3, 46 and 48 showed particularly attractive pharmacokinetic profiles.

Although the invention has been described with reference to embodiments and examples, it should be understood that numerous and various modifications can be made without departing from the spirit of the invention. Accordingly, the invention is limited only by the following claims.

What is claimed is:

1. A compound having the structure of formula IV:

(IV)

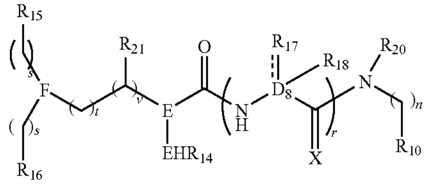

or a pharmaceutically acceptable salt thereof, wherein:

$D_8$ is C;

each E is independently CH or N;

F is selected from the group consisting of:

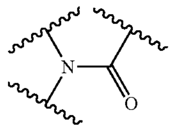, 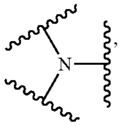, 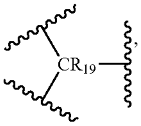,

-continued

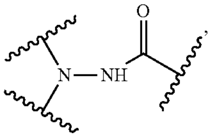, 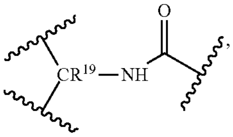, 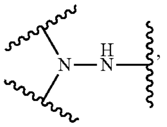, 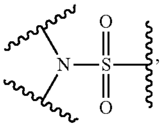, 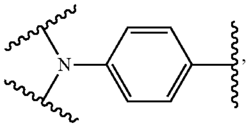, 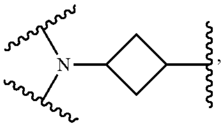, 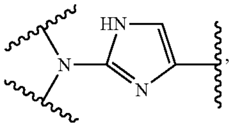, 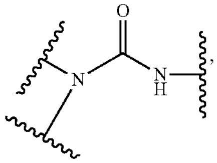, 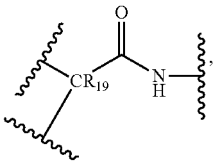, 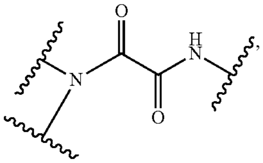, 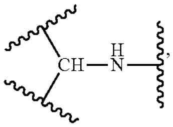, and

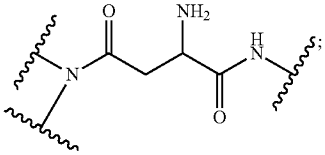;

X is O;

$R_{10}$ is selected from carbocyclyl, heterocyclyl, aryl, heteroaryl, —NHC(O)-aryl, and aralkyl, each optionally substituted with up to 3 substituents independently selected from the group consisting of a halide, alkyl optionally substituted with —$CF_3$ or —OH, alkylaminoalkoxy, —$CF_3$, —$OCF_3$, —$NO_2$, —CN, —OH, =O, carbocyclyl optionally substituted with halide, heterocyclyl, aryl optionally substituted with halide or —OH, heteroaryl optionally substituted with alkyl, —O-aryl optionally substituted with —O—$C_1$-$C_6$ alkyl, alkyl, or heterocyclyl, —O-heteroaryl optionally substituted with halide or —$CF_3$, —O—heterocyclyl, —$SO_2$NH-heteroaryl, —O—$C_1$-$C_6$ alkyl optionally substituted with halide, —$SO_2$N(alkyl)$_2$, —SMe, —$SO_2CF_3$, di($C_1$-$C_6$)alkylamino, —$CH_2$-heterocyclyl optionally substituted with alkyl, —$CH_2$-aryl, —C(O)aryl, and —CH=CH-aryl;

$R_{14}$ is selected from H, —C(O)—CH(Me)($NH_2$), —C(O)CH($NH_2$)(arylether), —C(O)CH($NH_2$)(aminoalkyl), —C(O)—CH($CH_2$OH)($NH_2$), and —($CH_2$)$_t$NH;

$R_{15}$ and $R_{16}$ are independently selected from —$NH_2$, —NHC(=NH)$NH_2$, $^+(CH_3)_3$, —$NHCH_2CH_2NH_2$, —N($CH_2CH_2NH_2$)$_2$, —C(O)N($CH_2CH_2NH_2$)$_2$, —CH($CH_2NH_2$)$_2$, and —$CH_2$($NH_2$)($CH_2NH_2$), or $R_{15}$ and $R_{16}$ together with F form a heterocyclyl substituted with one or more substituents independently selected from $—(CH_2)_sNH_2$, $—(CH_2)_sNHC(=NH)NH_2$, $—(CH_2)_sN^+(CH_3)_3$, $—(CH_2)_sNHCH_2CH_2NH_2$, $—(CH_2)_sN(CH_2CH_2NH_2)_2$, $—(CH_2)_sC(O)N(CH_2CH_2NH_2)_2$, and $—(CH_2)_sCH(CH_2NH_2)_2$;

$R_{17}$ is selected from alkyl, aralkyl, arylthioether, arylether, heteroaralkyl, carbocyclyl-alkyl, heterocyclyl-alkyl, aryl, and carbocyclyl, each optionally substituted with up to 3 substituents independently selected from the group consisting of $—CF_3$, —OH, $—OCF_3$, halide, —CN, alkyl, —O-aralkyl, aryl, $—S(CH_3)_2$, —C(O)aryl, —S-aralkyl optionally substituted with —OMe, =O, and =N—OH;

$R_{18}$ is H, $R_{19}$ is H, $—NH_2$, $—CH_2NH_2$, or $—CH_2CH_2NH_2$;

$R_{20}$ is H or $C_1$-$C_4$ alkyl;

$R_{21}$ is $—NH_2$, —OH, alkyl, t is an integer from 0 to 4;

each s is independently an integer from 0 to 3;

r is 1;

v is 0 or 1; and n is an integer from 0 to 4.

2. The compound of claim 1, having the structure:

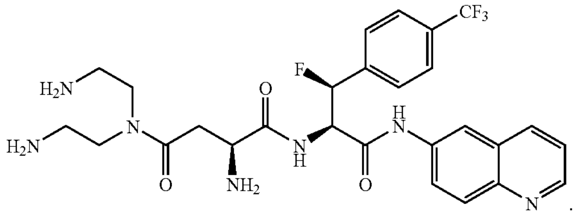

3. The compound of claim 1, having the structure:

279

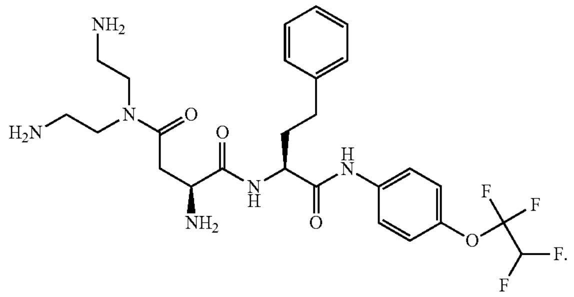

4. A method of inhibiting a bacterial efflux pump, comprising administering to a subject infected with a bacteria a compound according to claim 1.

5. A method of treating a bacterial infection, comprising co-administering to a subject infected with a bacteria or subject to infection with a bacteria, a compound according to claim 1 and another anti-bacterial agent.

6. The method of claim 5 wherein the bacteria is selected from *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus.*

7. The method of claim 5 wherein the bateria is selected from *Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii*, or *Bacteroides splanchnicus.*

8. The method of claim 5 wherein the anti-bacterial agent is selected from quinolones, tetracyclines, glycopeptides, aminoglycosides, β-lactams, rifamycins, macrolides/ketolides, oxazolidinones, coumermycins, and chloramphenicol.

9. A pharmaceutical composition, comprising a compound according to claim 1 and a pharmaceutically acceptable carrier, diluent, or excipient.

10. The compound of claim 1 having a structure selected from the group consisting of:

-continued
1
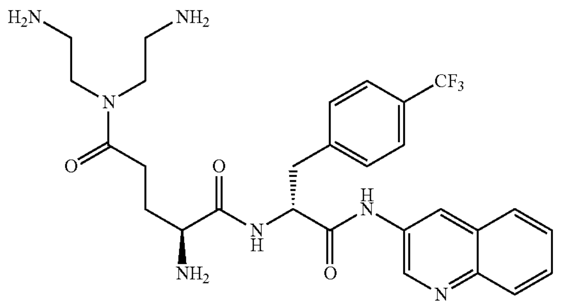
2
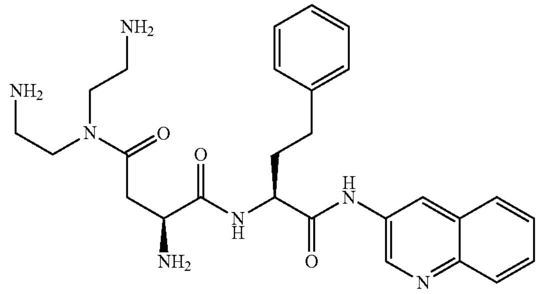
3
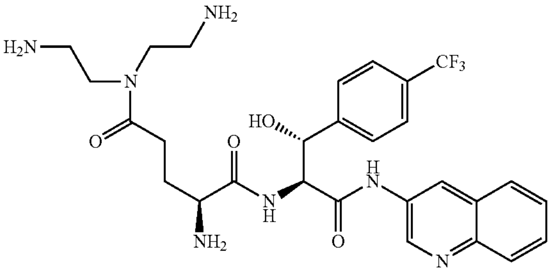
4
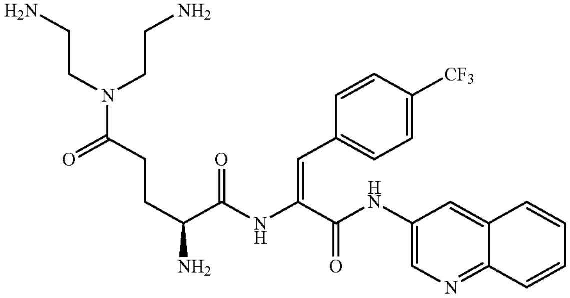
6
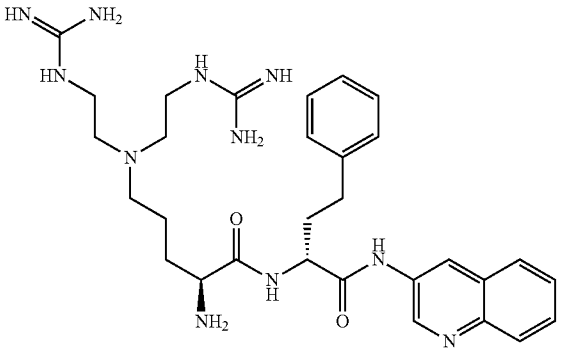
7
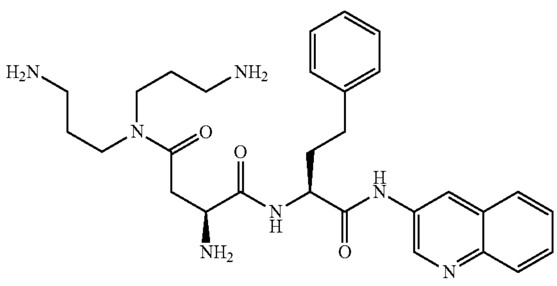
8
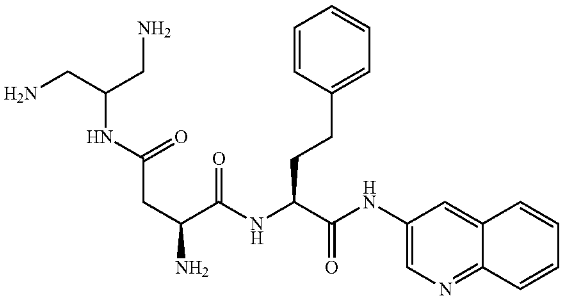
9
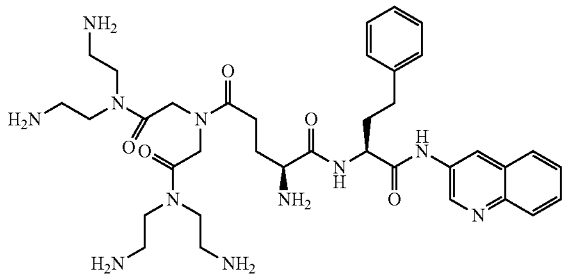
10
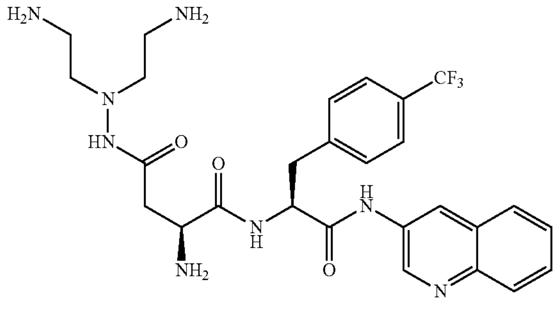
11
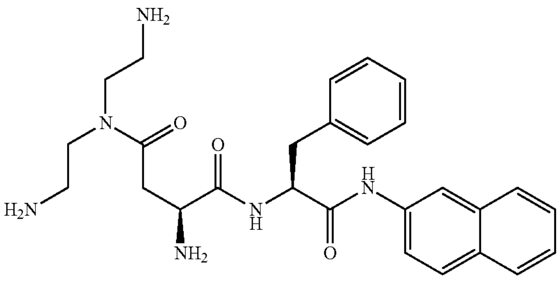

13
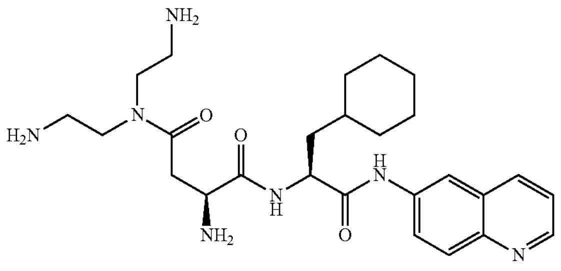
14
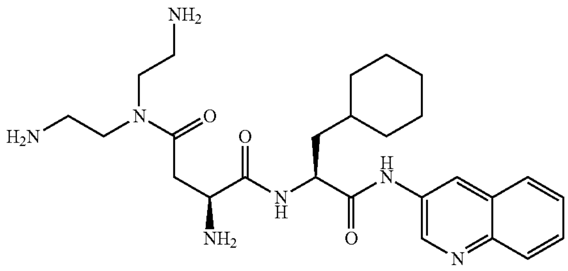
15
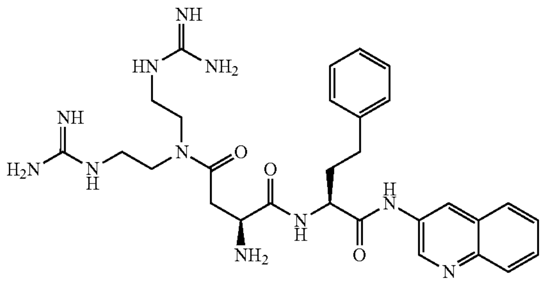
17
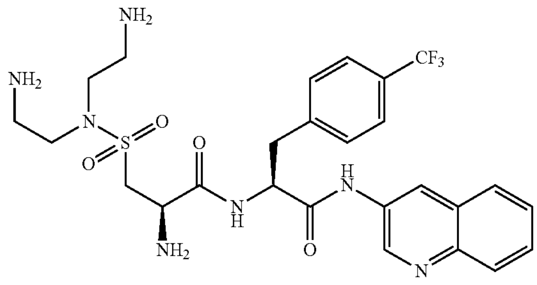
18
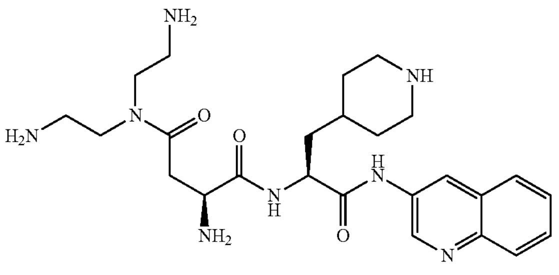
19
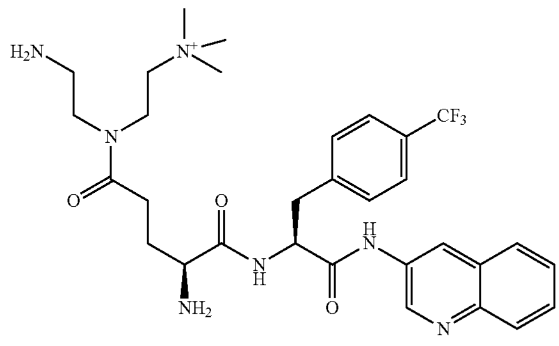
20
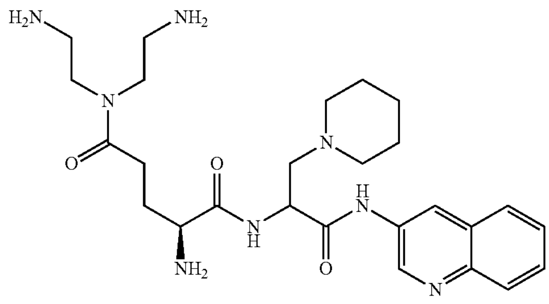
21
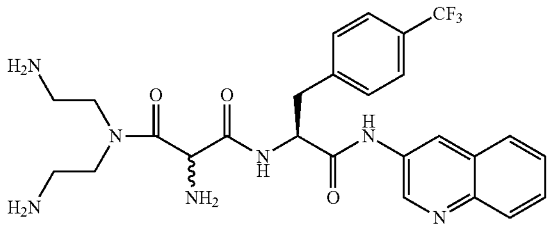
22
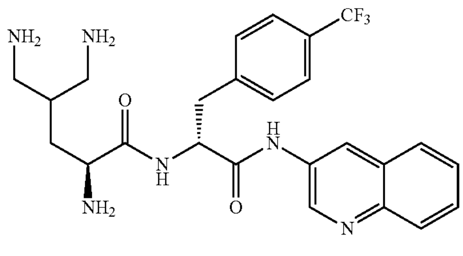
23
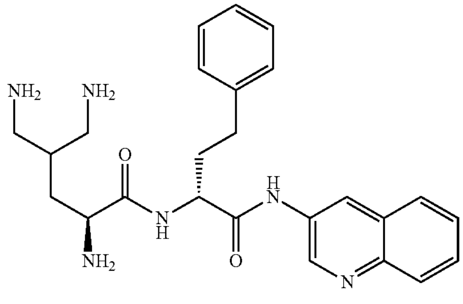

-continued
25
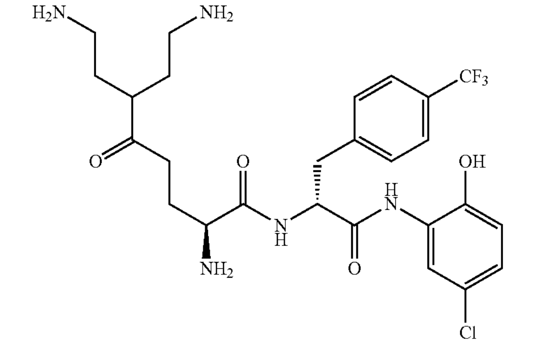
26
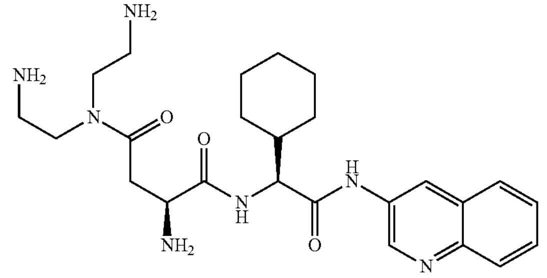
27
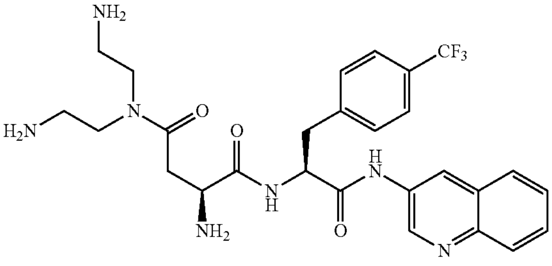
28
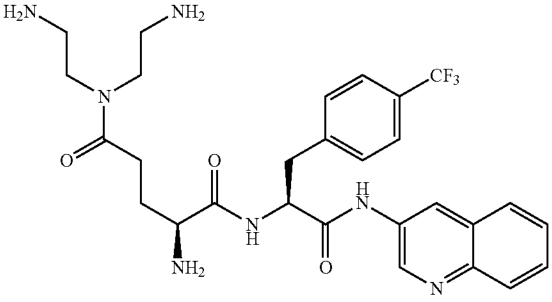
29
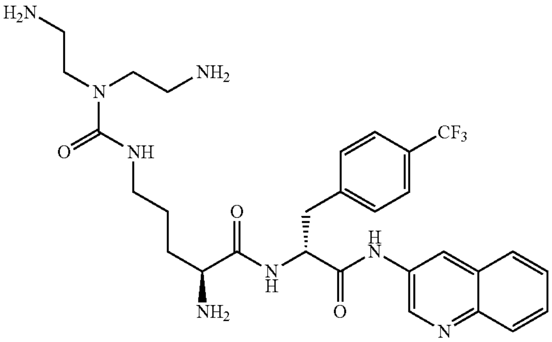
-continued
30
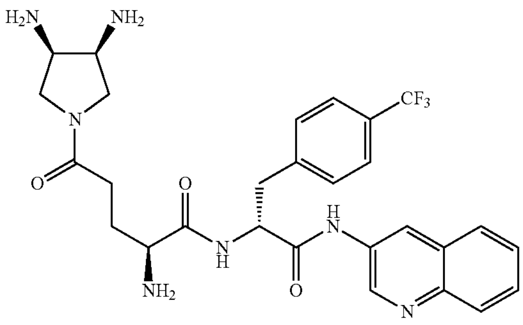
31
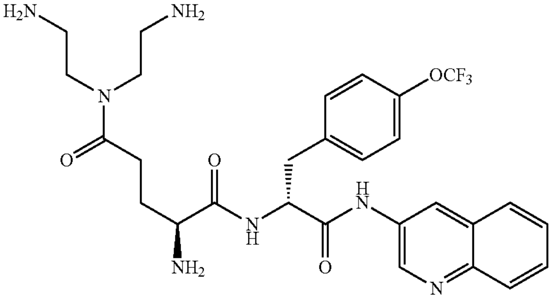
32
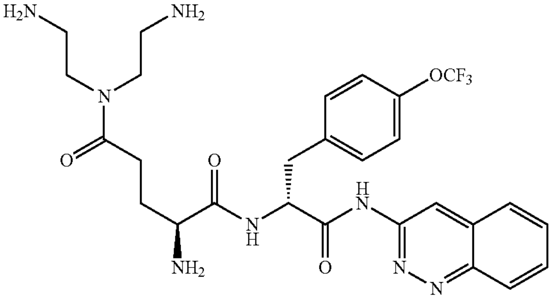
33
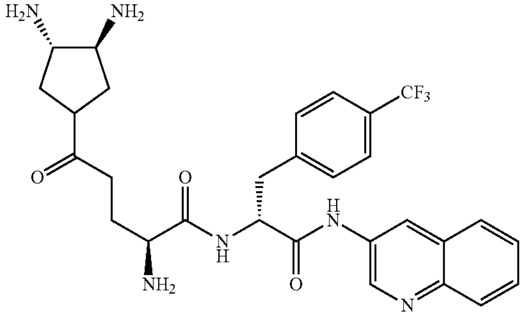
34
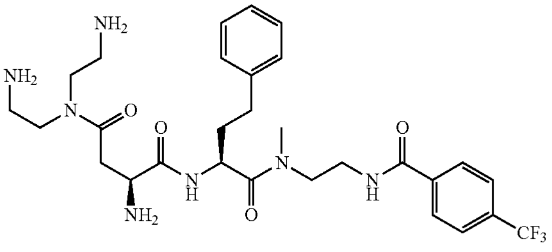

-continued
35
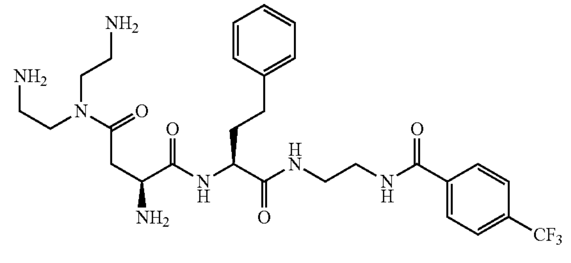
36
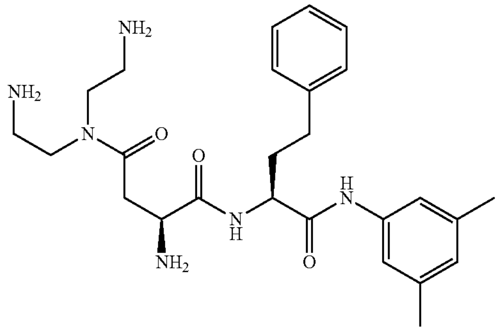
37
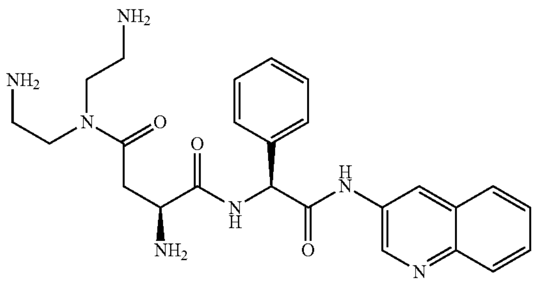
38
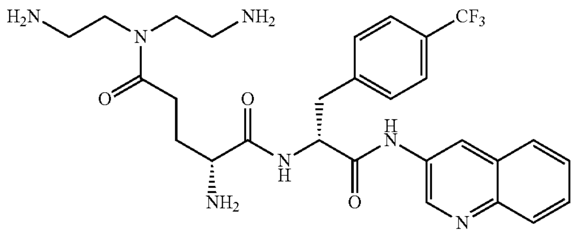
39
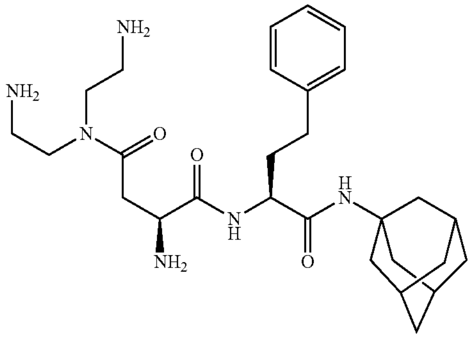
-continued
40
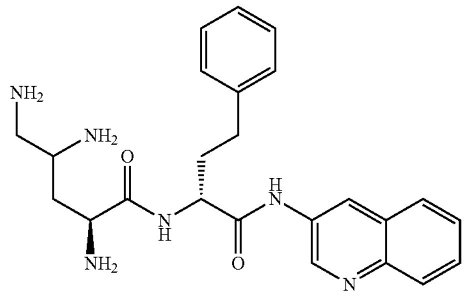
41
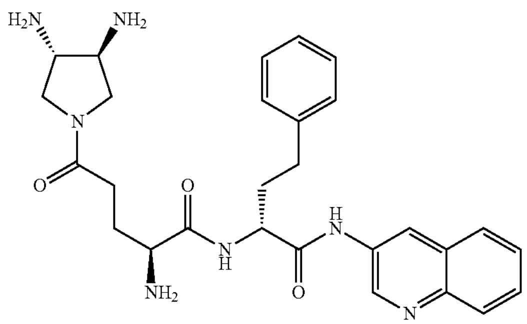
42
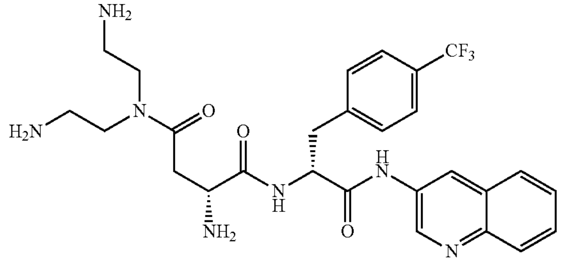
43
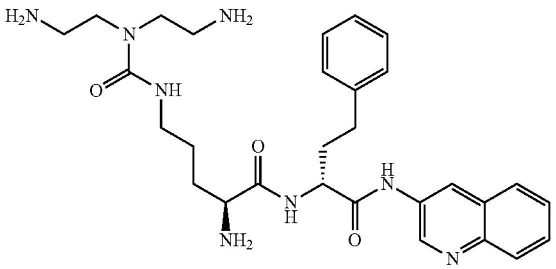
44
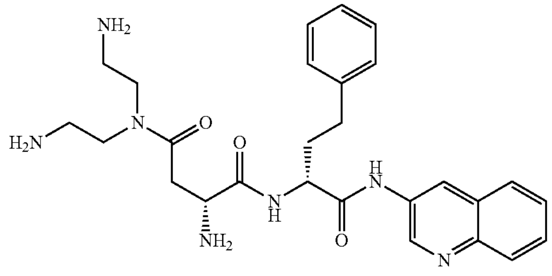

-continued
45
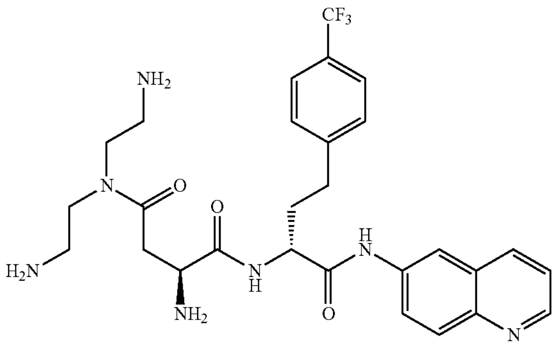
46
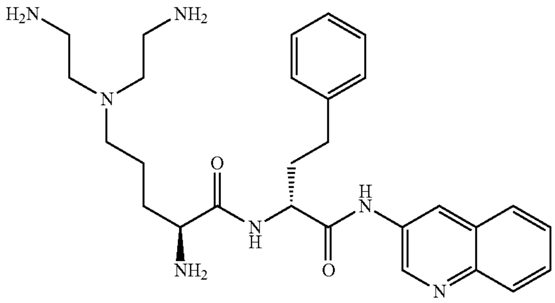
47
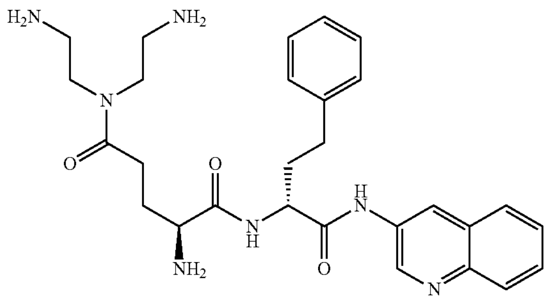
48
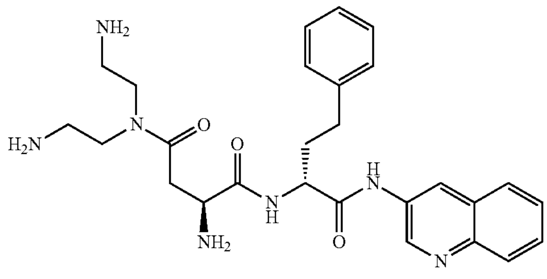
49
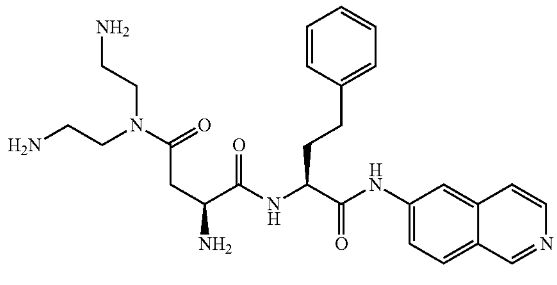
-continued
50
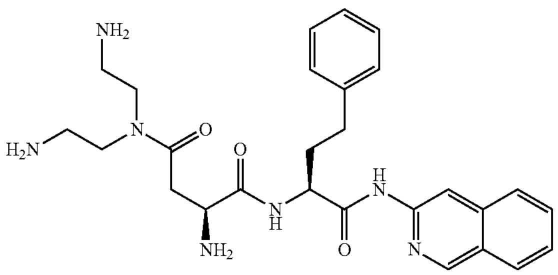
51
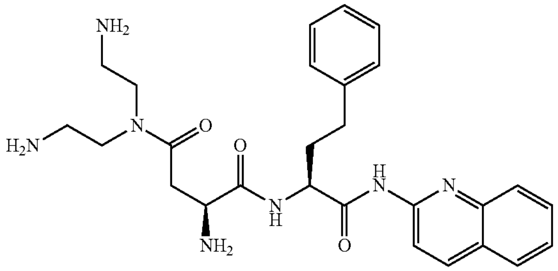
52
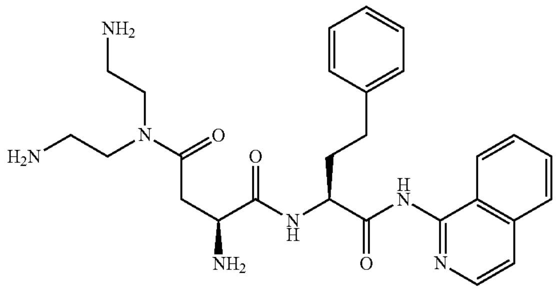
53
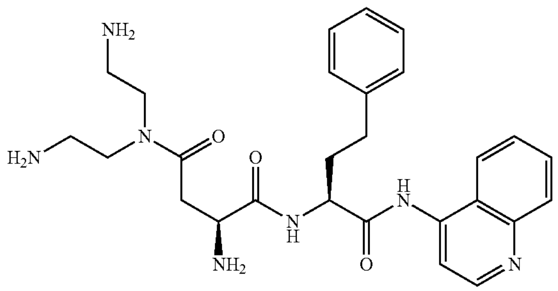
54
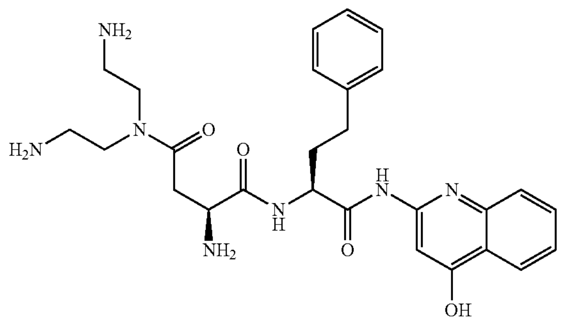

-continued
55
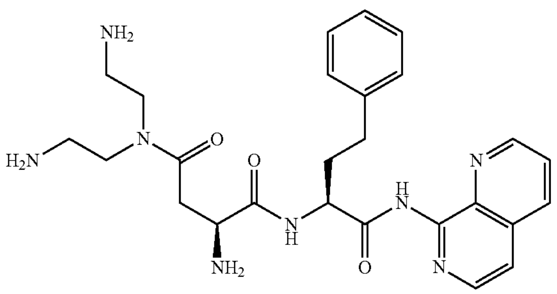
56
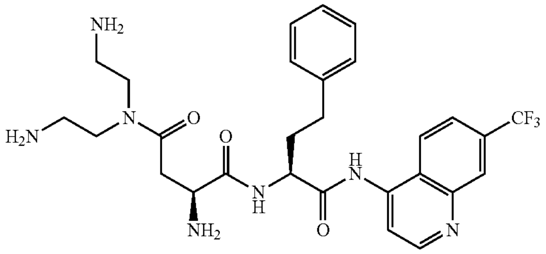
57
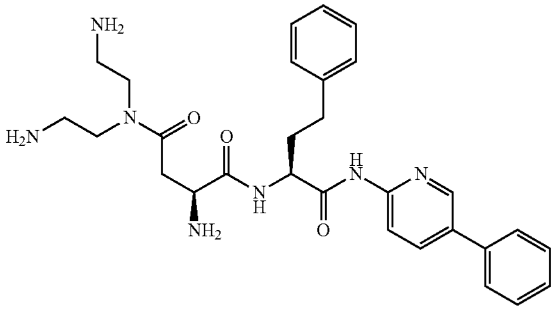
58
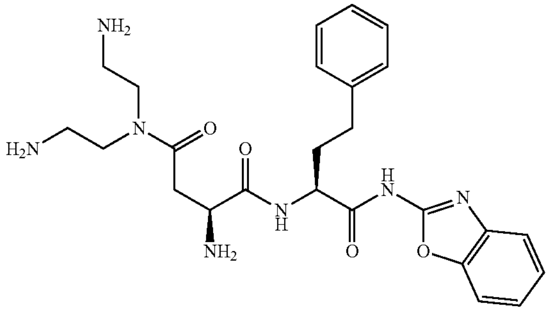
59
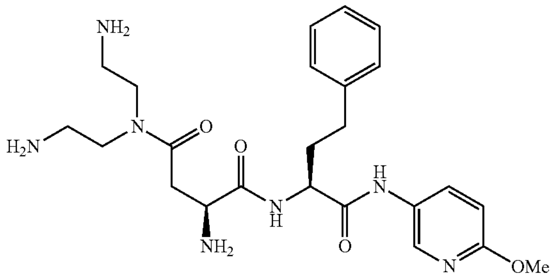
-continued
60
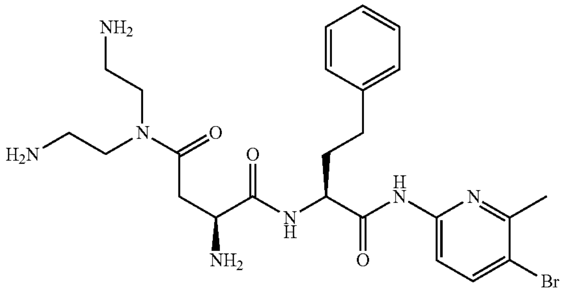
61
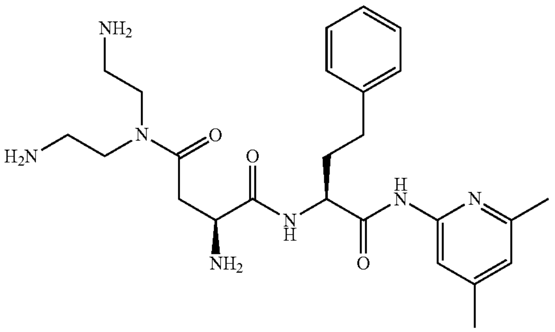
62
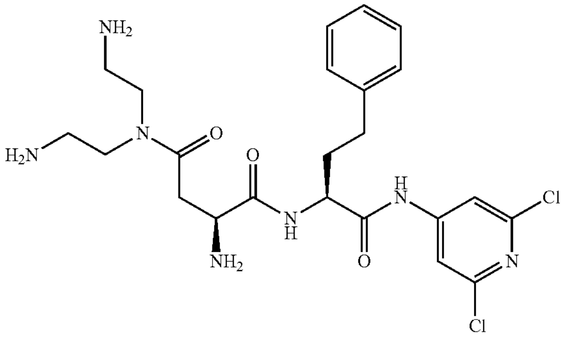
63
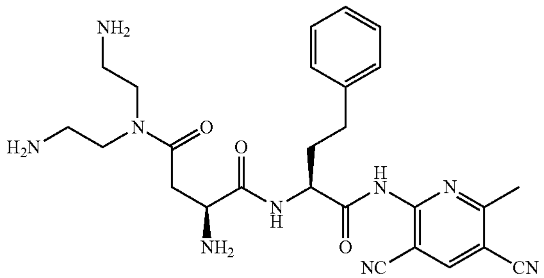
64
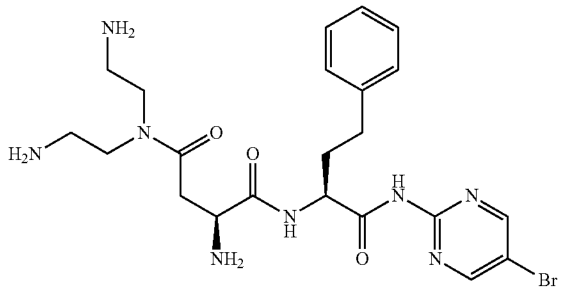

-continued
65
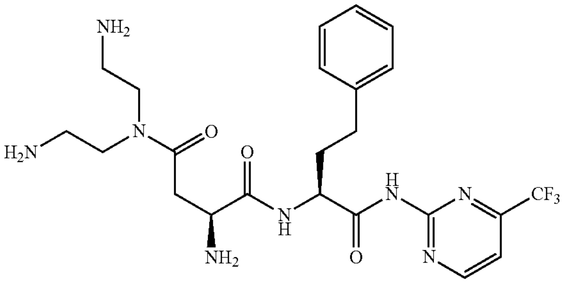
66
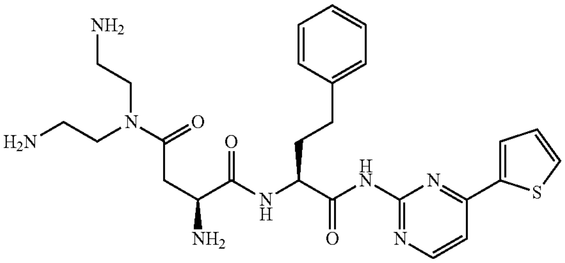
67
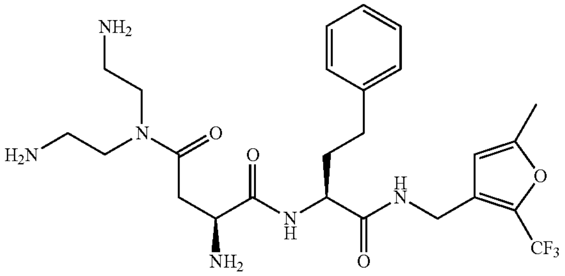
68
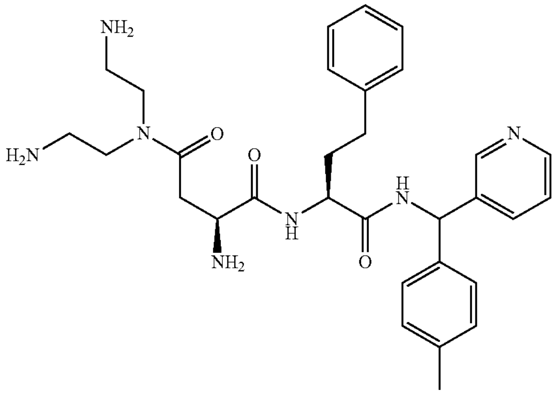
69
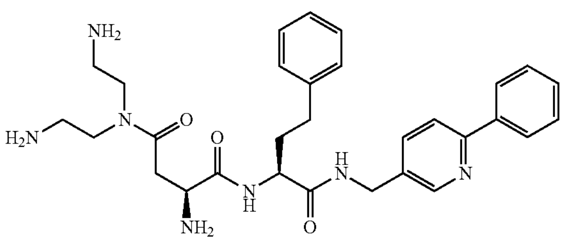
-continued
70
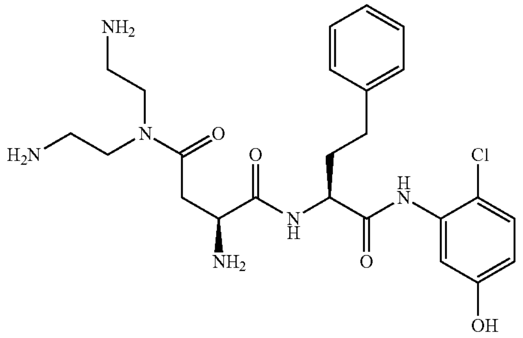
71
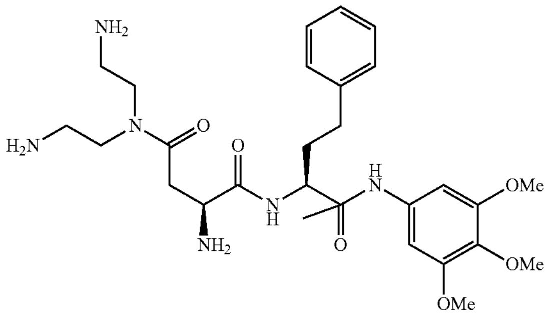
72
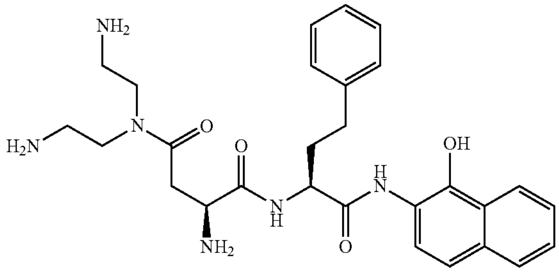
73
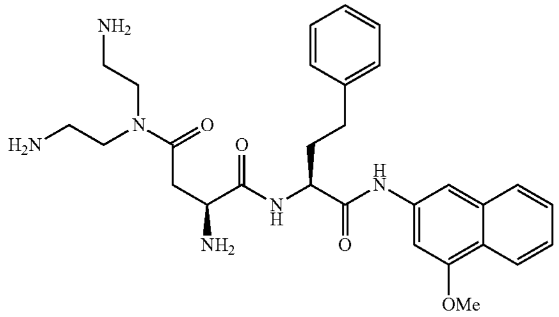

-continued
74
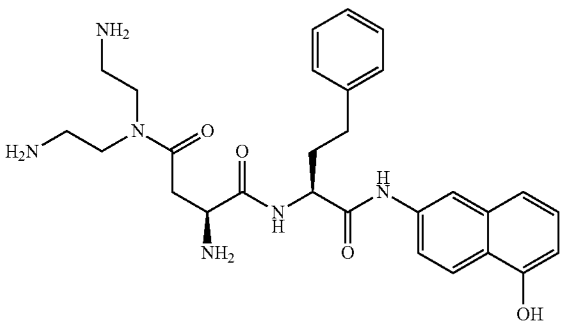
75
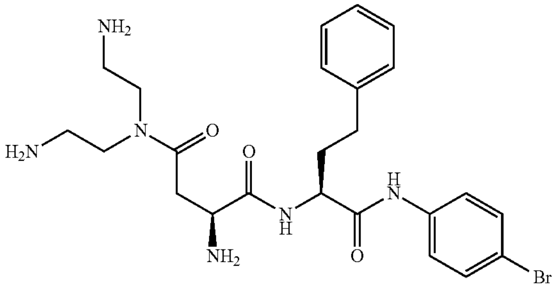
76
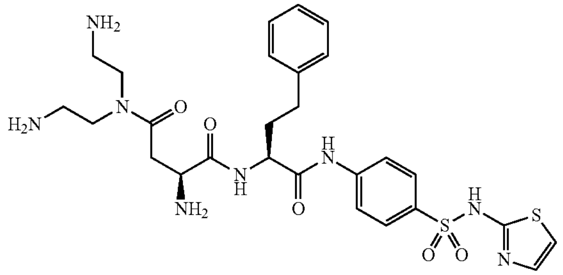
77
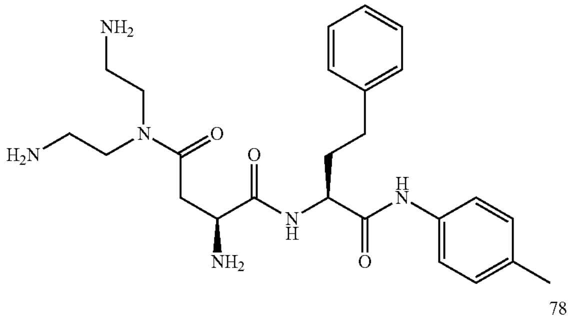
78
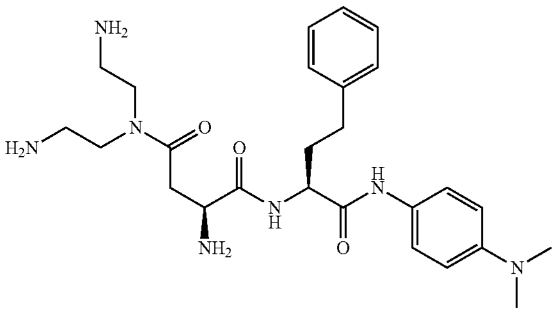
-continued
79
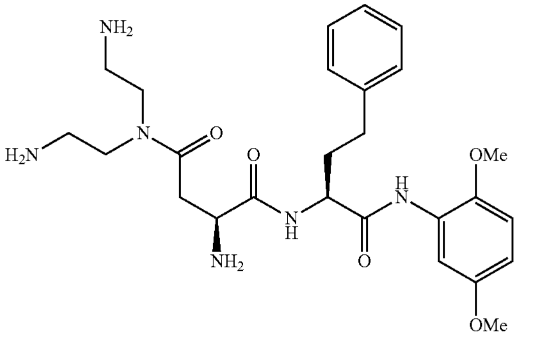
80
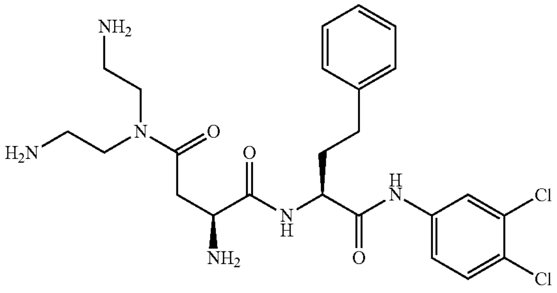
81
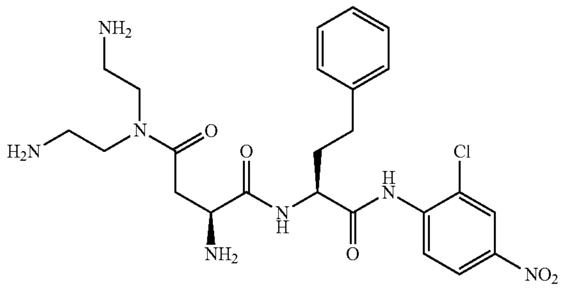
82
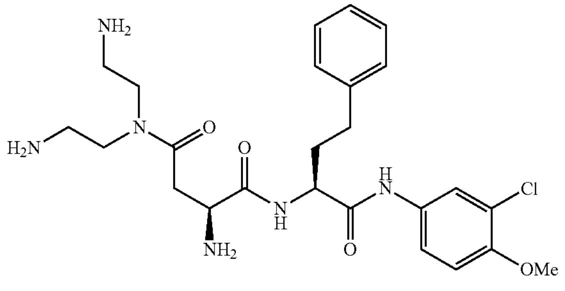
83
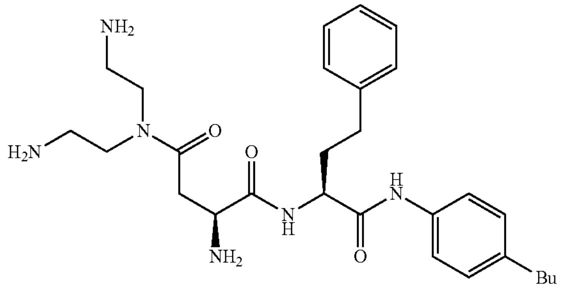

-continued
84
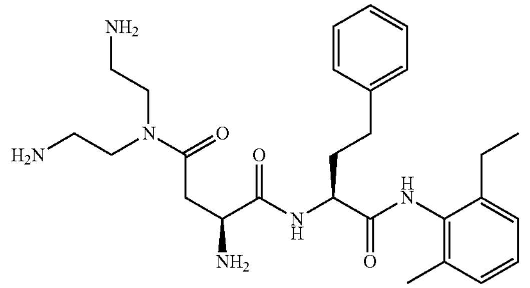
85
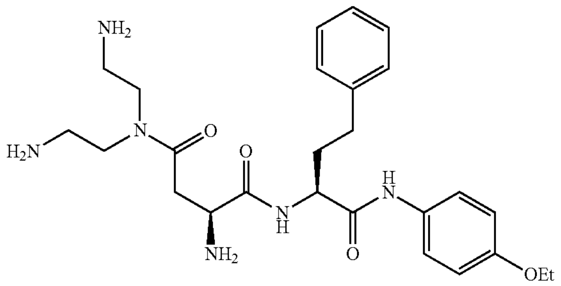
87
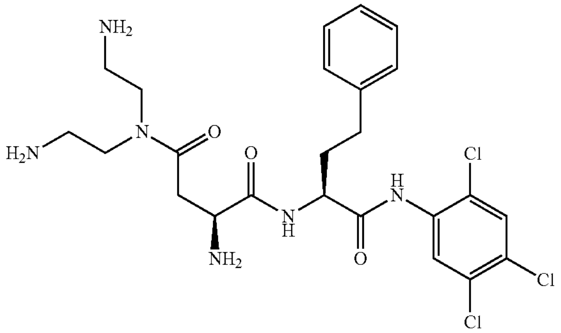
88
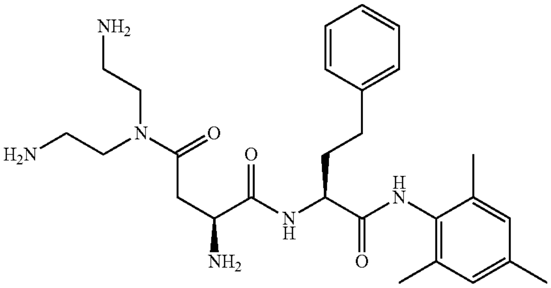
89
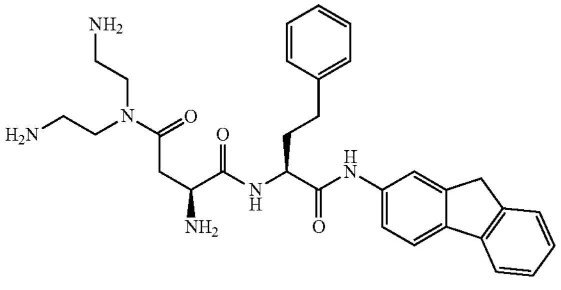
-continued
90
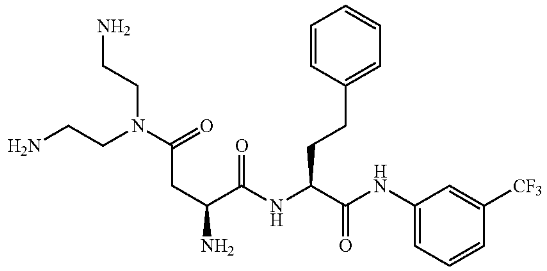
91
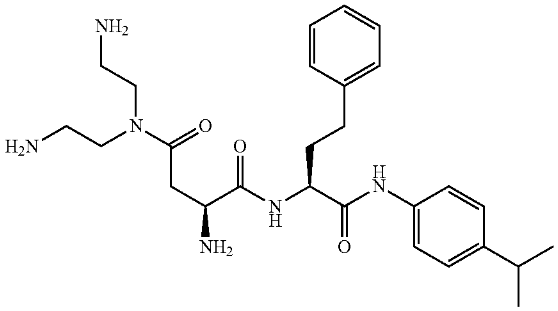
92
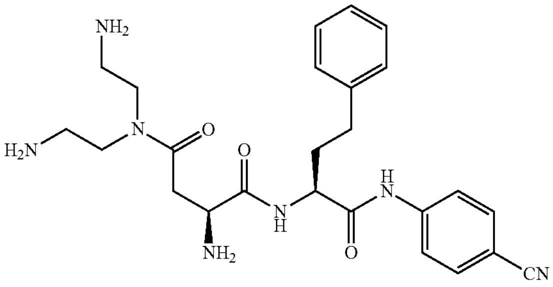
93
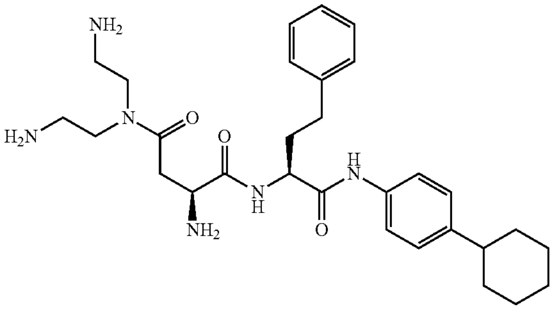
94
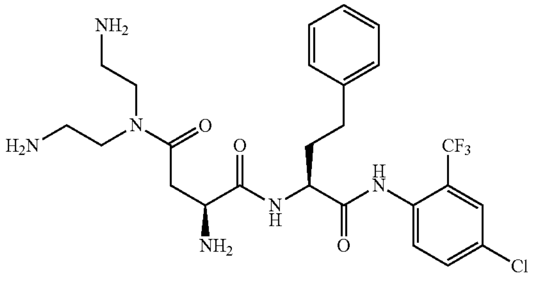

-continued
95
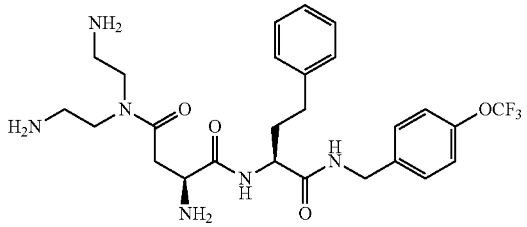
96
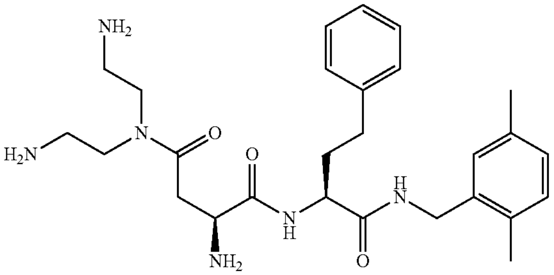
97
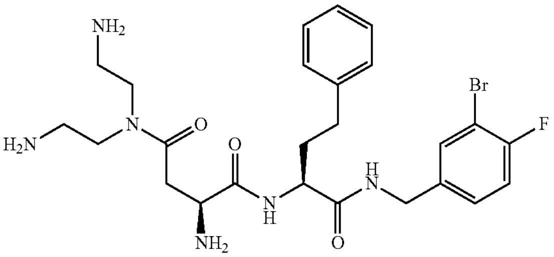
98
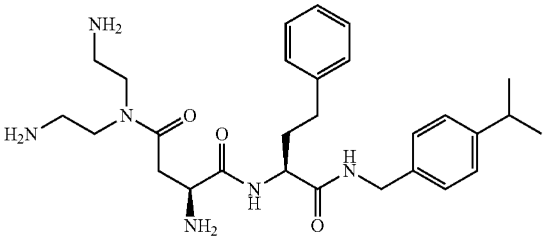
99
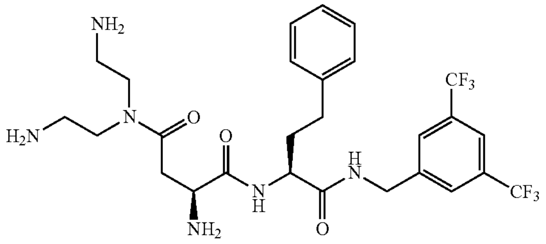
100
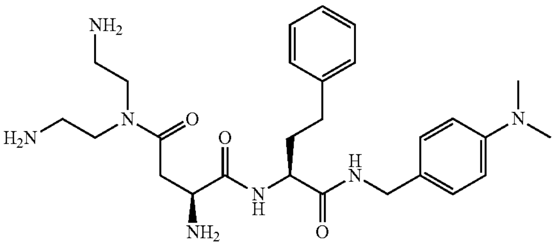
-continued
101
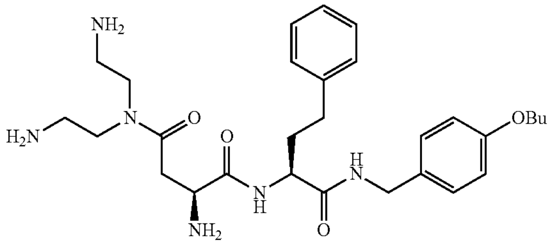
102
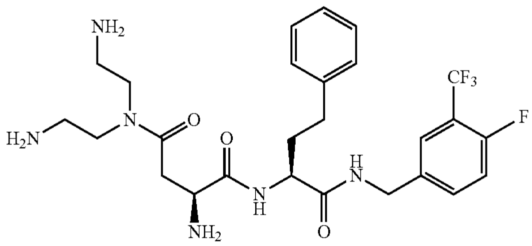
103
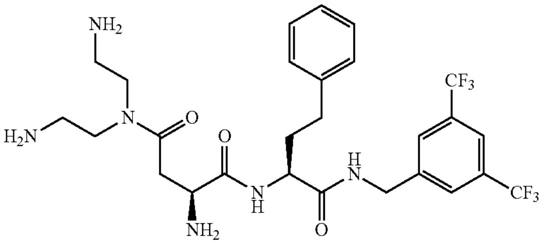
104
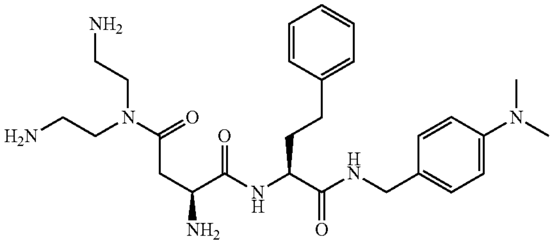
105
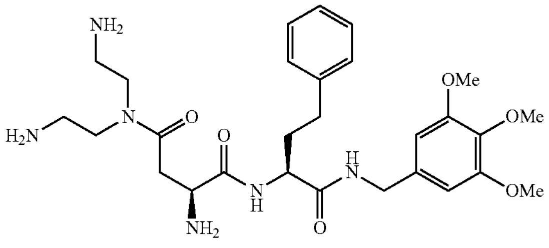
106
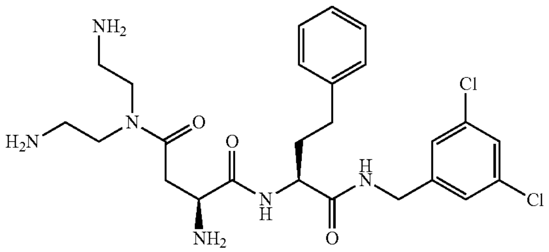

107
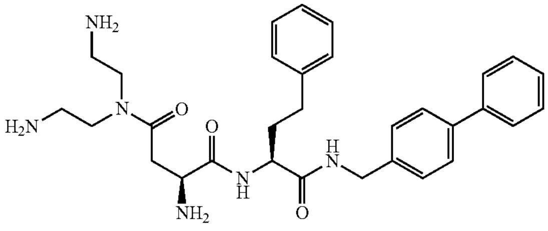
108
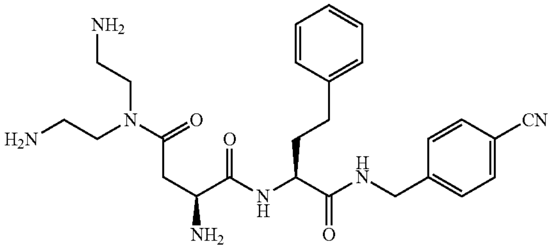
109
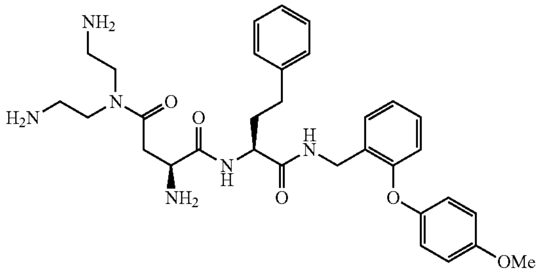
110
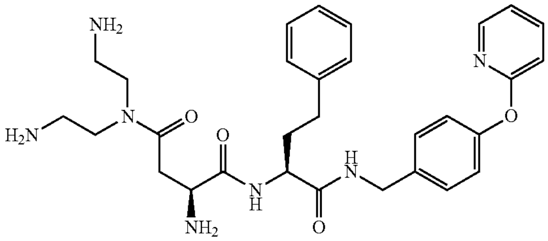
111
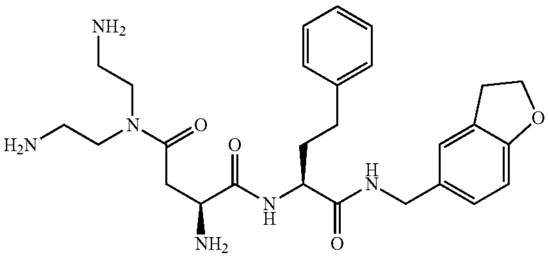
112
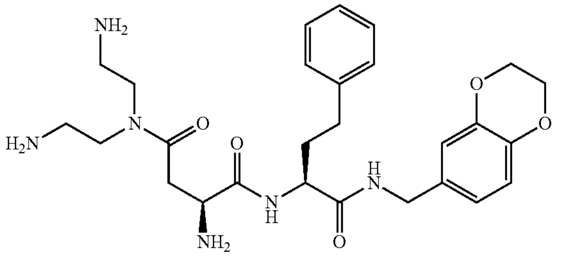
113
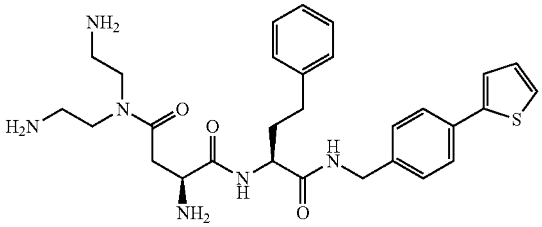
114
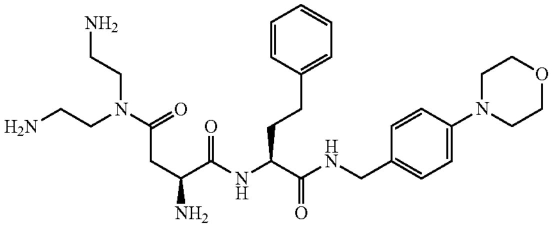
113
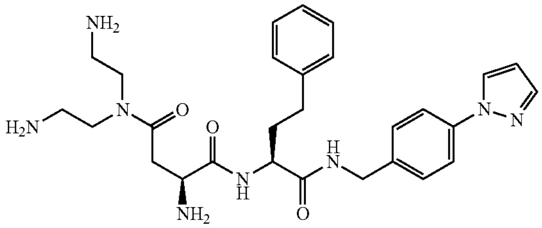
116
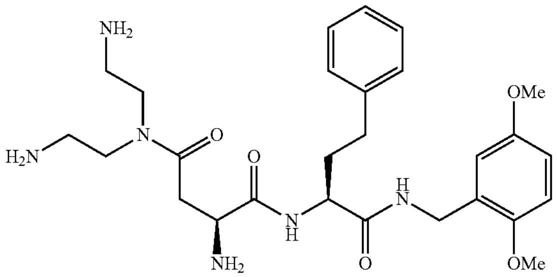
117
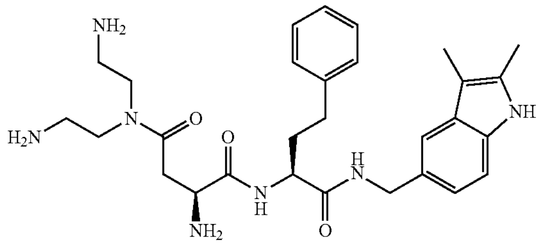

118
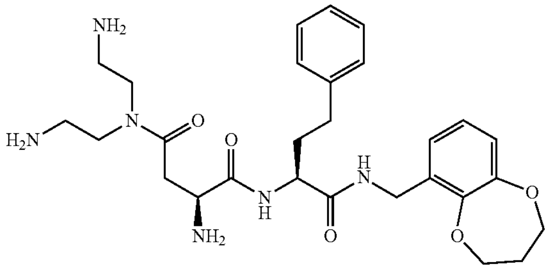
119
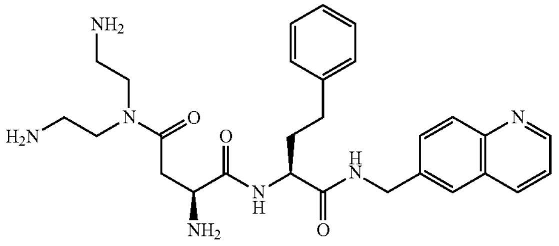
120
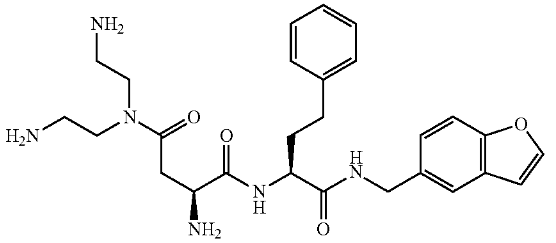
121
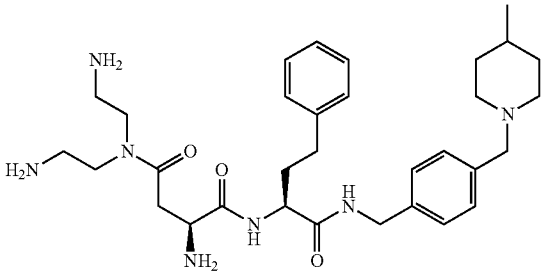
122
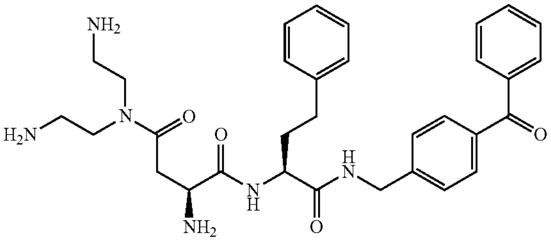
123
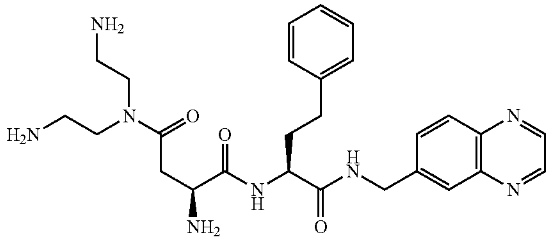
124
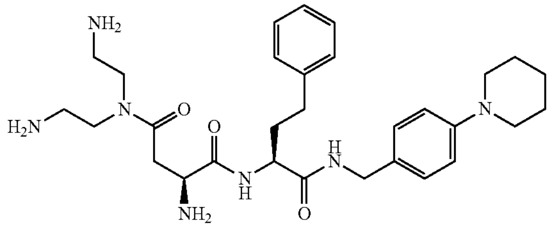
125
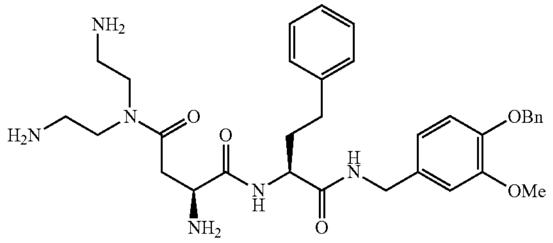
126
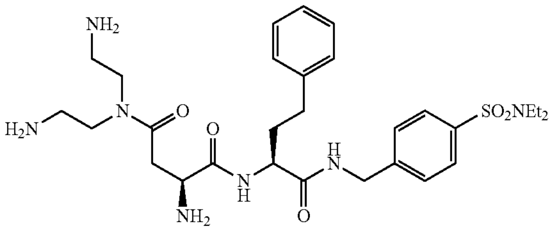
127
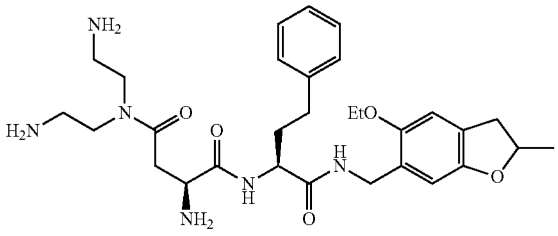
128
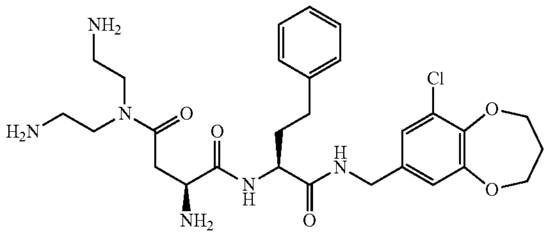

-continued
129
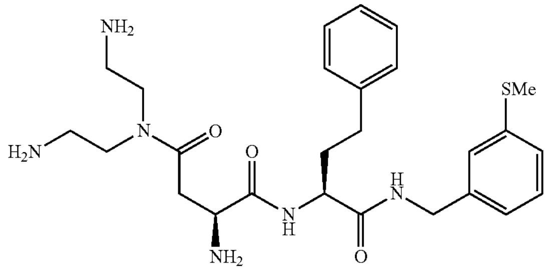
130
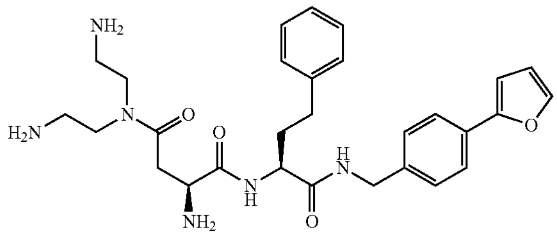
131
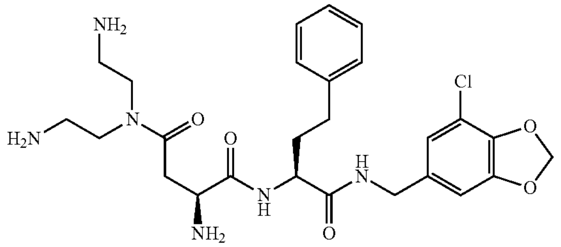
132
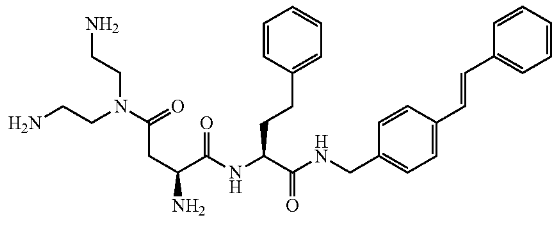
133
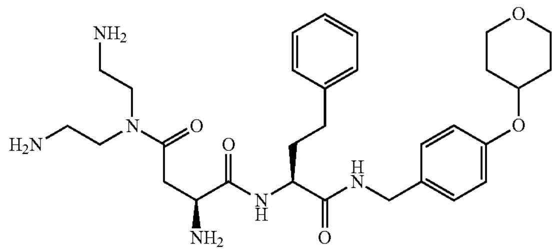
-continued
134
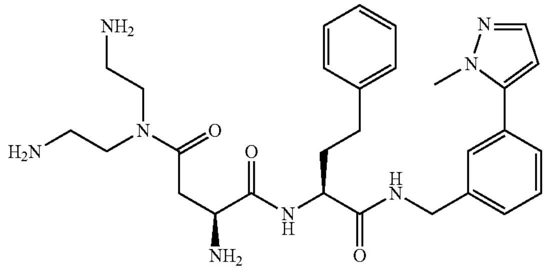
135
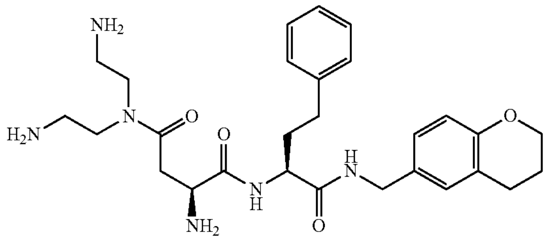
136
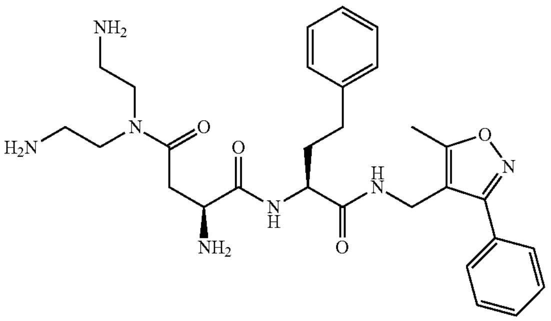
137
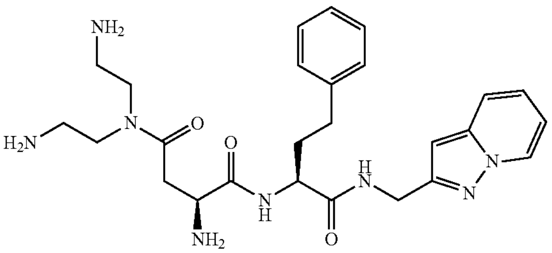
138
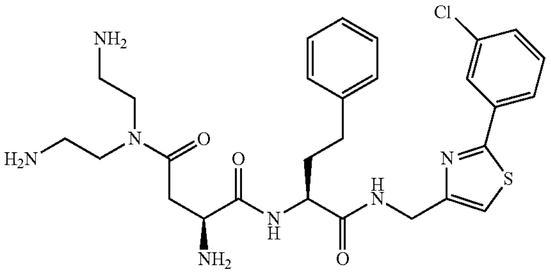

-continued
139
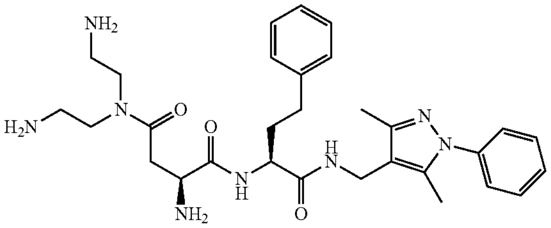
140
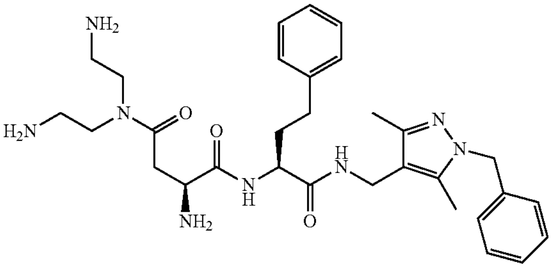
141
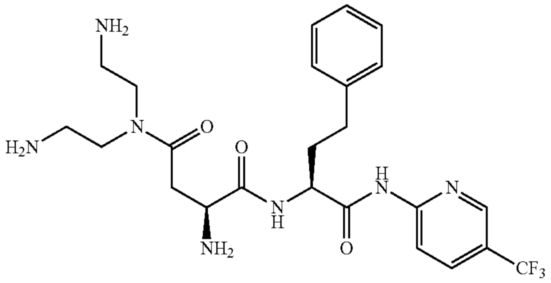
142
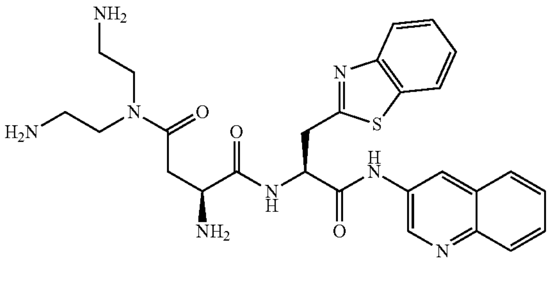
144
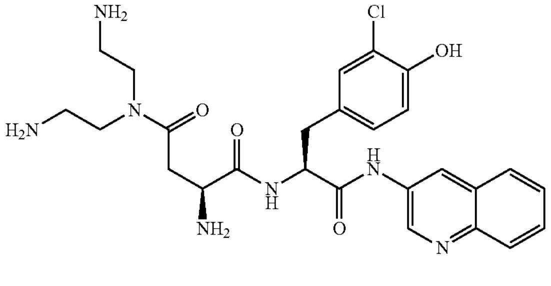
-continued
145
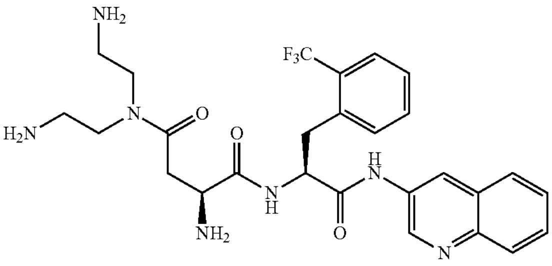
146
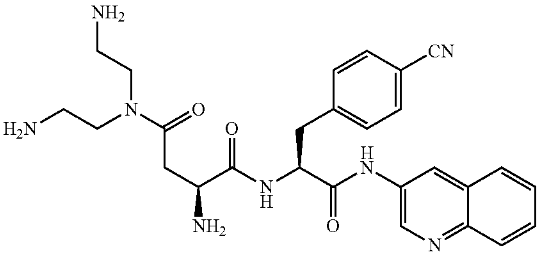
147
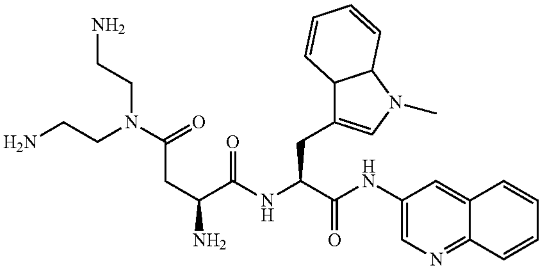
148
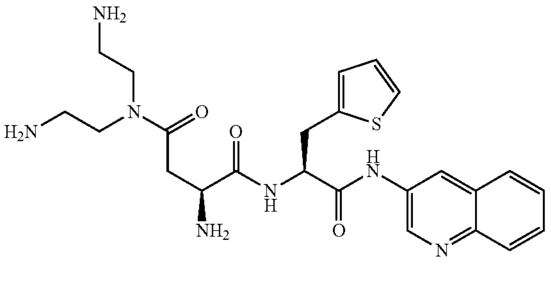
149
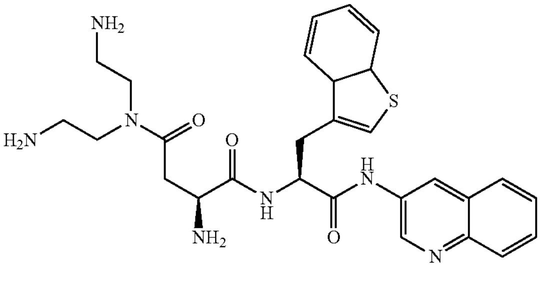

-continued
150
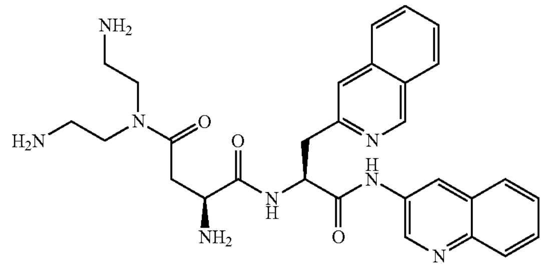
151
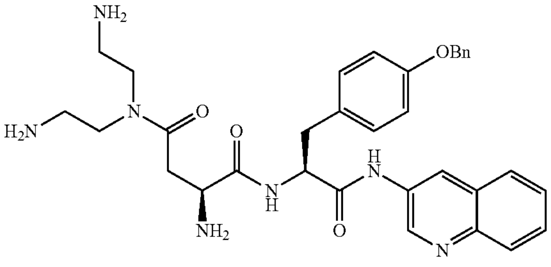
152
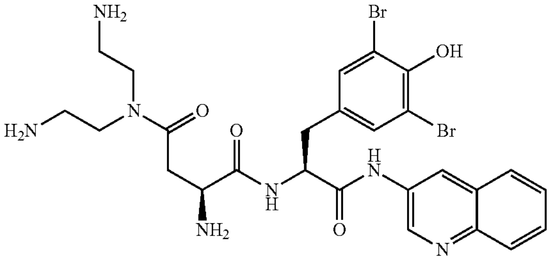
153
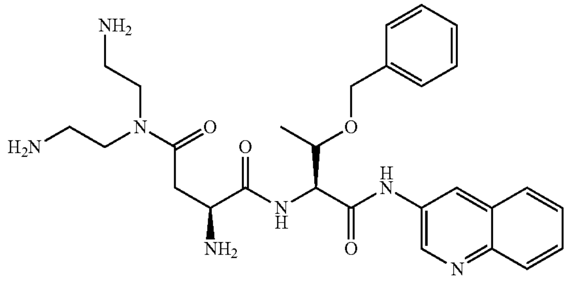
154
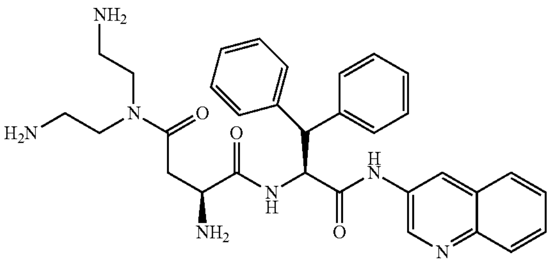
-continued
155
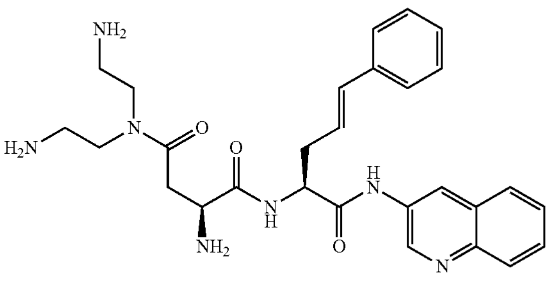
156
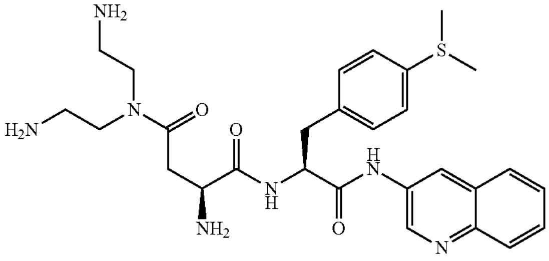
157
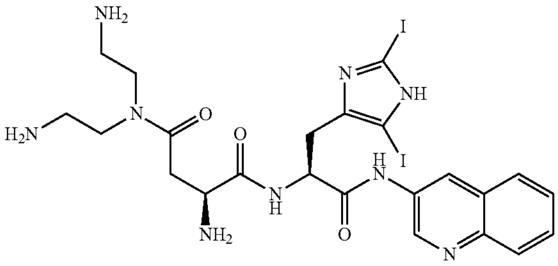
158
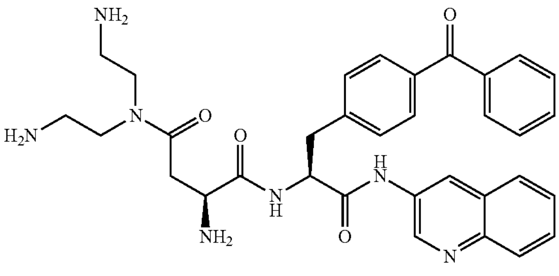
159
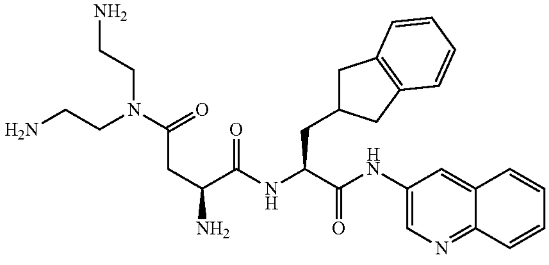

-continued
161
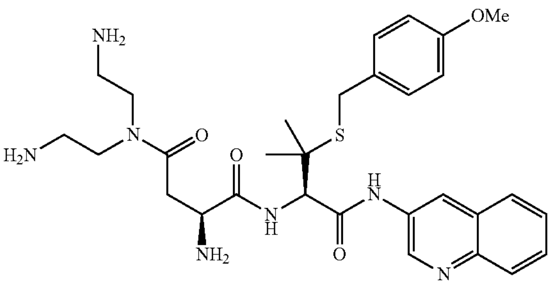
162
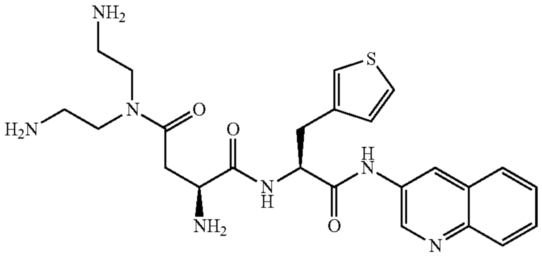
163
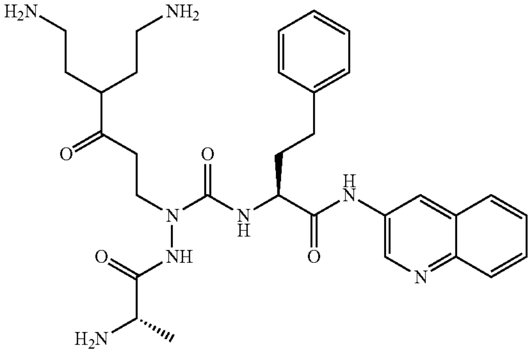
164
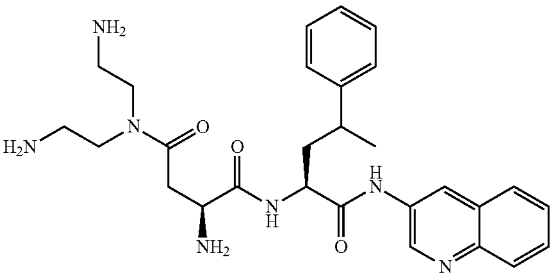
165
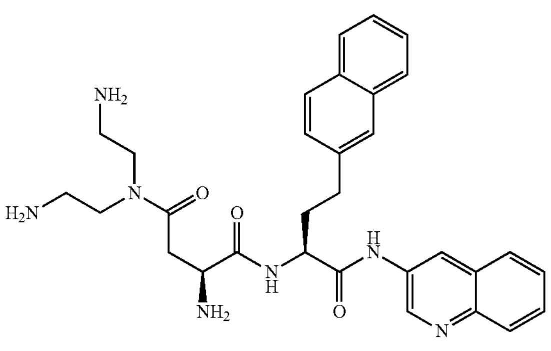
-continued
166
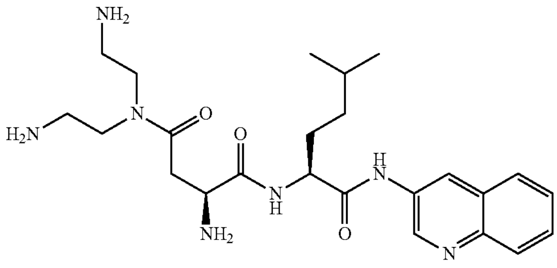
167
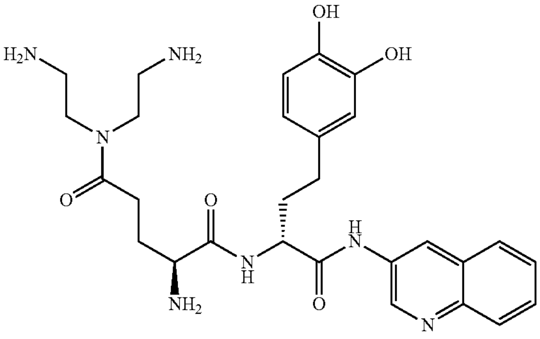
168
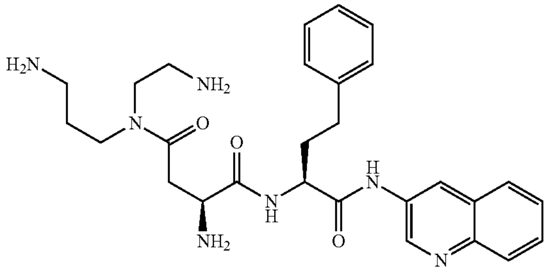
169
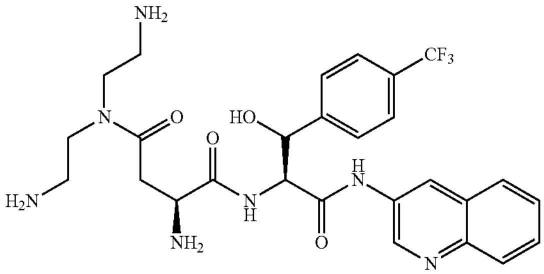
170
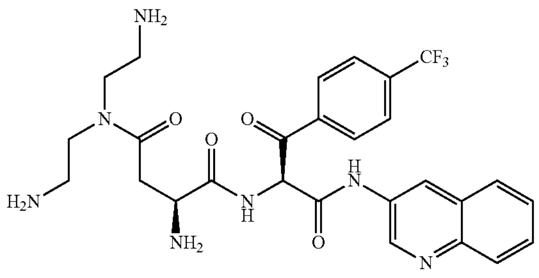

-continued
171
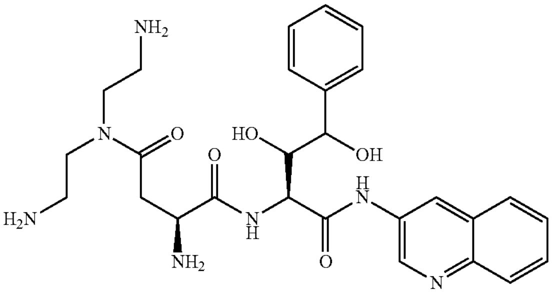
172
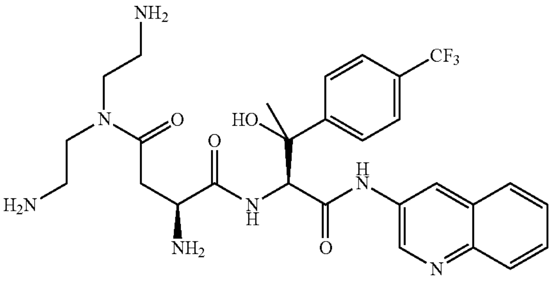
173
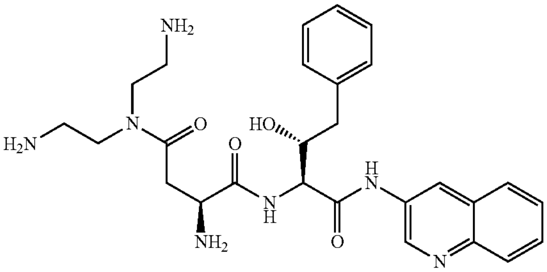
174
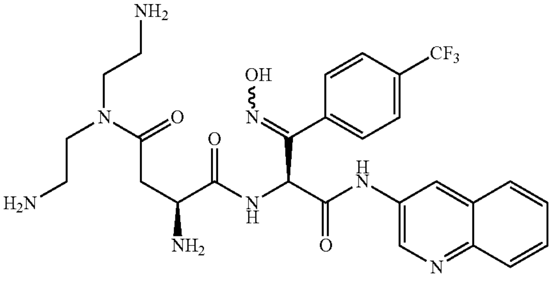
-continued
175
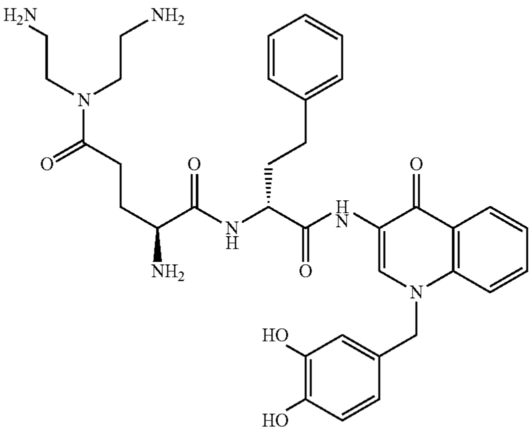
177
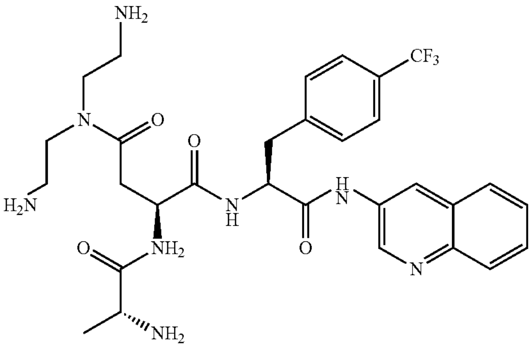
178
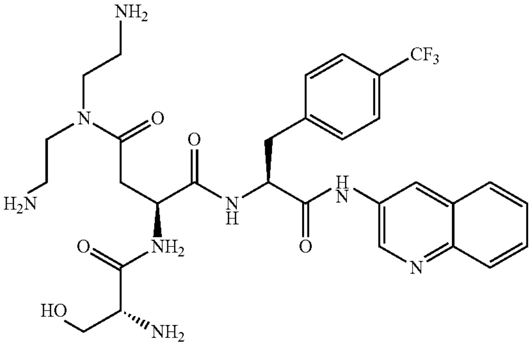
179
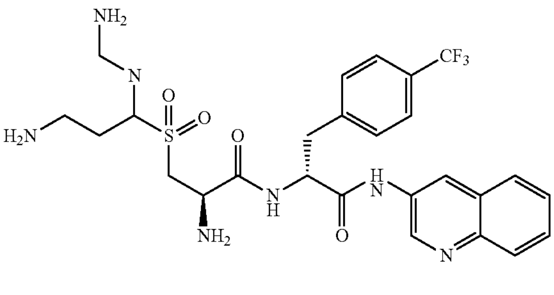

-continued
180
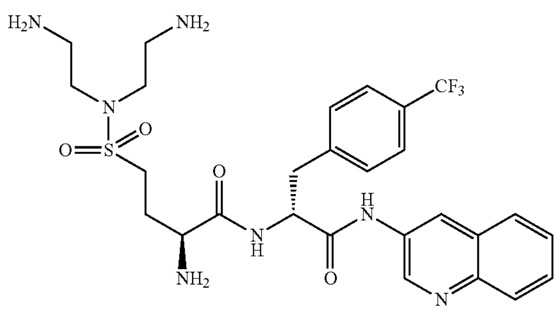
181
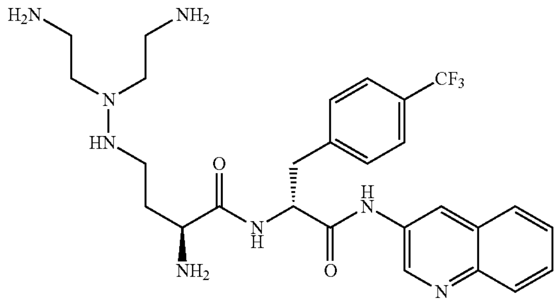
182
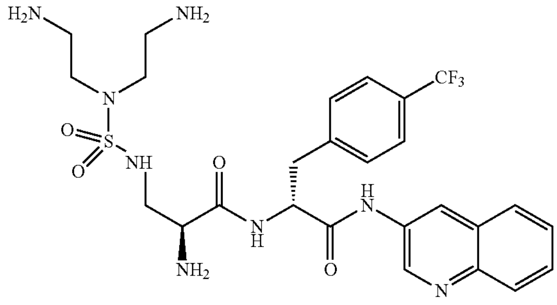
183
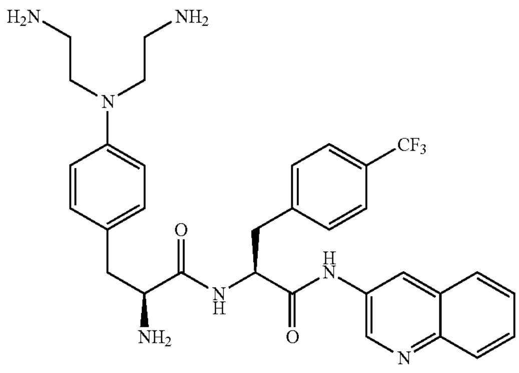
-continued
184
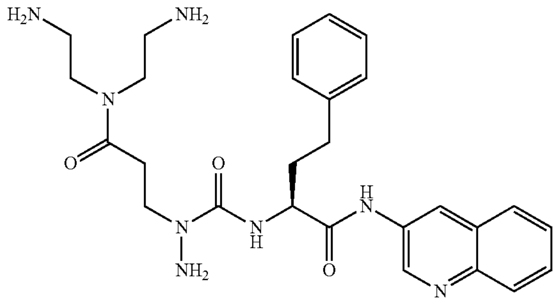
188
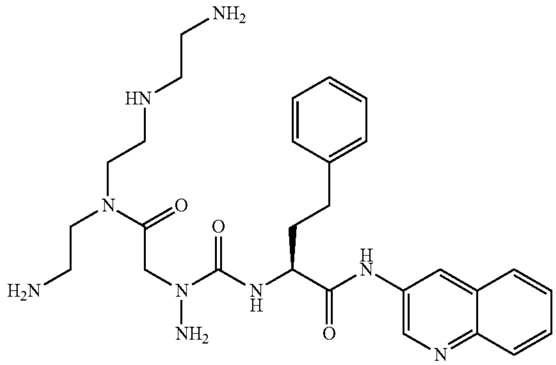
189
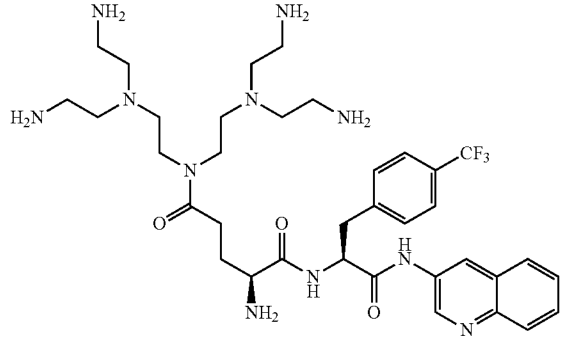
190
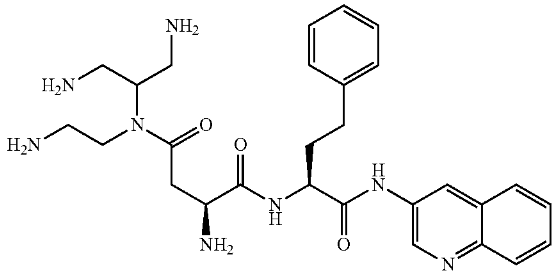

-continued
192
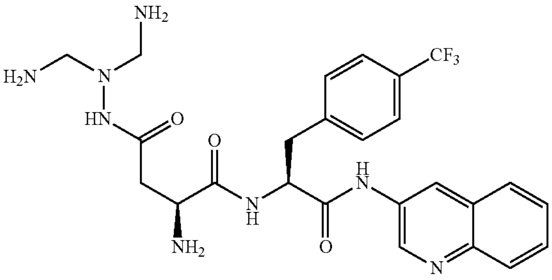
193
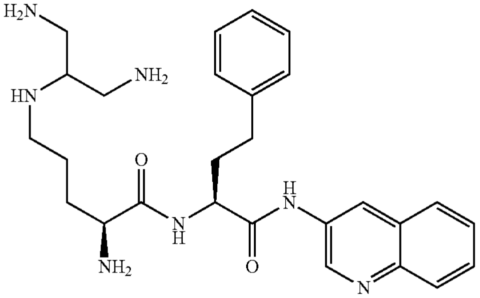
194
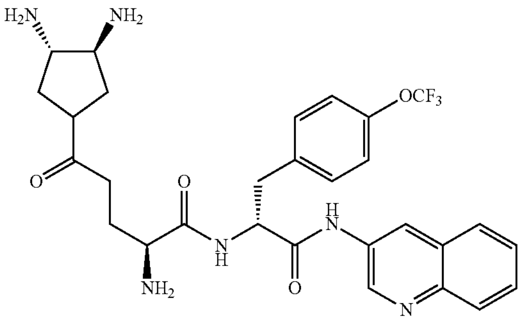
195
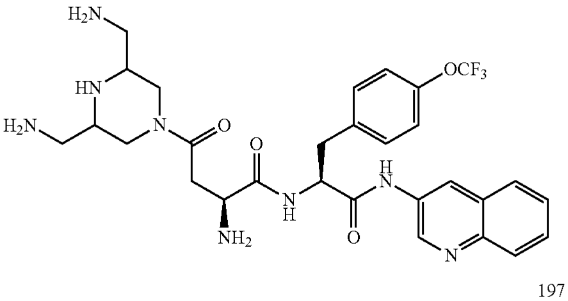
197
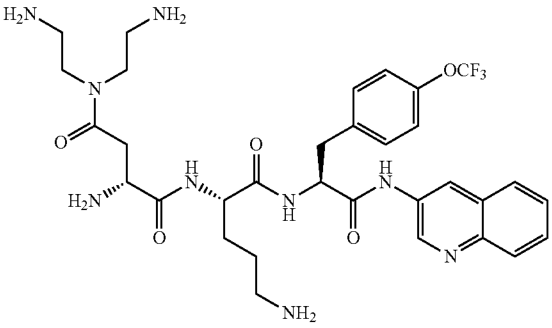
-continued
198
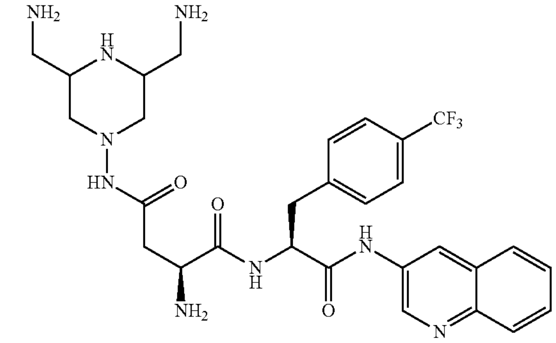
199
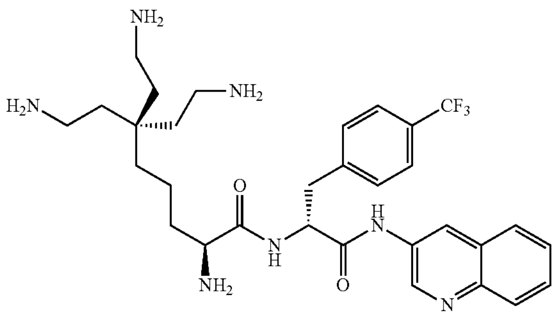
201
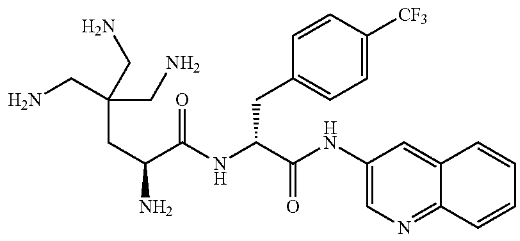
202
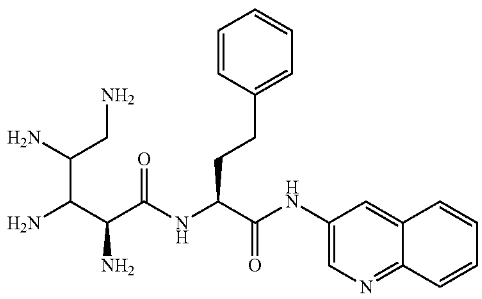
and
204
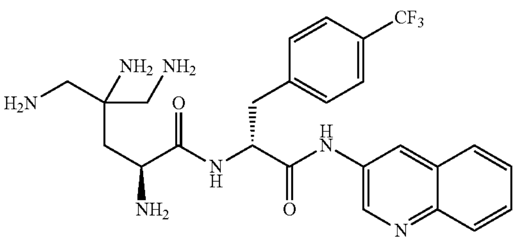
.
11. The compound of claim 1 having a structure selected from the group consisting of:

1
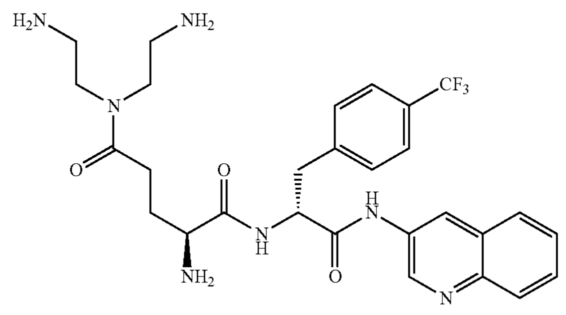
2
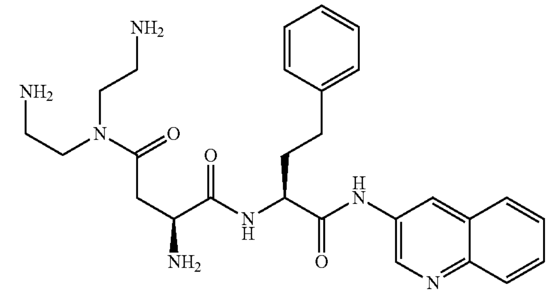
3
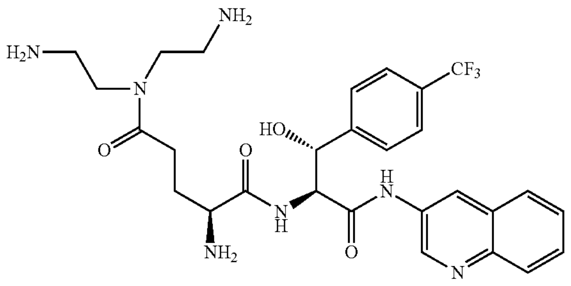
4
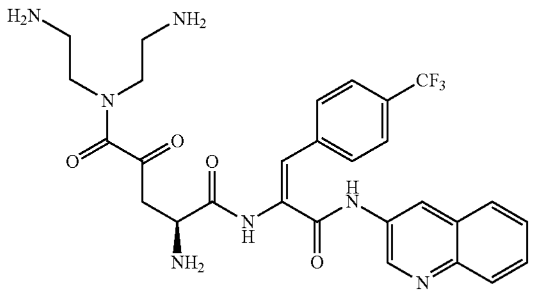
7
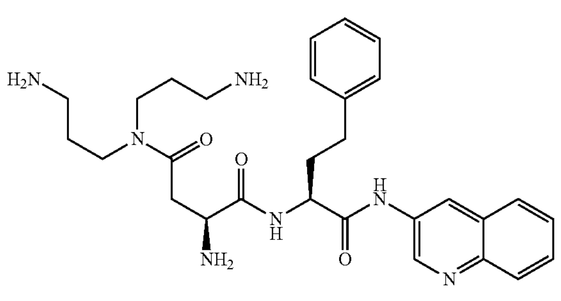
-continued
8
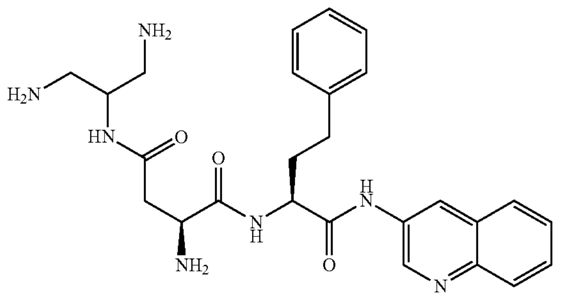
10
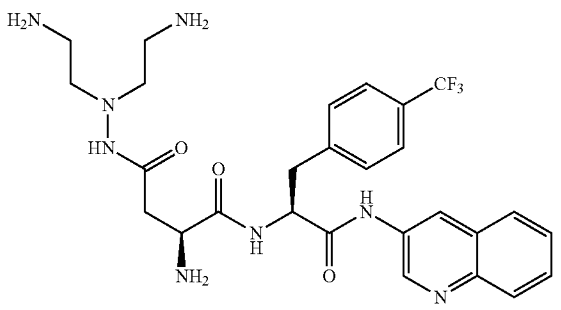
13
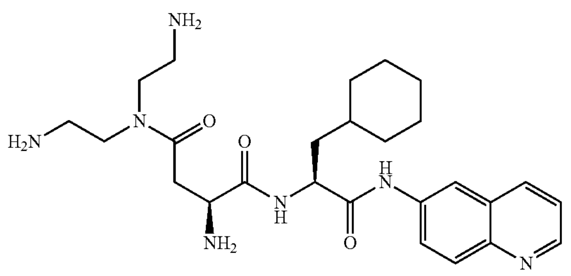
14
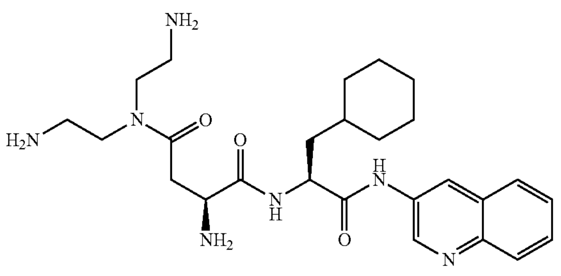
17
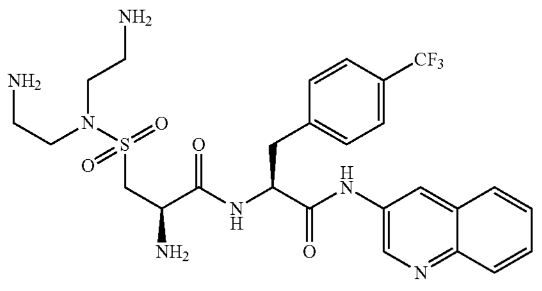

-continued
21
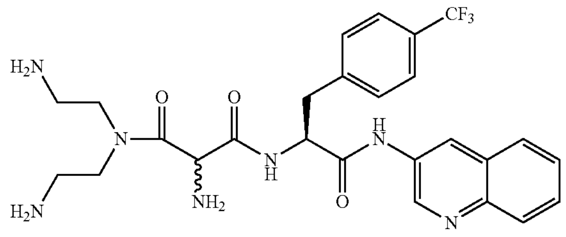
22
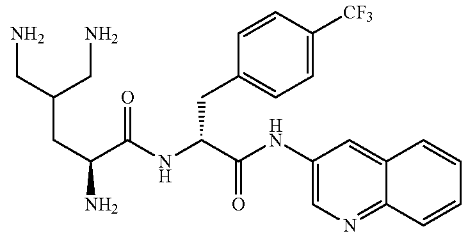
23
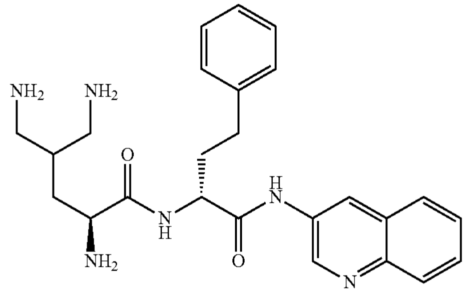
25
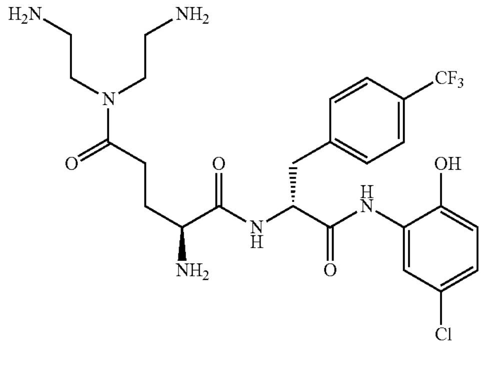
27
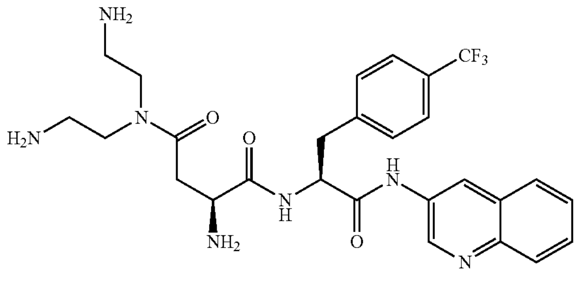
-continued
28
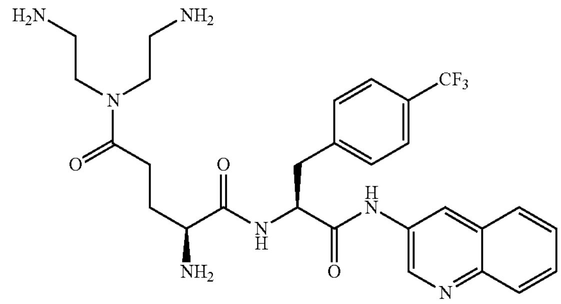
31
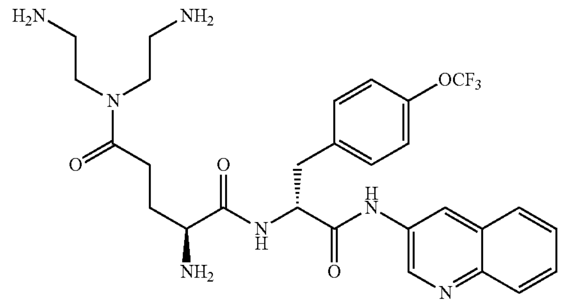
32
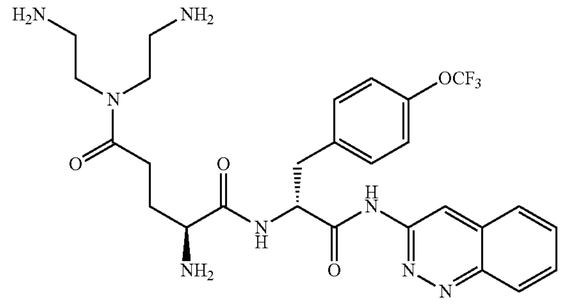
38
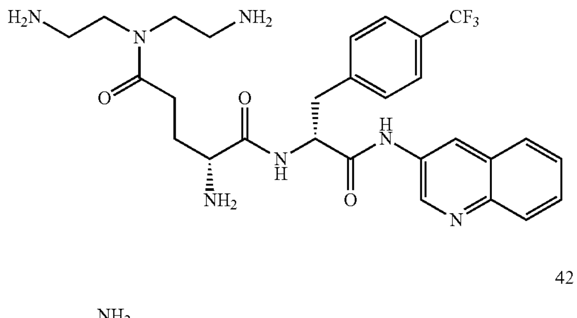
42
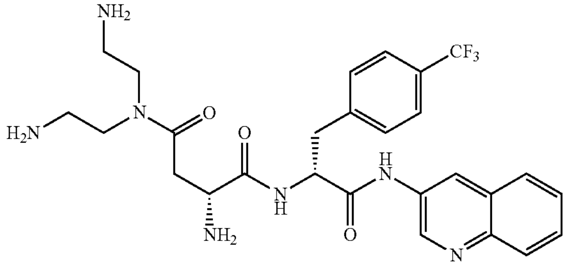

-continued
44
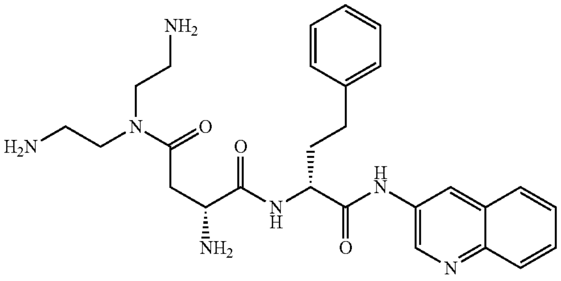
45
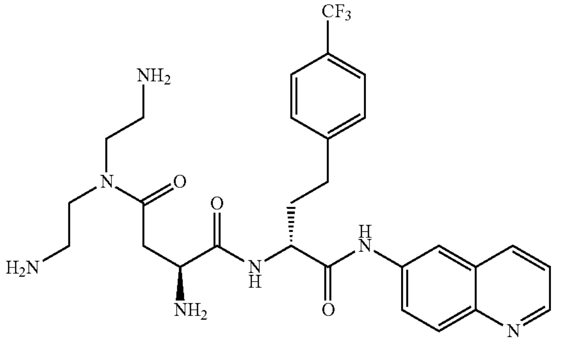
47
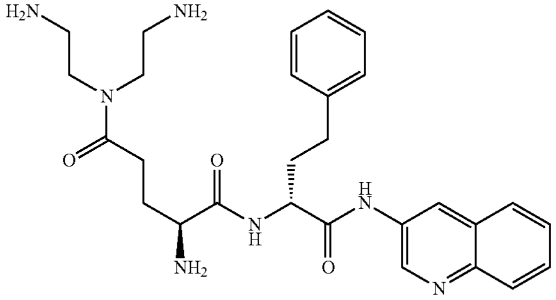
48
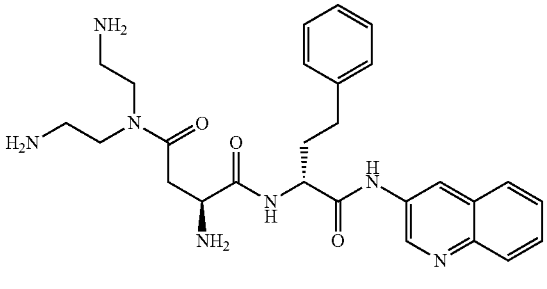
50
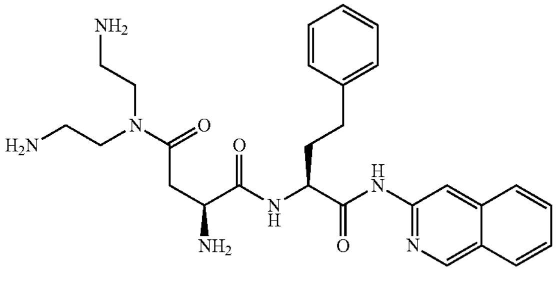
-continued
51
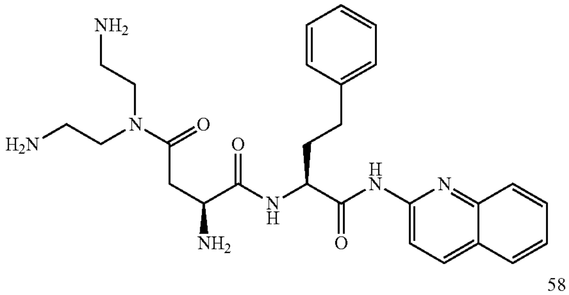
58
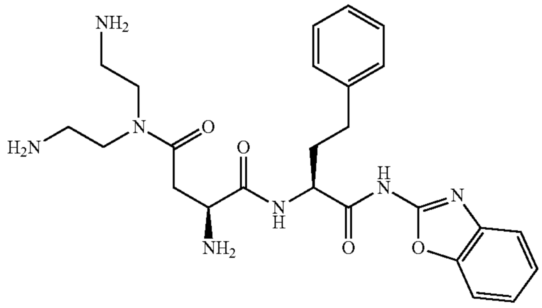
70
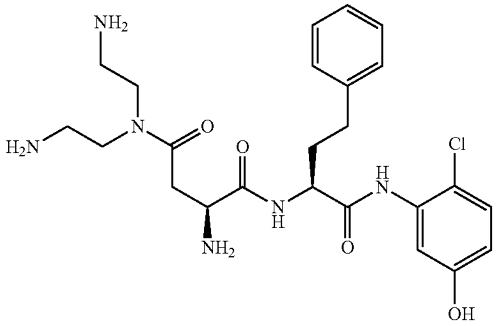
71
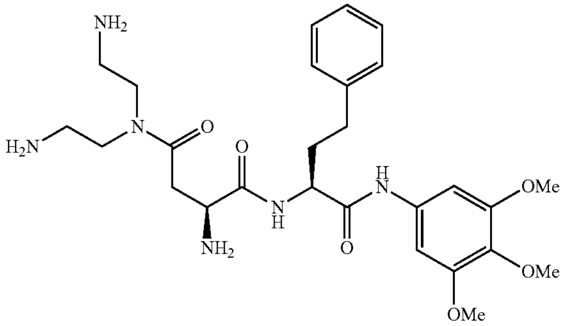
79
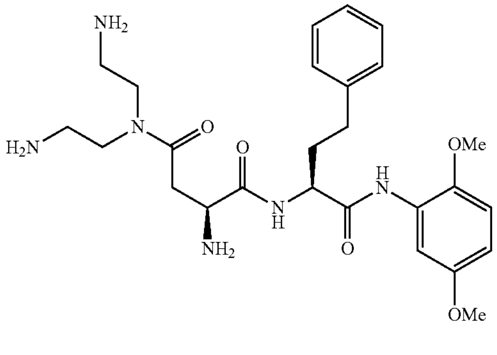

-continued
85
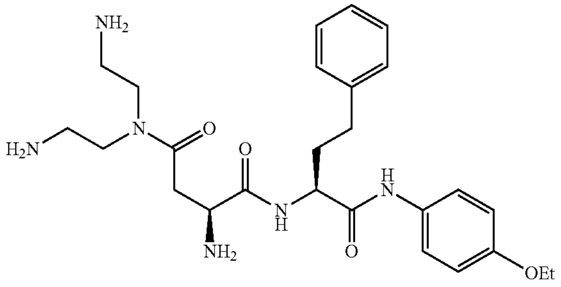
95
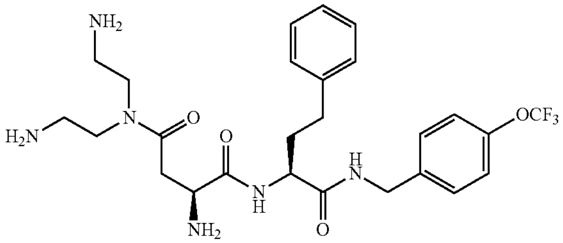
105
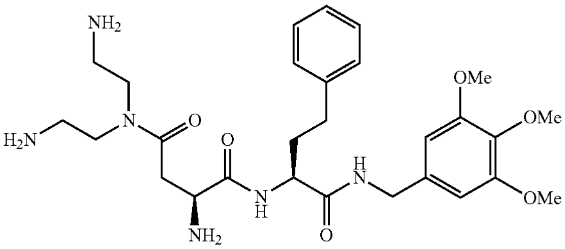
107
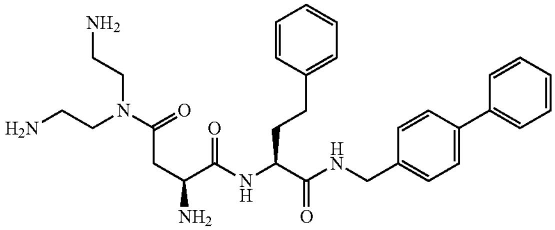
109
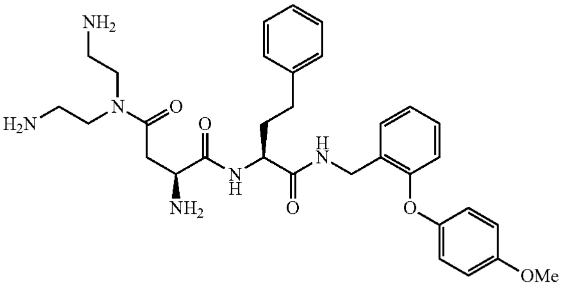
-continued
110
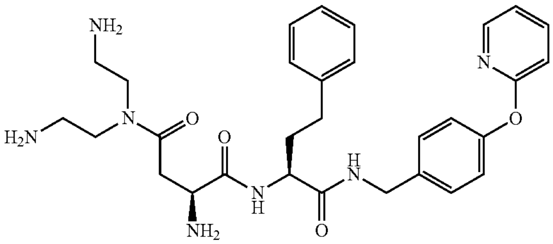
111
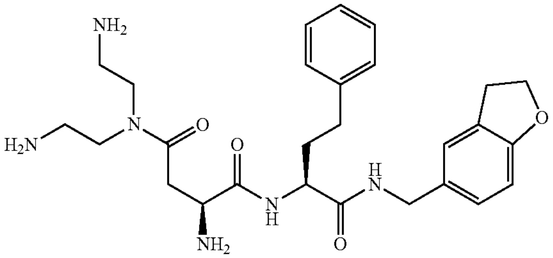
112
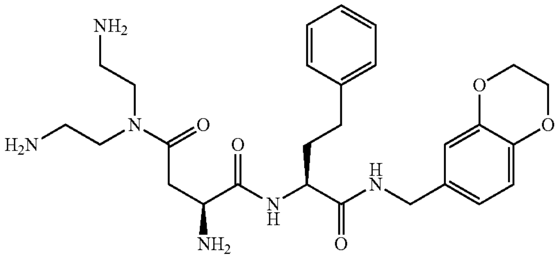
116
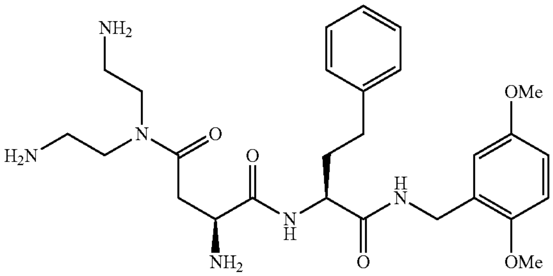
120
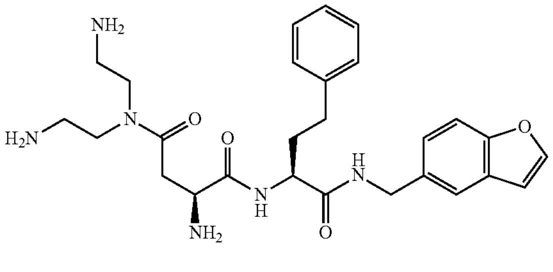

-continued
127
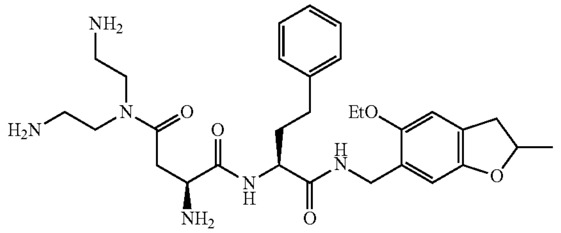
131
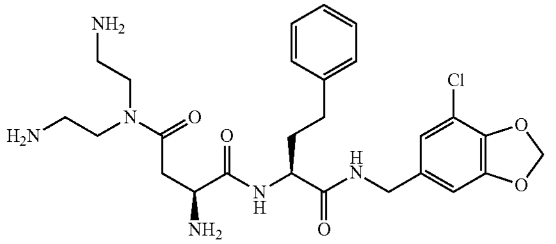
133
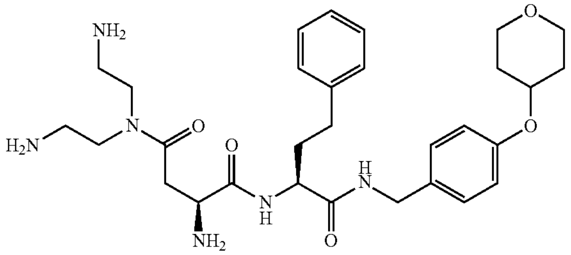
135
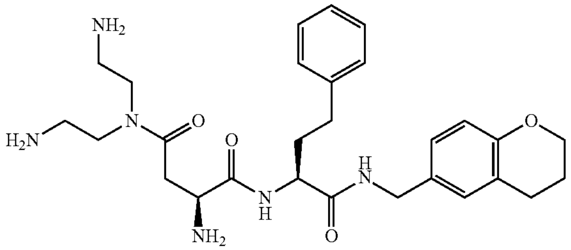
141
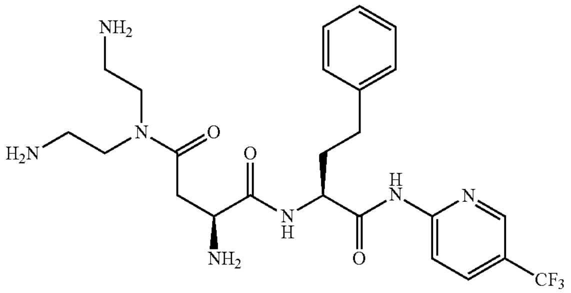
-continued
146
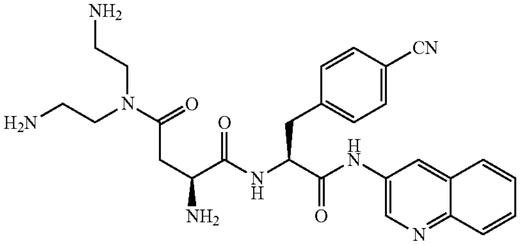
148
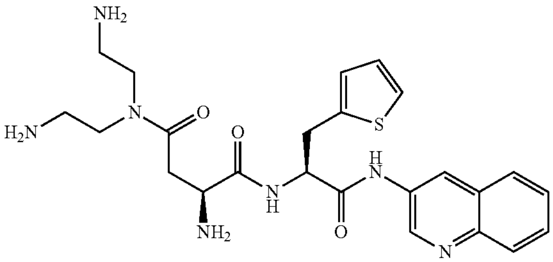
159
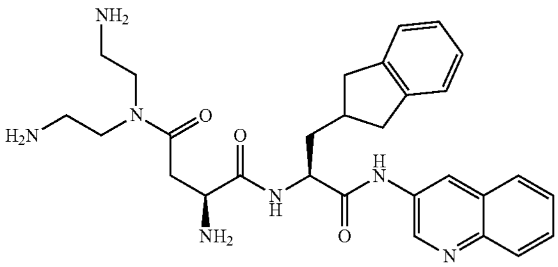
162
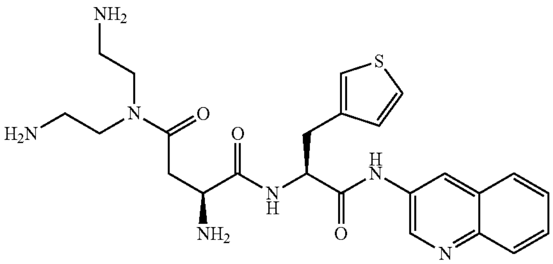
163
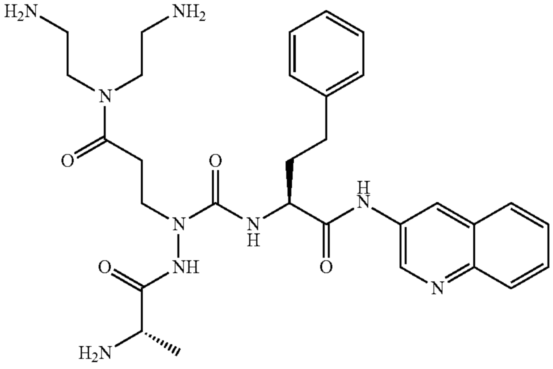

165
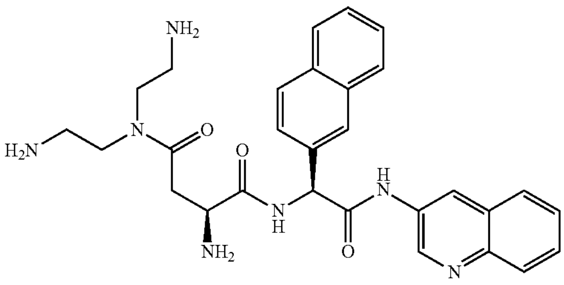
166
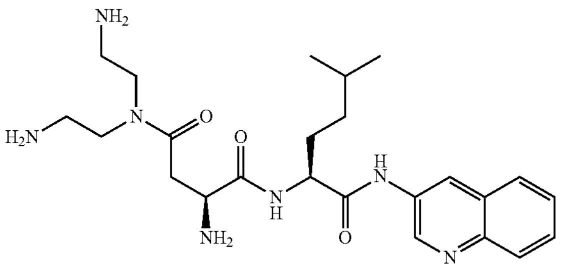
167
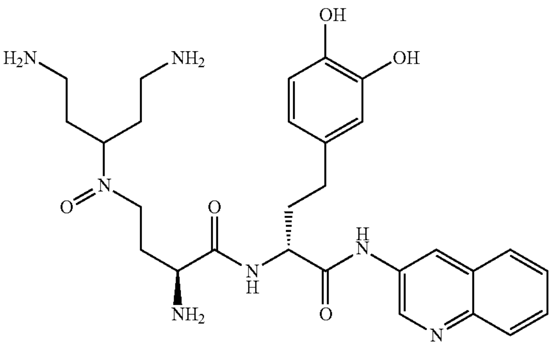
169
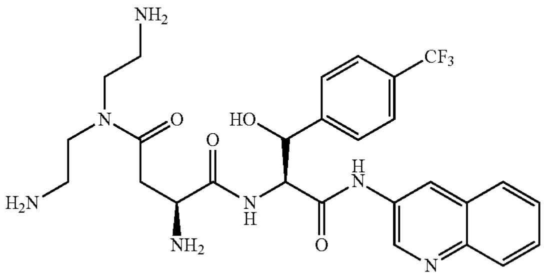
173
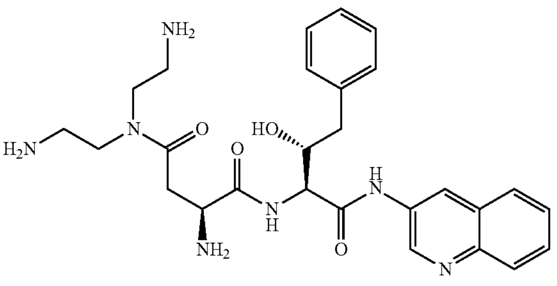
175
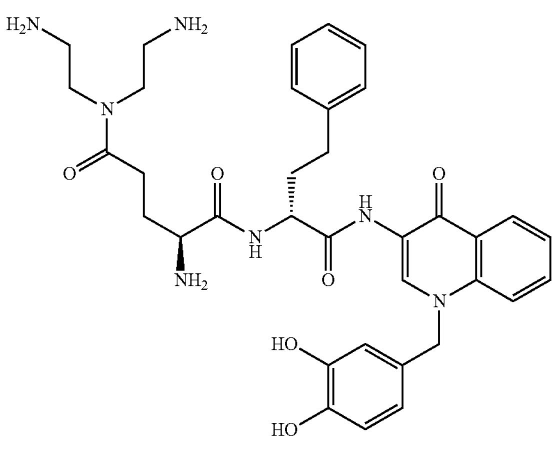
177
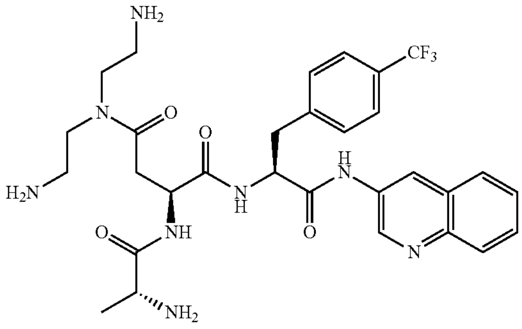
178
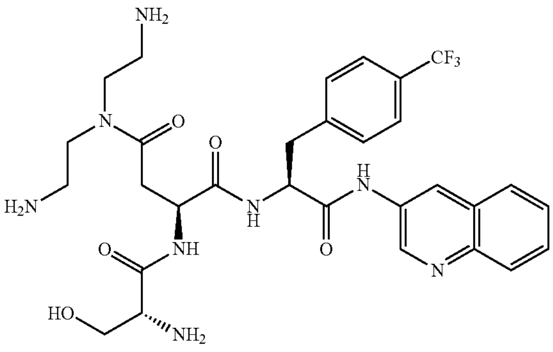
184
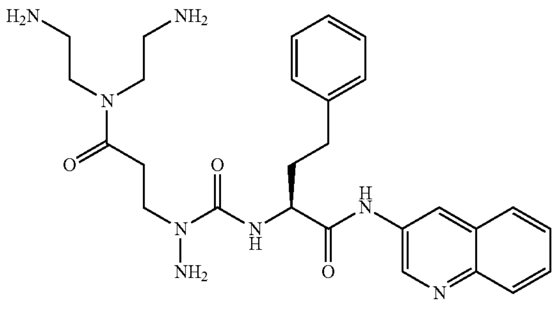

-continued
188
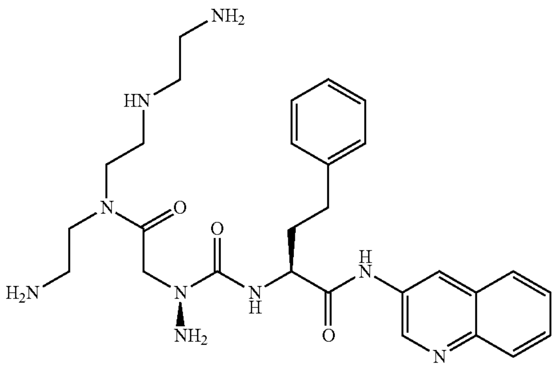
190
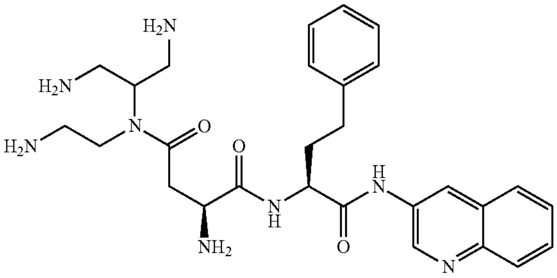
192
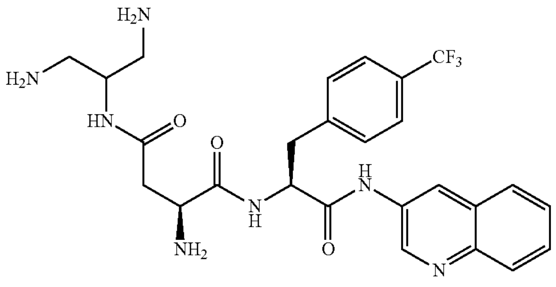
194
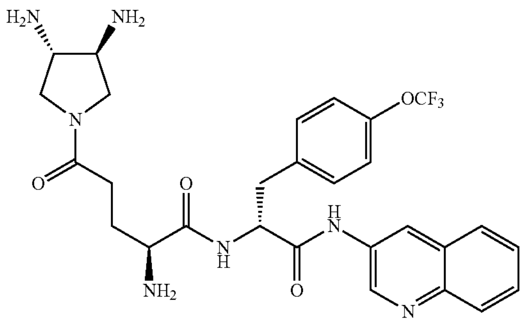
-continued
197
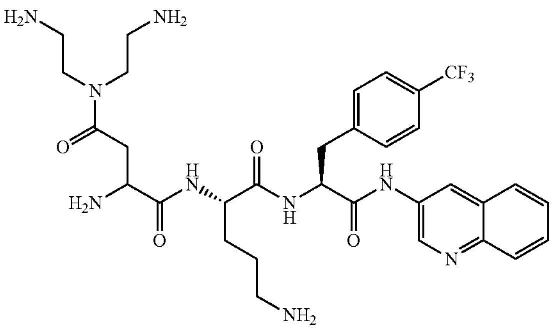
198
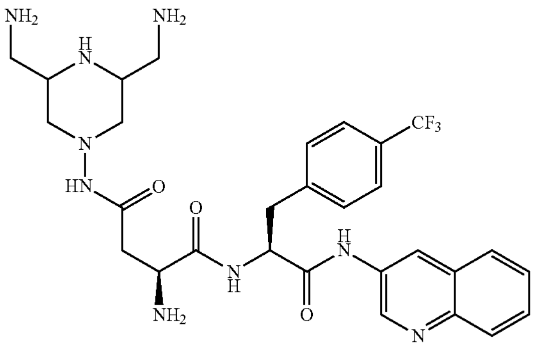
199
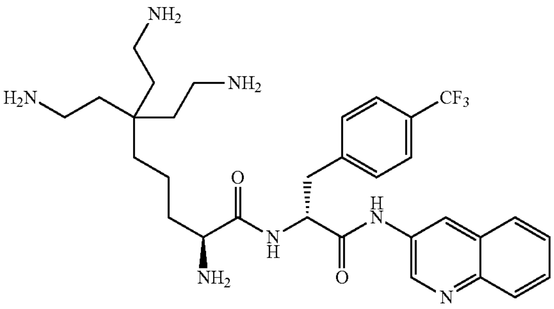
201
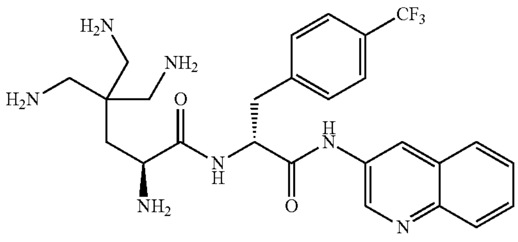
and
204
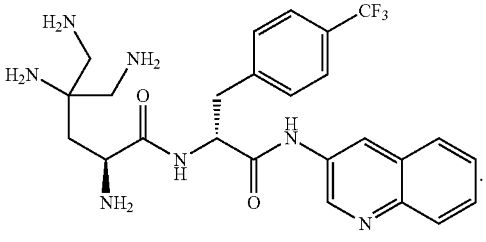
.
12. The compound of claim 1 having a structure selected from the group consisting of:

-continued
1
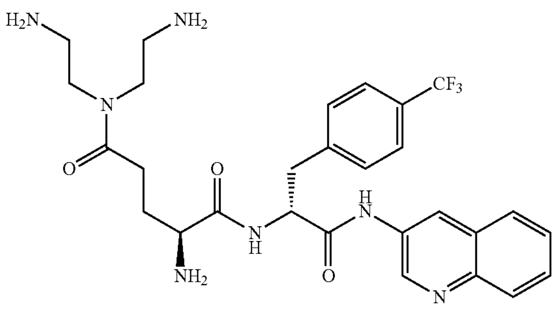
2
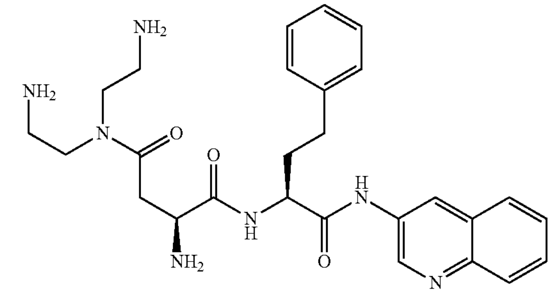
3
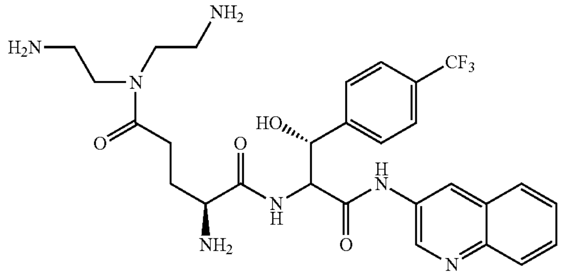
10
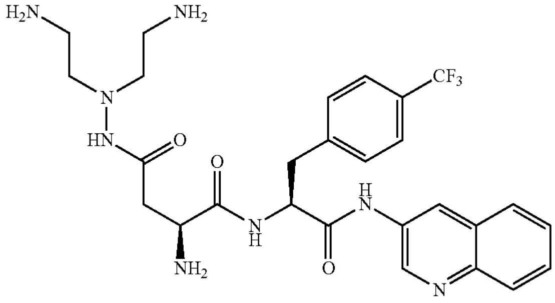
22
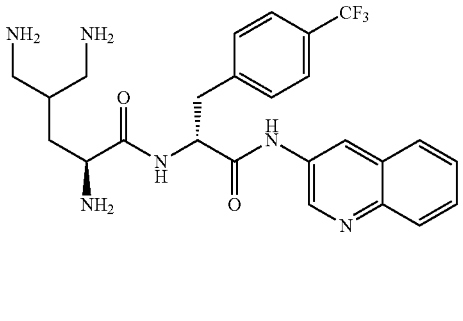
23
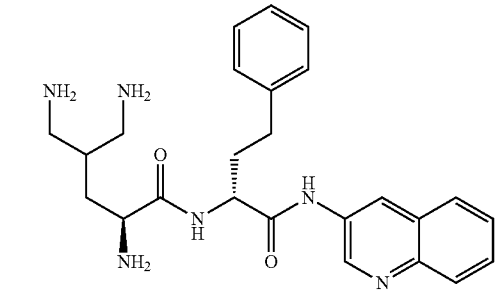
27
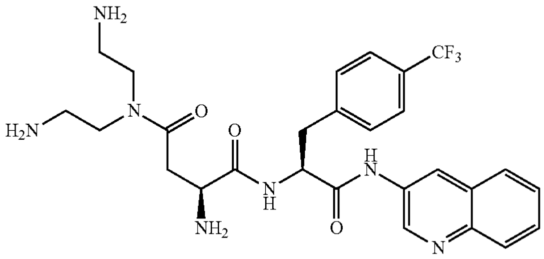
28
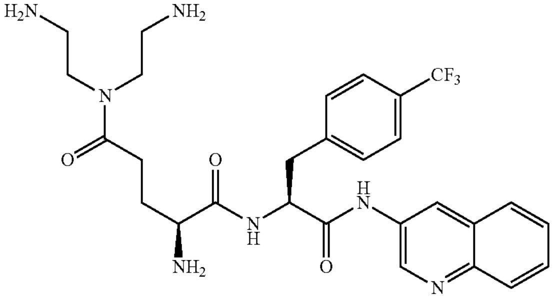
47
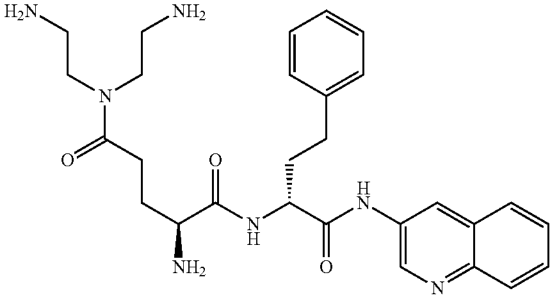
48
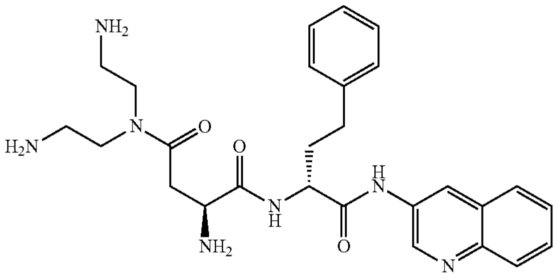

-continued
58
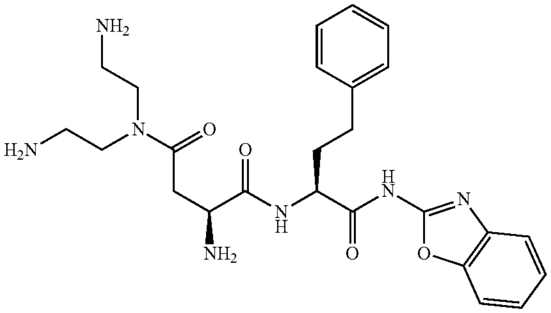
79
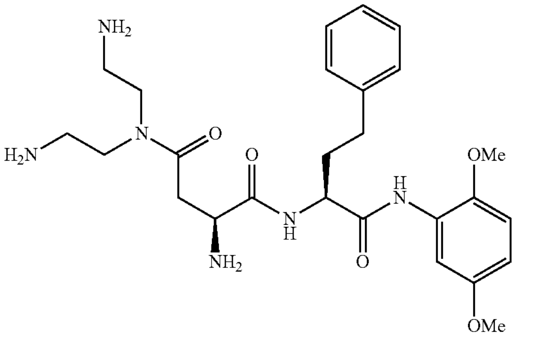
85
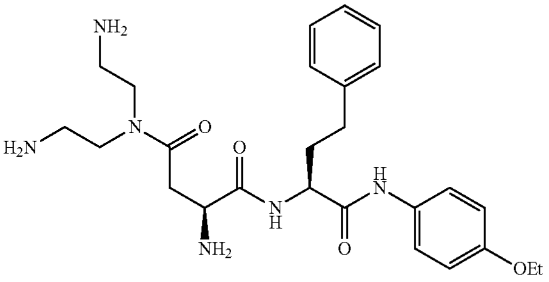
95
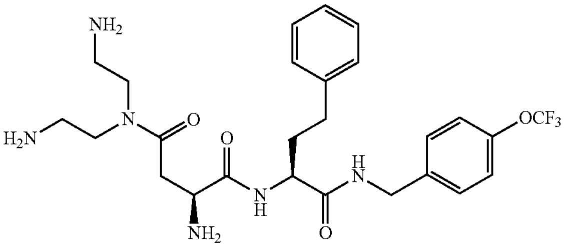
111
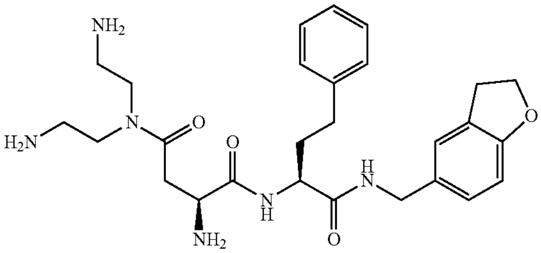
-continued
112
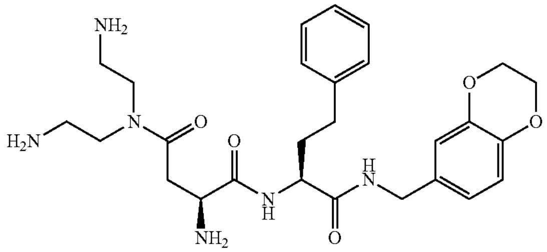
131
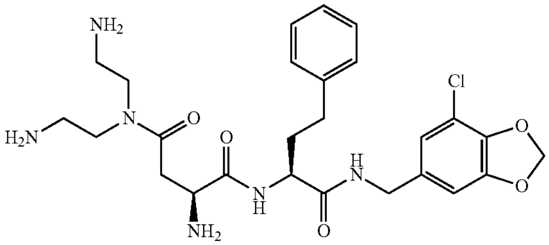
135
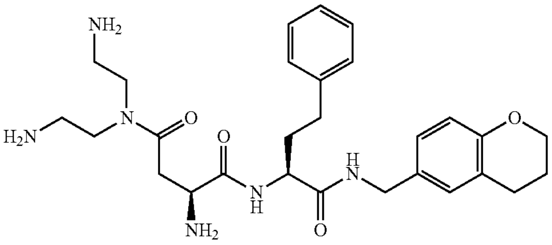
148
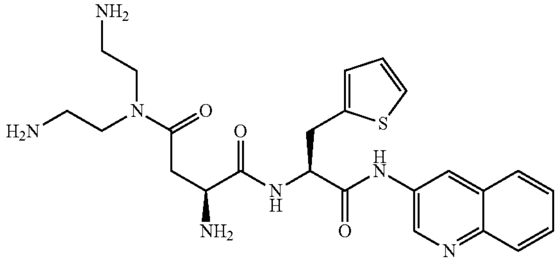
162
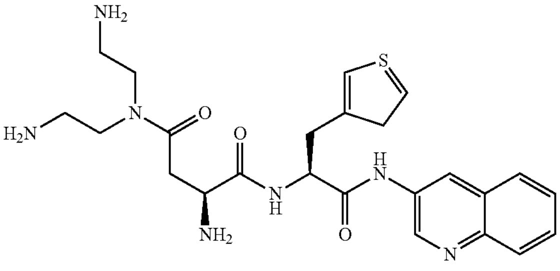

-continued
163
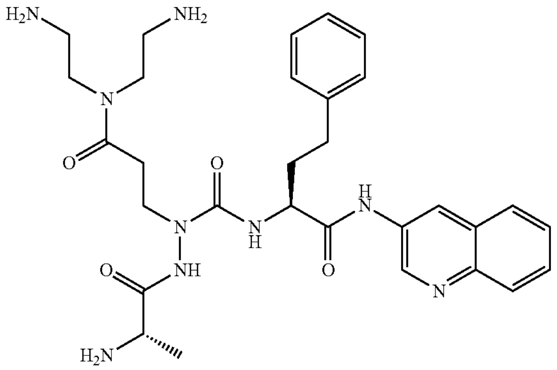
169
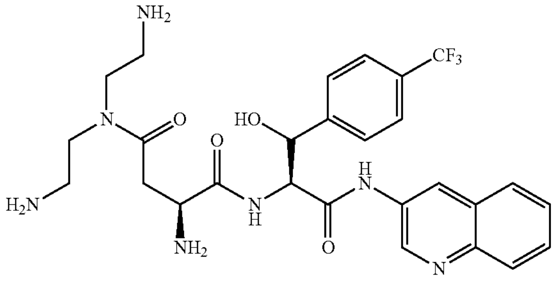
177
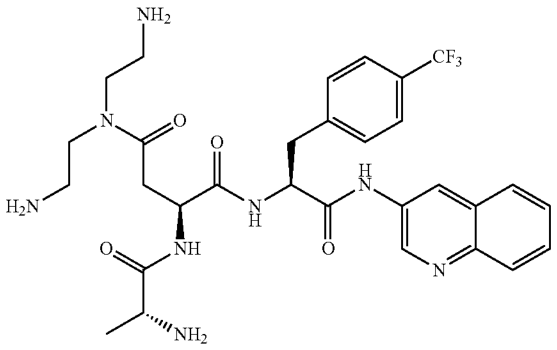
188
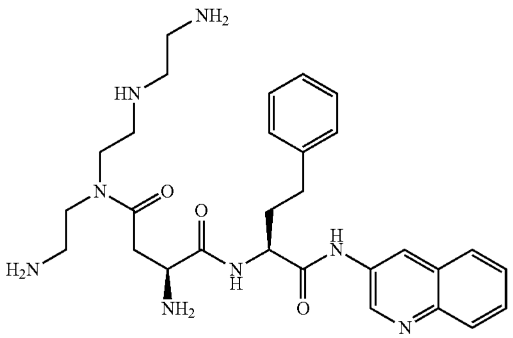
-continued
190
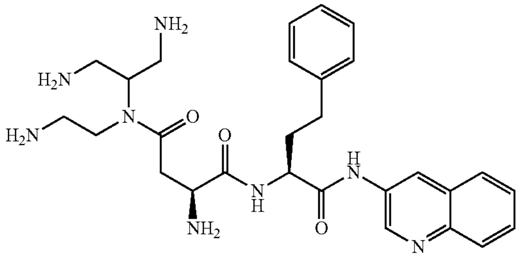
199
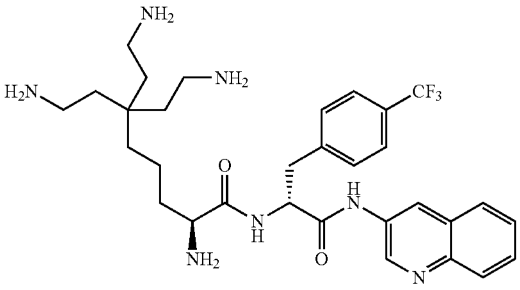
201
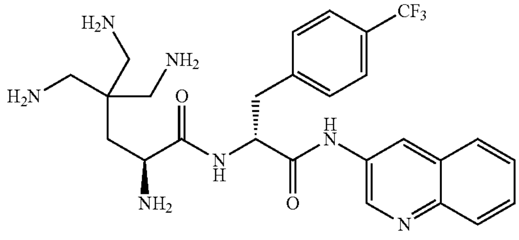
and
204
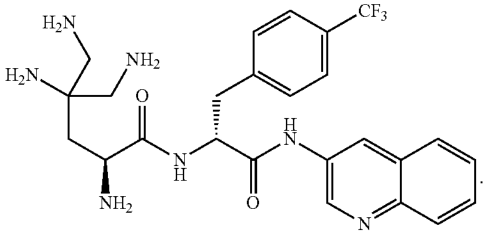
.
13. The compound of claim 1 having a structure selected from the group consisting of:
211
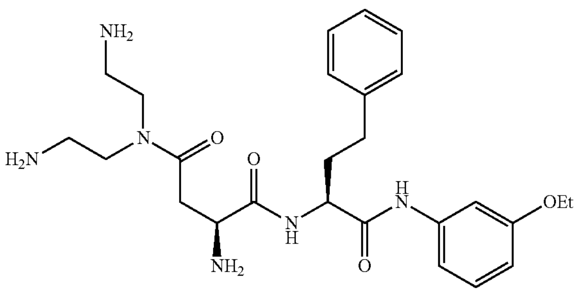

-continued
212
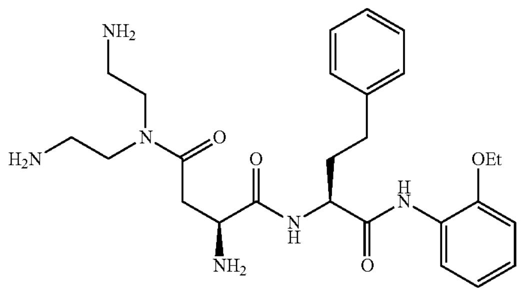
213
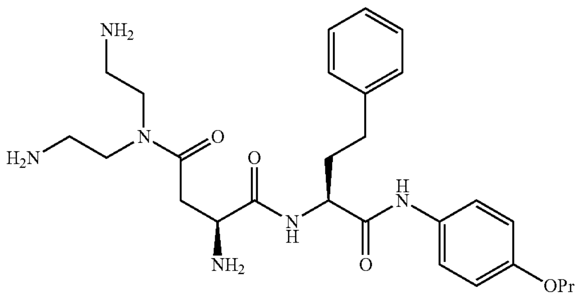
214
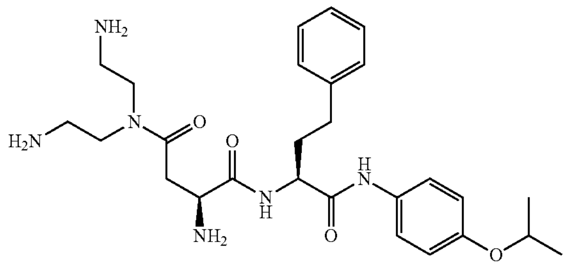
215
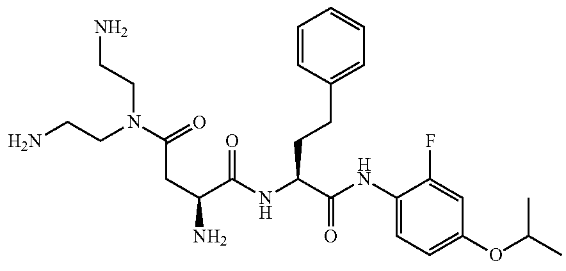
216
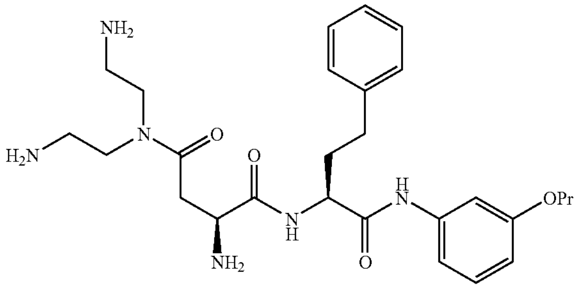
-continued
217
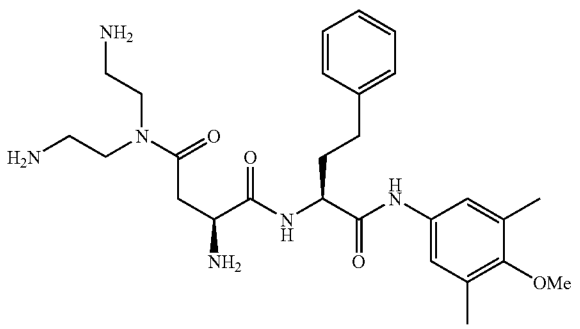
218
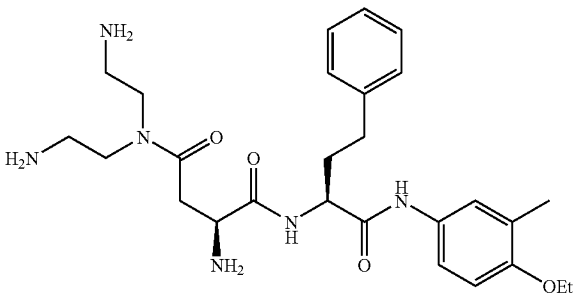
219
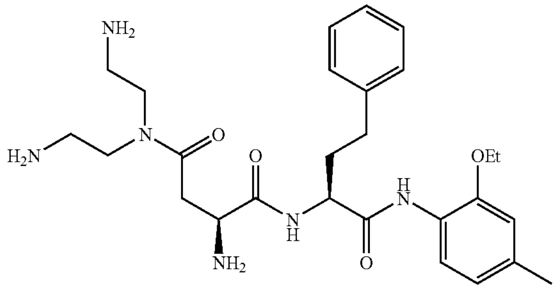
220
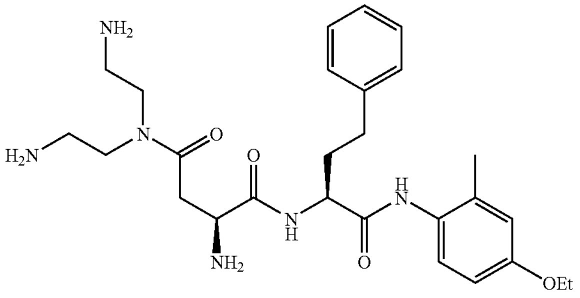
221
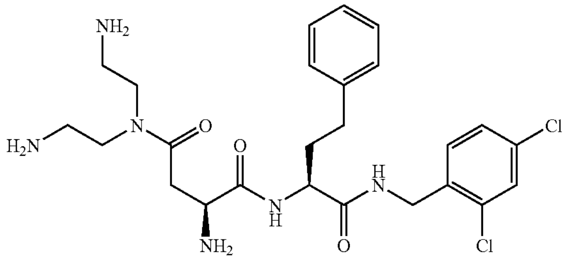

-continued
222
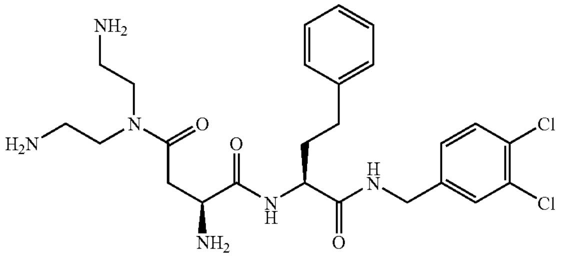
223
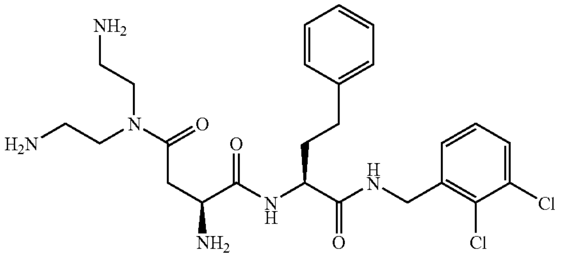
224
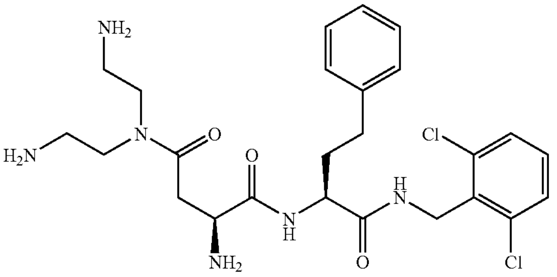
225
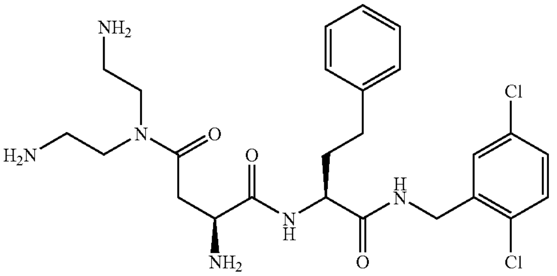
226
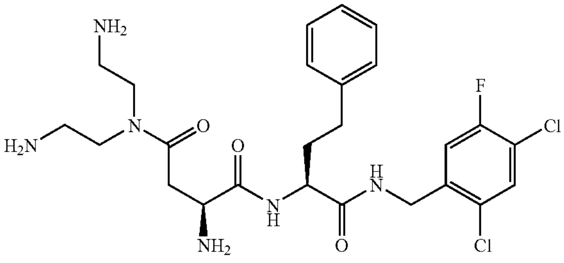
-continued
227
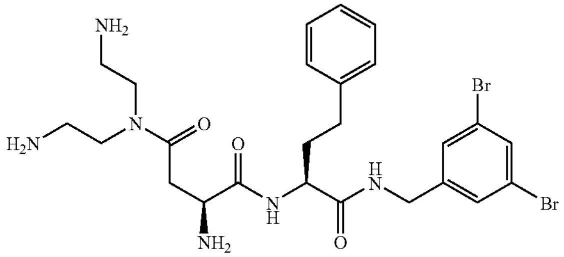
228
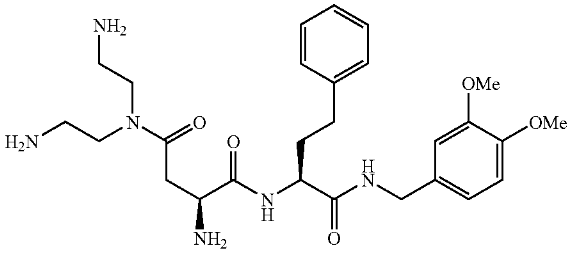
229
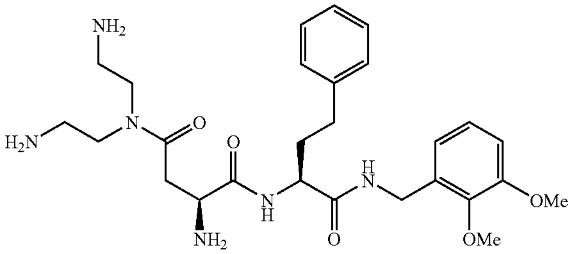
230
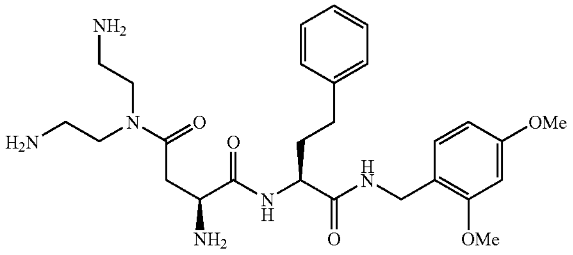
232
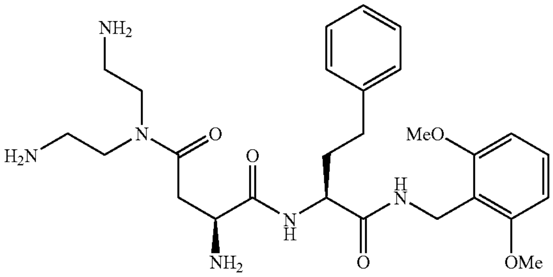

-continued
232
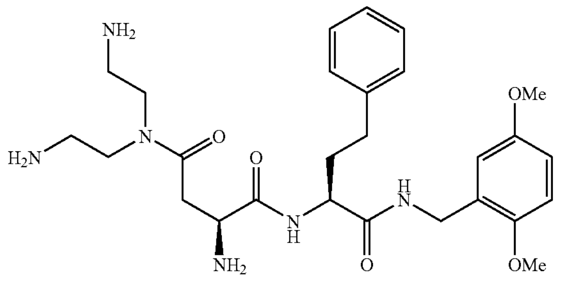
233
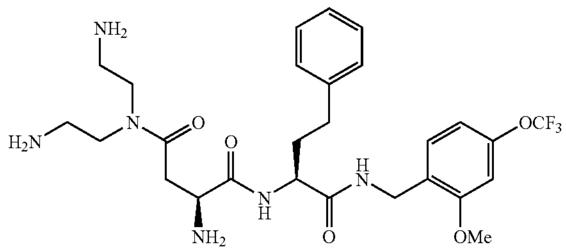
234
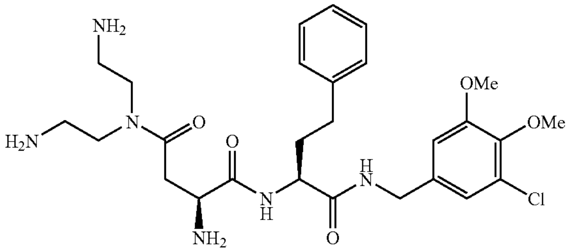
235
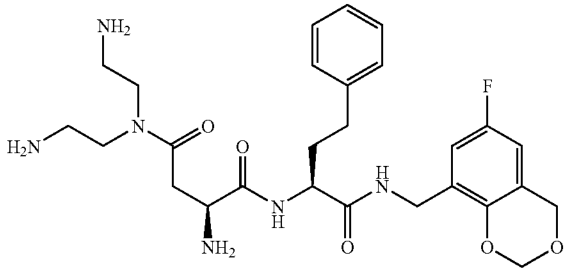
236
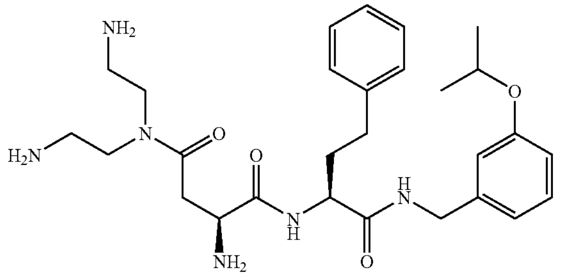
-continued
237
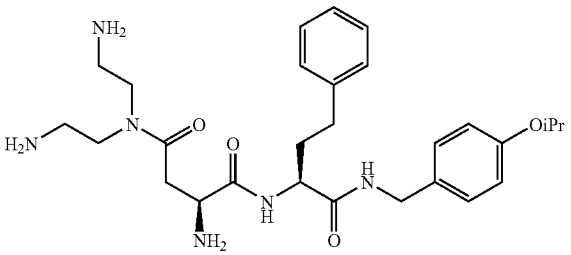
238
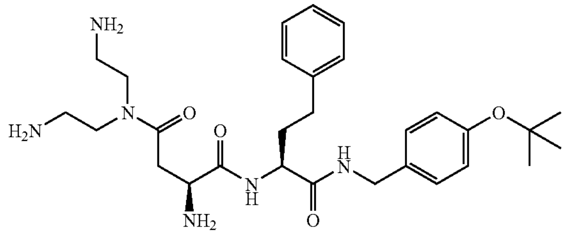
239
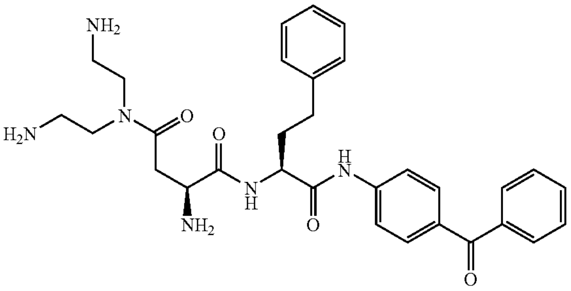
240
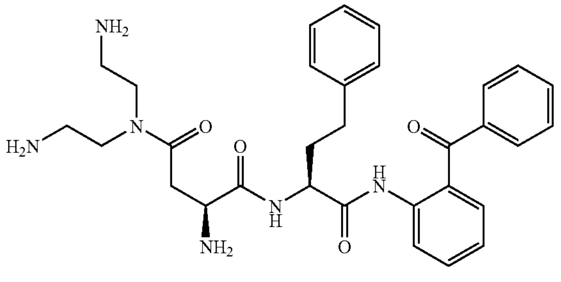
241
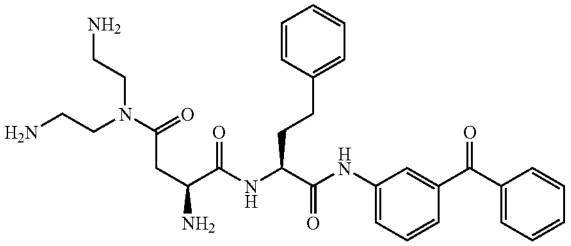

-continued
244
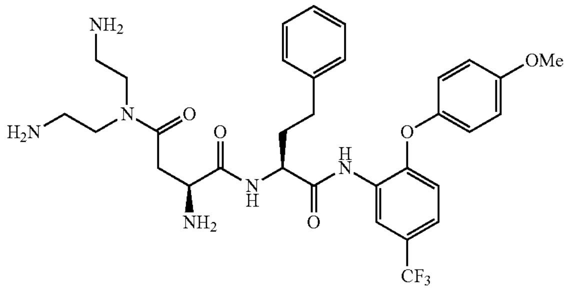
245
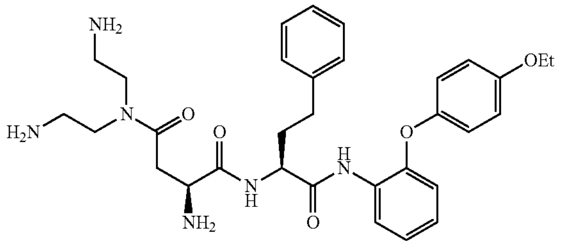
246
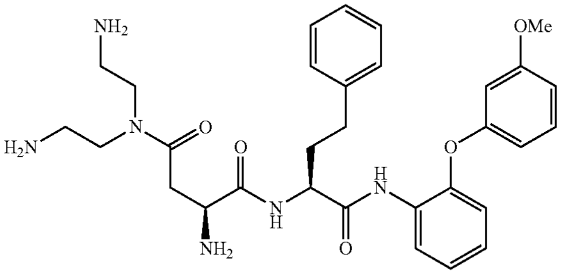
247
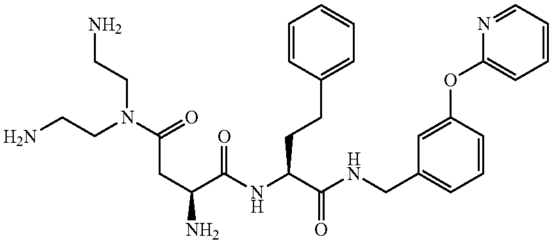
248
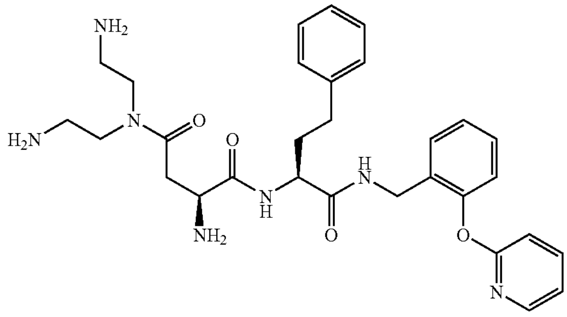
-continued
249
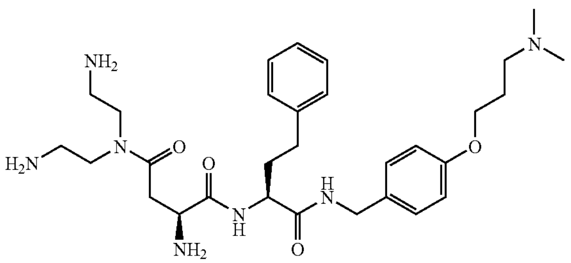
250
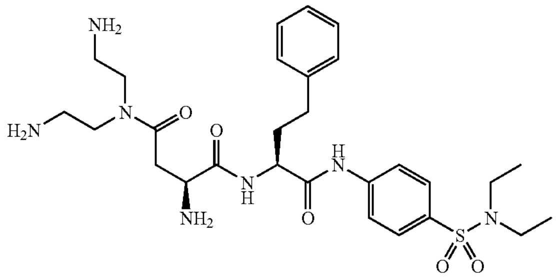
252
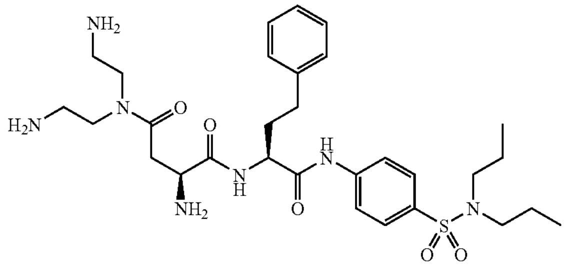
252
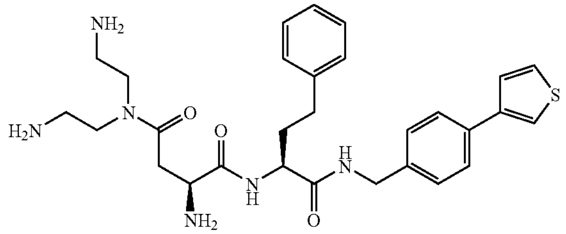
253
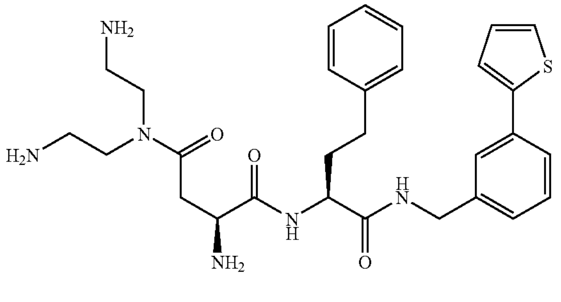

-continued
254
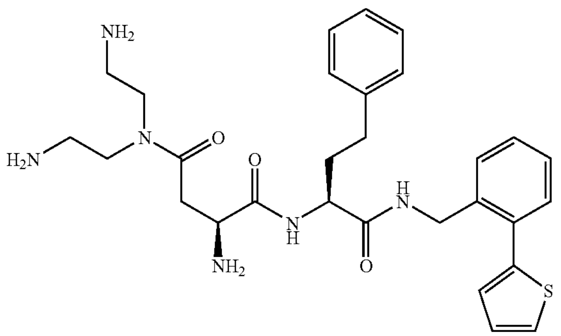
255
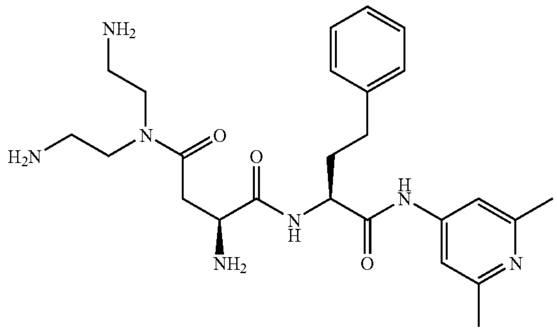
257
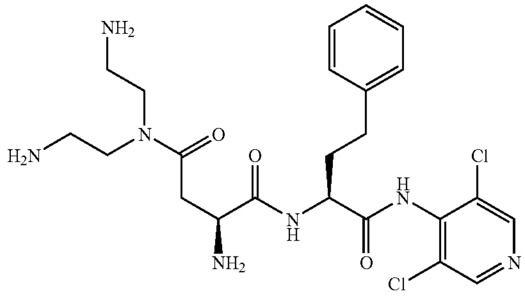
258
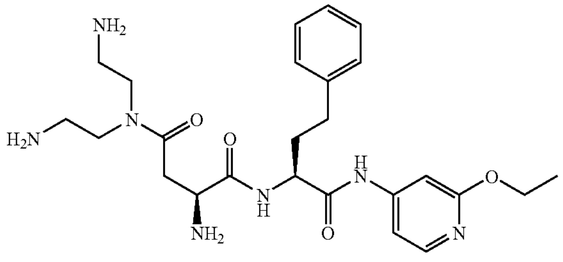
259
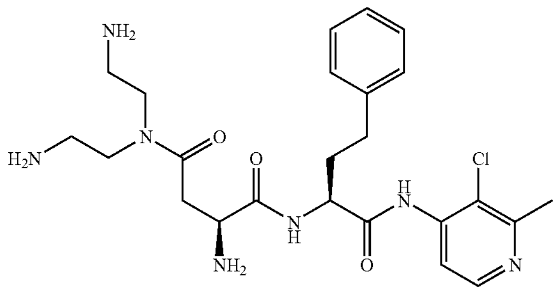
-continued
260
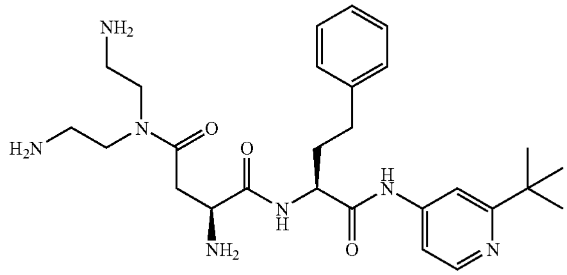
261
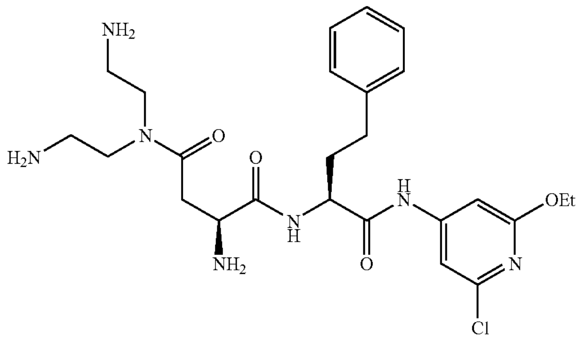
262
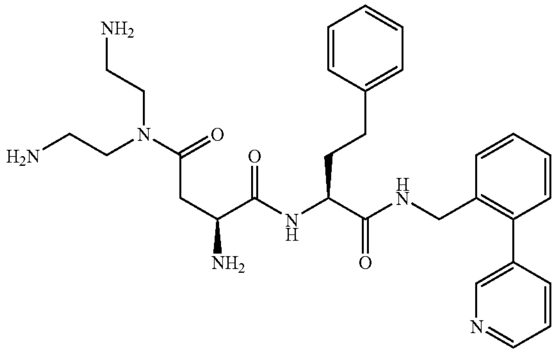
263
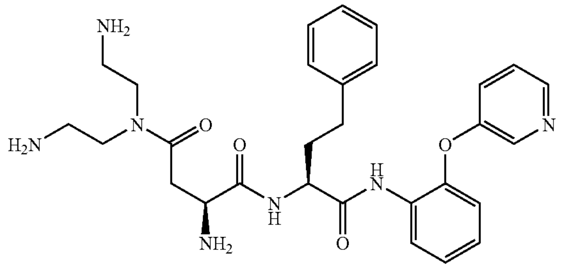
264
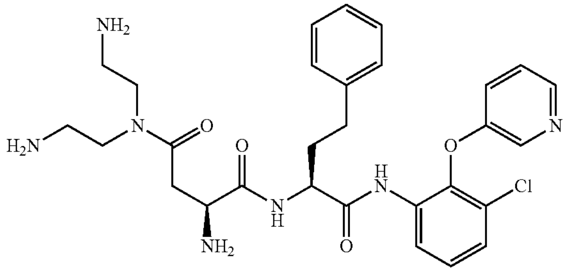

-continued
265
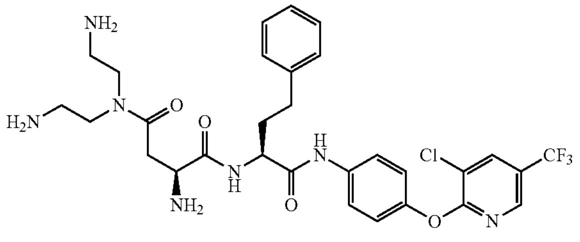
266
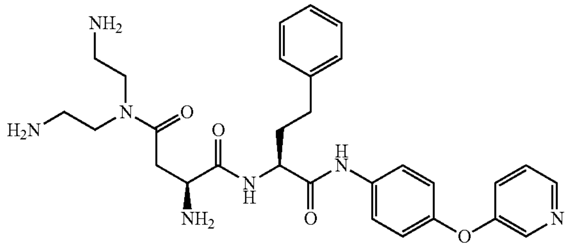
267
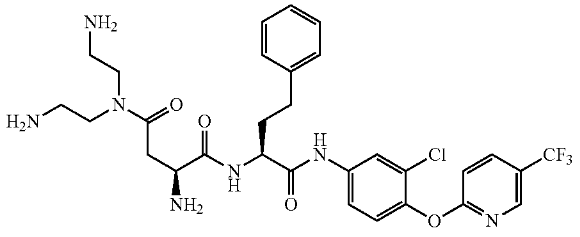
269
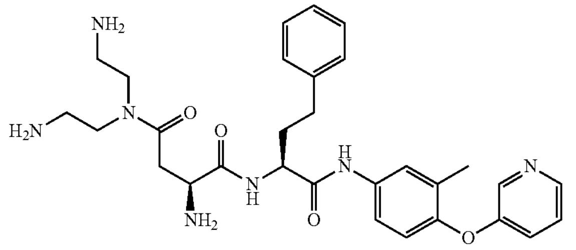
270
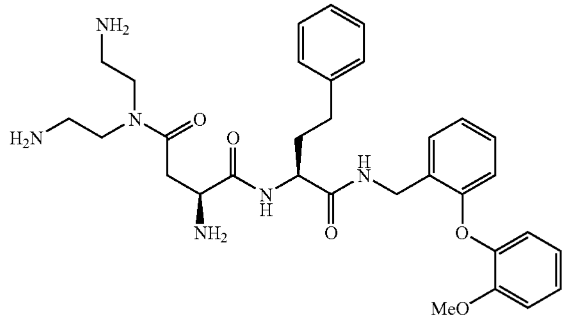
-continued
271
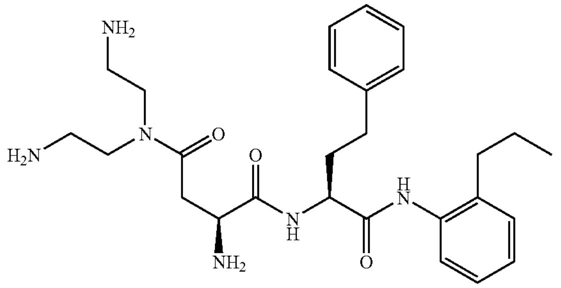
272
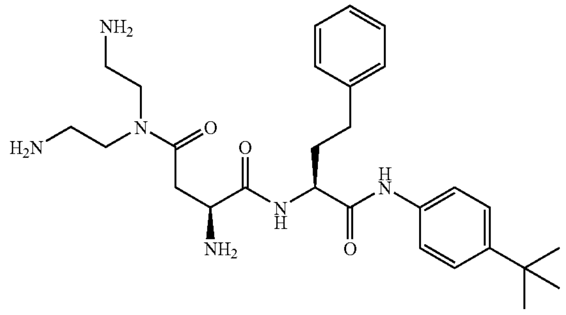
273
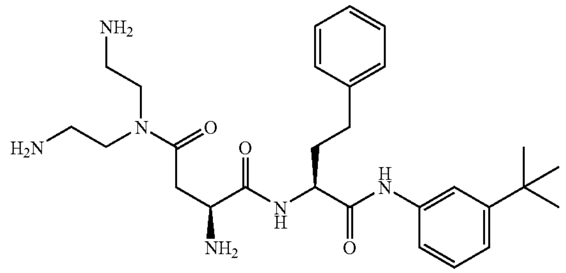
274
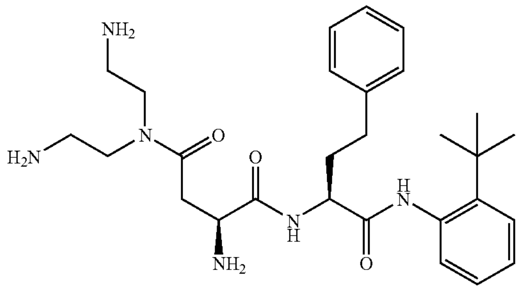
275
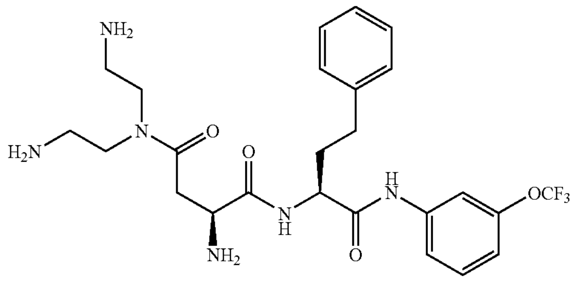

-continued
276
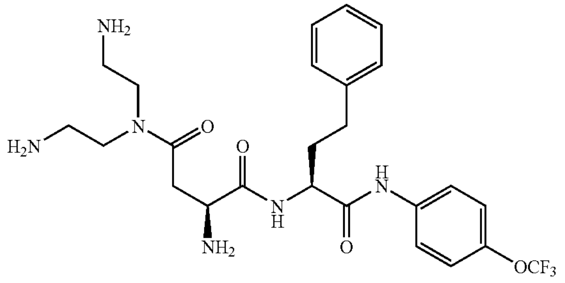
277
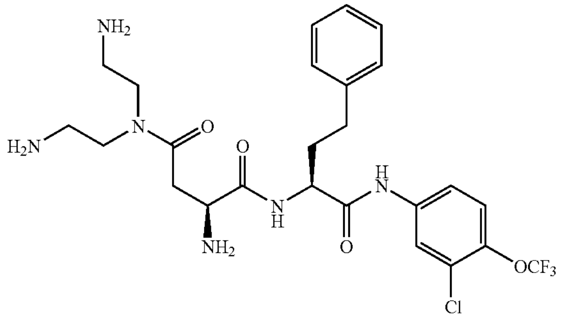
278
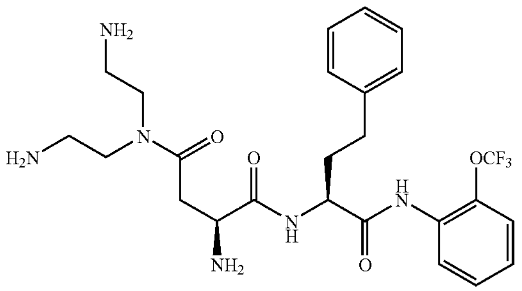
280
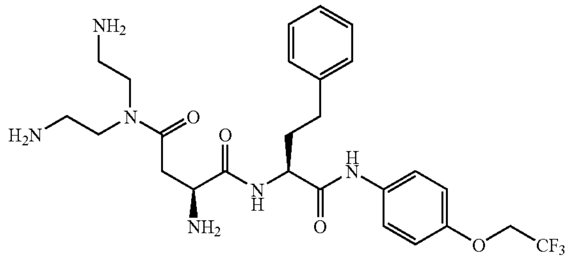
281
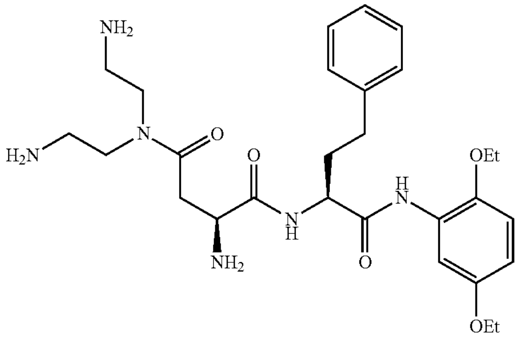
-continued
282
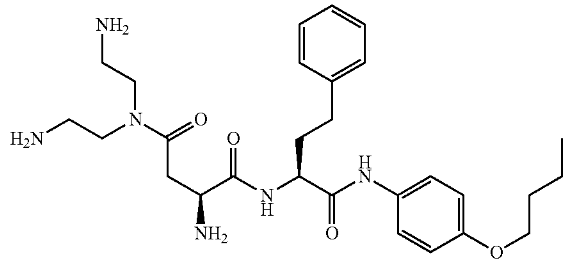
283
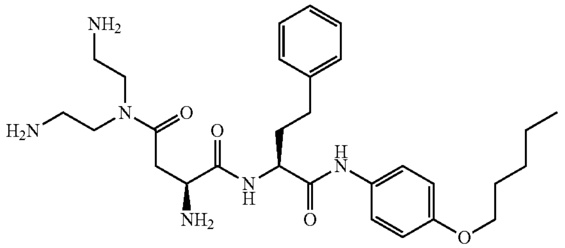
285
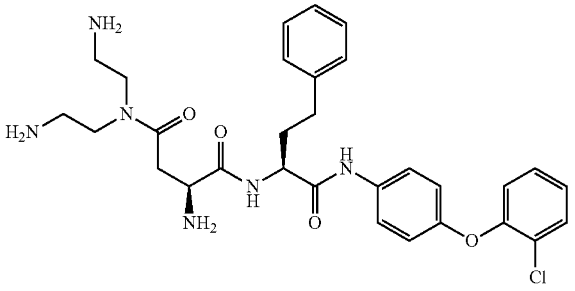
285
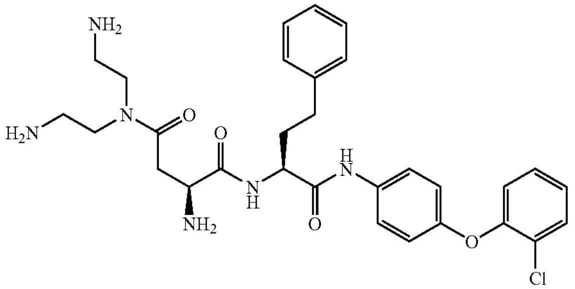
286
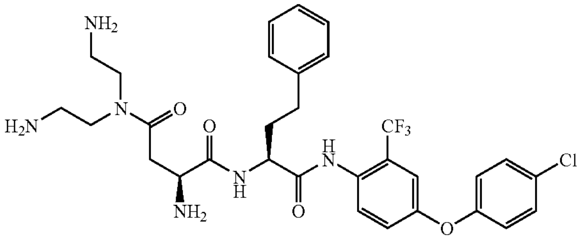

-continued
287
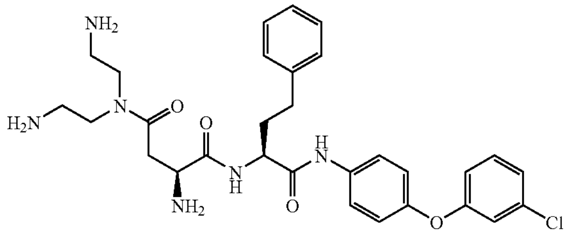
288
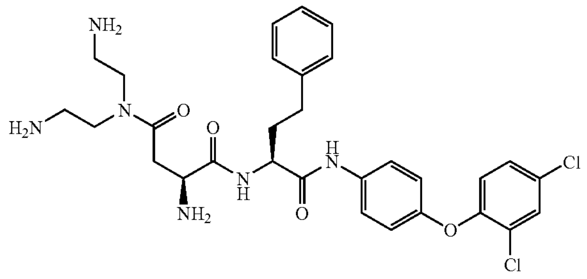
291
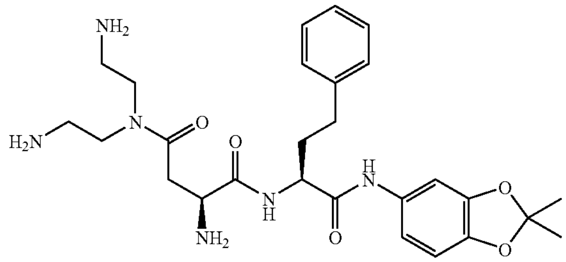
292
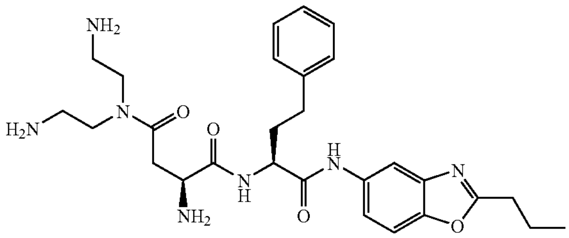
293
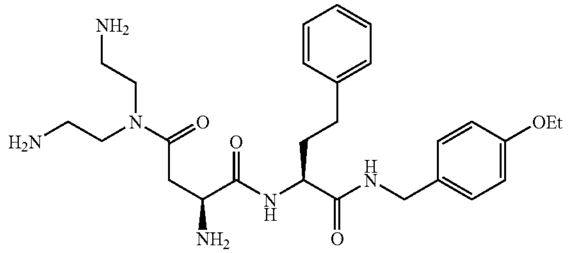
-continued
294
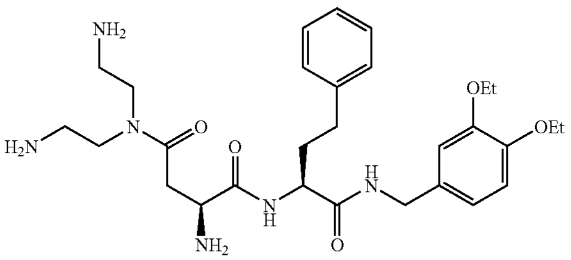
295
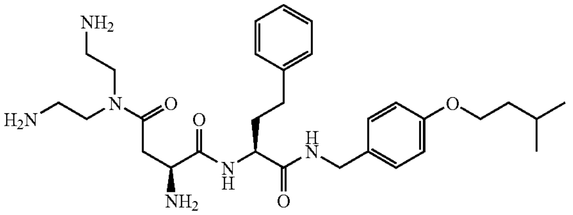
296
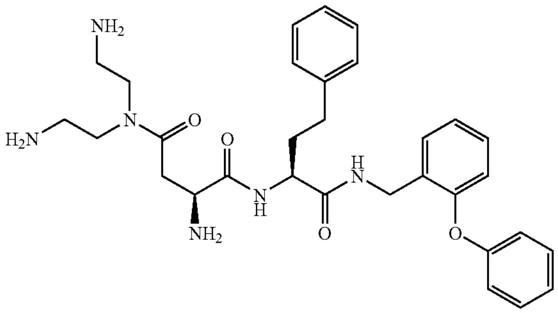
297
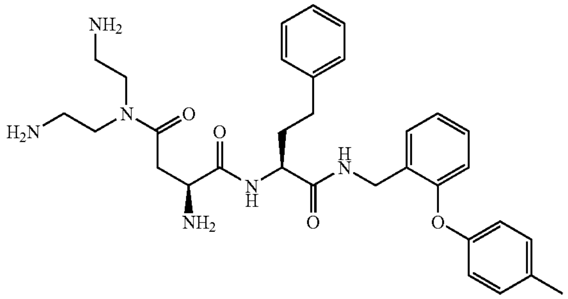
298
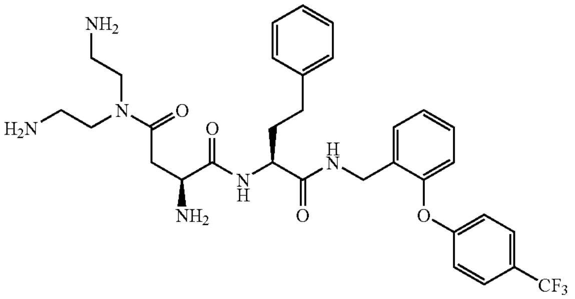

-continued
299
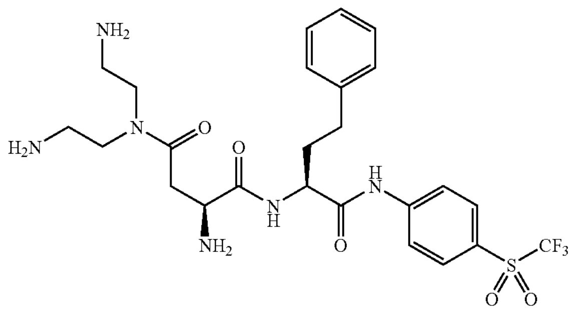
300
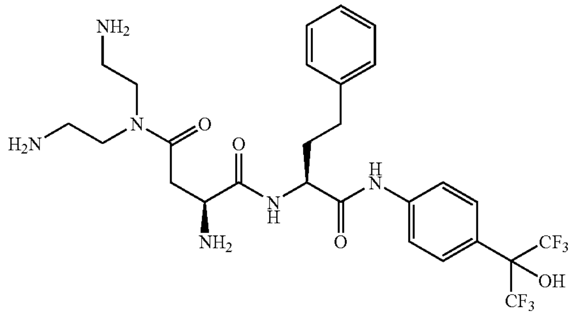
301
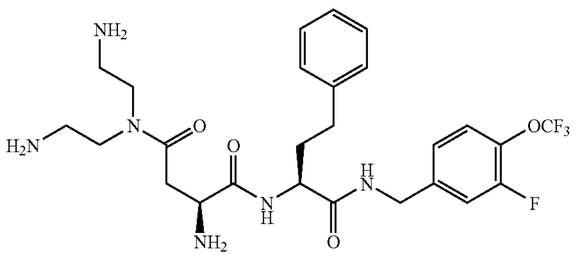
302
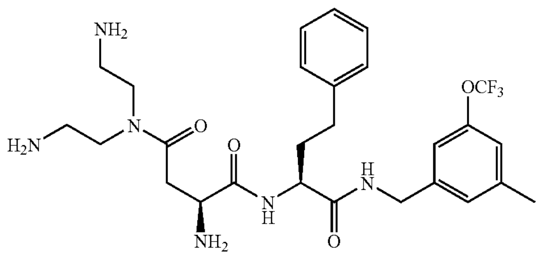
303
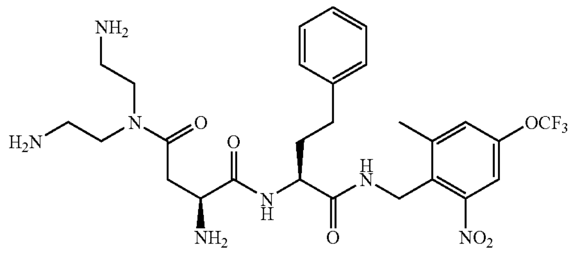
-continued
304
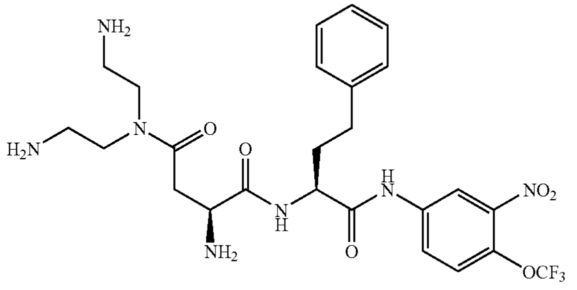
305
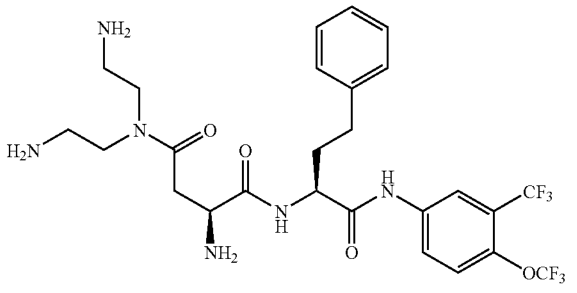
306
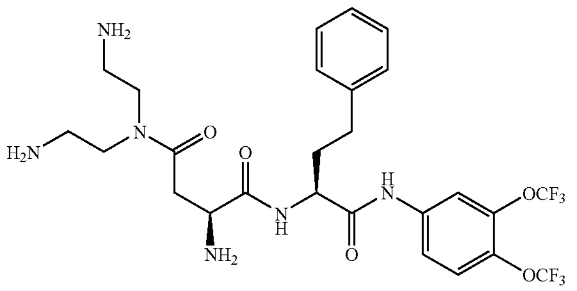
308
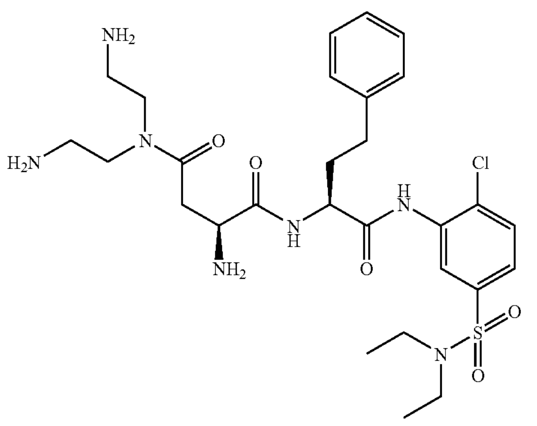
309
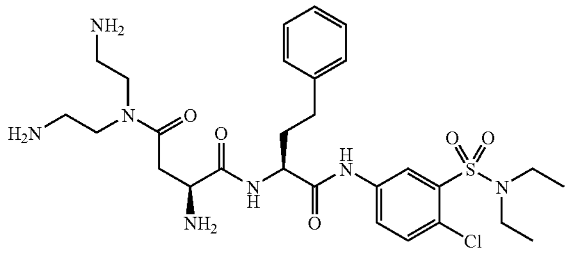

-continued
310
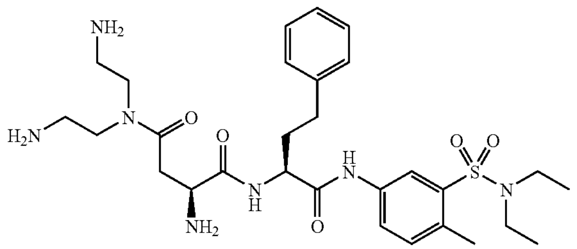
311
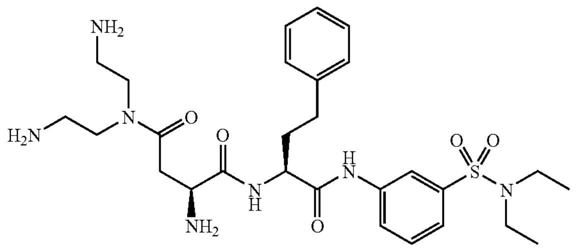
312
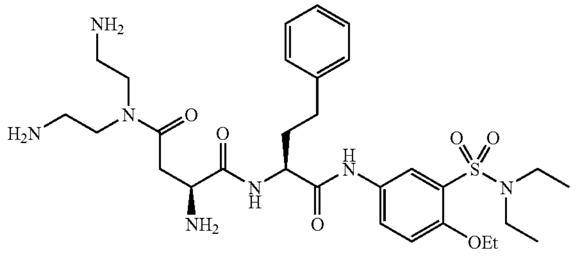
313
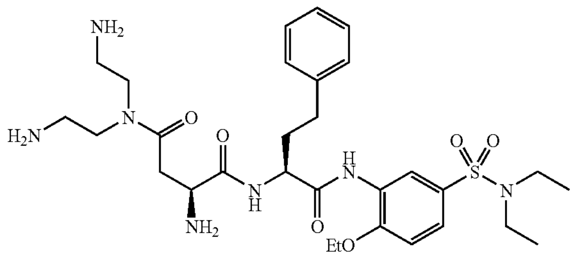
314
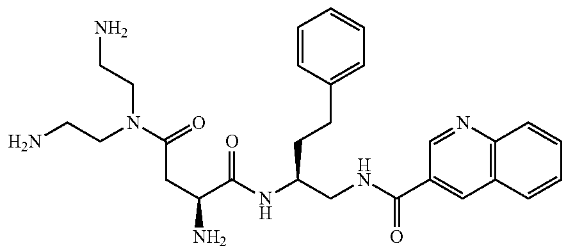
-continued
316
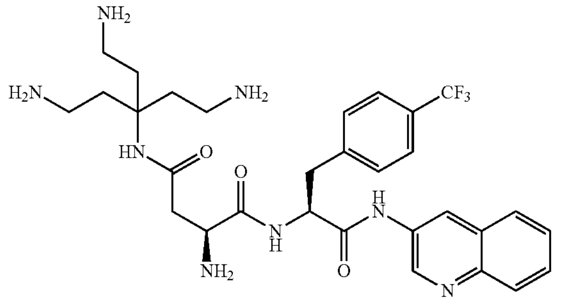
318
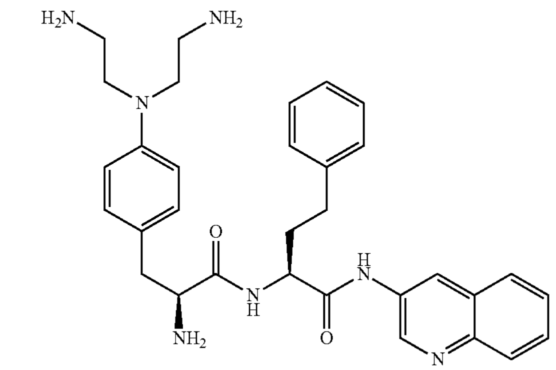
319
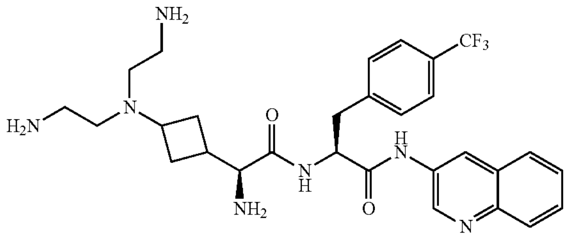
320
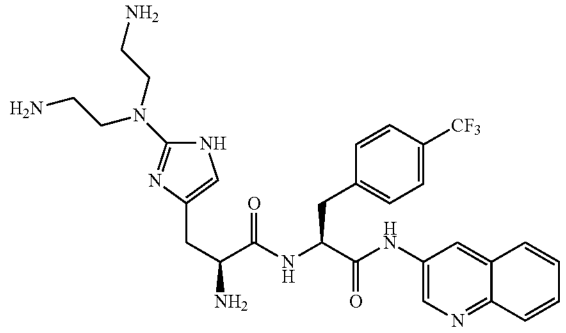
322
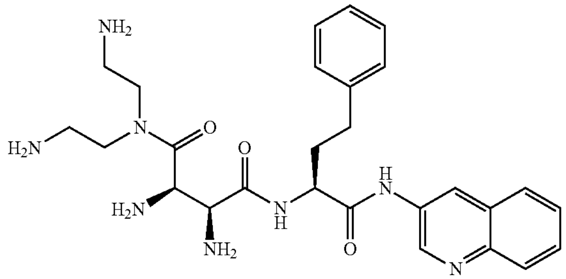

-continued
323
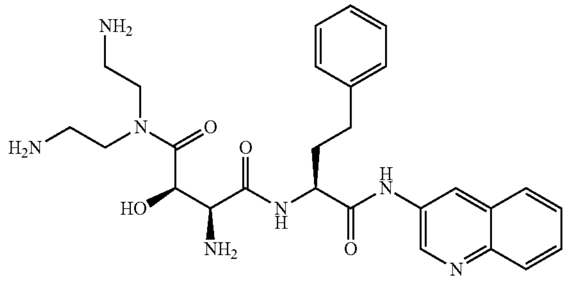
324
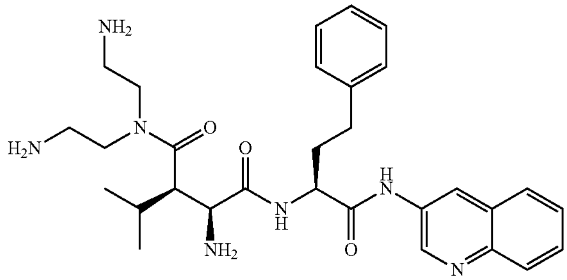
325
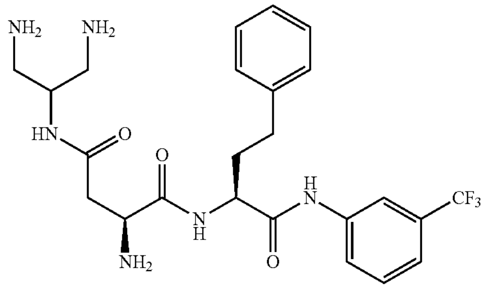
326
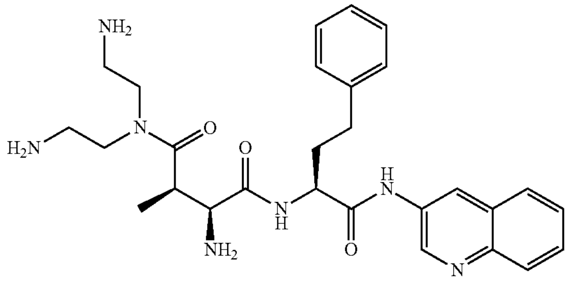
327
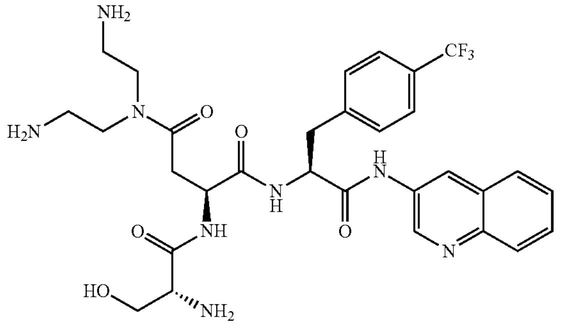
-continued
329
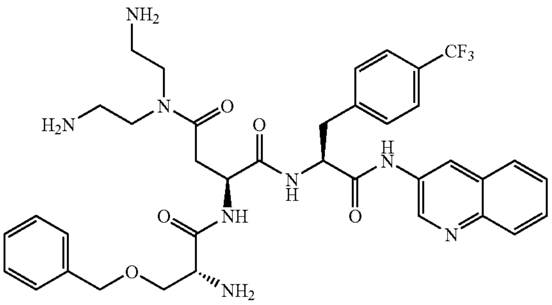
330
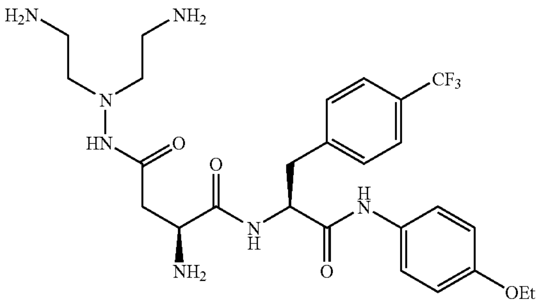
331
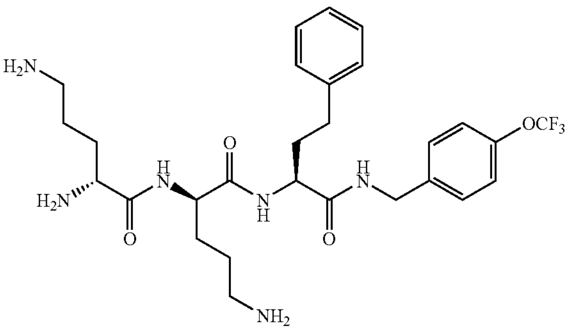
332
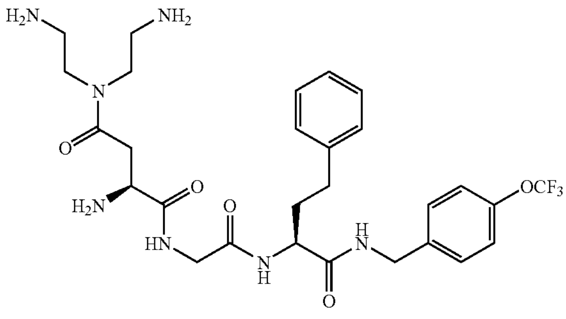
333
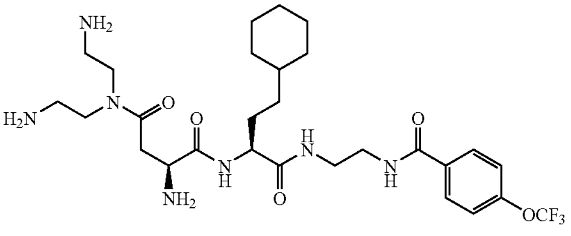

-continued
334
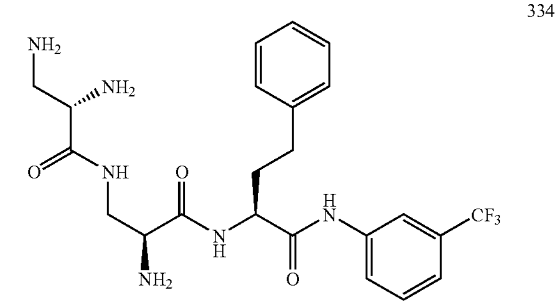
335
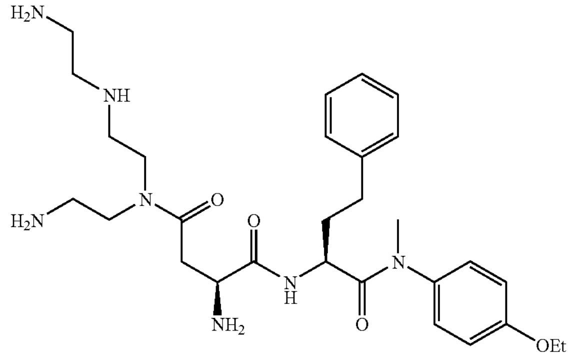
336
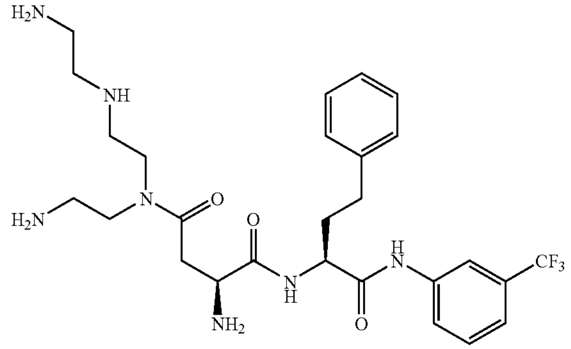
337
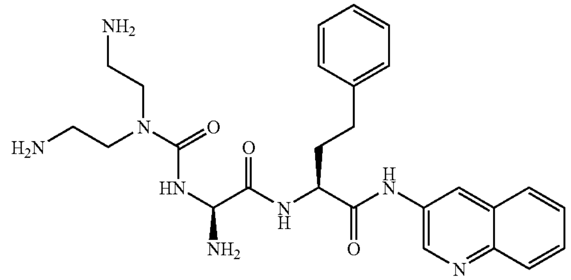
338
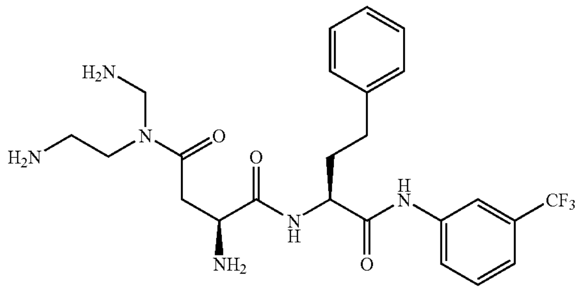
-continued
339
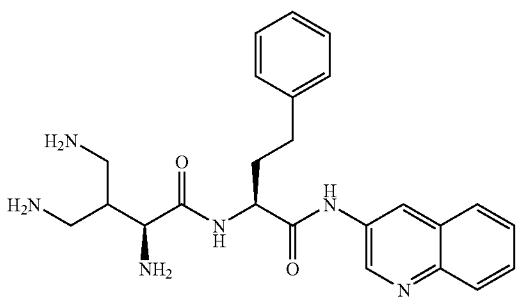
340
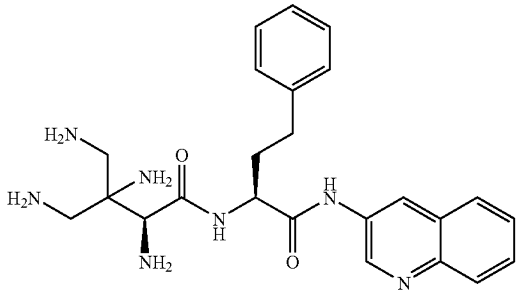
341
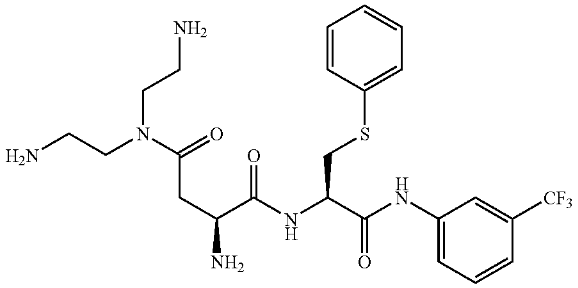
342
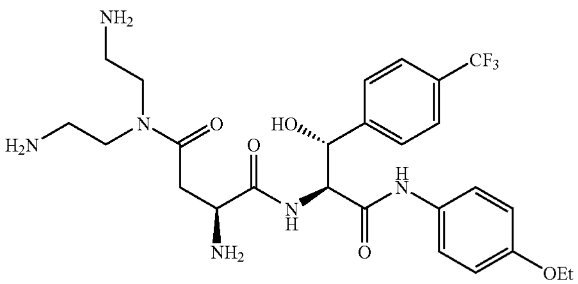
344
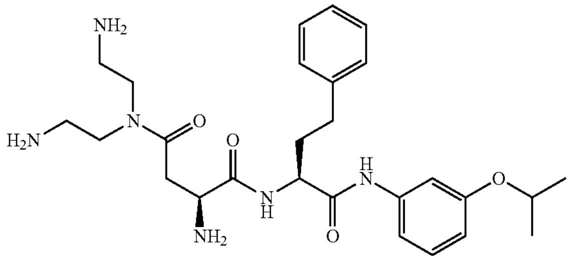

-continued
349
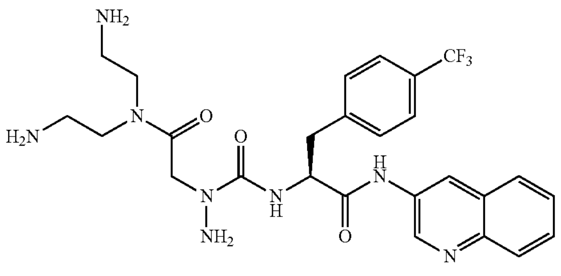
350
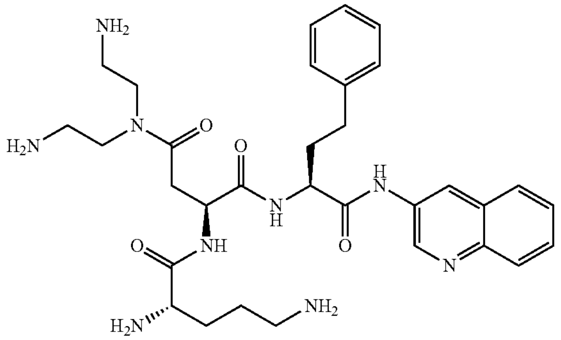
351
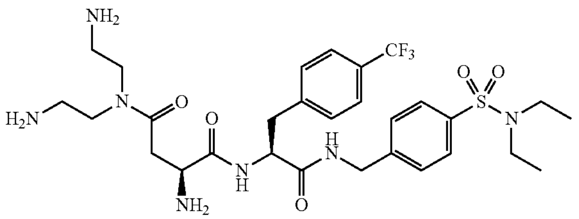
352
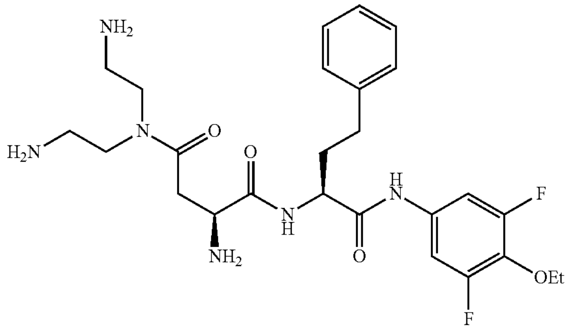
353
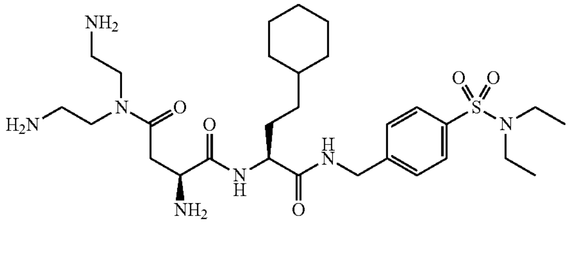
-continued
354
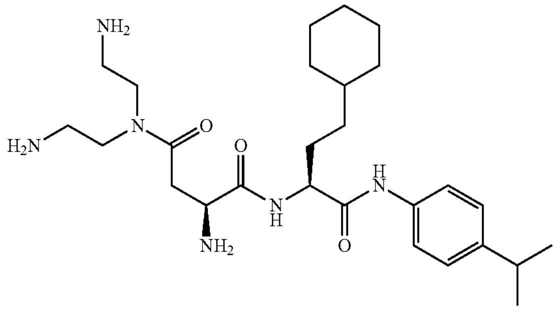
356
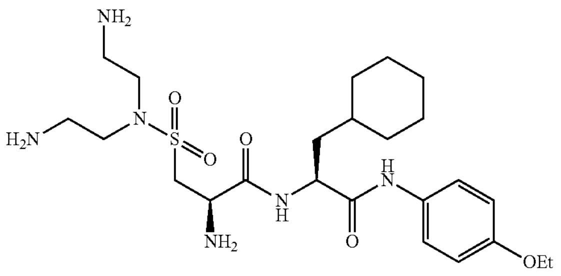
358
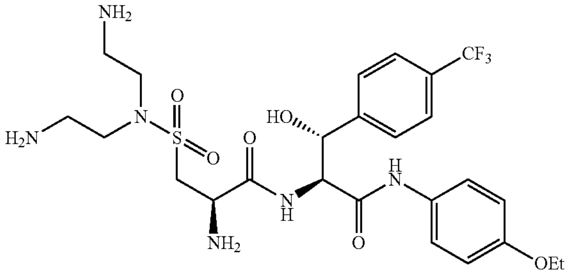
359
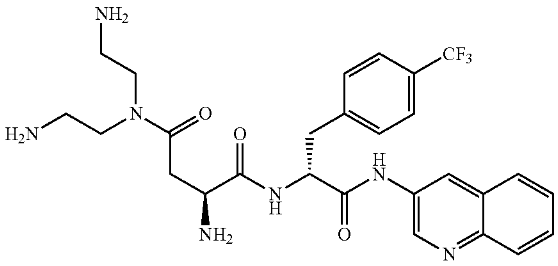
360
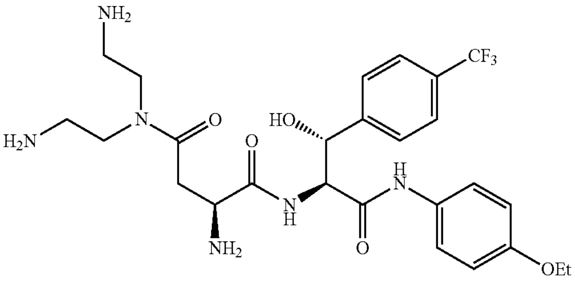

-continued
361
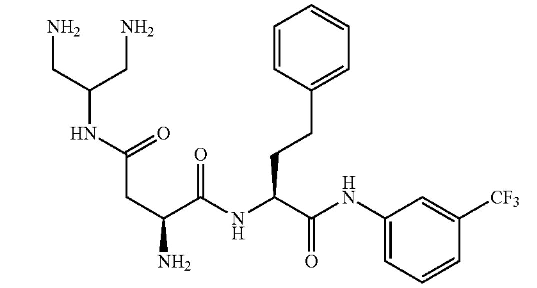
362
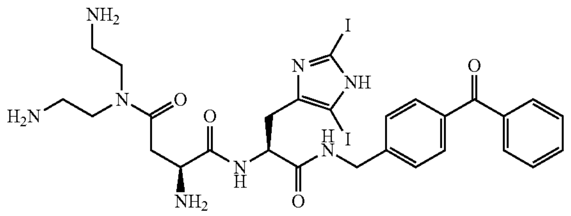
363
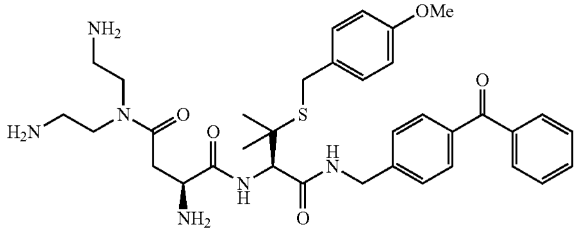
364
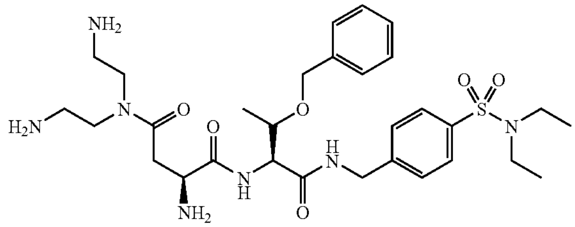
365
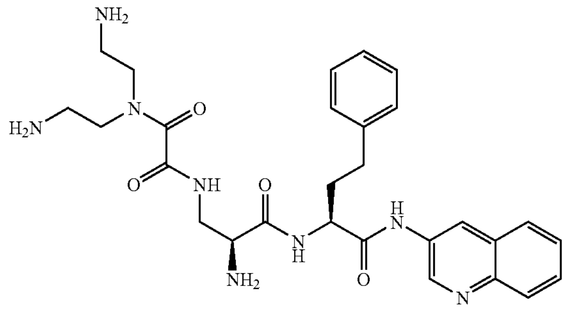
366
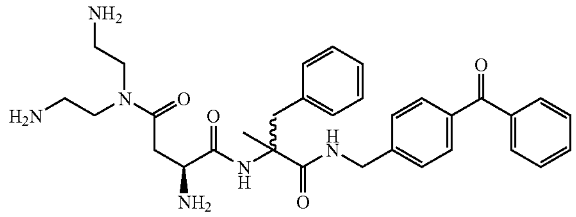
-continued
367
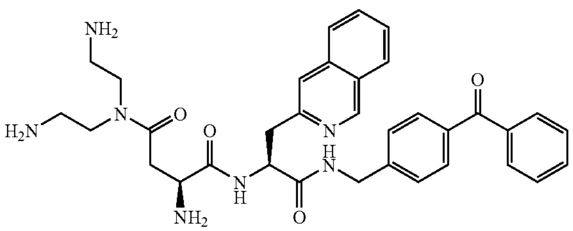
368
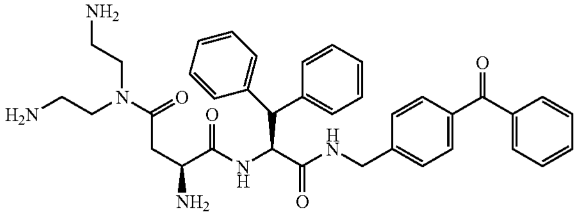
369
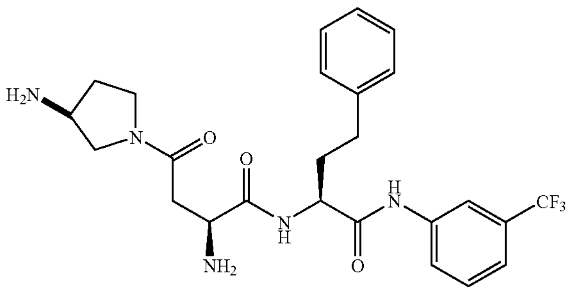
370
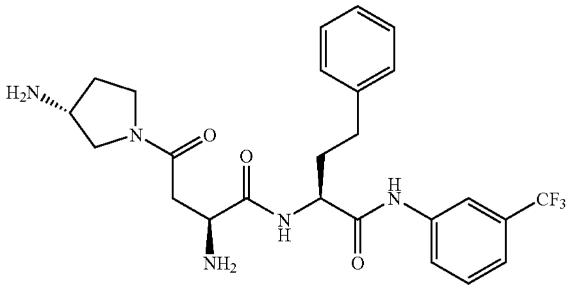
371
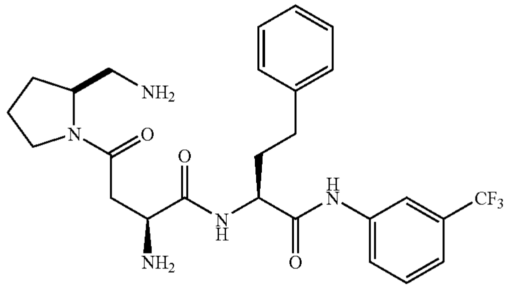

-continued
372
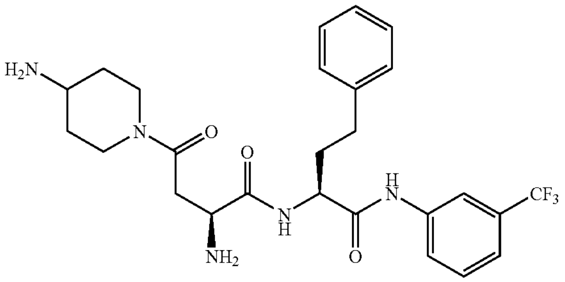
373
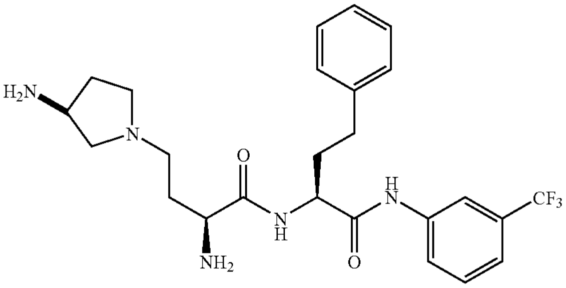
374
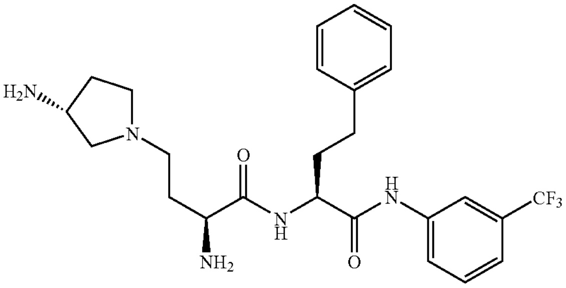
375
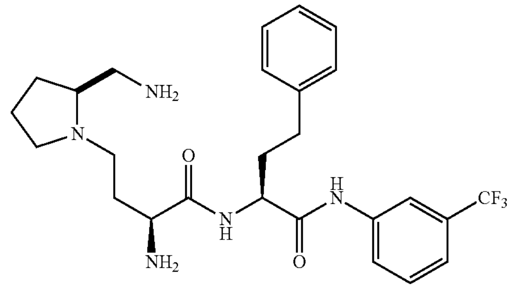
and
376
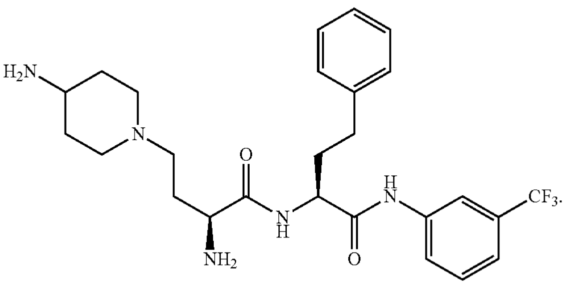
14. The compound of claim 1 having a structure selected from the group consisting of:
2
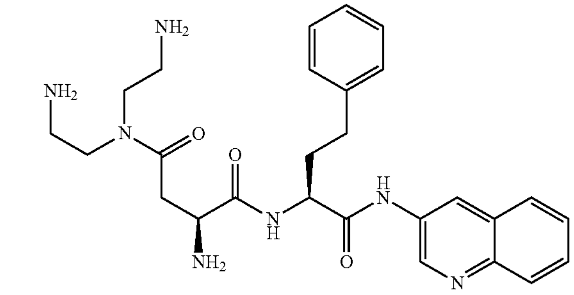
67
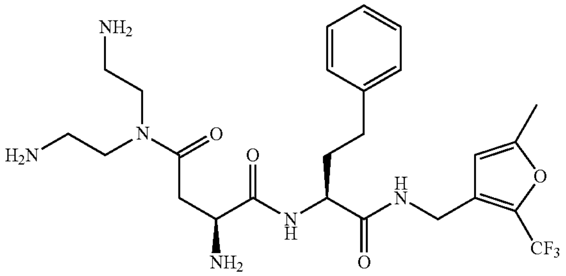
87
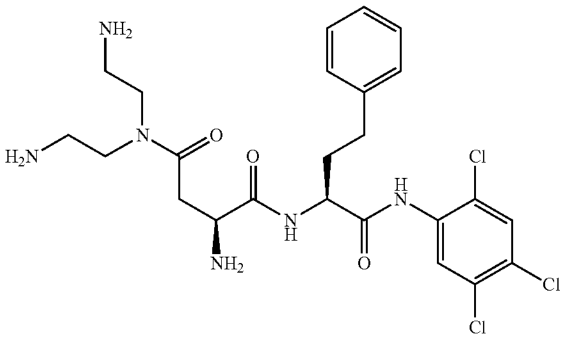
88
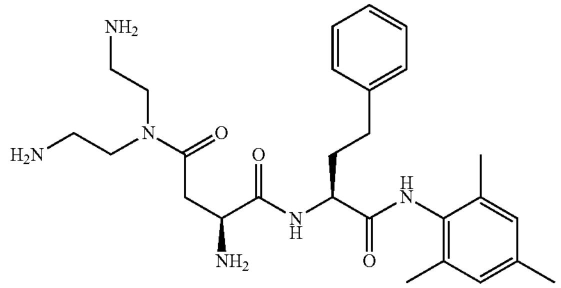
90
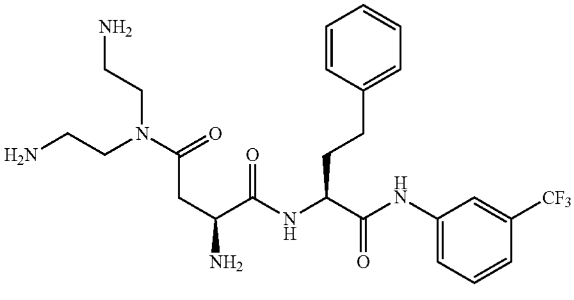

-continued
91
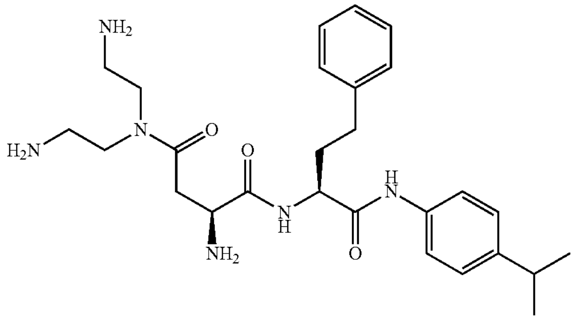
95
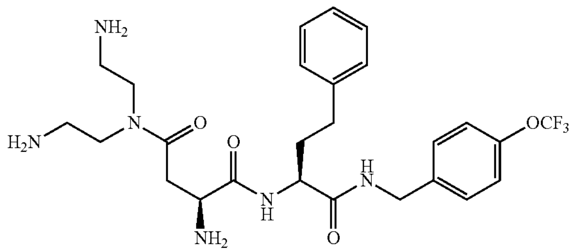
96
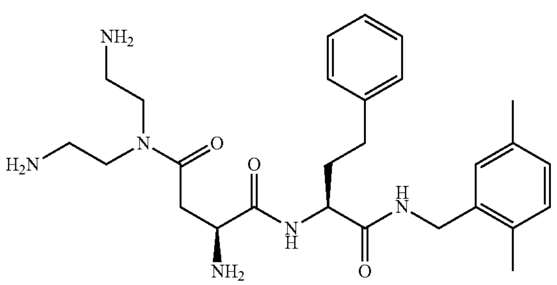
102
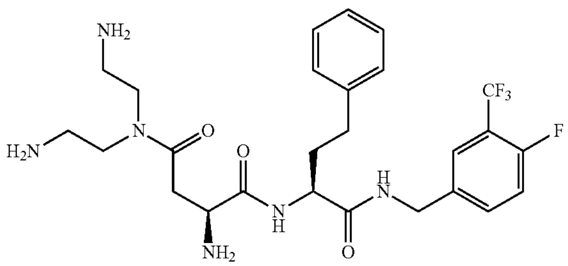
114
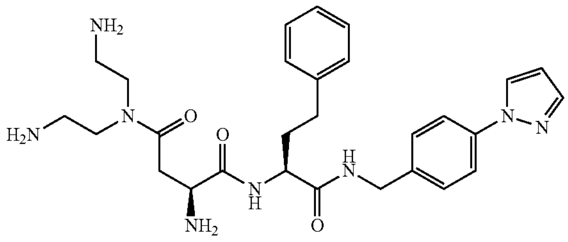
-continued
178
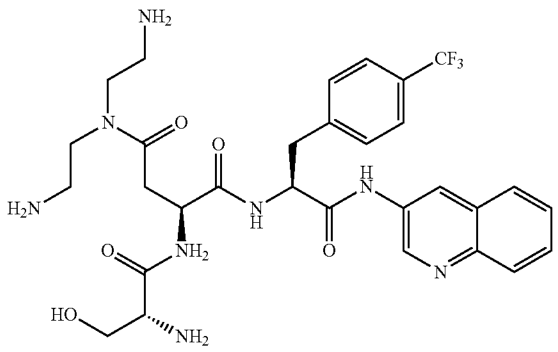
188
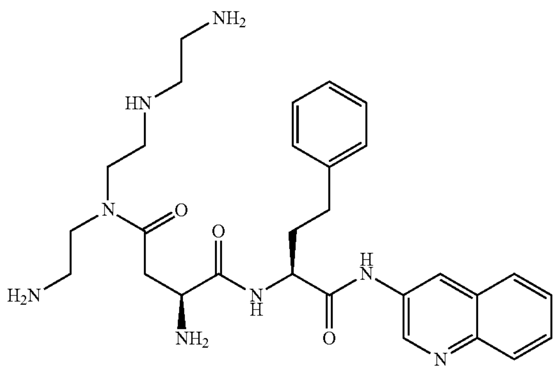
224
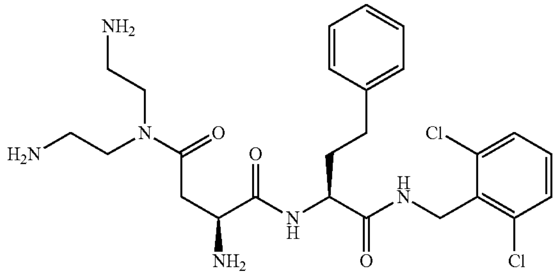
237
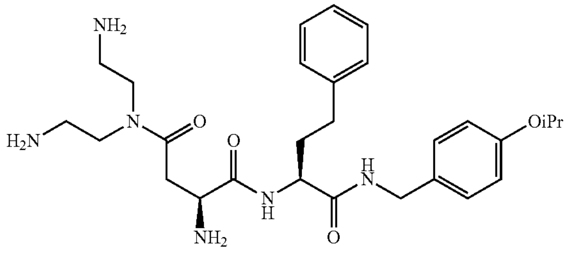

-continued
271
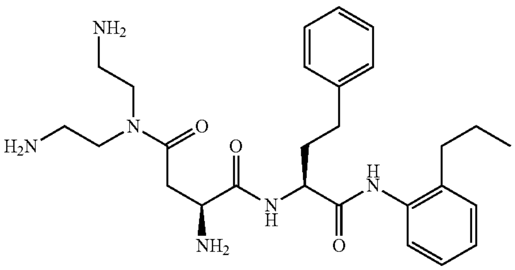
and
-continued
352
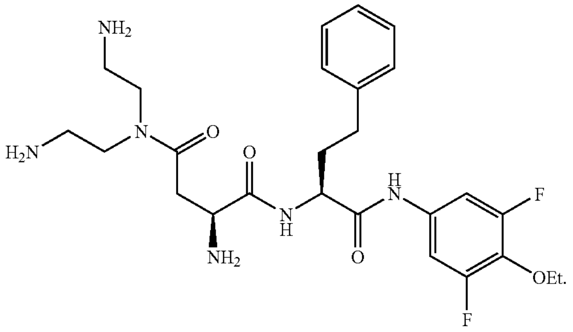
15. The compound of claim 1 having a structure selected from the group consisting of:
377
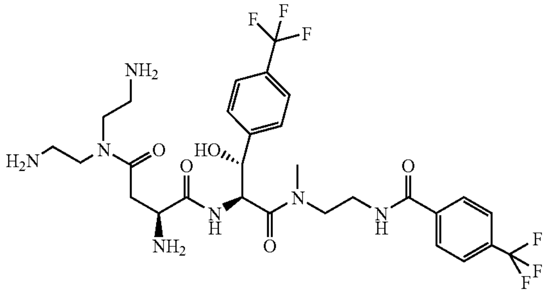
379
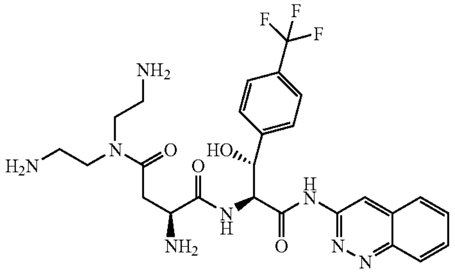
380
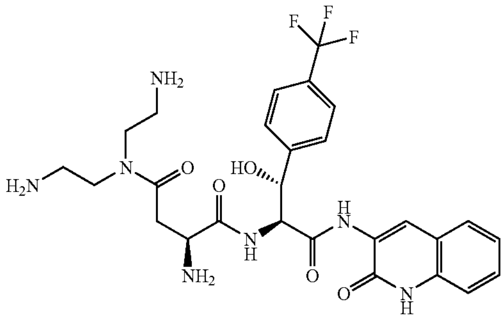
381
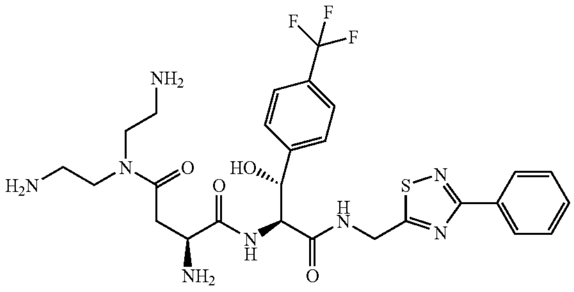
383
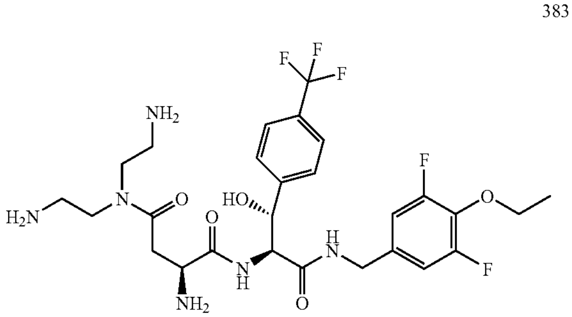
385
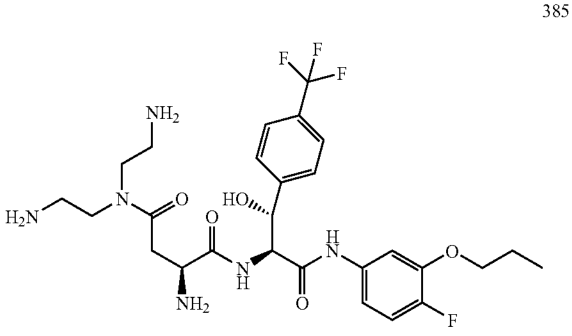

-continued
386
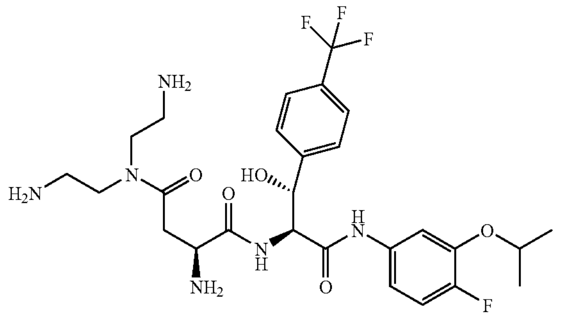
388
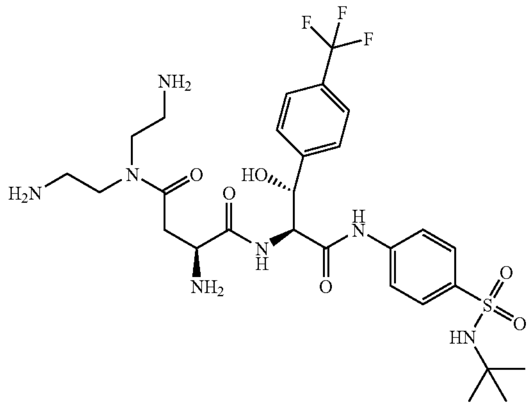
389
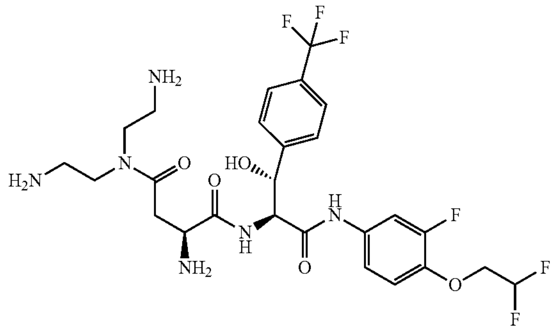
391
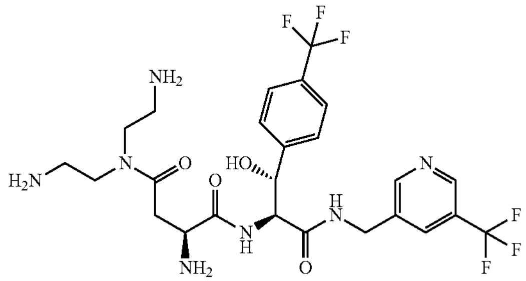
392
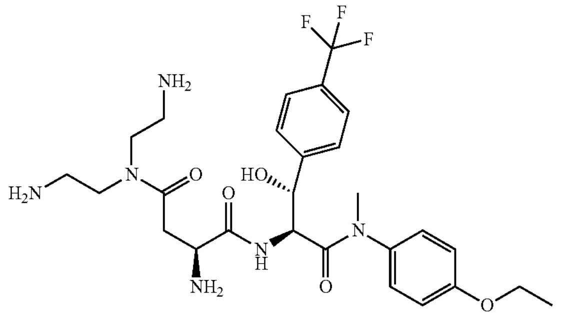
393
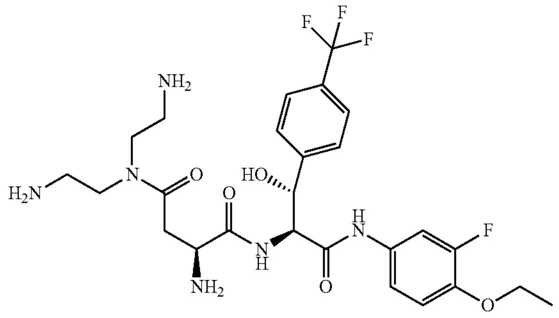
394
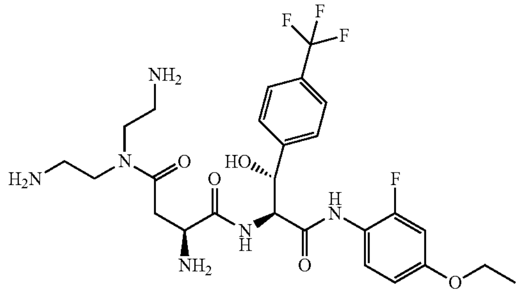
395
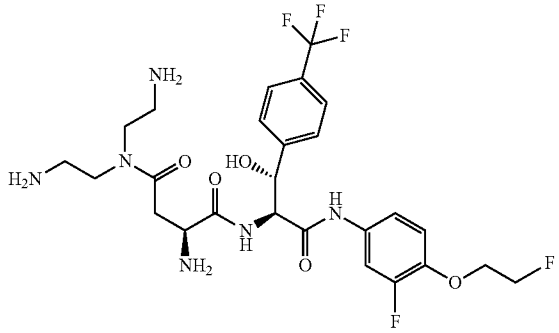

-continued
396
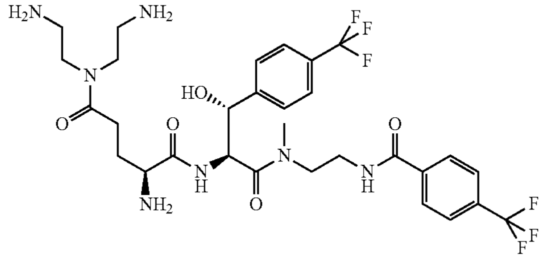
398
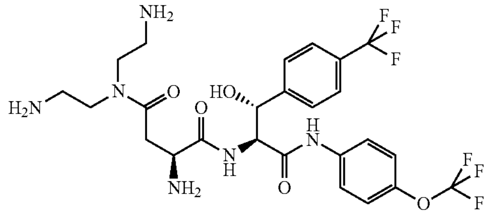
399
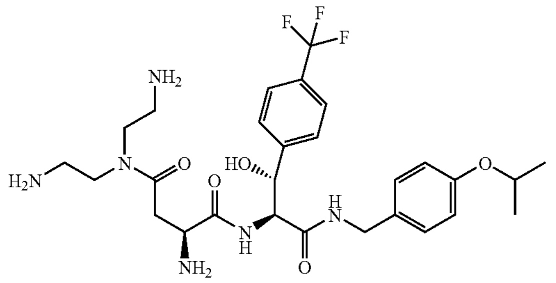
400
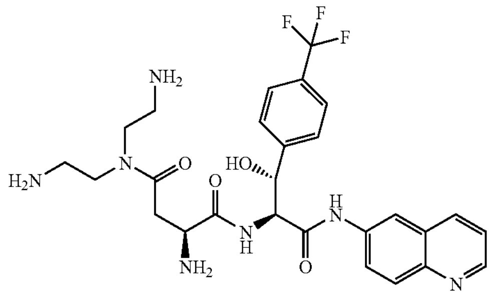
401
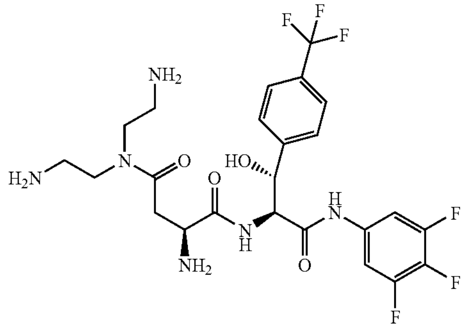
402
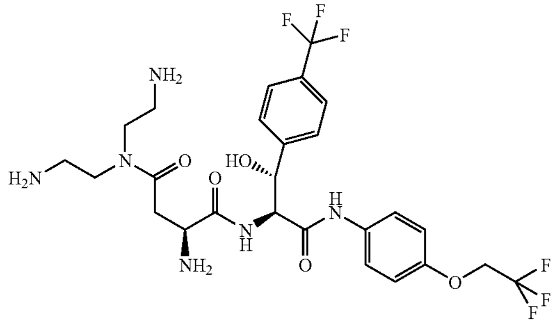
403
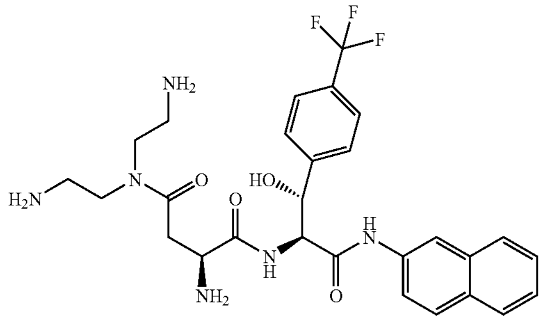
404
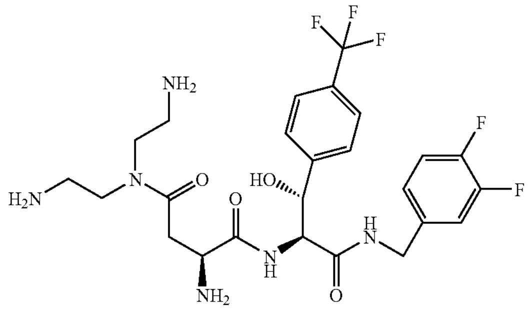
405
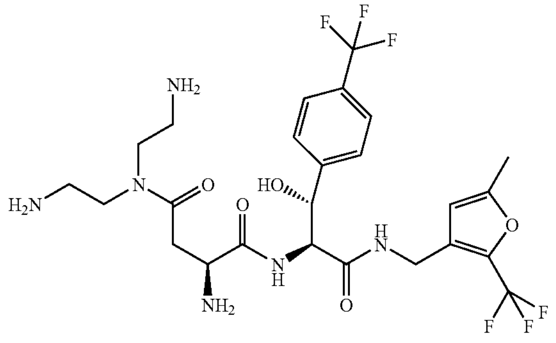
406
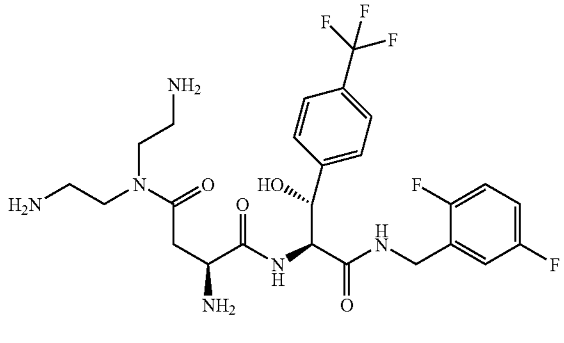

-continued
407
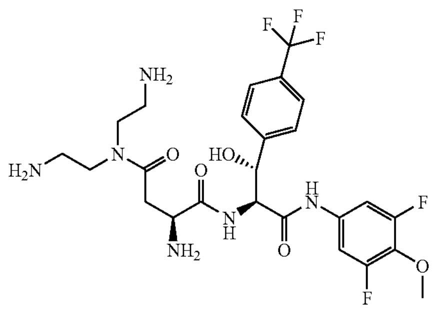
408
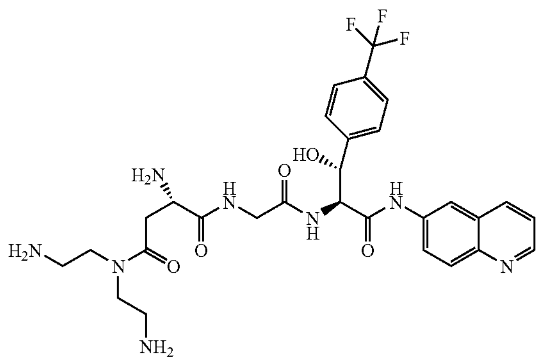
409
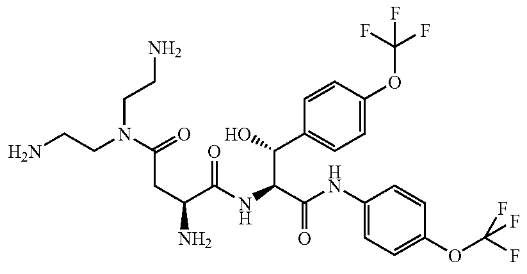
410
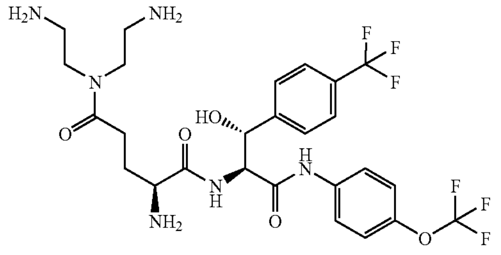
411
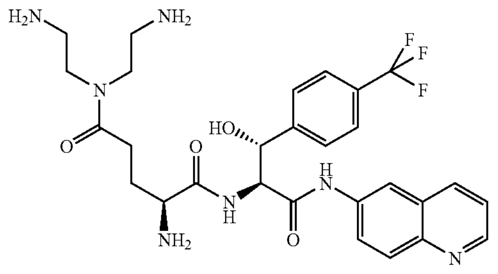
412
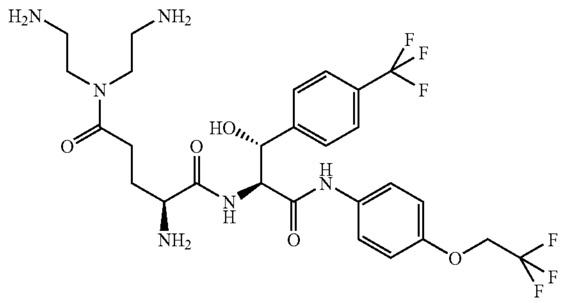
413
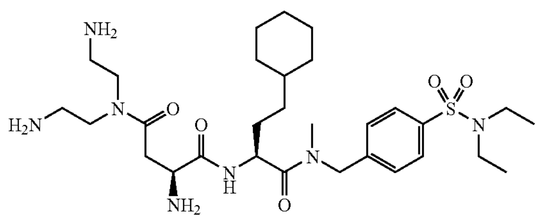
414
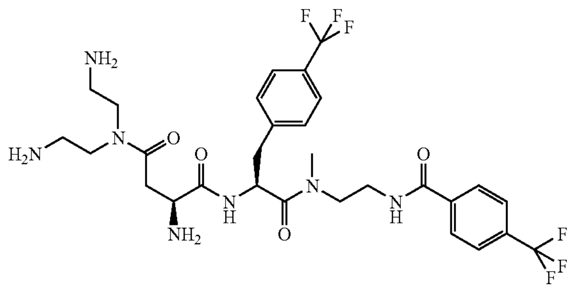
415
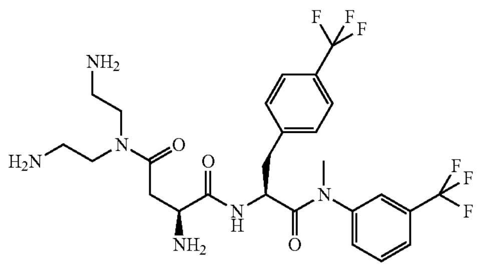
416
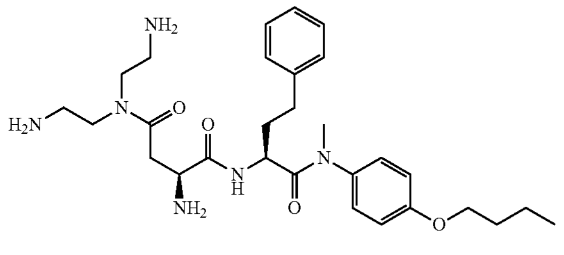

-continued
419
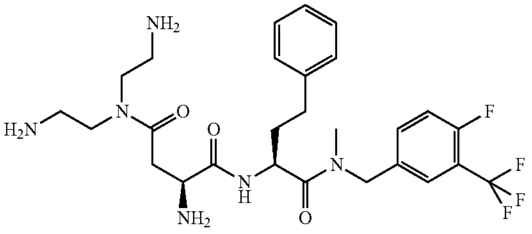
421
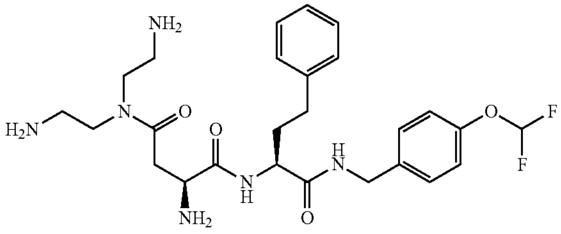
424
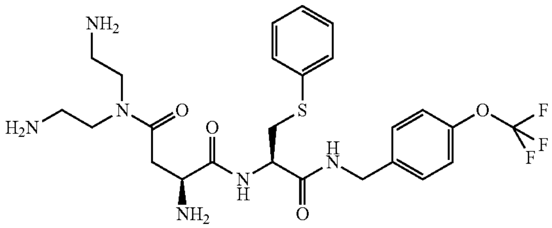
425
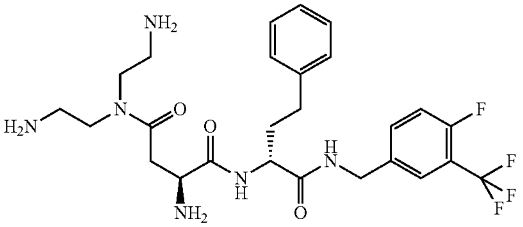
426
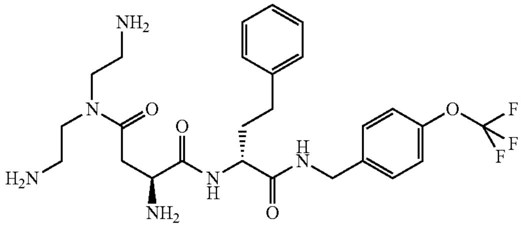
427
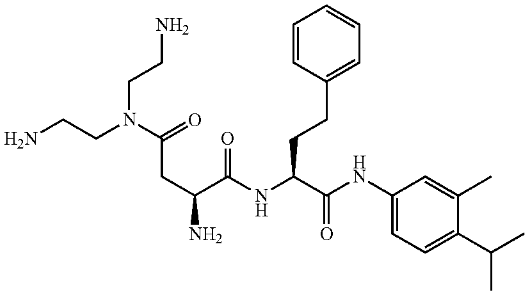
428
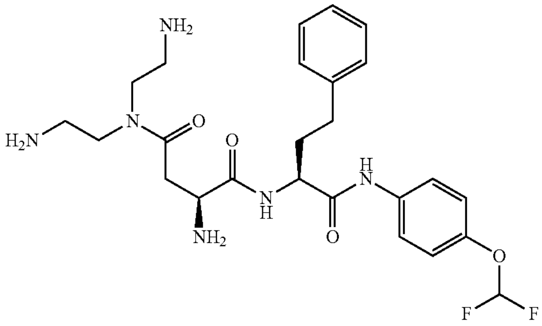
429
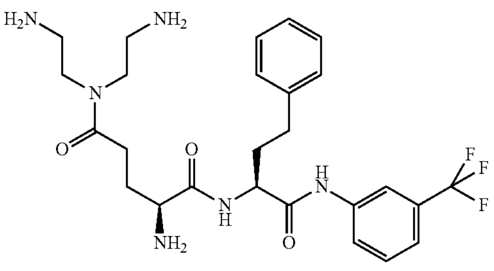
430
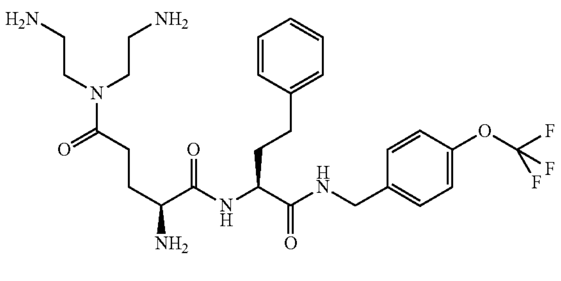

-continued
431
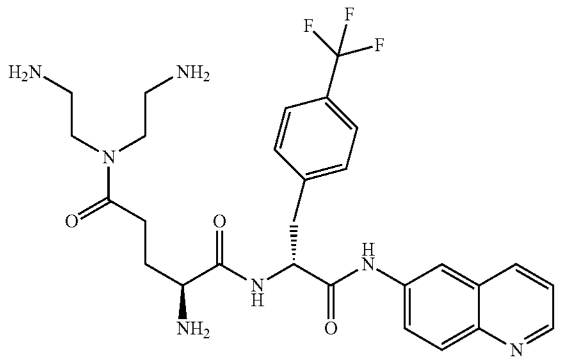
432
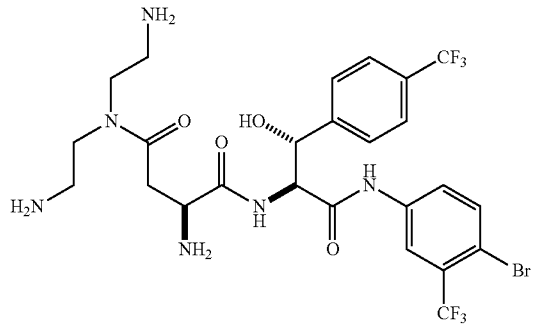
433
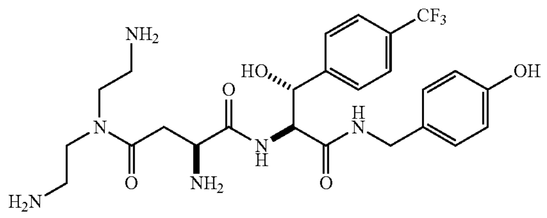
434
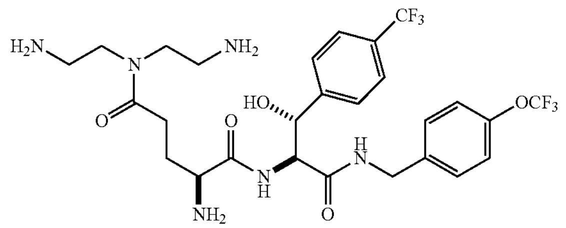
436
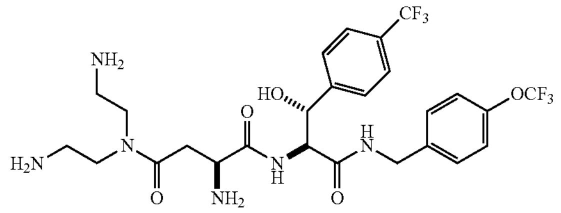
437
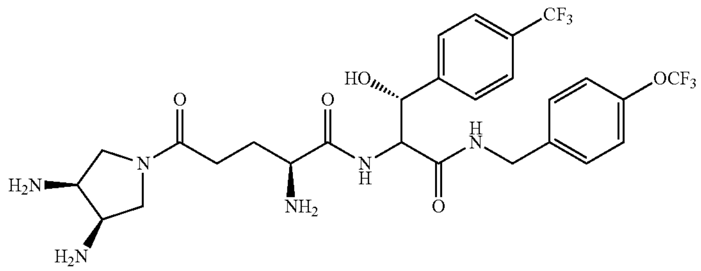
438
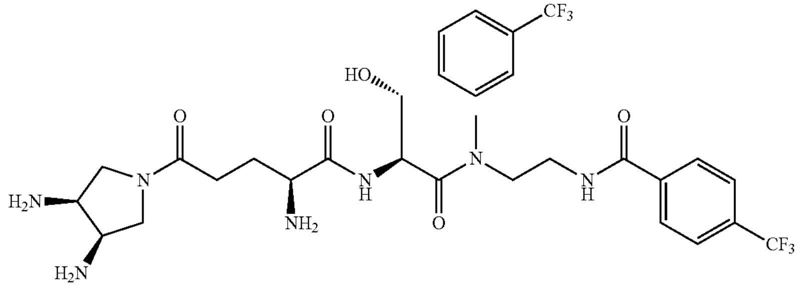

-continued
439
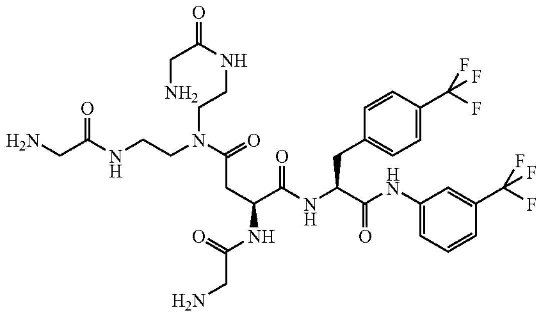
440
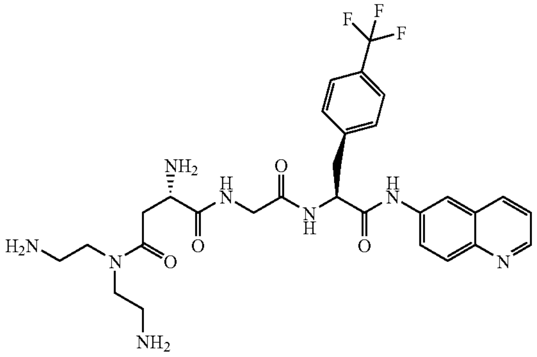
441
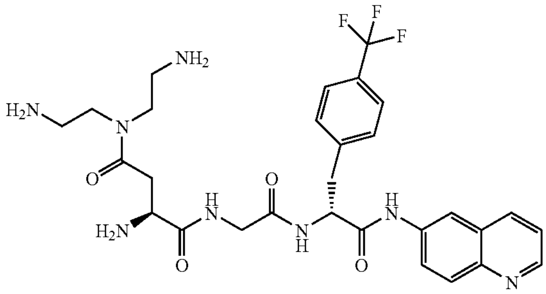
442
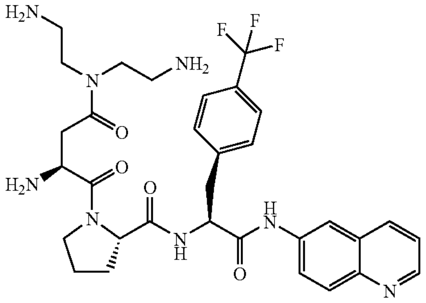
446
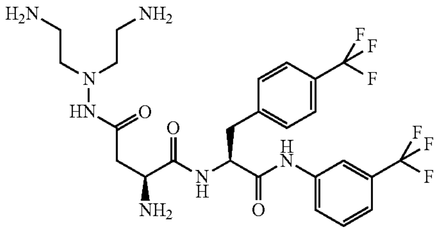
447
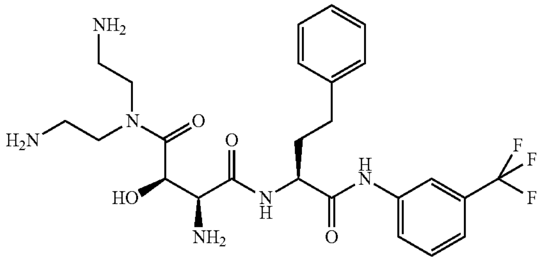
449
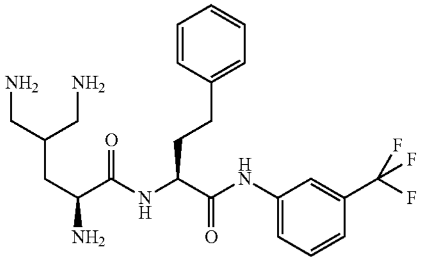
450
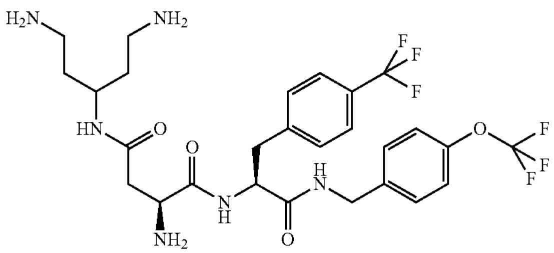
452
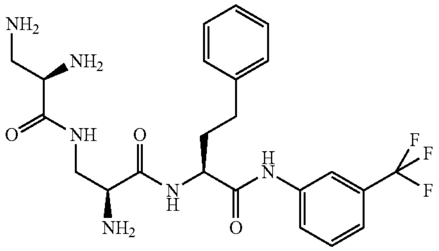

-continued
453
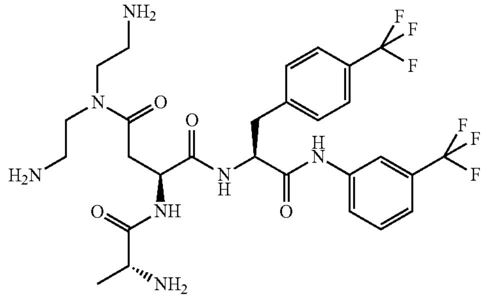
456
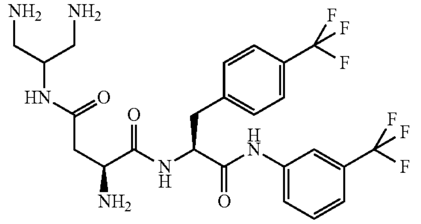
459
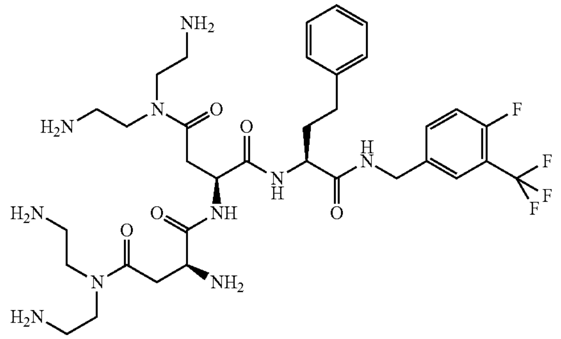
464
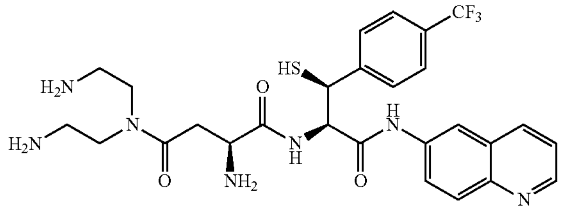
466
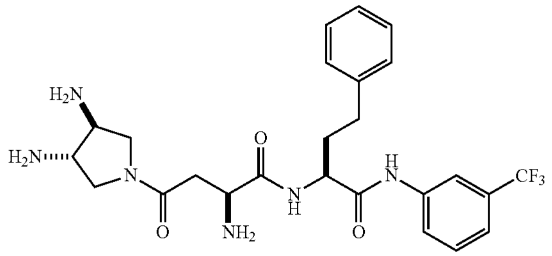
467
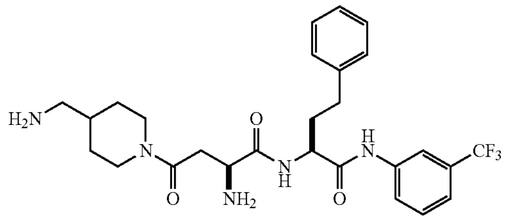
468
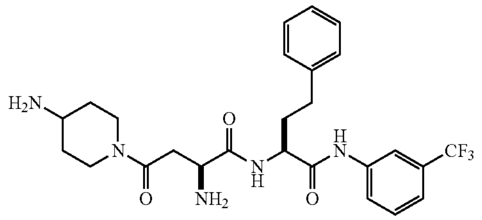
and
469
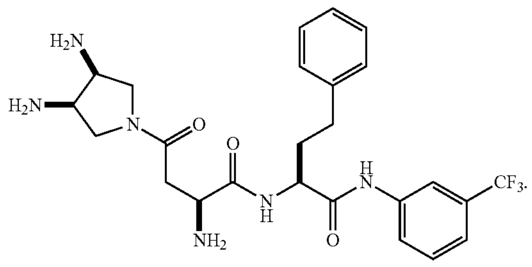
* * * * *

UNITED STATES PATENT AND TRADEMARK OFFICE

CERTIFICATE OF CORRECTION

PATENT NO. : 8,178,490 B2
APPLICATION NO. : 12/613329
DATED : May 15, 2012
INVENTOR(S) : Glinka et al.

It is certified that error appears in the above-identified patent and that said Letters Patent is hereby corrected as shown below:

In the Specifications:

At column 8, line 24, please delete “$NH_2$” and insert therefore, -- $-NH_2$--.

At column 11, line 17, please delete “heterocycyl” and insert therefore, --heterocyclyl--.

At column 11, line 21, please delete “heterocycicyl” and insert therefore, --heterocyclcyl--.

At column 11, line 25, please delete “heterocycyl” and insert therefore, --heterocyclyl--.

At column 17, line 26, after “$—S(R_2)_2$,” please insert -- $—SR_1$,--.
At column 93, lines 50-65, last chemical structure, please delete

354

“ 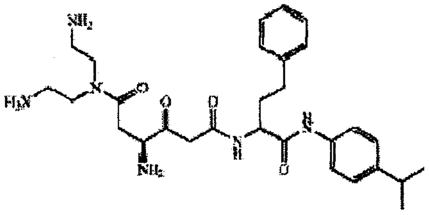 ”

354 and insert therefore, -- 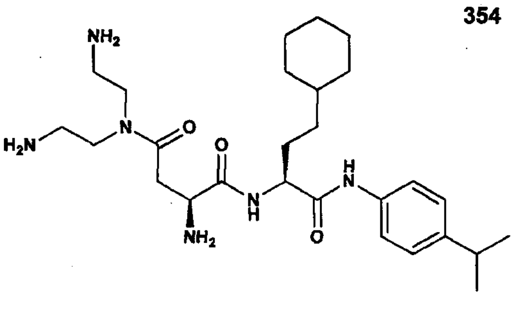 --.

At column 126, line 21, after “for” and before “min”, please insert --10--.

Signed and Sealed this
Thirtieth Day of July, 2013

Teresa Stanek Rea
*Acting Director of the United States Patent and Trademark Office*

At column 183-184, line 31, please delete
"
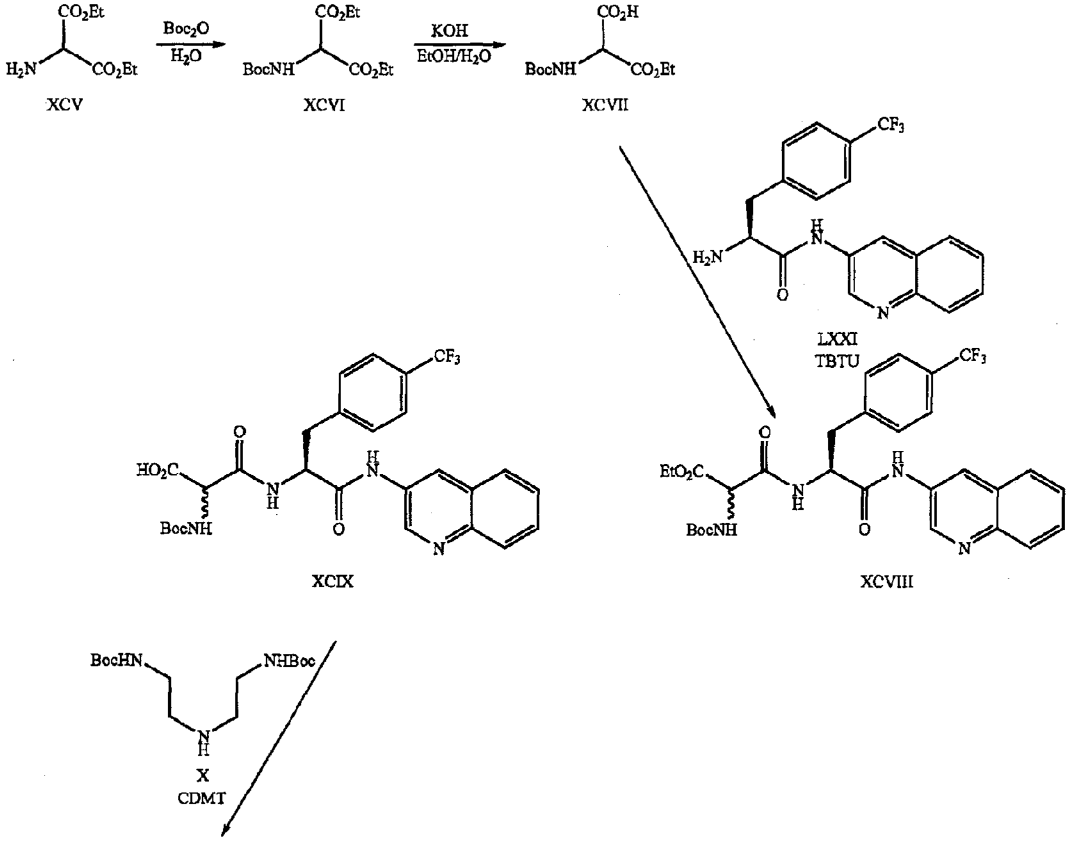
XCV XCVI XCVII LXXI XCIX XCVIII X
"
and insert therefore,
--
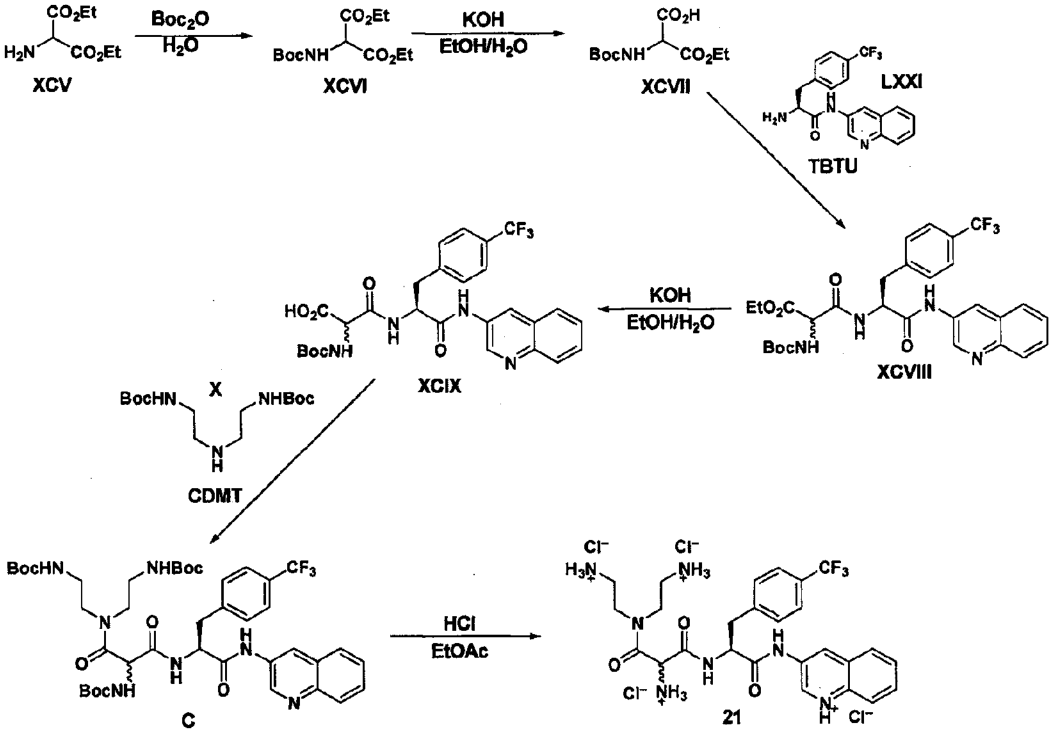
XCV XCVI XCVII LXXI XCVIII XCIX X C 21
--.

At column 187, second row of chemical structures, please delete
“ 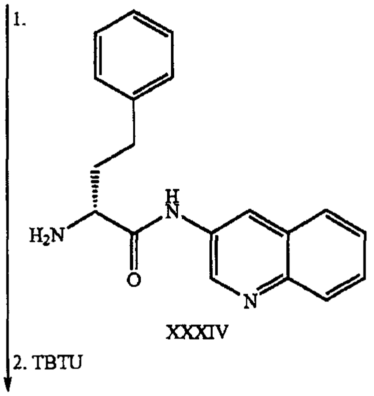
” and insert therefore, -- 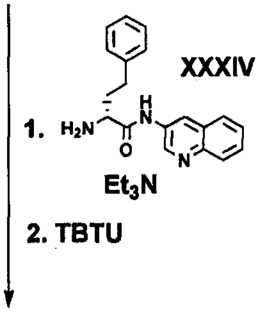
--.
At column 188, line 57, after “for” and before “min”, please insert --30--.
At column 201-202, lines 52-62, last row of chemical structures, please delete
“ 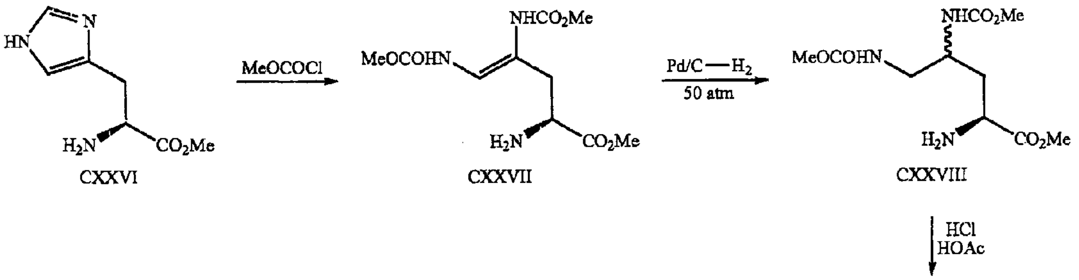
”
and insert therefore,
-- 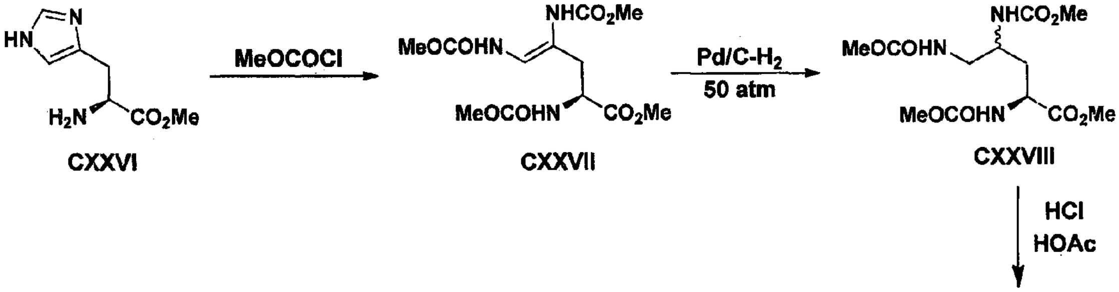
--.
At column 235-236, line 50, last line of chemical structures, please delete
“ 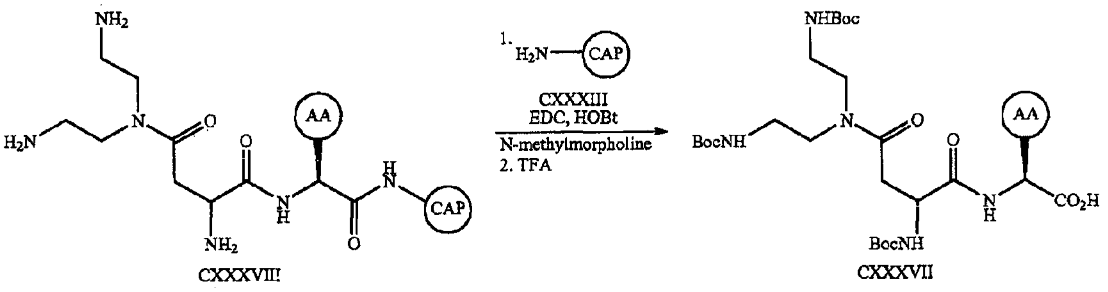
”
and insert therefore, -- 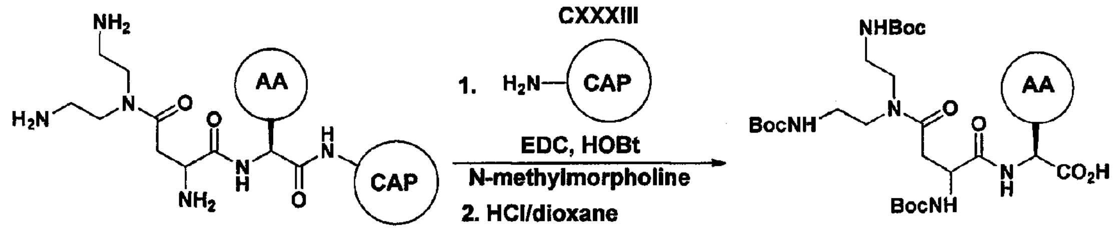
CXXXVIII CXXXVII --.
At column 254, line 37, please delete “diethylamide” and insert therefore, --triethylamine--.
At column 264, lines 18-30, second row of chemical structures, please delete
“ 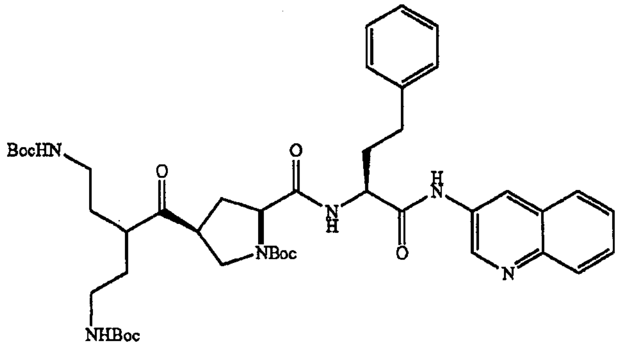 ”
and insert therefore, -- 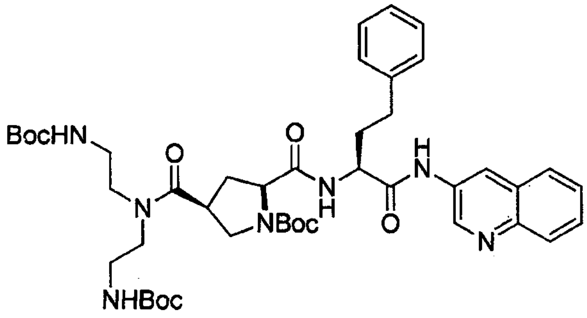 --.
At column 265-266, line 44, please delete
“ 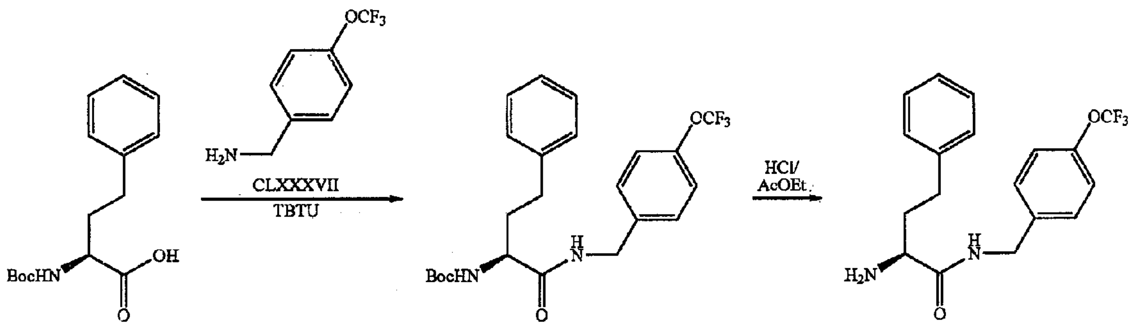
CLXXXVI CLXXXVIII CLXXXIX ”
and insert therefore, -- 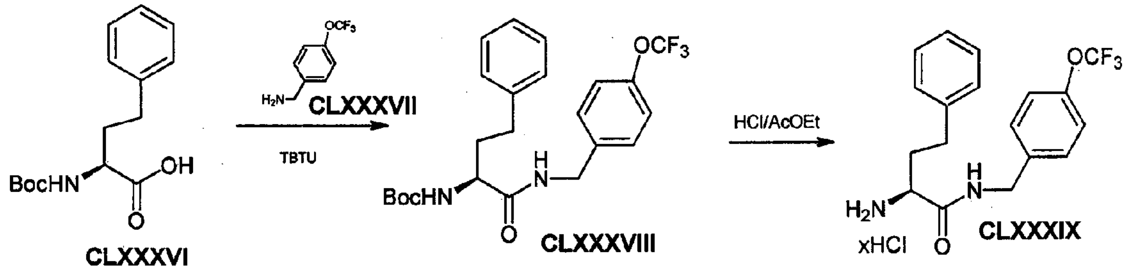
--.
At column 268, lines 35-40, third row of chemical structures, please delete
“ 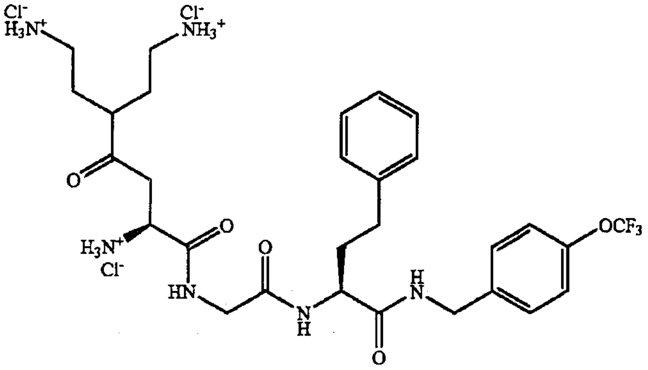 ” and insert therefore,
-- 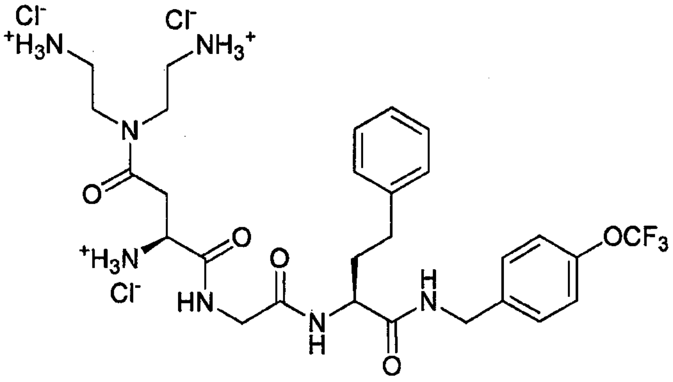 --.
At column 269-270, line 41, please delete
“ 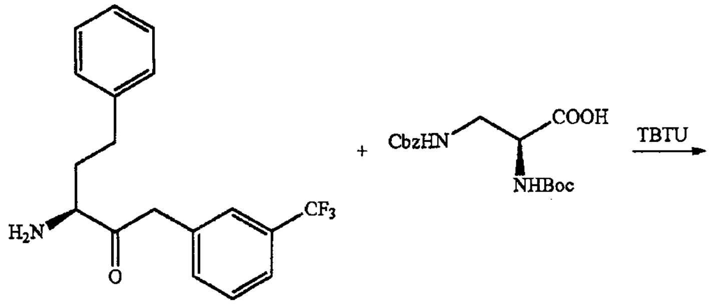
”
and insert therefore, -- 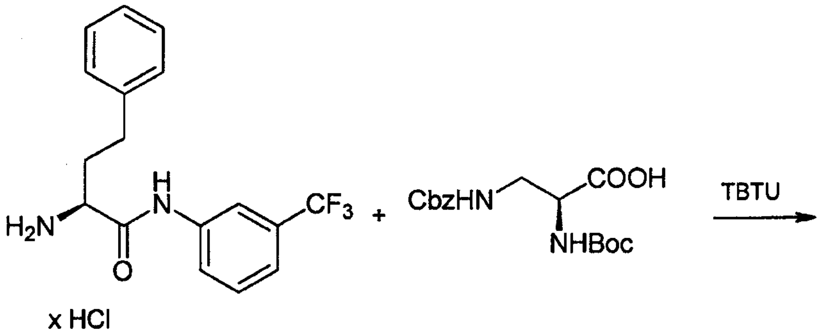
--.
At column 271-272, lines 35-40, third row of chemical structures, please delete
" 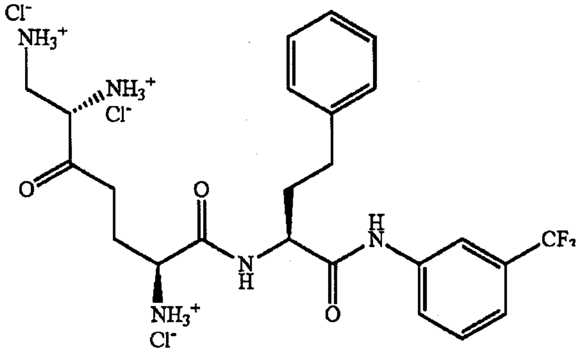 " and insert therefore,
-- 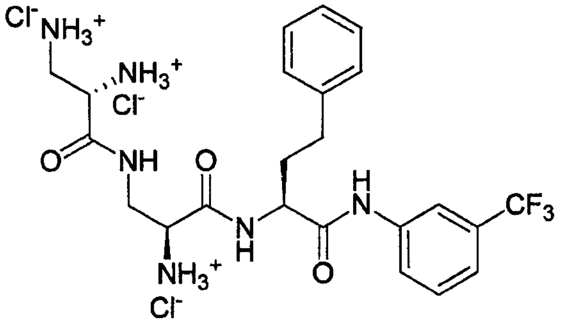 --.
At column 274, line 7, please delete "pethanediamide" and insert therefore, --ethanediamide--.
At column 290, line 67, please delete "3.89" and insert therefore, --63.89--.
At column 294, line 45, please delete " 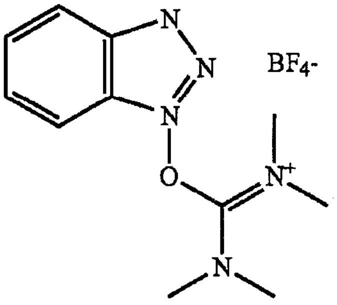 "

and insert therefore,

-- 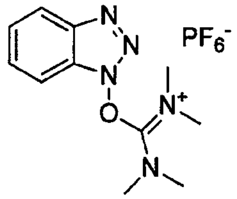 --.

At column 305, line 9, after “9:1,” and before “mL”, please insert --30--.

At column 489, lines 66-67, please delete “alcahgenes,” and insert therefore, --alcaligenes--.

In the Claims:

At column 502, line 47 in Claim 1, please delete “—OH,=O,” and insert therefore, -- —OH, =O,--.

At column 502, line 61 in Claim 1, please delete “—$(CH_2)_t$NH;” and insert therefore, -- —$(CH_2)_tNH_2$;--.

At column 502, line 63 in Claim 1, please delete “$^+(CH_3)_3$,” and insert therefore, -- —$N^+(CH_3)_3$,--.

At column 509, line 1 in Claim 10, please delete

“ 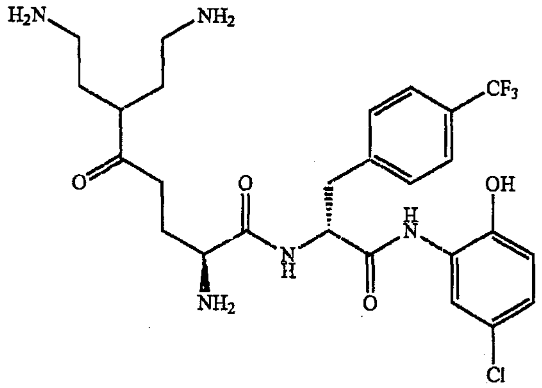 ”

and insert therefore,

-- 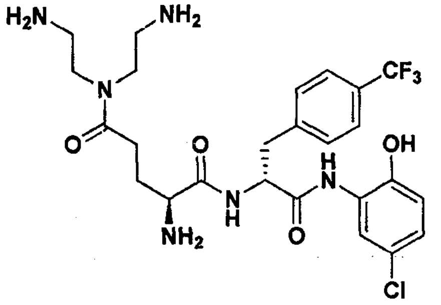 --.

At column 510, line 45 in Claim 10, please delete
"
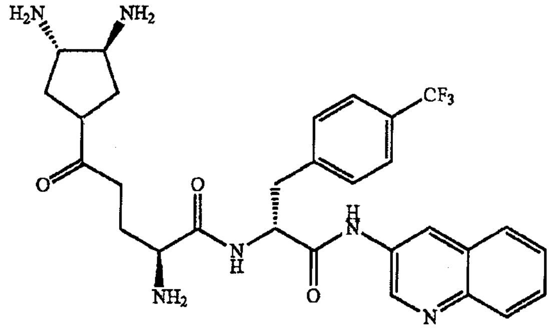
" and
insert therefore,
--
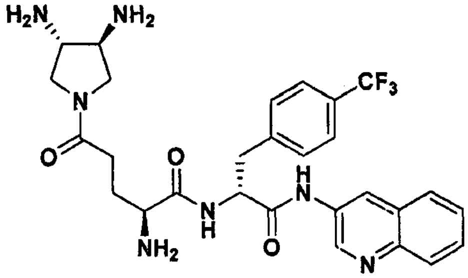
--.
At column 518, line 20 in Claim 10, please delete
"
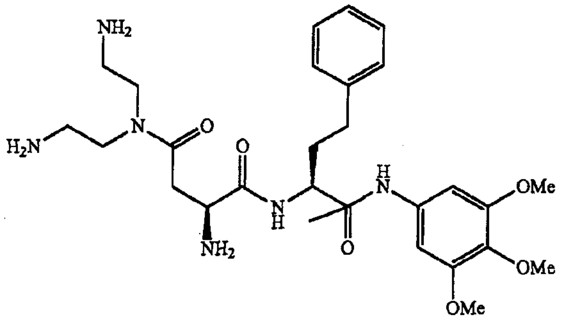
"
and insert therefore,
--
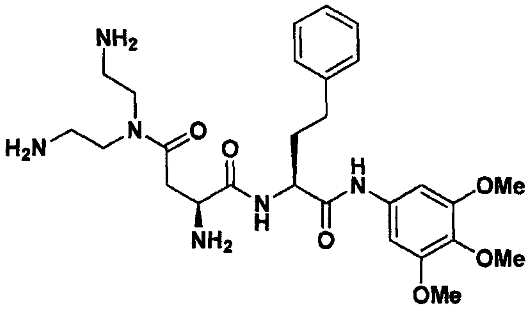
--.

At column 532, line 30 in Claim 10, please delete
"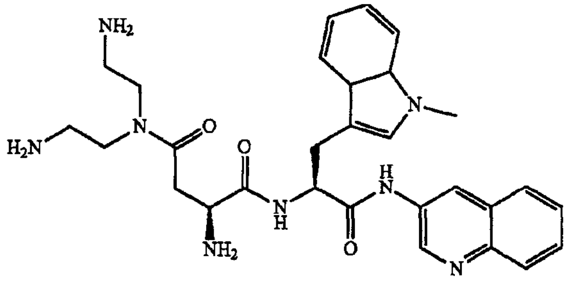" and
insert therefore,
--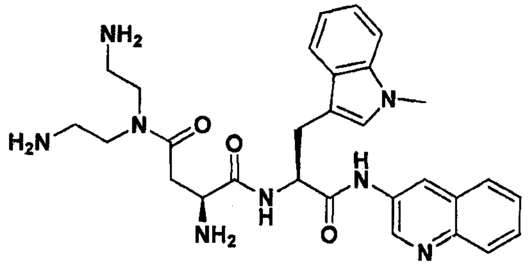--.
At column 532, line 60 in Claim 10, please delete
"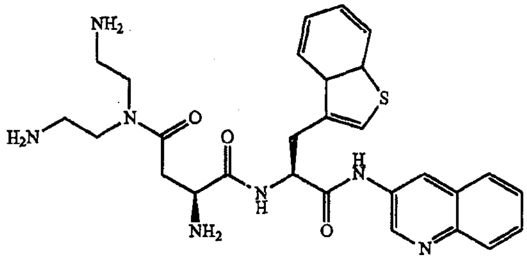"and
insert therefore,
--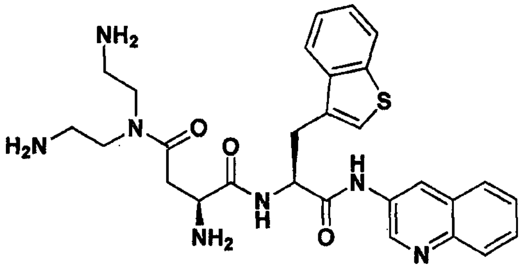--.

At column 535, line 30 in Claim 10, please delete
"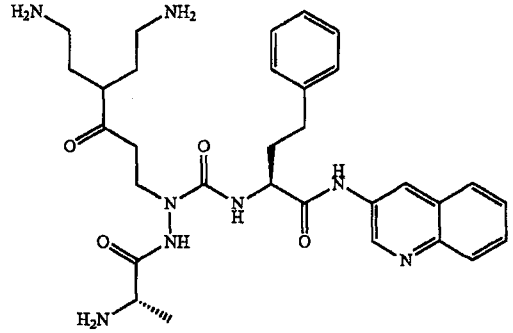" and insert therefore,
--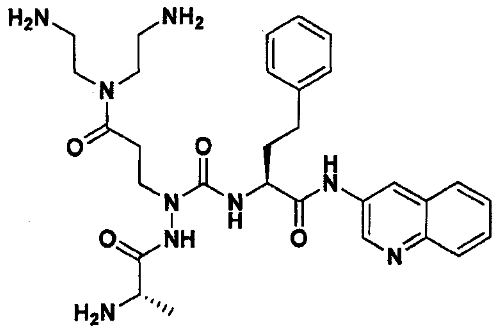--.
At column 538, line 25 in Claim 10, please delete
"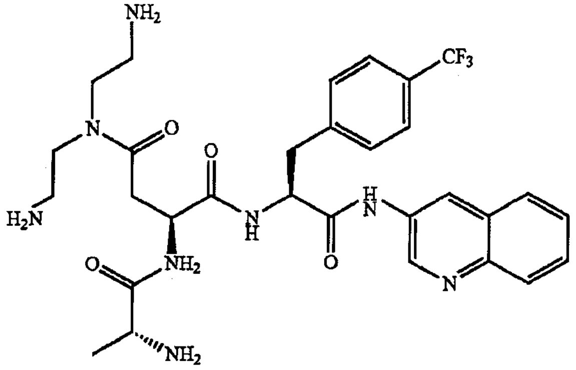"
and insert therefore,
--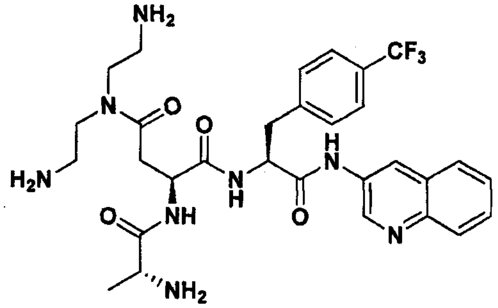--.

At column 538, line 60 in Claim 10, please delete
"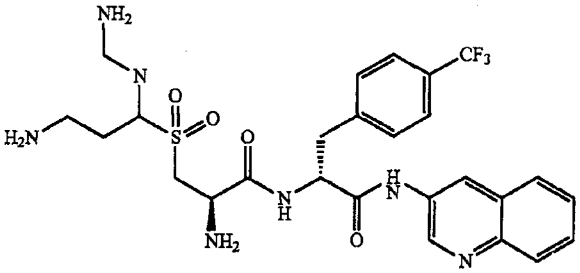"
and insert therefore,
--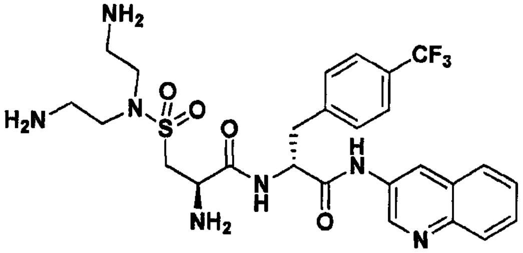--.
At column 539, line 40 in Claim 10, please delete
"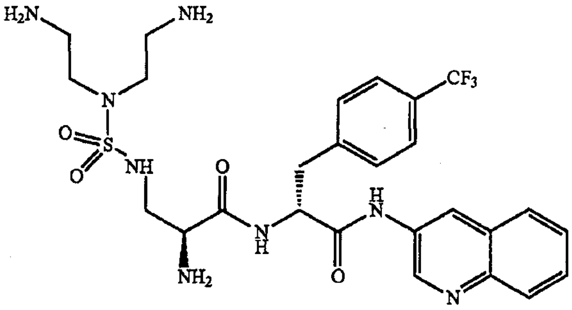" and
insert therefore,
--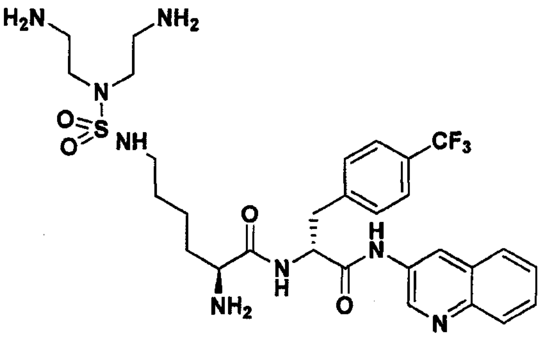--.

At column 540, line 20 in Claim 10, please delete
"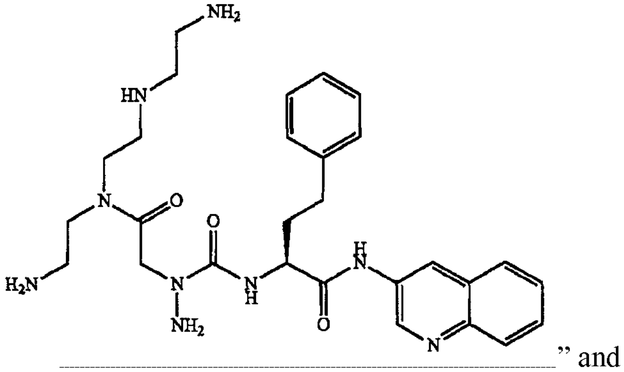" and insert therefore,
--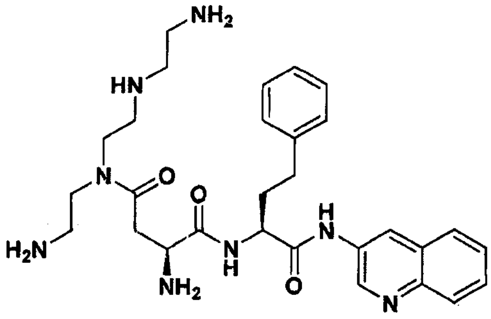--.
At column 541, line 30 in Claim 10, please delete
"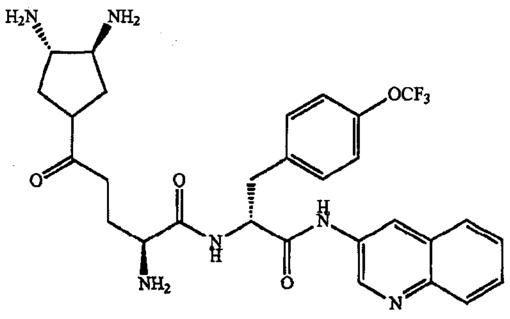" and insert therefore,
--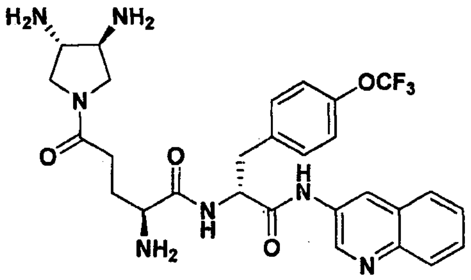--.

At column 541, line 45 in Claim 11, please delete
“ 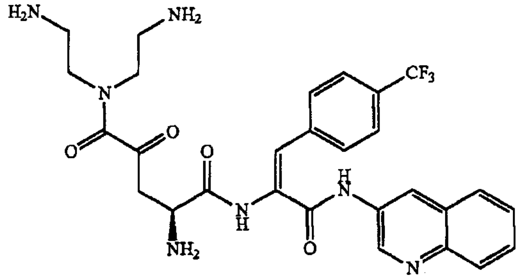 ” and
insert therefore,
-- 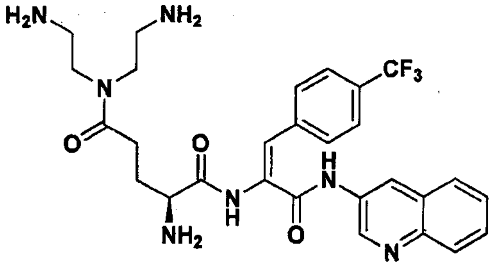 --.
At column 553, line 30 in Claim 11, please delete
“ 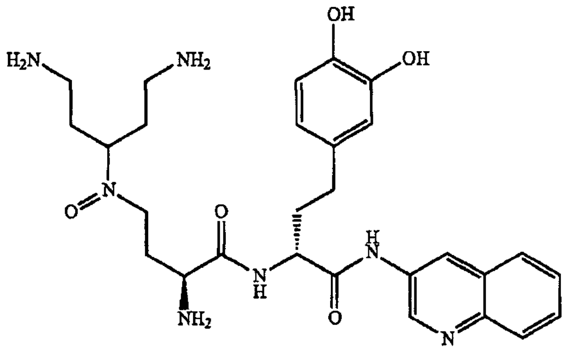 ” and
insert therefore,
-- 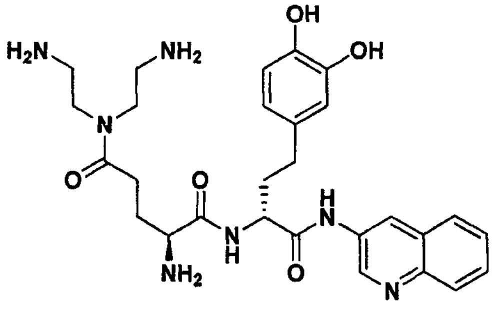 --.

At column 554, line 40 in Claim 11, please delete
" 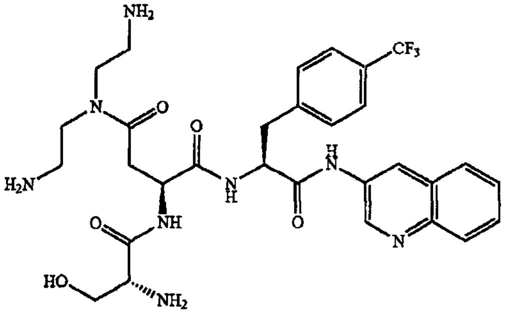 " and
insert therefore,
-- 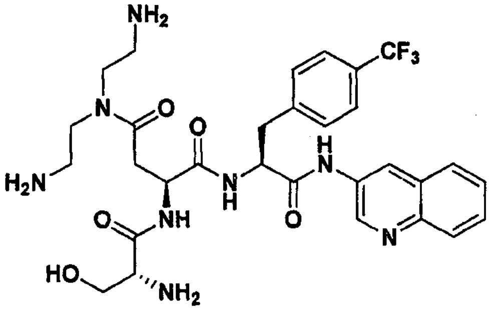 --.
At column 556, line 5 in Claim 11, please delete
" 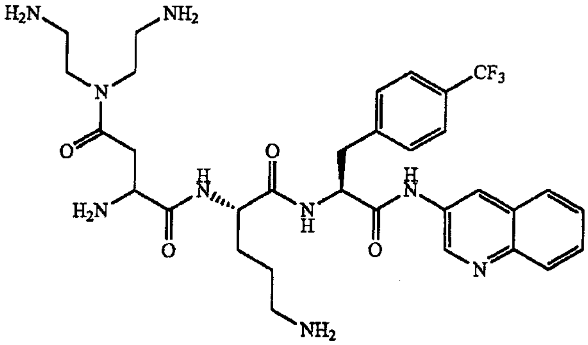 "
and insert therefore,
-- 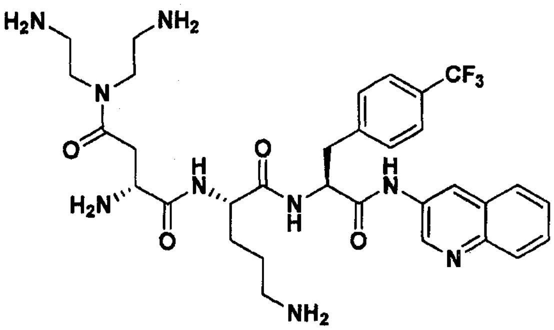 --.
At column 566, line 55 in Claim 13, please delete "232" and insert therefore --231--.
At column 570, line 29 in Claim 13, please delete "252" and insert therefore --251--.

At column 576, lines 41-54 in Claim 13, please delete
285
" 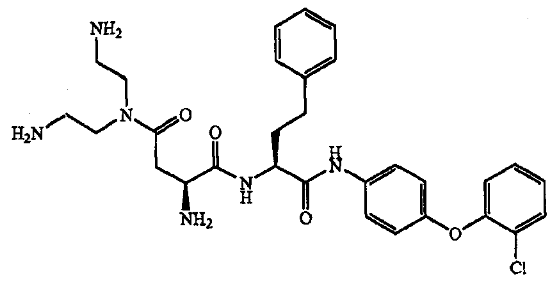 ".
At column 594, line 5 in Claim 14, please delete
" 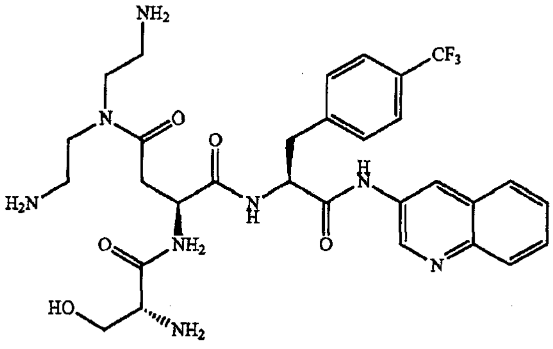 " and
insert therefore,
-- 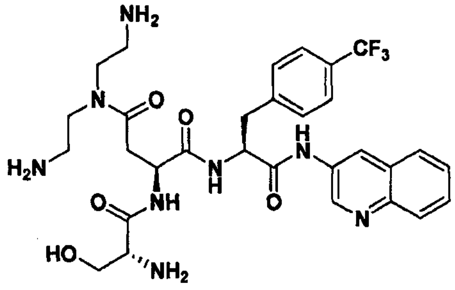 --.
At column 605-606, lines 50-65, last row of chemical structures in Claim 15, please delete
" 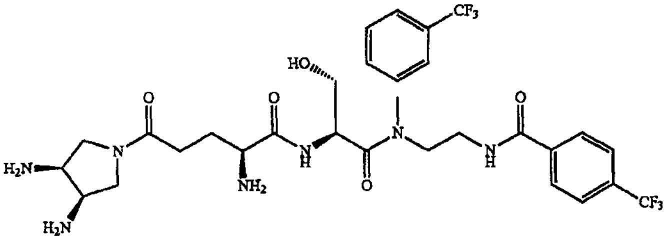 " and
insert therefore, -- 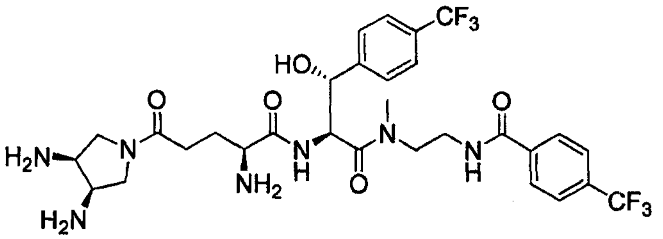 --.
Claim 15, first two rows of chemical structures, please delete
439
Col. 607, lines 1-15, " 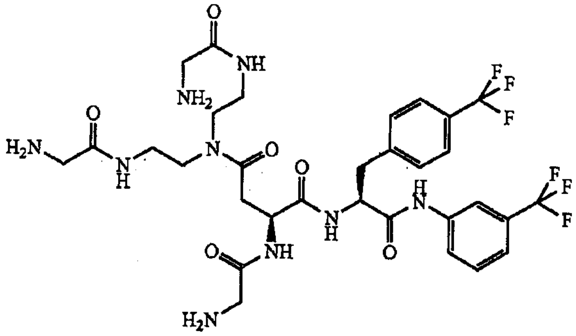 "
441
Col. 607, lines 20-35, " 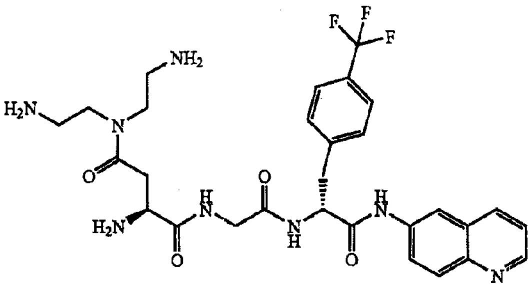 "
440
Col. 608, lines 1-18, " 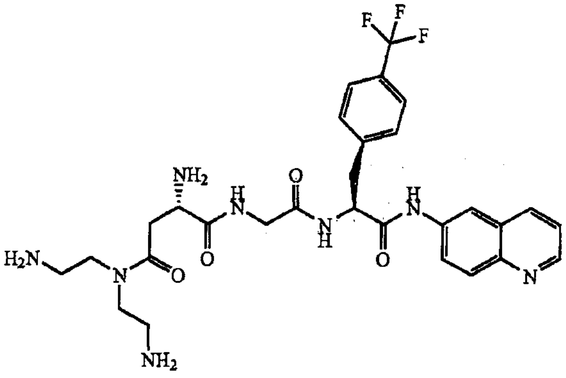 "

442
Col. 608, lines 20-35, " 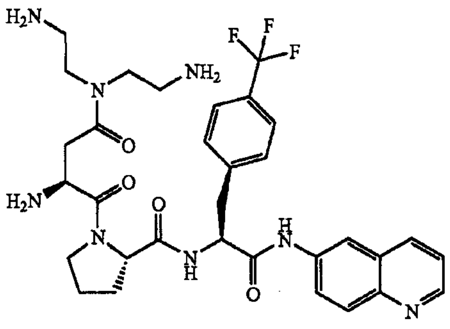 ".